US006492362B1

(12) United States Patent
Graupe et al.

(10) Patent No.: US 6,492,362 B1
(45) Date of Patent: Dec. 10, 2002

(54) COMPOUNDS AND COMPOSITIONS AS CATHEPSIN S INHIBITORS

(75) Inventors: Michael Graupe, San Mateo, CA (US); John O. Link, San Francisco, CA (US); John W. Patterson, Mountain View, CA (US); Sheila Zipfel, Palo Alto, CA (US)

(73) Assignee: Axys Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 09/663,449

(22) Filed: Sep. 15, 2000

Related U.S. Application Data

(60) Provisional application No. 60/154,245, filed on Sep. 16, 1999, provisional application No. 60/171,831, filed on Dec. 22, 1999, and provisional application No. 60/224,552, filed on Aug. 10, 2000.

(51) Int. Cl.$^7$ .................. A61K 31/5375; C07D 209/04; C07D 265/30
(52) U.S. Cl. ..................... 514/237.5; 514/415; 514/438; 514/448; 514/238; 544/169; 544/130; 544/160; 544/163; 548/504; 558/397; 549/71
(58) Field of Search .............................. 514/237.5, 415, 514/438, 448, 238; 544/169, 160, 130, 163; 548/504; 558/397; 549/71

(56) References Cited

U.S. PATENT DOCUMENTS 5,852,007 A    12/1998    Chatterjee ................... 514/183
6,124,333 A *   9/2000    Miller et al. ................ 514/369

FOREIGN PATENT DOCUMENTS

| EP | 0652009 A1 | 10/1995 |
|----|---|---|
| JP | 63 301868 | 12/1988 |
| WO | WO 98/23588 | 6/1998 |
| WO | WO 00/51998 | 9/2000 |

OTHER PUBLICATIONS

Picken, P. et al., "Inhibition of bovine cathepsin B by amino acid–derived nitriles" Biochemical Society Transactions, vol. 18, No. 2, p:316 (1990).

Chatterjee, S. et al., "D–Amino Acid Containing, High–Affinity Inhibitors of Recombinant Human Calpain I" Journal of Medicinal Chemistry, vol. 41, No. 15, p: 2663–2666 (1998).

* cited by examiner

Primary Examiner—Joseph K. McKane
Assistant Examiner—Donya Wright
(74) Attorney, Agent, or Firm—Wayne W. Montgomery; Rekha Bansal

(57) ABSTRACT

The present invention relates to novel selective cathepsin S inhibitors, the pharmaceutically acceptable salts and N-oxides thereof, their uses as therapeutic agents and the methods of their making.

9 Claims, No Drawings

COMPOUNDS AND COMPOSITIONS AS CATHEPSIN S INHIBITORS

This Application claims the right of priority under U.S.C. §119(e) of U.S. Provisional Applications Nos. 60/154,245, 60/171,831 and 60/224,552, filed Sep. 16, 1999, Dec. 22, 1999 and Aug. 10, 2000, respectively.

THE INVENTION

This Application relates to compounds and compositions for treating diseases associated with cysteine protease activity, particularly diseases associated with activity of cathepsin S.

DESCRIPTION OF THE FIELD

Cysteine proteases represent a class of peptidases characterized by the presence of a cysteine residue in the catalytic site of the enzyme. Cysteine proteases are associated with the normal degradation and processing of proteins. The aberrant activity of cysteine proteases, e.g., as a result of increase expression or enhanced activation, however, may have pathological consequences. In this regard, certain cysteine proteases are associated with a number of disease states, including arthritis, muscular dystrophy, inflammation, tumor invasion, glomerulonephritis, malaria, periodontal disease, metachromatic leukodystrophy and others. An increase in cathepsin S activity contributes to the pathology and/or symptomatology of a number of diseases. Accordingly, molecules that inhibit the activity of cathepsin S protease are useful as therapeutic agents in the treatment of such diseases.

SUMMARY OF THE INVENTION

This Application relates to compounds of Formula I:

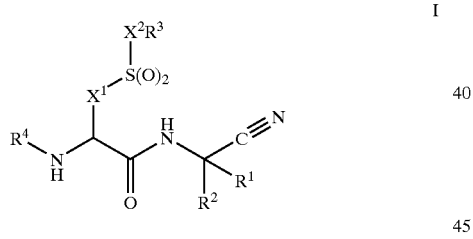

in which:

$X^1$ and $X^2$ are both methylene or $X^1$ is ethylene and $X^2$ is a bond;

$R^1$ is hydrogen and $R^2$ is cyano, hetero($C_5$)aryl or ($C_{1-4}$)alkyl-substituted hetero($C_5$)aryl or both $R^1$ and $R^2$ are hydrogen, halo, ($C_{1-4}$)alkyl or —$X^3OR^9$, wherein $X^3$ and $R^9$ are as defined below, or $R^1$ and $R^2$ together with the carbon atom to which both $R^1$ and $R^2$ are attached form ($C_{3-8}$)cycloalkylene or ($C_{3-8}$)heterocycloalkylene;

$R^3$ is —$CR^5$=$CHR^6$ or —$CR^7$=$NR^8$, wherein $R^5$ and $R^6$ together with the atoms to which $R^5$ and $R^6$ are attached form ($C_{2-6}$)alkenyl, ($C_{5-12}$)cycloalkenyl, hetero($C_{5-12}$) cycloalkenyl, ($C_{6-12}$)aryl, hetero($C_{6-12}$)aryl, ($C_{9-12}$) bicycloaryl or hetero($C_{8-12}$)bicycloaryl and $R^7$ and $R^8$ together with the atoms to which $R^7$ and $R^8$ are attached form hetero($C_{5-12}$)cycloalkenyl, hetero($C_{6-12}$)aryl or hetero($C_{8-12}$)bicycloaryl, wherein $R^3$ optionally is substituted by 1 to 5 radicals independently selected from a group consisting of ($C_{1-4}$)alkyl, cyano, halo, halo-substituted ($C_{1-4}$)alkyl, nitro, —$X^3NR^9R^9$, —$X^3OR^9$, —$X^3SR^9$, —$X^3C(O)NR^9R^9$, —$X^3C(O)OR^9$, —$X^3S$ (O)$R^{10}$, —$X^3S(O)_2R^{10}$ and —$X^3C(O)R^{10}$, wherein $X^3$ is a bond or ($C_{1-2}$)alkylene, $R^9$ at each occurrence independently is hydrogen, ($C_{1-3}$)alkyl or halo-substituted ($C_{1-3}$)alkyl and $R^{10}$ is ($C_{1-3}$)alkyl or halo-substituted ($C_{1-3}$)alkyl; and $R^4$ is —$C(O)X^4R^{11}$ or —$S(O)_2X^4R^{11}$, wherein $X^4$ is a bond, —O— or —$NR^{12}$—, wherein $R^{12}$ is hydrogen or ($C_{1-6}$)alkyl, and $R^{11}$ is (i) ($C_{1-6}$)alkyl optionally substituted by —$OR^3$, —$SR^3$, —$S(O)R^3$, —$S(O)_2R^{13}$, —$C(O)R^{13}$, —$C(O)OR^3$, —$C(O)NR^{13}R^{14}$, —$NR^{13}R^{14}$, —$NR^{14}C(O)R^{13}$, —$NR^{14}C(O)OR^{13}$, —$NR^{14}C(O)NR^{13}R^{14}$ or —$NR^{14}C(NR^{14})NR^{13}R^{14}$, wherein $R^{13}$ is ($C_{3-12}$)cycloalkyl($C_{0-3}$)alkyl, hetero($C_{5-12}$)cycloalkyl($C_{0-3}$)alkyl, ($C_{6-12}$)aryl($C_{0-3}$)alkyl, hetero ($C_{5-12}$)aryl($C_{0-3}$)alkyl, ($C_{9-12}$)bicycloaryl($C_{0-3}$)alkyl or hetero($C_{8-12}$)bicycloaryl($C_{0-3}$)alkyl and $R^{14}$ at each occurrence independently is hydrogen or ($C_{1-6}$)alkyl, or (ii) ($C_{3-12}$)cycloalkyl($C_{0-3}$)alkyl, hetero($C_{5-12}$) cycloalkyl($C_{0-3}$)alkyl, ($C_{6-12}$)aryl($C_{0-3}$)alkyl, hetero ($C_{5-12}$)aryl($C_{0-3}$)alkly, ($C_{9-12}$)bicycloaryl($C_{0-3}$)alkyl or hetero($C_{8-12}$)bicycloaryl($C_{0-3}$)alkyl or (iii) ($C_{3-6}$) cycloalkyl($C_{0-3}$)alkyl, hetero($C_{5-6}$)cycloalkyl($C_{0-3}$) alkyl, phenyl($C_{0-3}$)alkyl or hetero($C_{5-6}$)aryl($C_{0-3}$)alkyl substituted by —$X^5OR^{15}$, —$X^5SR^{15}$, —$X^5S(O)R^{15}$, —$X^5S(O)_2R^{15}$, —$X^5C(O)R^{15}$, —$X^5C(O)OR^{15}$, —$X^5C(O)NR^{15}R^{16}$, —$X^5NR^{15}R^{16}$, —$X^5NR^{16}C(O)$ $R^{15}$, —$X^5NR^{16}C(O)OR^{15}$, —$X^5NR^{16}C(O)NR^{15}R^{16}$ or —$X^5NR^{16}C(NR^{16})NR^{15}R^{16}$, wherein $X^5$ is a bond or methylene, $R^{15}$ is ($C_{3-6}$)cycloalkyl($C_{0-3}$)alkyl, hetero ($C_{5-6}$)cycloalkyl($C_{0-3}$)alkyl, phenyl($C_{0-3}$)alkyl or hetero($C_{5-6}$)aryl($C_{0-3}$)alkyl and $R^{16}$ is hydrogen or ($C_{1-6}$)alkyl; wherein $R^4$ optionally further contains 1 to 5 substituents which when occurring within an alicyclic or aromatic ring system are radicals independently selected from a group consisting of ($C_{1-6}$)alkyl, ($C_{1-6}$) alkylidene, cyano, halo, nitro, halo-substituted ($C_{1-3}$) alkyl, —$X^5NR^{17}R^{17}$, —$X^5NR^{17}C(O)OR^{17}$, —$X^5NR^{17}C(O)NR^{17}R^{17}$, —$X^5NR^{17}C(NR^{17})$ $NR^{17}R^{17}$, —$X^5OR^{17}$—$X^5SR^{17}$, —$X^5C(O)OR^{17}$, —$X^5C(O)NR^{17}R^{17}$, —$X^5S(O)_2NR^{17}R^{17}$, —$X^5P(O)$ $(OR^8)OR^{17}$, —$X^5OP(O)(OR^8)OR^{17}$, —$X^5NR^{17}C(O)$ $R^{18}$, —$X^5S(O)R^{18}$, —$X^5S(O)_2R^{18}$ and —$X^5C(O)R^{18}$ and when occurring within an aliphatic moiety are radicals independently selected from a group consisting of cyano, halo, nitro, —$NR^{17}R^{17}$, —$NR\ C(O)OR^{17}$, —$NR^{17}C(O)NR^{17}R^{17}$, —$NR^{17}C(NR^{17})NR^{17}R^{17}$, —$OR^{17}$, —$SR^{17}$, —$C(O)OR^{17}$, —$C(O)NR^{17}R^{17}$, —$S(O)_2NR^{17}R^{17}$, —$P(O)(OR^{17})OR^{17}$, —$OP(O)$ $(OR^{17}) OR^{17}$, —$NR^{17}C(O)R^{18}$, —$S(O)R^{18}$, —$S(O)_2$ $R^{18}$ and —$C(O)R^{18}$, wherein $X^5$ is a bond or ($C_{1-6}$) alkylene, $R^{17}$ at each occurrence independently is hydrogen, ($C_{1-6}$)alkyl or halo-substituted ($C_{1-3}$)alkyl and $R^{18}$ is ($C_{1-6}$)alkyl or halo-substituted ($C_{1-3}$)alkyl; and the N-oxide derivatives, prodrug derivatives, protected derivatives, individual isomers and mixtures of isomers thereof; and the pharmaceutically acceptable salts and solvates (e.g. hydrates) of such compounds and the N-oxide derivatives, prodrug derivatives, protected derivatives, individual isomers and mixtures of isomers thereof.

A second aspect of the invention is a pharmaceutical composition which contains a compound of Formula I or a N-oxide derivative, individual isomer or mixture of isomers thereof, or a pharmaceutically acceptable salt thereof, in admixture with one or more suitable excipients.

A third aspect of the invention is a method for treating a disease in an animal in which inhibition of cathepsin S can prevent, inhibit or ameliorate the pathology and/or symptomatology of the disease, which method comprises administering to the animal a therapeutically effective amount of compound of Formula I or a N-oxide derivative, individual isomer or mixture of isomers thereof; or a pharmaceutically acceptable salt thereof.

A fourth aspect of the invention is the processes for preparing compounds of Formula I and the N-oxide derivatives, prodrug derivatives, protected derivatives, individual isomers and mixtures of isomers thereof; and the pharmaceutically acceptable salts thereof.

DETAILED DESCRIPTION OF THE INVENTION

Definitions

Unless otherwise stated, the following terms used in the specification and claims are defined for the purposes of this Application and have the following meanings.

"Alicyclic" means a moiety characterized by arrangement of the carbon atoms in closed non-aromatic ring structures having properties resembling those of aliphatics and may be saturated or partially unsaturated with two or more double or triple bonds.

"Aliphatic" means a moiety characterized by a straight or branched chain arrangement of the constituent carbon atoms and may be saturated or partially unsaturated with two or more double or triple bonds.

"Alkyl" represented by itself means a straight or branched, saturated or unsaturated, aliphatic radical having the number of carbon atoms indicated (e.g., $(C_{1-6})$alkyl includes methyl, ethyl, propyl, isopropyl, butyl, sec-butyl, isobutyl, tert-butyl, vinyl, allyl, 1-propenyl, isopropenyl, 1-butenyl, 2-butenyl, 3-butenyl, 2-methylallyl, ethynyl, 1-propynyl, 2-propynyl, and the like). Alkyl represented along with another radical (e.g., as in arylalkyl) means a straight or branched, saturated or unsaturated aliphatic divalent radical having the number of atoms indicated or when no atoms are indicated means a bond (e.g., $(C_{6-12})$aryl$(C_{0-3})$alkyl includes phenyl, benzyl, phenethyl, 1-phenylethyl 3-phenylpropyl, and the like).

"Alkylene", unless indicated otherwise, means a straight or branched, saturated or unsaturated, aliphatic, divalent radical having the number of carbon atoms indicated (e.g., $(C_{1-6})$alkylene includes methylene (—CH$_2$—), ethylene (—CH$_2$CH$_2$—), trimethylene (—CH$_2$CH$_2$CH$_2$—), tetramethylene (—CH$_2$CH$_2$CH$_2$CH$_2$—) 2-butenylene (—CH$_2$CH=CHCH$_2$—), 2-methyltetramethylene (—CH$_2$CH(CH$_3$)CH$_2$CH$_2$—), pentamethylene (—CH$_2$CH$_2$CH$_2$CH$_2$CH$_2$—) and the like).

"Alkenyl" means alkyl, as defined in this Application, provided that the radical is comprised of at least one double bond. Hence, optionally substituted $(C_{2-6})$alkenyl as used in this Application to define R$^3$ includes 2-bromovinyl (—CH=CHBr), buta-1,3-dienyl (—CH=CH—CH=CH$_2$), 2-chloro-1-methylpropenyl (—C(CH$_3$)=CCl—CH$_3$), 2-chlorovinyl (—CH=CHCl), 4-isopropenyl (—C(CH$_3$)=CH$_2$), 1-methylpropenyl (—C(CH$_3$)=CH—CH$_3$), 2-methylpropenyl (—CH=C(CH$_3$)$_2$), 2-nitrovinyl (—CH=CHNO$_2$), propenyl (—CH=CH—CH$_3$), 2-trifluormethylvinyl (—CH=CH—CF$_3$), trifluorovinyl (—CF=CF$_2$), vinyl (—CH=CH$_2$), and the like).

"Alkylidene" means a straight or branched saturated or unsaturated, aliphatic, divalent radical having the number of carbon atoms indicated (e.g. $(C_{1-6})$alkylidene includes methylene (=CH$_2$), ethylidene (=CHCH$_3$), isopropylidene (=C(CH$_3$)$_2$), propylidene (=CHCH$_2$CH$_3$), allylidene (=CHCH=CH$_2$), and the like).

"Amino" means the radical —NH$_2$. Unless indicated otherwise, the compounds of the invention containing amino moieties include protected derivatives thereof. Suitable protecting groups for amino moieties include acetyl, tert-butoxycarbonyl, benzyloxycarbonyl, and the like.

"Animal" includes humans, non-human mammals (e.g., dogs, cats, rabbits, cattle, horses, sheep, goats, swine, deer, and the like) and non-mammals (e.g., birds, and the like).

"Aromatic" means a moiety wherein the constituent atoms make up an unsaturated ring system, all atoms in the ring system are sp$^2$ hybridized and the total number of pi electrons is equal to 4n+2.

"Aryl" means a monocyclic or bicyclic ring assembly (fused or linked by a single bond) containing the total number of ring carbon atoms indicated, wherein each ring is comprised of 6 ring carbon atoms and is aromatic or when fused with a second ring forms an aromatic ring assembly. For example, optionally substituted $(C_{6-12})$aryl as used in this Application to define R$^3$ includes biphenyl-2-yl, 2-bromophenyl, 2-bromocarbonylphenyl, 2-bromo-5-fluorophenyl, 4-tert-butylphenyl, 4-carbamoylphenyl, 4-carboxy-2-nitrophenyl, 2-chlorophenyl, 4-chlorophenyl, 3-chlorocarbonylphenyl, 4-chlorocarbonylphenyl, 2-chloro-4-fluorophenyl, 2-chloro-6-fluorophenyl, 4-chloro-2-nitrophenyl, 6-chloro-2-nitrophenyl, 2,6-dibromophenyl, 2,3-dichlorophenyl, 2,5-dichlorophenyl, 3,4-dichlorophenyl, 2-difluoromethoxyphenyl, 3,5-dimethylphenyl, 2-ethoxycarbonylphenyl, 2-fluoropheny, 2-Iodophenyl, 4-isopropylphenyl, 2-methoxyphenyl, 4-methoxyphenyl, 2-methylphenyl, 3-methylphenyl, 4-methylphenyl, 5-methyl-2-nitrophenyl, 4-methylsulfonylphenyl, naphth-2-yl, 2-nitrophenyl, 3-nitrophenyl, 4-nitrophenyl, 2,3,4,5,6-pentafluorophenyl, phenyl, 2-trifluoromethoxyphenyl, 3-trifluoromethoxyphenyl, 4-trifluoromethoxyphenyl, 2-trifluoromethylphenyl, 3-trifluoromethylphenyl, 4-trifluoromethylphenyl, 2-trifluoromethylsulfanylphenyl, 4-trifluoromethylsulfanylphenyl, and the like. Optionally substituted $(C_{6-12})$aryl as used in this Application to define R$^4$ includes 3-acetylphenyl, 3-tert-butoxycarbonylaminomethylphenyl, biphenyl-4-yl, 3-hydroxyphenyl, 4-hydroxyphenyl, 3-methoxyphenyl, naphth-2-yl, 3-phenoxyphenyl, phenyl, and the like.

"Bicycloaryl" means a bicyclic ring assembly containing the number of ring carbon atoms indicated, wherein the rings are linked by a single bond or fused and one, but not both, of the rings comprising the assembly is aromatic, and any carbocyclic ketone, thioketone or iminoketone derivative thereof (e.g., $(C_{9-12})$bicycloaryl includes cyclohexylphenyl, 1,2-dihydronaphthyl, 2,4-dioxo-1,2,3,4-tetrahydronaphthyl, indanyl, indenyl, phenylcyclohexyl, 1,2,3,4-tetrahydronaphthyl, and the like.

"Carbamoyl" means the radical —C(O)NH$_2$. Unless indicated otherwise, the compounds of the invention containing carbamoyl moieties include protected derivatives thereof. Suitable protecting groups for carbamoyl moieties include acetyl, tert-butoxycarbonyl, benzyloxycarbonyl, and the like and both the unprotected and protected derivatives fall within the scope of the invention.

"Carbocyclic ketone derivative" means a derivative containing the moiety —C(O)—.

"Carboxy" means the radical —C(O)OH. Unless indicated otherwise, the compounds of the invention containing carboxy moieties include protected derivatives thereof. Suitable protecting groups for carboxy moieties include benzyl, tert-butyl, and the like.

"Cycloalkenyl" means cycloalkyl, as defined in this Application, provided that the ring assembly is comprised of at least one double bond. Hence, optionally substituted $(C_{5-12})$cycloalkenyl as used in this Application to define $R^3$ includes cyclopent-1-enyl, 2-methylcyclopent-1-enyl, 2-nitrocyclopent-1-enyl, 2-fluorocyclopent-1-enyl, 2-chlorocyclopent-1-enyl, 2-trifluoromethylcyclopent-1-enyl, cyclohex-1-enyl, 2-methylcyclohex-1-enyl, 2-nitrocyclohex-1-enyl, 2-fluorocyclohex-1-enyl, 2-chlorocyclohex-1-enyl, 3-cyclohexa-1,3-dienyl, and the like).

"Cycloalkyl" means a saturated or partially unsaturated, monocyclic ring, bicyclic ring assembly (directly linked by a single bond or fused) or bridged polycyclic ring assembly containing the number of ring carbon atoms indicated, and any carbocyclic ketone, thioketone or iminoketone derivative thereof (e.g., $(C_{3-12})$cycloalkyl includes cyclopropyl, cyclobutyl, cyclopentyl, cyclohexyl, cyclohexenyl, 2,5-cyclohexadienyl, bicyclohexylyl, cyclopentylcyclohexyl, bicyclo[2.2.2]octyl, adamantan-1-yl, decahydronaphthyl, oxocyclohexyl, dioxocyclohexyl, thiocyclohexyl, 2-oxobicyclo[2.2.1]hept-1-yl, and the like).

"Cycloalkylene" means a divalent saturated or partially unsaturated, monocyclic ring or bridged polycyclic ring assembly containing the number of ring carbon atoms indicated, and any carbocyclic ketone, thioketone or iminoketone derivative thereof. For example, the instance wherein "$R^1$ and $R^2$ together with the carbon atom to which both $R^1$ and $R^2$ are attached form $(C_{3-8})$cycloalkylene" includes, but is not limited to, the following:

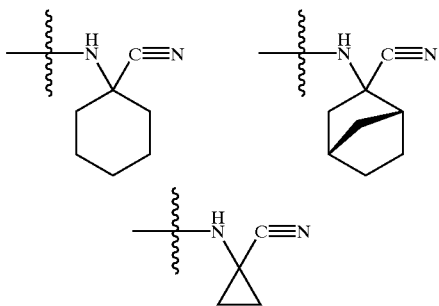

"Disease" specifically includes any unhealthy condition of an animal or part thereof and includes an unhealthy condition that may be caused by, or incident to, medical or veterinary therapy applied to that animal, i.e., the "side effects" of such therapy.

"Halo" means fluoro, chloro, bromo or iodo.

"Halo-substituted alkyl", as an isolated group or part of a larger group, means "alkyl" substituted by one or more "halo" atoms, as such terms are defined in this Application. Halo-substituted alkyl includes haloalkyl, dihaloalkyl, trihaloalkyl, perhaloalkyl and the like (e.g. halo-substituted $(C_{1-3})$alkyl includes chloromethyl, dichloromethyl, difluoromethyl, trifluoromethyl, 2,2,2-trifluoroethyl, perfluoroethyl, 2,2,2-trifluoro-1,1-dichloroethyl, and the like).

"Heteroatom moiety" includes —N=, —NR—, —O—, —S— or —S(O)$_2$—, wherein R is hydrogen, $(C_{1-6})$alkyl or a protecting group.

"Heterocycloalkylene" means cycloalkylene, as defined in this Application, provided that one or more of the ring member carbon atoms indicated, is replaced by heteroatom moiety selected from —N=, —NR—, —O—, —S— or —S(O)$_2$—, wherein R is hydrogen or $(C_{1-6})$alkyl. For example, the instance wherein $R^1$ and $R^2$ together with the carbon atom to which both $R^1$ and $R^2$ are attached form hetero$(C_{3-8})$cycloalkylene" includes, but is not limited to, the following:

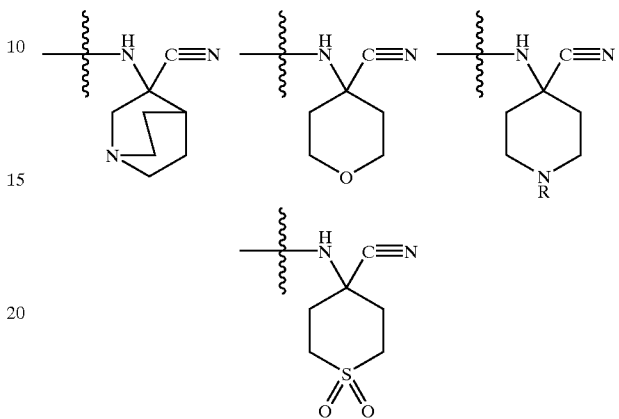

in which R is hydrogen, $(C_{1-6})$alkyl, or a protecting group.

"Heteroaryl" means aryl, as defined in this Application, provided that one or more of the ring carbon atoms indicated are replaced by a heteroatom moiety selected from —N=, —NR—, —O— or —S—, wherein R is hydrogen, $(C_{1-6})$alkyl, a protecting group or represents the free valence which serves as the point of attachment to a ring nitrogen, and each ring is comprised of 5 or 6 ring atoms. For example, optionally substituted hetero$(C_{5-12})$aryl as used in this Application to define $R^3$ includes 4-amino-2-hydroxypyrimidin-5-yl, benzothiazol-2-yl, 1H-benzoimidazol-2-yl, 2-bromopyrid-5-yl, 5-bromopyrid-2-yl, 4-carbamoylthiazol-2-yl, 3-carboxypyrid-4-yl, 5-carboxy-2,6-dimethylpyrid-3-yl, 3,5-dimethylisoxazol-4-yl, 5-ethoxy-2,6-dimethylpyrid-3-yl, 5-fluoro-6-hydroxypyrimidin-4-yl, fur-2-yl, fur-3-yl, 5-hydroxy-4,6-dimethylpyrid-3-yl, 8-hydroxy-5,7-dimethylquinolin-2-yl, 5-hydroxymethylisoxazol-3-yl, 3-hydroxy-6-methylpyrid-2-yl, 3-hydroxypyrid-2-yl, 1H-imidazol-2-yl, 1H-imidazol-4-yl, 1H-indol-3-yl, isothiazol-4-yl, isoxazol-4-yl, 2-methylfur-3-yl, 5-methylfur-2-yl, 1-methyl-1H-imidazol-2-yl, 5-methyl-3H-imidazol-4-yl, 5-methylisoxazol-3-yl, 5-methyl-2H-pyrazol-3-yl, 3-methylpyrid-2-yl, 4-methylpyrid-2-yl, 5-methylpyrid-2-yl, 6-methylpyrid-2-yl, 2-methylpyrid-3-yl, 2-methylthiazol-4-yl, 5-nitropyrid-2-yl, 2H-pyrazol-3-yl, 3H-pyrazol-4-yl, pyridazin-3-yl, pyrid-2-yl, pyrid-3-yl, pyrid-4-yl, 5-pyrid-3-yl-2H-[1,2,4]triazol-3-yl, pyrimidin-4-yl, pyrimidin-5-yl, 1H-pyrrol-3-yl, quinolin-2-yl, 1H-tetrazol-5-yl, thiazol-2-yl, thiazol-5-yl, thien-2-yl, thien-3-yl, 2H-[1,2,4]triazol-3-yl, 3H-[1,2,3]triazol-4-yl, 5-trifluoromethylpyrid-2-yl, and the like Suitable protecting groups include tert-butoxycarbonyl, benzyloxycarbonyl, benzyl, 4-methoxybenzyl, 2-nitrobenzyl, and the like. Optionally substituted hetero$(C_{5-12})$aryl as used in this Application to define $R^4$ includes benzofur-2-yl, fur-2-yl, fur-3-yl, pyrid-3-yl, pyrid-4-yl, quinol-2-yl, quinol-3-yl, thien-2-yl, thien-3-yl, and the like.

"Heterobicycloaryl" means bicycloaryl, as defined in this Application, provided that one or more of the ring carbon atoms indicated are replaced by a heteroatom moiety selected from —N=, —NR—, —O— or —S—, wherein R is hydrogen, $(C_{1-6})$alkyl, a protecting group or represents the free valence which serves as the point of attachment to a ring nitrogen, and any carbocyclic ketone, thioketone or iminoketone derivative thereof. For example, optionally substituted hetero($C_{8-12}$)bicycloaryl as used in this Application to define $R^3$ includes 2-amino-4-oxo-3,4-dihydropteridin-6-yl, and the like. In general, the term heterobicycloaryl as used in this Application includes, for example, benzo[1,3]dioxol-5-ylcarbonyl, 3,4-dihydro-2H-[1,8]naphthyridinyl, 3,4-dihydro-2H-quinolinyl, 2,4-dioxo-3,4-dihydro-2H-quinazolinyl, 1,2,3,4,5,6-hexahydro[2,2']bipyridinylyl, morpholinylpyridyl, 3-oxo-2,3-dihydrobenzo[1,4]oxazinyl, piperidinylphenyl, 5,6,7,8-tetrahydroquinolinyl, and the like. For example, hetero($C_{5-12}$)aryl as used in this Application to define $R^4$ includes benzo[1,3]dioxol-5-yl. For example, hetero($C_{8-12}$)bicycloaryl($C_{0-3}$)alkyl used to describe $R^{11}$ in this Application, includes 1-oxo-1,3-dihydroisoindol-2-yl, quinolin-3-yl, quinolin-2-yl, 3a,7a-dihydrobenzo[1,3]-dioxol-5-yl, naphthalen-2-yl, 3-chlorobenzo[b]thiophen-2-yl, benzo[b]thiophen-2-yl and 1H-indol-5-yl, and the like.

"Heterocycloalkenyl" means heterocycloalkyl, as defined in this Application, provided that the ring assembly is comprised of at least one double bond. Hence, optionally substituted hetero($C_{5-12}$)cycloalkenyl as used in this Application to define $R^3$ includes 2,4-dioxo-1,2,3,4-tetrahydropyrimidin-5-yl, 2,6-dioxo-1,2,3,6-tetrahydropyrimidin-4-yl, 5-hydroxy-4-oxo-4H-pyran-2-yl, 5-methoxy-4-oxo-4H-pyran-2-yl, 6-oxo-1,6-dihydropyrimidin-5-yl, 4-oxo-1,4-dihydropyrid-2-yl, 6-oxo-1,6-dihydropyrid-2-yl, 6-oxo-1,6-dihydropyrid-3-yl, and the like).

"Heterocycloalkyl" means cycloalkyl, as defined in this Application, provided that one or more of the ring carbon atoms indicated are replaced by a heteroatom moiety selected from —N=, —NR—, —O— or —S—, wherein R is hydrogen, ($C_{1-6}$)alkyl, a protecting group or represents the free valence which serves as the point of attachment to a ring nitrogen, and any carbocyclic ketone, thioketone or iminoketone derivative thereof (e.g., the term hetero($C_{5-12}$)cycloalkyl includes [1,4']bipiperidinylyl, 1',2'-dihydro-2H-[1,4']bipyridinylyl, imidazolidinyl, morpholinyl, 1-morpholin-4-ylpiperidinyl, piperazinyl, piperidyl, pyrrolidinyl, pyrrolinyl, quinuclidinyl, and the like). Thus, for example, optionally substituted hetero($C_{5-12}$)cycloalkyl as used in this Application to define $R^4$ includes 4-tert-butoxycarbonylpiperazin-1-yl, 4-ethoxycarbonylpiperazin-1-yl, 4-fur-2-ylcarbonylpiperazin-1-yl, morpholin-4-yl, and the like. Suitable protecting groups include tert-butoxycarbonyl, benzyloxycarbonyl, benzyl, 4-methoxybenzyl, 2-nitrobenzyl, and the like. For example, a compound of Formula I wherein $R^4$ is piperidin-4-ylcarbonyl may exist as either the unprotected or a protected derivative, e.g., wherein $R^4$ is 4-tert-butoxycarbonylpiperazin-1-ylcarbonyl, and both the unprotected and protected derivatives fall within the scope of the invention.

"Hydroxy" means the radical —OH. Unless indicated otherwise, the compounds of the invention containing hydroxy radicals include protected derivatives thereof. Suitable protecting groups for hydroxy moieties include benzyl and the like.

"iminoketone derivative" means a derivative containing the moiety —C(NR)—, wherein R is hydrogen or ($C_{1-6}$) alkyl.

"Isomers" mean compounds of Formula I having identical molecular formulae but differ in the nature or sequence of bonding of their atoms or in the arrangement of their atoms in space. Isomers that differ in the arrangement of their atoms in space are termed "stereoisomers". Stereoisomers that are not mirror images of one another are termed "diastereomers" and stereoisomers that are nonsuperimposable mirror images are termed "enantiomers" or sometimes "optical isomers". A carbon atom bonded to four nonidentical substituents is termed a "chiral center". A compound with one chiral center has two enantiomeric forms of opposite chirality is termed a "racemic mixture". A compound that has more than one chiral center has $2^{n-1}$ enantiomeric pairs, where n is the number of chiral centers. Compounds with more than one chiral center may exist as ether an individual diastereomers or as a mixture of diastereomers, termed a "diastereomeric mixture". When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992). It is understood that the names and illustration used in this Application to describe compounds of Formula I are meant to be encompassed all possible stereoisomers. Thus , for example, the name N-[1-cyanomethylcarbamoyl-2-(4-methylbenzylsulfonyl)ethyl]benzamide is meant to include N-[1S-cyanomethylcarbamoyl-2-(4-methylbenzylsulfonyl) ethyl]benzamide and N-[1R-cyanomethylcarbamoyl-2-(4-methylbenzylsulfonyl)ethyl]benzamide and any mixture, racemic or otherwise, thereof.

"Ketone derivative" means a derivative containing the moiety —C(O)—.

"Methylene" means the divalent radical —$CH_2$—.

"Nitro" means the radical —$NO_2$.

"Optional" or "optionally" means that the subsequently described event or circumstance may or may not occur, and that the description includes instances where the event or circumstance occurs and instances in which it does not. For example, the phrase "$R^3$ optionally is substituted by 1 to 5 radicals" means that $R^3$ may or may not be substituted in order to fall within the scope of the invention.

"Ortho" and "meta" have the meaning typically associated with their usage in organic chemistry. Hence, the phrase "$R^{22}$ at the first occurrence is attached at the ring carbon ortho or meta to the 1-position of the phenyl moiety", refers to the following illustrative example:

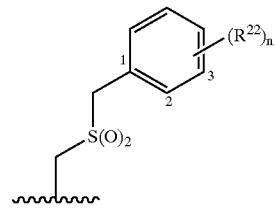

wherein $R^{22}$ is attached at the 2 or 3-position.

"N-oxide derivatives" means derivatives of compounds of Formula I in which nitrogens are in an oxidized state (i.e., O—N) and which possess the desired pharmacological activity.

"Pathology" of a disease means the essential nature, causes and development of the disease as well as the structural and functional changes that result from the disease processes.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of Formula I which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartatic acid, citric acid, benzoic acid, o-(4-hydroxybenzoyl)benzoic acid, cinnamic acid, madelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Prodrug" means a compound which is convertible in vivo by metabolic means (e.g. by hydrolysis) to a compound of Formula I. For example an ester of a compound of Formula I containing a hydroxy group may be convertible by hydrolysis in vivo to the parent molecule. Alternatively an ester of a compound of Formula I containing a carboxy group may be convertible by hydrolysis in vivo to the parent molecule. Suitable esters of compounds of Formula I containing a hydroxy group, are for example acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methanesulphonates, ethanesulphonates, benzenesulphonates, p-toluenesulphonates, cyclohexylsulphamates and quinates. Suitable esters of compounds of Formula I containing a carboxy group, are for example those described by F. J. Leinweber, Drug Metab. Res., 1987, 18, page 379. An especially useful class of esters of compounds of Formula I containing a hydroxy group, may be formed from acid moieties selected from those described by Bundgaard et al., J. Med. Chem., 1989, 32, page 2503–2507, and include substituted (aminomethyl)-benzoates, for example, dialkylamino-methylbenzoates in which the two alkyl groups may be joined together and/or interrupted by an oxygen atom or by an optionally substituted nitrogen atom, e.g. an alkylated nitrogen atom, more especially (morpholino-methyl)benzoates, e.g. 3- or 4-(morpholinomethyl)-benzoates, and (4-alkylpiperazin-1-yl)benzoates, e.g. 3- or 4-(4-alkylpiperazin-1-yl)benzoates.

"Protected derivatives" means derivatives of compounds of Formula I in which a reactive site or sites are blocked with protecting groups. Protected derivatives of compounds of Formula I are useful in the preparation of compounds of Formula I or in themselves may be active cathepsin S inhibitors. A comprehensive list of suitable protecting groups can be found in T. W. Greene, *Protecting Groups in Organic Synthesis*, 3rd edition, John Wiley & Sons, Inc. 1999.

"Therapeutically effective amount" means that amount which, when administered to an animal for treating a disease, is sufficient to effect such treatment for the disease.

"Thioketone derivative" means a derivative containing the moiety —C(S)—.

"Treatment" or "treating" means any administration of a compound of the present invention and includes:
(1) preventing the disease from occurring in an animal which may be predisposed to the disease but does not yet experience or display the pathology or symptomatology of the disease,
(2) inhibiting the disease in an animal that is experiencing or displaying the pathology or symptomatology of the diseased (i.e., arresting further development of the pathology and/or symptomatology), or
(3) ameliorating the disease in an animal that is experiencing or displaying the pathology or symptomatology of the diseased (i.e., reversing the pathology and/or symptomatology).

Nomenclature

The compounds of Formula I and the intermediates and starting materials used in their preparation are named in accordance with IUPAC rules of nomenclature in which the characteristic groups have decreasing priority for citation as the principle group as follows: acids, esters, amides, etc. Alternatively, the compounds are named by AutoNom 4.0 (Beilstein Information Systems, Inc.). For example, a compound of Formula I in which $R^1$ and $R^2$ are each hydrogen, $R^3$ is phenyl, $X^2$ is methylene and $R^4$ is naphthalen-2-yl-methanoyl; that is, a compound having the following structure:

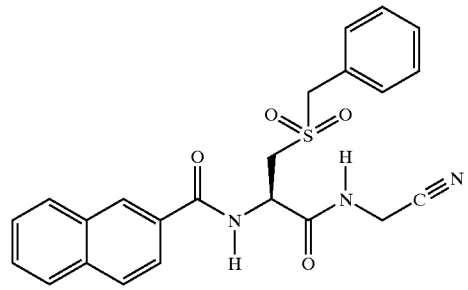

is named N-(2-benzylsulfonyl-1R-cyanomethylcarbamoylethyl)naphthalene-2-carboxamide or naphthalene-2-carboxylic acid [(R)-1-(cyanomethyl-carbamoyl)-2-phenylmethanesulfonyl-ethyl]-amide;

Presently Preferred Embodiments

While the broadest definition of the invention is set forth in the Summary of the Invention, certain aspects of the invention are preferred. For example, $R^1$ particularly represents hydrogen and $R^2$ represent hydrogen, hetero($C_5$)aryl or ($C_{1-4}$)alkyl-substituted hetero($C_5$)aryl or together with the carbon atom to which both $R^1$ and $R^2$ are attached form ($C_{3-5}$)cycloalkylene or ($C_{5-6}$)heterocycloalkylene.

Preferably $X^1$ and $X^2$ are both methylene and $R^3$ represents ($C_{2-6}$)alkenyl, ($C_{6-12}$)aryl or hetero($C_{5-12}$)aryl, each optionally substituted by 1 to 5 radicals selected from a group consisting of $(C_{1-4})$alkyl, cyano, halo, halo-substituted $(C_{1-4})$alkyl, nitro, —$X^3NR^9R^9$, —$X^3OR^9$, —$X^3SR^9$, —$X^3C(O)NR^9R^9$, —$X^3C(O)OR^9$, —$X^3S(O)R^{10}$, —$X^3S(O)_2R^{10}$ and —$X^3C(O)R^{10}$, wherein $X^3$ is a bond or $(C_{1-2})$alkylene, $R^9$ at each occurrence independently is hydrogen, $(C_{1-3})$alkyl or halo-substituted $(C_{1-3})$alkyl and $R^{10}$ is $(C_{1-3})$alkyl or halo-substituted $(C_{1-3})$alkyl. $R^3$ more preferably represents biphenyl, isooxazolyl, naphthyl, phenyl, pyridyl, thienyl or vinyl, each optionally substituted by 1 to 5 radicals selected from a group consisting of $(C_{1-4})$alkyl, cyano, halo, halo-substituted $(C_{1-4})$alkyl, nitro, —$X^3NR^9R^9$, —$X^3OR^9$, —$X^3SR^9$, —$X^3C(O)NR^9R^9$, —$X^3C(O)OR^9$, —$X^3S(O)R^{10}$, —$X^3S(O)_2R^{10}$ and —$X^3C(O)R^{10}$, wherein $X^3$ is a bond or $(C_{1-2})$alkylene, $R^9$ at each occurrence independently is hydrogen, $(C_{1-3})$alkyl or halo-substituted $(C_{1-3})$alkyl and $R^{10}$ is $(C_{1-3})$alkyl or halo-substituted $(C_{1-3})$alkyl. $R^3$ more preferably represents biphenyl-2-yl, 2,4-bistrifluoromethylphenyl, 2,5-bistrifluoromethylphenyl, 4-tert-butylphenyl, 2-bromophenyl, 3-bromophenyl, 4-bromophenyl, 2-bromo-5-fluorophenyl, 3-chloro-2-fluorophenyl, 2-chlorophenyl, 3-chlorophenyl, 4-chlorophenyl, 5-chlorothien-2-yl, 2-chloro-5-trifluoromethyl, 2-cyanophenyl, 3-cyanophenyl, 4-cyanophenyl, 1,5-dichlorophenyl, 2,6-dichlorophenyl, 3,4-dichlorophenyl, 2,3-difluorophenyl, 2,4-difluorophenyl, 3,4-difluorophenyl, 2-difluoromethoxyphenyl, 3-difluoromethoxyphenyl, 4-difluoromethoxyphenyl, 2,5-difluorophenyl, 2,6-difluorophenyl, 3,5-dimethylisooxaxol-4-yl, 3,5-dimethylphenyl, 2-fluoro-6-nitrophenyl, 2-fluorophenyl, 4-fluorophenyl, 2-fluoro-3-trifluoromethylphenyl, 2-fluoro-4-trifluoromethylphenyl, 2-fluoro-5-trifluoromethylphenyl, 2-fluoro-6-trifluoromethylphenyl, 4-fluoro-2-trifluoromethylphenyl, 4-fluoro-3-trifluoromethylphenyl, 2-iodophenyl, 3-iodophenyl, 4-iodophenyl, 2-methoxyphenyl, 4-methoxyphenyl, 2-methylphenyl, 3-methylphenyl, 4-methylphenyl, 3-methyl-2-fluorophenyl, naphth-2-yl, 2-nitrophenyl, 3-nitrophenyl, 4-nitrophenyl, 2,3,4,5,6-pentafluorophenyl, phenyl, prop-2-en-1-yl, pyrid-2-yl, pyrid-3-yl, pyrid-4-yl, 2-trifluoromethoxyphenyl, 3-trifluoromethoxyphenyl, 4-trifluoromethoxyphenyl, 3-trifluoromethylphenyl, 4-trifluoromethylphenyl, 2-trifluoromethylsulfanylphenyl, 3-trifluoromethylsulfanylphenyl, 4-trifluoromethylsulfanylphenyl, 2,3,4-trifluorophenyl, 2,3,5-trifluorophenyl, 2,4,6-trifluorophenyl, 2,4,5-trifluorophenyl or 2,3,6-trifluorophenyl.

In particular, $X^1$, $X^2$ and $R^3$ along with the sulfonyl moiety to which $X^1$ and $X^2$ are attached together represent a group having the following formula:

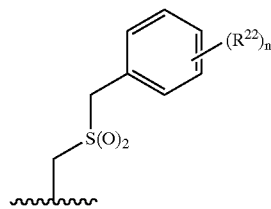

in which n is 0, 1, 2, 4 or 5 and $R^{22}$ at each occurrence independently is selected from a group consisting of $(C_{1-4})$alkyl, cyano, halo, halo-substituted $(C_{1-4})$alkyl, nitro, —$X^3NR^9R^9$, —$X^3OR^9$, —$X^3SR^9$, —$X^3C(O)NR^9R^9$, —$X^3C(O)OR^9$, —$X^3S(O)R^{10}$, —$X^3S(O)_2R^{10}$ and —$X^3C(O)R^{10}$, wherein $X^3$ is a bond or $(C_{1-2})$alkylene, $R^9$ at each occurrence independently is hydrogen, $(C_{1-3})$alkyl or halo-substituted $(C_{1-3})$alkyl and $R^{10}$ is $(C_{1-3})$alkyl or halo-substituted $(C_{1-3})$alkyl; more particularly in which n is 0, 1 or 2 and $R^{22}$ at each occurrence independently is selected from a group consisting of $(C_{1-4})$alkyl, cyano, halo, halo-substituted $(C_{1-4})$alkyl, nitro, —$OR^9$, —$SR^9$ and —$C(O)OR^9$, wherein $R^9$ at each occurrence independently is hydrogen, $(C_{1-3})$alkyl or halo-substituted $(C_{1-3})$alkyl; more particularly in which $R^{22}$ at each occurrence independently is selected from a group consisting of $(C_{1-4})$alkyl, bromo, carboxy, chloro, cyano, difluoromethoxy, fluoro, iodo, methoxy, nitro, trifluoromethoxy, trifluoromethyl and trifluorosulfanyl; more particularly in which at the first occurrence is attached at the ring carbon ortho or meta to the 1-position of the phenyl moiety.

Preferably n is 1 or 2 and $R^{22}$ at the first occurrence is selected from a group consisting of difluoromethoxy, trifluoromethoxy, trifluorosulfanyl and nitro and $R^{22}$ at the second occurrence, if present, is selected from a group consisting of $(C_{1-4})$alkyl, bromo, carboxy, chloro, cyano, difluoromethoxy, fluoro, iodo, methoxy, nitro, trifluoromethoxy, trifluoromethyl and trifluorosulfanyl. Preferably $R^{22}$ at the first occurrence is in the ortho position.

$R^4$ preferably may represent —$C(O)X^4R^{11}$ or —$S(O)_2X^4R^{11}$, wherein $X^4$ is a bond, —O— or —$NR^{12}$—, wherein $R^{12}$ is hydrogen or $(C_{1-6})$alkyl, and $R^{11}$ is $(C_{1-6})$alkyl, $(C_{3-12})$cycloalkyl$(C_{0-3})$alkyl, hetero$(C_{5-12})$cycloalkyl$(C_{0-3})$alkyl, $(C_{6-10})$aryl$(C_{0-3})$alkyl, hetero$(C_{5-10})$aryl$(C_{0-3})$alkyl, hetero$(C_{8-12})$bicycloaryl$(C_{0-3})$alkyl, hetero$(C_{5-6})$cycloalkyl$(C_{0-3})$alkyl or phenyl$(C_{0-3})$alkyl, wherein the hetero$(C_{5-6})$cycloalkyl or phenyl is substituted in the ring by —$X^5OR^{15}$ or —$X^5C(O)R^{15}$, wherein $X^5$ is a bond or methylene and $R^{15}$ is phenyl$(C_{0-3})$alkyl or hetero$(C_{5-6})$aryl$(C_{0-3})$alkyl, wherein any aryl or heteroaryl group comprising $R^4$ optionally is substituted in the ring by 1 to 2 substituents selected from $(C_{1-6})$alkyl, halo, halo-substituted $(C_{1-3})$alkyl, —$X^5OR^{17}$, —$X^5NR^{17}C(O)OR^{17}$, —$X^5C(O)OR^{17}$ or —$X^5C(O)R^{18}$, wherein $X^5$ is a bond or $(C_{1-6})$alkylene, $R^{17}$ is hydrogen, $(C_{1-6})$alkyl or halo-substituted $(C_{1-3})$alkyl and $R^{18}$ is $(C_{1-6})$alkyl or halo-substituted $(C_{1-3})$alkyl. $R^4$ more preferably may represent 3-acetylbenzoyl, allyloxycarbonyl, 2-aminopyrid-3-ylcarbonyl, 6-aminopyrid-3-ylcarbonyl, benzo[1,3]dioxol-5-ylcarbonyl, benzoyl, 4-benzoylbenzoylcarbonyl, benzo[1,3]dioxol-3-ylcarbonyl, benzofur-2-ylcarbonyl, biphenyl-4-ylcarbonyl, 4-bromobenzoyl, 3-bromothien-2-yl, tert-butoxycarbonyl, 3-tert-butoxycarbonylaminomethylbenzoyl, 4-teirbutoxycarbonylpiperazin-1-ylcarbonyl, 3-chlorobenzoyl, 4-chlorobenzoyl, 3-chlorothienylcarbonyl, cyclopentylcarbonyl, 3,4-difluorobenzoyl, 3,4-dimethoxybenzoyl, dimethylcarbamoyl, 4-ethoxycarbonylpiperazin-1-ylcarbonyl, 4-fluorobenzoyl, 3-fluoro-4-methoxybenzoyl, fur-2-ylcarbonyl, fur-3-ylcarbonyl, 4-fur-2-ylcarbonylpiperazin-1-ylcarbonyl, 3-hydroxybenzoyl, 4-hydroxybenzoyl, 4-hydroxypyrid-3-yl, 6-hydroxypyrid-3-yl, 1H-indol-4-ylcarbonyl, isopropylcarbamoyl, isobutyloxycarbonyl, isopropyloxycarbonyl, 3-methoxybenzoyl, 4-methoxybenzoyl, 3-methylbenzoyl, 5-methylthienylcarbonyl, 4-methylvaleryl, morpholin-4-ylcarbonyl, naphth-2-ylcarbonyl, naphth-2-ylsulfonyl, 3-phenoxybenzoyl, 3-phenylacryloyl, phenylsulfonyl, pyrazin-2-ylcarbonyl, 3-pyrid-3-ylacryl, pyrid-2-ylcarbonyl, pyrid-3-ylcarbonyl, pyrid-4-ylcarbonyl, quinol-2-ylcarbonyl, quinol-3-ylcarbonyl, thien-2-ylcarbonyl, thien-3-ylcarbonyl, thien-2-ylsulfonyl, 4-trifluoromethoxybenzoyl or 4-trifluoromethylbenzoyl.

R⁴ more preferably is benzoyl, morpholin-4-ylcarbonyl, thienylcarbonyl, indolylcarbonyl or pyridinylcarbonyl, optionally substituted in the ring by 1 to 2 substituents selected from fluoro and methyl. In particular, R⁴ represents one of the following formulae:

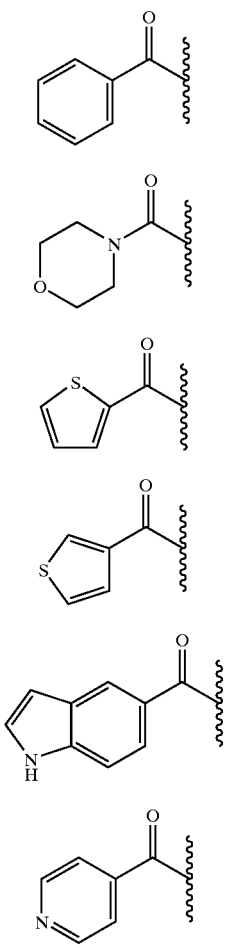

(a)
(b)
(c)
(d)
(e)
(f)

namely benzoyl, morpholin-4-ylcarbonyl, thien-2-yl, thien-3-yl, indol-4-yl and pyridin-4-yl, respectively, optionally substituted in the ring by 1 to 2 substituents selected from fluoro and methyl.

Preferred are compounds of Formula II:

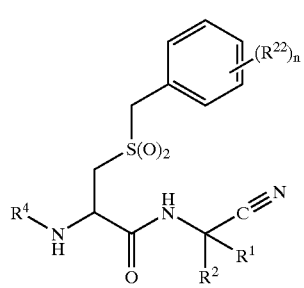

II in which n is 1, 2, 3, 4 or 5 and each $R^1$, $R^2$, $R^3$ and $R^{22}$ are as defined in the Summary of the Invention and in the preferred embodiments.

Reference to the preferred embodiments set forth above is meant to include all combinations of particular and preferred groups.

Particular compounds of the invention are selected from the compounds formed by joining the acyl carbon atom (C*) of one of the fragments (A1 to A36 or A40 to A71) shown in Table 1 to the nitrogen atom (N*) of one of the substituted aminoalkyl fragments (B1 to B75) shown in Table 2, and joining the methine carbon atom (CH*) of one of the substituted aminoalkyl fragments (B1 to B75) shown in Table 2 to the acyl carbon atom (C*) of one of the acyl-aminoalkylnitrile fragments(C1 to C9) depicted in Table 3.

Further particular compounds of the invention are selected from the compounds formed by joining the sulphonyl atom (SO₂*) of one of the fragments (A37 to A39) shown in Table 1 to the nitrogen atom (N*) of one of the substituted aminoalkyl fragments (B1 to B75) shown in Table 2, and joining the methine carbon atom (CH*) of one of the substituted aminoalkyl fragments (B1 to B75) shown in Table 2 to the acyl carbon atom (C*) of one of the acyl-aminoalkylnitrile fragments(C1 to C9) depicted in Table 3.

TABLE 1

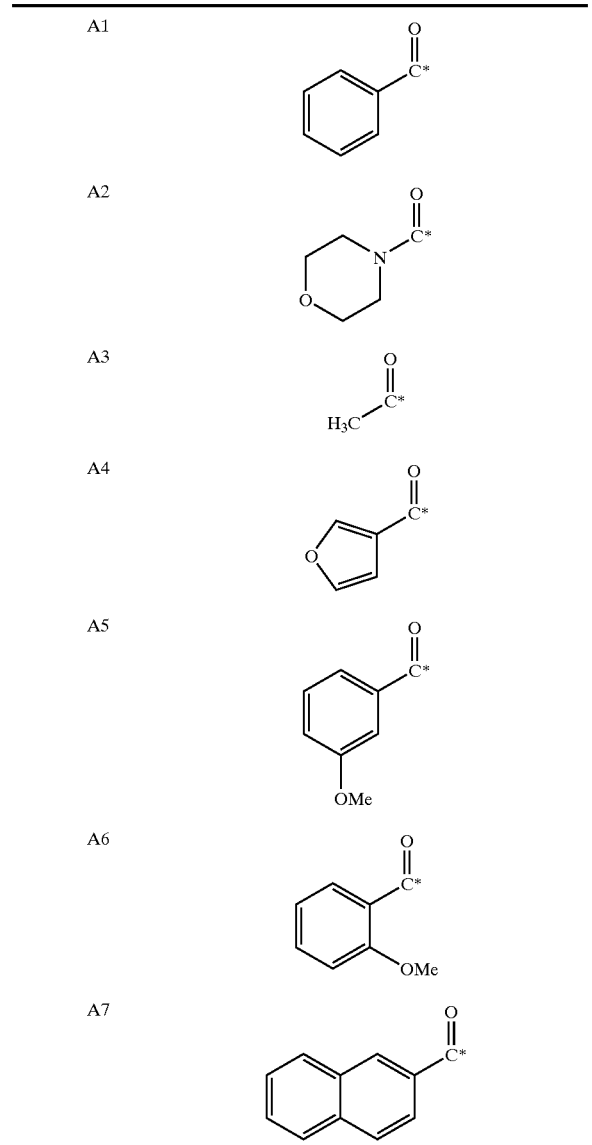

TABLE 1-continued
| | | | | |
|---|---|---|---|---|
| A8 | 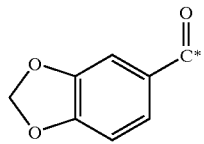 | | A18 | 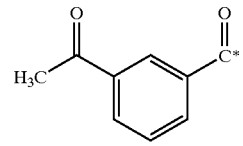 |
| A9 | 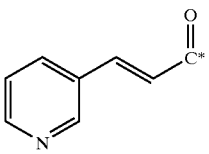 | | A19 | 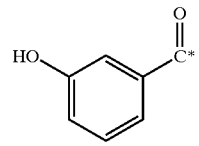 |
| A10 | 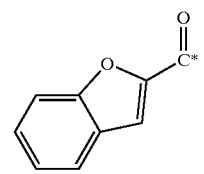 | | A20 | 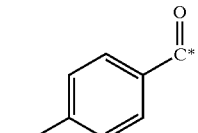 |
| A11 | 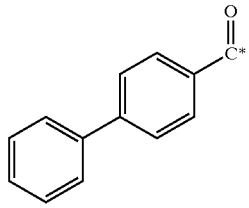 | | A21 | 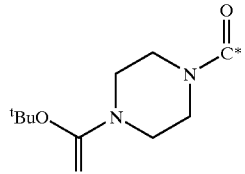 |
| A12 | 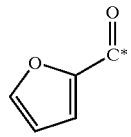 | | A22 | 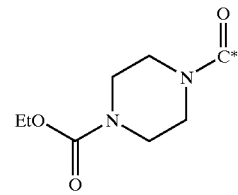 |
| A13 | 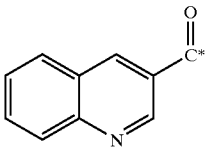 | | A23 | 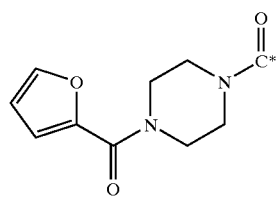 |
| A14 | 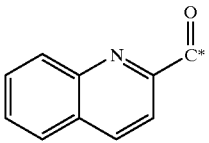 | | A24 | 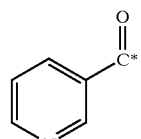 |
| A15 |  | | A25 | 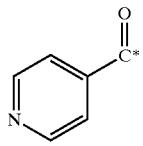 |
| A16 | 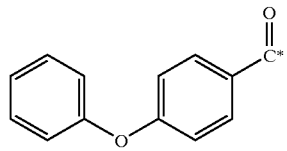 | | A26 | 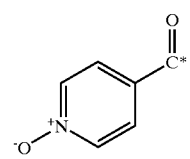 |
| A17 | 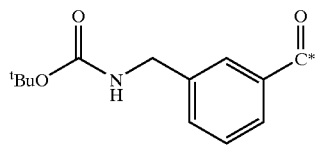 | | | |

TABLE 1-continued
| | | |
|---|---|---|
| A27 | 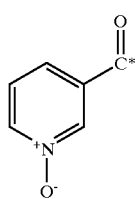 | |
| A28 | 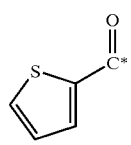 | |
| A29 | 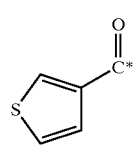 | |
| A30 | 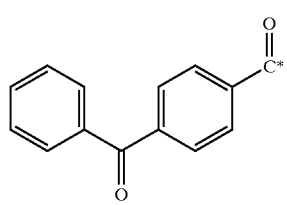 | |
| A31 | 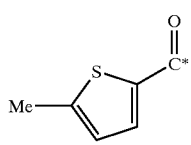 | |
| A32 | 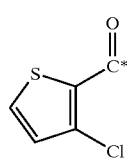 | |
| A33 | 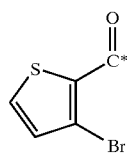 | |
| A34 | 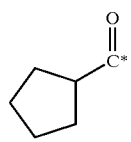 | |
| A35 | 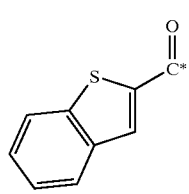 | |
TABLE 1-continued
| | | |
|---|---|---|
| A36 | 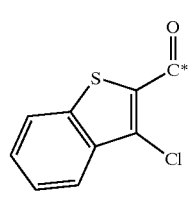 | |
| A37 | 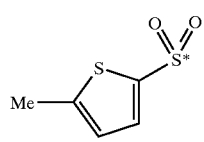 | |
| A38 | 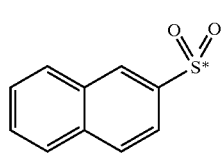 | |
| A39 | 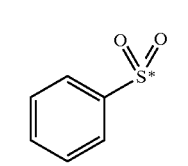 | |
| A40 | 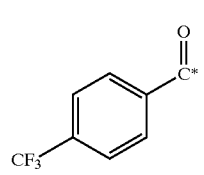 | |
| A41 | 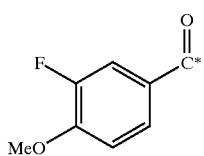 | |
| A42 | 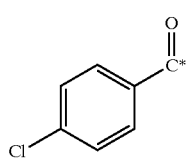 | |
| A43 | 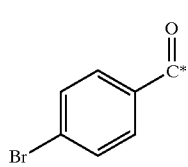 | |
| A44 | 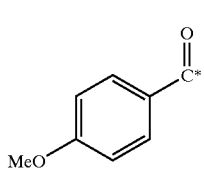 | |

TABLE 1-continued
| | |
|---|---|
| A45 |  |
| A46 |  |
| A47 |  |
| A48 |  |
| A49 |  |
| A50 | (CH$_3$)$_2$CHCH$_2$CH$_2$—C*(=O) |
| A51 | (CH$_3$)$_2$CHCH$_2$O—C*(=O) |
| A52 | CH$_3$O—C*(=O) |
| A53 | CH$_2$=CHCH$_2$O—C*(=O) |
| A54 | (CH$_3$)$_2$CHO—C*(=O) |
| A55 | (CH$_3$)$_2$CHNH—C*(=O) |
| A56 | (CH$_3$)$_2$N—C*(=O) |
TABLE 1-continued
| | |
|---|---|
| A57 |  |
| A58 |  |
| A59 |  |
| A60 |  |
| A61 | |
| A62 | |
| A63 | |
| A64 | |
| A65 | |
| A66 | |

TABLE 1-continued

A67 — 3-carbonyl-2-aminopyridine

A68 — 2-carbonyl-3-hydroxypyridine

A69 — 3-phenoxybenzoyl

A70 — 3-benzoylbenzoyl

A71 — pyridazine-4-carbonyl

A72 — thiophene-2-sulfonyl

TABLE 2

B1 — benzyl-CH2-S(O)2-CH2-CH(*NH)(*)

B2 — 2-(difluoromethoxy)benzyl-S(O)2-CH2-CH(*NH)(*)

TABLE 2-continued

B3 — phenyl-S(O)2-CH2-CH2-CH(*NH)(*)

B4 — pyridin-2-yl-S(O)2-CH2-CH2-CH(*NH)(*)

B5 — pyridin-4-yl-S(O)2-CH2-CH2-CH(*NH)(*)

B6 — benzyl-S(O)2-CH2-CH2-CH(*NH)(*)

B7 — (pyridin-2-yl N-oxide)-CH2-S(O)2-CH2-CH(*NH)(*)

B8 — allyl-S(O)2-CH2-CH(*NH)(*)

TABLE 2-continued

| | |
|---|---|
| B9 | 4-methoxybenzyl-CH2-S(O)2-CH(*NH*)(*) |
| B10 | 4-methylbenzyl-CH2-S(O)2-CH(*NH*)(*) |
| B11 | 4-chlorobenzyl-CH2-S(O)2-CH(*NH*)(*) |
| B12 | 2-methylbenzyl-CH2-S(O)2-CH(*NH*)(*) |
| B13 | 3,5-dimethylbenzyl-CH2-S(O)2-CH(*NH*)(*) |
| B14 | 4-trifluoromethylbenzyl-CH2-S(O)2-CH(*NH*)(*) |
| B15 | 4-trifluoromethoxybenzyl-CH2-S(O)2-CH(*NH*)(*) |
| B16 | 2-bromobenzyl-CH2-S(O)2-CH(*NH*)(*) |
| B17 | 2-naphthylmethyl-CH2-S(O)2-CH(*NH*)(*) |
| B18 | 2-pyridylmethyl-CH2-S(O)2-CH(*NH*)(*) |
| B19 | 4-pyridylmethyl-CH2-S(O)2-CH(*NH*)(*) |
| B20 | 3-pyridylmethyl-CH2-S(O)2-CH(*NH*)(*) |

TABLE 2-continued
B21 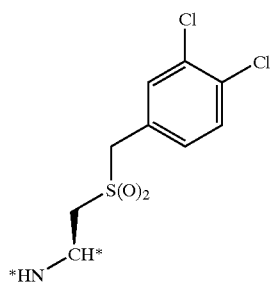
B22 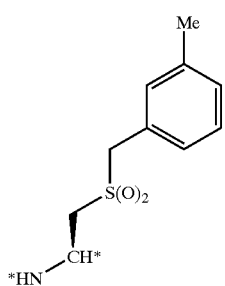
B23 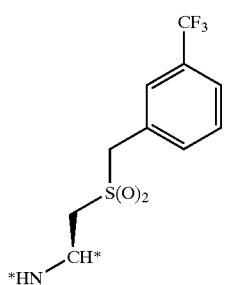
B24 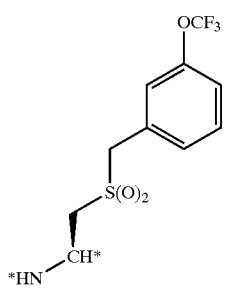
B25 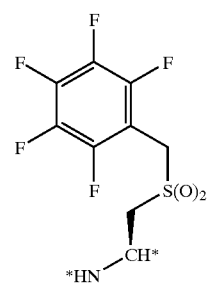
TABLE 2-continued
B26 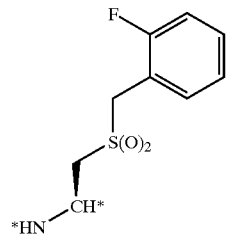
B27 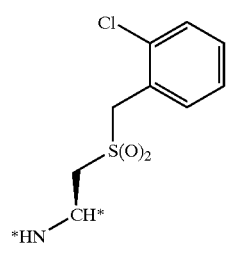
B28 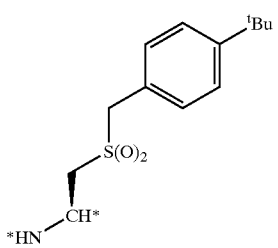
B29 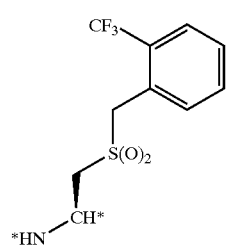
B30 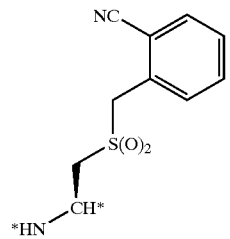
B31 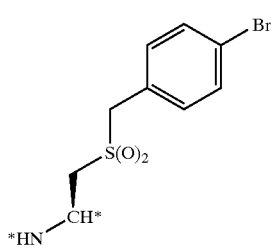

TABLE 2-continued
B32 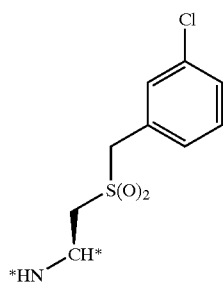
B33 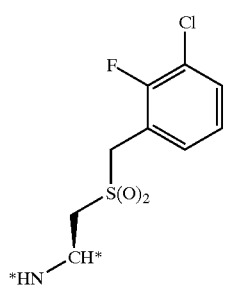
B34 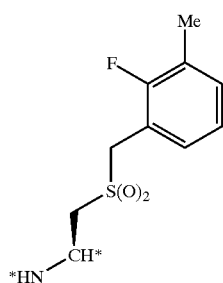
B35 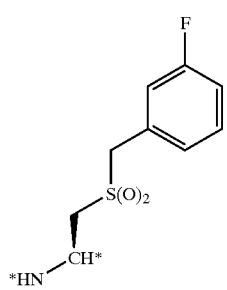
B36 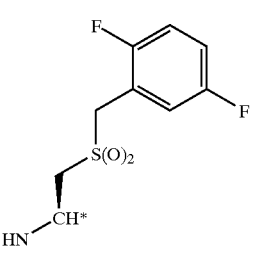
TABLE 2-continued
B37 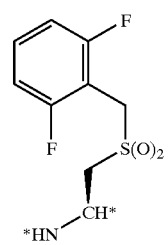
B38 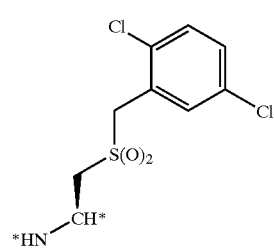
B39 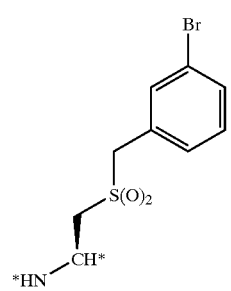
B40 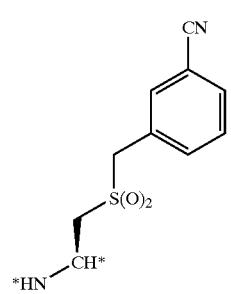
B41 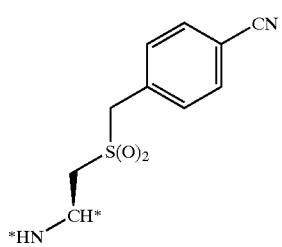
B42 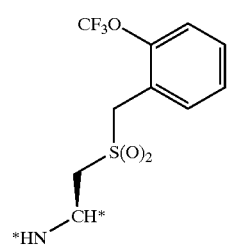

TABLE 2-continued
B43 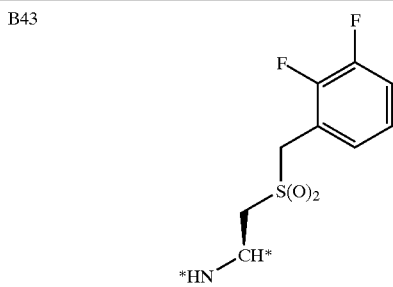
B44 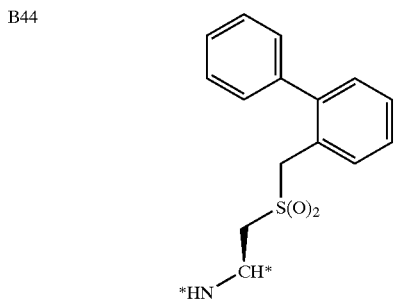
B45 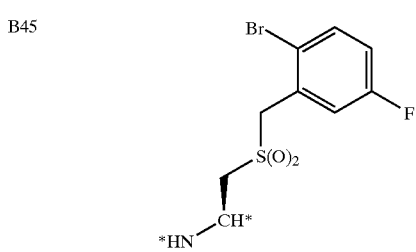
B46 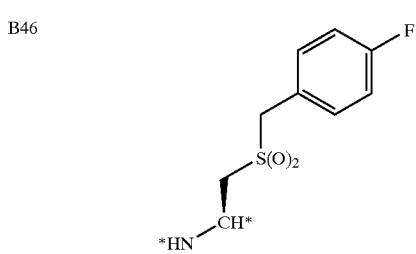
B47 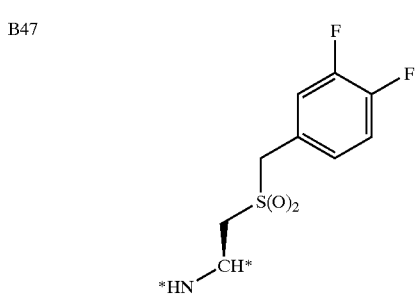
B48 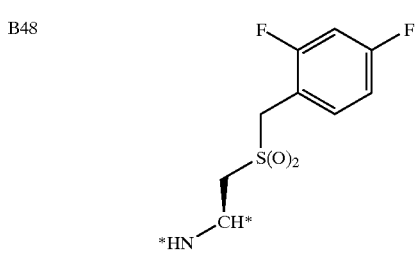
TABLE 2-continued
B49 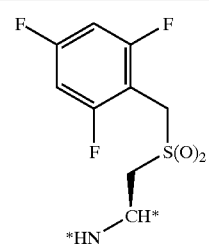
B50 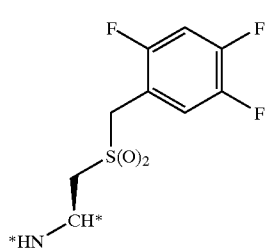
B51 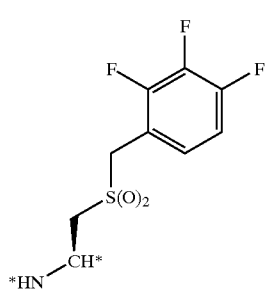
B52 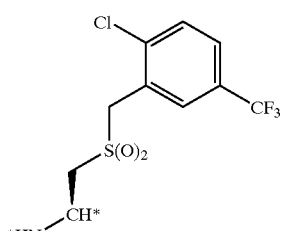
B53 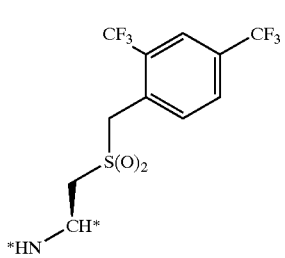
B54 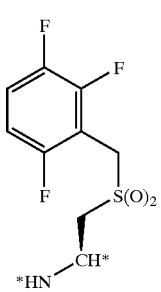

TABLE 2-continued
| | |
|---|---|
| B55 | 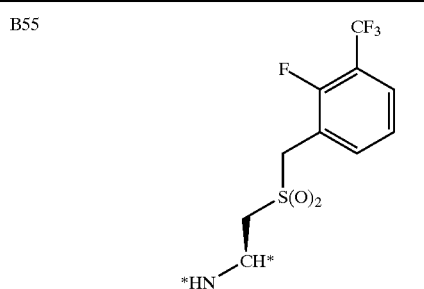 |
| B56 | 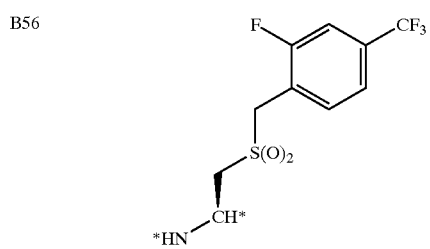 |
| B57 | 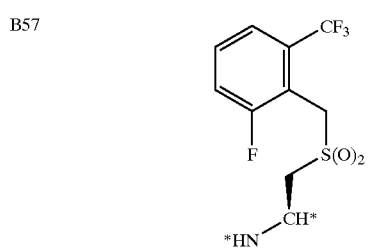 |
| B58 | 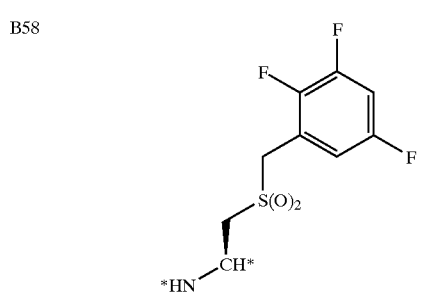 |
| B59 | 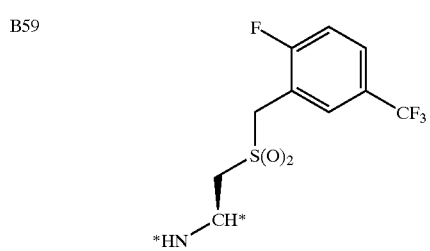 |
| B60 | 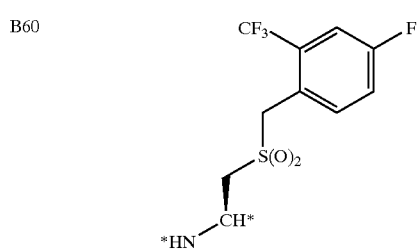 |
TABLE 2-continued
| | |
|---|---|
| B61 | 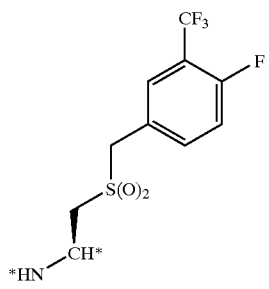 |
| B62 | 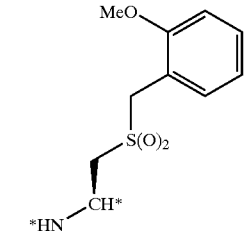 |
| B63 | 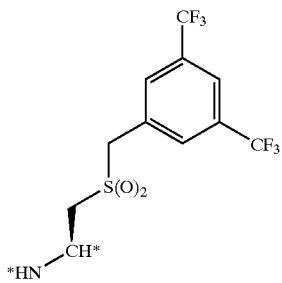 |
| B64 | 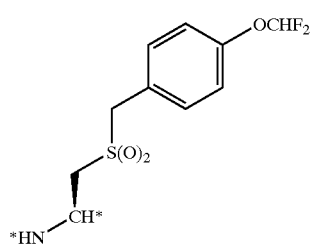 |
| B65 | 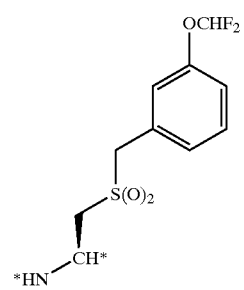 |
| B66 | 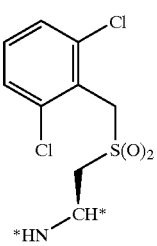 |

TABLE 2-continued
B67 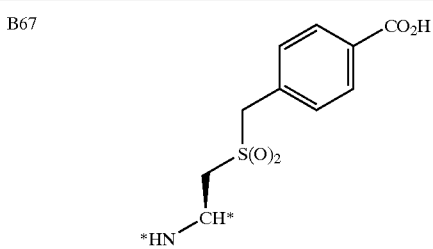
B68 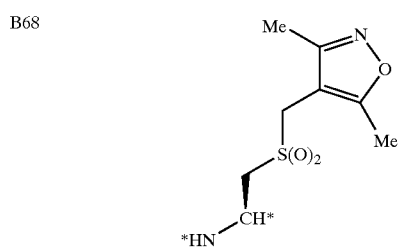
B69 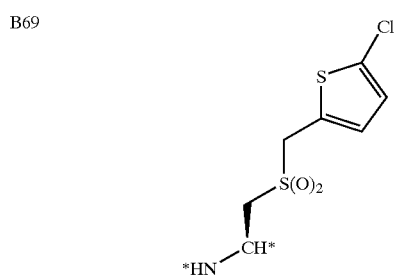
B70 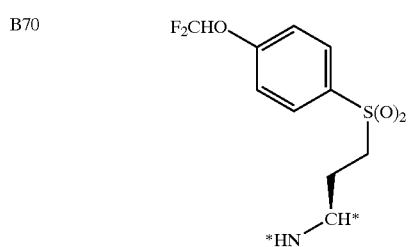
B71 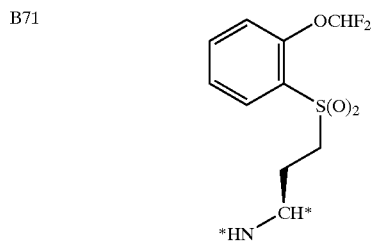
B72 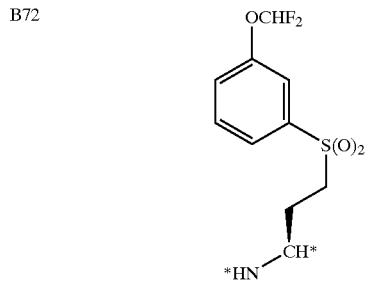
TABLE 2-continued
B73 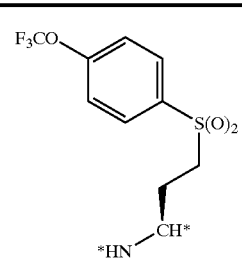
B74 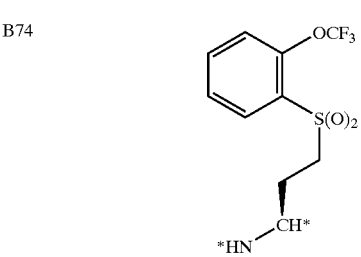
B75 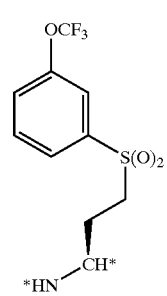
TABLE 3
C1 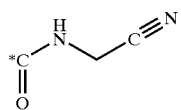
C2 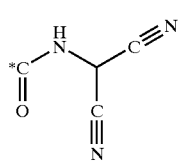
C3 

TABLE 3-continued

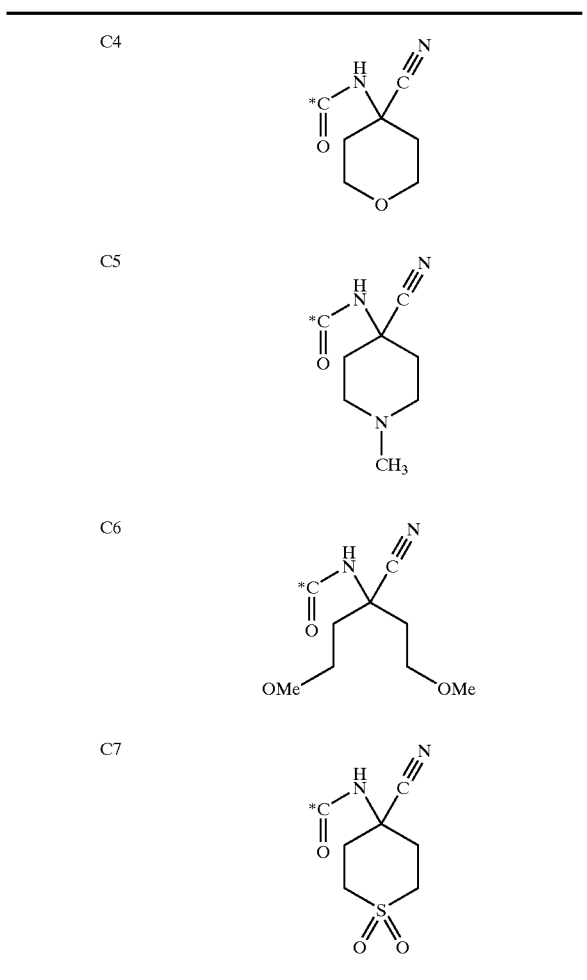

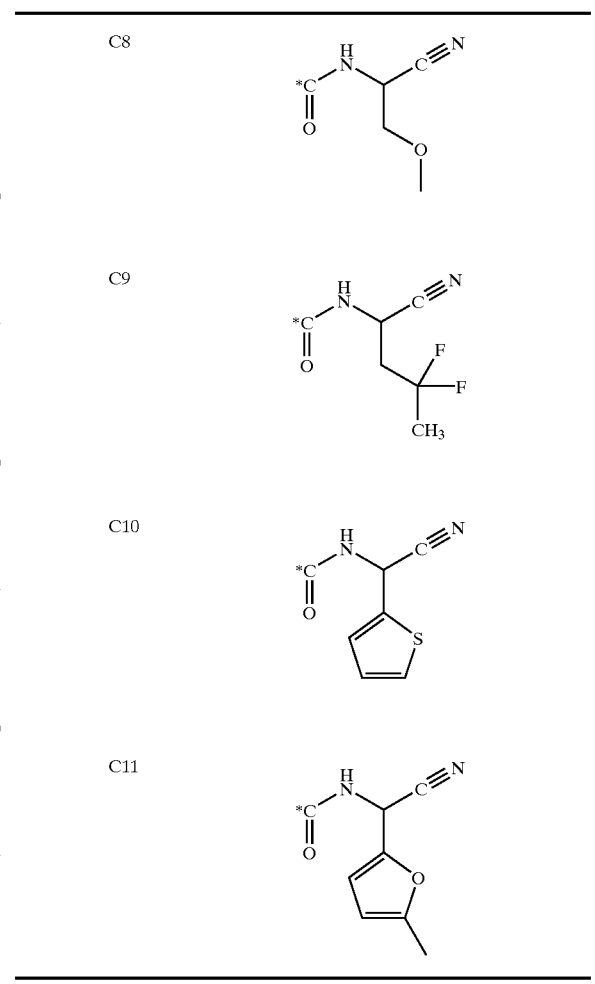

| | | | | | |
|---|---|---|---|---|---|
| A1-B1-C1; | A1-B1-C2; | A1-B1-C3; | A1-B1-C4; | A1-B1-C5; | A1-B1-C6; |
| A1-B1-C7; | A1-B1-C8; | A1-B1-C9; | A2-B1-C1; | A2-B1-C2; | A2-B1-C3; |
| A2-B1-C4; | A2-B1-C5; | A2-B1-C6; | A2-B1-C7; | A2-B1-C8; | A2-B1-C9; |
| A3-B1-C1; | A3-B1-C2; | A3-B1-C3; | A3-B1-C4; | A3-B1-C5; | A3-B1-C6; |
| A3-B1-C7; | A3-B1-C8; | A3-B1-C9; | A4-B1-C1; | A4-B1-C2; | A4-B1-C3; |
| A4-B1-C4; | A4-B1-C5; | A4-B1-C6; | A4-B1-C7; | A4-B1-C8; | A4-B1-C9; |
| A5-B1-C1; | A5-B1-C2; | A5-B1-C3; | A5-B1-C4; | A5-B1-C5; | A5-B1-C6; |
| A5-B1-C7; | A5-B1-C8; | A5-B1-C9; | A6-B1-C1; | A6-B1-C2; | A6-B1-C3; |
| A6-B1-C4; | A6-B1-C5; | A6-B1-C6; | A6-B1-C7; | A6-B1-C8; | A6-B1-C9; |
| A7-B1-C1; | A7-B1-C2; | A7-B1-C3; | A7-B1-C4; | A7-B1-C5; | A7-B1-C6; |
| A7-B1-C7; | A7-B1-C8; | A7-B1-C9; | A8-B1-C1; | A8-B1-C2; | A8-B1-C3; |
| A8-B1-C4; | A8-B1-C5; | A8-B1-C6; | A8-B1-C7; | A8-B1-C8; | A8-B1-C9; |
| A9-B1-C1; | A9-B1-C2; | A9-B1-C3; | A9-B1-C4; | A9-B1-C5; | A9-B1-C6; |
| A9-B1-C7; | A9-B1-C8; | A9-B1-C9; | A10-B1-C1; | A10-B1-C2; | A10-B1-C3; |
| A10-B1-C4; | A10-B1-C5; | A10-B1-C6; | A10-B1-C7; | A10-B1-C8; | A10-B1-C9; |
| A11-B1-C1; | A11-B1-C2; | A11-B1-C3; | A11-B1-C4; | A11-B1-C5; | A11-B1-C6; |
| A11-B1-C7; | A11-B1-C8; | A11-B1-C9; | A12-B1-C1; | A12-B1-C2; | A12-B1-C3; |
| A12-B1-C4; | A12-B1-C5; | A12-B1-C6; | A12-B1-C7; | A12-B1-C8; | A12-B1-C9; |
| A13-B1-C1; | A13-B1-C2; | A13-B1-C3; | A13-B1-C4; | A13-B1-C5; | A13-B1-C6; |
| A13-B1-C7; | A13-B1-C8; | A13-B1-C9; | A14-B1-C1; | A14-B1-C2; | A14-B1-C3; |
| A14-B1-C4; | A14-B1-C5; | A14-B1-C6; | A14-B1-C7; | A14-B1-C8; | A14-B1-C9; |
| A15-B1-C1; | A15-B1-C2; | A15-B1-C3; | A15-B1-C4; | A15-B1-C5; | A15-B1-C6; |
| A15-B1-C7; | A15-B1-C8; | A15-B1-C9; | A16-B1-C1; | A16-B1-C2; | A16-B1-C3; |
| A16-B1-C4; | A16-B1-C5; | A16-B1-C6; | A16-B1-C7; | A16-B1-C8; | A16-B1-C9; |
| A17-B1-C1; | A17-B1-C2; | A17-B1-C3; | A17-B1-C4; | A17-B1-C5; | A17-B1-C6; |
| A17-B1-C7; | A17-B1-C8; | A17-B1-C9; | A18-B1-C1; | A18-B1-C2; | A18-B1-C3; |
| A18-B1-C4; | A18-B1-C5; | A18-B1-C6; | A18-B1-C7; | A18-B1-C8; | A18-B1-C9; |

-continued

| | | | | | |
|---|---|---|---|---|---|
| A19-B1-C1; | A19-B1-C2; | A19-B1-C3; | A19-B1-C4; | A19-B1-C5; | A19-B1-C6; |
| A19-B1-C7; | A19-B1-C8; | A19-B1-C9; | A20-B1-C1; | A20-B1-C2; | A20-B1-C3; |
| A20-B1-C4; | A20-B1-C5; | A20-B1-C6; | A20-B1-C7; | A20-B1-C8; | A20-B1-C9; |
| A21-B1-C1; | A21-B1-C2; | A21-B1-C3; | A21-B1-C4; | A21-B1-C5; | A21-B1-C6; |
| A21-B1-C7; | A21-B1-C8; | A21-B1-C9; | A22-B1-C1; | A22-B1-C2; | A22-B1-C3; |
| A22-B1-C4; | A22-B1-C5; | A22-B1-C6; | A22-B1-C7; | A22-B1-C8; | A22-B1-C9; |
| A23-B1-C1; | A23-B1-C2; | A23-B1-C3; | A23-B1-C4; | A23-B1-C5; | A23-B1-C6; |
| A23-B1-C7; | A23-B1-C8; | A23-B1-C9; | A24-B1-C1; | A24-B1-C2; | A24-B1-C3; |
| A24-B1-C4; | A24-B1-C5; | A24-B1-C6; | A24-B1-C7; | A24-B1-C8; | A24-B1-C9; |
| A25-B1-C1; | A25-B1-C2; | A25-B1-C3; | A25-B1-C4; | A25-B1-C5; | A25-B1-C6; |
| A25-B1-C7; | A25-B1-C8; | A25-B1-C9; | A26-B1-C1; | A26-B1-C2; | A26-B1-C3; |
| A26-B1-C4; | A26-B1-C5; | A26-B1-C6; | A26-B1-C7; | A26-B1-C8; | A26-B1-C9; |
| A27-B1-C1; | A27-B1-C2; | A27-B1-C3; | A27-B1-C4; | A27-B1-C5; | A27-B1-C6; |
| A27-B1-C7; | A27-B1-C8; | A27-B1-C9; | A28-B1-C1; | A28-B1-C2; | A28-B1-C3; |
| A28-B1-C4; | A28-B1-C5; | A28-B1-C6; | A28-B1-C7; | A28-B1-C8; | A28-B1-C9; |
| A29-B1-C1; | A29-B1-C2; | A29-B1-C3; | A29-B1-C4; | A29-B1-C5; | A29-B1-C6; |
| A29-B1-C7; | A29-B1-C8; | A29-B1-C9; | A30-B1-C1; | A30-B1-C2; | A30-B1-C3; |
| A30-B1-C4; | A30-B1-C5; | A30-B1-C6; | A30-B1-C7; | A30-B1-C8; | A30-B1-C9; |
| A31-B1-C1; | A31-B1-C2; | A31-B1-C3; | A31-B1-C4; | A31-B1-C5; | A31-B1-C6; |
| A31-B1-C7; | A31-B1-C8; | A31-B1-C9; | A32-B1-C1; | A32-B1-C2; | A32-B1-C3; |
| A32-B1-C4; | A32-B1-C5; | A32-B1-C6; | A32-B1-C7; | A32-B1-C8; | A32-B1-C9; |
| A33-B1-C1; | A33-B1-C2; | A33-B1-C3; | A33-B1-C4; | A33-B1-C5; | A33-B1-C6; |
| A33-B1-C7; | A33-B1-C8; | A33-B1-C9; | A34-B1-C1; | A34-B1-C2; | A34-B1-C3; |
| A34-B1-C4; | A34-B1-C5; | A34-B1-C6; | A34-B1-C7; | A34-B1-C8; | A34-B1-C9; |
| A35-B1-C1; | A35-B1-C2; | A35-B1-C3; | A35-B1-C4; | A35-B1-C5; | A35-B1-C6; |
| A35-B1-C7; | A35-B1-C8; | A35-B1-C9; | A36-B1-C1; | A36-B1-C2; | A36-B1-C3; |
| A36-B1-C4; | A36-B1-C5; | A36-B1-C6; | A36-B1-C7; | A36-B1-C8; | A36-B1-C9; |
| A37-B1-C1; | A37-B1-C2; | A37-B1-C3; | A37-B1-C4; | A37-B1-C5; | A37-B1-C6; |
| A37-B1-C7; | A37-B1-C8; | A37-B1-C9; | A38-B1-C1; | A38-B1-C2; | A38-B1-C3; |
| A38-B1-C4; | A38-B1-C5; | A38-B1-C6; | A38-B1-C7; | A38-B1-C8; | A38-B1-C9; |
| A39-B1-C1; | A39-B1-C2; | A39-B1-C3; | A39-B1-C4; | A39-B1-C5; | A39-B1-C6; |
| A39-B1-C7; | A39-B1-C8; | A39-B1-C9; | A40-B1-C1; | A40-B1-C2; | A40-B1-C3; |
| A40-B1-C4; | A40-B1-C5; | A40-B1-C6; | A40-B1-C7; | A40-B1-C8; | A40-B1-C9; |
| A41-B1-C1; | A41-B1-C2; | A41-B1-C3; | A41-B1-C4; | A41-B1-C5; | A41-B1-C6; |
| A41-B1-C7; | A41-B1-C8; | A41-B1-C9; | A42-B1-C1; | A42-B1-C2; | A42-B1-C3; |
| A42-B1-C4; | A42-B1-C5; | A42-B1-C6; | A42-B1-C7; | A42-B1-C8; | A42-B1-C9; |
| A43-B1-C1; | A43-B1-C2; | A43-B1-C3; | A43-B1-C4; | A43-B1-C5; | A43-B1-C6; |
| A43-B1-C7; | A43-B1-C8; | A43-B1-C9; | A44-B1-C1; | A44-B1-C2; | A44-B1-C3; |
| A44-B1-C4; | A44-B1-C5; | A44-B1-C6; | A44-B1-C7; | A44-B1-C8; | A44-B1-C9; |
| A45-B1-C1; | A45-B1-C2; | A45-B1-C3; | A45-B1-C4; | A45-B1-C5; | A45-B1-C6; |
| A45-B1-C7; | A45-B1-C8; | A45-B1-C9; | A46-B1-C1; | A46-B1-C2; | A46-B1-C3; |
| A46-B1-C4; | A46-B1-C5; | A46-B1-C6; | A46-B1-C7; | A46-B1-C8; | A46-B1-C9; |
| A47-B1-C1; | A47-B1-C2; | A47-B1-C3; | A47-B1-C4; | A47-B1-C5; | A47-B1-C6; |
| A47-B1-C7; | A47-B1-C8; | A47-B1-C9; | A48-B1-C1; | A48-B1-C2; | A48-B1-C3; |
| A48-B1-C4; | A48-B1-C5; | A48-B1-C6; | A48-B1-C7; | A48-B1-C8; | A48-B1-C9; |
| A49-B1-C1; | A49-B1-C2; | A49-B1-C3; | A49-B1-C4; | A49-B1-C5; | A49-B1-C6; |
| A49-B1-C7; | A49-B1-C8; | A49-B1-C9; | A50-B1-C1; | A50-B1-C2; | A50-B1-C3; |
| A50-B1-C4; | A50-B1-C5; | A50-B1-C6; | A50-B1-C7; | A50-B1-C8; | A50-B1-C9; |
| A51-B1-C1; | A51-B1-C2; | A51-B1-C3; | A51-B1-C4; | A51-B1-C5; | A51-B1-C6; |
| A51-B1-C7; | A51-B1-C8; | A51-B1-C9; | A52-B1-C1; | A52-B1-C2; | A52-B1-C3; |
| A52-B1-C4; | A52-B1-C5; | A52-B1-C6; | A52-B1-C7; | A52-B1-C8; | A52-B1-C9; |
| A53-B1-C1; | A53-B1-C2; | A53-B1-C3; | A53-B1-C4; | A53-B1-C5; | A53-B1-C6; |
| A53-B1-C7; | A53-B1-C8; | A53-B1-C9; | A54-B1-C1; | A54-B1-C2; | A54-B1-C3; |
| A54-B1-C4; | A54-B1-C5; | A54-B1-C6; | A54-B1-C7; | A54-B1-C8; | A54-B1-C9; |
| A55-B1-C1; | A55-B1-C2; | A55-B1-C3; | A55-B1-C4; | A55-B1-C5; | A55-B1-C6; |
| A55-B1-C7; | A55-B1-C8; | A55-B1-C9; | A56-B1-C1; | A56-B1-C2; | A56-B1-C3; |
| A56-B1-C4; | A56-B1-C5; | A56-B1-C6; | A56-B1-C7; | A56-B1-C8; | A56-B1-C9; |
| A57-B1-C1; | A57-B1-C2; | A57-B1-C3; | A57-B1-C4; | A57-B1-C5; | A57-B1-C6; |
| A57-B1-C7; | A57-B1-C8; | A57-B1-C9; | A58-B1-C1; | A58-B1-C2; | A58-B1-C3; |
| A58-B1-C4; | A58-B1-C5; | A58-B1-C6; | A58-B1-C7; | A58-B1-C8; | A58-B1-C9; |
| A59-B1-C1; | A59-B1-C2; | A59-B1-C3; | A59-B1-C4; | A59-B1-C5; | A59-B1-C6; |
| A59-B1-C7; | A59-B1-C8; | A59-B1-C9; | A60-B1-C1; | A60-B1-C2; | A60-B1-C3; |
| A60-B1-C4; | A60-B1-C5; | A60-B1-C6; | A60-B1-C7; | A60-B1-C8; | A60-B1-C9; |
| A61-B1-C1; | A61-B1-C2; | A61-B1-C3; | A61-B1-C4; | A61-B1-C5; | A61-B1-C6; |
| A61-B1-C7; | A61-B1-C8; | A61-B1-C9; | A62-B1-C1; | A62-B1-C2; | A62-B1-C3; |
| A62-B1-C4; | A62-B1-C5; | A62-B1-C6; | A62-B1-C7; | A62-B1-C8; | A62-B1-C9; |
| A63-B1-C1; | A63-B1-C2; | A63-B1-C3; | A63-B1-C4; | A63-B1-C5; | A63-B1-C6; |
| A63-B1-C7; | A63-B1-C8; | A63-B1-C9; | A64-B1-C1; | A64-B1-C2; | A64-B1-C3; |
| A64-B1-C4; | A64-B1-C5; | A64-B1-C6; | A64-B1-C7; | A64-B1-C8; | A64-B1-C9; |
| A65-B1-C1; | A65-B1-C2; | A65-B1-C3; | A65-B1-C4; | A65-B1-C5; | A65-B1-C6; |
| A65-B1-C7; | A65-B1-C8; | A65-B1-C9; | A66-B1-C1; | A66-B1-C2; | A66-B1-C3; |
| A66-B1-C4; | A66-B1-C5; | A66-B1-C6; | A66-B1-C7; | A66-B1-C8; | A66-B1-C9; |
| A67-B1-C1; | A67-B1-C2; | A67-B1-C3; | A67-B1-C4; | A67-B1-C5; | A67-B1-C6; |
| A67-B1-C7; | A67-B1-C8; | A67-B1-C9; | A68-B1-C1; | A68-B1-C2; | A68-B1-C3; |
| A68-B1-C4; | A68-B1-C5; | A68-B1-C6; | A68-B1-C7; | A68-B1-C8; | A68-B1-C9; |
| A69-B1-C1; | A69-B1-C2; | A69-B1-C3; | A69-B1-C4; | A69-B1-C5; | A69-B1-C6; |
| A69-B1-C7; | A69-B1-C8; | A69-B1-C9; | A70-B1-C1; | A70-B1-C2; | A70-B1-C3; |
| A70-B1-C4; | A70-B1-C5; | A70-B1-C6; | A70-B1-C7; | A70-B1-C8; | A70-B1-C9; |
| A71-B1-C1; | A71-B1-C2; | A71-B1-C3; | A71-B1-C4; | A71-B1-C5; | A71-B1-C6; |

| | | | | | |
|---|---|---|---|---|---|
| A71-B1-C7; | A71-B1-C8; | A71-B1-C9; | A1-B2-C1; | A1-B2-C2; | A1-B2-C3; |
| A1-B2-C4; | A1-B2-C5; | A1-B2-C6; | A1-B2-C7; | A1-B2-C8; | A1-B2-C9; |
| A2-B2-C1; | A2-B2-C2; | A2-B2-C3; | A2-B2-C4; | A2-B2-C5; | A2-B2-C6; |
| A2-B2-C7; | A2-B2-C8; | A2-B2-C9; | A3-B2-C1; | A3-B2-C2; | A3-B2-C3; |
| A3-B2-C4; | A3-B2-C5; | A3-B2-C6; | A3-B2-C7; | A3-B2-C8; | A3-B2-C9; |
| A4-B2-C1; | A4-B2-C2; | A4-B2-C3; | A4-B2-C4; | A4-B2-C5; | A4-B2-C6; |
| A4-B2-C7; | A4-B2-C8; | A4-B2-C9; | A5-B2-C1; | A5-B2-C2; | A5-B2-C3; |
| A5-B2-C4; | A5-B2-C5; | A5-B2-C6; | A5-B2-C7; | A5-B2-C8; | A5-B2-C9; |
| A6-B2-C1; | A6-B2-C2; | A6-B2-C3; | A6-B2-C4; | A6-B2-C5; | A6-B2-C6; |
| A6-B2-C7; | A6-B2-C8; | A6-B2-C9; | A7-B2-C1; | A7-B2-C2; | A7-B2-C3; |
| A7-B2-C4; | A7-B2-C5; | A7-B2-C6; | A7-B2-C7; | A7-B2-C8; | A7-B2-C9; |
| A8-B2-C1; | A8-B2-C2; | A8-B2-C3; | A8-B2-C4; | A8-B2-C5; | A8-B2-C6; |
| A8-B2-C7; | A8-B2-C8; | A8-B2-C9; | A9-B2-C1; | A9-B2-C2; | A9-B2-C3; |
| A9-B2-C4; | A9-B2-C5; | A9-B2-C6; | A9-B2-C7; | A9-B2-C8; | A9-B2-C9; |
| A10-B2-C1; | A10-B2-C2; | A10-B2-C3; | A10-B2-C4; | A10-B2-C5; | A10-B2-C6; |
| A10-B2-C7; | A10-B2-C8; | A10-B2-C9; | A11-B2-C1; | A11-B2-C2; | A11-B2-C3; |
| A11-B2-C4; | A11-B2-C5; | A11-B2-C6; | A11-B2-C7; | A11-B2-C8; | A11-B2-C9; |
| A12-B2-C1; | A12-B2-C2; | A12-B2-C3; | A12-B2-C4; | A12-B2-C5; | A12-B2-C6; |
| A12-B2-C7; | A12-B2-C8; | A12-B2-C9; | A13-B2-C1; | A13-B2-C2; | A13-B2-C3; |
| A13-B2-C4; | A13-B2-C5; | A13-B2-C6; | A13-B2-C7; | A13-B2-C8; | A13-B2-C9; |
| A14-B2-C1; | A14-B2-C2; | A14-B2-C3; | A14-B2-C4; | A14-B2-C5; | A14-B2-C6; |
| A14-B2-C7; | A14-B2-C8; | A14-B2-C9; | A15-B2-C1; | A15-B2-C2; | A15-B2-C3; |
| A15-B2-C4; | A15-B2-C5; | A15-B2-C6; | A15-B2-C7; | A15-B2-C8; | A15-B2-C9; |
| A16-B2-C1; | A16-B2-C2; | A16-B2-C3; | A16-B2-C4; | A16-B2-C5; | A16-B2-C6; |
| A16-B2-C7; | A16-B2-C8; | A16-B2-C9; | A17-B2-C1; | A17-B2-C2; | A17-B2-C3; |
| A17-B2-C4; | A17-B2-C5; | A17-B2-C6; | A17-B2-C7; | A17-B2-C8; | A17-B2-C9; |
| A18-B2-C1; | A18-B2-C2; | A18-B2-C3; | A18-B2-C4; | A18-B2-C5; | A18-B2-C6; |
| A18-B2-C7; | A18-B2-C8; | A18-B2-C9; | A19-B2-C1; | A19-B2-C2; | A19-B2-C3; |
| A19-B2-C4; | A19-B2-C5; | A19-B2-C6; | A19-B2-C7; | A19-B2-C8; | A19-B2-C9; |
| A20-B2-C1; | A20-B2-C2; | A20-B2-C3; | A20-B2-C4; | A20-B2-C5; | A20-B2-C6; |
| A20-B2-C7; | A20-B2-C8; | A20-B2-C9; | A21-B2-C1; | A21-B2-C2; | A21-B2-C3; |
| A21-B2-C4; | A21-B2-C5; | A21-B2-C6; | A21-B2-C7; | A21-B2-C8; | A21-B2-C9; |
| A22-B2-C1; | A22-B2-C2; | A22-B2-C3; | A22-B2-C4; | A22-B2-C5; | A22-B2-C6; |
| A22-B2-C7; | A22-B2-C8; | A22-B2-C9; | A23-B2-C1; | A23-B2-C2; | A23-B2-C3; |
| A23-B2-C4; | A23-B2-C5; | A23-B2-C6; | A23-B2-C7; | A23-B2-C8; | A23-B2-C9; |
| A24-B2-C1; | A24-B2-C2; | A24-B2-C3; | A24-B2-C4; | A24-B2-C5; | A24-B2-C6; |
| A24-B2-C7; | A24-B2-C8; | A24-B2-C9; | A25-B2-C1; | A25-B2-C2; | A25-B2-C3; |
| A25-B2-C4; | A25-B2-C5; | A25-B2-C6; | A25-B2-C7; | A25-B2-C8; | A25-B2-C9; |
| A26-B2-C1; | A26-B2-C2; | A26-B2-C3; | A26-B2-C4; | A26-B2-C5; | A26-B2-C6; |
| A26-B2-C7; | A26-B2-C8; | A26-B2-C9; | A27-B2-C1; | A27-B2-C2; | A27-B2-C3; |
| A27-B2-C4; | A27-B2-C5; | A27-B2-C6; | A27-B2-C7; | A27-B2-C8; | A27-B2-C9; |
| A28-B2-C1; | A28-B2-C2; | A28-B2-C3; | A28-B2-C4; | A28-B2-C5; | A28-B2-C6; |
| A28-B2-C7; | A28-B2-C8; | A28-B2-C9; | A29-B2-C1; | A29-B2-C2; | A29-B2-C3; |
| A29-B2-C4; | A29-B2-C5; | A29-B2-C6; | A29-B2-C7; | A29-B2-C8; | A29-B2-C9; |
| A30-B2-C1; | A30-B2-C2; | A30-B2-C3; | A30-B2-C4; | A30-B2-C5; | A30-B2-C6; |
| A30-B2-C7; | A30-B2-C8; | A30-B2-C9; | A31-B2-C1; | A31-B2-C2; | A31-B2-C3; |
| A31-B2-C4; | A31-B2-C5; | A31-B2-C6; | A31-B2-C7; | A31-B2-C8; | A31-B2-C9; |
| A32-B2-C1; | A32-B2-C2; | A32-B2-C3; | A32-B2-C4; | A32-B2-C5; | A32-B2-C6; |
| A32-B2-C7; | A32-B2-C8; | A32-B2-C9; | A33-B2-C1; | A33-B2-C2; | A33-B2-C3; |
| A33-B2-C4; | A33-B2-C5; | A33-B2-C6; | A33-B2-C7; | A33-B2-C8; | A33-B2-C9; |
| A34-B2-C1; | A34-B2-C2; | A34-B2-C3; | A34-B2-C4; | A34-B2-C5; | A34-B2-C6; |
| A34-B2-C7; | A34-B2-C8; | A34-B2-C9; | A35-B2-C1; | A35-B2-C2; | A35-B2-C3; |
| A35-B2-C4; | A35-B2-C5; | A35-B2-C6; | A35-B2-C7; | A35-B2-C8; | A35-B2-C9; |
| A36-B2-C1; | A36-B2-C2; | A36-B2-C3; | A36-B2-C4; | A36-B2-C5; | A36-B2-C6; |
| A36-B2-C7; | A36-B2-C8; | A36-B2-C9; | A37-B2-C1; | A37-B2-C2; | A37-B2-C3; |
| A37-B2-C4; | A37-B2-C5; | A37-B2-C6; | A37-B2-C7; | A37-B2-C8; | A37-B2-C9; |
| A38-B2-C1; | A38-B2-C2; | A38-B2-C3; | A38-B2-C4; | A38-B2-C5; | A38-B2-C6; |
| A38-B2-C7; | A38-B2-C8; | A38-B2-C9; | A39-B2-C1; | A39-B2-C2; | A39-B2-C3; |
| A39-B2-C4; | A39-B2-C5; | A39-B2-C6; | A39-B2-C7; | A39-B2-C8; | A39-B2-C9; |
| A40-B2-C1; | A40-B2-C2; | A40-B2-C3; | A40-B2-C4; | A40-B2-C5; | A40-B2-C6; |
| A40-B2-C7; | A40-B2-C8; | A40-B2-C9; | A41-B2-C1; | A41-B2-C2; | A41-B2-C3; |
| A41-B2-C4; | A41-B2-C5; | A41-B2-C6; | A41-B2-C7; | A41-B2-C8; | A41-B2-C9; |
| A42-B2-C1; | A42-B2-C2; | A42-B2-C3; | A42-B2-C4; | A42-B2-C5; | A42-B2-C6; |
| A42-B2-C7; | A42-B2-C8; | A42-B2-C9; | A43-B2-C1; | A43-B2-C2; | A43-B2-C3; |
| A43-B2-C4; | A43-B2-C5; | A43-B2-C6; | A43-B2-C7; | A43-B2-C8; | A43-B2-C9; |
| A44-B2-C1; | A44-B2-C2; | A44-B2-C3; | A44-B2-C4; | A44-B2-C5; | A44-B2-C6; |
| A44-B2-C7; | A44-B2-C8; | A44-B2-C9; | A45-B2-C1; | A45-B2-C2; | A45-B2-C3; |
| A45-B2-C4; | A45-B2-C5; | A45-B2-C6; | A45-B2-C7; | A45-B2-C8; | A45-B2-C9; |
| A46-B2-C1; | A46-B2-C2; | A46-B2-C3; | A46-B2-C4; | A46-B2-C5; | A46-B2-C6; |
| A46-B2-C7; | A46-B2-C8; | A46-B2-C9; | A47-B2-C1; | A47-B2-C2; | A47-B2-C3; |
| A47-B2-C4; | A47-B2-C5; | A47-B2-C6; | A47-B2-C7; | A47-B2-C8; | A47-B2-C9; |
| A48-B2-C1; | A48-B2-C2; | A48-B2-C3; | A48-B2-C4; | A48-B2-C5; | A48-B2-C6; |
| A48-B2-C7; | A48-B2-C8; | A48-B2-C9; | A49-B2-C1; | A49-B2-C2; | A49-B2-C3; |
| A49-B2-C4; | A49-B2-C5; | A49-B2-C6; | A49-B2-C7; | A49-B2-C8; | A49-B2-C9; |
| A50-B2-C1; | A50-B2-C2; | A50-B2-C3; | A50-B2-C4; | A50-B2-C5; | A50-B2-C6; |
| A50-B2-C7; | A50-B2-C8; | A50-B2-C9; | A51-B2-C1; | A51-B2-C2; | A51-B2-C3; |
| A51-B2-C4; | A51-B2-C5; | A51-B2-C6; | A51-B2-C7; | A51-B2-C8; | A51-B2-C9; |
| A52-B2-C1; | A52-B2-C2; | A52-B2-C3; | A52-B2-C4; | A52-B2-C5; | A52-B2-C6; |
| A52-B2-C7; | A52-B2-C8; | A52-B2-C9; | A53-B2-C1; | A53-B2-C2; | A53-B2-C3; |

| | | | | | |
|---|---|---|---|---|---|
| A53-B2-C4; | A53-B2-C5; | A53-B2-C6; | A53-B2-C7; | A53-B2-C8; | A53-B2-C9; |
| A54-B2-C1; | A54-B2-C2; | A54-B2-C3; | A54-B2-C4; | A54-B2-C5; | A54-B2-C6; |
| A54-B2-C7; | A54-B2-C8; | A54-B2-C9; | A55-B2-C1; | A55-B2-C2; | A55-B2-C3; |
| A55-B2-C4; | A55-B2-C5; | A55-B2-C6; | A55-B2-C7; | A55-B2-C8; | A55-B2-C9; |
| A56-B2-C1; | A56-B2-C2; | A56-B2-C3; | A56-B2-C4; | A56-B2-C5; | A56-B2-C6; |
| A56-B2-C7; | A56-B2-C8; | A56-B2-C9; | A57-B2-C1; | A57-B2-C2; | A57-B2-C3; |
| A57-B2-C4; | A57-B2-C5; | A57-B2-C6; | A57-B2-C7; | A57-B2-C8; | A57-B2-C9; |
| A58-B2-C1; | A58-B2-C2; | A58-B2-C3; | A58-B2-C4; | A58-B2-C5; | A58-B2-C6; |
| A58-B2-C7; | A58-B2-C8; | A58-B2-C9; | A59-B2-C1; | A59-B2-C2; | A59-B2-C3; |
| A59-B2-C4; | A59-B2-C5; | A59-B2-C6; | A59-B2-C7; | A59-B2-C8; | A59-B2-C9; |
| A60-B2-C1; | A60-B2-C2; | A60-B2-C3; | A60-B2-C4; | A60-B2-C5; | A60-B2-C6; |
| A60-B2-C7; | A60-B2-C8; | A60-B2-C9; | A61-B2-C1; | A61-B2-C2; | A61-B2-C3; |
| A61-B2-C4; | A61-B2-C5; | A61-B2-C6; | A61-B2-C7; | A61-B2-C8; | A61-B2-C9; |
| A62-B2-C1; | A62-B2-C2; | A62-B2-C3; | A62-B2-C4; | A62-B2-C5; | A62-B2-C6; |
| A62-B2-C7; | A62-B2-C8; | A62-B2-C9; | A63-B2-C1; | A63-B2-C2; | A63-B2-C3; |
| A63-B2-C4; | A63-B2-C5; | A63-B2-C6; | A63-B2-C7; | A63-B2-C8; | A63-B2-C9; |
| A64-B2-C1; | A64-B2-C2; | A64-B2-C3; | A64-B2-C4; | A64-B2-C5; | A64-B2-C6; |
| A64-B2-C7; | A64-B2-C8; | A64-B2-C9; | A65-B2-C1; | A65-B2-C2; | A65-B2-C3; |
| A65-B2-C4; | A65-B2-C5; | A65-B2-C6; | A65-B2-C7; | A65-B2-C8; | A65-B2-C9; |
| A66-B2-C1; | A66-B2-C2; | A66-B2-C3; | A66-B2-C4; | A66-B2-C5; | A66-B2-C6; |
| A66-B2-C7; | A66-B2-C8; | A66-B2-C9; | A67-B2-C1; | A67-B2-C2; | A67-B2-C3; |
| A67-B2-C4; | A67-B2-C5; | A67-B2-C6; | A67-B2-C7; | A67-B2-C8; | A67-B2-C9; |
| A68-B2-C1; | A68-B2-C2; | A68-B2-C3; | A68-B2-C4; | A68-B2-C5; | A68-B2-C6; |
| A68-B2-C7; | A68-B2-C8; | A68-B2-C9; | A69-B2-C1; | A69-B2-C2; | A69-B2-C3; |
| A69-B2-C4; | A69-B2-C5; | A69-B2-C6; | A69-B2-C7; | A69-B2-C8; | A69-B2-C9; |
| A70-B2-C1; | A70-B2-C2; | A70-B2-C3; | A70-B2-C4; | A70-B2-C5; | A70-B2-C6; |
| A70-B2-C7; | A70-B2-C8; | A70-B2-C9; | A71-B2-C1; | A71-B2-C2; | A71-B2-C3; |
| A71-B2-C4; | A71-B2-C5; | A71-B2-C6; | A71-B2-C7; | A71-B2-C8; | A71-B2-C9; |
| A1-B3-C1; | A1-B3-C2; | A1-B3-C3; | A1-B3-C4; | A1-B3-C5; | A1-B3-C6; |
| A1-B3-C7; | A1-B3-C8; | A1-B3-C9; | A2-B3-C1; | A2-B3-C2; | A2-B3-C3; |
| A2-B3-C4; | A2-B3-C5; | A2-B3-C6; | A2-B3-C7; | A2-B3-C8; | A2-B3-C9; |
| A3-B3-C1; | A3-B3-C2; | A3-B3-C3; | A3-B3-C4; | A3-B3-C5; | A3-B3-C6; |
| A3-B3-C7; | A3-B3-C8; | A3-B3-C9; | A4-B3-C1; | A4-B3-C2; | A4-B3-C3; |
| A4-B3-C4; | A4-B3-C5; | A4-B3-C6; | A4-B3-C7; | A4-B3-C8; | A4-B3-C9; |
| A5-B3-C1; | A5-B3-C2; | A5-B3-C3; | A5-B3-C4; | A5-B3-C5; | A5-B3-C6; |
| A5-B3-C7; | A5-B3-C8; | A5-B3-C9; | A6-B3-C1; | A6-B3-C2; | A6-B3-C3; |
| A6-B3-C4; | A6-B3-C5; | A6-B3-C6; | A6-B3-C7; | A6-B3-C8; | A6-B3-C9; |
| A7-B3-C1; | A7-B3-C2; | A7-B3-C3; | A7-B3-C4; | A7-B3-C5; | A7-B3-C6; |
| A7-B3-C7; | A7-B3-C8; | A7-B3-C9; | A8-B3-C1; | A8-B3-C2; | A8-B3-C3; |
| A8-B3-C4; | A8-B3-C5; | A8-B3-C6; | A8-B3-C7; | A8-B3-C8; | A8-B3-C9; |
| A9-B3-C1; | A9-B3-C2; | A9-B3-C3; | A9-B3-C4; | A9-B3-C5; | A9-B3-C6; |
| A9-B3-C7; | A9-B3-C8; | A9-B3-C9; | A10-B3-C1; | A10-B3-C2; | A10-B3-C3; |
| A10-B3-C4; | A10-B3-C5; | A10-B3-C6; | A10-B3-C7; | A10-B3-C8; | A10-B3-C9; |
| A11-B3-C1; | A11-B3-C2; | A11-B3-C3; | A11-B3-C4; | A11-B3-C5; | A11-B3-C6; |
| A11-B3-C7; | A11-B3-C8; | A11-B3-C9; | A12-B3-C1; | A12-B3-C2; | A12-B3-C3; |
| A12-B3-C4; | A12-B3-C5; | A12-B3-C6; | A12-B3-C7; | A12-B3-C8; | A12-B3-C9; |
| A13-B3-C1; | A13-B3-C2; | A13-B3-C3; | A13-B3-C4; | A13-B3-C5; | A13-B3-C6; |
| A13-B3-C7; | A13-B3-C8; | A13-B3-C9; | A14-B3-C1; | A14-B3-C2; | A14-B3-C3; |
| A14-B3-C4; | A14-B3-C5; | A14-B3-C6; | A14-B3-C7; | A14-B3-C8; | A14-B3-C9; |
| A15-B3-C1; | A15-B3-C2; | A15-B3-C3; | A15-B3-C4; | A15-B3-C5; | A15-B3-C6; |
| A15-B3-C7; | A15-B3-C8; | A15-B3-C9; | A16-B3-C1; | A16-B3-C2; | A16-B3-C3; |
| A16-B3-C4; | A16-B3-C5; | A16-B3-C6; | A16-B3-C7; | A16-B3-C8; | A16-B3-C9; |
| A17-B3-C1; | A17-B3-C2; | A17-B3-C3; | A17-B3-C4; | A17-B3-C5; | A17-B3-C6; |
| A17-B3-C7; | A17-B3-C8; | A17-B3-C9; | A18-B3-C1; | A18-B3-C2; | A18-B3-C3; |
| A18-B3-C4; | A18-B3-C5; | A18-B3-C6; | A18-B3-C7; | A18-B3-C8; | A18-B3-C9; |
| A19-B3-C1; | A19-B3-C2; | A19-B3-C3; | A19-B3-C4; | A19-B3-C5; | A19-B3-C6; |
| A19-B3-C7; | A19-B3-C8; | A19-B3-C9; | A20-B3-C1; | A20-B3-C2; | A20-B3-C3; |
| A20-B3-C4; | A20-B3-C5; | A20-B3-C6; | A20-B3-C7; | A20-B3-C8; | A20-B3-C9; |
| A21-B3-C1; | A21-B3-C2; | A21-B3-C3; | A21-B3-C4; | A21-B3-C5; | A21-B3-C6; |
| A21-B3-C7; | A21-B3-C8; | A21-B3-C9; | A22-B3-C1; | A22-B3-C2; | A22-B3-C3; |
| A22-B3-C4; | A22-B3-C5; | A22-B3-C6; | A22-B3-C7; | A22-B3-C8; | A22-B3-C9; |
| A23-B3-C1; | A23-B3-C2; | A23-B3-C3; | A23-B3-C4; | A23-B3-C5; | A23-B3-C6; |
| A23-B3-C7; | A23-B3-C8; | A23-B3-C9; | A24-B3-C1; | A24-B3-C2; | A24-B3-C3; |
| A24-B3-C4; | A24-B3-C5; | A24-B3-C6; | A24-B3-C7; | A24-B3-C8; | A24-B3-C9; |
| A25-B3-C1; | A25-B3-C2; | A25-B3-C3; | A25-B3-C4; | A25-B3-C5; | A25-B3-C6; |
| A25-B3-C7; | A25-B3-C8; | A25-B3-C9; | A26-B3-C1; | A26-B3-C2; | A26-B3-C3; |
| A26-B3-C4; | A26-B3-C5; | A26-B3-C6; | A26-B3-C7; | A26-B3-C8; | A26-B3-C9; |
| A27-B3-C1; | A27-B3-C2; | A27-B3-C3; | A27-B3-C4; | A27-B3-C5; | A27-B3-C6; |
| A27-B3-C7; | A27-B3-C8; | A27-B3-C9; | A28-B3-C1; | A28-B3-C2; | A28-B3-C3; |
| A28-B3-C4; | A28-B3-C5; | A28-B3-C6; | A28-B3-C7; | A28-B3-C8; | A28-B3-C9; |
| A29-B3-C1; | A29-B3-C2; | A29-B3-C3; | A29-B3-C4; | A29-B3-C5; | A29-B3-C6; |
| A29-B3-C7; | A29-B3-C8; | A29-B3-C9; | A30-B3-C1; | A30-B3-C2; | A30-B3-C3; |
| A30-B3-C4; | A30-B3-C5; | A30-B3-C6; | A30-B3-C7; | A30-B3-C8; | A30-B3-C9; |
| A31-B3-C1; | A31-B3-C2; | A31-B3-C3; | A31-B3-C4; | A31-B3-C5; | A31-B3-C6; |
| A31-B3-C7; | A31-B3-C8; | A31-B3-C9; | A32-B3-C1; | A32-B3-C2; | A32-B3-C3; |
| A32-B3-C4; | A32-B3-C5; | A32-B3-C6; | A32-B3-C7; | A32-B3-C8; | A32-B3-C9; |
| A33-B3-C1; | A33-B3-C2; | A33-B3-C3; | A33-B3-C4; | A33-B3-C5; | A33-B3-C6; |
| A33-B3-C7; | A33-B3-C8; | A33-B3-C9; | A34-B3-C1; | A34-B3-C2; | A34-B3-C3; |
| A34-B3-C4; | A34-B3-C5; | A34-B3-C6; | A34-B3-C7; | A34-B3-C8; | A34-B3-C9; |

| | | | | | |
|---|---|---|---|---|---|
| A35-B3-C1; | A35-B3-C2; | A35-B3-C3; | A35-B3-C4; | A35-B3-C5; | A35-B3-C6; |
| A35-B3-C7; | A35-B3-C8; | A35-B3-C9; | A36-B3-C1; | A36-B3-C2; | A36-B3-C3; |
| A36-B3-C4; | A36-B3-C5; | A36-B3-C6; | A36-B3-C7; | A36-B3-C8; | A36-B3-C9; |
| A37-B3-C1; | A37-B3-C2; | A37-B3-C3; | A37-B3-C4; | A37-B3-C5; | A37-B3-C6; |
| A37-B3-C7; | A37-B3-C8; | A37-B3-C9; | A38-B3-C1; | A38-B3-C2; | A38-B3-C3; |
| A38-B3-C4; | A38-B3-C5; | A38-B3-C6; | A38-B3-C7; | A38-B3-C8; | A38-B3-C9; |
| A39-B3-C1; | A39-B3-C2; | A39-B3-C3; | A39-B3-C4; | A39-B3-C5; | A39-B3-C6; |
| A39-B3-C7; | A39-B3-C8; | A39-B3-C9; | A40-B3-C1; | A40-B3-C2; | A40-B3-C3; |
| A40-B3-C4; | A40-B3-C5; | A40-B3-C6; | A40-B3-C7; | A40-B3-C8; | A40-B3-C9; |
| A41-B3-C1; | A41-B3-C2; | A41-B3-C3; | A41-B3-C4; | A41-B3-C5; | A41-B3-C6; |
| A41-B3-C7; | A41-B3-C8; | A41-B3-C9; | A42-B3-C1; | A42-B3-C2; | A42-B3-C3; |
| A42-B3-C4; | A42-B3-C5; | A42-B3-C6; | A42-B3-C7; | A42-B3-C8; | A42-B3-C9; |
| A43-B3-C1; | A43-B3-C2; | A43-B3-C3; | A43-B3-C4; | A43-B3-C5; | A43-B3-C6; |
| A43-B3-C7; | A43-B3-C8; | A43-B3-C9; | A44-B3-C1; | A44-B3-C2; | A44-B3-C3; |
| A44-B3-C4; | A44-B3-C5; | A44-B3-C6; | A44-B3-C7; | A44-B3-C8; | A44-B3-C9; |
| A45-B3-C1; | A45-B3-C2; | A45-B3-C3; | A45-B3-C4; | A45-B3-C5; | A45-B3-C6; |
| A45-B3-C7; | A45-B3-C8; | A45-B3-C9; | A46-B3-C1; | A46-B3-C2; | A46-B3-C3; |
| A46-B3-C4; | A46-B3-C5; | A46-B3-C6; | A46-B3-C7; | A46-B3-C8; | A46-B3-C9; |
| A47-B3-C1; | A47-B3-C2; | A47-B3-C3; | A47-B3-C4; | A47-B3-C5; | A47-B3-C6; |
| A47-B3-C7; | A47-B3-C8; | A47-B3-C9; | A48-B3-C1; | A48-B3-C2; | A48-B3-C3; |
| A48-B3-C4; | A48-B3-C5; | A48-B3-C6; | A48-B3-C7; | A48-B3-C8; | A48-B3-C9; |
| A49-B3-C1; | A49-B3-C2; | A49-B3-C3; | A49-B3-C4; | A49-B3-C5; | A49-B3-C6; |
| A49-B3-C7; | A49-B3-C8; | A49-B3-C9; | A50-B3-C1; | A50-B3-C2; | A50-B3-C3; |
| A50-B3-C4; | A50-B3-C5; | A50-B3-C6; | A50-B3-C7; | A50-B3-C8; | A50-B3-C9; |
| A51-B3-C1; | A51-B3-C2; | A51-B3-C3; | A51-B3-C4; | A51-B3-C5; | A51-B3-C6; |
| A51-B3-C7; | A51-B3-C8; | A51-B3-C9; | A52-B3-C1; | A52-B3-C2; | A52-B3-C3; |
| A52-B3-C4; | A52-B3-C5; | A52-B3-C6; | A52-B3-C7; | A52-B3-C8; | A52-B3-C9; |
| A53-B3-C1; | A53-B3-C2; | A53-B3-C3; | A53-B3-C4; | A53-B3-C5; | A53-B3-C6; |
| A53-B3-C7; | A53-B3-C8; | A53-B3-C9; | A54-B3-C1; | A54-B3-C2; | A54-B3-C3; |
| A54-B3-C4; | A54-B3-C5; | A54-B3-C6; | A54-B3-C7; | A54-B3-C8; | A54-B3-C9; |
| A55-B3-C1; | A55-B3-C2; | A55-B3-C3; | A55-B3-C4; | A55-B3-C5; | A55-B3-C6; |
| A55-B3-C7; | A55-B3-C8; | A55-B3-C9; | A56-B3-C1; | A56-B3-C2; | A56-B3-C3; |
| A56-B3-C4; | A56-B3-C5; | A56-B3-C6; | A56-B3-C7; | A56-B3-C8; | A56-B3-C9; |
| A57-B3-C1; | A57-B3-C2; | A57-B3-C3; | A57-B3-C4; | A57-B3-C5; | A57-B3-C6; |
| A57-B3-C7; | A57-B3-C8; | A57-B3-C9; | A58-B3-C1; | A58-B3-C2; | A58-B3-C3; |
| A58-B3-C4; | A58-B3-C5; | A58-B3-C6; | A58-B3-C7; | A58-B3-C8; | A58-B3-C9; |
| A59-B3-C1; | A59-B3-C2; | A59-B3-C3; | A59-B3-C4; | A59-B3-C5; | A59-B3-C6; |
| A59-B3-C7; | A59-B3-C8; | A59-B3-C9; | A60-B3-C1; | A60-B3-C2; | A60-B3-C3; |
| A60-B3-C4; | A60-B3-C5; | A60-B3-C6; | A60-B3-C7; | A60-B3-C8; | A60-B3-C9; |
| A61-B3-C1; | A61-B3-C2; | A61-B3-C3; | A61-B3-C4; | A61-B3-C5; | A61-B3-C6; |
| A61-B3-C7; | A61-B3-C8; | A61-B3-C9; | A62-B3-C1; | A62-B3-C2; | A62-B3-C3; |
| A62-B3-C4; | A62-B3-C5; | A62-B3-C6; | A62-B3-C7; | A62-B3-C8; | A62-B3-C9; |
| A63-B3-C1; | A63-B3-C2; | A63-B3-C3; | A63-B3-C4; | A63-B3-C5; | A63-B3-C6; |
| A63-B3-C7; | A63-B3-C8; | A63-B3-C9; | A64-B3-C1; | A64-B3-C2; | A64-B3-C3; |
| A64-B3-C4; | A64-B3-C5; | A64-B3-C6; | A64-B3-C7; | A64-B3-C8; | A64-B3-C9; |
| A65-B3-C1; | A65-B3-C2; | A65-B3-C3; | A65-B3-C4; | A65-B3-C5; | A65-B3-C6; |
| A65-B3-C7; | A65-B3-C8; | A65-B3-C9; | A66-B3-C1; | A66-B3-C2; | A66-B3-C3; |
| A66-B3-C4; | A66-B3-C5; | A66-B3-C6; | A66-B3-C7; | A66-B3-C8; | A66-B3-C9; |
| A67-B3-C1; | A67-B3-C2; | A67-B3-C3; | A67-B3-C4; | A67-B3-C5; | A67-B3-C6; |
| A67-B3-C7; | A67-B3-C8; | A67-B3-C9; | A68-B3-C1; | A68-B3-C2; | A68-B3-C3; |
| A68-B3-C4; | A68-B3-C5; | A68-B3-C6; | A68-B3-C7; | A68-B3-C8; | A68-B3-C9; |
| A69-B3-C1; | A69-B3-C2; | A69-B3-C3; | A69-B3-C4; | A69-B3-C5; | A69-B3-C6; |
| A69-B3-C7; | A69-B3-C8; | A69-B3-C9; | A70-B3-C1; | A70-B3-C2; | A70-B3-C3; |
| A70-B3-C4; | A70-B3-C5; | A70-B3-C6; | A70-B3-C7; | A70-B3-C8; | A70-B3-C9; |
| A71-B3-C1; | A71-B3-C2; | A71-B3-C3; | A71-B3-C4; | A71-B3-C5; | A71-B3-C6; |
| A71-B3-C7; | A71-B3-C8; | A71-B3-C9; | A1-B4-C1; | A1-B4-C2; | A1-B4-C3; |
| A1-B4-C4; | A1-B4-C5; | A1-B4-C6; | A1-B4-C7; | A1-B4-C8; | A1-B4-C9; |
| A2-B4-C1; | A2-B4-C2; | A2-B4-C3; | A2-B4-C4; | A2-B4-C5; | A2-B4-C6; |
| A2-B4-C7; | A2-B4-C8; | A2-B4-C9; | A3-B4-C1; | A3-B4-C2; | A3-B4-C3; |
| A3-B4-C4; | A3-B4-C5; | A3-B4-C6; | A3-B4-C7; | A3-B4-C8; | A3-B4-C9; |
| A4-B4-C1; | A4-B4-C2; | A4-B4-C3; | A4-B4-C4; | A4-B4-C5; | A4-B4-C6; |
| A4-B4-C7; | A4-B4-C8; | A4-B4-C9; | A5-B4-C1; | A5-B4-C2; | A5-B4-C3; |
| A5-B4-C4; | A5-B4-C5; | A5-B4-C6; | A5-B4-C7; | A5-B4-C8; | A5-B4-C9; |
| A6-B4-C1; | A6-B4-C2; | A6-B4-C3; | A6-B4-C4; | A6-B4-C5; | A6-B4-C6; |
| A6-B4-C7; | A6-B4-C8; | A6-B4-C9; | A7-B4-C1; | A7-B4-C2; | A7-B4-C3; |
| A7-B4-C4; | A7-B4-C5; | A7-B4-C6; | A7-B4-C7; | A7-B4-C8; | A7-B4-C9; |
| A8-B4-C1; | A8-B4-C2; | A8-B4-C3; | A8-B4-C4; | A8-B4-C5; | A8-B4-C6; |
| A8-B4-C7; | A8-B4-C8; | A8-B4-C9; | A9-B4-C1; | A9-B4-C2; | A9-B4-C3; |
| A9-B4-C4; | A9-B4-C5; | A9-B4-C6; | A9-B4-C7; | A9-B4-C8; | A9-B4-C9; |
| A10-B4-C1; | A10-B4-C2; | A10-B4-C3; | A10-B4-C4; | A10-B4-C5; | A10-B4-C6; |
| A10-B4-C7; | A10-B4-C8; | A10-B4-C9; | A11-B4-C1; | A11-B4-C2; | A11-B4-C3; |
| A11-B4-C4; | A11-B4-C5; | A11-B4-C6; | A11-B4-C7; | A11-B4-C8; | A11-B4-C9; |
| A12-B4-C1; | A12-B4-C2; | A12-B4-C3; | A12-B4-C4; | A12-B4-C5; | A12-B4-C6; |
| A12-B4-C7; | A12-B4-C8; | A12-B4-C9; | A13-B4-C1; | A13-B4-C2; | A13-B4-C3; |
| A13-B4-C4; | A13-B4-C5; | A13-B4-C6; | A13-B4-C7; | A13-B4-C8; | A13-B4-C9; |
| A14-B4-C1; | A14-B4-C2; | A14-B4-C3; | A14-B4-C4; | A14-B4-C5; | A14-B4-C6; |
| A14-B4-C7; | A14-B4-C8; | A14-B4-C9; | A15-B4-C1; | A15-B4-C2; | A15-B4-C3; |
| A15-B4-C4; | A15-B4-C5; | A15-B4-C6; | A15-B4-C7; | A15-B4-C8; | A15-B4-C9; |
| A16-B4-C1; | A16-B4-C2; | A16-B4-C3; | A16-B4-C4; | A16-B4-C5; | A16-B4-C6; |

-continued

| | | | | | |
|---|---|---|---|---|---|
| A16-B4-C7; | A16-B4-C8; | A16-B4-C9; | A17-B4-C1; | A17-B4-C2; | A17-B4-C3; |
| A17-B4-C4; | A17-B4-C5; | A17-B4-C6; | A17-B4-C7; | A17-B4-C8; | A17-B4-C9; |
| A18-B4-C1; | A18-B4-C2; | A18-B4-C3; | A18-B4-C4; | A18-B4-C5; | A18-B4-C6; |
| A18-B4-C7; | A18-B4-C8; | A18-B4-C9; | A19-B4-C1; | A19-B4-C2; | A19-B4-C3; |
| A19-B4-C4; | A19-B4-C5; | A19-B4-C6; | A19-B4-C7; | A19-B4-C8; | A19-B4-C9; |
| A20-B4-C1; | A20-B4-C2; | A20-B4-C3; | A20-B4-C4; | A20-B4-C5; | A20-B4-C6; |
| A20-B4-C7; | A20-B4-C8; | A20-B4-C9; | A21-B4-C1; | A21-B4-C2; | A21-B4-C3; |
| A21-B4-C4; | A21-B4-C5; | A21-B4-C6; | A21-B4-C7; | A21-B4-C8; | A21-B4-C9; |
| A22-B4-C1; | A22-B4-C2; | A22-B4-C3; | A22-B4-C4; | A22-B4-C5; | A22-B4-C6; |
| A22-B4-C7; | A22-B4-C8; | A22-B4-C9; | A23-B4-C1; | A23-B4-C2; | A23-B4-C3; |
| A23-B4-C4; | A23-B4-C5; | A23-B4-C6; | A23-B4-C7; | A23-B4-C8; | A23-B4-C9; |
| A24-B4-C1; | A24-B4-C2; | A24-B4-C3; | A24-B4-C4; | A24-B4-C5; | A24-B4-C6; |
| A24-B4-C7; | A24-B4-C8; | A24-B4-C9; | A25-B4-C1; | A25-B4-C2; | A25-B4-C3; |
| A25-B4-C4; | A25-B4-C5; | A25-B4-C6; | A25-B4-C7; | A25-B4-C8; | A25-B4-C9; |
| A26-B4-C1; | A26-B4-C2; | A26-B4-C3; | A26-B4-C4; | A26-B4-C5; | A26-B4-C6; |
| A26-B4-C7; | A26-B4-C8; | A26-B4-C9; | A27-B4-C1; | A27-B4-C2; | A27-B4-C3; |
| A27-B4-C4; | A27-B4-C5; | A27-B4-C6; | A27-B4-C7; | A27-B4-C8; | A27-B4-C9; |
| A28-B4-C1; | A28-B4-C2; | A28-B4-C3; | A28-B4-C4; | A28-B4-C5; | A28-B4-C6; |
| A28-B4-C7; | A28-B4-C8; | A28-B4-C9; | A29-B4-C1; | A29-B4-C2; | A29-B4-C3; |
| A29-B4-C4; | A29-B4-C5; | A29-B4-C6; | A29-B4-C7; | A29-B4-C8; | A29-B4-C9; |
| A30-B4-C1; | A30-B4-C2; | A30-B4-C3; | A30-B4-C4; | A30-B4-C5; | A30-B4-C6; |
| A30-B4-C7; | A30-B4-C8; | A30-B4-C9; | A31-B4-C1; | A31-B4-C2; | A31-B4-C3; |
| A31-B4-C4; | A31-B4-C5; | A31-B4-C6; | A31-B4-C7; | A31-B4-C8; | A31-B4-C9; |
| A32-B4-C1; | A32-B4-C2; | A32-B4-C3; | A32-B4-C4; | A32-B4-C5; | A32-B4-C6; |
| A32-B4-C7; | A32-B4-C8; | A32-B4-C9; | A33-B4-C1; | A33-B4-C2; | A33-B4-C3; |
| A33-B4-C4; | A33-B4-C5; | A33-B4-C6; | A33-B4-C7; | A33-B4-C8; | A33-B4-C9; |
| A34-B4-C1; | A34-B4-C2; | A34-B4-C3; | A34-B4-C4; | A34-B4-C5; | A34-B4-C6; |
| A34-B4-C7; | A34-B4-C8; | A34-B4-C9; | A35-B4-C1; | A35-B4-C2; | A35-B4-C3; |
| A35-B4-C4; | A35-B4-C5; | A35-B4-C6; | A35-B4-C7; | A35-B4-C8; | A35-B4-C9; |
| A36-B4-C1; | A36-B4-C2; | A36-B4-C3; | A36-B4-C4; | A36-B4-C5; | A36-B4-C6; |
| A36-B4-C7; | A36-B4-C8; | A36-B4-C9; | A37-B4-C1; | A37-B4-C2; | A37-B4-C3; |
| A37-B4-C4; | A37-B4-C5; | A37-B4-C6; | A37-B4-C7; | A37-B4-C8; | A37-B4-C9; |
| A38-B4-C1; | A38-B4-C2; | A38-B4-C3; | A38-B4-C4; | A38-B4-C5; | A38-B4-C6; |
| A38-B4-C7; | A38-B4-C8; | A38-B4-C9; | A39-B4-C1; | A39-B4-C2; | A39-B4-C3; |
| A39-B4-C4; | A39-B4-C5; | A39-B4-C6; | A39-B4-C7; | A39-B4-C8; | A39-B4-C9; |
| A40-B4-C1; | A40-B4-C2; | A40-B4-C3; | A40-B4-C4; | A40-B4-C5; | A40-B4-C6; |
| A40-B4-C7; | A40-B4-C8; | A40-B4-C9; | A41-B4-C1; | A41-B4-C2; | A41-B4-C3; |
| A41-B4-C4; | A41-B4-C5; | A41-B4-C6; | A41-B4-C7; | A41-B4-C8; | A41-B4-C9; |
| A42-B4-C1; | A42-B4-C2; | A42-B4-C3; | A42-B4-C4; | A42-B4-C5; | A42-B4-C6; |
| A42-B4-C7; | A42-B4-C8; | A42-B4-C9; | A43-B4-C1; | A43-B4-C2; | A43-B4-C3; |
| A43-B4-C4; | A43-B4-C5; | A43-B4-C6; | A43-B4-C7; | A43-B4-C8; | A43-B4-C9; |
| A44-B4-C1; | A44-B4-C2; | A44-B4-C3; | A44-B4-C4; | A44-B4-C5; | A44-B4-C6; |
| A44-B4-C7; | A44-B4-C8; | A44-B4-C9; | A45-B4-C1; | A45-B4-C2; | A45-B4-C3; |
| A45-B4-C4; | A45-B4-C5; | A45-B4-C6; | A45-B4-C7; | A45-B4-C8; | A45-B4-C9; |
| A46-B4-C1; | A46-B4-C2; | A46-B4-C3; | A46-B4-C4; | A46-B4-C5; | A46-B4-C6; |
| A46-B4-C7; | A46-B4-C8; | A46-B4-C9; | A47-B4-C1; | A47-B4-C2; | A47-B4-C3; |
| A47-B4-C4; | A47-B4-C5; | A47-B4-C6; | A47-B4-C7; | A47-B4-C8; | A47-B4-C9; |
| A48-B4-C1; | A48-B4-C2; | A48-B4-C3; | A48-B4-C4; | A48-B4-C5; | A48-B4-C6; |
| A48-B4-C7; | A48-B4-C8; | A48-B4-C9; | A49-B4-C1; | A49-B4-C2; | A49-B4-C3; |
| A49-B4-C4; | A49-B4-C5; | A49-B4-C6; | A49-B4-C7; | A49-B4-C8; | A49-B4-C9; |
| A50-B4-C1; | A50-B4-C2; | A50-B4-C3; | A50-B4-C4; | A50-B4-C5; | A50-B4-C6; |
| A50-B4-C7; | A50-B4-C8; | A50-B4-C9; | A51-B4-C1; | A51-B4-C2; | A51-B4-C3; |
| A51-B4-C4; | A51-B4-C5; | A51-B4-C6; | A51-B4-C7; | A51-B4-C8; | A51-B4-C9; |
| A52-B4-C1; | A52-B4-C2; | A52-B4-C3; | A52-B4-C4; | A52-B4-C5; | A52-B4-C6; |
| A52-B4-C7; | A52-B4-C8; | A52-B4-C9; | A53-B4-C1; | A53-B4-C2; | A53-B4-C3; |
| A53-B4-C4; | A53-B4-C5; | A53-B4-C6; | A53-B4-C7; | A53-B4-C8; | A53-B4-C9; |
| A54-B4-C1; | A54-B4-C2; | A54-B4-C3; | A54-B4-C4; | A54-B4-C5; | A54-B4-C6; |
| A54-B4-C7; | A54-B4-C8; | A54-B4-C9; | A55-B4-C1; | A55-B4-C2; | A55-B4-C3; |
| A55-B4-C4; | A55-B4-C5; | A55-B4-C6; | A55-B4-C7; | A55-B4-C8; | A55-B4-C9; |
| A56-B4-C1; | A56-B4-C2; | A56-B4-C3; | A56-B4-C4; | A56-B4-C5; | A56-B4-C6; |
| A56-B4-C7; | A56-B4-C8; | A56-B4-C9; | A57-B4-C1; | A57-B4-C2; | A57-B4-C3; |
| A57-B4-C4; | A57-B4-C5; | A57-B4-C6; | A57-B4-C7; | A57-B4-C8; | A57-B4-C9; |
| A58-B4-C1; | A58-B4-C2; | A58-B4-C3; | A58-B4-C4; | A58-B4-C5; | A58-B4-C6; |
| A58-B4-C7; | A58-B4-C8; | A58-B4-C9; | A59-B4-C1; | A59-B4-C2; | A59-B4-C3; |
| A59-B4-C4; | A59-B4-C5; | A59-B4-C6; | A59-B4-C7; | A59-B4-C8; | A59-B4-C9; |
| A60-B4-C1; | A60-B4-C2; | A60-B4-C3; | A60-B4-C4; | A60-B4-C5; | A60-B4-C6; |
| A60-B4-C7; | A60-B4-C8; | A60-B4-C9; | A61-B4-C1; | A61-B4-C2; | A61-B4-C3; |
| A61-B4-C4; | A61-B4-C5; | A61-B4-C6; | A61-B4-C7; | A61-B4-C8; | A61-B4-C9; |
| A62-B4-C1; | A62-B4-C2; | A62-B4-C3; | A62-B4-C4; | A62-B4-C5; | A62-B4-C6; |
| A62-B4-C7; | A62-B4-C8; | A62-B4-C9; | A63-B4-C1; | A63-B4-C2; | A63-B4-C3; |
| A63-B4-C4; | A63-B4-C5; | A63-B4-C6; | A63-B4-C7; | A63-B4-C8; | A63-B4-C9; |
| A64-B4-C1; | A64-B4-C2; | A64-B4-C3; | A64-B4-C4; | A64-B4-C5; | A64-B4-C6; |
| A64-B4-C7; | A64-B4-C8; | A64-B4-C9; | A65-B4-C1; | A65-B4-C2; | A65-B4-C3; |
| A65-B4-C4; | A65-B4-C5; | A65-B4-C6; | A65-B4-C7; | A65-B4-C8; | A65-B4-C9; |
| A66-B4-C1; | A66-B4-C2; | A66-B4-C3; | A66-B4-C4; | A66-B4-C5; | A66-B4-C6; |
| A66-B4-C7; | A66-B4-C8; | A66-B4-C9; | A67-B4-C1; | A67-B4-C2; | A67-B4-C3; |
| A67-B4-C4; | A67-B4-C5; | A67-B4-C6; | A67-B4-C7; | A67-B4-C8; | A67-B4-C9; |
| A68-B4-C1; | A68-B4-C2; | A68-B4-C3; | A68-B4-C4; | A68-B4-C5; | A68-B4-C6; |
| A68-B4-C7; | A68-B4-C8; | A68-B4-C9; | A69-B4-C1; | A69-B4-C2; | A69-B4-C3; |

| | | | | | |
|---|---|---|---|---|---|
| A69-B4-C4; | A69-B4-C5; | A69-B4-C6; | A69-B4-C7; | A69-B4-C8; | A69-B4-C9; |
| A70-B4-C1; | A70-B4-C2; | A70-B4-C3; | A70-B4-C4; | A70-B4-C5; | A70-B4-C6; |
| A70-B4-C7; | A70-B4-C8; | A70-B4-C9; | A71-B4-C1; | A71-B4-C2; | A71-B4-C3; |
| A71-B4-C4; | A71-B4-C5; | A71-B4-C6; | A71-B4-C7; | A71-B4-C8; | A71-B4-C9; |
| A1-B5-C1; | A1-B5-C2; | A1-B5-C3; | A1-B5-C4; | A1-B5-C5; | A1-B5-C6; |
| A1-B5-C7; | A1-B5-C8; | A1-B5-C9; | A2-B5-C1; | A2-B5-C2; | A2-B5-C3; |
| A2-B5-C4; | A2-B5-C5; | A2-B5-C6; | A2-B5-C7; | A2-B5-C8; | A2-B5-C9; |
| A3-B5-C1; | A3-B5-C2; | A3-B5-C3; | A3-B5-C4; | A3-B5-C5; | A3-B5-C6; |
| A3-B5-C7; | A3-B5-C8; | A3-B5-C9; | A4-B5-C1; | A4-B5-C2; | A4-B5-C3; |
| A4-B5-C4; | A4-B5-C5; | A4-B5-C6; | A4-B5-C7; | A4-B5-C8; | A4-B5-C9; |
| A5-B5-C1; | A5-B5-C2; | A5-B5-C3; | A5-B5-C4; | A5-B5-C5; | A5-B5-C6; |
| A5-B5-C7; | A5-B5-C8; | A5-B5-C9; | A6-B5-C1; | A6-B5-C2; | A6-B5-C3; |
| A6-B5-C4; | A6-B5-C5; | A6-B5-C6; | A6-B5-C7; | A6-B5-C8; | A6-B5-C9; |
| A7-B5-C1; | A7-B5-C2; | A7-B5-C3; | A7-B5-C4; | A7-B5-C5; | A7-B5-C6; |
| A7-B5-C7; | A7-B5-C8; | A7-B5-C9; | A8-B5-C1; | A8-B5-C2; | A8-B5-C3; |
| A8-B5-C4; | A8-B5-C5; | A8-B5-C6; | A8-B5-C7; | A8-B5-C8; | A8-B5-C9; |
| A9-B5-C1; | A9-B5-C2; | A9-B5-C3; | A9-B5-C4; | A9-B5-C5; | A9-B5-C6; |
| A9-B5-C7; | A9-B5-C8; | A9-B5-C9; | A10-B5-C1; | A10-B5-C2; | A10-B5-C3; |
| A10-B5-C4; | A10-B5-C5; | A10-B5-C6; | A10-B5-C7; | A10-B5-C8; | A10-B5-C9; |
| A11-B5-C1; | A11-B5-C2; | A11-B5-C3; | A11-B5-C4; | A11-B5-C5; | A11-B5-C6; |
| A11-B5-C7; | A11-B5-C8; | A11-B5-C9; | A12-B5-C1; | A12-B5-C2; | A12-B5-C3; |
| A12-B5-C4; | A12-B5-C5; | A12-B5-C6; | A12-B5-C7; | A12-B5-C8; | A12-B5-C9; |
| A13-B5-C1; | A13-B5-C2; | A13-B5-C3; | A13-B5-C4; | A13-B5-C5; | A13-B5-C6; |
| A13-B5-C7; | A13-B5-C8; | A13-B5-C9; | A14-B5-C1; | A14-B5-C2; | A14-B5-C3; |
| A14-B5-C4; | A14-B5-C5; | A14-B5-C6; | A14-B5-C7; | A14-B5-C8; | A14-B5-C9; |
| A15-B5-C1; | A15-B5-C2; | A15-B5-C3; | A15-B5-C4; | A15-B5-C5; | A15-B5-C6; |
| A15-B5-C7; | A15-B5-C8; | A15-B5-C9; | A16-B5-C1; | A16-B5-C2; | A16-B5-C3; |
| A16-B5-C4; | A16-B5-C5; | A16-B5-C6; | A16-B5-C7; | A16-B5-C8; | A16-B5-C9; |
| A17-B5-C1; | A17-B5-C2; | A17-B5-C3; | A17-B5-C4; | A17-B5-C5; | A17-B5-C6; |
| A17-B5-C7; | A17-B5-C8; | A17-B5-C9; | A18-B5-C1; | A18-B5-C2; | A18-B5-C3; |
| A18-B5-C4; | A18-B5-C5; | A18-B5-C6; | A18-B5-C7; | A18-B5-C8; | A18-B5-C9; |
| A19-B5-C1; | A19-B5-C2; | A19-B5-C3; | A19-B5-C4; | A19-B5-C5; | A19-B5-C6; |
| A19-B5-C7; | A19-B5-C8; | A19-B5-C9; | A20-B5-C1; | A20-B5-C2; | A20-B5-C3; |
| A20-B5-C4; | A20-B5-C5; | A20-B5-C6; | A20-B5-C7; | A20-B5-C8; | A20-B5-C9; |
| A21-B5-C1; | A21-B5-C2; | A21-B5-C3; | A21-B5-C4; | A21-B5-C5; | A21-B5-C6; |
| A21-B5-C7; | A21-B5-C8; | A21-B5-C9; | A22-B5-C1; | A22-B5-C2; | A22-B5-C3; |
| A22-B5-C4; | A22-B5-C5; | A22-B5-C6; | A22-B5-C7; | A22-B5-C8; | A22-B5-C9; |
| A23-B5-C1; | A23-B5-C2; | A23-B5-C3; | A23-B5-C4; | A23-B5-C5; | A23-B5-C6; |
| A23-B5-C7; | A23-B5-C8; | A23-B5-C9; | A24-B5-C1; | A24-B5-C2; | A24-B5-C3; |
| A24-B5-C4; | A24-B5-C5; | A24-B5-C6; | A24-B5-C7; | A24-B5-C8; | A24-B5-C9; |
| A25-B5-C1; | A25-B5-C2; | A25-B5-C3; | A25-B5-C4; | A25-B5-C5; | A25-B5-C6; |
| A25-B5-C7; | A25-B5-C8; | A25-B5-C9; | A26-B5-C1; | A26-B5-C2; | A26-B5-C3; |
| A26-B5-C4; | A26-B5-C5; | A26-B5-C6; | A26-B5-C7; | A26-B5-C8; | A26-B5-C9; |
| A27-B5-C1; | A27-B5-C2; | A27-B5-C3; | A27-B5-C4; | A27-B5-C5; | A27-B5-C6; |
| A27-B5-C7; | A27-B5-C8; | A27-B5-C9; | A28-B5-C1; | A28-B5-C2; | A28-B5-C3; |
| A28-B5-C4; | A28-B5-C5; | A28-B5-C6; | A28-B5-C7; | A28-B5-C8; | A28-B5-C9; |
| A29-B5-C1; | A29-B5-C2; | A29-B5-C3; | A29-B5-C4; | A29-B5-C5; | A29-B5-C6; |
| A29-B5-C7; | A29-B5-C8; | A29-B5-C9; | A30-B5-C1; | A30-B5-C2; | A30-B5-C3; |
| A30-B5-C4; | A30-B5-C5; | A30-B5-C6; | A30-B5-C7; | A30-B5-C8; | A30-B5-C9; |
| A31-B5-C1; | A31-B5-C2; | A31-B5-C3; | A31-B5-C4; | A31-B5-C5; | A31-B5-C6; |
| A31-B5-C7; | A31-B5-C8; | A31-B5-C9; | A32-B5-C1; | A32-B5-C2; | A32-B5-C3; |
| A32-B5-C4; | A32-B5-C5; | A32-B5-C6; | A32-B5-C7; | A32-B5-C8; | A32-B5-C9; |
| A33-B5-C1; | A33-B5-C2; | A33-B5-C3; | A33-B5-C4; | A33-B5-C5; | A33-B5-C6; |
| A33-B5-C7; | A33-B5-C8; | A33-B5-C9; | A34-B5-C1; | A34-B5-C2; | A34-B5-C3; |
| A34-B5-C4; | A34-B5-C5; | A34-B5-C6; | A34-B5-C7; | A34-B5-C8; | A34-B5-C9; |
| A35-B5-C1; | A35-B5-C2; | A35-B5-C3; | A35-B5-C4; | A35-B5-C5; | A35-B5-C6; |
| A35-B5-C7; | A35-B5-C8; | A35-B5-C9; | A36-B5-C1; | A36-B5-C2; | A36-B5-C3; |
| A36-B5-C4; | A36-B5-C5; | A36-B5-C6; | A36-B5-C7; | A36-B5-C8; | A36-B5-C9; |
| A37-B5-C1; | A37-B5-C2; | A37-B5-C3; | A37-B5-C4; | A37-B5-C5; | A37-B5-C6; |
| A37-B5-C7; | A37-B5-C8; | A37-B5-C9; | A38-B5-C1; | A38-B5-C2; | A38-B5-C3; |
| A38-B5-C4; | A38-B5-C5; | A38-B5-C6; | A38-B5-C7; | A38-B5-C8; | A38-B5-C9; |
| A39-B5-C1; | A39-B5-C2; | A39-B5-C3; | A39-B5-C4; | A39-B5-C5; | A39-B5-C6; |
| A39-B5-C7; | A39-B5-C8; | A39-B5-C9; | A40-B5-C1; | A40-B5-C2; | A40-B5-C3; |
| A40-B5-C4; | A40-B5-C5; | A40-B5-C6; | A40-B5-C7; | A40-B5-C8; | A40-B5-C9; |
| A41-B5-C1; | A41-B5-C2; | A41-B5-C3; | A41-B5-C4; | A41-B5-C5; | A41-B5-C6; |
| A41-B5-C7; | A41-B5-C8; | A41-B5-C9; | A42-B5-C1; | A42-B5-C2; | A42-B5-C3; |
| A42-B5-C4; | A42-B5-C5; | A42-B5-C6; | A42-B5-C7; | A42-B5-C8; | A42-B5-C9; |
| A43-B5-C1; | A43-B5-C2; | A43-B5-C3; | A43-B5-C4; | A43-B5-C5; | A43-B5-C6; |
| A43-B5-C7; | A43-B5-C8; | A43-B5-C9; | A44-B5-C1; | A44-B5-C2; | A44-B5-C3; |
| A44-B5-C4; | A44-B5-C5; | A44-B5-C6; | A44-B5-C7; | A44-B5-C8; | A44-B5-C9; |
| A45-B5-C1; | A45-B5-C2; | A45-B5-C3; | A45-B5-C4; | A45-B5-C5; | A45-B5-C6; |
| A45-B5-C7; | A45-B5-C8; | A45-B5-C9; | A46-B5-C1; | A46-B5-C2; | A46-B5-C3; |
| A46-B5-C4; | A46-B5-C5; | A46-B5-C6; | A46-B5-C7; | A46-B5-C8; | A46-B5-C9; |
| A47-B5-C1; | A47-B5-C2; | A47-B5-C3; | A47-B5-C4; | A47-B5-C5; | A47-B5-C6; |
| A47-B5-C7; | A47-B5-C8; | A47-B5-C9; | A48-B5-C1; | A48-B5-C2; | A48-B5-C3; |
| A48-B5-C4; | A48-B5-C5; | A48-B5-C6; | A48-B5-C7; | A48-B5-C8; | A48-B5-C9; |
| A49-B5-C1; | A49-B5-C2; | A49-B5-C3; | A49-B5-C4; | A49-B5-C5; | A49-B5-C6; |
| A49-B5-C7; | A49-B5-C8; | A49-B5-C9; | A50-B5-C1; | A50-B5-C2; | A50-B5-C3; |
| A50-B5-C4; | A50-B5-C5; | A50-B5-C6; | A50-B5-C7; | A50-B5-C8; | A50-B5-C9; |

| | | | | | |
|---|---|---|---|---|---|
| A51-B5-C1; | A51-B5-C2; | A51-B5-C3; | A51-B5-C4; | A51-B5-C5; | A51-B5-C6; |
| A51-B5-C7; | A51-B5-C8; | A51-B5-C9; | A52-B5-C1; | A52-B5-C2; | A52-B5-C3; |
| A52-B5-C4; | A52-B5-C5; | A52-B5-C6; | A52-B5-C7; | A52-B5-C8; | A52-B5-C9; |
| A53-B5-C1; | A53-B5-C2; | A53-B5-C3; | A53-B5-C4; | A53-B5-C5; | A53-B5-C6; |
| A53-B5-C7; | A53-B5-C8; | A53-B5-C9; | A54-B5-C1; | A54-B5-C2; | A54-B5-C3; |
| A54-B5-C4; | A54-B5-C5; | A54-B5-C6; | A54-B5-C7; | A54-B5-C8; | A54-B5-C9; |
| A55-B5-C1; | A55-B5-C2; | A55-B5-C3; | A55-B5-C4; | A55-B5-C5; | A55-B5-C6; |
| A55-B5-C7; | A55-B5-C8; | A55-B5-C9; | A56-B5-C1; | A56-B5-C2; | A56-B5-C3; |
| A56-B5-C4; | A56-B5-C5; | A56-B5-C6; | A56-B5-C7; | A56-B5-C8; | A56-B5-C9; |
| A57-B5-C1; | A57-B5-C2; | A57-B5-C3; | A57-B5-C4; | A57-B5-C5; | A57-B5-C6; |
| A57-B5-C7; | A57-B5-C8; | A57-B5-C9; | A58-B5-C1; | A58-B5-C2; | A58-B5-C3; |
| A58-B5-C4; | A58-B5-C5; | A58-B5-C6; | A58-B5-C7; | A58-B5-C8; | A58-B5-C9; |
| A59-B5-C1; | A59-B5-C2; | A59-B5-C3; | A59-B5-C4; | A59-B5-C5; | A59-B5-C6; |
| A59-B5-C7; | A59-B5-C8; | A59-B5-C9; | A60-B5-C1; | A60-B5-C2; | A60-B5-C3; |
| A60-B5-C4; | A60-B5-C5; | A60-B5-C6; | A60-B5-C7; | A60-B5-C8; | A60-B5-C9; |
| A61-B5-C1; | A61-B5-C2; | A61-B5-C3; | A61-B5-C4; | A61-B5-C5; | A61-B5-C6; |
| A61-B5-C7; | A61-B5-C8; | A61-B5-C9; | A62-B5-C1; | A62-B5-C2; | A62-B5-C3; |
| A62-B5-C4; | A62-B5-C5; | A62-B5-C6; | A62-B5-C7; | A62-B5-C8; | A62-B5-C9; |
| A63-B5-C1; | A63-B5-C2; | A63-B5-C3; | A63-B5-C4; | A63-B5-C5; | A63-B5-C6; |
| A63-B5-C7; | A63-B5-C8; | A63-B5-C9; | A64-B5-C1; | A64-B5-C2; | A64-B5-C3; |
| A64-B5-C4; | A64-B5-C5; | A64-B5-C6; | A64-B5-C7; | A64-B5-C8; | A64-B5-C9; |
| A65-B5-C1; | A65-B5-C2; | A65-B5-C3; | A65-B5-C4; | A65-B5-C5; | A65-B5-C6; |
| A65-B5-C7; | A65-B5-C8; | A65-B5-C9; | A66-B5-C1; | A66-B5-C2; | A66-B5-C3; |
| A66-B5-C4; | A66-B5-C5; | A66-B5-C6; | A66-B5-C7; | A66-B5-C8; | A66-B5-C9; |
| A67-B5-C1; | A67-B5-C2; | A67-B5-C3; | A67-B5-C4; | A67-B5-C5; | A67-B5-C6; |
| A67-B5-C7; | A67-B5-C8; | A67-B5-C9; | A68-B5-C1; | A68-B5-C2; | A68-B5-C3; |
| A68-B5-C4; | A68-B5-C5; | A68-B5-C6; | A68-B5-C7; | A68-B5-C8; | A68-B5-C9; |
| A69-B5-C1; | A69-B5-C2; | A69-B5-C3; | A69-B5-C4; | A69-B5-C5; | A69-B5-C6; |
| A69-B5-C7; | A69-B5-C8; | A69-B5-C9; | A70-B5-C1; | A70-B5-C2; | A70-B5-C3; |
| A70-B5-C4; | A70-B5-C5; | A70-B5-C6; | A70-B5-C7; | A70-B5-C8; | A70-B5-C9; |
| A71-B5-C1; | A71-B5-C2; | A71-B5-C3; | A71-B5-C4; | A71-B5-C5; | A71-B5-C6; |
| A71-B5-C7; | A71-B5-C8; | A71-B5-C9; | A1-B6-C1; | A1-B6-C2; | A1-B6-C3; |
| A1-B6-C4; | A1-B6-C5; | A1-B6-C6; | A1-B6-C7; | A1-B6-C8; | A1-B6-C9; |
| A2-B6-C1; | A2-B6-C2; | A2-B6-C3; | A2-B6-C4; | A2-B6-C5; | A2-B6-C6; |
| A2-B6-C7; | A2-B6-C8; | A2-B6-C9; | A3-B6-C1; | A3-B6-C2; | A3-B6-C3; |
| A3-B6-C4; | A3-B6-C5; | A3-B6-C6; | A3-B6-C7; | A3-B6-C8; | A3-B6-C9; |
| A4-B6-C1; | A4-B6-C2; | A4-B6-C3; | A4-B6-C4; | A4-B6-C5; | A4-B6-C6; |
| A4-B6-C7; | A4-B6-C8; | A4-B6-C9; | A5-B6-C1; | A5-B6-C2; | A5-B6-C3; |
| A5-B6-C4; | A5-B6-C5; | A5-B6-C6; | A5-B6-C7; | A5-B6-C8; | A5-B6-C9; |
| A6-B6-C1; | A6-B6-C2; | A6-B6-C3; | A6-B6-C4; | A6-B6-C5; | A6-B6-C6; |
| A6-B6-C7; | A6-B6-C8; | A6-B6-C9; | A7-B6-C1; | A7-B6-C2; | A7-B6-C3; |
| A7-B6-C4; | A7-B6-C5; | A7-B6-C6; | A7-B6-C7; | A7-B6-C8; | A7-B6-C9; |
| A8-B6-C1; | A8-B6-C2; | A8-B6-C3; | A8-B6-C4; | A8-B6-C5; | A8-B6-C6; |
| A8-B6-C7; | A8-B6-C8; | A8-B6-C9; | A9-B6-C1; | A9-B6-C2; | A9-B6-C3; |
| A9-B6-C4; | A9-B6-C5; | A9-B6-C6; | A9-B6-C7; | A9-B6-C8; | A9-B6-C9; |
| A10-B6-C1; | A10-B6-C2; | A10-B6-C3; | A10-B6-C4; | A10-B6-C5; | A10-B6-C6; |
| A10-B6-C7; | A10-B6-C8; | A10-B6-C9; | A11-B6-C1; | A11-B6-C2; | A11-B6-C3; |
| A11-B6-C4; | A11-B6-C5; | A11-B6-C6; | A11-B6-C7; | A11-B6-C8; | A11-B6-C9; |
| A12-B6-C1; | A12-B6-C2; | A12-B6-C3; | A12-B6-C4; | A12-B6-C5; | A12-B6-C6; |
| A12-B6-C7; | A12-B6-C8; | A12-B6-C9; | A13-B6-C1; | A13-B6-C2; | A13-B6-C3; |
| A13-B6-C4; | A13-B6-C5; | A13-B6-C6; | A13-B6-C7; | A13-B6-C8; | A13-B6-C9; |
| A14-B6-C1; | A14-B6-C2; | A14-B6-C3; | A14-B6-C4; | A14-B6-C5; | A14-B6-C6; |
| A14-B6-C7; | A14-B6-C8; | A14-B6-C9; | A15-B6-C1; | A15-B6-C2; | A15-B6-C3; |
| A15-B6-C4; | A15-B6-C5; | A15-B6-C6; | A15-B6-C7; | A15-B6-C8; | A15-B6-C9; |
| A16-B6-C1; | A16-B6-C2; | A16-B6-C3; | A16-B6-C4; | A16-B6-C5; | A16-B6-C6; |
| A16-B6-C7; | A16-B6-C8; | A16-B6-C9; | A17-B6-C1; | A17-B6-C2; | A17-B6-C3; |
| A17-B6-C4; | A17-B6-C5; | A17-B6-C6; | A17-B6-C7; | A17-B6-C8; | A17-B6-C9; |
| A18-B6-C1; | A18-B6-C2; | A18-B6-C3; | A18-B6-C4; | A18-B6-C5; | A18-B6-C6; |
| A18-B6-C7; | A18-B6-C8; | A18-B6-C9; | A19-B6-C1; | A19-B6-C2; | A19-B6-C3; |
| A19-B6-C4; | A19-B6-C5; | A19-B6-C6; | A19-B6-C7; | A19-B6-C8; | A19-B6-C9; |
| A20-B6-C1; | A20-B6-C2; | A20-B6-C3; | A20-B6-C4; | A20-B6-C5; | A20-B6-C6; |
| A20-B6-C7; | A20-B6-C8; | A20-B6-C9; | A21-B6-C1; | A21-B6-C2; | A21-B6-C3; |
| A21-B6-C4; | A21-B6-C5; | A21-B6-C6; | A21-B6-C7; | A21-B6-C8; | A21-B6-C9; |
| A22-B6-C1; | A22-B6-C2; | A22-B6-C3; | A22-B6-C4; | A22-B6-C5; | A22-B6-C6; |
| A22-B6-C7; | A22-B6-C8; | A22-B6-C9; | A23-B6-C1; | A23-B6-C2; | A23-B6-C3; |
| A23-B6-C4; | A23-B6-C5; | A23-B6-C6; | A23-B6-C7; | A23-B6-C8; | A23-B6-C9; |
| A24-B6-C1; | A24-B6-C2; | A24-B6-C3; | A24-B6-C4; | A24-B6-C5; | A24-B6-C6; |
| A24-B6-C7; | A24-B6-C8; | A24-B6-C9; | A25-B6-C1; | A25-B6-C2; | A25-B6-C3; |
| A25-B6-C4; | A25-B6-C5; | A25-B6-C6; | A25-B6-C7; | A25-B6-C8; | A25-B6-C9; |
| A26-B6-C1; | A26-B6-C2; | A26-B6-C3; | A26-B6-C4; | A26-B6-C5; | A26-B6-C6; |
| A26-B6-C7; | A26-B6-C8; | A26-B6-C9; | A27-B6-C1; | A27-B6-C2; | A27-B6-C3; |
| A27-B6-C4; | A27-B6-C5; | A27-B6-C6; | A27-B6-C7; | A27-B6-C8; | A27-B6-C9; |
| A28-B6-C1; | A28-B6-C2; | A28-B6-C3; | A28-B6-C4; | A28-B6-C5; | A28-B6-C6; |
| A28-B6-C7; | A28-B6-C8; | A28-B6-C9; | A29-B6-C1; | A29-B6-C2; | A29-B6-C3; |
| A29-B6-C4; | A29-B6-C5; | A29-B6-C6; | A29-B6-C7; | A29-B6-C8; | A29-B6-C9; |
| A30-B6-C1; | A30-B6-C2; | A30-B6-C3; | A30-B6-C4; | A30-B6-C5; | A30-B6-C6; |
| A30-B6-C7; | A30-B6-C8; | A30-B6-C9; | A31-B6-C1; | A31-B6-C2; | A31-B6-C3; |
| A31-B6-C4; | A31-B6-C5; | A31-B6-C6; | A31-B6-C7; | A31-B6-C8; | A31-B6-C9; |
| A32-B6-C1; | A32-B6-C2; | A32-B6-C3; | A32-B6-C4; | A32-B6-C5; | A32-B6-C6; |

-continued

| | | | | | |
|---|---|---|---|---|---|
| A32-B6-C7; | A32-B6-C8; | A32-B6-C9; | A33-B6-C1; | A33-B6-C2; | A33-B6-C3; |
| A33-B6-C4; | A33-B6-C5; | A33-B6-C6; | A33-B6-C7; | A33-B6-C8; | A33-B6-C9; |
| A34-B6-C1; | A34-B6-C2; | A34-B6-C3; | A34-B6-C4; | A34-B6-C5; | A34-B6-C6; |
| A34-B6-C7; | A34-B6-C8; | A34-B6-C9; | A35-B6-C1; | A35-B6-C2; | A35-B6-C3; |
| A35-B6-C4; | A35-B6-C5; | A35-B6-C6; | A35-B6-C7; | A35-B6-C8; | A35-B6-C9; |
| A36-B6-C1; | A36-B6-C2; | A36-B6-C3; | A36-B6-C4; | A36-B6-C5; | A36-B6-C6; |
| A36-B6-C7; | A36-B6-C8; | A36-B6-C9; | A37-B6-C1; | A37-B6-C2; | A37-B6-C3; |
| A37-B6-C4; | A37-B6-C5; | A37-B6-C6; | A37-B6-C7; | A37-B6-C8; | A37-B6-C9; |
| A38-B6-C1; | A38-B6-C2; | A38-B6-C3; | A38-B6-C4; | A38-B6-C5; | A38-B6-C6; |
| A38-B6-C7; | A38-B6-C8; | A38-B6-C9; | A39-B6-C1; | A39-B6-C2; | A39-B6-C3; |
| A39-B6-C4; | A39-B6-C5; | A39-B6-C6; | A39-B6-C7; | A39-B6-C8; | A39-B6-C9; |
| A40-B6-C1; | A40-B6-C2; | A40-B6-C3; | A40-B6-C4; | A40-B6-C5; | A40-B6-C6; |
| A40-B6-C7; | A40-B6-C8; | A40-B6-C9; | A41-B6-C1; | A41-B6-C2; | A41-B6-C3; |
| A41-B6-C4; | A41-B6-C5; | A41-B6-C6; | A41-B6-C7; | A41-B6-C8; | A41-B6-C9; |
| A42-B6-C1; | A42-B6-C2; | A42-B6-C3; | A42-B6-C4; | A42-B6-C5; | A42-B6-C6; |
| A42-B6-C7; | A42-B6-C8; | A42-B6-C9; | A43-B6-C1; | A43-B6-C2; | A43-B6-C3; |
| A43-B6-C4; | A43-B6-C5; | A43-B6-C6; | A43-B6-C7; | A43-B6-C8; | A43-B6-C9; |
| A44-B6-C1; | A44-B6-C2; | A44-B6-C3; | A44-B6-C4; | A44-B6-C5; | A44-B6-C6; |
| A44-B6-C7; | A44-B6-C8; | A44-B6-C9; | A45-B6-C1; | A45-B6-C2; | A45-B6-C3; |
| A45-B6-C4; | A45-B6-C5; | A45-B6-C6; | A45-B6-C7; | A45-B6-C8; | A45-B6-C9; |
| A46-B6-C1; | A46-B6-C2; | A46-B6-C3; | A46-B6-C4; | A46-B6-C5; | A46-B6-C6; |
| A46-B6-C7; | A46-B6-C8; | A46-B6-C9; | A47-B6-C1; | A47-B6-C2; | A47-B6-C3; |
| A47-B6-C4; | A47-B6-C5; | A47-B6-C6; | A47-B6-C7; | A47-B6-C8; | A47-B6-C9; |
| A48-B6-C1; | A48-B6-C2; | A48-B6-C3; | A48-B6-C4; | A48-B6-C5; | A48-B6-C6; |
| A48-B6-C7; | A48-B6-C8; | A48-B6-C9; | A49-B6-C1; | A49-B6-C2; | A49-B6-C3; |
| A49-B6-C4; | A49-B6-C5; | A49-B6-C6; | A49-B6-C7; | A49-B6-C8; | A49-B6-C9; |
| A50-B6-C1; | A50-B6-C2; | A50-B6-C3; | A50-B6-C4; | A50-B6-C5; | A50-B6-C6; |
| A50-B6-C7; | A50-B6-C8; | A50-B6-C9; | A51-B6-C1; | A51-B6-C2; | A51-B6-C3; |
| A51-B6-C4; | A51-B6-C5; | A51-B6-C6; | A51-B6-C7; | A51-B6-C8; | A51-B6-C9; |
| A52-B6-C1; | A52-B6-C2; | A52-B6-C3; | A52-B6-C4; | A52-B6-C5; | A52-B6-C6; |
| A52-B6-C7; | A52-B6-C8; | A52-B6-C9; | A53-B6-C1; | A53-B6-C2; | A53-B6-C3; |
| A53-B6-C4; | A53-B6-C5; | A53-B6-C6; | A53-B6-C7; | A53-B6-C8; | A53-B6-C9; |
| A54-B6-C1; | A54-B6-C2; | A54-B6-C3; | A54-B6-C4; | A54-B6-C5; | A54-B6-C6; |
| A54-B6-C7; | A54-B6-C8; | A54-B6-C9; | A55-B6-C1; | A55-B6-C2; | A55-B6-C3; |
| A55-B6-C4; | A55-B6-C5; | A55-B6-C6; | A55-B6-C7; | A55-B6-C8; | A55-B6-C9; |
| A56-B6-C1; | A56-B6-C2; | A56-B6-C3; | A56-B6-C4; | A56-B6-C5; | A56-B6-C6; |
| A56-B6-C7; | A56-B6-C8; | A56-B6-C9; | A57-B6-C1; | A57-B6-C2; | A57-B6-C3; |
| A57-B6-C4; | A57-B6-C5; | A57-B6-C6; | A57-B6-C7; | A57-B6-C8; | A57-B6-C9; |
| A58-B6-C1; | A58-B6-C2; | A58-B6-C3; | A58-B6-C4; | A58-B6-C5; | A58-B6-C6; |
| A58-B6-C7; | A58-B6-C8; | A58-B6-C9; | A59-B6-C1; | A59-B6-C2; | A59-B6-C3; |
| A59-B6-C4; | A59-B6-C5; | A59-B6-C6; | A59-B6-C7; | A59-B6-C8; | A59-B6-C9; |
| A60-B6-C1; | A60-B6-C2; | A60-B6-C3; | A60-B6-C4; | A60-B6-C5; | A60-B6-C6; |
| A60-B6-C7; | A60-B6-C8; | A60-B6-C9; | A61-B6-C1; | A61-B6-C2; | A61-B6-C3; |
| A61-B6-C4; | A61-B6-C5; | A61-B6-C6; | A61-B6-C7; | A61-B6-C8; | A61-B6-C9; |
| A62-B6-C1; | A62-B6-C2; | A62-B6-C3; | A62-B6-C4; | A62-B6-C5; | A62-B6-C6; |
| A62-B6-C7; | A62-B6-C8; | A62-B6-C9; | A63-B6-C1; | A63-B6-C2; | A63-B6-C3; |
| A63-B6-C4; | A63-B6-C5; | A63-B6-C6; | A63-B6-C7; | A63-B6-C8; | A63-B6-C9; |
| A64-B6-C1; | A64-B6-C2; | A64-B6-C3; | A64-B6-C4; | A64-B6-C5; | A64-B6-C6; |
| A64-B6-C7; | A64-B6-C8; | A64-B6-C9; | A65-B6-C1; | A65-B6-C2; | A65-B6-C3; |
| A65-B6-C4; | A65-B6-C5; | A65-B6-C6; | A65-B6-C7; | A65-B6-C8; | A65-B6-C9; |
| A66-B6-C1; | A66-B6-C2; | A66-B6-C3; | A66-B6-C4; | A66-B6-C5; | A66-B6-C6; |
| A66-B6-C7; | A66-B6-C8; | A66-B6-C9; | A67-B6-C1; | A67-B6-C2; | A67-B6-C3; |
| A67-B6-C4; | A67-B6-C5; | A67-B6-C6; | A67-B6-C7; | A67-B6-C8; | A67-B6-C9; |
| A68-B6-C1; | A68-B6-C2; | A68-B6-C3; | A68-B6-C4; | A68-B6-C5; | A68-B6-C6; |
| A68-B6-C7; | A68-B6-C8; | A68-B6-C9; | A69-B6-C1; | A69-B6-C2; | A69-B6-C3; |
| A69-B6-C4; | A69-B6-C5; | A69-B6-C6; | A69-B6-C7; | A69-B6-C8; | A69-B6-C9; |
| A70-B6-C1; | A70-B6-C2; | A70-B6-C3; | A70-B6-C4; | A70-B6-C5; | A70-B6-C6; |
| A70-B6-C7; | A70-B6-C8; | A70-B6-C9; | A71-B6-C1; | A71-B6-C2; | A71-B6-C3; |
| A71-B6-C4; | A71-B6-C5; | A71-B6-C6; | A71-B6-C7; | A71-B6-C8; | A71-B6-C9; |
| A1-B7-C1; | A1-B7-C2; | A1-B7-C3; | A1-B7-C4; | A1-B7-C5; | A1-B7-C6; |
| A1-B7-C7; | A1-B7-C8; | A1-B7-C9; | A2-B7-C1; | A2-B7-C2; | A2-B7-C3; |
| A2-B7-C4; | A2-B7-C5; | A2-B7-C6; | A2-B7-C7; | A2-B7-C8; | A2-B7-C9; |
| A3-B7-C1; | A3-B7-C2; | A3-B7-C3; | A3-B7-C4; | A3-B7-C5; | A3-B7-C6; |
| A3-B7-C7; | A3-B7-C8; | A3-B7-C9; | A4-B7-C1; | A4-B7-C2; | A4-B7-C3; |
| A4-B7-C4; | A4-B7-C5; | A4-B7-C6; | A4-B7-C7; | A4-B7-C8; | A4-B7-C9; |
| A5-B7-C1; | A5-B7-C2; | A5-B7-C3; | A5-B7-C4; | A5-B7-C5; | A5-B7-C6; |
| A5-B7-C7; | A5-B7-C8; | A5-B7-C9; | A6-B7-C1; | A6-B7-C2; | A6-B7-C3; |
| A6-B7-C4; | A6-B7-C5; | A6-B7-C6; | A6-B7-C7; | A6-B7-C8; | A6-B7-C9; |
| A7-B7-C1; | A7-B7-C2; | A7-B7-C3; | A7-B7-C4; | A7-B7-C5; | A7-B7-C6; |
| A7-B7-C7; | A7-B7-C8; | A7-B7-C9; | A8-B7-C1; | A8-B7-C2; | A8-B7-C3; |
| A8-B7-C4; | A8-B7-C5; | A8-B7-C6; | A8-B7-C7; | A8-B7-C8; | A8-B7-C9; |
| A9-B7-C1; | A9-B7-C2; | A9-B7-C3; | A9-B7-C4; | A9-B7-C5; | A9-B7-C6; |
| A9-B7-C7; | A9-B7-C8; | A9-B7-C9; | A10-B7-C1; | A10-B7-C2; | A10-B7-C3; |
| A10-B7-C4; | A10-B7-C5; | A10-B7-C6; | A10-B7-C7; | A10-B7-C8; | A10-B7-C9; |
| A11-B7-C1; | A11-B7-C2; | A11-B7-C3; | A11-B7-C4; | A11-B7-C5; | A11-B7-C6; |
| A11-B7-C7; | A11-B7-C8; | A11-B7-C9; | A12-B7-C1; | A12-B7-C2; | A12-B7-C3; |
| A12-B7-C4; | A12-B7-C5; | A12-B7-C6; | A12-B7-C7; | A12-B7-C8; | A12-B7-C9; |
| A13-B7-C1; | A13-B7-C2; | A13-B7-C3; | A13-B7-C4; | A13-B7-C5; | A13-B7-C6; |
| A13-B7-C7; | A13-B7-C8; | A13-B7-C9; | A14-B7-C1; | A14-B7-C2; | A14-B7-C3; |

-continued

| | | | | | |
|---|---|---|---|---|---|
| A14-B7-C4; | A14-B7-C5; | A14-B7-C6; | A14-B7-C7; | A14-B7-C8; | A14-B7-C9; |
| A15-B7-C1; | A15-B7-C2; | A15-B7-C3; | A15-B7-C4; | A15-B7-C5; | A15-B7-C6; |
| A15-B7-C7; | A15-B7-C8; | A15-B7-C9; | A16-B7-C1; | A16-B7-C2; | A16-B7-C3; |
| A16-B7-C4; | A16-B7-C5; | A16-B7-C6; | A16-B7-C7; | A16-B7-C8; | A16-B7-C9; |
| A17-B7-C1; | A17-B7-C2; | A17-B7-C3; | A17-B7-C4; | A17-B7-C5; | A17-B7-C6; |
| A17-B7-C7; | A17-B7-C8; | A17-B7-C9; | A18-B7-C1; | A18-B7-C2; | A18-B7-C3; |
| A18-B7-C4; | A18-B7-C5; | A18-B7-C6; | A18-B7-C7; | A18-B7-C8; | A18-B7-C9; |
| A19-B7-C1; | A19-B7-C2; | A19-B7-C3; | A19-B7-C4; | A19-B7-C5; | A19-B7-C6; |
| A19-B7-C7; | A19-B7-C8; | A19-B7-C9; | A20-B7-C1; | A20-B7-C2; | A20-B7-C3; |
| A20-B7-C4; | A20-B7-C5; | A20-B7-C6; | A20-B7-C7; | A20-B7-C8; | A20-B7-C9; |
| A21-B7-C1; | A21-B7-C2; | A21-B7-C3; | A21-B7-C4; | A21-B7-C5; | A21-B7-C6; |
| A21-B7-C7; | A21-B7-C8; | A21-B7-C9; | A22-B7-C1; | A22-B7-C2; | A22-B7-C3; |
| A22-B7-C4; | A22-B7-C5; | A22-B7-C6; | A22-B7-C7; | A22-B7-C8; | A22-B7-C9; |
| A23-B7-C1; | A23-B7-C2; | A23-B7-C3; | A23-B7-C4; | A23-B7-C5; | A23-B7-C6; |
| A23-B7-C7; | A23-B7-C8; | A23-B7-C9; | A24-B7-C1; | A24-B7-C2; | A24-B7-C3; |
| A24-B7-C4; | A24-B7-C5; | A24-B7-C6; | A24-B7-C7; | A24-B7-C8; | A24-B7-C9; |
| A25-B7-C1; | A25-B7-C2; | A25-B7-C3; | A25-B7-C4; | A25-B7-C5; | A25-B7-C6; |
| A25-B7-C7; | A25-B7-C8; | A25-B7-C9; | A26-B7-C1; | A26-B7-C2; | A26-B7-C3; |
| A26-B7-C4; | A26-B7-C5; | A26-B7-C6; | A26-B7-C7; | A26-B7-C8; | A26-B7-C9; |
| A27-B7-C1; | A27-B7-C2; | A27-B7-C3; | A27-B7-C4; | A27-B7-C5; | A27-B7-C6; |
| A27-B7-C7; | A27-B7-C8; | A27-B7-C9; | A28-B7-C1; | A28-B7-C2; | A28-B7-C3; |
| A28-B7-C4; | A28-B7-C5; | A28-B7-C6; | A28-B7-C7; | A28-B7-C8; | A28-B7-C9; |
| A29-B7-C1; | A29-B7-C2; | A29-B7-C3; | A29-B7-C4; | A29-B7-C5; | A29-B7-C6; |
| A29-B7-C7; | A29-B7-C8; | A29-B7-C9; | A30-B7-C1; | A30-B7-C2; | A30-B7-C3; |
| A30-B7-C4; | A30-B7-C5; | A30-B7-C6; | A30-B7-C7; | A30-B7-C8; | A30-B7-C9; |
| A31-B7-C1; | A31-B7-C2; | A31-B7-C3; | A31-B7-C4; | A31-B7-C5; | A31-B7-C6; |
| A31-B7-C7; | A31-B7-C8; | A31-B7-C9; | A32-B7-C1; | A32-B7-C2; | A32-B7-C3; |
| A32-B7-C4; | A32-B7-C5; | A32-B7-C6; | A32-B7-C7; | A32-B7-C8; | A32-B7-C9; |
| A33-B7-C1; | A33-B7-C2; | A33-B7-C3; | A33-B7-C4; | A33-B7-C5; | A33-B7-C6; |
| A33-B7-C7; | A33-B7-C8; | A33-B7-C9; | A34-B7-C1; | A34-B7-C2; | A34-B7-C3; |
| A34-B7-C4; | A34-B7-C5; | A34-B7-C6; | A34-B7-C7; | A34-B7-C8; | A34-B7-C9; |
| A35-B7-C1; | A35-B7-C2; | A35-B7-C3; | A35-B7-C4; | A35-B7-C5; | A35-B7-C6; |
| A35-B7-C7; | A35-B7-C8; | A35-B7-C9; | A36-B7-C1; | A36-B7-C2; | A36-B7-C3; |
| A36-B7-C4; | A36-B7-C5; | A36-B7-C6; | A36-B7-C7; | A36-B7-C8; | A36-B7-C9; |
| A37-B7-C1; | A37-B7-C2; | A37-B7-C3; | A37-B7-C4; | A37-B7-C5; | A37-B7-C6; |
| A37-B7-C7; | A37-B7-C8; | A37-B7-C9; | A38-B7-C1; | A38-B7-C2; | A38-B7-C3; |
| A38-B7-C4; | A38-B7-C5; | A38-B7-C6; | A38-B7-C7; | A38-B7-C8; | A38-B7-C9; |
| A39-B7-C1; | A39-B7-C2; | A39-B7-C3; | A39-B7-C4; | A39-B7-C5; | A39-B7-C6; |
| A39-B7-C7; | A39-B7-C8; | A39-B7-C9; | A40-B7-C1; | A40-B7-C2; | A40-B7-C3; |
| A40-B7-C4; | A40-B7-C5; | A40-B7-C6; | A40-B7-C7; | A40-B7-C8; | A40-B7-C9; |
| A41-B7-C1; | A41-B7-C2; | A41-B7-C3; | A41-B7-C4; | A41-B7-C5; | A41-B7-C6; |
| A41-B7-C7; | A41-B7-C8; | A41-B7-C9; | A42-B7-C1; | A42-B7-C2; | A42-B7-C3; |
| A42-B7-C4; | A42-B7-C5; | A42-B7-C6; | A42-B7-C7; | A42-B7-C8; | A42-B7-C9; |
| A43-B7-C1; | A43-B7-C2; | A43-B7-C3; | A43-B7-C4; | A43-B7-C5; | A43-B7-C6; |
| A43-B7-C7; | A43-B7-C8; | A43-B7-C9; | A44-B7-C1; | A44-B7-C2; | A44-B7-C3; |
| A44-B7-C4; | A44-B7-C5; | A44-B7-C6; | A44-B7-C7; | A44-B7-C8; | A44-B7-C9; |
| A45-B7-C1; | A45-B7-C2; | A45-B7-C3; | A45-B7-C4; | A45-B7-C5; | A45-B7-C6; |
| A45-B7-C7; | A45-B7-C8; | A45-B7-C9; | A46-B7-C1; | A46-B7-C2; | A46-B7-C3; |
| A46-B7-C4; | A46-B7-C5; | A46-B7-C6; | A46-B7-C7; | A46-B7-C8; | A46-B7-C9; |
| A47-B7-C1; | A47-B7-C2; | A47-B7-C3; | A47-B7-C4; | A47-B7-C5; | A47-B7-C6; |
| A47-B7-C7; | A47-B7-C8; | A47-B7-C9; | A48-B7-C1; | A48-B7-C2; | A48-B7-C3; |
| A48-B7-C4; | A48-B7-C5; | A48-B7-C6; | A48-B7-C7; | A48-B7-C8; | A48-B7-C9; |
| A49-B7-C1; | A49-B7-C2; | A49-B7-C3; | A49-B7-C4; | A49-B7-C5; | A49-B7-C6; |
| A49-B7-C7; | A49-B7-C8; | A49-B7-C9; | A50-B7-C1; | A50-B7-C2; | A50-B7-C3; |
| A50-B7-C4; | A50-B7-C5; | A50-B7-C6; | A50-B7-C7; | A50-B7-C8; | A50-B7-C9; |
| A51-B7-C1; | A51-B7-C2; | A51-B7-C3; | A51-B7-C4; | A51-B7-C5; | A51-B7-C6; |
| A51-B7-C7; | A51-B7-C8; | A51-B7-C9; | A52-B7-C1; | A52-B7-C2; | A52-B7-C3; |
| A52-B7-C4; | A52-B7-C5; | A52-B7-C6; | A52-B7-C7; | A52-B7-C8; | A52-B7-C9; |
| A53-B7-C1; | A53-B7-C2; | A53-B7-C3; | A53-B7-C4; | A53-B7-C5; | A53-B7-C6; |
| A53-B7-C7; | A53-B7-C8; | A53-B7-C9; | A54-B7-C1; | A54-B7-C2; | A54-B7-C3; |
| A54-B7-C4; | A54-B7-C5; | A54-B7-C6; | A54-B7-C7; | A54-B7-C8; | A54-B7-C9; |
| A55-B7-C1; | A55-B7-C2; | A55-B7-C3; | A55-B7-C4; | A55-B7-C5; | A55-B7-C6; |
| A55-B7-C7; | A55-B7-C8; | A55-B7-C9; | A56-B7-C1; | A56-B7-C2; | A56-B7-C3; |
| A56-B7-C4; | A56-B7-C5; | A56-B7-C6; | A56-B7-C7; | A56-B7-C8; | A56-B7-C9; |
| A57-B7-C1; | A57-B7-C2; | A57-B7-C3; | A57-B7-C4; | A57-B7-C5; | A57-B7-C6; |
| A57-B7-C7; | A57-B7-C8; | A57-B7-C9; | A58-B7-C1; | A58-B7-C2; | A58-B7-C3; |
| A58-B7-C4; | A58-B7-C5; | A58-B7-C6; | A58-B7-C7; | A58-B7-C8; | A58-B7-C9; |
| A59-B7-C1; | A59-B7-C2; | A59-B7-C3; | A59-B7-C4; | A59-B7-C5; | A59-B7-C6; |
| A59-B7-C7; | A59-B7-C8; | A59-B7-C9; | A60-B7-C1; | A60-B7-C2; | A60-B7-C3; |
| A60-B7-C4; | A60-B7-C5; | A60-B7-C6; | A60-B7-C7; | A60-B7-C8; | A60-B7-C9; |
| A61-B7-C1; | A61-B7-C2; | A61-B7-C3; | A61-B7-C4; | A61-B7-C5; | A61-B7-C6; |
| A61-B7-C7; | A61-B7-C8; | A61-B7-C9; | A62-B7-C1; | A62-B7-C2; | A62-B7-C3; |
| A62-B7-C4; | A62-B7-C5; | A62-B7-C6; | A62-B7-C7; | A62-B7-C8; | A62-B7-C9; |
| A63-B7-C1; | A63-B7-C2; | A63-B7-C3; | A63-B7-C4; | A63-B7-C5; | A63-B7-C6; |
| A63-B7-C7; | A63-B7-C8; | A63-B7-C9; | A64-B7-C1; | A64-B7-C2; | A64-B7-C3; |
| A64-B7-C4; | A64-B7-C5; | A64-B7-C6; | A64-B7-C7; | A64-B7-C8; | A64-B7-C9; |
| A65-B7-C1; | A65-B7-C2; | A65-B7-C3; | A65-B7-C4; | A65-B7-C5; | A65-B7-C6; |
| A65-B7-C7; | A65-B7-C8; | A65-B7-C9; | A66-B7-C1; | A66-B7-C2; | A66-B7-C3; |
| A66-B7-C4; | A66-B7-C5; | A66-B7-C6; | A66-B7-C7; | A66-B7-C8; | A66-B7-C9; |

| | | | | | |
|---|---|---|---|---|---|
| A67-B7-C1; | A67-B7-C2; | A67-B7-C3; | A67-B7-C4; | A67-B7-C5; | A67-B7-C6; |
| A67-B7-C7; | A67-B7-C8; | A67-B7-C9; | A68-B7-C1; | A68-B7-C2; | A68-B7-C3; |
| A68-B7-C4; | A68-B7-C5; | A68-B7-C6; | A68-B7-C7; | A68-B7-C8; | A68-B7-C9; |
| A69-B7-C1; | A69-B7-C2; | A69-B7-C3; | A69-B7-C4; | A69-B7-C5; | A69-B7-C6; |
| A69-B7-C7; | A69-B7-C8; | A69-B7-C9; | A70-B7-C1; | A70-B7-C2; | A70-B7-C3; |
| A70-B7-C4; | A70-B7-C5; | A70-B7-C6; | A70-B7-C7; | A70-B7-C8; | A70-B7-C9; |
| A71-B7-C1; | A71-B7-C2; | A71-B7-C3; | A71-B7-C4; | A71-B7-C5; | A71-B7-C6; |
| A71-B7-C7; | A71-B7-C8; | A71-B7-C9; | A1-B8-C1; | A1-B8-C2; | A1-B8-C3; |
| A1-B8-C4; | A1-B8-C5; | A1-B8-C6; | A1-B8-C7; | A1-B8-C8; | A1-B8-C9; |
| A2-B8-C1; | A2-B8-C2; | A2-B8-C3; | A2-B8-C4; | A2-B8-C5; | A2-B8-C6; |
| A2-B8-C7; | A2-B8-C8; | A2-B8-C9; | A3-B8-C1; | A3-B8-C2; | A3-B8-C3; |
| A3-B8-C4; | A3-B8-C5; | A3-B8-C6; | A3-B8-C7; | A3-B8-C8; | A3-B8-C9; |
| A4-B8-C1; | A4-B8-C2; | A4-B8-C3; | A4-B8-C4; | A4-B8-C5; | A4-B8-C6; |
| A4-B8-C7; | A4-B8-C8; | A4-B8-C9; | A5-B8-C1; | A5-B8-C2; | A5-B8-C3; |
| A5-B8-C4; | A5-B8-C5; | A5-B8-C6; | A5-B8-C7; | A5-B8-C8; | A5-B8-C9; |
| A6-B8-C1; | A6-B8-C2; | A6-B8-C3; | A6-B8-C4; | A6-B8-C5; | A6-B8-C6; |
| A6-B8-C7; | A6-B8-C8; | A6-B8-C9; | A7-B8-C1; | A7-B8-C2; | A7-B8-C3; |
| A7-B8-C4; | A7-B8-C5; | A7-B8-C6; | A7-B8-C7; | A7-B8-C8; | A7-B8-C9; |
| A8-B8-C1; | A8-B8-C2; | A8-B8-C3; | A8-B8-C4; | A8-B8-C5; | A8-B8-C6; |
| A8-B8-C7; | A8-B8-C8; | A8-B8-C9; | A9-B8-C1; | A9-B8-C2; | A9-B8-C3; |
| A9-B8-C4; | A9-B8-C5; | A9-B8-C6; | A9-B8-C7; | A9-B8-C8; | A9-B8-C9; |
| A10-B8-C1; | A10-B8-C2; | A10-B8-C3; | A10-B8-C4; | A10-B8-C5; | A10-B8-C6; |
| A10-B8-C7; | A10-B8-C8; | A10-B8-C9; | A11-B8-C1; | A11-B8-C2; | A11-B8-C3; |
| A11-B8-C4; | A11-B8-C5; | A11-B8-C6; | A11-B8-C7; | A11-B8-C8; | A11-B8-C9; |
| A12-B8-C1; | A12-B8-C2; | A12-B8-C3; | A12-B8-C4; | A12-B8-C5; | A12-B8-C6; |
| A12-B8-C7; | A12-B8-C8; | A12-B8-C9; | A13-B8-C1; | A13-B8-C2; | A13-B8-C3; |
| A13-B8-C4; | A13-B8-C5; | A13-B8-C6; | A13-B8-C7; | A13-B8-C8; | A13-B8-C9; |
| A14-B8-C1; | A14-B8-C2; | A14-B8-C3; | A14-B8-C4; | A14-B8-C5; | A14-B8-C6; |
| A14-B8-C7; | A14-B8-C8; | A14-B8-C9; | A15-B8-C1; | A15-B8-C2; | A15-B8-C3; |
| A15-B8-C4; | A15-B8-C5; | A15-B8-C6; | A15-B8-C7; | A15-B8-C8; | A15-B8-C9; |
| A16-B8-C1; | A16-B8-C2; | A16-B8-C3; | A16-B8-C4; | A16-B8-C5; | A16-B8-C6; |
| A16-B8-C7; | A16-B8-C8; | A16-B8-C9; | A17-B8-C1; | A17-B8-C2; | A17-B8-C3; |
| A17-B8-C4; | A17-B8-C5; | A17-B8-C6; | A17-B8-C7; | A17-B8-C8; | A17-B8-C9; |
| A18-B8-C1; | A18-B8-C2; | A18-B8-C3; | A18-B8-C4; | A18-B8-C5; | A18-B8-C6; |
| A18-B8-C7; | A18-B8-C8; | A18-B8-C9; | A19-B8-C1; | A19-B8-C2; | A19-B8-C3; |
| A19-B8-C4; | A19-B8-C5; | A19-B8-C6; | A19-B8-C7; | A19-B8-C8; | A19-B8-C9; |
| A20-B8-C1; | A20-B8-C2; | A20-B8-C3; | A20-B8-C4; | A20-B8-C5; | A20-B8-C6; |
| A20-B8-C7; | A20-B8-C8; | A20-B8-C9; | A21-B8-C1; | A21-B8-C2; | A21-B8-C3; |
| A21-B8-C4; | A21-B8-C5; | A21-B8-C6; | A21-B8-C7; | A21-B8-C8; | A21-B8-C9; |
| A22-B8-C1; | A22-B8-C2; | A22-B8-C3; | A22-B8-C4; | A22-B8-C5; | A22-B8-C6; |
| A22-B8-C7; | A22-B8-C8; | A22-B8-C9; | A23-B8-C1; | A23-B8-C2; | A23-B8-C3; |
| A23-B8-C4; | A23-B8-C5; | A23-B8-C6; | A23-B8-C7; | A23-B8-C8; | A23-B8-C9; |
| A24-B8-C1; | A24-B8-C2; | A24-B8-C3; | A24-B8-C4; | A24-B8-C5; | A24-B8-C6; |
| A24-B8-C7; | A24-B8-C8; | A24-B8-C9; | A25-B8-C1; | A25-B8-C2; | A25-B8-C3; |
| A25-B8-C4; | A25-B8-C5; | A25-B8-C6; | A25-B8-C7; | A25-B8-C8; | A25-B8-C9; |
| A26-B8-C1; | A26-B8-C2; | A26-B8-C3; | A26-B8-C4; | A26-B8-C5; | A26-B8-C6; |
| A26-B8-C7; | A26-B8-C8; | A26-B8-C9; | A27-B8-C1; | A27-B8-C2; | A27-B8-C3; |
| A27-B8-C4; | A27-B8-C5; | A27-B8-C6; | A27-B8-C7; | A27-B8-C8; | A27-B8-C9; |
| A28-B8-C1; | A28-B8-C2; | A28-B8-C3; | A28-B8-C4; | A28-B8-C5; | A28-B8-C6; |
| A28-B8-C7; | A28-B8-C8; | A28-B8-C9; | A29-B8-C1; | A29-B8-C2; | A29-B8-C3; |
| A29-B8-C4; | A29-B8-C5; | A29-B8-C6; | A29-B8-C7; | A29-B8-C8; | A29-B8-C9; |
| A30-B8-C1; | A30-B8-C2; | A30-B8-C3; | A30-B8-C4; | A30-B8-C5; | A30-B8-C6; |
| A30-B8-C7; | A30-B8-C8; | A30-B8-C9; | A31-B8-C1; | A31-B8-C2; | A31-B8-C3; |
| A31-B8-C4; | A31-B8-C5; | A31-B8-C6; | A31-B8-C7; | A31-B8-C8; | A31-B8-C9; |
| A32-B8-C1; | A32-B8-C2; | A32-B8-C3; | A32-B8-C4; | A32-B8-C5; | A32-B8-C6; |
| A32-B8-C7; | A32-B8-C8; | A32-B8-C9; | A33-B8-C1; | A33-B8-C2; | A33-B8-C3; |
| A33-B8-C4; | A33-B8-C5; | A33-B8-C6; | A33-B8-C7; | A33-B8-C8; | A33-B8-C9; |
| A34-B8-C1; | A34-B8-C2; | A34-B8-C3; | A34-B8-C4; | A34-B8-C5; | A34-B8-C6; |
| A34-B8-C7; | A34-B8-C8; | A34-B8-C9; | A35-B8-C1; | A35-B8-C2; | A35-B8-C3; |
| A35-B8-C4; | A35-B8-C5; | A35-B8-C6; | A35-B8-C7; | A35-B8-C8; | A35-B8-C9; |
| A36-B8-C1; | A36-B8-C2; | A36-B8-C3; | A36-B8-C4; | A36-B8-C5; | A36-B8-C6; |
| A36-B8-C7; | A36-B8-C8; | A36-B8-C9; | A37-B8-C1; | A37-B8-C2; | A37-B8-C3; |
| A37-B8-C4; | A37-B8-C5; | A37-B8-C6; | A37-B8-C7; | A37-B8-C8; | A37-B8-C9; |
| A38-B8-C1; | A38-B8-C2; | A38-B8-C3; | A38-B8-C4; | A38-B8-C5; | A38-B8-C6; |
| A38-B8-C7; | A38-B8-C8; | A38-B8-C9; | A39-B8-C1; | A39-B8-C2; | A39-B8-C3; |
| A39-B8-C4; | A39-B8-C5; | A39-B8-C6; | A39-B8-C7; | A39-B8-C8; | A39-B8-C9; |
| A40-B8-C1; | A40-B8-C2; | A40-B8-C3; | A40-B8-C4; | A40-B8-C5; | A40-B8-C6; |
| A40-B8-C7; | A40-B8-C8; | A40-B8-C9; | A41-B8-C1; | A41-B8-C2; | A41-B8-C3; |
| A41-B8-C4; | A41-B8-C5; | A41-B8-C6; | A41-B8-C7; | A41-B8-C8; | A41-B8-C9; |
| A42-B8-C1; | A42-B8-C2; | A42-B8-C3; | A42-B8-C4; | A42-B8-C5; | A42-B8-C6; |
| A42-B8-C7; | A42-B8-C8; | A42-B8-C9; | A43-B8-C1; | A43-B8-C2; | A43-B8-C3; |
| A43-B8-C4; | A43-B8-C5; | A43-B8-C6; | A43-B8-C7; | A43-B8-C8; | A43-B8-C9; |
| A44-B8-C1; | A44-B8-C2; | A44-B8-C3; | A44-B8-C4; | A44-B8-C5; | A44-B8-C6; |
| A44-B8-C7; | A44-B8-C8; | A44-B8-C9; | A45-B8-C1; | A45-B8-C2; | A45-B8-C3; |
| A45-B8-C4; | A45-B8-C5; | A45-B8-C6; | A45-B8-C7; | A45-B8-C8; | A45-B8-C9; |
| A46-B8-C1; | A46-B8-C2; | A46-B8-C3; | A46-B8-C4; | A46-B8-C5; | A46-B8-C6; |
| A46-B8-C7; | A46-B8-C8; | A46-B8-C9; | A47-B8-C1; | A47-B8-C2; | A47-B8-C3; |
| A47-B8-C4; | A47-B8-C5; | A47-B8-C6; | A47-B8-C7; | A47-B8-C8; | A47-B8-C9; |
| A48-B8-C1; | A48-B8-C2; | A48-B8-C3; | A48-B8-C4; | A48-B8-C5; | A48-B8-C6; |

| | | | | | |
|---|---|---|---|---|---|
| A48-B8-C7; | A48-B8-C8; | A48-B8-C9; | A49-B8-C1; | A49-B8-C2; | A49-B8-C3; |
| A49-B8-C4; | A49-B8-C5; | A49-B8-C6; | A49-B8-C7; | A49-B8-C8; | A49-B8-C9; |
| A50-B8-C1; | A50-B8-C2; | A50-B8-C3; | A50-B8-C4; | A50-B8-C5; | A50-B8-C6; |
| A50-B8-C7; | A50-B8-C8; | A50-B8-C9; | A51-B8-C1; | A51-B8-C2; | A51-B8-C3; |
| A51-B8-C4; | A51-B8-C5; | A51-B8-C6; | A51-B8-C7; | A51-B8-C8; | A51-B8-C9; |
| A52-B8-C1; | A52-B8-C2; | A52-B8-C3; | A52-B8-C4; | A52-B8-C5; | A52-B8-C6; |
| A52-B8-C7; | A52-B8-C8; | A52-B8-C9; | A53-B8-C1; | A53-B8-C2; | A53-B8-C3; |
| A53-B8-C4; | A53-B8-C5; | A53-B8-C6; | A53-B8-C7; | A53-B8-C8; | A53-B8-C9; |
| A54-B8-C1; | A54-B8-C2; | A54-B8-C3; | A54-B8-C4; | A54-B8-C5; | A54-B8-C6; |
| A54-B8-C7; | A54-B8-C8; | A54-B8-C9; | A55-B8-C1; | A55-B8-C2; | A55-B8-C3; |
| A55-B8-C4; | A55-B8-C5; | A55-B8-C6; | A55-B8-C7; | A55-B8-C8; | A55-B8-C9; |
| A56-B8-C1; | A56-B8-C2; | A56-B8-C3; | A56-B8-C4; | A56-B8-C5; | A56-B8-C6; |
| A56-B8-C7; | A56-B8-C8; | A56-B8-C9; | A57-B8-C1; | A57-B8-C2; | A57-B8-C3; |
| A57-B8-C4; | A57-B8-C5; | A57-B8-C6; | A57-B8-C7; | A57-B8-C8; | A57-B8-C9; |
| A58-B8-C1; | A58-B8-C2; | A58-B8-C3; | A58-B8-C4; | A58-B8-C5; | A58-B8-C6; |
| A58-B8-C7; | A58-B8-C8; | A58-B8-C9; | A59-B8-C1; | A59-B8-C2; | A59-B8-C3; |
| A59-B8-C4; | A59-B8-C5; | A59-B8-C6; | A59-B8-C7; | A59-B8-C8; | A59-B8-C9; |
| A60-B8-C1; | A60-B8-C2; | A60-B8-C3; | A60-B8-C4; | A60-B8-C5; | A60-B8-C6; |
| A60-B8-C7; | A60-B8-C8; | A60-B8-C9; | A61-B8-C1; | A61-B8-C2; | A61-B8-C3; |
| A61-B8-C4; | A61-B8-C5; | A61-B8-C6; | A61-B8-C7; | A61-B8-C8; | A61-B8-C9; |
| A62-B8-C1; | A62-B8-C2; | A62-B8-C3; | A62-B8-C4; | A62-B8-C5; | A62-B8-C6; |
| A62-B8-C7; | A62-B8-C8; | A62-B8-C9; | A63-B8-C1; | A63-B8-C2; | A63-B8-C3; |
| A63-B8-C4; | A63-B8-C5; | A63-B8-C6; | A63-B8-C7; | A63-B8-C8; | A63-B8-C9; |
| A64-B8-C1; | A64-B8-C2; | A64-B8-C3; | A64-B8-C4; | A64-B8-C5; | A64-B8-C6; |
| A64-B8-C7; | A64-B8-C8; | A64-B8-C9; | A65-B8-C1; | A65-B8-C2; | A65-B8-C3; |
| A65-B8-C4; | A65-B8-C5; | A65-B8-C6; | A65-B8-C7; | A65-B8-C8; | A65-B8-C9; |
| A66-B8-C1; | A66-B8-C2; | A66-B8-C3; | A66-B8-C4; | A66-B8-C5; | A66-B8-C6; |
| A66-B8-C7; | A66-B8-C8; | A66-B8-C9; | A67-B8-C1; | A67-B8-C2; | A67-B8-C3; |
| A67-B8-C4; | A67-B8-C5; | A67-B8-C6; | A67-B8-C7; | A67-B8-C8; | A67-B8-C9; |
| A68-B8-C1; | A68-B8-C2; | A68-B8-C3; | A68-B8-C4; | A68-B8-C5; | A68-B8-C6; |
| A68-B8-C7; | A68-B8-C8; | A68-B8-C9; | A69-B8-C1; | A69-B8-C2; | A69-B8-C3; |
| A69-B8-C4; | A69-B8-C5; | A69-B8-C6; | A69-B8-C7; | A69-B8-C8; | A69-B8-C9; |
| A70-B8-C1; | A70-B8-C2; | A70-B8-C3; | A70-B8-C4; | A70-B8-C5; | A70-B8-C6; |
| A70-B8-C7; | A70-B8-C8; | A70-B8-C9; | A71-B8-C1; | A71-B8-C2; | A71-B8-C3; |
| A71-B8-C4; | A71-B8-C5; | A71-B8-C6; | A71-B8-C7; | A71-B8-C8; | A71-B8-C9; |
| A1-B9-C1; | A1-B9-C2; | A1-B9-C3; | A1-B9-C4; | A1-B9-C5; | A1-B9-C6; |
| A1-B9-C7; | A1-B9-C8; | A1-B9-C9; | A2-B9-C1; | A2-B9-C2; | A2-B9-C3; |
| A2-B9-C4; | A2-B9-C5; | A2-B9-C6; | A2-B9-C7; | A2-B9-C8; | A2-B9-C9; |
| A3-B9-C1; | A3-B9-C2; | A3-B9-C3; | A3-B9-C4; | A3-B9-C5; | A3-B9-C6; |
| A3-B9-C7; | A3-B9-C8; | A3-B9-C9; | A4-B9-C1; | A4-B9-C2; | A4-B9-C3; |
| A4-B9-C4; | A4-B9-C5; | A4-B9-C6; | A4-B9-C7; | A4-B9-C8; | A4-B9-C9; |
| A5-B9-C1; | A5-B9-C2; | A5-B9-C3; | A5-B9-C4; | A5-B9-C5; | A5-B9-C6; |
| A5-B9-C7; | A5-B9-C8; | A5-B9-C9; | A6-B9-C1; | A6-B9-C2; | A6-B9-C3; |
| A6-B9-C4; | A6-B9-C5; | A6-B9-C6; | A6-B9-C7; | A6-B9-C8; | A6-B9-C9; |
| A7-B9-C1; | A7-B9-C2; | A7-B9-C3; | A7-B9-C4; | A7-B9-C5; | A7-B9-C6; |
| A7-B9-C7; | A7-B9-C8; | A7-B9-C9; | A8-B9-C1; | A8-B9-C2; | A8-B9-C3; |
| A8-B9-C4; | A8-B9-C5; | A8-B9-C6; | A8-B9-C7; | A8-B9-C8; | A8-B9-C9; |
| A9-B9-C1; | A9-B9-C2; | A9-B9-C3; | A9-B9-C4; | A9-B9-C5; | A9-B9-C6; |
| A9-B9-C7; | A9-B9-C8; | A9-B9-C9; | A10-B9-C1; | A10-B9-C2; | A10-B9-C3; |
| A10-B9-C4; | A10-B9-C5; | A10-B9-C6; | A10-B9-C7; | A10-B9-C8; | A10-B9-C9; |
| A11-B9-C1; | A11-B9-C2; | A11-B9-C3; | A11-B9-C4; | A11-B9-C5; | A11-B9-C6; |
| A11-B9-C7; | A11-B9-C8; | A11-B9-C9; | A12-B9-C1; | A12-B9-C2; | A12-B9-C3; |
| A12-B9-C4; | A12-B9-C5; | A12-B9-C6; | A12-B9-C7; | A12-B9-C8; | A12-B9-C9; |
| A13-B9-C1; | A13-B9-C2; | A13-B9-C3; | A13-B9-C4; | A13-B9-C5; | A13-B9-C6; |
| A13-B9-C7; | A13-B9-C8; | A13-B9-C9; | A14-B9-C1; | A14-B9-C2; | A14-B9-C3; |
| A14-B9-C4; | A14-B9-C5; | A14-B9-C6; | A14-B9-C7; | A14-B9-C8; | A14-B9-C9; |
| A15-B9-C1; | A15-B9-C2; | A15-B9-C3; | A15-B9-C4; | A15-B9-C5; | A15-B9-C6; |
| A15-B9-C7; | A15-B9-C8; | A15-B9-C9; | A16-B9-C1; | A16-B9-C2; | A16-B9-C3; |
| A16-B9-C4; | A16-B9-C5; | A16-B9-C6; | A16-B9-C7; | A16-B9-C8; | A16-B9-C9; |
| A17-B9-C1; | A17-B9-C2; | A17-B9-C3; | A17-B9-C4; | A17-B9-C5; | A17-B9-C6; |
| A17-B9-C7; | A17-B9-C8; | A17-B9-C9; | A18-B9-C1; | A18-B9-C2; | A18-B9-C3; |
| A18-B9-C4; | A18-B9-C5; | A18-B9-C6; | A18-B9-C7; | A18-B9-C8; | A18-B9-C9; |
| A19-B9-C1; | A19-B9-C2; | A19-B9-C3; | A19-B9-C4; | A19-B9-C5; | A19-B9-C6; |
| A19-B9-C7; | A19-B9-C8; | A19-B9-C9; | A20-B9-C1; | A20-B9-C2; | A20-B9-C3; |
| A20-B9-C4; | A20-B9-C5; | A20-B9-C6; | A20-B9-C7; | A20-B9-C8; | A20-B9-C9; |
| A21-B9-C1; | A21-B9-C2; | A21-B9-C3; | A21-B9-C4; | A21-B9-C5; | A21-B9-C6; |
| A21-B9-C7; | A21-B9-C8; | A21-B9-C9; | A22-B9-C1; | A22-B9-C2; | A22-B9-C3; |
| A22-B9-C4; | A22-B9-C5; | A22-B9-C6; | A22-B9-C7; | A22-B9-C8; | A22-B9-C9; |
| A23-B9-C1; | A23-B9-C2; | A23-B9-C3; | A23-B9-C4; | A23-B9-C5; | A23-B9-C6; |
| A23-B9-C7; | A23-B9-C8; | A23-B9-C9; | A24-B9-C1; | A24-B9-C2; | A24-B9-C3; |
| A24-B9-C4; | A24-B9-C5; | A24-B9-C6; | A24-B9-C7; | A24-B9-C8; | A24-B9-C9; |
| A25-B9-C1; | A25-B9-C2; | A25-B9-C3; | A25-B9-C4; | A25-B9-C5; | A25-B9-C6; |
| A25-B9-C7; | A25-B9-C8; | A25-B9-C9; | A26-B9-C1; | A26-B9-C2; | A26-B9-C3; |
| A26-B9-C4; | A26-B9-C5; | A26-B9-C6; | A26-B9-C7; | A26-B9-C8; | A26-B9-C9; |
| A27-B9-C1; | A27-B9-C2; | A27-B9-C3; | A27-B9-C4; | A27-B9-C5; | A27-B9-C6; |
| A27-B9-C7; | A27-B9-C8; | A27-B9-C9; | A28-B9-C1; | A28-B9-C2; | A28-B9-C3; |
| A28-B9-C4; | A28-B9-C5; | A28-B9-C6; | A28-B9-C7; | A28-B9-C8; | A28-B9-C9; |
| A29-B9-C1; | A29-B9-C2; | A29-B9-C3; | A29-B9-C4; | A29-B9-C5; | A29-B9-C6; |
| A29-B9-C7; | A29-B9-C8; | A29-B9-C9; | A30-B9-C1; | A30-B9-C2; | A30-B9-C3; |

-continued

| | | | | | |
|---|---|---|---|---|---|
| A30-B9-C4; | A30-B9-C5; | A30-B9-C6; | A30-B9-C7; | A30-B9-C8; | A30-B9-C9; |
| A31-B9-C1; | A31-B9-C2; | A31-B9-C3; | A31-B9-C4; | A31-B9-C5; | A31-B9-C6; |
| A31-B9-C7; | A31-B9-C8; | A31-B9-C9; | A32-B9-C1; | A32-B9-C2; | A32-B9-C3; |
| A32-B9-C4; | A32-B9-C5; | A32-B9-C6; | A32-B9-C7; | A32-B9-C8; | A32-B9-C9; |
| A33-B9-C1; | A33-B9-C2; | A33-B9-C3; | A33-B9-C4; | A33-B9-C5; | A33-B9-C6; |
| A33-B9-C7; | A33-B9-C8; | A33-B9-C9; | A34-B9-C1; | A34-B9-C2; | A34-B9-C3; |
| A34-B9-C4; | A34-B9-C5; | A34-B9-C6; | A34-B9-C7; | A34-B9-C8; | A34-B9-C9; |
| A35-B9-C1; | A35-B9-C2; | A35-B9-C3; | A35-B9-C4; | A35-B9-C5; | A35-B9-C6; |
| A35-B9-C7; | A35-B9-C8; | A35-B9-C9; | A36-B9-C1; | A36-B9-C2; | A36-B9-C3; |
| A36-B9-C4; | A36-B9-C5; | A36-B9-C6; | A36-B9-C7; | A36-B9-C8; | A36-B9-C9; |
| A37-B9-C1; | A37-B9-C2; | A37-B9-C3; | A37-B9-C4; | A37-B9-C5; | A37-B9-C6; |
| A37-B9-C7; | A37-B9-C8; | A37-B9-C9; | A38-B9-C1; | A38-B9-C2; | A38-B9-C3; |
| A38-B9-C4; | A38-B9-C5; | A38-B9-C6; | A38-B9-C7; | A38-B9-C8; | A38-B9-C9; |
| A39-B9-C1; | A39-B9-C2; | A39-B9-C3; | A39-B9-C4; | A39-B9-C5; | A39-B9-C6; |
| A39-B9-C7; | A39-B9-C8; | A39-B9-C9; | A40-B9-C1; | A40-B9-C2; | A40-B9-C3; |
| A40-B9-C4; | A40-B9-C5; | A40-B9-C6; | A40-B9-C7; | A40-B9-C8; | A40-B9-C9; |
| A41-B9-C1; | A41-B9-C2; | A41-B9-C3; | A41-B9-C4; | A41-B9-C5; | A41-B9-C6; |
| A41-B9-C7; | A41-B9-C8; | A41-B9-C9; | A42-B9-C1; | A42-B9-C2; | A42-B9-C3; |
| A42-B9-C4; | A42-B9-C5; | A42-B9-C6; | A42-B9-C7; | A42-B9-C8; | A42-B9-C9; |
| A43-B9-C1; | A43-B9-C2; | A43-B9-C3; | A43-B9-C4; | A43-B9-C5; | A43-B9-C6; |
| A43-B9-C7; | A43-B9-C8; | A43-B9-C9; | A44-B9-C1; | A44-B9-C2; | A44-B9-C3; |
| A44-B9-C4; | A44-B9-C5; | A44-B9-C6; | A44-B9-C7; | A44-B9-C8; | A44-B9-C9; |
| A45-B9-C1; | A45-B9-C2; | A45-B9-C3; | A45-B9-C4; | A45-B9-C5; | A45-B9-C6; |
| A45-B9-C7; | A45-B9-C8; | A45-B9-C9; | A46-B9-C1; | A46-B9-C2; | A46-B9-C3; |
| A46-B9-C4; | A46-B9-C5; | A46-B9-C6; | A46-B9-C7; | A46-B9-C8; | A46-B9-C9; |
| A47-B9-C1; | A47-B9-C2; | A47-B9-C3; | A47-B9-C4; | A47-B9-C5; | A47-B9-C6; |
| A47-B9-C7; | A47-B9-C8; | A47-B9-C9; | A48-B9-C1; | A48-B9-C2; | A48-B9-C3; |
| A48-B9-C4; | A48-B9-C5; | A48-B9-C6; | A48-B9-C7; | A48-B9-C8; | A48-B9-C9; |
| A49-B9-C1; | A49-B9-C2; | A49-B9-C3; | A49-B9-C4; | A49-B9-C5; | A49-B9-C6; |
| A49-B9-C7; | A49-B9-C8; | A49-B9-C9; | A50-B9-C1; | A50-B9-C2; | A50-B9-C3; |
| A50-B9-C4; | A50-B9-C5; | A50-B9-C6; | A50-B9-C7; | A50-B9-C8; | A50-B9-C9; |
| A51-B9-C1; | A51-B9-C2; | A51-B9-C3; | A51-B9-C4; | A51-B9-C5; | A51-B9-C6; |
| A51-B9-C7; | A51-B9-C8; | A51-B9-C9; | A52-B9-C1; | A52-B9-C2; | A52-B9-C3; |
| A52-B9-C4; | A52-B9-C5; | A52-B9-C6; | A52-B9-C7; | A52-B9-C8; | A52-B9-C9; |
| A53-B9-C1; | A53-B9-C2; | A53-B9-C3; | A53-B9-C4; | A53-B9-C5; | A53-B9-C6; |
| A53-B9-C7; | A53-B9-C8; | A53-B9-C9; | A54-B9-C1; | A54-B9-C2; | A54-B9-C3; |
| A54-B9-C4; | A54-B9-C5; | A54-B9-C6; | A54-B9-C7; | A54-B9-C8; | A54-B9-C9; |
| A55-B9-C1; | A55-B9-C2; | A55-B9-C3; | A55-B9-C4; | A55-B9-C5; | A55-B9-C6; |
| A55-B9-C7; | A55-B9-C8; | A55-B9-C9; | A56-B9-C1; | A56-B9-C2; | A56-B9-C3; |
| A56-B9-C4; | A56-B9-C5; | A56-B9-C6; | A56-B9-C7; | A56-B9-C8; | A56-B9-C9; |
| A57-B9-C1; | A57-B9-C2; | A57-B9-C3; | A57-B9-C4; | A57-B9-C5; | A57-B9-C6; |
| A57-B9-C7; | A57-B9-C8; | A57-B9-C9; | A58-B9-C1; | A58-B9-C2; | A58-B9-C3; |
| A58-B9-C4; | A58-B9-C5; | A58-B9-C6; | A58-B9-C7; | A58-B9-C8; | A58-B9-C9; |
| A59-B9-C1; | A59-B9-C2; | A59-B9-C3; | A59-B9-C4; | A59-B9-C5; | A59-B9-C6; |
| A59-B9-C7; | A59-B9-C8; | A59-B9-C9; | A60-B9-C1; | A60-B9-C2; | A60-B9-C3; |
| A60-B9-C4; | A60-B9-C5; | A60-B9-C6; | A60-B9-C7; | A60-B9-C8; | A60-B9-C9; |
| A61-B9-C1; | A61-B9-C2; | A61-B9-C3; | A61-B9-C4; | A61-B9-C5; | A61-B9-C6; |
| A61-B9-C7; | A61-B9-C8; | A61-B9-C9; | A62-B9-C1; | A62-B9-C2; | A62-B9-C3; |
| A62-B9-C4; | A62-B9-C5; | A62-B9-C6; | A62-B9-C7; | A62-B9-C8; | A62-B9-C9; |
| A63-B9-C1; | A63-B9-C2; | A63-B9-C3; | A63-B9-C4; | A63-B9-C5; | A63-B9-C6; |
| A63-B9-C7; | A63-B9-C8; | A63-B9-C9; | A64-B9-C1; | A64-B9-C2; | A64-B9-C3; |
| A64-B9-C4; | A64-B9-C5; | A64-B9-C6; | A64-B9-C7; | A64-B9-C8; | A64-B9-C9; |
| A65-B9-C1; | A65-B9-C2; | A65-B9-C3; | A65-B9-C4; | A65-B9-C5; | A65-B9-C6; |
| A65-B9-C7; | A65-B9-C8; | A65-B9-C9; | A66-B9-C1; | A66-B9-C2; | A66-B9-C3; |
| A66-B9-C4; | A66-B9-C5; | A66-B9-C6; | A66-B9-C7; | A66-B9-C8; | A66-B9-C9; |
| A67-B9-C1; | A67-B9-C2; | A67-B9-C3; | A67-B9-C4; | A67-B9-C5; | A67-B9-C6; |
| A67-B9-C7; | A67-B9-C8; | A67-B9-C9; | A68-B9-C1; | A68-B9-C2; | A68-B9-C3; |
| A68-B9-C4; | A68-B9-C5; | A68-B9-C6; | A68-B9-C7; | A68-B9-C8; | A68-B9-C9; |
| A69-B9-C1; | A69-B9-C2; | A69-B9-C3; | A69-B9-C4; | A69-B9-C5; | A69-B9-C6; |
| A69-B9-C7; | A69-B9-C8; | A69-B9-C9; | A70-B9-C1; | A70-B9-C2; | A70-B9-C3; |
| A70-B9-C4; | A70-B9-C5; | A70-B9-C6; | A70-B9-C7; | A70-B9-C8; | A70-B9-C9; |
| A71-B9-C1; | A71-B9-C2; | A71-B9-C3; | A71-B9-C4; | A71-B9-C5; | A71-B9-C6; |
| A71-B9-C7; | A71-B9-C8; | A71-B9-C9; | A1-B10-C1; | A1-B10-C2; | A1-B10-C3; |
| A1-B10-C4; | A1-B10-C5; | A1-B10-C6; | A1-B10-C7; | A1-B10-C8; | A1-B10-C9; |
| A2-B10-C1; | A2-B10-C2; | A2-B10-C3; | A2-B10-C4; | A2-B10-C5; | A2-B10-C6; |
| A2-B10-C7; | A2-B10-C8; | A2-B10-C9; | A3-B10-C1; | A3-B10-C2; | A3-B10-C3; |
| A3-B10-C4; | A3-B10-C5; | A3-B10-C6; | A3-B10-C7; | A3-B10-C8; | A3-B10-C9; |
| A4-B10-C1; | A4-B10-C2; | A4-B10-C3; | A4-B10-C4; | A4-B10-C5; | A4-B10-C6; |
| A4-B10-C7; | A4-B10-C8; | A4-B10-C9; | A5-B10-C1; | A5-B10-C2; | A5-B10-C3; |
| A5-B10-C4; | A5-B10-C5; | A5-B10-C6; | A5-B10-C7; | A5-B10-C8; | A5-B10-C9; |
| A6-B10-C1; | A6-B10-C2; | A6-B10-C3; | A6-B10-C4; | A6-B10-C5; | A6-B10-C6; |
| A6-B10-C7; | A6-B10-C8; | A6-B10-C9; | A7-B10-C1; | A7-B10-C2; | A7-B10-C3; |
| A7-B10-C4; | A7-B10-C5; | A7-B10-C6; | A7-B10-C7; | A7-B10-C8; | A7-B10-C9; |
| A8-B10-C1; | A8-B10-C2; | A8-B10-C3; | A8-B10-C4; | A8-B10-C5; | A8-B10-C6; |
| A8-B10-C7; | A8-B10-C8; | A8-B10-C9; | A9-B10-C1; | A9-B10-C2; | A9-B10-C3; |
| A9-B10-C4; | A9-B10-C5; | A9-B10-C6; | A9-B10-C7; | A9-B10-C8; | A9-B10-C9; |
| A10-B10-C1; | A10-B10-C2; | A10-B10-C3; | A10-B10-C4; | A10-B10-C5; | A10-B10-C6; |
| A10-B10-C7; | A10-B10-C8; | A10-B10-C9; | A11-B10-C1; | A11-B10-C2; | A11-B10-C3; |
| A11-B10-C4; | A11-B10-C5; | A11-B10-C6; | A11-B10-C7; | A11-B10-C8; | A11-B10-C9; |

-continued

| | | | | | |
|---|---|---|---|---|---|
| A12-B10-C1; | A12-B10-C2; | A12-B10-C3; | A12-B10-C4; | A12-B10-C5; | A12-B10-C6; |
| A12-B10-C7; | A12-B10-C8; | A12-B10-C9; | A13-B10-C1; | A13-B10-C2; | A13-B10-C3; |
| A13-B10-C4; | A13-B10-C5; | A13-B10-C6; | A13-B10-C7; | A13-B10-C8; | A13-B10-C9; |
| A14-B10-C1; | A14-B10-C2; | A14-B10-C3; | A14-B10-C4; | A14-B10-C5; | A14-B10-C6; |
| A14-B10-C7; | A14-B10-C8; | A14-B10-C9; | A15-B10-C1; | A15-B10-C2; | A15-B10-C3; |
| A15-B10-C4; | A15-B10-C5; | A15-B10-C6; | A15-B10-C7; | A15-B10-C8; | A15-B10-C9; |
| A16-B10-C1; | A16-B10-C2; | A16-B10-C3; | A16-B10-C4; | A16-B10-C5; | A16-B10-C6; |
| A16-B10-C7; | A16-B10-C8; | A16-B10-C9; | A17-B10-C1; | A17-B10-C2; | A17-B10-C3; |
| A17-B10-C4; | A17-B10-C5; | A17-B10-C6; | A17-B10-C7; | A17-B10-C8; | A17-B10-C9; |
| A18-B10-C1; | A18-B10-C2; | A18-B10-C3; | A18-B10-C4; | A18-B10-C5; | A18-B10-C6; |
| A18-B10-C7; | A18-B10-C8; | A18-B10-C9; | A19-B10-C1; | A19-B10-C2; | A19-B10-C3; |
| A19-B10-C4; | A19-B10-C5; | A19-B10-C6; | A19-B10-C7; | A19-B10-C8; | A19-B10-C9; |
| A20-B10-C1; | A20-B10-C2; | A20-B10-C3; | A20-B10-C4; | A20-B10-C5; | A20-B10-C6; |
| A20-B10-C7; | A20-B10-C8; | A20-B10-C9; | A21-B10-C1; | A21-B10-C2; | A21-B10-C3; |
| A21-B10-C4; | A21-B10-C5; | A21-B10-C6; | A21-B10-C7; | A21-B10-C8; | A21-B10-C9; |
| A22-B10-C1; | A22-B10-C2; | A22-B10-C3; | A22-B10-C4; | A22-B10-C5; | A22-B10-C6; |
| A22-B10-C7; | A22-B10-C8; | A22-B10-C9; | A23-B10-C1; | A23-B10-C2; | A23-B10-C3; |
| A23-B10-C4; | A23-B10-C5; | A23-B10-C6; | A23-B10-C7; | A23-B10-C8; | A23-B10-C9; |
| A24-B10-C1; | A24-B10-C2; | A24-B10-C3; | A24-B10-C4; | A24-B10-C5; | A24-B10-C6; |
| A24-B10-C7; | A24-B10-C8; | A24-B10-C9; | A25-B10-C1; | A25-B10-C2; | A25-B10-C3; |
| A25-B10-C4; | A25-B10-C5; | A25-B10-C6; | A25-B10-C7; | A25-B10-C8; | A25-B10-C9; |
| A26-B10-C1; | A26-B10-C2; | A26-B10-C3; | A26-B10-C4; | A26-B10-C5; | A26-B10-C6; |
| A26-B10-C7; | A26-B10-C8; | A26-B10-C9; | A27-B10-C1; | A27-B10-C2; | A27-B10-C3; |
| A27-B10-C4; | A27-B10-C5; | A27-B10-C6; | A27-B10-C7; | A27-B10-C8; | A27-B10-C9; |
| A28-B10-C1; | A28-B10-C2; | A28-B10-C3; | A28-B10-C4; | A28-B10-C5; | A28-B10-C6; |
| A28-B10-C7; | A28-B10-C8; | A28-B10-C9; | A29-B10-C1; | A29-B10-C2; | A29-B10-C3; |
| A29-B10-C4; | A29-B10-C5; | A29-B10-C6; | A29-B10-C7; | A29-B10-C8; | A29-B10-C9; |
| A30-B10-C1; | A30-B10-C2; | A30-B10-C3; | A30-B10-C4; | A30-B10-C5; | A30-B10-C6; |
| A30-B10-C7; | A30-B10-C8; | A30-B10-C9; | A31-B10-C1; | A31-B10-C2; | A31-B10-C3; |
| A31-B10-C4; | A31-B10-C5; | A31-B10-C6; | A31-B10-C7; | A31-B10-C8; | A31-B10-C9; |
| A32-B10-C1; | A32-B10-C2; | A32-B10-C3; | A32-B10-C4; | A32-B10-C5; | A32-B10-C6; |
| A32-B10-C7; | A32-B10-C8; | A32-B10-C9; | A33-B10-C1; | A33-B10-C2; | A33-B10-C3; |
| A33-B10-C4; | A33-B10-C5; | A33-B10-C6; | A33-B10-C7; | A33-B10-C8; | A33-B10-C9; |
| A34-B10-C1; | A34-B10-C2; | A34-B10-C3; | A34-B10-C4; | A34-B10-C5; | A34-B10-C6; |
| A34-B10-C7; | A34-B10-C8; | A34-B10-C9; | A35-B10-C1; | A35-B10-C2; | A35-B10-C3; |
| A35-B10-C4; | A35-B10-C5; | A35-B10-C6; | A35-B10-C7; | A35-B10-C8; | A35-B10-C9; |
| A36-B10-C1; | A36-B10-C2; | A36-B10-C3; | A36-B10-C4; | A36-B10-C5; | A36-B10-C6; |
| A36-B10-C7; | A36-B10-C8; | A36-B10-C9; | A37-B10-C1; | A37-B10-C2; | A37-B10-C3; |
| A37-B10-C4; | A37-B10-C5; | A37-B10-C6; | A37-B10-C7; | A37-B10-C8; | A37-B10-C9; |
| A38-B10-C1; | A38-B10-C2; | A38-B10-C3; | A38-B10-C4; | A38-B10-C5; | A38-B10-C6; |
| A38-B10-C7; | A38-B10-C8; | A38-B10-C9; | A39-B10-C1; | A39-B10-C2; | A39-B10-C3; |
| A39-B10-C4; | A39-B10-C5; | A39-B10-C6; | A39-B10-C7; | A39-B10-C8; | A39-B10-C9; |
| A40-B10-C1; | A40-B10-C2; | A40-B10-C3; | A40-B10-C4; | A40-B10-C5; | A40-B10-C6; |
| A40-B10-C7; | A40-B10-C8; | A40-B10-C9; | A41-B10-C1; | A41-B10-C2; | A41-B10-C3; |
| A41-B10-C4; | A41-B10-C5; | A41-B10-C6; | A41-B10-C7; | A41-B10-C8; | A41-B10-C9; |
| A42-B10-C1; | A42-B10-C2; | A42-B10-C3; | A42-B10-C4; | A42-B10-C5; | A42-B10-C6; |
| A42-B10-C7; | A42-B10-C8; | A42-B10-C9; | A43-B10-C1; | A43-B10-C2; | A43-B10-C3; |
| A43-B10-C4; | A43-B10-C5; | A43-B10-C6; | A43-B10-C7; | A43-B10-C8; | A43-B10-C9; |
| A44-B10-C1; | A44-B10-C2; | A44-B10-C3; | A44-B10-C4; | A44-B10-C5; | A44-B10-C6; |
| A44-B10-C7; | A44-B10-C8; | A44-B10-C9; | A45-B10-C1; | A45-B10-C2; | A45-B10-C3; |
| A45-B10-C4; | A45-B10-C5; | A45-B10-C6; | A45-B10-C7; | A45-B10-C8; | A45-B10-C9; |
| A46-B10-C1; | A46-B10-C2; | A46-B10-C3; | A46-B10-C4; | A46-B10-C5; | A46-B10-C6; |
| A46-B10-C7; | A46-B10-C8; | A46-B10-C9; | A47-B10-C1; | A47-B10-C2; | A47-B10-C3; |
| A47-B10-C4; | A47-B10-C5; | A47-B10-C6; | A47-B10-C7; | A47-B10-C8; | A47-B10-C9; |
| A48-B10-C1; | A48-B10-C2; | A48-B10-C3; | A48-B10-C4; | A48-B10-C5; | A48-B10-C6; |
| A48-B10-C7; | A48-B10-C8; | A48-B10-C9; | A49-B10-C1; | A49-B10-C2; | A49-B10-C3; |
| A49-B10-C4; | A49-B10-C5; | A49-B10-C6; | A49-B10-C7; | A49-B10-C8; | A49-B10-C9; |
| A50-B10-C1; | A50-B10-C2; | A50-B10-C3; | A50-B10-C4; | A50-B10-C5; | A50-B10-C6; |
| A50-B10-C7; | A50-B10-C8; | A50-B10-C9; | A51-B10-C1; | A51-B10-C2; | A51-B10-C3; |
| A51-B10-C4; | A51-B10-C5; | A51-B10-C6; | A51-B10-C7; | A51-B10-C8; | A51-B10-C9; |
| A52-B10-C1; | A52-B10-C2; | A52-B10-C3; | A52-B10-C4; | A52-B10-C5; | A52-B10-C6; |
| A52-B10-C7; | A52-B10-C8; | A52-B10-C9; | A53-B10-C1; | A53-B10-C2; | A53-B10-C3; |
| A53-B10-C4; | A53-B10-C5; | A53-B10-C6; | A53-B10-C7; | A53-B10-C8; | A53-B10-C9; |
| A54-B10-C1; | A54-B10-C2; | A54-B10-C3; | A54-B10-C4; | A54-B10-C5; | A54-B10-C6; |
| A54-B10-C7; | A54-B10-C8; | A54-B10-C9; | A55-B10-C1; | A55-B10-C2; | A55-B10-C3; |
| A55-B10-C4; | A55-B10-C5; | A55-B10-C6; | A55-B10-C7; | A55-B10-C8; | A55-B10-C9; |
| A56-B10-C1; | A56-B10-C2; | A56-B10-C3; | A56-B10-C4; | A56-B10-C5; | A56-B10-C6; |
| A56-B10-C7; | A56-B10-C8; | A56-B10-C9; | A57-B10-C1; | A57-B10-C2; | A57-B10-C3; |
| A57-B10-C4; | A57-B10-C5; | A57-B10-C6; | A57-B10-C7; | A57-B10-C8; | A57-B10-C9; |
| A58-B10-C1; | A58-B10-C2; | A58-B10-C3; | A58-B10-C4; | A58-B10-C5; | A58-B10-C6; |
| A58-B10-C7; | A58-B10-C8; | A58-B10-C9; | A59-B10-C1; | A59-B10-C2; | A59-B10-C3; |
| A59-B10-C4; | A59-B10-C5; | A59-B10-C6; | A59-B10-C7; | A59-B10-C8; | A59-B10-C9; |
| A60-B10-C1; | A60-B10-C2; | A60-B10-C3; | A60-B10-C4; | A60-B10-C5; | A60-B10-C6; |
| A60-B10-C7; | A60-B10-C8; | A60-B10-C9; | A61-B10-C1; | A61-B10-C2; | A61-B10-C3; |
| A61-B10-C4; | A61-B10-C5; | A61-B10-C6; | A61-B10-C7; | A61-B10-C8; | A61-B10-C9; |
| A62-B10-C1; | A62-B10-C2; | A62-B10-C3; | A62-B10-C4; | A62-B10-C5; | A62-B10-C6; |
| A62-B10-C7; | A62-B10-C8; | A62-B10-C9; | A63-B10-C1; | A63-B10-C2; | A63-B10-C3; |
| A63-B10-C4; | A63-B10-C5; | A63-B10-C6; | A63-B10-C7; | A63-B10-C8; | A63-B10-C9; |
| A64-B10-C1; | A64-B10-C2; | A64-B10-C3; | A64-B10-C4; | A64-B10-C5; | A64-B10-C6; |

| | | | | | |
|---|---|---|---|---|---|
| A64-B10-C7; | A64-B10-C8; | A64-B10-C9; | A65-B10-C1; | A65-B10-C2; | A65-B10-C3; |
| A65-B10-C4; | A65-B10-C5; | A65-B10-C6; | A65-B10-C7; | A65-B10-C8; | A65-B10-C9; |
| A66-B10-C1; | A66-B10-C2; | A66-B10-C3; | A66-B10-C4; | A66-B10-C5; | A66-B10-C6; |
| A66-B10-C7; | A66-B10-C8; | A66-B10-C9; | A67-B10-C1; | A67-B10-C2; | A67-B10-C3; |
| A67-B10-C4; | A67-B10-C5; | A67-B10-C6; | A67-B10-C7; | A67-B10-C8; | A67-B10-C9; |
| A68-B10-C1; | A68-B10-C2; | A68-B10-C3; | A68-B10-C4; | A68-B10-C5; | A68-B10-C6; |
| A68-B10-C7; | A68-B10-C8; | A68-B10-C9; | A69-B10-C1; | A69-B10-C2; | A69-B10-C3; |
| A69-B10-C4; | A69-B10-C5; | A69-B10-C6; | A69-B10-C7; | A69-B10-C8; | A69-B10-C9; |
| A70-B10-C1; | A70-B10-C2; | A70-B10-C3; | A70-B10-C4; | A70-B10-C5; | A70-B10-C6; |
| A70-B10-C7; | A70-B10-C8; | A70-B10-C9; | A71-B10-C1; | A71-B10-C2; | A71-B10-C3; |
| A71-B10-C4; | A71-B10-C5; | A71-B10-C6; | A71-B10-C7; | A71-B10-C8; | A71-B10-C9; |
| A1-B11-C1; | A1-B11-C2; | A1-B11-C3; | A1-B11-C4; | A1-B11-C5; | A1-B11-C6; |
| A1-B11-C7; | A1-B11-C8; | A1-B11-C9; | A2-B11-C1; | A2-B11-C2; | A2-B11-C3; |
| A2-B11-C4; | A2-B11-C5; | A2-B11-C6; | A2-B11-C7; | A2-B11-C8; | A2-B11-C9; |
| A3-B11-C1; | A3-B11-C2; | A3-B11-C3; | A3-B11-C4; | A3-B11-C5; | A3-B11-C6; |
| A3-B11-C7; | A3-B11-C8; | A3-B11-C9; | A4-B11-C1; | A4-B11-C2; | A4-B11-C3; |
| A4-B11-C4; | A4-B11-C5; | A4-B11-C6; | A4-B11-C7; | A4-B11-C8; | A4-B11-C9; |
| A5-B11-C1; | A5-B11-C2; | A5-B11-C3; | A5-B11-C4; | A5-B11-C5; | A5-B11-C6; |
| A5-B11-C7; | A5-B11-C8; | A5-B11-C9; | A6-B11-C1; | A6-B11-C2; | A6-B11-C3; |
| A6-B11-C4; | A6-B11-C5; | A6-B11-C6; | A6-B11-C7; | A6-B11-C8; | A6-B11-C9; |
| A7-B11-C1; | A7-B11-C2; | A7-B11-C3; | A7-B11-C4; | A7-B11-C5; | A7-B11-C6; |
| A7-B11-C7; | A7-B11-C8; | A7-B11-C9; | A8-B11-C1; | A8-B11-C2; | A8-B11-C3; |
| A8-B11-C4; | A8-B11-C5; | A8-B11-C6; | A8-B11-C7; | A8-B11-C8; | A8-B11-C9; |
| A9-B11-C1; | A9-B11-C2; | A9-B11-C3; | A9-B11-C4; | A9-B11-C5; | A9-B11-C6; |
| A9-B11-C7; | A9-B11-C8; | A9-B11-C9; | A10-B11-C1; | A10-B11-C2; | A10-B11-C3; |
| A10-B11-C4; | A10-B11-C5; | A10-B11-C6; | A10-B11-C7; | A10-B11-C8; | A10-B11-C9; |
| A11-B11-C1; | A11-B11-C2; | A11-B11-C3; | A11-B11-C4; | A11-B11-C5; | A11-B11-C6; |
| A11-B11-C7; | A11-B11-C8; | A11-B11-C9; | A12-B11-C1; | A12-B11-C2; | A12-B11-C3; |
| A12-B11-C4; | A12-B11-C5; | A12-B11-C6; | A12-B11-C7; | A12-B11-C8; | A12-B11-C9; |
| A13-B11-C1; | A13-B11-C2; | A13-B11-C3; | A13-B11-C4; | A13-B11-C5; | A13-B11-C6; |
| A13-B11-C7; | A13-B11-C8; | A13-B11-C9; | A14-B11-C1; | A14-B11-C2; | A14-B11-C3; |
| A14-B11-C4; | A14-B11-C5; | A14-B11-C6; | A14-B11-C7; | A14-B11-C8; | A14-B11-C9; |
| A15-B11-C1; | A15-B11-C2; | A15-B11-C3; | A15-B11-C4; | A15-B11-C5; | A15-B11-C6; |
| A15-B11-C7; | A15-B11-C8; | A15-B11-C9; | A16-B11-C1; | A16-B11-C2; | A16-B11-C3; |
| A16-B11-C4; | A16-B11-C5; | A16-B11-C6; | A16-B11-C7; | A16-B11-C8; | A16-B11-C9; |
| A17-B11-C1; | A17-B11-C2; | A17-B11-C3; | A17-B11-C4; | A17-B11-C5; | A17-B11-C6; |
| A17-B11-C7; | A17-B11-C8; | A17-B11-C9; | A18-B11-C1; | A18-B11-C2; | A18-B11-C3; |
| A18-B11-C4; | A18-B11-C5; | A18-B11-C6; | A18-B11-C7; | A18-B11-C8; | A18-B11-C9; |
| A19-B11-C1; | A19-B11-C2; | A19-B11-C3; | A19-B11-C4; | A19-B11-C5; | A19-B11-C6; |
| A19-B11-C7; | A19-B11-C8; | A19-B11-C9; | A20-B11-C1; | A20-B11-C2; | A20-B11-C3; |
| A20-B11-C4; | A20-B11-C5; | A20-B11-C6; | A20-B11-C7; | A20-B11-C8; | A20-B11-C9; |
| A21-B11-C1; | A21-B11-C2; | A21-B11-C3; | A21-B11-C4; | A21-B11-C5; | A21-B11-C6; |
| A21-B11-C7; | A21-B11-C8; | A21-B11-C9; | A22-B11-C1; | A22-B11-C2; | A22-B11-C3; |
| A22-B11-C4; | A22-B11-C5; | A22-B11-C6; | A22-B11-C7; | A22-B11-C8; | A22-B11-C9; |
| A23-B11-C1; | A23-B11-C2; | A23-B11-C3; | A23-B11-C4; | A23-B11-C5; | A23-B11-C6; |
| A23-B11-C7; | A23-B11-C8; | A23-B11-C9; | A24-B11-C1; | A24-B11-C2; | A24-B11-C3; |
| A24-B11-C4; | A24-B11-C5; | A24-B11-C6; | A24-B11-C7; | A24-B11-C8; | A24-B11-C9; |
| A25-B11-C1; | A25-B11-C2; | A25-B11-C3; | A25-B11-C4; | A25-B11-C5; | A25-B11-C6; |
| A25-B11-C7; | A25-B11-C8; | A25-B11-C9; | A26-B11-C1; | A26-B11-C2; | A26-B11-C3; |
| A26-B11-C4; | A26-B11-C5; | A26-B11-C6; | A26-B11-C7; | A26-B11-C8; | A26-B11-C9; |
| A27-B11-C1; | A27-B11-C2; | A27-B11-C3; | A27-B11-C4; | A27-B11-C5; | A27-B11-C6; |
| A27-B11-C7; | A27-B11-C8; | A27-B11-C9; | A28-B11-C1; | A28-B11-C2; | A28-B11-C3; |
| A28-B11-C4; | A28-B11-C5; | A28-B11-C6; | A28-B11-C7; | A28-B11-C8; | A28-B11-C9; |
| A29-B11-C1; | A29-B11-C2; | A29-B11-C3; | A29-B11-C4; | A29-B11-C5; | A29-B11-C6; |
| A29-B11-C7; | A29-B11-C8; | A29-B11-C9; | A30-B11-C1; | A30-B11-C2; | A30-B11-C3; |
| A30-B11-C4; | A30-B11-C5; | A30-B11-C6; | A30-B11-C7; | A30-B11-C8; | A30-B11-C9; |
| A31-B11-C1; | A31-B11-C2; | A31-B11-C3; | A31-B11-C4; | A31-B11-C5; | A31-B11-C6; |
| A31-B11-C7; | A31-B11-C8; | A31-B11-C9; | A32-B11-C1; | A32-B11-C2; | A32-B11-C3; |
| A32-B11-C4; | A32-B11-C5; | A32-B11-C6; | A32-B11-C7; | A32-B11-C8; | A32-B11-C9; |
| A33-B11-C1; | A33-B11-C2; | A33-B11-C3; | A33-B11-C4; | A33-B11-C5; | A33-B11-C6; |
| A33-B11-C7; | A33-B11-C8; | A33-B11-C9; | A34-B11-C1; | A34-B11-C2; | A34-B11-C3; |
| A34-B11-C4; | A34-B11-C5; | A34-B11-C6; | A34-B11-C7; | A34-B11-C8; | A34-B11-C9; |
| A35-B11-C1; | A35-B11-C2; | A35-B11-C3; | A35-B11-C4; | A35-B11-C5; | A35-B11-C6; |
| A35-B11-C7; | A35-B11-C8; | A35-B11-C9; | A36-B11-C1; | A36-B11-C2; | A36-B11-C3; |
| A36-B11-C4; | A36-B11-C5; | A36-B11-C6; | A36-B11-C7; | A36-B11-C8; | A36-B11-C9; |
| A37-B11-C1; | A37-B11-C2; | A37-B11-C3; | A37-B11-C4; | A37-B11-C5; | A37-B11-C6; |
| A37-B11-C7; | A37-B11-C8; | A37-B11-C9; | A38-B11-C1; | A38-B11-C2; | A38-B11-C3; |
| A38-B11-C4; | A38-B11-C5; | A38-B11-C6; | A38-B11-C7; | A38-B11-C8; | A38-B11-C9; |
| A39-B11-C1; | A39-B11-C2; | A39-B11-C3; | A39-B11-C4; | A39-B11-C5; | A39-B11-C6; |
| A39-B11-C7; | A39-B11-C8; | A39-B11-C9; | A40-B11-C1; | A40-B11-C2; | A40-B11-C3; |
| A40-B11-C4; | A40-B11-C5; | A40-B11-C6; | A40-B11-C7; | A40-B11-C8; | A40-B11-C9; |
| A41-B11-C1; | A41-B11-C2; | A41-B11-C3; | A41-B11-C4; | A41-B11-C5; | A41-B11-C6; |
| A41-B11-C7; | A41-B11-C8; | A41-B11-C9; | A42-B11-C1; | A42-B11-C2; | A42-B11-C3; |
| A42-B11-C4; | A42-B11-C5; | A42-B11-C6; | A42-B11-C7; | A42-B11-C8; | A42-B11-C9; |
| A43-B11-C1; | A43-B11-C2; | A43-B11-C3; | A43-B11-C4; | A43-B11-C5; | A43-B11-C6; |
| A43-B11-C7; | A43-B11-C8; | A43-B11-C9; | A44-B11-C1; | A44-B11-C2; | A44-B11-C3; |
| A44-B11-C4; | A44-B11-C5; | A44-B11-C6; | A44-B11-C7; | A44-B11-C8; | A44-B11-C9; |
| A45-B11-C1; | A45-B11-C2; | A45-B11-C3; | A45-B11-C4; | A45-B11-C5; | A45-B11-C6; |
| A45-B11-C7; | A45-B11-C8; | A45-B11-C9; | A46-B11-C1; | A46-B11-C2; | A46-B11-C3; |

-continued

| | | | | | |
|---|---|---|---|---|---|
| A46-B11-C4; | A46-B11-C5; | A46-B11-C6; | A46-B11-C7; | A46-B11-C8; | A46-B11-C9; |
| A47-B11-C1; | A47-B11-C2; | A47-B11-C3; | A47-B11-C4; | A47-B11-C5; | A47-B11-C6; |
| A47-B11-C7; | A47-B11-C8; | A47-B11-C9; | A48-B11-C1; | A48-B11-C2; | A48-B11-C3; |
| A48-B11-C4; | A48-B11-C5; | A48-B11-C6; | A48-B11-C7; | A48-B11-C8; | A48-B11-C9; |
| A49-B11-C1; | A49-B11-C2; | A49-B11-C3; | A49-B11-C4; | A49-B11-C5; | A49-B11-C6; |
| A49-B11-C7; | A49-B11-C8; | A49-B11-C9; | A50-B11-C1; | A50-B11-C2; | A50-B11-C3; |
| A50-B11-C4; | A50-B11-C5; | A50-B11-C6; | A50-B11-C7; | A50-B11-C8; | A50-B11-C9; |
| A51-B11-C1; | A51-B11-C2; | A51-B11-C3; | A51-B11-C4; | A51-B11-C5; | A51-B11-C6; |
| A51-B11-C7; | A51-B11-C8; | A51-B11-C9; | A52-B11-C1; | A52-B11-C2; | A52-B11-C3; |
| A52-B11-C4; | A52-B11-C5; | A52-B11-C6; | A52-B11-C7; | A52-B11-C8; | A52-B11-C9; |
| A53-B11-C1; | A53-B11-C2; | A53-B11-C3; | A53-B11-C4; | A53-B11-C5; | A53-B11-C6; |
| A53-B11-C7; | A53-B11-C8; | A53-B11-C9; | A54-B11-C1; | A54-B11-C2; | A54-B11-C3; |
| A54-B11-C4; | A54-B11-C5; | A54-B11-C6; | A54-B11-C7; | A54-B11-C8; | A54-B11-C9; |
| A55-B11-C1; | A55-B11-C2; | A55-B11-C3; | A55-B11-C4; | A55-B11-C5; | A55-B11-C6; |
| A55-B11-C7; | A55-B11-C8; | A55-B11-C9; | A56-B11-C1; | A56-B11-C2; | A56-B11-C3; |
| A56-B11-C4; | A56-B11-C5; | A56-B11-C6; | A56-B11-C7; | A56-B11-C8; | A56-B11-C9; |
| A57-B11-C1; | A57-B11-C2; | A57-B11-C3; | A57-B11-C4; | A57-B11-C5; | A57-B11-C6; |
| A57-B11-C7; | A57-B11-C8; | A57-B11-C9; | A58-B11-C1; | A58-B11-C2; | A58-B11-C3; |
| A58-B11-C4; | A58-B11-C5; | A58-B11-C6; | A58-B11-C7; | A58-B11-C8; | A58-B11-C9; |
| A59-B11-C1; | A59-B11-C2; | A59-B11-C3; | A59-B11-C4; | A59-B11-C5; | A59-B11-C6; |
| A59-B11-C7; | A59-B11-C8; | A59-B11-C9; | A60-B11-C1; | A60-B11-C2; | A60-B11-C3; |
| A60-B11-C4; | A60-B11-C5; | A60-B11-C6; | A60-B11-C7; | A60-B11-C8; | A60-B11-C9; |
| A61-B11-C1; | A61-B11-C2; | A61-B11-C3; | A61-B11-C4; | A61-B11-C5; | A61-B11-C6; |
| A61-B11-C7; | A61-B11-C8; | A61-B11-C9; | A62-B11-C1; | A62-B11-C2; | A62-B11-C3; |
| A62-B11-C4; | A62-B11-C5; | A62-B11-C6; | A62-B11-C7; | A62-B11-C8; | A62-B11-C9; |
| A63-B11-C1; | A63-B11-C2; | A63-B11-C3; | A63-B11-C4; | A63-B11-C5; | A63-B11-C6; |
| A63-B11-C7; | A63-B11-C8; | A63-B11-C9; | A64-B11-C1; | A64-B11-C2; | A64-B11-C3; |
| A64-B11-C4; | A64-B11-C5; | A64-B11-C6; | A64-B11-C7; | A64-B11-C8; | A64-B11-C9; |
| A65-B11-C1; | A65-B11-C2; | A65-B11-C3; | A65-B11-C4; | A65-B11-C5; | A65-B11-C6; |
| A65-B11-C7; | A65-B11-C8; | A65-B11-C9; | A66-B11-C1; | A66-B11-C2; | A66-B11-C3; |
| A66-B11-C4; | A66-B11-C5; | A66-B11-C6; | A66-B11-C7; | A66-B11-C8; | A66-B11-C9; |
| A67-B11-C1; | A67-B11-C2; | A67-B11-C3; | A67-B11-C4; | A67-B11-C5; | A67-B11-C6; |
| A67-B11-C7; | A67-B11-C8; | A67-B11-C9; | A68-B11-C1; | A68-B11-C2; | A68-B11-C3; |
| A68-B11-C4; | A68-B11-C5; | A68-B11-C6; | A68-B11-C7; | A68-B11-C8; | A68-B11-C9; |
| A69-B11-C1; | A69-B11-C2; | A69-B11-C3; | A69-B11-C4; | A69-B11-C5; | A69-B11-C6; |
| A69-B11-C7; | A69-B11-C8; | A69-B11-C9; | A70-B11-C1; | A70-B11-C2; | A70-B11-C3; |
| A70-B11-C4; | A70-B11-C5; | A70-B11-C6; | A70-B11-C7; | A70-B11-C8; | A70-B11-C9; |
| A71-B11-C1; | A71-B11-C2; | A71-B11-C3; | A71-B11-C4; | A71-B11-C5; | A71-B11-C6; |
| A71-B11-C7; | A71-B11-C8; | A71-B11-C9; | A1-B12-C1; | A1-B12-C2; | A1-B12-C3; |
| A1-B12-C4; | A1-B12-C5; | A1-B12-C6; | A1-B12-C7; | A1-B12-C8; | A1-B12-C9; |
| A2-B12-C1; | A2-B12-C2; | A2-B12-C3; | A2-B12-C4; | A2-B12-C5; | A2-B12-C6; |
| A2-B12-C7; | A2-B12-C8; | A2-B12-C9; | A3-B12-C1; | A3-B12-C2; | A3-B12-C3; |
| A3-B12-C4; | A3-B12-C5; | A3-B12-C6; | A3-B12-C7; | A3-B12-C8; | A3-B12-C9; |
| A4-B12-C1; | A4-B12-C2; | A4-B12-C3; | A4-B12-C4; | A4-B12-C5; | A4-B12-C6; |
| A4-B12-C7; | A4-B12-C8; | A4-B12-C9; | A5-B12-C1; | A5-B12-C2; | A5-B12-C3; |
| A5-B12-C4; | A5-B12-C5; | A5-B12-C6; | A5-B12-C7; | A5-B12-C8; | A5-B12-C9; |
| A6-B12-C1; | A6-B12-C2; | A6-B12-C3; | A6-B12-C4; | A6-B12-C5; | A6-B12-C6; |
| A6-B12-C7; | A6-B12-C8; | A6-B12-C9; | A7-B12-C1; | A7-B12-C2; | A7-B12-C3; |
| A7-B12-C4; | A7-B12-C5; | A7-B12-C6; | A7-B12-C7; | A7-B12-C8; | A7-B12-C9; |
| A8-B12-C1; | A8-B12-C2; | A8-B12-C3; | A8-B12-C4; | A8-B12-C5; | A8-B12-C6; |
| A8-B12-C7; | A8-B12-C8; | A8-B12-C9; | A9-B12-C1; | A9-B12-C2; | A9-B12-C3; |
| A9-B12-C4; | A9-B12-C5; | A9-B12-C6; | A9-B12-C7; | A9-B12-C8; | A9-B12-C9; |
| A10-B12-C1; | A10-B12-C2; | A10-B12-C3; | A10-B12-C4; | A10-B12-C5; | A10-B12-C6; |
| A10-B12-C7; | A10-B12-C8; | A10-B12-C9; | A11-B12-C1; | A11-B12-C2; | A11-B12-C3; |
| A11-B12-C4; | A11-B12-C5; | A11-B12-C6; | A11-B12-C7; | A11-B12-C8; | A11-B12-C9; |
| A12-B12-C1; | A12-B12-C2; | A12-B12-C3; | A12-B12-C4; | A12-B12-C5; | A12-B12-C6; |
| A12-B12-C7; | A12-B12-C8; | A12-B12-C9; | A13-B12-C1; | A13-B12-C2; | A13-B12-C3; |
| A13-B12-C4; | A13-B12-C5; | A13-B12-C6; | A13-B12-C7; | A13-B12-C8; | A13-B12-C9; |
| A14-B12-C1; | A14-B12-C2; | A14-B12-C3; | A14-B12-C4; | A14-B12-C5; | A14-B12-C6; |
| A14-B12-C7; | A14-B12-C8; | A14-B12-C9; | A15-B12-C1; | A15-B12-C2; | A15-B12-C3; |
| A15-B12-C4; | A15-B12-C5; | A15-B12-C6; | A15-B12-C7; | A15-B12-C8; | A15-B12-C9; |
| A16-B12-C1; | A16-B12-C2; | A16-B12-C3; | A16-B12-C4; | A16-B12-C5; | A16-B12-C6; |
| A16-B12-C7; | A16-B12-C8; | A16-B12-C9; | A17-B12-C1; | A17-B12-C2; | A17-B12-C3; |
| A17-B12-C4; | A17-B12-C5; | A17-B12-C6; | A17-B12-C7; | A17-B12-C8; | A17-B12-C9; |
| A18-B12-C1; | A18-B12-C2; | A18-B12-C3; | A18-B12-C4; | A18-B12-C5; | A18-B12-C6; |
| A18-B12-C7; | A18-B12-C8; | A18-B12-C9; | A19-B12-C1; | A19-B12-C2; | A19-B12-C3; |
| A19-B12-C4; | A19-B12-C5; | A19-B12-C6; | A19-B12-C7; | A19-B12-C8; | A19-B12-C9; |
| A20-B12-C1; | A20-B12-C2; | A20-B12-C3; | A20-B12-C4; | A20-B12-C5; | A20-B12-C6; |
| A20-B12-C7; | A20-B12-C8; | A20-B12-C9; | A21-B12-C1; | A21-B12-C2; | A21-B12-C3; |
| A21-B12-C4; | A21-B12-C5; | A21-B12-C6; | A21-B12-C7; | A21-B12-C8; | A21-B12-C9; |
| A22-B12-C1; | A22-B12-C2; | A22-B12-C3; | A22-B12-C4; | A22-B12-C5; | A22-B12-C6; |
| A22-B12-C7; | A22-B12-C8; | A22-B12-C9; | A23-B12-C1; | A23-B12-C2; | A23-B12-C3; |
| A23-B12-C4; | A23-B12-C5; | A23-B12-C6; | A23-B12-C7; | A23-B12-C8; | A23-B12-C9; |
| A24-B12-C1; | A24-B12-C2; | A24-B12-C3; | A24-B12-C4; | A24-B12-C5; | A24-B12-C6; |
| A24-B12-C7; | A24-B12-C8; | A24-B12-C9; | A25-B12-C1; | A25-B12-C2; | A25-B12-C3; |
| A25-B12-C4; | A25-B12-C5; | A25-B12-C6; | A25-B12-C7; | A25-B12-C8; | A25-B12-C9; |
| A26-B12-C1; | A26-B12-C2; | A26-B12-C3; | A26-B12-C4; | A26-B12-C5; | A26-B12-C6; |
| A26-B12-C7; | A26-B12-C8; | A26-B12-C9; | A27-B12-C1; | A27-B12-C2; | A27-B12-C3; |
| A27-B12-C4; | A27-B12-C5; | A27-B12-C6; | A27-B12-C7; | A27-B12-C8; | A27-B12-C9; |

| | | | | | |
|---|---|---|---|---|---|
| A28-B12-C1; | A28-B12-C2; | A28-B12-C3; | A28-B12-C4; | A28-B12-C5; | A28-B12-C6; |
| A28-B12-C7; | A28-B12-C8; | A28-B12-C9; | A29-B12-C1; | A29-B12-C2; | A29-B12-C3; |
| A29-B12-C4; | A29-B12-C5; | A29-B12-C6; | A29-B12-C7; | A29-B12-C8; | A29-B12-C9; |
| A30-B12-C1; | A30-B12-C2; | A30-B12-C3; | A30-B12-C4; | A30-B12-C5; | A30-B12-C6; |
| A30-B12-C7; | A30-B12-C8; | A30-B12-C9; | A31-B12-C1; | A31-B12-C2; | A31-B12-C3; |
| A31-B12-C4; | A31-B12-C5; | A31-B12-C6; | A31-B12-C7; | A31-B12-C8; | A31-B12-C9; |
| A32-B12-C1; | A32-B12-C2; | A32-B12-C3; | A32-B12-C4; | A32-B12-C5; | A32-B12-C6; |
| A32-B12-C7; | A32-B12-C8; | A32-B12-C9; | A33-B12-C1; | A33-B12-C2; | A33-B12-C3; |
| A33-B12-C4; | A33-B12-C5; | A33-B12-C6; | A33-B12-C7; | A33-B12-C8; | A33-B12-C9; |
| A34-B12-C1; | A34-B12-C2; | A34-B12-C3; | A34-B12-C4; | A34-B12-C5; | A34-B12-C6; |
| A34-B12-C7; | A34-B12-C8; | A34-B12-C9; | A35-B12-C1; | A35-B12-C2; | A35-B12-C3; |
| A35-B12-C4; | A35-B12-C5; | A35-B12-C6; | A35-B12-C7; | A35-B12-C8; | A35-B12-C9; |
| A36-B12-C1; | A36-B12-C2; | A36-B12-C3; | A36-B12-C4; | A36-B12-C5; | A36-B12-C6; |
| A36-B12-C7; | A36-B12-C8; | A36-B12-C9; | A37-B12-C1; | A37-B12-C2; | A37-B12-C3; |
| A37-B12-C4; | A37-B12-C5; | A37-B12-C6; | A37-B12-C7; | A37-B12-C8; | A37-B12-C9; |
| A38-B12-C1; | A38-B12-C2; | A38-B12-C3; | A38-B12-C4; | A38-B12-C5; | A38-B12-C6; |
| A38-B12-C7; | A38-B12-C8; | A38-B12-C9; | A39-B12-C1; | A39-B12-C2; | A39-B12-C3; |
| A39-B12-C4; | A39-B12-C5; | A39-B12-C6; | A39-B12-C7; | A39-B12-C8; | A39-B12-C9; |
| A40-B12-C1; | A40-B12-C2; | A40-B12-C3; | A40-B12-C4; | A40-B12-C5; | A40-B12-C6; |
| A40-B12-C7; | A40-B12-C8; | A40-B12-C9; | A41-B12-C1; | A41-B12-C2; | A41-B12-C3; |
| A41-B12-C4; | A41-B12-C5; | A41-B12-C6; | A41-B12-C7; | A41-B12-C8; | A41-B12-C9; |
| A42-B12-C1; | A42-B12-C2; | A42-B12-C3; | A42-B12-C4; | A42-B12-C5; | A42-B12-C6; |
| A42-B12-C7; | A42-B12-C8; | A42-B12-C9; | A43-B12-C1; | A43-B12-C2; | A43-B12-C3; |
| A43-B12-C4; | A43-B12-C5; | A43-B12-C6; | A43-B12-C7; | A43-B12-C8; | A43-B12-C9; |
| A44-B12-C1; | A44-B12-C2; | A44-B12-C3; | A44-B12-C4; | A44-B12-C5; | A44-B12-C6; |
| A44-B12-C7; | A44-B12-C8; | A44-B12-C9; | A45-B12-C1; | A45-B12-C2; | A45-B12-C3; |
| A45-B12-C4; | A45-B12-C5; | A45-B12-C6; | A45-B12-C7; | A45-B12-C8; | A45-B12-C9; |
| A46-B12-C1; | A46-B12-C2; | A46-B12-C3; | A46-B12-C4; | A46-B12-C5; | A46-B12-C6; |
| A46-B12-C7; | A46-B12-C8; | A46-B12-C9; | A47-B12-C1; | A47-B12-C2; | A47-B12-C3; |
| A47-B12-C4; | A47-B12-C5; | A47-B12-C6; | A47-B12-C7; | A47-B12-C8; | A47-B12-C9; |
| A48-B12-C1; | A48-B12-C2; | A48-B12-C3; | A48-B12-C4; | A48-B12-C5; | A48-B12-C6; |
| A48-B12-C7; | A48-B12-C8; | A48-B12-C9; | A49-B12-C1; | A49-B12-C2; | A49-B12-C3; |
| A49-B12-C4; | A49-B12-C5; | A49-B12-C6; | A49-B12-C7; | A49-B12-C8; | A49-B12-C9; |
| A50-B12-C1; | A50-B12-C2; | A50-B12-C3; | A50-B12-C4; | A50-B12-C5; | A50-B12-C6; |
| A50-B12-C7; | A50-B12-C8; | A50-B12-C9; | A51-B12-C1; | A51-B12-C2; | A51-B12-C3; |
| A51-B12-C4; | A51-B12-C5; | A51-B12-C6; | A51-B12-C7; | A51-B12-C8; | A51-B12-C9; |
| A52-B12-C1; | A52-B12-C2; | A52-B12-C3; | A52-B12-C4; | A52-B12-C5; | A52-B12-C6; |
| A52-B12-C7; | A52-B12-C8; | A52-B12-C9; | A53-B12-C1; | A53-B12-C2; | A53-B12-C3; |
| A53-B12-C4; | A53-B12-C5; | A53-B12-C6; | A53-B12-C7; | A53-B12-C8; | A53-B12-C9; |
| A54-B12-C1; | A54-B12-C2; | A54-B12-C3; | A54-B12-C4; | A54-B12-C5; | A54-B12-C6; |
| A54-B12-C7; | A54-B12-C8; | A54-B12-C9; | A55-B12-C1; | A55-B12-C2; | A55-B12-C3; |
| A55-B12-C4; | A55-B12-C5; | A55-B12-C6; | A55-B12-C7; | A55-B12-C8; | A55-B12-C9; |
| A56-B12-C1; | A56-B12-C2; | A56-B12-C3; | A56-B12-C4; | A56-B12-C5; | A56-B12-C6; |
| A56-B12-C7; | A56-B12-C8; | A56-B12-C9; | A57-B12-C1; | A57-B12-C2; | A57-B12-C3; |
| A57-B12-C4; | A57-B12-C5; | A57-B12-C6; | A57-B12-C7; | A57-B12-C8; | A57-B12-C9; |
| A58-B12-C1; | A58-B12-C2; | A58-B12-C3; | A58-B12-C4; | A58-B12-C5; | A58-B12-C6; |
| A58-B12-C7; | A58-B12-C8; | A58-B12-C9; | A59-B12-C1; | A59-B12-C2; | A59-B12-C3; |
| A59-B12-C4; | A59-B12-C5; | A59-B12-C6; | A59-B12-C7; | A59-B12-C8; | A59-B12-C9; |
| A60-B12-C1; | A60-B12-C2; | A60-B12-C3; | A60-B12-C4; | A60-B12-C5; | A60-B12-C6; |
| A60-B12-C7; | A60-B12-C8; | A60-B12-C9; | A61-B12-C1; | A61-B12-C2; | A61-B12-C3; |
| A61-B12-C4; | A61-B12-C5; | A61-B12-C6; | A61-B12-C7; | A61-B12-C8; | A61-B12-C9; |
| A62-B12-C1; | A62-B12-C2; | A62-B12-C3; | A62-B12-C4; | A62-B12-C5; | A62-B12-C6; |
| A62-B12-C7; | A62-B12-C8; | A62-B12-C9; | A63-B12-C1; | A63-B12-C2; | A63-B12-C3; |
| A63-B12-C4; | A63-B12-C5; | A63-B12-C6; | A63-B12-C7; | A63-B12-C8; | A63-B12-C9; |
| A64-B12-C1; | A64-B12-C2; | A64-B12-C3; | A64-B12-C4; | A64-B12-C5; | A64-B12-C6; |
| A64-B12-C7; | A64-B12-C8; | A64-B12-C9; | A65-B12-C1; | A65-B12-C2; | A65-B12-C3; |
| A65-B12-C4; | A65-B12-C5; | A65-B12-C6; | A65-B12-C7; | A65-B12-C8; | A65-B12-C9; |
| A66-B12-C1; | A66-B12-C2; | A66-B12-C3; | A66-B12-C4; | A66-B12-C5; | A66-B12-C6; |
| A66-B12-C7; | A66-B12-C8; | A66-B12-C9; | A67-B12-C1; | A67-B12-C2; | A67-B12-C3; |
| A67-B12-C4; | A67-B12-C5; | A67-B12-C6; | A67-B12-C7; | A67-B12-C8; | A67-B12-C9; |
| A68-B12-C1; | A68-B12-C2; | A68-B12-C3; | A68-B12-C4; | A68-B12-C5; | A68-B12-C6; |
| A68-B12-C7; | A68-B12-C8; | A68-B12-C9; | A69-B12-C1; | A69-B12-C2; | A69-B12-C3; |
| A69-B12-C4; | A69-B12-C5; | A69-B12-C6; | A69-B12-C7; | A69-B12-C8; | A69-B12-C9; |
| A70-B12-C1; | A70-B12-C2; | A70-B12-C3; | A70-B12-C4; | A70-B12-C5; | A70-B12-C6; |
| A70-B12-C7; | A70-B12-C8; | A70-B12-C9; | A71-B12-C1; | A71-B12-C2; | A71-B12-C3; |
| A71-B12-C4; | A71-B12-C5; | A71-B12-C6; | A71-B12-C7; | A71-B12-C8; | A71-B12-C9; |
| A1-B13-C1; | A1-B13-C2; | A1-B13-C3; | A1-B13-C4; | A1-B13-C5; | A1-B13-C6; |
| A1-B13-C7; | A1-B13-C8; | A1-B13-C9; | A2-B13-C1; | A2-B13-C2; | A2-B13-C3; |
| A2-B13-C4; | A2-B13-C5; | A2-B13-C6; | A2-B13-C7; | A2-B13-C8; | A2-B13-C9; |
| A3-B13-C1; | A3-B13-C2; | A3-B13-C3; | A3-B13-C4; | A3-B13-C5; | A3-B13-C6; |
| A3-B13-C7; | A3-B13-C8; | A3-B13-C9; | A4-B13-C1; | A4-B13-C2; | A4-B13-C3; |
| A4-B13-C4; | A4-B13-C5; | A4-B13-C6; | A4-B13-C7; | A4-B13-C8; | A4-B13-C9; |
| A5-B13-C1; | A5-B13-C2; | A5-B13-C3; | A5-B13-C4; | A5-B13-C5; | A5-B13-C6; |
| A5-B13-C7; | A5-B13-C8; | A5-B13-C9; | A6-B13-C1; | A6-B13-C2; | A6-B13-C3; |
| A6-B13-C4; | A6-B13-C5; | A6-B13-C6; | A6-B13-C7; | A6-B13-C8; | A6-B13-C9; |
| A7-B13-C1; | A7-B13-C2; | A7-B13-C3; | A7-B13-C4; | A7-B13-C5; | A7-B13-C6; |
| A7-B13-C7; | A7-B13-C8; | A7-B13-C9; | A8-B13-C1; | A8-B13-C2; | A8-B13-C3; |
| A8-B13-C4; | A8-B13-C5; | A8-B13-C6; | A8-B13-C7; | A8-B13-C8; | A8-B13-C9; |
| A9-B13-C1; | A9-B13-C2; | A9-B13-C3; | A9-B13-C4; | A9-B13-C5; | A9-B13-C6; |

-continued

| | | | | | |
|---|---|---|---|---|---|
| A9-B13-C7; | A9-B13-C8; | A9-B13-C9; | A10-B13-C1; | A10-B13-C2; | A10-B13-C3; |
| A10-B13-C4; | A10-B13-C5; | A10-B13-C6; | A10-B13-C7; | A10-B13-C8; | A10-B13-C9; |
| A11-B13-C1; | A11-B13-C2; | A11-B13-C3; | A11-B13-C4; | A11-B13-C5; | A11-B13-C6; |
| A11-B13-C7; | A11-B13-C8; | A11-B13-C9; | A12-B13-C1; | A12-B13-C2; | A12-B13-C3; |
| A12-B13-C4; | A12-B13-C5; | A12-B13-C6; | A12-B13-C7; | A12-B13-C8; | A12-B13-C9; |
| A13-B13-C1; | A13-B13-C2; | A13-B13-C3; | A13-B13-C4; | A13-B13-C5; | A13-B13-C6; |
| A13-B13-C7; | A13-B13-C8; | A13-B13-C9; | A14-B13-C1; | A14-B13-C2; | A14-B13-C3; |
| A14-B13-C4; | A14-B13-C5; | A14-B13-C6; | A14-B13-C7; | A14-B13-C8; | A14-B13-C9; |
| A15-B13-C1; | A15-B13-C2; | A15-B13-C3; | A15-B13-C4; | A15-B13-C5; | A15-B13-C6; |
| A15-B13-C7; | A15-B13-C8; | A15-B13-C9; | A16-B13-C1; | A16-B13-C2; | A16-B13-C3; |
| A16-B13-C4; | A16-B13-C5; | A16-B13-C6; | A16-B13-C7; | A16-B13-C8; | A16-B13-C9; |
| A17-B13-C1; | A17-B13-C2; | A17-B13-C3; | A17-B13-C4; | A17-B13-C5; | A17-B13-C6; |
| A17-B13-C7; | A17-B13-C8; | A17-B13-C9; | A18-B13-C1; | A18-B13-C2; | A18-B13-C3; |
| A18-B13-C4; | A18-B13-C5; | A18-B13-C6; | A18-B13-C7; | A18-B13-C8; | A18-B13-C9; |
| A19-B13-C1; | A19-B13-C2; | A19-B13-C3; | A19-B13-C4; | A19-B13-C5; | A19-B13-C6; |
| A19-B13-C7; | A19-B13-C8; | A19-B13-C9; | A20-B13-C1; | A20-B13-C2; | A20-B13-C3; |
| A20-B13-C4; | A20-B13-C5; | A20-B13-C6; | A20-B13-C7; | A20-B13-C8; | A20-B13-C9; |
| A21-B13-C1; | A21-B13-C2; | A21-B13-C3; | A21-B13-C4; | A21-B13-C5; | A21-B13-C6; |
| A21-B13-C7; | A21-B13-C8; | A21-B13-C9; | A22-B13-C1; | A22-B13-C2; | A22-B13-C3; |
| A22-B13-C4; | A22-B13-C5; | A22-B13-C6; | A22-B13-C7; | A22-B13-C8; | A22-B13-C9; |
| A23-B13-C1; | A23-B13-C2; | A23-B13-C3; | A23-B13-C4; | A23-B13-C5; | A23-B13-C6; |
| A23-B13-C7; | A23-B13-C8; | A23-B13-C9; | A24-B13-C1; | A24-B13-C2; | A24-B13-C3; |
| A24-B13-C4; | A24-B13-C5; | A24-B13-C6; | A24-B13-C7; | A24-B13-C8; | A24-B13-C9; |
| A25-B13-C1; | A25-B13-C2; | A25-B13-C3; | A25-B13-C4; | A25-B13-C5; | A25-B13-C6; |
| A25-B13-C7; | A25-B13-C8; | A25-B13-C9; | A26-B13-C1; | A26-B13-C2; | A26-B13-C3; |
| A26-B13-C4; | A26-B13-C5; | A26-B13-C6; | A26-B13-C7; | A26-B13-C8; | A26-B13-C9; |
| A27-B13-C1; | A27-B13-C2; | A27-B13-C3; | A27-B13-C4; | A27-B13-C5; | A27-B13-C6; |
| A27-B13-C7; | A27-B13-C8; | A27-B13-C9; | A28-B13-C1; | A28-B13-C2; | A28-B13-C3; |
| A28-B13-C4; | A28-B13-C5; | A28-B13-C6; | A28-B13-C7; | A28-B13-C8; | A28-B13-C9; |
| A29-B13-C1; | A29-B13-C2; | A29-B13-C3; | A29-B13-C4; | A29-B13-C5; | A29-B13-C6; |
| A29-B13-C7; | A29-B13-C8; | A29-B13-C9; | A30-B13-C1; | A30-B13-C2; | A30-B13-C3; |
| A30-B13-C4; | A30-B13-C5; | A30-B13-C6; | A30-B13-C7; | A30-B13-C8; | A30-B13-C9; |
| A31-B13-C1; | A31-B13-C2; | A31-B13-C3; | A31-B13-C4; | A31-B13-C5; | A31-B13-C6; |
| A31-B13-C7; | A31-B13-C8; | A31-B13-C9; | A32-B13-C1; | A32-B13-C2; | A32-B13-C3; |
| A32-B13-C4; | A32-B13-C5; | A32-B13-C6; | A32-B13-C7; | A32-B13-C8; | A32-B13-C9; |
| A33-B13-C1; | A33-B13-C2; | A33-B13-C3; | A33-B13-C4; | A33-B13-C5; | A33-B13-C6; |
| A33-B13-C7; | A33-B13-C8; | A33-B13-C9; | A34-B13-C1; | A34-B13-C2; | A34-B13-C3; |
| A34-B13-C4; | A34-B13-C5; | A34-B13-C6; | A34-B13-C7; | A34-B13-C8; | A34-B13-C9; |
| A35-B13-C1; | A35-B13-C2; | A35-B13-C3; | A35-B13-C4; | A35-B13-C5; | A35-B13-C6; |
| A35-B13-C7; | A35-B13-C8; | A35-B13-C9; | A36-B13-C1; | A36-B13-C2; | A36-B13-C3; |
| A36-B13-C4; | A36-B13-C5; | A36-B13-C6; | A36-B13-C7; | A36-B13-C8; | A36-B13-C9; |
| A37-B13-C1; | A37-B13-C2; | A37-B13-C3; | A37-B13-C4; | A37-B13-C5; | A37-B13-C6; |
| A37-B13-C7; | A37-B13-C8; | A37-B13-C9; | A38-B13-C1; | A38-B13-C2; | A38-B13-C3; |
| A38-B13-C4; | A38-B13-C5; | A38-B13-C6; | A38-B13-C7; | A38-B13-C8; | A38-B13-C9; |
| A39-B13-C1; | A39-B13-C2; | A39-B13-C3; | A39-B13-C4; | A39-B13-C5; | A39-B13-C6; |
| A39-B13-C7; | A39-B13-C8; | A39-B13-C9; | A40-B13-C1; | A40-B13-C2; | A40-B13-C3; |
| A40-B13-C4; | A40-B13-C5; | A40-B13-C6; | A40-B13-C7; | A40-B13-C8; | A40-B13-C9; |
| A41-B13-C1; | A41-B13-C2; | A41-B13-C3; | A41-B13-C4; | A41-B13-C5; | A41-B13-C6; |
| A41-B13-C7; | A41-B13-C8; | A41-B13-C9; | A42-B13-C1; | A42-B13-C2; | A42-B13-C3; |
| A42-B13-C4; | A42-B13-C5; | A42-B13-C6; | A42-B13-C7; | A42-B13-C8; | A42-B13-C9; |
| A43-B13-C1; | A43-B13-C2; | A43-B13-C3; | A43-B13-C4; | A43-B13-C5; | A43-B13-C6; |
| A43-B13-C7; | A43-B13-C8; | A43-B13-C9; | A44-B13-C1; | A44-B13-C2; | A44-B13-C3; |
| A44-B13-C4; | A44-B13-C5; | A44-B13-C6; | A44-B13-C7; | A44-B13-C8; | A44-B13-C9; |
| A45-B13-C1; | A45-B13-C2; | A45-B13-C3; | A45-B13-C4; | A45-B13-C5; | A45-B13-C6; |
| A45-B13-C7; | A45-B13-C8; | A45-B13-C9; | A46-B13-C1; | A46-B13-C2; | A46-B13-C3; |
| A46-B13-C4; | A46-B13-C5; | A46-B13-C6; | A46-B13-C7; | A46-B13-C8; | A46-B13-C9; |
| A47-B13-C1; | A47-B13-C2; | A47-B13-C3; | A47-B13-C4; | A47-B13-C5; | A47-B13-C6; |
| A47-B13-C7; | A47-B13-C8; | A47-B13-C9; | A48-B13-C1; | A48-B13-C2; | A48-B13-C3; |
| A48-B13-C4; | A48-B13-C5; | A48-B13-C6; | A48-B13-C7; | A48-B13-C8; | A48-B13-C9; |
| A49-B13-C1; | A49-B13-C2; | A49-B13-C3; | A49-B13-C4; | A49-B13-C5; | A49-B13-C6; |
| A49-B13-C7; | A49-B13-C8; | A49-B13-C9; | A50-B13-C1; | A50-B13-C2; | A50-B13-C3; |
| A50-B13-C4; | A50-B13-C5; | A50-B13-C6; | A50-B13-C7; | A50-B13-C8; | A50-B13-C9; |
| A51-B13-C1; | A51-B13-C2; | A51-B13-C3; | A51-B13-C4; | A51-B13-C5; | A51-B13-C6; |
| A51-B13-C7; | A51-B13-C8; | A51-B13-C9; | A52-B13-C1; | A52-B13-C2; | A52-B13-C3; |
| A52-B13-C4; | A52-B13-C5; | A52-B13-C6; | A52-B13-C7; | A52-B13-C8; | A52-B13-C9; |
| A53-B13-C1; | A53-B13-C2; | A53-B13-C3; | A53-B13-C4; | A53-B13-C5; | A53-B13-C6; |
| A53-B13-C7; | A53-B13-C8; | A53-B13-C9; | A54-B13-C1; | A54-B13-C2; | A54-B13-C3; |
| A54-B13-C4; | A54-B13-C5; | A54-B13-C6; | A54-B13-C7; | A54-B13-C8; | A54-B13-C9; |
| A55-B13-C1; | A55-B13-C2; | A55-B13-C3; | A55-B13-C4; | A55-B13-C5; | A55-B13-C6; |
| A55-B13-C7; | A55-B13-C8; | A55-B13-C9; | A56-B13-C1; | A56-B13-C2; | A56-B13-C3; |
| A56-B13-C4; | A56-B13-C5; | A56-B13-C6; | A56-B13-C7; | A56-B13-C8; | A56-B13-C9; |
| A57-B13-C1; | A57-B13-C2; | A57-B13-C3; | A57-B13-C4; | A57-B13-C5; | A57-B13-C6; |
| A57-B13-C7; | A57-B13-C8; | A57-B13-C9; | A58-B13-C1; | A58-B13-C2; | A58-B13-C3; |
| A58-B13-C4; | A58-B13-C5; | A58-B13-C6; | A58-B13-C7; | A58-B13-C8; | A58-B13-C9; |
| A59-B13-C1; | A59-B13-C2; | A59-B13-C3; | A59-B13-C4; | A59-B13-C5; | A59-B13-C6; |
| A59-B13-C7; | A59-B13-C8; | A59-B13-C9; | A60-B13-C1; | A60-B13-C2; | A60-B13-C3; |
| A60-B13-C4; | A60-B13-C5; | A60-B13-C6; | A60-B13-C7; | A60-B13-C8; | A60-B13-C9; |
| A61-B13-C1; | A61-B13-C2; | A61-B13-C3; | A61-B13-C4; | A61-B13-C5; | A61-B13-C6; |
| A61-B13-C7; | A61-B13-C8; | A61-B13-C9; | A62-B13-C1; | A62-B13-C2; | A62-B13-C3; |

-continued

| | | | | | |
|---|---|---|---|---|---|
| A62-B13-C4; | A62-B13-C5; | A62-B13-C6; | A62-B13-C7; | A62-B13-C8; | A62-B13-C9; |
| A63-B13-C1; | A63-B13-C2; | A63-B13-C3; | A63-B13-C4; | A63-B13-C5; | A63-B13-C6; |
| A63-B13-C7; | A63-B13-C8; | A63-B13-C9; | A64-B13-C1; | A64-B13-C2; | A64-B13-C3; |
| A64-B13-C4; | A64-B13-C5; | A64-B13-C6; | A64-B13-C7; | A64-B13-C8; | A64-B13-C9; |
| A65-B13-C1; | A65-B13-C2; | A65-B13-C3; | A65-B13-C4; | A65-B13-C5; | A65-B13-C6; |
| A65-B13-C7; | A65-B13-C8; | A65-B13-C9; | A66-B13-C1; | A66-B13-C2; | A66-B13-C3; |
| A66-B13-C4; | A66-B13-C5; | A66-B13-C6; | A66-B13-C7; | A66-B13-C8; | A66-B13-C9; |
| A67-B13-C1; | A67-B13-C2; | A67-B13-C3; | A67-B13-C4; | A67-B13-C5; | A67-B13-C6; |
| A67-B13-C7; | A67-B13-C8; | A67-B13-C9; | A68-B13-C1; | A68-B13-C2; | A68-B13-C3; |
| A68-B13-C4; | A68-B13-C5; | A68-B13-C6; | A68-B13-C7; | A68-B13-C8; | A68-B13-C9; |
| A69-B13-C1; | A69-B13-C2; | A69-B13-C3; | A69-B13-C4; | A69-B13-C5; | A69-B13-C6; |
| A69-B13-C7; | A69-B13-C8; | A69-B13-C9; | A70-B13-C1; | A70-B13-C2; | A70-B13-C3; |
| A70-B13-C4; | A70-B13-C5; | A70-B13-C6; | A70-B13-C7; | A70-B13-C8; | A70-B13-C9; |
| A71-B13-C1; | A71-B13-C2; | A71-B13-C3; | A71-B13-C4; | A71-B13-C5; | A71-B13-C6; |
| A71-B13-C7; | A71-B13-C8; | A71-B13-C9; | A1-B14-C1; | A1-B14-C2; | A1-B14-C3; |
| A1-B14-C4; | A1-B14-C5; | A1-B14-C6; | A1-B14-C7; | A1-B14-C8; | A1-B14-C9; |
| A2-B14-C1; | A2-B14-C2; | A2-B14-C3; | A2-B14-C4; | A2-B14-C5; | A2-B14-C6; |
| A2-B14-C7; | A2-B14-C8; | A2-B14-C9; | A3-B14-C1; | A3-B14-C2; | A3-B14-C3; |
| A3-B14-C4; | A3-B14-C5; | A3-B14-C6; | A3-B14-C7; | A3-B14-C8; | A3-B14-C9; |
| A4-B14-C1; | A4-B14-C2; | A4-B14-C3; | A4-B14-C4; | A4-B14-C5; | A4-B14-C6; |
| A4-B14-C7; | A4-B14-C8; | A4-B14-C9; | A5-B14-C1; | A5-B14-C2; | A5-B14-C3; |
| A5-B14-C4; | A5-B14-C5; | A5-B14-C6; | A5-B14-C7; | A5-B14-C8; | A5-B14-C9; |
| A6-B14-C1; | A6-B14-C2; | A6-B14-C3; | A6-B14-C4; | A6-B14-C5; | A6-B14-C6; |
| A6-B14-C7; | A6-B14-C8; | A6-B14-C9; | A7-B14-C1; | A7-B14-C2; | A7-B14-C3; |
| A7-B14-C4; | A7-B14-C5; | A7-B14-C6; | A7-B14-C7; | A7-B14-C8; | A7-B14-C9; |
| A8-B14-C1; | A8-B14-C2; | A8-B14-C3; | A8-B14-C4; | A8-B14-C5; | A8-B14-C6; |
| A8-B14-C7; | A8-B14-C8; | A8-B14-C9; | A9-B14-C1; | A9-B14-C2; | A9-B14-C3; |
| A9-B14-C4; | A9-B14-C5; | A9-B14-C6; | | | |
| A10-B14-C1; | A10-B14-C2; | A10-B14-C3; | A10-B14-C4; | A10-B14-C5; | A10-B14-C6; |
| A10-B14-C7; | A10-B14-C8; | A10-B14-C9; | A11-B14-C1; | A11-B14-C2; | A11-B14-C3; |
| A11-B14-C4; | A11-B14-C5; | A11-B14-C6; | A11-B14-C7; | A11-B14-C8; | A11-B14-C9; |
| A12-B14-C1; | A12-B14-C2; | A12-B14-C3; | A12-B14-C4; | A12-B14-C5; | A12-B14-C6; |
| A12-B14-C7; | A12-B14-C8; | A12-B14-C9; | A13-B14-C1; | A13-B14-C2; | A13-B14-C3; |
| A13-B14-C4; | A13-B14-C5; | A13-B14-C6; | A13-B14-C7; | A13-B14-C8; | A13-B14-C9; |
| A14-B14-C1; | A14-B14-C2; | A14-B14-C3; | A14-B14-C4; | A14-B14-C5; | A14-B14-C6; |
| A14-B14-C7; | A14-B14-C8; | A14-B14-C9; | A15-B14-C1; | A15-B14-C2; | A15-B14-C3; |
| A15-B14-C4; | A15-B14-C5; | A15-B14-C6; | A15-B14-C7; | A15-B14-C8; | A15-B14-C9; |
| A16-B14-C1; | A16-B14-C2; | A16-B14-C3; | A16-B14-C4; | A16-B14-C5; | A16-B14-C6; |
| A16-B14-C7; | A16-B14-C8; | A16-B14-C9; | A17-B14-C1; | A17-B14-C2; | A17-B14-C3; |
| A17-B14-C4; | A17-B14-C5; | A17-B14-C6; | A17-B14-C7; | A17-B14-C8; | A17-B14-C9; |
| A18-B14-C1; | A18-B14-C2; | A18-B14-C3; | A18-B14-C4; | A18-B14-C5; | A18-B14-C6; |
| A18-B14-C7; | A18-B14-C8; | A18-B14-C9; | A19-B14-C1; | A19-B14-C2; | A19-B14-C3; |
| A19-B14-C4; | A19-B14-C5; | A19-B14-C6; | A19-B14-C7; | A19-B14-C8; | A19-B14-C9; |
| A20-B14-C1; | A20-B14-C2; | A20-B14-C3; | A20-B14-C4; | A20-B14-C5; | A20-B14-C6; |
| A20-B14-C7; | A20-B14-C8; | A20-B14-C9; | A21-B14-C1; | A21-B14-C2; | A21-B14-C3; |
| A21-B14-C4; | A21-B14-C5; | A21-B14-C6; | A21-B14-C7; | A21-B14-C8; | A21-B14-C9; |
| A22-B14-C1; | A22-B14-C2; | A22-B14-C3; | A22-B14-C4; | A22-B14-C5; | A22-B14-C6; |
| A22-B14-C7; | A22-B14-C8; | A22-B14-C9; | A23-B14-C1; | A23-B14-C2; | A23-B14-C3; |
| A23-B14-C4; | A23-B14-C5; | A23-B14-C6; | A23-B14-C7; | A23-B14-C8; | A23-B14-C9; |
| A24-B14-C1; | A24-B14-C2; | A24-B14-C3; | A24-B14-C4; | A24-B14-C5; | A24-B14-C6; |
| A24-B14-C7; | A24-B14-C8; | A24-B14-C9; | A25-B14-C1; | A25-B14-C2; | A25-B14-C3; |
| A25-B14-C4; | A25-B14-C5; | A25-B14-C6; | A25-B14-C7; | A25-B14-C8; | A25-B14-C9; |
| A26-B14-C1; | A26-B14-C2; | A26-B14-C3; | A26-B14-C4; | A26-B14-C5; | A26-B14-C6; |
| A26-B14-C7; | A26-B14-C8; | A26-B14-C9; | A27-B14-C1; | A27-B14-C2; | A27-B14-C3; |
| A27-B14-C4; | A27-B14-C5; | A27-B14-C6; | A27-B14-C7; | A27-B14-C8; | A27-B14-C9; |
| A28-B14-C1; | A28-B14-C2; | A28-B14-C3; | A28-B14-C4; | A28-B14-C5; | A28-B14-C6; |
| A28-B14-C7; | A28-B14-C8; | A28-B14-C9; | A29-B14-C1; | A29-B14-C2; | A29-B14-C3; |
| A29-B14-C4; | A29-B14-C5; | A29-B14-C6; | A29-B14-C7; | A29-B14-C8; | A29-B14-C9; |
| A30-B14-C1; | A30-B14-C2; | A30-B14-C3; | A30-B14-C4; | A30-B14-C5; | A30-B14-C6; |
| A30-B14-C7; | A30-B14-C8; | A30-B14-C9; | A31-B14-C1; | A31-B14-C2; | A31-B14-C3; |
| A31-B14-C4; | A31-B14-C5; | A31-B14-C6; | A31-B14-C7; | A31-B14-C8; | A31-B14-C9; |
| A32-B14-C1; | A32-B14-C2; | A32-B14-C3; | A32-B14-C4; | A32-B14-C5; | A32-B14-C6; |
| A32-B14-C7; | A32-B14-C8; | A32-B14-C9; | A33-B14-C1; | A33-B14-C2; | A33-B14-C3; |
| A33-B14-C4; | A33-B14-C5; | A33-B14-C6; | A33-B14-C7; | A33-B14-C8; | A33-B14-C9; |
| A34-B14-C1; | A34-B14-C2; | A34-B14-C3; | A34-B14-C4; | A34-B14-C5; | A34-B14-C6; |
| A34-B14-C7; | A34-B14-C8; | A34-B14-C9; | A35-B14-C1; | A35-B14-C2; | A35-B14-C3; |
| A35-B14-C4; | A35-B14-C5; | A35-B14-C6; | A35-B14-C7; | A35-B14-C8; | A35-B14-C9; |
| A36-B14-C1; | A36-B14-C2; | A36-B14-C3; | A36-B14-C4; | A36-B14-C5; | A36-B14-C6; |
| A36-B14-C7; | A36-B14-C8; | A36-B14-C9; | A37-B14-C1; | A37-B14-C2; | A37-B14-C3; |
| A37-B14-C4; | A37-B14-C5; | A37-B14-C6; | A37-B14-C7; | A37-B14-C8; | A37-B14-C9; |
| A38-B14-C1; | A38-B14-C2; | A38-B14-C3; | A38-B14-C4; | A38-B14-C5; | A38-B14-C6; |
| A38-B14-C7; | A38-B14-C8; | A38-B14-C9; | A39-B14-C1; | A39-B14-C2; | A39-B14-C3; |
| A39-B14-C4; | A39-B14-C5; | A39-B14-C6; | A39-B14-C7; | A39-B14-C8; | A39-B14-C9; |
| A40-B14-C1; | A40-B14-C2; | A40-B14-C3; | A40-B14-C4; | A40-B14-C5; | A40-B14-C6; |
| A40-B14-C7; | A40-B14-C8; | A40-B14-C9; | A41-B14-C1; | A41-B14-C2; | A41-B14-C3; |
| A41-B14-C4; | A41-B14-C5; | A41-B14-C6; | A41-B14-C7; | A41-B14-C8; | A41-B14-C9; |
| A42-B14-C1; | A42-B14-C2; | A42-B14-C3; | A42-B14-C4; | A42-B14-C5; | A42-B14-C6; |
| A42-B14-C7; | A42-B14-C8; | A42-B14-C9; | A43-B14-C1; | A43-B14-C2; | A43-B14-C3; |
| A43-B14-C4; | A43-B14-C5; | A43-B14-C6; | A43-B14-C7; | A43-B14-C8; | A43-B14-C9; |

-continued

| | | | | | |
|---|---|---|---|---|---|
| A44-B14-C1; | A44-B14-C2; | A44-B14-C3; | A44-B14-C4; | A44-B14-C5; | A44-B14-C6; |
| A44-B14-C7; | A44-B14-C8; | A44-B14-C9; | A45-B14-C1; | A45-B14-C2; | A45-B14-C3; |
| A45-B14-C4; | A45-B14-C5; | A45-B14-C6; | A45-B14-C7; | A45-B14-C8; | A45-B14-C9; |
| A46-B14-C1; | A46-B14-C2; | A46-B14-C3; | A46-B14-C4; | A46-B14-C5; | A46-B14-C6; |
| A46-B14-C7; | A46-B14-C8; | A46-B14-C9; | A47-B14-C1; | A47-B14-C2; | A47-B14-C3; |
| A47-B14-C4; | A47-B14-C5; | A47-B14-C6; | A47-B14-C7; | A47-B14-C8; | A47-B14-C9; |
| A48-B14-C1; | A48-B14-C2; | A48-B14-C3; | A48-B14-C4; | A48-B14-C5; | A48-B14-C6; |
| A48-B14-C7; | A48-B14-C8; | A48-B14-C9; | A49-B14-C1; | A49-B14-C2; | A49-B14-C3; |
| A49-B14-C4; | A49-B14-C5; | A49-B14-C6; | A49-B14-C7; | A49-B14-C8; | A49-B14-C9; |
| A50-B14-C1; | A50-B14-C2; | A50-B14-C3; | A50-B14-C4; | A50-B14-C5; | A50-B14-C6; |
| A50-B14-C7; | A50-B14-C8; | A50-B14-C9; | A51-B14-C1; | A51-B14-C2; | A51-B14-C3; |
| A51-B14-C4; | A51-B14-C5; | A51-B14-C6; | A51-B14-C7; | A51-B14-C8; | A51-B14-C9; |
| A52-B14-C1; | A52-B14-C2; | A52-B14-C3; | A52-B14-C4; | A52-B14-C5; | A52-B14-C6; |
| A52-B14-C7; | A52-B14-C8; | A52-B14-C9; | A53-B14-C1; | A53-B14-C2; | A53-B14-C3; |
| A53-B14-C4; | A53-B14-C5; | A53-B14-C6; | A53-B14-C7; | A53-B14-C8; | A53-B14-C9; |
| A54-B14-C1; | A54-B14-C2; | A54-B14-C3; | A54-B14-C4; | A54-B14-C5; | A54-B14-C6; |
| A54-B14-C7; | A54-B14-C8; | A54-B14-C9; | A55-B14-C1; | A55-B14-C2; | A55-B14-C3; |
| A55-B14-C4; | A55-B14-C5; | A55-B14-C6; | A55-B14-C7; | A55-B14-C8; | A55-B14-C9; |
| A56-B14-C1; | A56-B14-C2; | A56-B14-C3; | A56-B14-C4; | A56-B14-C5; | A56-B14-C6; |
| A56-B14-C7; | A56-B14-C8; | A56-B14-C9; | A57-B14-C1; | A57-B14-C2; | A57-B14-C3; |
| A57-B14-C4; | A57-B14-C5; | A57-B14-C6; | A57-B14-C7; | A57-B14-C8; | A57-B14-C9; |
| A58-B14-C1; | A58-B14-C2; | A58-B14-C3; | A58-B14-C4; | A58-B14-C5; | A58-B14-C6; |
| A58-B14-C7; | A58-B14-C8; | A58-B14-C9; | A59-B14-C1; | A59-B14-C2; | A59-B14-C3; |
| A59-B14-C4; | A59-B14-C5; | A59-B14-C6; | A59-B14-C7; | A59-B14-C8; | A59-B14-C9; |
| A60-B14-C1; | A60-B14-C2; | A60-B14-C3; | A60-B14-C4; | A60-B14-C5; | A60-B14-C6; |
| A60-B14-C7; | A60-B14-C8; | A60-B14-C9; | A61-B14-C1; | A61-B14-C2; | A61-B14-C3; |
| A61-B14-C4; | A61-B14-C5; | A61-B14-C6; | A61-B14-C7; | A61-B14-C8; | A61-B14-C9; |
| A62-B14-C1; | A62-B14-C2; | A62-B14-C3; | A62-B14-C4; | A62-B14-C5; | A62-B14-C6; |
| A62-B14-C7; | A62-B14-C8; | A62-B14-C9; | A63-B14-C1; | A63-B14-C2; | A63-B14-C3; |
| A63-B14-C4; | A63-B14-C5; | A63-B14-C6; | A63-B14-C7; | A63-B14-C8; | A63-B14-C9; |
| A64-B14-C1; | A64-B14-C2; | A64-B14-C3; | A64-B14-C4; | A64-B14-C5; | A64-B14-C6; |
| A64-B14-C7; | A64-B14-C8; | A64-B14-C9; | A65-B14-C1; | A65-B14-C2; | A65-B14-C3; |
| A65-B14-C4; | A65-B14-C5; | A65-B14-C6; | A65-B14-C7; | A65-B14-C8; | A65-B14-C9; |
| A66-B14-C1; | A66-B14-C2; | A66-B14-C3; | A66-B14-C4; | A66-B14-C5; | A66-B14-C6; |
| A66-B14-C7; | A66-B14-C8; | A66-B14-C9; | A67-B14-C1; | A67-B14-C2; | A67-B14-C3; |
| A67-B14-C4; | A67-B14-C5; | A67-B14-C6; | A67-B14-C7; | A67-B14-C8; | A67-B14-C9; |
| A68-B14-C1; | A68-B14-C2; | A68-B14-C3; | A68-B14-C4; | A68-B14-C5; | A68-B14-C6; |
| A68-B14-C7; | A68-B14-C8; | A68-B14-C9; | A69-B14-C1; | A69-B14-C2; | A69-B14-C3; |
| A69-B14-C4; | A69-B14-C5; | A69-B14-C6; | A69-B14-C7; | A69-B14-C8; | A69-B14-C9; |
| A70-B14-C1; | A70-B14-C2; | A70-B14-C3; | A70-B14-C4; | A70-B14-C5; | A70-B14-C6; |
| A70-B14-C7; | A70-B14-C8; | A70-B14-C9; | A71-B14-C1; | A71-B14-C2; | A71-B14-C3; |
| A71-B14-C4; | A71-B14-C5; | A71-B14-C6; | A71-B14-C7; | A71-B14-C8; | A71-B14-C9; |
| A1-B15-C1; | A1-B15-C2; | A1-B15-C3; | A1-B15-C4; | A1-B15-C5; | A1-B15-C6; |
| A1-B15-C7; | A1-B15-C8; | A1-B15-C9; | A2-B15-C1; | A2-B15-C2; | A2-B15-C3; |
| A2-B15-C4; | A2-B15-C5; | A2-B15-C6; | A2-B15-C7; | A2-B15-C8; | A2-B15-C9; |
| A3-B15-C1; | A3-B15-C2; | A3-B15-C3; | A3-B15-C4; | A3-B15-C5; | A3-B15-C6; |
| A3-B15-C7; | A3-B15-C8; | A3-B15-C9; | A4-B15-C1; | A4-B15-C2; | A4-B15-C3; |
| A4-B15-C4; | A4-B15-C5; | A4-B15-C6; | A4-B15-C7; | A4-B15-C8; | A4-B15-C9; |
| A5-B15-C1; | A5-B15-C2; | A5-B15-C3; | A5-B15-C4; | A5-B15-C5; | A5-B15-C6; |
| A5-B15-C7; | A5-B15-C8; | A5-B15-C9; | A6-B15-C1; | A6-B15-C2; | A6-B15-C3; |
| A6-B15-C4; | A6-B15-C5; | A6-B15-C6; | A6-B15-C7; | A6-B15-C8; | A6-B15-C9; |
| A7-B15-C1; | A7-B15-C2; | A7-B15-C3; | A7-B15-C4; | A7-B15-C5; | A7-B15-C6; |
| A7-B15-C7; | A7-B15-C8; | A7-B15-C9; | A8-B15-C1; | A8-B15-C2; | A8-B15-C3; |
| A8-B15-C4; | A8-B15-C5; | A8-B15-C6; | A8-B15-C7; | A8-B15-C8; | A8-B15-C9; |
| A9-B15-C1; | A9-B15-C2; | A9-B15-C3; | A9-B15-C4; | A9-B15-C5; | A9-B15-C6; |
| A9-B15-C7; | A9-B15-C8; | A9-B15-C9; | A10-B15-C1; | A10-B15-C2; | A10-B15-C3; |
| A10-B15-C4; | A10-B15-C5; | A10-B15-C6; | A10-B15-C7; | A10-B15-C8; | A10-B15-C9; |
| A11-B15-C1; | A11-B15-C2; | A11-B15-C3; | A11-B15-C4; | A11-B15-C5; | A11-B15-C6; |
| A11-B15-C7; | A11-B15-C8; | A11-B15-C9; | A12-B15-C1; | A12-B15-C2; | A12-B15-C3; |
| A12-B15-C4; | A12-B15-C5; | A12-B15-C6; | A12-B15-C7; | A12-B15-C8; | A12-B15-C9; |
| A13-B15-C1; | A13-B15-C2; | A13-B15-C3; | A13-B15-C4; | A13-B15-C5; | A13-B15-C6; |
| A13-B15-C7; | A13-B15-C8; | A13-B15-C9; | A14-B15-C1; | A14-B15-C2; | A14-B15-C3; |
| A14-B15-C4; | A14-B15-C5; | A14-B15-C6; | A14-B15-C7; | A14-B15-C8; | A14-B15-C9; |
| A15-B15-C1; | A15-B15-C2; | A15-B15-C3; | A15-B15-C4; | A15-B15-C5; | A15-B15-C6; |
| A15-B15-C7; | A15-B15-C8; | A15-B15-C9; | A16-B15-C1; | A16-B15-C2; | A16-B15-C3; |
| A16-B15-C4; | A16-B15-C5; | A16-B15-C6; | A16-B15-C7; | A16-B15-C8; | A16-B15-C9; |
| A17-B15-C1; | A17-B15-C2; | A17-B15-C3; | A17-B15-C4; | A17-B15-C5; | A17-B15-C6; |
| A17-B15-C7; | A17-B15-C8; | A17-B15-C9; | A18-B15-C1; | A18-B15-C2; | A18-B15-C3; |
| A18-B15-C4; | A18-B15-C5; | A18-B15-C6; | A18-B15-C7; | A18-B15-C8; | A18-B15-C9; |
| A19-B15-C1; | A19-B15-C2; | A19-B15-C3; | A19-B15-C4; | A19-B15-C5; | A19-B15-C6; |
| A19-B15-C7; | A19-B15-C8; | A19-B15-C9; | A20-B15-C1; | A20-B15-C2; | A20-B15-C3; |
| A20-B15-C4; | A20-B15-C5; | A20-B15-C6; | A20-B15-C7; | A20-B15-C8; | A20-B15-C9; |
| A21-B15-C1; | A21-B15-C2; | A21-B15-C3; | A21-B15-C4; | A21-B15-C5; | A21-B15-C6; |
| A21-B15-C7; | A21-B15-C8; | A21-B15-C9; | A22-B15-C1; | A22-B15-C2; | A22-B15-C3; |
| A22-B15-C4; | A22-B15-C5; | A22-B15-C6; | A22-B15-C7; | A22-B15-C8; | A22-B15-C9; |
| A23-B15-C1; | A23-B15-C2; | A23-B15-C3; | A23-B15-C4; | A23-B15-C5; | A23-B15-C6; |
| A23-B15-C7; | A23-B15-C8; | A23-B15-C9; | A24-B15-C1; | A24-B15-C2; | A24-B15-C3; |
| A24-B15-C4; | A24-B15-C5; | A24-B15-C6; | A24-B15-C7; | A24-B15-C8; | A24-B15-C9; |
| A25-B15-C1; | A25-B15-C2; | A25-B15-C3; | A25-B15-C4; | A25-B15-C5; | A25-B15-C6; |

-continued

| | | | | | |
|---|---|---|---|---|---|
| A25-B15-C7; | A25-B15-C8; | A25-B15-C9; | A26-B15-C1; | A26-B15-C2; | A26-B15-C3; |
| A26-B15-C4; | A26-B15-C5; | A26-B15-C6; | A26-B15-C7; | A26-B15-C8; | A26-B15-C9; |
| A27-B15-C1; | A27-B15-C2; | A27-B15-C3; | A27-B15-C4; | A27-B15-C5; | A27-B15-C6; |
| A27-B15-C7; | A27-B15-C8; | A27-B15-C9; | A28-B15-C1; | A28-B15-C2; | A28-B15-C3; |
| A28-B15-C4; | A28-B15-C5; | A28-B15-C6; | A28-B15-C7; | A28-B15-C8; | A28-B15-C9; |
| A29-B15-C1; | A29-B15-C2; | A29-B15-C3; | A29-B15-C4; | A29-B15-C5; | A29-B15-C6; |
| A29-B15-C7; | A29-B15-C8; | A29-B15-C9; | A30-B15-C1; | A30-B15-C2; | A30-B15-C3; |
| A30-B15-C4; | A30-B15-C5; | A30-B15-C6; | A30-B15-C7; | A30-B15-C8; | A30-B15-C9; |
| A31-B15-C1; | A31-B15-C2; | A31-B15-C3; | A31-B15-C4; | A31-B15-C5; | A31-B15-C6; |
| A31-B15-C7; | A31-B15-C8; | A31-B15-C9; | A32-B15-C1; | A32-B15-C2; | A32-B15-C3; |
| A32-B15-C4; | A32-B15-C5; | A32-B15-C6; | A32-B15-C7; | A32-B15-C8; | A32-B15-C9; |
| A33-B15-C1; | A33-B15-C2; | A33-B15-C3; | A33-B15-C4; | A33-B15-C5; | A33-B15-C6; |
| A33-B15-C7; | A33-B15-C8; | A33-B15-C9; | A34-B15-C1; | A34-B15-C2; | A34-B15-C3; |
| A34-B15-C4; | A34-B15-C5; | A34-B15-C6; | A34-B15-C7; | A34-B15-C8; | A34-B15-C9; |
| A35-B15-C1; | A35-B15-C2; | A35-B15-C3; | A35-B15-C4; | A35-B15-C5; | A35-B15-C6; |
| A35-B15-C7; | A35-B15-C8; | A35-B15-C9; | A36-B15-C1; | A36-B15-C2; | A36-B15-C3; |
| A36-B15-C4; | A36-B15-C5; | A36-B15-C6; | A36-B15-C7; | A36-B15-C8; | A36-B15-C9; |
| A37-B15-C1; | A37-B15-C2; | A37-B15-C3; | A37-B15-C4; | A37-B15-C5; | A37-B15-C6; |
| A37-B15-C7; | A37-B15-C8; | A37-B15-C9; | A38-B15-C1; | A38-B15-C2; | A38-B15-C3; |
| A38-B15-C4; | A38-B15-C5; | A38-B15-C6; | A38-B15-C7; | A38-B15-C8; | A38-B15-C9; |
| A39-B15-C1; | A39-B15-C2; | A39-B15-C3; | A39-B15-C4; | A39-B15-C5; | A39-B15-C6; |
| A39-B15-C7; | A39-B15-C8; | A39-B15-C9; | A40-B15-C1; | A40-B15-C2; | A40-B15-C3; |
| A40-B15-C4; | A40-B15-C5; | A40-B15-C6; | A40-B15-C7; | A40-B15-C8; | A40-B15-C9; |
| A41-B15-C1; | A41-B15-C2; | A41-B15-C3; | A41-B15-C4; | A41-B15-C5; | A41-B15-C6; |
| A41-B15-C7; | A41-B15-C8; | A41-B15-C9; | A42-B15-C1; | A42-B15-C2; | A42-B15-C3; |
| A42-B15-C4; | A42-B15-C5; | A42-B15-C6; | A42-B15-C7; | A42-B15-C8; | A42-B15-C9; |
| A43-B15-C1; | A43-B15-C2; | A43-B15-C3; | A43-B15-C4; | A43-B15-C5; | A43-B15-C6; |
| A43-B15-C7; | A43-B15-C8; | A43-B15-C9; | A44-B15-C1; | A44-B15-C2; | A44-B15-C3; |
| A44-B15-C4; | A44-B15-C5; | A44-B15-C6; | A44-B15-C7; | A44-B15-C8; | A44-B15-C9; |
| A45-B15-C1; | A45-B15-C2; | A45-B15-C3; | A45-B15-C4; | A45-B15-C5; | A45-B15-C6; |
| A45-B15-C7; | A45-B15-C8; | A45-B15-C9; | A46-B15-C1; | A46-B15-C2; | A46-B15-C3; |
| A46-B15-C4; | A46-B15-C5; | A46-B15-C6; | A46-B15-C7; | A46-B15-C8; | A46-B15-C9; |
| A47-B15-C1; | A47-B15-C2; | A47-B15-C3; | A47-B15-C4; | A47-B15-C5; | A47-B15-C6; |
| A47-B15-C7; | A47-B15-C8; | A47-B15-C9; | A48-B15-C1; | A48-B15-C2; | A48-B15-C3; |
| A48-B15-C4; | A48-B15-C5; | A48-B15-C6; | A48-B15-C7; | A48-B15-C8; | A48-B15-C9; |
| A49-B15-C1; | A49-B15-C2; | A49-B15-C3; | A49-B15-C4; | A49-B15-C5; | A49-B15-C6; |
| A49-B15-C7; | A49-B15-C8; | A49-B15-C9; | A50-B15-C1; | A50-B15-C2; | A50-B15-C3; |
| A50-B15-C4; | A50-B15-C5; | A50-B15-C6; | A50-B15-C7; | A50-B15-C8; | A50-B15-C9; |
| A51-B15-C1; | A51-B15-C2; | A51-B15-C3; | A51-B15-C4; | A51-B15-C5; | A51-B15-C6; |
| A51-B15-C7; | A51-B15-C8; | A51-B15-C9; | A52-B15-C1; | A52-B15-C2; | A52-B15-C3; |
| A52-B15-C4; | A52-B15-C5; | A52-B15-C6; | A52-B15-C7; | A52-B15-C8; | A52-B15-C9; |
| A53-B15-C1; | A53-B15-C2; | A53-B15-C3; | A53-B15-C4; | A53-B15-C5; | A53-B15-C6; |
| A53-B15-C7; | A53-B15-C8; | A53-B15-C9; | A54-B15-C1; | A54-B15-C2; | A54-B15-C3; |
| A54-B15-C4; | A54-B15-C5; | A54-B15-C6; | A54-B15-C7; | A54-B15-C8; | A54-B15-C9; |
| A55-B15-C1; | A55-B15-C2; | A55-B15-C3; | A55-B15-C4; | A55-B15-C5; | A55-B15-C6; |
| A55-B15-C7; | A55-B15-C8; | A55-B15-C9; | A56-B15-C1; | A56-B15-C2; | A56-B15-C3; |
| A56-B15-C4; | A56-B15-C5; | A56-B15-C6; | A56-B15-C7; | A56-B15-C8; | A56-B15-C9; |
| A57-B15-C1; | A57-B15-C2; | A57-B15-C3; | A57-B15-C4; | A57-B15-C5; | A57-B15-C6; |
| A57-B15-C7; | A57-B15-C8; | A57-B15-C9; | A58-B15-C1; | A58-B15-C2; | A58-B15-C3; |
| A58-B15-C4; | A58-B15-C5; | A58-B15-C6; | A58-B15-C7; | A58-B15-C8; | A58-B15-C9; |
| A59-B15-C1; | A59-B15-C2; | A59-B15-C3; | A59-B15-C4; | A59-B15-C5; | A59-B15-C6; |
| A59-B15-C7; | A59-B15-C8; | A59-B15-C9; | A60-B15-C1; | A60-B15-C2; | A60-B15-C3; |
| A60-B15-C4; | A60-B15-C5; | A60-B15-C6; | A60-B15-C7; | A60-B15-C8; | A60-B15-C9; |
| A61-B15-C1; | A61-B15-C2; | A61-B15-C3; | A61-B15-C4; | A61-B15-C5; | A61-B15-C6; |
| A61-B15-C7; | A61-B15-C8; | A61-B15-C9; | A62-B15-C1; | A62-B15-C2; | A62-B15-C3; |
| A62-B15-C4; | A62-B15-C5; | A62-B15-C6; | A62-B15-C7; | A62-B15-C8; | A62-B15-C9; |
| A63-B15-C1; | A63-B15-C2; | A63-B15-C3; | A63-B15-C4; | A63-B15-C5; | A63-B15-C6; |
| A63-B15-C7; | A63-B15-C8; | A63-B15-C9; | A64-B15-C1; | A64-B15-C2; | A64-B15-C3; |
| A64-B15-C4; | A64-B15-C5; | A64-B15-C6; | A64-B15-C7; | A64-B15-C8; | A64-B15-C9; |
| A65-B15-C1; | A65-B15-C2; | A65-B15-C3; | A65-B15-C4; | A65-B15-C5; | A65-B15-C6; |
| A65-B15-C7; | A65-B15-C8; | A65-B15-C9; | A66-B15-C1; | A66-B15-C2; | A66-B15-C3; |
| A66-B15-C4; | A66-B15-C5; | A66-B15-C6; | A66-B15-C7; | A66-B15-C8; | A66-B15-C9; |
| A67-B15-C1; | A67-B15-C2; | A67-B15-C3; | A67-B15-C4; | A67-B15-C5; | A67-B15-C6; |
| A67-B15-C7; | A67-B15-C8; | A67-B15-C9; | A68-B15-C1; | A68-B15-C2; | A68-B15-C3; |
| A68-B15-C4; | A68-B15-C5; | A68-B15-C6; | A68-B15-C7; | A68-B15-C8; | A68-B15-C9; |
| A69-B15-C1; | A69-B15-C2; | A69-B15-C3; | A69-B15-C4; | A69-B15-C5; | A69-B15-C6; |
| A69-B15-C7; | A69-B15-C8; | A69-B15-C9; | A70-B15-C1; | A70-B15-C2; | A70-B15-C3; |
| A70-B15-C4; | A70-B15-C5; | A70-B15-C6; | A70-B15-C7; | A70-B15-C8; | A70-B15-C9; |
| A71-B15-C1; | A71-B15-C2; | A71-B15-C3; | A71-B15-C4; | A71-B15-C5; | A71-B15-C6; |
| A71-B15-C7; | A71-B15-C8; | A71-B15-C9; | A1-B16-C1; | A1-B16-C2; | A1-B16-C3; |
| A1-B16-C4; | A1-B16-C5; | A1-B16-C6; | A1-B16-C7; | A1-B16-C8; | A1-B16-C9; |
| A2-B16-C1; | A2-B16-C2; | A2-B16-C3; | A2-B16-C4; | A2-B16-C5; | A2-B16-C6; |
| A2-B16-C7; | A2-B16-C8; | A2-B16-C9; | A3-B16-C1; | A3-B16-C2; | A3-B16-C3; |
| A3-B16-C4; | A3-B16-C5; | A3-B16-C6; | A3-B16-C7; | A3-B16-C8; | A3-B16-C9; |
| A4-B16-C1; | A4-B16-C2; | A4-B16-C3; | A4-B16-C4; | A4-B16-C5; | A4-B16-C6; |
| A4-B16-C7; | A4-B16-C8; | A4-B16-C9; | A5-B16-C1; | A5-B16-C2; | A5-B16-C3; |
| A5-B16-C4; | A5-B16-C5; | A5-B16-C6; | A5-B16-C7; | A5-B16-C8; | A5-B16-C9; |
| A6-B16-C1; | A6-B16-C2; | A6-B16-C3; | A6-B16-C4; | A6-B16-C5; | A6-B16-C6; |
| A6-B16-C7; | A6-B16-C8; | A6-B16-C9; | A7-B16-C1; | A7-B16-C2; | A7-B16-C3; |

-continued

A7-B16-C4; A7-B16-C5; A7-B16-C6; A7-B16-C7; A7-B16-C8; A7-B16-C9;
A8-B16-C1; A8-B16-C2; A8-B16-C3; A8-B16-C4; A8-B16-C5; A8-B16-C6;
A8-B16-C7; A8-B16-C8; A8-B16-C9; A9-B16-C1; A9-B16-C2; A9-B16-C3;
A9-B16-C4; A9-B16-C5; A9-B16-C6; A9-B16-C7; A9-B16-C8; A9-B16-C9;
A10-B16-C1; A10-B16-C2; A10-B16-C3; A10-B16-C4; A10-B16-C5; A10-B16-C6;
A10-B16-C7; A10-B16-C8; A10-B16-C9; A11-B16-C1; A11-B16-C2; A11-B16-C3;
A11-B16-C4; A11-B16-C5; A11-B16-C6; A11-B16-C7; A11-B16-C8; A11-B16-C9;
A12-B16-C1; A12-B16-C2; A12-B16-C3; A12-B16-C4; A12-B16-C5; A12-B16-C6;
A12-B16-C7; A12-B16-C8; A12-B16-C9; A13-B16-C1; A13-B16-C2; A13-B16-C3;
A13-B16-C4; A13-B16-C5; A13-B16-C6; A13-B16-C7; A13-B16-C8; A13-B16-C9;
A14-B16-C1; A14-B16-C2; A14-B16-C3; A14-B16-C4; A14-B16-C5; A14-B16-C6;
A14-B16-C7; A14-B16-C8; A14-B16-C9; A15-B16-C1; A15-B16-C2; A15-B16-C3;
A15-B16-C4; A15-B16-C5; A15-B16-C6; A15-B16-C7; A15-B16-C8; A15-B16-C9;
A16-B16-C1; A16-B16-C2; A16-B16-C3; A16-B16-C4; A16-B16-C5; A16-B16-C6;
A16-B16-C7; A16-B16-C8; A16-B16-C9; A17-B16-C1; A17-B16-C2; A17-B16-C3;
A17-B16-C4; A17-B16-C5; A17-B16-C6; A17-B16-C7; A17-B16-C8; A17-B16-C9;
A18-B16-C1; A18-B16-C2; A18-B16-C3; A18-B16-C4; A18-B16-C5; A18-B16-C6;
A18-B16-C7; A18-B16-C8; A18-B16-C9; A19-B16-C1; A19-B16-C2; A19-B16-C3;
A19-B16-C4; A19-B16-C5; A19-B16-C6; A19-B16-C7; A19-B16-C8; A19-B16-C9;
A20-B16-C1; A20-B16-C2; A20-B16-C3; A20-B16-C4; A20-B16-C5; A20-B16-C6;
A20-B16-C7; A20-B16-C8; A20-B16-C9; A21-B16-C1; A21-B16-C2; A21-B16-C3;
A21-B16-C4; A21-B16-C5; A21-B16-C6; A21-B16-C7; A21-B16-C8; A21-B16-C9;
A22-B16-C1; A22-B16-C2; A22-B16-C3; A22-B16-C4; A22-B16-C5; A22-B16-C6;
A22-B16-C7; A22-B16-C8; A22-B16-C9; A23-B16-C1; A23-B16-C2; A23-B16-C3;
A23-B16-C4; A23-B16-C5; A23-B16-C6; A23-B16-C7; A23-B16-C8; A23-B16-C9;
A24-B16-C1; A24-B16-C2; A24-B16-C3; A24-B16-C4; A24-B16-C5; A24-B16-C6;
A24-B16-C7; A24-B16-C8; A24-B16-C9; A25-B16-C1; A25-B16-C2; A25-B16-C3;
A25-B16-C4; A25-B16-C5; A25-B16-C6; A25-B16-C7; A25-B16-C8; A25-B16-C9;
A26-B16-C1; A26-B16-C2; A26-B16-C3; A26-B16-C4; A26-B16-C5; A26-B16-C6;
A26-B16-C7; A26-B16-C8; A26-B16-C9; A27-B16-C1; A27-B16-C2; A27-B16-C3;
A27-B16-C4; A27-B16-C5; A27-B16-C6; A27-B16-C7; A27-B16-C8; A27-B16-C9;
A28-B16-C1; A28-B16-C2; A28-B16-C3; A28-B16-C4; A28-B16-C5; A28-B16-C6;
A28-B16-C7; A28-B16-C8; A28-B16-C9; A29-B16-C1; A29-B16-C2; A29-B16-C3;
A29-B16-C4; A29-B16-C5; A29-B16-C6; A29-B16-C7; A29-B16-C8; A29-B16-C9;
A30-B16-C1; A30-B16-C2; A30-B16-C3; A30-B16-C4; A30-B16-C5; A30-B16-C6;
A30-B16-C7; A30-B16-C8; A30-B16-C9; A31-B16-C1; A31-B16-C2; A31-B16-C3;
A31-B16-C4; A31-B16-C5; A31-B16-C6; A31-B16-C7; A31-B16-C8; A31-B16-C9;
A32-B16-C1; A32-B16-C2; A32-B16-C3; A32-B16-C4; A32-B16-C5; A32-B16-C6;
A32-B16-C7; A32-B16-C8; A32-B16-C9; A33-B16-C1; A33-B16-C2; A33-B16-C3;
A33-B16-C4; A33-B16-C5; A33-B16-C6; A33-B16-C7; A33-B16-C8; A33-B16-C9;
A34-B16-C1; A34-B16-C2; A34-B16-C3; A34-B16-C4; A34-B16-C5; A34-B16-C6;
A34-B16-C7; A34-B16-C8; A34-B16-C9; A35-B16-C1; A35-B16-C2; A35-B16-C3;
A35-B16-C4; A35-B16-C5; A35-B16-C6; A35-B16-C7; A35-B16-C8; A35-B16-C9;
A36-B16-C4; A36-B16-C2; A36-B16-C3; A36-B16-C4; A36-B16-C5; A36-B16-C6;
A36-B16-C7; A36-B16-C8; A36-B16-C9; A37-B16-C1; A37-B16-C2; A37-B16-C3;
A37-B16-C4; A37-B16-C5; A37-B16-C6; A37-B16-C7; A37-B16-C8; A37-B16-C9;
A38-B16-C1; A38-B16-C2; A38-B16-C3; A38-B16-C4; A38-B16-C5; A38-B16-C6;
A38-B16-C7; A38-B16-C8; A38-B16-C9; A39-B16-C1; A39-B16-C2; A39-B16-C3;
A39-B16-C4; A39-B16-C5; A39-B16-C6; A39-B16-C7; A39-B16-C8; A39-B16-C9;
A40-B16-C1; A40-B16-C2; A40-B16-C3; A40-B16-C4; A40-B16-C5; A40-B16-C6;
A40-B16-C7; A40-B16-C8; A40-B16-C9; A41-B16-C1; A41-B16-C2; A41-B16-C3;
A41-B16-C4; A41-B16-C5; A41-B16-C6; A41-B16-C7; A41-B16-C8; A41-B16-C9;
A42-B16-C1; A42-B16-C2; A42-B16-C3; A42-B16-C4; A42-B16-C5; A42-B16-C6;
A42-B16-C7; A42-B16-C8; A42-B16-C9; A43-B16-C1; A43-B16-C2; A43-B16-C3;
A43-B16-C4; A43-B16-C5; A43-B16-C6; A43-B16-C7; A43-B16-C8; A43-B16-C9;
A44-B16-C1; A44-B16-C2; A44-B16-C3; A44-B16-C4; A44-B16-C5; A44-B16-C6;
A44-B16-C7; A44-B16-C8; A44-B16-C9; A45-B16-C1; A45-B16-C2; A45-B16-C3;
A45-B16-C4; A45-B16-C5; A45-B16-C6; A45-B16-C7; A45-B16-C8; A45-B16-C9;
A46-B16-C1; A46-B16-C2; A46-B16-C3; A46-B16-C4; A46-B16-C5; A46-B16-C6;
A46-B16-C7; A46-B16-C8; A46-B16-C9; A47-B16-C1; A47-B16-C2; A47-B16-C3;
A47-B16-C4; A47-B16-C5; A47-B16-C6; A47-B16-C7; A47-B16-C8; A47-B16-C9;
A48-B16-C1; A48-B16-C2; A48-B16-C3; A48-B16-C4; A48-B16-C5; A48-B16-C6;
A48-B16-C7; A48-B16-C8; A48-B16-C9; A49-B16-C1; A49-B16-C2; A49-B16-C3;
A49-B16-C4; A49-B16-C5; A49-B16-C6; A49-B16-C7; A49-B16-C8; A49-B16-C9;
A50-B16-C2; A50-B16-C3; A50-B16-C4; A50-B16-C5; A50-B16-C6;
A50-B16-C7; A50-B16-C8; A50-B16-C9; A51-B16-C1; A51-B16-C2; A51-B16-C3;
A51-B16-C4; A51-B16-C5; A51-B16-C6; A51-B16-C7; A51-B16-C8; A51-B16-C9;
A52-B16-C1; A52-B16-C2; A52-B16-C3; A52-B16-C4; A52-B16-C5; A52-B16-C6;
A52-B16-C7; A52-B16-C8; A52-B16-C9; A53-B16-C1; A53-B16-C2; A53-B16-C3;
A53-B16-C4; A53-B16-C5; A53-B16-C6; A53-B16-C7; A53-B16-C8; A53-B16-C9;
A54-B16-C1; A54-B16-C2; A54-B16-C3; A54-B16-C4; A54-B16-C5; A54-B16-C6;
A54-B16-C7; A54-B16-C8; A54-B16-C9; A55-B16-C1; A55-B16-C2; A55-B16-C3;
A55-B16-C4; A55-B16-C5; A55-B16-C6; A55-B16-C7; A55-B16-C8; A55-B16-C9;
A56-B16-C1; A56-B16-C2; A56-B16-C3; A56-B16-C4; A56-B16-C5; A56-B16-C6;
A56-B16-C7; A56-B16-C8; A56-B16-C9; A57-B16-C1; A57-B16-C2; A57-B16-C3;
A57-B16-C4; A57-B16-C5; A57-B16-C6; A57-B16-C7; A57-B16-C8; A57-B16-C9;
A58-B16-C1; A58-B16-C2; A58-B16-C3; A58-B16-C4; A58-B16-C5; A58-B16-C6;
A58-B16-C7; A58-B16-C8; A58-B16-C9; A59-B16-C1; A59-B16-C2; A59-B16-C3;
A59-B16-C4; A59-B16-C5; A59-B16-C6; A59-B16-C7; A59-B16-C8; A59-B16-C9;

-continued

| | | | | | |
|---|---|---|---|---|---|
| A60-B16-C1; | A60-B16-C2; | A60-B16-C3; | A60-B16-C4; | A60-B16-C5; | A60-B16-C6; |
| A60-B16-C7; | A60-B16-C8; | A60-B16-C9; | A61-B16-C1; | A61-B16-C2; | A61-B16-C3; |
| A61-B16-C4; | A61-B16-C5; | A61-B16-C6; | A61-B16-C7; | A61-B16-C8; | A61-B16-C9; |
| A62-B16-C1; | A62-B16-C2; | A62-B16-C3; | A62-B16-C4; | A62-B16-C5; | A62-B16-C6; |
| A62-B16-C7; | A62-B16-C8; | A62-B16-C9; | A63-B16-C1; | A63-B16-C2; | A63-B16-C3; |
| A63-B16-C4; | A63-B16-C5; | A63-B16-C6; | A63-B16-C7; | A63-B16-C8; | A63-B16-C9; |
| A64-B16-C1; | A64-B16-C2; | A64-B16-C3; | A64-B16-C4; | A64-B16-C5; | A64-B16-C6; |
| A64-B16-C7; | A64-B16-C8; | A64-B16-C9; | A65-B16-C1; | A65-B16-C2; | A65-B16-C3; |
| A65-B16-C4; | A65-B16-C5; | A65-B16-C6; | A65-B16-C7; | A65-B16-C8; | A65-B16-C9; |
| A66-B16-C1; | A66-B16-C2; | A66-B16-C3; | A66-B16-C4; | A66-B16-C5; | A66-B16-C6; |
| A66-B16-C7; | A66-B16-C8; | A66-B16-C9; | A67-B16-C1; | A67-B16-C2; | A67-B16-C3; |
| A67-B16-C4; | A67-B16-C5; | A67-B16-C6; | A67-B16-C7; | A67-B16-C8; | A67-B16-C9; |
| A68-B16-C1; | A68-B16-C2; | A68-B16-C3; | A68-B16-C4; | A68-B16-C5; | A68-B16-C6; |
| A68-B16-C7; | A68-B16-C8; | A68-B16-C9; | A69-B16-C1; | A69-B16-C2; | A69-B16-C3; |
| A69-B16-C4; | A69-B16-C5; | A69-B16-C6; | A69-B16-C7; | A69-B16-C8; | A69-B16-C9; |
| A70-B16-C1; | A70-B16-C2; | A70-B16-C3; | A70-B16-C4; | A70-B16-C5; | A70-B16-C6; |
| A70-B16-C7; | A70-B16-C8; | A70-B16-C9; | A71-B16-C1; | A71-B16-C2; | A71-B16-C3; |
| A71-B16-C4; | A71-B16-C5; | A71-B16-C6; | A71-B16-C7; | A71-B16-C8; | A71-B16-C9; |
| A1-B17-C1; | A1-B17-C2; | A1-B17-C3; | A1-B17-C4; | A1-B17-C5; | A1-B17-C6; |
| A1-B17-C7; | A1-B17-C8; | A1-B17-C9; | A2-B17-C1; | A2-B17-C2; | A2-B17-C3; |
| A2-B17-C4; | A2-B17-C5; | A2-B17-C6; | A2-B17-C7; | A2-B17-C8; | A2-B17-C9; |
| A3-B17-C1; | A3-B17-C2; | A3-B17-C3; | A3-B17-C4; | A3-B17-C5; | A3-B17-C6; |
| A3-B17-C7; | A3-B17-C8; | A3-B17-C9; | A4-B17-C1; | A4-B17-C2; | A4-B17-C3; |
| A4-B17-C4; | A4-B17-C5; | A4-B17-C6; | A4-B17-C7; | A4-B17-C8; | A4-B17-C9; |
| A5-B17-C1; | A5-B17-C2; | A5-B17-C3; | A5-B17-C4; | A5-B17-C5; | A5-B17-C6; |
| A5-B17-C7; | A5-B17-C8; | A5-B17-C9; | A6-B17-C1; | A6-B17-C2; | A6-B17-C3; |
| A6-B17-C4; | A6-B17-C5; | A6-B17-C6; | A6-B17-C7; | A6-B17-C8; | A6-B17-C9; |
| A7-B17-C1; | A7-B17-C2; | A7-B17-C3; | A7-B17-C4; | A7-B17-C5; | A7-B17-C6; |
| A7-B17-C7; | A7-B17-C8; | A7-B17-C9; | A8-B17-C1; | A8-B17-C2; | A8-B17-C3; |
| A8-B17-C4; | A8-B17-C5; | A8-B17-C6; | A8-B17-C7; | A8-B17-C8; | A8-B17-C9; |
| A9-B17-C1; | A9-B17-C2; | A9-B17-C3; | A9-B17-C4; | A9-B17-C5; | A9-B17-C6; |
| A9-B17-C7; | A9-B17-C8; | A9-B17-C9; | A10-B17-C1; | A10-B17-C2; | A10-B17-C3; |
| A10-B17-C4; | A10-B17-C5; | A10-B17-C6; | A10-B17-C7; | A10-B17-C8; | A10-B17-C9; |
| A11-B17-C1; | A11-B17-C2; | A11-B17-C3; | A11-B17-C4; | A11-B17-C5; | A11-B17-C6; |
| A11-B17-C7; | A11-B17-C8; | A11-B17-C9; | A12-B17-C1; | A12-B17-C2; | A12-B17-C3; |
| A12-B17-C4; | A12-B17-C5; | A12-B17-C6; | A12-B17-C7; | A12-B17-C8; | A12-B17-C9; |
| A13-B17-C1; | A13-B17-C2; | A13-B17-C3; | A13-B17-C4; | A13-B17-C5; | A13-B17-C6; |
| A13-B17-C7; | A13-B17-C8; | A13-B17-C9; | A14-B17-C1; | A14-B17-C2; | A14-B17-C3; |
| A14-B17-C4; | A14-B17-C5; | A14-B17-C6; | A14-B17-C7; | A14-B17-C8; | A14-B17-C9; |
| A15-B17-C1; | A15-B17-C2; | A15-B17-C3; | A15-B17-C4; | A15-B17-C5; | A15-B17-C6; |
| A15-B17-C7; | A15-B17-C8; | A15-B17-C9; | A16-B17-C1; | A16-B17-C2; | A16-B17-C3; |
| A16-B17-C4; | A16-B17-C5; | A16-B17-C6; | A16-B17-C7; | A16-B17-C8; | A16-B17-C9; |
| A17-B17-C1; | A17-B17-C2; | A17-B17-C3; | A17-B17-C4; | A17-B17-C5; | A17-B17-C6; |
| A17-B17-C7; | A17-B17-C8; | A17-B17-C9; | A18-B17-C1; | A18-B17-C2; | A18-B17-C3; |
| A18-B17-C4; | A18-B17-C5; | A18-B17-C6; | A18-B17-C7; | A18-B17-C8; | A18-B17-C9; |
| A19-B17-C1; | A19-B17-C2; | A19-B17-C3; | A19-B17-C4; | A19-B17-C5; | A19-B17-C6; |
| A19-B17-C7; | A19-B17-C8; | A19-B17-C9; | A20-B17-C1; | A20-B17-C2; | A20-B17-C3; |
| A20-B17-C4; | A20-B17-C5; | A20-B17-C6; | A20-B17-C7; | A20-B17-C8; | A20-B17-C9; |
| A21-B17-C1; | A21-B17-C2; | A21-B17-C3; | A21-B17-C4; | A21-B17-C5; | A21-B17-C6; |
| A21-B17-C7; | A21-B17-C8; | A21-B17-C9; | A22-B17-C1; | A22-B17-C2; | A22-B17-C3; |
| A22-B17-C4; | A22-B17-C5; | A22-B17-C6; | A22-B17-C7; | A22-B17-C8; | A22-B17-C9; |
| A23-B17-C1; | A23-B17-C2; | A23-B17-C3; | A23-B17-C4; | A23-B17-C5; | A23-B17-C6; |
| A23-B17-C7; | A23-B17-C8; | A23-B17-C9; | A24-B17-C1; | A24-B17-C2; | A24-B17-C3; |
| A24-B17-C4; | A24-B17-C5; | A24-B17-C6; | A24-B17-C7; | A24-B17-C8; | A24-B17-C9; |
| A25-B17-C1; | A25-B17-C2; | A25-B17-C3; | A25-B17-C4; | A25-B17-C5; | A25-B17-C6; |
| A25-B17-C7; | A25-B17-C8; | A25-B17-C9; | A26-B17-C1; | A26-B17-C2; | A26-B17-C3; |
| A26-B17-C4; | A26-B17-C5; | A26-B17-C6; | A26-B17-C7; | A26-B17-C8; | A26-B17-C9; |
| A27-B17-C1; | A27-B17-C2; | A27-B17-C3; | A27-B17-C4; | A27-B17-C5; | A27-B17-C6; |
| A27-B17-C7; | A27-B17-C8; | A27-B17-C9; | A28-B17-C1; | A28-B17-C2; | A28-B17-C3; |
| A28-B17-C4; | A28-B17-C5; | A28-B17-C6; | A28-B17-C7; | A28-B17-C8; | A28-B17-C9; |
| A29-B17-C1; | A29-B17-C2; | A29-B17-C3; | A29-B17-C4; | A29-B17-C5; | A29-B17-C6; |
| A29-B17-C7; | A29-B17-C8; | A29-B17-C9; | A30-B17-C1; | A30-B17-C2; | A30-B17-C3; |
| A30-B17-C4; | A30-B17-C5; | A30-B17-C6; | A30-B17-C7; | A30-B17-C8; | A30-B17-C9; |
| A31-B17-C1; | A31-B17-C2; | A31-B17-C3; | A31-B17-C4; | A31-B17-C5; | A31-B17-C6; |
| A31-B17-C7; | A31-B17-C8; | A31-B17-C9; | A32-B17-C1; | A32-B17-C2; | A32-B17-C3; |
| A32-B17-C4; | A32-B17-C5; | A32-B17-C6; | A32-B17-C7; | A32-B17-C8; | A32-B17-C9; |
| A33-B17-C1; | A33-B17-C2; | A33-B17-C3; | A33-B17-C4; | A33-B17-C5; | A33-B17-C6; |
| A33-B17-C7; | A33-B17-C8; | A33-B17-C9; | A34-B17-C1; | A34-B17-C2; | A34-B17-C3; |
| A34-B17-C4; | A34-B17-C5; | A34-B17-C6; | A34-B17-C7; | A34-B17-C8; | A34-B17-C9; |
| A35-B17-C1; | A35-B17-C2; | A35-B17-C3; | A35-B17-C4; | A35-B17-C5; | A35-B17-C6; |
| A35-B17-C7; | A35-B17-C8; | A35-B17-C9; | A36-B17-C1; | A36-B17-C2; | A36-B17-C3; |
| A36-B17-C4; | A36-B17-C5; | A36-B17-C6; | A36-B17-C7; | A36-B17-C8; | A36-B17-C9; |
| A37-B17-C1; | A37-B17-C2; | A37-B17-C3; | A37-B17-C4; | A37-B17-C5; | A37-B17-C6; |
| A37-B17-C7; | A37-B17-C8; | A37-B17-C9; | A38-B17-C1; | A38-B17-C2; | A38-B17-C3; |
| A38-B17-C4; | A38-B17-C5; | A38-B17-C6; | A38-B17-C7; | A38-B17-C8; | A38-B17-C9; |
| A39-B17-C1; | A39-B17-C2; | A39-B17-C3; | A39-B17-C4; | A39-B17-C5; | A39-B17-C6; |
| A39-B17-C7; | A39-B17-C8; | A39-B17-C9; | A40-B17-C1; | A40-B17-C2; | A40-B17-C3; |
| A40-B17-C4; | A40-B17-C5; | A40-B17-C6; | A40-B17-C7; | A40-B17-C8; | A40-B17-C9; |
| A41-B17-C1; | A41-B17-C2; | A41-B17-C3; | A41-B17-C4; | A41-B17-C5; | A41-B17-C6; |

| | | | | | |
|---|---|---|---|---|---|
| A41-B17-C7; | A41-B17-C8; | A41-B17-C9; | A42-B17-C1; | A42-B17-C2; | A42-B17-C3; |
| A42-B17-C4; | A42-B17-C5; | A42-B17-C6; | A42-B17-C7; | A42-B17-C8; | A42-B17-C9; |
| A43-B17-C1; | A43-B17-C2; | A43-B17-C3; | A43-B17-C4; | A43-B17-C5; | A43-B17-C6; |
| A43-B17-C7; | A43-B17-C8; | A43-B17-C9; | A44-B17-C1; | A44-B17-C2; | A44-B17-C3; |
| A44-B17-C4; | A44-B17-C5; | A44-B17-C6; | A44-B17-C7; | A44-B17-C8; | A44-B17-C9; |
| A45-B17-C1; | A45-B17-C2; | A45-B17-C3; | A45-B17-C4; | A45-B17-C5; | A45-B17-C6; |
| A45-B17-C7; | A45-B17-C8; | A45-B17-C9; | A46-B17-C1; | A46-B17-C2; | A46-B17-C3; |
| A46-B17-C4; | A46-B17-C5; | A46-B17-C6; | A46-B17-C7; | A46-B17-C8; | A46-B17-C9; |
| A47-B17-C1; | A47-B17-C2; | A47-B17-C3; | A47-B17-C4; | A47-B17-C5; | A47-B17-C6; |
| A47-B17-C7; | A47-B17-C8; | A47-B17-C9; | A48-B17-C1; | A48-B17-C2; | A48-B17-C3; |
| A48-B17-C4; | A48-B17-C5; | A48-B17-C6; | A48-B17-C7; | A48-B17-C8; | A48-B17-C9; |
| A49-B17-C1; | A49-B17-C2; | A49-B17-C3; | A49-B17-C4; | A49-B17-C5; | A49-B17-C6; |
| A49-B17-C7; | A49-B17-C8; | A49-B17-C9; | A50-B17-C1; | A50-B17-C2; | A50-B17-C3; |
| A50-B17-C4; | A50-B17-C5; | A50-B17-C6; | A50-B17-C7; | A50-B17-C8; | A50-B17-C9; |
| A51-B17-C1; | A51-B17-C2; | A51-B17-C3; | A51-B17-C4; | A51-B17-C5; | A51-B17-C6; |
| A51-B17-C7; | A51-B17-C8; | A51-B17-C9; | A52-B17-C1; | A52-B17-C2; | A52-B17-C3; |
| A52-B17-C4; | A52-B17-C5; | A52-B17-C6; | A52-B17-C7; | A52-B17-C8; | A52-B17-C9; |
| A53-B17-C1; | A53-B17-C2; | A53-B17-C3; | A53-B17-C4; | A53-B17-C5; | A53-B17-C6; |
| A53-B17-C7; | A53-B17-C8; | A53-B17-C9; | A54-B17-C1; | A54-B17-C2; | A54-B17-C3; |
| A54-B17-C4; | A54-B17-C5; | A54-B17-C6; | A54-B17-C7; | A54-B17-C8; | A54-B17-C9; |
| A55-B17-C1; | A55-B17-C2; | A55-B17-C3; | A55-B17-C4; | A55-B17-C5; | A55-B17-C6; |
| A55-B17-C7; | A55-B17-C8; | A55-B17-C9; | A56-B17-C1; | A56-B17-C2; | A56-B17-C3; |
| A56-B17-C4; | A56-B17-C5; | A56-B17-C6; | A56-B17-C7; | A56-B17-C8; | A56-B17-C9; |
| A57-B17-C1; | A57-B17-C2; | A57-B17-C3; | A57-B17-C4; | A57-B17-C5; | A57-B17-C6; |
| A57-B17-C7; | A57-B17-C8; | A57-B17-C9; | A58-B17-C1; | A58-B17-C2; | A58-B17-C3; |
| A58-B17-C4; | A58-B17-C5; | A58-B17-C6; | A58-B17-C7; | A58-B17-C8; | A58-B17-C9; |
| A59-B17-C1; | A59-B17-C2; | A59-B17-C3; | A59-B17-C4; | A59-B17-C5; | A59-B17-C6; |
| A59-B17-C7; | A59-B17-C8; | A59-B17-C9; | A60-B17-C1; | A60-B17-C2; | A60-B17-C3; |
| A60-B17-C4; | A60-B17-C5; | A60-B17-C6; | A60-B17-C7; | A60-B17-C8; | A60-B17-C9; |
| A61-B17-C1; | A61-B17-C2; | A61-B17-C3; | A61-B17-C4; | A61-B17-C5; | A61-B17-C6; |
| A61-B17-C7; | A61-B17-C8; | A61-B17-C9; | A62-B17-C1; | A62-B17-C2; | A62-B17-C3; |
| A62-B17-C4; | A62-B17-C5; | A62-B17-C6; | A62-B17-C7; | A62-B17-C8; | A62-B17-C9; |
| A63-B17-C1; | A63-B17-C2; | A63-B17-C3; | A63-B17-C4; | A63-B17-C5; | A63-B17-C6; |
| A63-B17-C7; | A63-B17-C8; | A63-B17-C9; | A64-B17-C1; | A64-B17-C2; | A64-B17-C3; |
| A64-B17-C4; | A64-B17-C5; | A64-B17-C6; | A64-B17-C7; | A64-B17-C8; | A64-B17-C9; |
| A65-B17-C1; | A65-B17-C2; | A65-B17-C3; | A65-B17-C4; | A65-B17-C5; | A65-B17-C6; |
| A65-B17-C7; | A65-B17-C8; | A65-B17-C9; | A66-B17-C1; | A66-B17-C2; | A66-B17-C3; |
| A66-B17-C4; | A66-B17-C5; | A66-B17-C6; | A66-B17-C7; | A66-B17-C8; | A66-B17-C9; |
| A67-B17-C1; | A67-B17-C2; | A67-B17-C3; | A67-B17-C4; | A67-B17-C5; | A67-B17-C6; |
| A67-B17-C7; | A67-B17-C8; | A67-B17-C9; | A68-B17-C1; | A68-B17-C2; | A68-B17-C3; |
| A68-B17-C4; | A68-B17-C5; | A68-B17-C6; | A68-B17-C7; | A68-B17-C8; | A68-B17-C9; |
| A69-B17-C1; | A69-B17-C2; | A69-B17-C3; | A69-B17-C4; | A69-B17-C5; | A69-B17-C6; |
| A69-B17-C7; | A69-B17-C8; | A69-B17-C9; | A70-B17-C1; | A70-B17-C2; | A70-B17-C3; |
| A70-B17-C4; | A70-B17-C5; | A70-B17-C6; | A70-B17-C7; | A70-B17-C8; | A70-B17-C9; |
| A71-B17-C1; | A71-B17-C2; | A71-B17-C3; | A71-B17-C4; | A71-B17-C5; | A71-B17-C6; |
| A71-B17-C7; | A71-B17-C8; | A71-B17-C9; | A1-B18-C1; | A1-B18-C2; | A1-B18-C3; |
| A1-B18-C4; | A1-B18-C5; | A1-B18-C6; | A1-B18-C7; | A1-B18-C8; | A1-B18-C9; |
| A2-B18-C1; | A2-B18-C2; | A2-B18-C3; | A2-B18-C4; | A2-B18-C5; | A2-B18-C6; |
| A2-B18-C7; | A2-B18-C8; | A2-B18-C9; | A3-B18-C1; | A3-B18-C2; | A3-B18-C3; |
| A3-B18-C4; | A3-B18-C5; | A3-B18-C6; | A3-B18-C7; | A3-B18-C8; | A3-B18-C9; |
| A4-B18-C1; | A4-B18-C2; | A4-B18-C3; | A4-B18-C4; | A4-B18-C5; | A4-B18-C6; |
| A4-B18-C7; | A4-B18-C8; | A4-B18-C9; | A5-B18-C1; | A5-B18-C2; | A5-B18-C3; |
| A5-B18-C4; | A5-B18-C5; | A5-B18-C6; | A5-B18-C7; | A5-B18-C8; | A5-B18-C9; |
| A6-B18-C1; | A6-B18-C2; | A6-B18-C3; | A6-B18-C4; | A6-B18-C5; | A6-B18-C6; |
| A6-B18-C7; | A6-B18-C8; | A6-B18-C9; | A7-B18-C1; | A7-B18-C2; | A7-B18-C3; |
| A7-B18-C4; | A7-B18-C5; | A7-B18-C6; | A7-B18-C7; | A7-B18-C8; | A7-B18-C9; |
| A8-B18-C1; | A8-B18-C2; | A8-B18-C3; | A8-B18-C4; | A8-B18-C5; | A8-B18-C6; |
| A8-B18-C7; | A8-B18-C8; | A8-B18-C9; | A9-B18-C1; | A9-B18-C2; | A9-B18-C3; |
| A9-B18-C4; | A9-B18-C5; | A9-B18-C6; | A9-B18-C7; | A9-B18-C8; | A9-B18-C9; |
| A10-B18-C1; | A10-B18-C2; | A10-B18-C3; | A10-B18-C4; | A10-B18-C5; | A10-B18-C6; |
| A10-B18-C7; | A10-B18-C8; | A10-B18-C9; | A11-B18-C1; | A11-B18-C2; | A11-B18-C3; |
| A11-B18-C4; | A11-B18-C5; | A11-B18-C6; | A11-B18-C7; | A11-B18-C8; | A11-B18-C9; |
| A12-B18-C1; | A12-B18-C2; | A12-B18-C3; | A12-B18-C4; | A12-B18-C5; | A12-B18-C6; |
| A12-B18-C7; | A12-B18-C8; | A12-B18-C9; | A13-B18-C1; | A13-B18-C2; | A13-B18-C3; |
| A13-B18-C4; | A13-B18-C5; | A13-B18-C6; | A13-B18-C7; | A13-B18-C8; | A13-B18-C9; |
| A14-B18-C1; | A14-B18-C2; | A14-B18-C3; | A14-B18-C4; | A14-B18-C5; | A14-B18-C6; |
| A14-B18-C7; | A14-B18-C8; | A14-B18-C9; | A15-B18-C1; | A15-B18-C2; | A15-B18-C3; |
| A15-B18-C4; | A15-B18-C5; | A15-B18-C6; | A15-B18-C7; | A15-B18-C8; | A15-B18-C9; |
| A16-B18-C1; | A16-B18-C2; | A16-B18-C3; | A16-B18-C4; | A16-B18-C5; | A16-B18-C6; |
| A16-B18-C7; | A16-B18-C8; | A16-B18-C9; | A17-B18-C1; | A17-B18-C2; | A17-B18-C3; |
| A17-B18-C4; | A17-B18-C5; | A17-B18-C6; | A17-B18-C7; | A17-B18-C8; | A17-B18-C9; |
| A18-B18-C1; | A18-B18-C2; | A18-B18-C3; | A18-B18-C4; | A18-B18-C5; | A18-B18-C6; |
| A18-B18-C7; | A18-B18-C8; | A18-B18-C9; | A19-B18-C1; | A19-B18-C2; | A19-B18-C3; |
| A19-B18-C4; | A19-B18-C5; | A19-B18-C6; | A19-B18-C7; | A19-B18-C8; | A19-B18-C9; |
| A20-B18-C1; | A20-B18-C2; | A20-B18-C3; | A20-B18-C4; | A20-B18-C5; | A20-B18-C6; |
| A20-B18-C7; | A20-B18-C8; | A20-B18-C9; | A21-B18-C1; | A21-B18-C2; | A21-B18-C3; |
| A21-B18-C4; | A21-B18-C5; | A21-B18-C6; | A21-B18-C7; | A21-B18-C8; | A21-B18-C9; |
| A22-B18-C1; | A22-B18-C2; | A22-B18-C3; | A22-B18-C4; | A22-B18-C5; | A22-B18-C6; |
| A22-B18-C7; | A22-B18-C8; | A22-B18-C9; | A23-B18-C1; | A23-B18-C2; | A23-B18-C3; |

| | | | | | |
|---|---|---|---|---|---|
| A23-B18-C4; | A23-B18-C5; | A23-B18-C6; | A23-B18-C7; | A23-B18-C8; | A23-B18-C9; |
| A24-B18-C1; | A24-B18-C2; | A24-B18-C3; | A24-B18-C4; | A24-B18-C5; | A24-B18-C6; |
| A24-B18-C7; | A24-B18-C8; | A24-B18-C9; | A25-B18-C1; | A25-B18-C2; | A25-B18-C3; |
| A25-B18-C4; | A25-B18-C5; | A25-B18-C6; | A25-B18-C7; | A25-B18-C8; | A25-B18-C9; |
| A26-B18-C1; | A26-B18-C2; | A26-B18-C3; | A26-B18-C4; | A26-B18-C5; | A26-B18-C6; |
| A26-B18-C7; | A26-B18-C8; | A26-B18-C9; | A27-B18-C1; | A27-B18-C2; | A27-B18-C3; |
| A27-B18-C4; | A27-B18-C5; | A27-B18-C6; | A27-B18-C7; | A27-B18-C8; | A27-B18-C9; |
| A28-B18-C1; | A28-B18-C2; | A28-B18-C3; | A28-B18-C4; | A28-B18-C5; | A28-B18-C6; |
| A28-B18-C7; | A28-B18-C8; | A28-B18-C9; | A29-B18-C1; | A29-B18-C2; | A29-B18-C3; |
| A29-B18-C4; | A29-B18-C5; | A29-B18-C6; | A29-B18-C7; | A29-B18-C8; | A29-B18-C9; |
| A30-B18-C1; | A30-B18-C2; | A30-B18-C3; | A30-B18-C4; | A30-B18-C5; | A30-B18-C6; |
| A30-B18-C7; | A30-B18-C8; | A30-B18-C9; | A31-B18-C1; | A31-B18-C2; | A31-B18-C3; |
| A31-B18-C4; | A31-B18-C5; | A31-B18-C6; | A31-B18-C7; | A31-B18-C8; | A31-B18-C9; |
| A32-B18-C1; | A32-B18-C2; | A32-B18-C3; | A32-B18-C4; | A32-B18-C5; | A32-B18-C6; |
| A32-B18-C7; | A32-B18-C8; | A32-B18-C9; | A33-B18-C1; | A33-B18-C2; | A33-B18-C3; |
| A33-B18-C4; | A33-B18-C5; | A33-B18-C6; | A33-B18-C7; | A33-B18-C8; | A33-B18-C9; |
| A34-B18-C1; | A34-B18-C2; | A34-B18-C3; | A34-B18-C4; | A34-B18-C5; | A34-B18-C6; |
| A34-B18-C7; | A34-B18-C8; | A34-B18-C9; | A35-B18-C1; | A35-B18-C2; | A35-B18-C3; |
| A35-B18-C4; | A35-B18-C5; | A35-B18-C6; | A35-B18-C7; | A35-B18-C8; | A35-B18-C9; |
| A36-B18-C1; | A36-B18-C2; | A36-B18-C3; | A36-B18-C4; | A36-B18-C5; | A36-B18-C6; |
| A36-B18-C7; | A36-B18-C8; | A36-B18-C9; | A37-B18-C1; | A37-B18-C2; | A37-B18-C3; |
| A37-B18-C4; | A37-B18-C5; | A37-B18-C6; | A37-B18-C7; | A37-B18-C8; | A37-B18-C9; |
| A38-B18-C1; | A38-B18-C2; | A38-B18-C3; | A38-B18-C4; | A38-B18-C5; | A38-B18-C6; |
| A38-B18-C7; | A38-B18-C8; | A38-B18-C9; | A39-B18-C1; | A39-B18-C2; | A39-B18-C3; |
| A39-B18-C4; | A39-B18-C5; | A39-B18-C6; | A39-B18-C7; | A39-B18-C8; | A39-B18-C9; |
| A40-B18-C1; | A40-B18-C2; | A40-B18-C3; | A40-B18-C4; | A40-B18-C5; | A40-B18-C6; |
| A40-B18-C7; | A40-B18-C8; | A40-B18-C9; | A41-B18-C1; | A41-B18-C2; | A41-B18-C3; |
| A41-B18-C4; | A41-B18-C5; | A41-B18-C6; | A41-B18-C7; | A41-B18-C8; | A41-B18-C9; |
| A42-B18-C1; | A42-B18-C2; | A42-B18-C3; | A42-B18-C4; | A42-B18-C5; | A42-B18-C6; |
| A42-B18-C7; | A42-B18-C8; | A42-B18-C9; | A43-B18-C1; | A43-B18-C2; | A43-B18-C3; |
| A43-B18-C4; | A43-B18-C5; | A43-B18-C6; | A43-B18-C7; | A43-B18-C8; | A43-B18-C9; |
| A44-B18-C1; | A44-B18-C2; | A44-B18-C3; | A44-B18-C4; | A44-B18-C5; | A44-B18-C6; |
| A44-B18-C7; | A44-B18-C8; | A44-B18-C9; | A45-B18-C1; | A45-B18-C2; | A45-B18-C3; |
| A45-B18-C4; | A45-B18-C5; | A45-B18-C6; | A45-B18-C7; | A45-B18-C8; | A45-B18-C9; |
| A46-B18-C1; | A46-B18-C2; | A46-B18-C3; | A46-B18-C4; | A46-B18-C5; | A46-B18-C6; |
| A46-B18-C7; | A46-B18-C8; | A46-B18-C9; | A47-B18-C1; | A47-B18-C2; | A47-B18-C3; |
| A47-B18-C4; | A47-B18-C5; | A47-B18-C6; | A47-B18-C7; | A47-B18-C8; | A47-B18-C9; |
| A48-B18-C1; | A48-B18-C2; | A48-B18-C3; | A48-B18-C4; | A48-B18-C5; | A48-B18-C6; |
| A48-B18-C7; | A48-B18-C8; | A48-B18-C9; | A49-B18-C1; | A49-B18-C2; | A49-B18-C3; |
| A49-B18-C4; | A49-B18-C5; | A49-B18-C6; | A49-B18-C7; | A49-B18-C8; | A49-B18-C9; |
| A50-B18-C1; | A50-B18-C2; | A50-B18-C3; | A50-B18-C4; | A50-B18-C5; | A50-B18-C6; |
| A50-B18-C7; | A50-B18-C8; | A50-B18-C9; | A51-B18-C1; | A51-B18-C2; | A51-B18-C3; |
| A51-B18-C4; | A51-B18-C5; | A51-B18-C6; | A51-B18-C7; | A51-B18-C8; | A51-B18-C9; |
| A52-B18-C1; | A52-B18-C2; | A52-B18-C3; | A52-B18-C4; | A52-B18-C5; | A52-B18-C6; |
| A52-B18-C7; | A52-B18-C8; | A52-B18-C9; | A53-B18-C1; | A53-B18-C2; | A53-B18-C3; |
| A53-B18-C4; | A53-B18-C5; | A53-B18-C6; | A53-B18-C7; | A53-B18-C8; | A53-B18-C9; |
| A54-B18-C1; | A54-B18-C2; | A54-B18-C3; | A54-B18-C4; | A54-B18-C5; | A54-B18-C6; |
| A54-B18-C7; | A54-B18-C8; | A54-B18-C9; | A55-B18-C1; | A55-B18-C2; | A55-B18-C3; |
| A55-B18-C4; | A55-B18-C5; | A55-B18-C6; | A55-B18-C7; | A55-B18-C8; | A55-B18-C9; |
| A56-B18-C1; | A56-B18-C2; | A56-B18-C3; | A56-B18-C4; | A56-B18-C5; | A56-B18-C6; |
| A56-B18-C7; | A56-B18-C8; | A56-B18-C9; | A57-B18-C1; | A57-B18-C2; | A57-B18-C3; |
| A57-B18-C4; | A57-B18-C5; | A57-B18-C6; | A57-B18-C7; | A57-B18-C8; | A57-B18-C9; |
| A58-B18-C1; | A58-B18-C2; | A58-B18-C3; | A58-B18-C4; | A58-B18-C5; | A58-B18-C6; |
| A58-B18-C7; | A58-B18-C8; | A58-B18-C9; | A59-B18-C1; | A59-B18-C2; | A59-B18-C3; |
| A59-B18-C4; | A59-B18-C5; | A59-B18-C6; | A59-B18-C7; | A59-B18-C8; | A59-B18-C9; |
| A60-B18-C1; | A60-B18-C2; | A60-B18-C3; | A60-B18-C4; | A60-B18-C5; | A60-B18-C6; |
| A60-B18-C7; | A60-B18-C8; | A60-B18-C9; | A61-B18-C1; | A61-B18-C2; | A61-B18-C3; |
| A61-B18-C4; | A61-B18-C5; | A61-B18-C6; | A61-B18-C7; | A61-B18-C8; | A61-B18-C9; |
| A62-B18-C1; | A62-B18-C2; | A62-B18-C3; | A62-B18-C4; | A62-B18-C5; | A62-B18-C6; |
| A62-B18-C7; | A62-B18-C8; | A62-B18-C9; | A63-B18-C1; | A63-B18-C2; | A63-B18-C3; |
| A63-B18-C4; | A63-B18-C5; | A63-B18-C6; | A63-B18-C7; | A63-B18-C8; | A63-B18-C9; |
| A64-B18-C1; | A64-B18-C2; | A64-B18-C3; | A64-B18-C4; | A64-B18-C5; | A64-B18-C6; |
| A64-B18-C7; | A64-B18-C8; | A64-B18-C9; | A65-B18-C1; | A65-B18-C2; | A65-B18-C3; |
| A65-B18-C4; | A65-B18-C5; | A65-B18-C6; | A65-B18-C7; | A65-B18-C8; | A65-B18-C9; |
| A66-B18-C1; | A66-B18-C2; | A66-B18-C3; | A66-B18-C4; | A66-B18-C5; | A66-B18-C6; |
| A66-B18-C7; | A66-B18-C8; | A66-B18-C9; | A67-B18-C1; | A67-B18-C2; | A67-B18-C3; |
| A67-B18-C4; | A67-B18-C5; | A67-B18-C6; | A67-B18-C7; | A67-B18-C8; | A67-B18-C9; |
| A68-B18-C1; | A68-B18-C2; | A68-B18-C3; | A68-B18-C4; | A68-B18-C5; | A68-B18-C6; |
| A68-B18-C7; | A68-B18-C8; | A68-B18-C9; | A69-B18-C1; | A69-B18-C2; | A69-B18-C3; |
| A69-B18-C4; | A69-B18-C5; | A69-B18-C6; | A69-B18-C7; | A69-B18-C8; | A69-B18-C9; |
| A70-B18-C1; | A70-B18-C2; | A70-B18-C3; | A70-B18-C4; | A70-B18-C5; | A70-B18-C6; |
| A70-B18-C7; | A70-B18-C8; | A70-B18-C9; | A71-B18-C1; | A71-B18-C2; | A71-B18-C3; |
| A71-B18-C4; | A71-B18-C5; | A71-B18-C6; | A71-B18-C7; | A71-B18-C8; | A71-B18-C9; |
| A1-B19-C1; | A1-B19-C2; | A1-B19-C3; | A1-B19-C4; | A1-B19-C5; | A1-B19-C6; |
| A1-B19-C7; | A1-B19-C8; | A1-B19-C9; | A2-B19-C1; | A2-B19-C2; | A2-B19-C3; |
| A2-B19-C4; | A2-B19-C5; | A2-B19-C6; | A2-B19-C7; | A2-B19-C8; | A2-B19-C9; |
| A3-B19-C1; | A3-B19-C2; | A3-B19-C3; | A3-B19-C4; | A3-B19-C5; | A3-B19-C6; |
| A3-B19-C7; | A3-B19-C8; | A3-B19-C9; | A4-B19-C1; | A4-B19-C2; | A4-B19-C3; |
| A4-B19-C4; | A4-B19-C5; | A4-B19-C6; | A4-B19-C7; | A4-B19-C8; | A4-B19-C9; |

-continued

| | | | | | |
|---|---|---|---|---|---|
| A5-B19-C1; | A5-B19-C2; | A5-B19-C3; | A5-B19-C4; | A5-B19-C5; | A5-B19-C6; |
| A5-B19-C7; | A5-B19-C8; | A5-B19-C9; | A6-B19-C1; | A6-B19-C2; | A6-B19-C3; |
| A6-B19-C4; | A6-B19-C5; | A6-B19-C6; | A6-B19-C7; | A6-B19-C8; | A6-B19-C9; |
| A7-B19-C1; | A7-B19-C2; | A7-B19-C3; | A7-B19-C4; | A7-B19-C5; | A7-B19-C6; |
| A7-B19-C7; | A7-B19-C8; | A7-B19-C9; | A8-B19-C1; | A8-B19-C2; | A8-B19-C3; |
| A8-B19-C4; | A8-B19-C5; | A8-B19-C6; | A8-B19-C7; | A8-B19-C8; | A8-B19-C9; |
| A9-B19-C1; | A9-B19-C2; | A9-B19-C3; | A9-B19-C4; | A9-B19-C5; | A9-B19-C6; |
| A9-B19-C7; | A9-B19-C8; | A9-B19-C9; | A10-B19-C1; | A10-B19-C2; | A10-B19-C3; |
| A10-B19-C4; | A10-B19-C5; | A10-B19-C6; | A10-B19-C7; | A10-B19-C8; | A10-B19-C9; |
| A11-B19-C1; | A11-B19-C2; | A11-B19-C3; | A11-B19-C4; | A11-B19-C5; | A11-B19-C6; |
| A11-B19-C7; | A11-B19-C8; | A11-B19-C9; | A12-B19-C1; | A12-B19-C2; | A12-B19-C3; |
| A12-B19-C4; | A12-B19-C5; | A12-B19-C6; | A12-B19-C7; | A12-B19-C8; | A12-B19-C9; |
| A13-B19-C1; | A13-B19-C2; | A13-B19-C3; | A13-B19-C4; | A13-B19-C5; | A13-B19-C6; |
| A13-B19-C7; | A13-B19-C8; | A13-B19-C9; | A14-B19-C1; | A14-B19-C2; | A14-B19-C3; |
| A14-B19-C4; | A14-B19-C5; | A14-B19-C6; | A14-B19-C7; | A14-B19-C8; | A14-B19-C9; |
| A15-B19-C1; | A15-B19-C2; | A15-B19-C3; | A15-B19-C4; | A15-B19-C5; | A15-B19-C6; |
| A15-B19-C7; | A15-B19-C8; | A15-B19-C9; | A16-B19-C1; | A16-B19-C2; | A16-B19-C3; |
| A16-B19-C4; | A16-B19-C5; | A16-B19-C6; | A16-B19-C7; | A16-B19-C8; | A16-B19-C9; |
| A17-B19-C1; | A17-B19-C2; | A17-B19-C3; | A17-B19-C4; | A17-B19-C5; | A17-B19-C6; |
| A17-B19-C7; | A17-B19-C8; | A17-B19-C9; | A18-B19-C1; | A18-B19-C2; | A18-B19-C3; |
| A18-B19-C4; | A18-B19-C5; | A18-B19-C6; | A18-B19-C7; | A18-B19-C8; | A18-B19-C9; |
| A19-B19-C1; | A19-B19-C2; | A19-B19-C3; | A19-B19-C4; | A19-B19-C5; | A19-B19-C6; |
| A19-B19-C7; | A19-B19-C8; | A19-B19-C9; | A20-B19-C1; | A20-B19-C2; | A20-B19-C3; |
| A20-B19-C4; | A20-B19-C5; | A20-B19-C6; | A20-B19-C7; | A20-B19-C8; | A20-B19-C9; |
| A21-B19-C1; | A21-B19-C2; | A21-B19-C3; | A21-B19-C4; | A21-B19-C5; | A21-B19-C6; |
| A21-B19-C7; | A21-B19-C8; | A21-B19-C9; | A22-B19-C1; | A22-B19-C2; | A22-B19-C3; |
| A22-B19-C4; | A22-B19-C5; | A22-B19-C6; | A22-B19-C7; | A22-B19-C8; | A22-B19-C9; |
| A23-B19-C1; | A23-B19-C2; | A23-B19-C3; | A23-B19-C4; | A23-B19-C5; | A23-B19-C6; |
| A23-B19-C7; | A23-B19-C8; | A23-B19-C9; | A24-B19-C1; | A24-B19-C2; | A24-B19-C3; |
| A24-B19-C4; | A24-B19-C5; | A24-B19-C6; | A24-B19-C7; | A24-B19-C8; | A24-B19-C9; |
| A25-B19-C1; | A25-B19-C2; | A25-B19-C3; | A25-B19-C4; | A25-B19-C5; | A25-B19-C6; |
| A25-B19-C7; | A25-B19-C8; | A25-B19-C9; | A26-B19-C1; | A26-B19-C2; | A26-B19-C3; |
| A26-B19-C4; | A26-B19-C5; | A26-B19-C6; | A26-B19-C7; | A26-B19-C8; | A26-B19-C9; |
| A27-B19-C1; | A27-B19-C2; | A27-B19-C3; | A27-B19-C4; | A27-B19-C5; | A27-B19-C6; |
| A27-B19-C7; | A27-B19-C8; | A27-B19-C9; | A28-B19-C1; | A28-B19-C2; | A28-B19-C3; |
| A28-B19-C4; | A28-B19-C5; | A28-B19-C6; | A28-B19-C7; | A28-B19-C8; | A28-B19-C9; |
| A29-B19-C1; | A29-B19-C2; | A29-B19-C3; | A29-B19-C4; | A29-B19-C5; | A29-B19-C6; |
| A29-B19-C7; | A29-B19-C8; | A29-B19-C9; | A30-B19-C1; | A30-B19-C2; | A30-B19-C3; |
| A30-B19-C4; | A30-B19-C5; | A30-B19-C6; | A30-B19-C7; | A30-B19-C8; | A30-B19-C9; |
| A31-B19-C1; | A31-B19-C2; | A31-B19-C3; | A31-B19-C4; | A31-B19-C5; | A31-B19-C6; |
| A31-B19-C7; | A31-B19-C8; | A31-B19-C9; | A32-B19-C1; | A32-B19-C2; | A32-B19-C3; |
| A32-B19-C4; | A32-B19-C5; | A32-B19-C6; | A32-B19-C7; | A32-B19-C8; | A32-B19-C9; |
| A33-B19-C1; | A33-B19-C2; | A33-B19-C3; | A33-B19-C4; | A33-B19-C5; | A33-B19-C6; |
| A33-B19-C7; | A33-B19-C8; | A33-B19-C9; | A34-B19-C1; | A34-B19-C2; | A34-B19-C3; |
| A34-B19-C4; | A34-B19-C5; | A34-B19-C6; | A34-B19-C7; | A34-B19-C8; | A34-B19-C9; |
| A35-B19-C1; | A35-B19-C2; | A35-B19-C3; | A35-B19-C4; | A35-B19-C5; | A35-B19-C6; |
| A35-B19-C7; | A35-B19-C8; | A35-B19-C9; | A36-B19-C1; | A36-B19-C2; | A36-B19-C3; |
| A36-B19-C4; | A36-B19-C5; | A36-B19-C6; | A36-B19-C7; | A36-B19-C8; | A36-B19-C9; |
| A37-B19-C1; | A37-B19-C2; | A37-B19-C3; | A37-B19-C4; | A37-B19-C5; | A37-B19-C6; |
| A37-B19-C7; | A37-B19-C8; | A37-B19-C9; | A38-B19-C1; | A38-B19-C2; | A38-B19-C3; |
| A38-B19-C4; | A38-B19-C5; | A38-B19-C6; | A38-B19-C7; | A38-B19-C8; | A38-B19-C9; |
| A39-B19-C1; | A39-B19-C2; | A39-B19-C3; | A39-B19-C4; | A39-B19-C5; | A39-B19-C6; |
| A39-B19-C7; | A39-B19-C8; | A39-B19-C9; | A40-B19-C1; | A40-B19-C2; | A40-B19-C3; |
| A40-B19-C4; | A40-B19-C5; | A40-B19-C6; | A40-B19-C7; | A40-B19-C8; | A40-B19-C9; |
| A41-B19-C1; | A41-B19-C2; | A41-B19-C3; | A41-B19-C4; | A41-B19-C5; | A41-B19-C6; |
| A41-B19-C7; | A41-B19-C8; | A41-B19-C9; | A42-B19-C1; | A42-B19-C2; | A42-B19-C3; |
| A42-B19-C4; | A42-B19-C5; | A42-B19-C6; | A42-B19-C7; | A42-B19-C8; | A42-B19-C9; |
| A43-B19-C1; | A43-B19-C2; | A43-B19-C3; | A43-B19-C4; | A43-B19-C5; | A43-B19-C6; |
| A43-B19-C7; | A43-B19-C8; | A43-B19-C9; | A44-B19-C1; | A44-B19-C2; | A44-B19-C3; |
| A44-B19-C4; | A44-B19-C5; | A44-B19-C6; | A44-B19-C7; | A44-B19-C8; | A44-B19-C9; |
| A45-B19-C1; | A45-B19-C2; | A45-B19-C3; | A45-B19-C4; | A45-B19-C5; | A45-B19-C6; |
| A45-B19-C7; | A45-B19-C8; | A45-B19-C9; | A46-B19-C1; | A46-B19-C2; | A46-B19-C3; |
| A46-B19-C4; | A46-B19-C5; | A46-B19-C6; | A46-B19-C7; | A46-B19-C8; | A46-B19-C9; |
| A47-B19-C1; | A47-B19-C2; | A47-B19-C3; | A47-B19-C4; | A47-B19-C5; | A47-B19-C6; |
| A47-B19-C7; | A47-B19-C8; | A47-B19-C9; | A48-B19-C1; | A48-B19-C2; | A48-B19-C3; |
| A48-B19-C4; | A48-B19-C5; | A48-B19-C6; | A48-B19-C7; | A48-B19-C8; | A48-B19-C9; |
| A49-B19-C1; | A49-B19-C2; | A49-B19-C3; | A49-B19-C4; | A49-B19-C5; | A49-B19-C6; |
| A49-B19-C7; | A49-B19-C8; | A49-B19-C9; | A50-B19-C1; | A50-B19-C2; | A50-B19-C3; |
| A50-B19-C4; | A50-B19-C5; | A50-B19-C6; | A50-B19-C7; | A50-B19-C8; | A50-B19-C9; |
| A51-B19-C1; | A51-B19-C2; | A51-B19-C3; | A51-B19-C4; | A51-B19-C5; | A51-B19-C6; |
| A51-B19-C7; | A51-B19-C8; | A51-B19-C9; | A52-B19-C1; | A52-B19-C2; | A52-B19-C3; |
| A52-B19-C4; | A52-B19-C5; | A52-B19-C6; | A52-B19-C7; | A52-B19-C8; | A52-B19-C9; |
| A53-B19-C1; | A53-B19-C2; | A53-B19-C3; | A53-B19-C4; | A53-B19-C5; | A53-B19-C6; |
| A53-B19-C7; | A53-B19-C8; | A53-B19-C9; | A54-B19-C1; | A54-B19-C2; | A54-B19-C3; |
| A54-B19-C4; | A54-B19-C5; | A54-B19-C6; | A54-B19-C7; | A54-B19-C8; | A54-B19-C9; |
| A55-B19-C1; | A55-B19-C2; | A55-B19-C3; | A55-B19-C4; | A55-B19-C5; | A55-B19-C6; |
| A55-B19-C7; | A55-B19-C8; | A55-B19-C9; | A56-B19-C1; | A56-B19-C2; | A56-B19-C3; |
| A56-B19-C4; | A56-B19-C5; | A56-B19-C6; | A56-B19-C7; | A56-B19-C8; | A56-B19-C9; |
| A57-B19-C1; | A57-B19-C2; | A57-B19-C3; | A57-B19-C4; | A57-B19-C5; | A57-B19-C6; |

-continued

| | | | | | |
|---|---|---|---|---|---|
| A57-B19-C7; | A57-B19-C8; | A57-B19-C9; | A58-B19-C1; | A58-B19-C2; | A58-B19-C3; |
| A58-B19-C4; | A58-B19-C5; | A58-B19-C6; | A58-B19-C7; | A58-B19-C8; | A58-B19-C9; |
| A59-B19-C1; | A59-B19-C2; | A59-B19-C3; | A59-B19-C4; | A59-B19-C5; | A59-B19-C6; |
| A59-B19-C7; | A59-B19-C8; | A59-B19-C9; | A60-B19-C1; | A60-B19-C2; | A60-B19-C3; |
| A60-B19-C4; | A60-B19-C5; | A60-B19-C6; | A60-B19-C7; | A60-B19-C8; | A60-B19-C9; |
| A61-B19-C1; | A61-B19-C2; | A61-B19-C3; | A61-B19-C4; | A61-B19-C5; | A61-B19-C6; |
| A61-B19-C7; | A61-B19-C8; | A61-B19-C9; | A62-B19-C1; | A62-B19-C2; | A62-B19-C3; |
| A62-B19-C4; | A62-B19-C5; | A62-B19-C6; | A62-B19-C7; | A62-B19-C8; | A62-B19-C9; |
| A63-B19-C1; | A63-B19-C2; | A63-B19-C3; | A63-B19-C4; | A63-B19-C5; | A63-B19-C6; |
| A63-B19-C7; | A63-B19-C8; | A63-B19-C9; | A64-B19-C1; | A64-B19-C2; | A64-B19-C3; |
| A64-B19-C4; | A64-B19-C5; | A64-B19-C6; | A64-B19-C7; | A64-B19-C8; | A64-B19-C9; |
| A65-B19-C1; | A65-B19-C2; | A65-B19-C3; | A65-B19-C4; | A65-B19-C5; | A65-B19-C6; |
| A65-B19-C7; | A65-B19-C8; | A65-B19-C9; | A66-B19-C1; | A66-B19-C2; | A66-B19-C3; |
| A66-B19-C4; | A66-B19-C5; | A66-B19-C6; | A66-B19-C7; | A66-B19-C8; | A66-B19-C9; |
| A67-B19-C1; | A67-B19-C2; | A67-B19-C3; | A67-B19-C4; | A67-B19-C5; | A67-B19-C6; |
| A67-B19-C7; | A67-B19-C8; | A67-B19-C9; | A68-B19-C1; | A68-B19-C2; | A68-B19-C3; |
| A68-B19-C4; | A68-B19-C5; | A68-B19-C6; | A68-B19-C7; | A68-B19-C8; | A68-B19-C9; |
| A69-B19-C1; | A69-B19-C2; | A69-B19-C3; | A69-B19-C4; | A69-B19-C5; | A69-B19-C6; |
| A69-B19-C7; | A69-B19-C8; | A69-B19-C9; | A70-B19-C1; | A70-B19-C2; | A70-B19-C3; |
| A70-B19-C4; | A70-B19-C5; | A70-B19-C6; | A70-B19-C7; | A70-B19-C8; | A70-B19-C9; |
| A71-B19-C1; | A71-B19-C2; | A71-B19-C3; | A71-B19-C4; | A71-B19-C5; | A71-B19-C6; |
| A71-B19-C7; | A71-B19-C8; | A71-B19-C9; | A1-B20-C1; | A1-B20-C2; | A1-B20-C3; |
| A1-B20-C4; | A1-B20-C5; | A1-B20-C6; | A1-B20-C7; | A1-B20-C8; | A1-B20-C9; |
| A2-B20-C1; | A2-B20-C2; | A2-B20-C3; | A2-B20-C4; | A2-B20-C5; | A2-B20-C6; |
| A2-B20-C7; | A2-B20-C8; | A2-B20-C9; | A3-B20-C1; | A3-B20-C2; | A3-B20-C3; |
| A3-B20-C4; | A3-B20-C5; | A3-B20-C6; | A3-B20-C7; | A3-B20-C8; | A3-B20-C9; |
| A4-B20-C1; | A4-B20-C2; | A4-B20-C3; | A4-B20-C4; | A4-B20-C5; | A4-B20-C6; |
| A4-B20-C7; | A4-B20-C8; | A4-B20-C9; | A5-B20-C1; | A5-B20-C2; | A5-B20-C3; |
| A5-B20-C4; | A5-B20-C5; | A5-B20-C6; | A5-B20-C7; | A5-B20-C8; | A5-B20-C9; |
| A6-B20-C1; | A6-B20-C2; | A6-B20-C3; | A6-B20-C4; | A6-B20-C5; | A6-B20-C6; |
| A6-B20-C7; | A6-B20-C8; | A6-B20-C9; | A7-B20-C1; | A7-B20-C2; | A7-B20-C3; |
| A7-B20-C4; | A7-B20-C5; | A7-B20-C6; | A7-B20-C7; | A7-B20-C8; | A7-B20-C9; |
| A8-B20-C1; | A8-B20-C2; | A8-B20-C3; | A8-B20-C4; | A8-B20-C5; | A8-B20-C6; |
| A8-B20-C7; | A8-B20-C8; | A8-B20-C9; | A9-B20-C1; | A9-B20-C2; | A9-B20-C3; |
| A9-B20-C4; | A9-B20-C5; | A9-B20-C6; | A9-B20-C7; | A9-B20-C8; | A9-B20-C9; |
| A10-B20-C1; | A10-B20-C2; | A10-B20-C3; | A10-B20-C4; | A10-B20-C5; | A10-B20-C6; |
| A10-B20-C7; | A10-B20-C8; | A10-B20-C9; | A11-B20-C1; | A11-B20-C2; | A11-B20-C3; |
| A11-B20-C4; | A11-B20-C5; | A11-B20-C6; | A11-B20-C7; | A11-B20-C8; | A11-B20-C9; |
| A12-B20-C1; | A12-B20-C2; | A12-B20-C3; | A12-B20-C4; | A12-B20-C5; | A12-B20-C6; |
| A12-B20-C7; | A12-B20-C8; | A12-B20-C9; | A13-B20-C1; | A13-B20-C2; | A13-B20-C3; |
| A13-B20-C4; | A13-B20-C5; | A13-B20-C6; | A13-B20-C7; | A13-B20-C8; | A13-B20-C9; |
| A14-B20-C1; | A14-B20-C2; | A14-B20-C3; | A14-B20-C4; | A14-B20-C5; | A14-B20-C6; |
| A14-B20-C7; | A14-B20-C8; | A14-B20-C9; | A15-B20-C1; | A15-B20-C2; | A15-B20-C3; |
| A15-B20-C4; | A15-B20-C5; | A15-B20-C6; | A15-B20-C7; | A15-B20-C8; | A15-B20-C9; |
| A16-B20-C1; | A16-B20-C2; | A16-B20-C3; | A16-B20-C4; | A16-B20-C5; | A16-B20-C6; |
| A16-B20-C7; | A16-B20-C8; | A16-B20-C9; | A17-B20-C1; | A17-B20-C2; | A17-B20-C3; |
| A17-B20-C4; | A17-B20-C5; | A17-B20-C6; | A17-B20-C7; | A17-B20-C8; | A17-B20-C9; |
| A18-B20-C1; | A18-B20-C2; | A18-B20-C3; | A18-B20-C4; | A18-B20-C5; | A18-B20-C6; |
| A18-B20-C7; | A18-B20-C8; | A18-B20-C9; | A19-B20-C1; | A19-B20-C2; | A19-B20-C3; |
| A19-B20-C4; | A19-B20-C5; | A19-B20-C6; | A19-B20-C7; | A19-B20-C8; | A19-B20-C9; |
| A20-B20-C1; | A20-B20-C2; | A20-B20-C3; | A20-B20-C4; | A20-B20-C5; | A20-B20-C6; |
| A20-B20-C7; | A20-B20-C8; | A20-B20-C9; | A21-B20-C1; | A21-B20-C2; | A21-B20-C3; |
| A21-B20-C4; | A21-B20-C5; | A21-B20-C6; | A21-B20-C7; | A21-B20-C8; | A21-B20-C9; |
| A22-B20-C1; | A22-B20-C2; | A22-B20-C3; | A22-B20-C4; | A22-B20-C5; | A22-B20-C6; |
| A22-B20-C7; | A22-B20-C8; | A22-B20-C9; | A23-B20-C1; | A23-B20-C2; | A23-B20-C3; |
| A23-B20-C4; | A23-B20-C5; | A23-B20-C6; | A23-B20-C7; | A23-B20-C8; | A23-B20-C9; |
| A24-B20-C1; | A24-B20-C2; | A24-B20-C3; | A24-B20-C4; | A24-B20-C5; | A24-B20-C6; |
| A24-B20-C7; | A24-B20-C8; | A24-B20-C9; | A25-B20-C1; | A25-B20-C2; | A25-B20-C3; |
| A25-B20-C4; | A25-B20-C5; | A25-B20-C6; | A25-B20-C7; | A25-B20-C8; | A25-B20-C9; |
| A26-B20-C1; | A26-B20-C2; | A26-B20-C3; | A26-B20-C4; | A26-B20-C5; | A26-B20-C6; |
| A26-B20-C7; | A26-B20-C8; | A26-B20-C9; | A27-B20-C1; | A27-B20-C2; | A27-B20-C3; |
| A27-B20-C4; | A27-B20-C5; | A27-B20-C6; | A27-B20-C7; | A27-B20-C8; | A27-B20-C9; |
| A28-B20-C1; | A28-B20-C2; | A28-B20-C3; | A28-B20-C4; | A28-B20-C5; | A28-B20-C6; |
| A28-B20-C7; | A28-B20-C8; | A28-B20-C9; | A29-B20-C1; | A29-B20-C2; | A29-B20-C3; |
| A29-B20-C4; | A29-B20-C5; | A29-B20-C6; | A29-B20-C7; | A29-B20-C8; | A29-B20-C9; |
| A30-B20-C1; | A30-B20-C2; | A30-B20-C3; | A30-B20-C4; | A30-B20-C5; | A30-B20-C6; |
| A30-B20-C7; | A30-B20-C8; | A30-B20-C9; | A31-B20-C1; | A31-B20-C2; | A31-B20-C3; |
| A31-B20-C4; | A31-B20-C5; | A31-B20-C6; | A31-B20-C7; | A31-B20-C8; | A31-B20-C9; |
| A32-B20-C1; | A32-B20-C2; | A32-B20-C3; | A32-B20-C4; | A32-B20-C5; | A32-B20-C6; |
| A32-B20-C7; | A32-B20-C8; | A32-B20-C9; | A33-B20-C1; | A33-B20-C2; | A33-B20-C3; |
| A33-B20-C4; | A33-B20-C5; | A33-B20-C6; | A33-B20-C7; | A33-B20-C8; | A33-B20-C9; |
| A34-B20-C1; | A34-B20-C2; | A34-B20-C3; | A34-B20-C4; | A34-B20-C5; | A34-B20-C6; |
| A34-B20-C7; | A34-B20-C8; | A34-B20-C9; | A35-B20-C1; | A35-B20-C2; | A35-B20-C3; |
| A35-B20-C4; | A35-B20-C5; | A35-B20-C6; | A35-B20-C7; | A35-B20-C8; | A35-B20-C9; |
| A36-B20-C1; | A36-B20-C2; | A36-B20-C3; | A36-B20-C4; | A36-B20-C5; | A36-B20-C6; |
| A36-B20-C7; | A36-B20-C8; | A36-B20-C9; | A37-B20-C1; | A37-B20-C2; | A37-B20-C3; |
| A37-B20-C4; | A37-B20-C5; | A37-B20-C6; | A37-B20-C7; | A37-B20-C8; | A37-B20-C9; |
| A38-B20-C1; | A38-B20-C2; | A38-B20-C3; | A38-B20-C4; | A38-B20-C5; | A38-B20-C6; |
| A38-B20-C7; | A38-B20-C8; | A38-B20-C9; | A39-B20-C1; | A39-B20-C2; | A39-B20-C3; |

-continued

| | | | | | |
|---|---|---|---|---|---|
| A39-B20-C4; | A39-B20-C5; | A39-B20-C6; | A39-B20-C7; | A39-B20-C8; | A39-B20-C9; |
| A40-B20-C1; | A40-B20-C2; | A40-B20-C3; | A40-B20-C4; | A40-B20-C5; | A40-B20-C6; |
| A40-B20-C7; | A40-B20-C8; | A40-B20-C9; | A41-B20-C1; | A41-B20-C2; | A41-B20-C3; |
| A41-B20-C4; | A41-B20-C5; | A41-B20-C6; | A41-B20-C7; | A41-B20-C8; | A41-B20-C9; |
| A42-B20-C1; | A42-B20-C2; | A42-B20-C3; | A42-B20-C4; | A42-B20-C5; | A42-B20-C6; |
| A42-B20-C7; | A42-B20-C8; | A42-B20-C9; | A43-B20-C1; | A43-B20-C2; | A43-B20-C3; |
| A43-B20-C4; | A43-B20-C5; | A43-B20-C6; | A43-B20-C7; | A43-B20-C8; | A43-B20-C9; |
| A44-B20-C1; | A44-B20-C2; | A44-B20-C3; | A44-B20-C4; | A44-B20-C5; | A44-B20-C6; |
| A44-B20-C7; | A44-B20-C8; | A44-B20-C9; | A45-B20-C1; | A45-B20-C2; | A45-B20-C3; |
| A45-B20-C4; | A45-B20-C5; | A45-B20-C6; | A45-B20-C7; | A45-B20-C8; | A45-B20-C9; |
| A46-B20-C1; | A46-B20-C2; | A46-B20-C3; | A46-B20-C4; | A46-B20-C5; | A46-B20-C6; |
| A46-B20-C7; | A46-B20-C8; | A46-B20-C9; | A47-B20-C1; | A47-B20-C2; | A47-B20-C3; |
| A47-B20-C4; | A47-B20-C5; | A47-B20-C6; | A47-B20-C7; | A47-B20-C8; | A47-B20-C9; |
| A48-B20-C1; | A48-B20-C2; | A48-B20-C3; | A48-B20-C4; | A48-B20-C5; | A48-B20-C6; |
| A48-B20-C7; | A48-B20-C8; | A48-B20-C9; | A49-B20-C1; | A49-B20-C2; | A49-B20-C3; |
| A49-B20-C4; | A49-B20-C5; | A49-B20-C6; | A49-B20-C7; | A49-B20-C8; | A49-B20-C9; |
| A50-B20-C1; | A50-B20-C2; | A50-B20-C3; | A50-B20-C4; | A50-B20-C5; | A50-B20-C6; |
| A50-B20-C7; | A50-B20-C8; | A50-B20-C9; | A51-B20-C1; | A51-B20-C2; | A51-B20-C3; |
| A51-B20-C4; | A51-B20-C5; | A51-B20-C6; | A51-B20-C7; | A51-B20-C8; | A51-B20-C9; |
| A52-B20-C1; | A52-B20-C2; | A52-B20-C3; | A52-B20-C4; | A52-B20-C5; | A52-B20-C6; |
| A52-B20-C7; | A52-B20-C8; | A52-B20-C9; | A53-B20-C1; | A53-B20-C2; | A53-B20-C3; |
| A53-B20-C4; | A53-B20-C5; | A53-B20-C6; | A53-B20-C7; | A53-B20-C8; | A53-B20-C9; |
| A54-B20-C1; | A54-B20-C2; | A54-B20-C3; | A54-B20-C4; | A54-B20-C5; | A54-B20-C6; |
| A54-B20-C7; | A54-B20-C8; | A54-B20-C9; | A55-B20-C1; | A55-B20-C2; | A55-B20-C3; |
| A55-B20-C4; | A55-B20-C5; | A55-B20-C6; | A55-B20-C7; | A55-B20-C8; | A55-B20-C9; |
| A56-B20-C1; | A56-B20-C2; | A56-B20-C3; | A56-B20-C4; | A56-B20-C5; | A56-B20-C6; |
| A56-B20-C7; | A56-B20-C8; | A56-B20-C9; | A57-B20-C1; | A57-B20-C2; | A57-B20-C3; |
| A57-B20-C4; | A57-B20-C5; | A57-B20-C6; | A57-B20-C7; | A57-B20-C8; | A57-B20-C9; |
| A58-B20-C1; | A58-B20-C2; | A58-B20-C3; | A58-B20-C4; | A58-B20-C5; | A58-B20-C6; |
| A58-B20-C7; | A58-B20-C8; | A58-B20-C9; | A59-B20-C1; | A59-B20-C2; | A59-B20-C3; |
| A59-B20-C4; | A59-B20-C5; | A59-B20-C6; | A59-B20-C7; | A59-B20-C8; | A59-B20-C9; |
| A60-B20-C1; | A60-B20-C2; | A60-B20-C3; | A60-B20-C4; | A60-B20-C5; | A60-B20-C6; |
| A60-B20-C7; | A60-B20-C8; | A60-B20-C9; | A61-B20-C1; | A61-B20-C2; | A61-B20-C3; |
| A61-B20-C4; | A61-B20-C5; | A61-B20-C6; | A61-B20-C7; | A61-B20-C8; | A61-B20-C9; |
| A62-B20-C1; | A62-B20-C2; | A62-B20-C3; | A62-B20-C4; | A62-B20-C5; | A62-B20-C6; |
| A62-B20-C7; | A62-B20-C8; | A62-B20-C9; | A63-B20-C1; | A63-B20-C2; | A63-B20-C3; |
| A63-B20-C4; | A63-B20-C5; | A63-B20-C6; | A63-B20-C7; | A63-B20-C8; | A63-B20-C9; |
| A64-B20-C1; | A64-B20-C2; | A64-B20-C3; | A64-B20-C4; | A64-B20-C5; | A64-B20-C6; |
| A64-B20-C7; | A64-B20-C8; | A64-B20-C9; | A65-B20-C1; | A65-B20-C2; | A65-B20-C3; |
| A65-B20-C4; | A65-B20-C5; | A65-B20-C6; | A65-B20-C7; | A65-B20-C8; | A65-B20-C9; |
| A66-B20-C1; | A66-B20-C2; | A66-B20-C3; | A66-B20-C4; | A66-B20-C5; | A66-B20-C6; |
| A66-B20-C7; | A66-B20-C8; | A66-B20-C9; | A67-B20-C1; | A67-B20-C2; | A67-B20-C3; |
| A67-B20-C4; | A67-B20-C5; | A67-B20-C6; | A67-B20-C7; | A67-B20-C8; | A67-B20-C9; |
| A68-B20-C1; | A68-B20-C2; | A68-B20-C3; | A68-B20-C4; | A68-B20-C5; | A68-B20-C6; |
| A68-B20-C7; | A68-B20-C8; | A68-B20-C9; | A69-B20-C1; | A69-B20-C2; | A69-B20-C3; |
| A69-B20-C4; | A69-B20-C5; | A69-B20-C6; | A69-B20-C7; | A69-B20-C8; | A69-B20-C9; |
| A70-B20-C1; | A70-B20-C2; | A70-B20-C3; | A70-B20-C4; | A70-B20-C5; | A70-B20-C6; |
| A70-B20-C7; | A70-B20-C8; | A70-B20-C9; | A71-B20-C1; | A71-B20-C2; | A71-B20-C3; |
| A71-B20-C4; | A71-B20-C5; | A71-B20-C6; | A71-B20-C7; | A71-B20-C8; | A71-B20-C9; |
| A1-B21-C1; | A1-B21-C2; | A1-B21-C3; | A1-B21-C4; | A1-B21-C5; | A1-B21-C6; |
| A1-B21-C7; | A1-B21-C8; | A1-B21-C9; | A2-B21-C1; | A2-B21-C2; | A2-B21-C3; |
| A2-B21-C4; | A2-B21-C5; | A2-B21-C6; | A2-B21-C7; | A2-B21-C8; | A2-B21-C9; |
| A3-B21-C1; | A3-B21-C2; | A3-B21-C3; | A3-B21-C4; | A3-B21-C5; | A3-B21-C6; |
| A3-B21-C7; | A3-B21-C8; | A3-B21-C9; | A4-B21-C1; | A4-B21-C2; | A4-B21-C3; |
| A4-B21-C4; | A4-B21-C5; | A4-B21-C6; | A4-B21-C7; | A4-B21-C8; | A4-B21-C9; |
| A5-B21-C1; | A5-B21-C2; | A5-B21-C3; | A5-B21-C4; | A5-B21-C5; | A5-B21-C6; |
| A5-B21-C7; | A5-B21-C8; | A5-B21-C9; | A6-B21-C1; | A6-B21-C2; | A6-B21-C3; |
| A6-B21-C4; | A6-B21-C5; | A6-B21-C6; | A6-B21-C7; | A6-B21-C8; | A6-B21-C9; |
| A7-B21-C1; | A7-B21-C2; | A7-B21-C3; | A7-B21-C4; | A7-B21-C5; | A7-B21-C6; |
| A7-B21-C7; | A7-B21-C8; | A7-B21-C9; | A8-B21-C1; | A8-B21-C2; | A8-B21-C3; |
| A8-B21-C4; | A8-B21-C5; | A8-B21-C6; | A8-B21-C7; | A8-B21-C8; | A8-B21-C9; |
| A9-B21-C1; | A9-B21-C2; | A9-B21-C3; | A9-B21-C4; | A9-B21-C5; | A9-B21-C6; |
| A9-B21-C7; | A9-B21-C8; | A9-B21-C9; | A10-B21-C1; | A10-B21-C2; | A10-B21-C3; |
| A10-B21-C4; | A10-B21-C5; | A10-B21-C6; | A10-B21-C7; | A10-B21-C8; | A10-B21-C9; |
| A11-B21-C1; | A11-B21-C2; | A11-B21-C3; | A11-B21-C4; | A11-B21-C5; | A11-B21-C6; |
| A11-B21-C7; | A11-B21-C8; | A11-B21-C9; | A12-B21-C1; | A12-B21-C2; | A12-B21-C3; |
| A12-B21-C4; | A12-B21-C5; | A12-B21-C6; | A12-B21-C7; | A12-B21-C8; | A12-B21-C9; |
| A13-B21-C1; | A13-B21-C2; | A13-B21-C3; | A13-B21-C4; | A13-B21-C5; | A13-B21-C6; |
| A13-B21-C7; | A13-B21-C8; | A13-B21-C9; | A14-B21-C1; | A14-B21-C2; | A14-B21-C3; |
| A14-B21-C4; | A14-B21-C5; | A14-B21-C6; | A14-B21-C7; | A14-B21-C8; | A14-B21-C9; |
| A15-B21-C1; | A15-B21-C2; | A15-B21-C3; | A15-B21-C4; | A15-B21-C5; | A15-B21-C6; |
| A15-B21-C7; | A15-B21-C8; | A15-B21-C9; | A16-B21-C1; | A16-B21-C2; | A16-B21-C3; |
| A16-B21-C4; | A16-B21-C5; | A16-B21-C6; | A16-B21-C7; | A16-B21-C8; | A16-B21-C9; |
| A17-B21-C1; | A17-B21-C2; | A17-B21-C3; | A17-B21-C4; | A17-B21-C5; | A17-B21-C6; |
| A17-B21-C7; | A17-B21-C8; | A17-B21-C9; | A18-B21-C1; | A18-B21-C2; | A18-B21-C3; |
| A18-B21-C4; | A18-B21-C5; | A18-B21-C6; | A18-B21-C7; | A18-B21-C8; | A18-B21-C9; |
| A19-B21-C1; | A19-B21-C2; | A19-B21-C3; | A19-B21-C4; | A19-B21-C5; | A19-B21-C6; |
| A19-B21-C7; | A19-B21-C8; | A19-B21-C9; | A20-B21-C1; | A20-B21-C2; | A20-B21-C3; |
| A20-B21-C4; | A20-B21-C5; | A20-B21-C6; | A20-B21-C7; | A20-B21-C8; | A20-B21-C9; |

-continued

| | | | | | |
|---|---|---|---|---|---|
| A21-B21-C1; | A21-B21-C2; | A21-B21-C3; | A21-B21-C4; | A21-B21-C5; | A21-B21-C6; |
| A21-B21-C7; | A21-B21-C8; | A21-B21-C9; | A22-B21-C1; | A22-B21-C2; | A22-B21-C3; |
| A22-B21-C4; | A22-B21-C5; | A22-B21-C6; | A22-B21-C7; | A22-B21-C8; | A22-B21-C9; |
| A23-B21-C1; | A23-B21-C2; | A23-B21-C3; | A23-B21-C4; | A23-B21-C5; | A23-B21-C6; |
| A23-B21-C7; | A23-B21-C8; | A23-B21-C9; | A24-B21-C1; | A24-B21-C2; | A24-B21-C3; |
| A24-B21-C4; | A24-B21-C5; | A24-B21-C6; | A24-B21-C7; | A24-B21-C8; | A24-B21-C9; |
| A25-B21-C1; | A25-B21-C2; | A25-B21-C3; | A25-B21-C4; | A25-B21-C5; | A25-B21-C6; |
| A25-B21-C7; | A25-B21-C8; | A25-B21-C9; | A26-B21-C1; | A26-B21-C2; | A26-B21-C3; |
| A26-B21-C4; | A26-B21-C5; | A26-B21-C6; | A26-B21-C7; | A26-B21-C8; | A26-B21-C9; |
| A27-B21-C1; | A27-B21-C2; | A27-B21-C3; | A27-B21-C4; | A27-B21-C5; | A27-B21-C6; |
| A27-B21-C7; | A27-B21-C8; | A27-B21-C9; | A28-B21-C1; | A28-B21-C2; | A28-B21-C3; |
| A28-B21-C4; | A28-B21-C5; | A28-B21-C6; | A28-B21-C7; | A28-B21-C8; | A28-B21-C9; |
| A29-B21-C1; | A29-B21-C2; | A29-B21-C3; | A29-B21-C4; | A29-B21-C5; | A29-B21-C6; |
| A29-B21-C7; | A29-B21-C8; | A29-B21-C9; | A30-B21-C1; | A30-B21-C2; | A30-B21-C3; |
| A30-B21-C4; | A30-B21-C5; | A30-B21-C6; | A30-B21-C7; | A30-B21-C8; | A30-B21-C9; |
| A31-B21-C1; | A31-B21-C2; | A31-B21-C3; | A31-B21-C4; | A31-B21-C5; | A31-B21-C6; |
| A31-B21-C7; | A31-B21-C8; | A31-B21-C9; | A32-B21-C1; | A32-B21-C2; | A32-B21-C3; |
| A32-B21-C4; | A32-B21-C5; | A32-B21-C6; | A32-B21-C7; | A32-B21-C8; | A32-B21-C9; |
| A33-B21-C1; | A33-B21-C2; | A33-B21-C3; | A33-B21-C4; | A33-B21-C5; | A33-B21-C6; |
| A33-B21-C7; | A33-B21-C8; | A33-B21-C9; | A34-B21-C1; | A34-B21-C2; | A34-B21-C3; |
| A34-B21-C4; | A34-B21-C5; | A34-B21-C6; | A34-B21-C7; | A34-B21-C8; | A34-B21-C9; |
| A35-B21-C1; | A35-B21-C2; | A35-B21-C3; | A35-B21-C4; | A35-B21-C5; | A35-B21-C6; |
| A35-B21-C7; | A35-B21-C8; | A35-B21-C9; | A36-B21-C1; | A36-B21-C2; | A36-B21-C3; |
| A36-B21-C4; | A36-B21-C5; | A36-B21-C6; | A36-B21-C7; | A36-B21-C8; | A36-B21-C9; |
| A37-B21-C1; | A37-B21-C2; | A37-B21-C3; | A37-B21-C4; | A37-B21-C5; | A37-B21-C6; |
| A37-B21-C7; | A37-B21-C8; | A37-B21-C9; | A38-B21-C1; | A38-B21-C2; | A38-B21-C3; |
| A38-B21-C4; | A38-B21-C5; | A38-B21-C6; | A38-B21-C7; | A38-B21-C8; | A38-B21-C9; |
| A39-B21-C1; | A39-B21-C2; | A39-B21-C3; | A39-B21-C4; | A39-B21-C5; | A39-B21-C6; |
| A39-B21-C7; | A39-B21-C8; | A39-B21-C9; | A40-B21-C1; | A40-B21-C2; | A40-B21-C3; |
| A40-B21-C4; | A40-B21-C5; | A40-B21-C6; | A40-B21-C7; | A40-B21-C8; | A40-B21-C9; |
| A41-B21-C1; | A41-B21-C2; | A41-B21-C3; | A41-B21-C4; | A41-B21-C5; | A41-B21-C6; |
| A41-B21-C7; | A41-B21-C8; | A41-B21-C9; | A42-B21-C1; | A42-B21-C2; | A42-B21-C3; |
| A42-B21-C4; | A42-B21-C5; | A42-B21-C6; | A42-B21-C7; | A42-B21-C8; | A42-B21-C9; |
| A43-B21-C1; | A43-B21-C2; | A43-B21-C3; | A43-B21-C4; | A43-B21-C5; | A43-B21-C6; |
| A43-B21-C7; | A43-B21-C8; | A43-B21-C9; | A44-B21-C1; | A44-B21-C2; | A44-B21-C3; |
| A44-B21-C4; | A44-B21-C5; | A44-B21-C6; | A44-B21-C7; | A44-B21-C8; | A44-B21-C9; |
| A45-B21-C1; | A45-B21-C2; | A45-B21-C3; | A45-B21-C4; | A45-B21-C5; | A45-B21-C6; |
| A45-B21-C7; | A45-B21-C8; | A45-B21-C9; | A46-B21-C1; | A46-B21-C2; | A46-B21-C3; |
| A46-B21-C4; | A46-B21-C5; | A46-B21-C6; | A46-B21-C7; | A46-B21-C8; | A46-B21-C9; |
| A47-B21-C1; | A47-B21-C2; | A47-B21-C3; | A47-B21-C4; | A47-B21-C5; | A47-B21-C6; |
| A47-B21-C7; | A47-B21-C8; | A47-B21-C9; | A48-B21-C1; | A48-B21-C2; | A48-B21-C3; |
| A48-B21-C4; | A48-B21-C5; | A48-B21-C6; | A48-B21-C7; | A48-B21-C8; | A48-B21-C9; |
| A49-B21-C1; | A49-B21-C2; | A49-B21-C3; | A49-B21-C4; | A49-B21-C5; | A49-B21-C6; |
| A49-B21-C7; | A49-B21-C8; | A49-B21-C9; | A50-B21-C1; | A50-B21-C2; | A50-B21-C3; |
| A50-B21-C4; | A50-B21-C5; | A50-B21-C6; | A50-B21-C7; | A50-B21-C8; | A50-B21-C9; |
| A51-B21-C1; | A51-B21-C2; | A51-B21-C3; | A51-B21-C4; | A51-B21-C5; | A51-B21-C6; |
| A51-B21-C7; | A51-B21-C8; | A51-B21-C9; | A52-B21-C1; | A52-B21-C2; | A52-B21-C3; |
| A52-B21-C4; | A52-B21-C5; | A52-B21-C6; | A52-B21-C7; | A52-B21-C8; | A52-B21-C9; |
| A53-B21-C1; | A53-B21-C2; | A53-B21-C3; | A53-B21-C4; | A53-B21-C5; | A53-B21-C6; |
| A53-B21-C7; | A53-B21-C8; | A53-B21-C9; | A54-B21-C1; | A54-B21-C2; | A54-B21-C3; |
| A54-B21-C4; | A54-B21-C5; | A54-B21-C6; | A54-B21-C7; | A54-B21-C8; | A54-B21-C9; |
| A55-B21-C1; | A55-B21-C2; | A55-B21-C3; | A55-B21-C4; | A55-B21-C5; | A55-B21-C6; |
| A55-B21-C7; | A55-B21-C8; | A55-B21-C9; | A56-B21-C1; | A56-B21-C2; | A56-B21-C3; |
| A56-B21-C4; | A56-B21-C5; | A56-B21-C6; | A56-B21-C7; | A56-B21-C8; | A56-B21-C9; |
| A57-B21-C1; | A57-B21-C2; | A57-B21-C3; | A57-B21-C4; | A57-B21-C5; | A57-B21-C6; |
| A57-B21-C7; | A57-B21-C8; | A57-B21-C9; | A58-B21-C1; | A58-B21-C2; | A58-B21-C3; |
| A58-B21-C4; | A58-B21-C5; | A58-B21-C6; | A58-B21-C7; | A58-B21-C8; | A58-B21-C9; |
| A59-B21-C1; | A59-B21-C2; | A59-B21-C3; | A59-B21-C4; | A59-B21-C5; | A59-B21-C6; |
| A59-B21-C7; | A59-B21-C8; | A59-B21-C9; | A60-B21-C1; | A60-B21-C2; | A60-B21-C3; |
| A60-B21-C4; | A60-B21-C5; | A60-B21-C6; | A60-B21-C7; | A60-B21-C8; | A60-B21-C9; |
| A61-B21-C1; | A61-B21-C2; | A61-B21-C3; | A61-B21-C4; | A61-B21-C5; | A61-B21-C6; |
| A61-B21-C7; | A61-B21-C8; | A61-B21-C9; | A62-B21-C1; | A62-B21-C2; | A62-B21-C3; |
| A62-B21-C4; | A62-B21-C5; | A62-B21-C6; | A62-B21-C7; | A62-B21-C8; | A62-B21-C9; |
| A63-B21-C1; | A63-B21-C2; | A63-B21-C3; | A63-B21-C4; | A63-B21-C5; | A63-B21-C6; |
| A63-B21-C7; | A63-B21-C8; | A63-B21-C9; | A64-B21-C1; | A64-B21-C2; | A64-B21-C3; |
| A64-B21-C4; | A64-B21-C5; | A64-B21-C6; | A64-B21-C7; | A64-B21-C8; | A64-B21-C9; |
| A65-B21-C1; | A65-B21-C2; | A65-B21-C3; | A65-B21-C4; | A65-B21-C5; | A65-B21-C6; |
| A65-B21-C7; | A65-B21-C8; | A65-B21-C9; | A66-B21-C1; | A66-B21-C2; | A66-B21-C3; |
| A66-B21-C4; | A66-B21-C5; | A66-B21-C6; | A66-B21-C7; | A66-B21-C8; | A66-B21-C9; |
| A67-B21-C1; | A67-B21-C2; | A67-B21-C3; | A67-B21-C4; | A67-B21-C5; | A67-B21-C6; |
| A67-B21-C7; | A67-B21-C8; | A67-B21-C9; | A68-B21-C1; | A68-B21-C2; | A68-B21-C3; |
| A68-B21-C4; | A68-B21-C5; | A68-B21-C6; | A68-B21-C7; | A68-B21-C8; | A68-B21-C9; |
| A69-B21-C1; | A69-B21-C2; | A69-B21-C3; | A69-B21-C4; | A69-B21-C5; | A69-B21-C6; |
| A69-B21-C7; | A69-B21-C8; | A69-B21-C9; | A70-B21-C1; | A70-B21-C2; | A70-B21-C3; |
| A70-B21-C4; | A70-B21-C5; | A70-B21-C6; | A70-B21-C7; | A70-B21-C8; | A70-B21-C9; |
| A71-B21-C1; | A71-B21-C2; | A71-B21-C3; | A71-B21-C4; | A71-B21-C5; | A71-B21-C6; |
| A71-B21-C7; | A71-B21-C8; | A71-B21-C9; | A1-B22-C1; | A1-B22-C2; | A1-B22-C3; |
| A1-B22-C4; | A1-B22-C5; | A1-B22-C6; | A1-B22-C7; | A1-B22-C8; | A1-B22-C9; |
| A2-B22-C1; | A2-B22-C2; | A2-B22-C3; | A2-B22-C4; | A2-B22-C5; | A2-B22-C6; |

-continued

| | | | | | |
|---|---|---|---|---|---|
| A2-B22-C7; | A2-B22-C8; | A2-B22-C9; | A3-B22-C1; | A3-B22-C2; | A3-B22-C3; |
| A3-B22-C4; | A3-B22-C5; | A3-B22-C6; | A3-B22-C7; | A3-B22-C8; | A3-B22-C9; |
| A4-B22-C1; | A4-B22-C2; | A4-B22-C3; | A4-B22-C4; | A4-B22-C5; | A4-B22-C6; |
| A4-B22-C7; | A4-B22-C8; | A4-B22-C9; | A5-B22-C1; | A5-B22-C2; | A5-B22-C3; |
| A5-B22-C4; | A5-B22-C5; | A5-B22-C6; | A5-B22-C7; | A5-B22-C8; | A5-B22-C9; |
| A6-B22-C1; | A6-B22-C2; | A6-B22-C3; | A6-B22-C4; | A6-B22-C5; | A6-B22-C6; |
| A6-B22-C7; | A6-B22-C8; | A6-B22-C9; | A7-B22-C1; | A7-B22-C2; | A7-B22-C3; |
| A7-B22-C4; | A7-B22-C5; | A7-B22-C6; | A7-B22-C7; | A7-B22-C8; | A7-B22-C9; |
| A8-B22-C1; | A8-B22-C2; | A8-B22-C3; | A8-B22-C4; | A8-B22-C5; | A8-B22-C6; |
| A8-B22-C7; | A8-B22-C8; | A8-B22-C9; | A9-B22-C1; | A9-B22-C2; | A9-B22-C3; |
| A9-B22-C4; | A9-B22-C5; | A9-B22-C6; | A9-B22-C7; | A9-B22-C8; | A9-B22-C9; |
| A10-B22-C1; | A10-B22-C2; | A10-B22-C3; | A10-B22-C4; | A10-B22-C5; | A10-B22-C6; |
| A10-B22-C7; | A10-B22-C8; | A10-B22-C9; | A11-B22-C1; | A11-B22-C2; | A11-B22-C3; |
| A11-B22-C4; | A11-B22-C5; | A11-B22-C6; | A11-B22-C7; | A11-B22-C8; | A11-B22-C9; |
| A12-B22-C1; | A12-B22-C2; | A12-B22-C3; | A12-B22-C4; | A12-B22-C5; | A12-B22-C6; |
| A12-B22-C7; | A12-B22-C8; | A12-B22-C9; | A13-B22-C1; | A13-B22-C2; | A13-B22-C3; |
| A13-B22-C4; | A13-B22-C5; | A13-B22-C6; | A13-B22-C7; | A13-B22-C8; | A13-B22-C9; |
| A14-B22-C1; | A14-B22-C2; | A14-B22-C3; | A14-B22-C4; | A14-B22-C5; | A14-B22-C6; |
| A14-B22-C7; | A14-B22-C8; | A14-B22-C9; | A15-B22-C1; | A15-B22-C2; | A15-B22-C3; |
| A15-B22-C4; | A15-B22-C5; | A15-B22-C6; | A15-B22-C7; | A15-B22-C8; | A15-B22-C9; |
| A16-B22-C1; | A16-B22-C2; | A16-B22-C3; | A16-B22-C4; | A16-B22-C5; | A16-B22-C6; |
| A16-B22-C7; | A16-B22-C8; | A16-B22-C9; | A17-B22-C1; | A17-B22-C2; | A17-B22-C3; |
| A17-B22-C4; | A17-B22-C5; | A17-B22-C6; | A17-B22-C7; | A17-B22-C8; | A17-B22-C9; |
| A18-B22-C1; | A18-B22-C2; | A18-B22-C3; | A18-B22-C4; | A18-B22-C5; | A18-B22-C6; |
| A18-B22-C7; | A18-B22-C8; | A18-B22-C9; | A19-B22-C1; | A19-B22-C2; | A19-B22-C3; |
| A19-B22-C4; | A19-B22-C5; | A19-B22-C6; | A19-B22-C7; | A19-B22-C8; | A19-B22-C9; |
| A20-B22-C1; | A20-B22-C2; | A20-B22-C3; | A20-B22-C4; | A20-B22-C5; | A20-B22-C6; |
| A20-B22-C7; | A20-B22-C8; | A20-B22-C9; | A21-B22-C1; | A21-B22-C2; | A21-B22-C3; |
| A21-B22-C4; | A21-B22-C5; | A21-B22-C6; | A21-B22-C7; | A21-B22-C8; | A21-B22-C9; |
| A22-B22-C1; | A22-B22-C2; | A22-B22-C3; | A22-B22-C4; | A22-B22-C5; | A22-B22-C6; |
| A22-B22-C7; | A22-B22-C8; | A22-B22-C9; | A23-B22-C1; | A23-B22-C2; | A23-B22-C3; |
| A23-B22-C4; | A23-B22-C5; | A23-B22-C6; | A23-B22-C7; | A23-B22-C8; | A23-B22-C9; |
| A24-B22-C1; | A24-B22-C2; | A24-B22-C3; | A24-B22-C4; | A24-B22-C5; | A24-B22-C6; |
| A24-B22-C7; | A24-B22-C8; | A24-B22-C9; | A25-B22-C1; | A25-B22-C2; | A25-B22-C3; |
| A25-B22-C4; | A25-B22-C5; | A25-B22-C6; | A25-B22-C7; | A25-B22-C8; | A25-B22-C9; |
| A26-B22-C1; | A26-B22-C2; | A26-B22-C3; | A26-B22-C4; | A26-B22-C5; | A26-B22-C6; |
| A26-B22-C7; | A26-B22-C8; | A26-B22-C9; | A27-B22-C1; | A27-B22-C2; | A27-B22-C3; |
| A27-B22-C4; | A27-B22-C5; | A27-B22-C6; | A27-B22-C7; | A27-B22-C8; | A27-B22-C9; |
| A28-B22-C1; | A28-B22-C2; | A28-B22-C3; | A28-B22-C4; | A28-B22-C5; | A28-B22-C6; |
| A28-B22-C7; | A28-B22-C8; | A28-B22-C9; | A29-B22-C1; | A29-B22-C2; | A29-B22-C3; |
| A29-B22-C4; | A29-B22-C5; | A29-B22-C6; | A29-B22-C7; | A29-B22-C8; | A29-B22-C9; |
| A30-B22-C1; | A30-B22-C2; | A30-B22-C3; | A30-B22-C4; | A30-B22-C5; | A30-B22-C6; |
| A30-B22-C7; | A30-B22-C8; | A30-B22-C9; | A31-B22-C1; | A31-B22-C2; | A31-B22-C3; |
| A31-B22-C4; | A31-B22-C5; | A31-B22-C6; | A31-B22-C7; | A31-B22-C8; | A31-B22-C9; |
| A32-B22-C1; | A32-B22-C2; | A32-B22-C3; | A32-B22-C4; | A32-B22-C5; | A32-B22-C6; |
| A32-B22-C7; | A32-B22-C8; | A32-B22-C9; | A33-B22-C1; | A33-B22-C2; | A33-B22-C3; |
| A33-B22-C4; | A33-B22-C5; | A33-B22-C6; | A33-B22-C7; | A33-B22-C8; | A33-B22-C9; |
| A34-B22-C1; | A34-B22-C2; | A34-B22-C3; | A34-B22-C4; | A34-B22-C5; | A34-B22-C6; |
| A34-B22-C7; | A34-B22-C8; | A34-B22-C9; | A35-B22-C1; | A35-B22-C2; | A35-B22-C3; |
| A35-B22-C4; | A35-B22-C5; | A35-B22-C6; | A35-B22-C7; | A35-B22-C8; | A35-B22-C9; |
| A36-B22-C1; | A36-B22-C2; | A36-B22-C3; | A36-B22-C4; | A36-B22-C5; | A36-B22-C6; |
| A36-B22-C7; | A36-B22-C8; | A36-B22-C9; | A37-B22-C1; | A37-B22-C2; | A37-B22-C3; |
| A37-B22-C4; | A37-B22-C5; | A37-B22-C6; | A37-B22-C7; | A37-B22-C8; | A37-B22-C9; |
| A38-B22-C1; | A38-B22-C2; | A38-B22-C3; | A38-B22-C4; | A38-B22-C5; | A38-B22-C6; |
| A38-B22-C7; | A38-B22-C8; | A38-B22-C9; | A39-B22-C1; | A39-B22-C2; | A39-B22-C3; |
| A39-B22-C4; | A39-B22-C5; | A39-B22-C6; | A39-B22-C7; | A39-B22-C8; | A39-B22-C9; |
| A40-B22-C1; | A40-B22-C2; | A40-B22-C3; | A40-B22-C4; | A40-B22-C5; | A40-B22-C6; |
| A40-B22-C7; | A40-B22-C8; | A40-B22-C9; | A41-B22-C1; | A41-B22-C2; | A41-B22-C3; |
| A41-B22-C4; | A41-B22-C5; | A41-B22-C6; | A41-B22-C7; | A41-B22-C8; | A41-B22-C9; |
| A42-B22-C1; | A42-B22-C2; | A42-B22-C3; | A42-B22-C4; | A42-B22-C5; | A42-B22-C6; |
| A42-B22-C7; | A42-B22-C8; | A42-B22-C9; | A43-B22-C1; | A43-B22-C2; | A43-B22-C3; |
| A43-B22-C4; | A43-B22-C5; | A43-B22-C6; | A43-B22-C7; | A43-B22-C8; | A43-B22-C9; |
| A44-B22-C1; | A44-B22-C2; | A44-B22-C3; | A44-B22-C4; | A44-B22-C5; | A44-B22-C6; |
| A44-B22-C7; | A44-B22-C8; | A44-B22-C9; | A45-B22-C1; | A45-B22-C2; | A45-B22-C3; |
| A45-B22-C4; | A45-B22-C5; | A45-B22-C6; | A45-B22-C7; | A45-B22-C8; | A45-B22-C9; |
| A46-B22-C1; | A46-B22-C2; | A46-B22-C3; | A46-B22-C4; | A46-B22-C5; | A46-B22-C6; |
| A46-B22-C7; | A46-B22-C8; | A46-B22-C9; | A47-B22-C1; | A47-B22-C2; | A47-B22-C3; |
| A47-B22-C4; | A47-B22-C5; | A47-B22-C6; | A47-B22-C7; | A47-B22-C8; | A47-B22-C9; |
| A48-B22-C1; | A48-B22-C2; | A48-B22-C3; | A48-B22-C4; | A48-B22-C5; | A48-B22-C6; |
| A48-B22-C7; | A48-B22-C8; | A48-B22-C9; | A49-B22-C1; | A49-B22-C2; | A49-B22-C3; |
| A49-B22-C4; | A49-B22-C5; | A49-B22-C6; | A49-B22-C7; | A49-B22-C8; | A49-B22-C9; |
| A50-B22-C1; | A50-B22-C2; | A50-B22-C3; | A50-B22-C4; | A50-B22-C5; | A50-B22-C6; |
| A50-B22-C7; | A50-B22-C8; | A50-B22-C9; | A51-B22-C1; | A51-B22-C2; | A51-B22-C3; |
| A51-B22-C4; | A51-B22-C5; | A51-B22-C6; | A51-B22-C7; | A51-B22-C8; | A51-B22-C9; |
| A52-B22-C1; | A52-B22-C2; | A52-B22-C3; | A52-B22-C4; | A52-B22-C5; | A52-B22-C6; |
| A52-B22-C7; | A52-B22-C8; | A52-B22-C9; | A53-B22-C1; | A53-B22-C2; | A53-B22-C3; |
| A53-B22-C4; | A53-B22-C5; | A53-B22-C6; | A53-B22-C7; | A53-B22-C8; | A53-B22-C9; |
| A54-B22-C1; | A54-B22-C2; | A54-B22-C3; | A54-B22-C4; | A54-B22-C5; | A54-B22-C6; |
| A54-B22-C7; | A54-B22-C8; | A54-B22-C9; | A55-B22-C1; | A55-B22-C2; | A55-B22-C3; |

-continued

| | | | | | |
|---|---|---|---|---|---|
| A55-B22-C4; | A55-B22-C5; | A55-B22-C6; | A55-B22-C7; | A55-B22-C8; | A55-B22-C9; |
| A56-B22-C1; | A56-B22-C2; | A56-B22-C3; | A56-B22-C4; | A56-B22-C5; | A56-B22-C6; |
| A56-B22-C7; | A56-B22-C8; | A56-B22-C9; | A57-B22-C1; | A57-B22-C2; | A57-B22-C3; |
| A57-B22-C4; | A57-B22-C5; | A57-B22-C6; | A57-B22-C7; | A57-B22-C8; | A57-B22-C9; |
| A58-B22-C1; | A58-B22-C2; | A58-B22-C3; | A58-B22-C4; | A58-B22-C5; | A58-B22-C6; |
| A58-B22-C7; | A58-B22-C8; | A58-B22-C9; | A59-B22-C1; | A59-B22-C2; | A59-B22-C3; |
| A59-B22-C4; | A59-B22-C5; | A59-B22-C6; | A59-B22-C7; | A59-B22-C8; | A59-B22-C9; |
| A60-B22-C1; | A60-B22-C2; | A60-B22-C3; | A60-B22-C4; | A60-B22-C5; | A60-B22-C6; |
| A60-B22-C7; | A60-B22-C8; | A60-B22-C9; | A61-B22-C1; | A61-B22-C2; | A61-B22-C3; |
| A61-B22-C4; | A61-B22-C5; | A61-B22-C6; | A61-B22-C7; | A61-B22-C8; | A61-B22-C9; |
| A62-B22-C1; | A62-B22-C2; | A62-B22-C3; | A62-B22-C4; | A62-B22-C5; | A62-B22-C6; |
| A62-B22-C7; | A62-B22-C8; | A62-B22-C9; | A63-B22-C1; | A63-B22-C2; | A63-B22-C3; |
| A63-B22-C4; | A63-B22-C5; | A63-B22-C6; | A63-B22-C7; | A63-B22-C8; | A63-B22-C9; |
| A64-B22-C1; | A64-B22-C2; | A64-B22-C3; | A64-B22-C4; | A64-B22-C5; | A64-B22-C6; |
| A64-B22-C7; | A64-B22-C8; | A64-B22-C9; | A65-B22-C1; | A65-B22-C2; | A65-B22-C3; |
| A65-B22-C4; | A65-B22-C5; | A65-B22-C6; | A65-B22-C7; | A65-B22-C8; | A65-B22-C9; |
| A66-B22-C1; | A66-B22-C2; | A66-B22-C3; | A66-B22-C4; | A66-B22-C5; | A66-B22-C6; |
| A66-B22-C7; | A66-B22-C8; | A66-B22-C9; | A67-B22-C1; | A67-B22-C2; | A67-B22-C3; |
| A67-B22-C4; | A67-B22-C5; | A67-B22-C6; | A67-B22-C7; | A67-B22-C8; | A67-B22-C9; |
| A68-B22-C1; | A68-B22-C2; | A68-B22-C3; | A68-B22-C4; | A68-B22-C5; | A68-B22-C6; |
| A68-B22-C7; | A68-B22-C8; | A68-B22-C9; | A69-B22-C1; | A69-B22-C2; | A69-B22-C3; |
| A69-B22-C4; | A69-B22-C5; | A69-B22-C6; | A69-B22-C7; | A69-B22-C8; | A69-B22-C9; |
| A70-B22-C1; | A70-B22-C2; | A70-B22-C3; | A70-B22-C4; | A70-B22-C5; | A70-B22-C6; |
| A70-B22-C7; | A70-B22-C8; | A70-B22-C9; | A71-B22-C1; | A71-B22-C2; | A71-B22-C3; |
| A71-B22-C4; | A71-B22-C5; | A71-B22-C6; | A71-B22-C7; | A71-B22-C8; | A71-B22-C9; |
| A1-B23-C1; | A1-B23-C2; | A1-B23-C3; | A1-B23-C4; | A1-B23-C5; | A1-B23-C6; |
| A1-B23-C7; | A1-B23-C8; | A1-B23-C9; | A2-B23-C1; | A2-B23-C2; | A2-B23-C3; |
| A2-B23-C4; | A2-B23-C5; | A2-B23-C6; | A2-B23-C7; | A2-B23-C8; | A2-B23-C9; |
| A3-B23-C1; | A3-B23-C2; | A3-B23-C3; | A3-B23-C4; | A3-B23-C5; | A3-B23-C6; |
| A3-B23-C7; | A3-B23-C8; | A3-B23-C9; | A4-B23-C1; | A4-B23-C2; | A4-B23-C3; |
| A4-B23-C4; | A4-B23-C5; | A4-B23-C6; | A4-B23-C7; | A4-B23-C8; | A4-B23-C9; |
| A5-B23-C1; | A5-B23-C2; | A5-B23-C3; | A5-B23-C4; | A5-B23-C5; | A5-B23-C6; |
| A5-B23-C7; | A5-B23-C8; | A5-B23-C9; | A6-B23-C1; | A6-B23-C2; | A6-B23-C3; |
| A6-B23-C4; | A6-B23-C5; | A6-B23-C6; | A6-B23-C7; | A6-B23-C8; | A6-B23-C9; |
| A7-B23-C1; | A7-B23-C2; | A7-B23-C3; | A7-B23-C4; | A7-B23-C5; | A7-B23-C6; |
| A7-B23-C7; | A7-B23-C8; | A7-B23-C9; | A8-B23-C1; | A8-B23-C2; | A8-B23-C3; |
| A8-B23-C4; | A8-B23-C5; | A8-B23-C6; | A8-B23-C7; | A8-B23-C8; | A8-B23-C9; |
| A9-B23-C1; | A9-B23-C2; | A9-B23-C3; | A9-B23-C4; | A9-B23-C5; | A9-B23-C6; |
| A9-B23-C7; | A9-B23-C8; | A9-B23-C9; | A10-B23-C1; | A10-B23-C2; | A10-B23-C3; |
| A10-B23-C4; | A10-B23-C5; | A10-B23-C6; | A10-B23-C7; | A10-B23-C8; | A10-B23-C9; |
| A11-B23-C1; | A11-B23-C2; | A11-B23-C3; | A11-B23-C4; | A11-B23-C5; | A11-B23-C6; |
| A11-B23-C7; | A11-B23-C8; | A11-B23-C9; | A12-B23-C1; | A12-B23-C2; | A12-B23-C3; |
| A12-B23-C4; | A12-B23-C5; | A12-B23-C6; | A12-B23-C7; | A12-B23-C8; | A12-B23-C9; |
| A13-B23-C1; | A13-B23-C2; | A13-B23-C3; | A13-B23-C4; | A13-B23-C5; | A13-B23-C6; |
| A13-B23-C7; | A13-B23-C8; | A13-B23-C9; | A14-B23-C1; | A14-B23-C2; | A14-B23-C3; |
| A14-B23-C4; | A14-B23-C5; | A14-B23-C6; | A14-B23-C7; | A14-B23-C8; | A14-B23-C9; |
| A15-B23-C1; | A15-B23-C2; | A15-B23-C3; | A15-B23-C4; | A15-B23-C5; | A15-B23-C6; |
| A15-B23-C7; | A15-B23-C8; | A15-B23-C9; | A16-B23-C1; | A16-B23-C2; | A16-B23-C3; |
| A16-B23-C4; | A16-B23-C5; | A16-B23-C6; | A16-B23-C7; | A16-B23-C8; | A16-B23-C9; |
| A17-B23-C1; | A17-B23-C2; | A17-B23-C3; | A17-B23-C4; | A17-B23-C5; | A17-B23-C6; |
| A17-B23-C7; | A17-B23-C8; | A17-B23-C9; | A18-B23-C1; | A18-B23-C2; | A18-B23-C3; |
| A18-B23-C4; | A18-B23-C5; | A18-B23-C6; | A18-B23-C7; | A18-B23-C8; | A18-B23-C9; |
| A19-B23-C1; | A19-B23-C2; | A19-B23-C3; | A19-B23-C4; | A19-B23-C5; | A19-B23-C6; |
| A19-B23-C7; | A19-B23-C8; | A19-B23-C9; | A20-B23-C1; | A20-B23-C2; | A20-B23-C3; |
| A20-B23-C4; | A20-B23-C5; | A20-B23-C6; | A20-B23-C7; | A20-B23-C8; | A20-B23-C9; |
| A21-B23-C1; | A21-B23-C2; | A21-B23-C3; | A21-B23-C4; | A21-B23-C5; | A21-B23-C6; |
| A21-B23-C7; | A21-B23-C8; | A21-B23-C9; | A22-B23-C1; | A22-B23-C2; | A22-B23-C3; |
| A22-B23-C4; | A22-B23-C5; | A22-B23-C6; | A22-B23-C7; | A22-B23-C8; | A22-B23-C9; |
| A23-B23-C1; | A23-B23-C2; | A23-B23-C3; | A23-B23-C4; | A23-B23-C5; | A23-B23-C6; |
| A23-B23-C7; | A23-B23-C8; | A23-B23-C9; | A24-B23-C1; | A24-B23-C2; | A24-B23-C3; |
| A24-B23-C4; | A24-B23-C5; | A24-B23-C6; | A24-B23-C7; | A24-B23-C8; | A24-B23-C9; |
| A25-B23-C1; | A25-B23-C2; | A25-B23-C3; | A25-B23-C4; | A25-B23-C5; | A25-B23-C6; |
| A25-B23-C7; | A25-B23-C8; | A25-B23-C9; | A26-B23-C1; | A26-B23-C2; | A26-B23-C3; |
| A26-B23-C4; | A26-B23-C5; | A26-B23-C6; | A26-B23-C7; | A26-B23-C8; | A26-B23-C9; |
| A27-B23-C1; | A27-B23-C2; | A27-B23-C3; | A27-B23-C4; | A27-B23-C5; | A27-B23-C6; |
| A27-B23-C7; | A27-B23-C8; | A27-B23-C9; | A28-B23-C1; | A28-B23-C2; | A28-B23-C3; |
| A28-B23-C4; | A28-B23-C5; | A28-B23-C6; | A28-B23-C7; | A28-B23-C8; | A28-B23-C9; |
| A29-B23-C1; | A29-B23-C2; | A29-B23-C3; | A29-B23-C4; | A29-B23-C5; | A29-B23-C6; |
| A29-B23-C7; | A29-B23-C8; | A29-B23-C9; | A30-B23-C1; | A30-B23-C2; | A30-B23-C3; |
| A30-B23-C4; | A30-B23-C5; | A30-B23-C6; | A30-B23-C7; | A30-B23-C8; | A30-B23-C9; |
| A31-B23-C1; | A31-B23-C2; | A31-B23-C3; | A31-B23-C4; | A31-B23-C5; | A31-B23-C6; |
| A31-B23-C7; | A31-B23-C8; | A31-B23-C9; | A32-B23-C1; | A32-B23-C2; | A32-B23-C3; |
| A32-B23-C4; | A32-B23-C5; | A32-B23-C6; | A32-B23-C7; | A32-B23-C8; | A32-B23-C9; |
| A33-B23-C1; | A33-B23-C2; | A33-B23-C3; | A33-B23-C4; | A33-B23-C5; | A33-B23-C6; |
| A33-B23-C7; | A33-B23-C8; | A33-B23-C9; | A34-B23-C1; | A34-B23-C2; | A34-B23-C3; |
| A34-B23-C4; | A34-B23-C5; | A34-B23-C6; | A34-B23-C7; | A34-B23-C8; | A34-B23-C9; |
| A35-B23-C1; | A35-B23-C2; | A35-B23-C3; | A35-B23-C4; | A35-B23-C5; | A35-B23-C6; |
| A35-B23-C7; | A35-B23-C8; | A35-B23-C9; | A36-B23-C1; | A36-B23-C2; | A36-B23-C3; |
| A36-B23-C4; | A36-B23-C5; | A36-B23-C6; | A36-B23-C7; | A36-B23-C8; | A36-B23-C9; |

-continued

| | | | | | |
|---|---|---|---|---|---|
| A37-B23-C1; | A37-B23-C2; | A37-B23-C3; | A37-B23-C4; | A37-B23-C5; | A37-B23-C6; |
| A37-B23-C7; | A37-B23-C8; | A37-B23-C9; | A38-B23-C1; | A38-B23-C2; | A38-B23-C3; |
| A38-B23-C4; | A38-B23-C5; | A38-B23-C6; | A38-B23-C7; | A38-B23-C8; | A38-B23-C9; |
| A39-B23-C1; | A39-B23-C2; | A39-B23-C3; | A39-B23-C4; | A39-B23-C5; | A39-B23-C6; |
| A39-B23-C7; | A39-B23-C8; | A39-B23-C9; | A40-B23-C1; | A40-B23-C2; | A40-B23-C3; |
| A40-B23-C4; | A40-B23-C5; | A40-B23-C6; | A40-B23-C7; | A40-B23-C8; | A40-B23-C9; |
| A41-B23-C1; | A41-B23-C2; | A41-B23-C3; | A41-B23-C4; | A41-B23-C5; | A41-B23-C6; |
| A41-B23-C7; | A41-B23-C8; | A41-B23-C9; | A42-B23-C1; | A42-B23-C2; | A42-B23-C3; |
| A42-B23-C4; | A42-B23-C5; | A42-B23-C6; | A42-B23-C7; | A42-B23-C8; | A42-B23-C9; |
| A43-B23-C1; | A43-B23-C2; | A43-B23-C3; | A43-B23-C4; | A43-B23-C5; | A43-B23-C6; |
| A43-B23-C7; | A43-B23-C8; | A43-B23-C9; | A44-B23-C1; | A44-B23-C2; | A44-B23-C3; |
| A44-B23-C4; | A44-B23-C5; | A44-B23-C6; | A44-B23-C7; | A44-B23-C8; | A44-B23-C9; |
| A45-B23-C1; | A45-B23-C2; | A45-B23-C3; | A45-B23-C4; | A45-B23-C5; | A45-B23-C6; |
| A45-B23-C7; | A45-B23-C8; | A45-B23-C9; | A46-B23-C1; | A46-B23-C2; | A46-B23-C3; |
| A46-B23-C4; | A46-B23-C5; | A46-B23-C6; | A46-B23-C7; | A46-B23-C8; | A46-B23-C9; |
| A47-B23-C1; | A47-B23-C2; | A47-B23-C3; | A47-B23-C4; | A47-B23-C5; | A47-B23-C6; |
| A47-B23-C7; | A47-B23-C8; | A47-B23-C9; | A48-B23-C1; | A48-B23-C2; | A48-B23-C3; |
| A48-B23-C4; | A48-B23-C5; | A48-B23-C6; | A48-B23-C7; | A48-B23-C8; | A48-B23-C9; |
| A49-B23-C1; | A49-B23-C2; | A49-B23-C3; | A49-B23-C4; | A49-B23-C5; | A49-B23-C6; |
| A49-B23-C7; | A49-B23-C8; | A49-B23-C9; | A50-B23-C1; | A50-B23-C2; | A50-B23-C3; |
| A50-B23-C4; | A50-B23-C5; | A50-B23-C6; | A50-B23-C7; | A50-B23-C8; | A50-B23-C9; |
| A51-B23-C1; | A51-B23-C2; | A51-B23-C3; | A51-B23-C4; | A51-B23-C5; | A51-B23-C6; |
| A51-B23-C7; | A51-B23-C8; | A51-B23-C9; | A52-B23-C1; | A52-B23-C2; | A52-B23-C3; |
| A52-B23-C4; | A52-B23-C5; | A52-B23-C6; | A52-B23-C7; | A52-B23-C8; | A52-B23-C9; |
| A53-B23-C1; | A53-B23-C2; | A53-B23-C3; | A53-B23-C4; | A53-B23-C5; | A53-B23-C6; |
| A53-B23-C7; | A53-B23-C8; | A53-B23-C9; | A54-B23-C1; | A54-B23-C2; | A54-B23-C3; |
| A54-B23-C4; | A54-B23-C5; | A54-B23-C6; | A54-B23-C7; | A54-B23-C8; | A54-B23-C9; |
| A55-B23-C1; | A55-B23-C2; | A55-B23-C3; | A55-B23-C4; | A55-B23-C5; | A55-B23-C6; |
| A55-B23-C7; | A55-B23-C8; | A55-B23-C9; | A56-B23-C1; | A56-B23-C2; | A56-B23-C3; |
| A56-B23-C4; | A56-B23-C5; | A56-B23-C6; | A56-B23-C7; | A56-B23-C8; | A56-B23-C9; |
| A57-B23-C1; | A57-B23-C2; | A57-B23-C3; | A57-B23-C4; | A57-B23-C5; | A57-B23-C6; |
| A57-B23-C7; | A57-B23-C8; | A57-B23-C9; | A58-B23-C1; | A58-B23-C2; | A58-B23-C3; |
| A58-B23-C4; | A58-B23-C5; | A58-B23-C6; | A58-B23-C7; | A58-B23-C8; | A58-B23-C9; |
| A59-B23-C1; | A59-B23-C2; | A59-B23-C3; | A59-B23-C4; | A59-B23-C5; | A59-B23-C6; |
| A59-B23-C7; | A59-B23-C8; | A59-B23-C9; | A60-B23-C1; | A60-B23-C2; | A60-B23-C3; |
| A60-B23-C4; | A60-B23-C5; | A60-B23-C6; | A60-B23-C7; | A60-B23-C8; | A60-B23-C9; |
| A61-B23-C1; | A61-B23-C2; | A61-B23-C3; | A61-B23-C4; | A61-B23-C5; | A61-B23-C6; |
| A61-B23-C7; | A61-B23-C8; | A61-B23-C9; | A62-B23-C1; | A62-B23-C2; | A62-B23-C3; |
| A62-B23-C4; | A62-B23-C5; | A62-B23-C6; | A62-B23-C7; | A62-B23-C8; | A62-B23-C9; |
| A63-B23-C1; | A63-B23-C2; | A63-B23-C3; | A63-B23-C4; | A63-B23-C5; | A63-B23-C6; |
| A63-B23-C7; | A63-B23-C8; | A63-B23-C9; | A64-B23-C1; | A64-B23-C2; | A64-B23-C3; |
| A64-B23-C4; | A64-B23-C5; | A64-B23-C6; | A64-B23-C7; | A64-B23-C8; | A64-B23-C9; |
| A65-B23-C1; | A65-B23-C2; | A65-B23-C3; | A65-B23-C4; | A65-B23-C5; | A65-B23-C6; |
| A65-B23-C7; | A65-B23-C8; | A65-B23-C9; | A66-B23-C1; | A66-B23-C2; | A66-B23-C3; |
| A66-B23-C4; | A66-B23-C5; | A66-B23-C6; | A66-B23-C7; | A66-B23-C8; | A66-B23-C9; |
| A67-B23-C1; | A67-B23-C2; | A67-B23-C3; | A67-B23-C4; | A67-B23-C5; | A67-B23-C6; |
| A67-B23-C7; | A67-B23-C8; | A67-B23-C9; | A68-B23-C1; | A68-B23-C2; | A68-B23-C3; |
| A68-B23-C4; | A68-B23-C5; | A68-B23-C6; | A68-B23-C7; | A68-B23-C8; | A68-B23-C9; |
| A69-B23-C1; | A69-B23-C2; | A69-B23-C3; | A69-B23-C4; | A69-B23-C5; | A69-B23-C6; |
| A69-B23-C7; | A69-B23-C8; | A69-B23-C9; | A70-B23-C1; | A70-B23-C2; | A70-B23-C3; |
| A70-B23-C4; | A70-B23-C5; | A70-B23-C6; | A70-B23-C7; | A70-B23-C8; | A70-B23-C9; |
| A71-B23-C1; | A71-B23-C2; | A71-B23-C3; | A71-B23-C4; | A71-B23-C5; | A71-B23-C6; |
| A71-B23-C7; | A71-B23-C8; | A71-B23-C9; | A1-B24-C1; | A1-B24-C2; | A1-B24-C3; |
| A1-B24-C4; | A1-B24-C5; | A1-B24-C6; | A1-B24-C7; | A1-B24-C8; | A1-B24-C9; |
| A2-B24-C1; | A2-B24-C2; | A2-B24-C3; | A2-B24-C4; | A2-B24-C5; | A2-B24-C6; |
| A2-B24-C7; | A2-B24-C8; | A2-B24-C9; | A3-B24-C1; | A3-B24-C2; | A3-B24-C3; |
| A3-B24-C4; | A3-B24-C5; | A3-B24-C6; | A3-B24-C7; | A3-B24-C8; | A3-B24-C9; |
| A4-B24-C1; | A4-B24-C2; | A4-B24-C3; | A4-B24-C4; | A4-B24-C5; | A4-B24-C6; |
| A4-B24-C7; | A4-B24-C8; | A4-B24-C9; | A5-B24-C1; | A5-B24-C2; | A5-B24-C3; |
| A5-B24-C4; | A5-B24-C5; | A5-B24-C6; | A5-B24-C7; | A5-B24-C8; | A5-B24-C9; |
| A6-B24-C1; | A6-B24-C2; | A6-B24-C3; | A6-B24-C4; | A6-B24-C5; | A6-B24-C6; |
| A6-B24-C7; | A6-B24-C8; | A6-B24-C9; | A7-B24-C1; | A7-B24-C2; | A7-B24-C3; |
| A7-B24-C4; | A7-B24-C5; | A7-B24-C6; | A7-B24-C7; | A7-B24-C8; | A7-B24-C9; |
| A8-B24-C1; | A8-B24-C2; | A8-B24-C3; | A8-B24-C4; | A8-B24-C5; | A8-B24-C6; |
| A8-B24-C7; | A8-B24-C8; | A8-B24-C9; | A9-B24-C1; | A9-B24-C2; | A9-B24-C3; |
| A9-B24-C4; | A9-B24-C5; | A9-B24-C6; | A9-B24-C7; | A9-B24-C8; | A9-B24-C9; |
| A10-B24-C1; | A10-B24-C2; | A10-B24-C3; | A10-B24-C4; | A10-B24-C5; | A10-B24-C6; |
| A10-B24-C7; | A10-B24-C8; | A10-B24-C9; | A11-B24-C1; | A11-B24-C2; | A11-B24-C3; |
| A11-B24-C4; | A11-B24-C5; | A11-B24-C6; | A11-B24-C7; | A11-B24-C8; | A11-B24-C9; |
| A12-B24-C1; | A12-B24-C2; | A12-B24-C3; | A12-B24-C4; | A12-B24-C5; | A12-B24-C6; |
| A12-B24-C7; | A12-B24-C8; | A12-B24-C9; | A13-B24-C1; | A13-B24-C2; | A13-B24-C3; |
| A13-B24-C4; | A13-B24-C5; | A13-B24-C6; | A13-B24-C7; | A13-B24-C8; | A13-B24-C9; |
| A14-B24-C1; | A14-B24-C2; | A14-B24-C3; | A14-B24-C4; | A14-B24-C5; | A14-B24-C6; |
| A14-B24-C7; | A14-B24-C8; | A14-B24-C9; | A15-B24-C1; | A15-B24-C2; | A15-B24-C3; |
| A15-B24-C4; | A15-B24-C5; | A15-B24-C6; | A15-B24-C7; | A15-B24-C8; | A15-B24-C9; |
| A16-B24-C1; | A16-B24-C2; | A16-B24-C3; | A16-B24-C4; | A16-B24-C5; | A16-B24-C6; |
| A16-B24-C7; | A16-B24-C8; | A16-B24-C9; | A17-B24-C1; | A17-B24-C2; | A17-B24-C3; |
| A17-B24-C4; | A17-B24-C5; | A17-B24-C6; | A17-B24-C7; | A17-B24-C8; | A17-B24-C9; |
| A18-B24-C1; | A18-B24-C2; | A18-B24-C3; | A18-B24-C4; | A18-B24-C5; | A18-B24-C6; |

-continued

| | | | | | |
|---|---|---|---|---|---|
| A18-B24-C7; | A18-B24-C8; | A18-B24-C9; | A19-B24-C1; | A19-B24-C2; | A19-B24-C3; |
| A19-B24-C4; | A19-B24-C5; | A19-B24-C6; | A19-B24-C7; | A19-B24-C8; | A19-B24-C9; |
| A20-B24-C1; | A20-B24-C2; | A20-B24-C3; | A20-B24-C4; | A20-B24-C5; | A20-B24-C6; |
| A20-B24-C7; | A20-B24-C8; | A20-B24-C9; | A21-B24-C1; | A21-B24-C2; | A21-B24-C3; |
| A21-B24-C4; | A21-B24-C5; | A21-B24-C6; | A21-B24-C7; | A21-B24-C8; | A21-B24-C9; |
| A22-B24-C1; | A22-B24-C2; | A22-B24-C3; | A22-B24-C4; | A22-B24-C5; | A22-B24-C6; |
| A22-B24-C7; | A22-B24-C8; | A22-B24-C9; | A23-B24-C1; | A23-B24-C2; | A23-B24-C3; |
| A23-B24-C4; | A23-B24-C5; | A23-B24-C6; | A23-B24-C7; | A23-B24-C8; | A23-B24-C9; |
| A24-B24-C1; | A24-B24-C2; | A24-B24-C3; | A24-B24-C4; | A24-B24-C5; | A24-B24-C6; |
| A24-B24-C7; | A24-B24-C8; | A24-B24-C9; | A25-B24-C1; | A25-B24-C2; | A25-B24-C3; |
| A25-B24-C4; | A25-B24-C5; | A25-B24-C6; | A25-B24-C7; | A25-B24-C8; | A25-B24-C9; |
| A26-B24-C1; | A26-B24-C2; | A26-B24-C3; | A26-B24-C4; | A26-B24-C5; | A26-B24-C6; |
| A26-B24-C7; | A26-B24-C8; | A26-B24-C9; | A27-B24-C1; | A27-B24-C2; | A27-B24-C3; |
| A27-B24-C4; | A27-B24-C5; | A27-B24-C6; | A27-B24-C7; | A27-B24-C8; | A27-B24-C9; |
| A28-B24-C1; | A28-B24-C2; | A28-B24-C3; | A28-B24-C4; | A28-B24-C5; | A28-B24-C6; |
| A28-B24-C7; | A28-B24-C8; | A28-B24-C9; | A29-B24-C1; | A29-B24-C2; | A29-B24-C3; |
| A29-B24-C4; | A29-B24-C5; | A29-B24-C6; | A29-B24-C7; | A29-B24-C8; | A29-B24-C9; |
| A30-B24-C1; | A30-B24-C2; | A30-B24-C3; | A30-B24-C4; | A30-B24-C5; | A30-B24-C6; |
| A30-B24-C7; | A30-B24-C8; | A30-B24-C9; | A31-B24-C1; | A31-B24-C2; | A31-B24-C3; |
| A31-B24-C4; | A31-B24-C5; | A31-B24-C6; | A31-B24-C7; | A31-B24-C8; | A31-B24-C9; |
| A32-B24-C1; | A32-B24-C2; | A32-B24-C3; | A32-B24-C4; | A32-B24-C5; | A32-B24-C6; |
| A32-B24-C7; | A32-B24-C8; | A32-B24-C9; | A33-B24-C1; | A33-B24-C2; | A33-B24-C3; |
| A33-B24-C4; | A33-B24-C5; | A33-B24-C6; | A33-B24-C7; | A33-B24-C8; | A33-B24-C9; |
| A34-B24-C1; | A34-B24-C2; | A34-B24-C3; | A34-B24-C4; | A34-B24-C5; | A34-B24-C6; |
| A34-B24-C7; | A34-B24-C8; | A34-B24-C9; | A35-B24-C1; | A35-B24-C2; | A35-B24-C3; |
| A35-B24-C4; | A35-B24-C5; | A35-B24-C6; | A35-B24-C7; | A35-B24-C8; | A35-B24-C9; |
| A36-B24-C1; | A36-B24-C2; | A36-B24-C3; | A36-B24-C4; | A36-B24-C5; | A36-B24-C6; |
| A36-B24-C7; | A36-B24-C8; | A36-B24-C9; | A37-B24-C1; | A37-B24-C2; | A37-B24-C3; |
| A37-B24-C4; | A37-B24-C5; | A37-B24-C6; | A37-B24-C7; | A37-B24-C8; | A37-B24-C9; |
| A38-B24-C1; | A38-B24-C2; | A38-B24-C3; | A38-B24-C4; | A38-B24-C5; | A38-B24-C6; |
| A38-B24-C7; | A38-B24-C8; | A38-B24-C9; | A39-B24-C1; | A39-B24-C2; | A39-B24-C3; |
| A39-B24-C4; | A39-B24-C5; | A39-B24-C6; | A39-B24-C7; | A39-B24-C8; | A39-B24-C9; |
| A40-B24-C1; | A40-B24-C2; | A40-B24-C3; | A40-B24-C4; | A40-B24-C5; | A40-B24-C6; |
| A40-B24-C7; | A40-B24-C8; | A40-B24-C9; | A41-B24-C1; | A41-B24-C2; | A41-B24-C3; |
| A41-B24-C4; | A41-B24-C5; | A41-B24-C6; | A41-B24-C7; | A41-B24-C8; | A41-B24-C9; |
| A42-B24-C1; | A42-B24-C2; | A42-B24-C3; | A42-B24-C4; | A42-B24-C5; | A42-B24-C6; |
| A42-B24-C7; | A42-B24-C8; | A42-B24-C9; | A43-B24-C1; | A43-B24-C2; | A43-B24-C3; |
| A43-B24-C4; | A43-B24-C5; | A43-B24-C6; | A43-B24-C7; | A43-B24-C8; | A43-B24-C9; |
| A44-B24-C1; | A44-B24-C2; | A44-B24-C3; | A44-B24-C4; | A44-B24-C5; | A44-B24-C6; |
| A44-B24-C7; | A44-B24-C8; | A44-B24-C9; | A45-B24-C1; | A45-B24-C2; | A45-B24-C3; |
| A45-B24-C4; | A45-B24-C5; | A45-B24-C6; | A45-B24-C7; | A45-B24-C8; | A45-B24-C9; |
| A46-B24-C1; | A46-B24-C2; | A46-B24-C3; | A46-B24-C4; | A46-B24-C5; | A46-B24-C6; |
| A46-B24-C7; | A46-B24-C8; | A46-B24-C9; | A47-B24-C1; | A47-B24-C2; | A47-B24-C3; |
| A47-B24-C4; | A47-B24-C5; | A47-B24-C6; | A47-B24-C7; | A47-B24-C8; | A47-B24-C9; |
| A48-B24-C1; | A48-B24-C2; | A48-B24-C3; | A48-B24-C4; | A48-B24-C5; | A48-B24-C6; |
| A48-B24-C7; | A48-B24-C8; | A48-B24-C9; | A49-B24-C1; | A49-B24-C2; | A49-B24-C3; |
| A49-B24-C4; | A49-B24-C5; | A49-B24-C6; | A49-B24-C7; | A49-B24-C8; | A49-B24-C9; |
| A50-B24-C1; | A50-B24-C2; | A50-B24-C3; | A50-B24-C4; | A50-B24-C5; | A50-B24-C6; |
| A50-B24-C7; | A50-B24-C8; | A50-B24-C9; | A51-B24-C1; | A51-B24-C2; | A51-B24-C3; |
| A51-B24-C4; | A51-B24-C5; | A51-B24-C6; | A51-B24-C7; | A51-B24-C8; | A51-B24-C9; |
| A52-B24-C1; | A52-B24-C2; | A52-B24-C3; | A52-B24-C4; | A52-B24-C5; | A52-B24-C6; |
| A52-B24-C7; | A52-B24-C8; | A52-B24-C9; | A53-B24-C1; | A53-B24-C2; | A53-B24-C3; |
| A53-B24-C4; | A53-B24-C5; | A53-B24-C6; | A53-B24-C7; | A53-B24-C8; | A53-B24-C9; |
| A54-B24-C1; | A54-B24-C2; | A54-B24-C3; | A54-B24-C4; | A54-B24-C5; | A54-B24-C6; |
| A54-B24-C7; | A54-B24-C8; | A54-B24-C9; | A55-B24-C1; | A55-B24-C2; | A55-B24-C3; |
| A55-B24-C4; | A55-B24-C5; | A55-B24-C6; | A55-B24-C7; | A55-B24-C8; | A55-B24-C9; |
| A56-B24-C1; | A56-B24-C2; | A56-B24-C3; | A56-B24-C4; | A56-B24-C5; | A56-B24-C6; |
| A56-B24-C7; | A56-B24-C8; | A56-B24-C9; | A57-B24-C1; | A57-B24-C2; | A57-B24-C3; |
| A57-B24-C4; | A57-B24-C5; | A57-B24-C6; | A57-B24-C7; | A57-B24-C8; | A57-B24-C9; |
| A58-B24-C1; | A58-B24-C2; | A58-B24-C3; | A58-B24-C4; | A58-B24-C5; | A58-B24-C6; |
| A58-B24-C7; | A58-B24-C8; | A58-B24-C9; | A59-B24-C1; | A59-B24-C2; | A59-B24-C3; |
| A59-B24-C4; | A59-B24-C5; | A59-B24-C6; | A59-B24-C7; | A59-B24-C8; | A59-B24-C9; |
| A60-B24-C1; | A60-B24-C2; | A60-B24-C3; | A60-B24-C4; | A60-B24-C5; | A60-B24-C6; |
| A60-B24-C7; | A60-B24-C8; | A60-B24-C9; | A61-B24-C1; | A61-B24-C2; | A61-B24-C3; |
| A61-B24-C4; | A61-B24-C5; | A61-B24-C6; | A61-B24-C7; | A61-B24-C8; | A61-B24-C9; |
| A62-B24-C1; | A62-B24-C2; | A62-B24-C3; | A62-B24-C4; | A62-B24-C5; | A62-B24-C6; |
| A62-B24-C7; | A62-B24-C8; | A62-B24-C9; | A63-B24-C1; | A63-B24-C2; | A63-B24-C3; |
| A63-B24-C4; | A63-B24-C5; | A63-B24-C6; | A63-B24-C7; | A63-B24-C8; | A63-B24-C9; |
| A64-B24-C1; | A64-B24-C2; | A64-B24-C3; | A64-B24-C4; | A64-B24-C5; | A64-B24-C6; |
| A64-B24-C7; | A64-B24-C8; | A64-B24-C9; | A65-B24-C1; | A65-B24-C2; | A65-B24-C3; |
| A65-B24-C4; | A65-B24-C5; | A65-B24-C6; | A65-B24-C7; | A65-B24-C8; | A65-B24-C9; |
| A66-B24-C1; | A66-B24-C2; | A66-B24-C3; | A66-B24-C4; | A66-B24-C5; | A66-B24-C6; |
| A66-B24-C7; | A66-B24-C8; | A66-B24-C9; | A67-B24-C1; | A67-B24-C2; | A67-B24-C3; |
| A67-B24-C4; | A67-B24-C5; | A67-B24-C6; | A67-B24-C7; | A67-B24-C8; | A67-B24-C9; |
| A68-B24-C1; | A68-B24-C2; | A68-B24-C3; | A68-B24-C4; | A68-B24-C5; | A68-B24-C6; |
| A68-B24-C7; | A68-B24-C8; | A68-B24-C9; | A69-B24-C1; | A69-B24-C2; | A69-B24-C3; |
| A69-B24-C4; | A69-B24-C5; | A69-B24-C6; | A69-B24-C7; | A69-B24-C8; | A69-B24-C9; |
| A70-B24-C1; | A70-B24-C2; | A70-B24-C3; | A70-B24-C4; | A70-B24-C5; | A70-B24-C6; |
| A70-B24-C7; | A70-B24-C8; | A70-B24-C9; | A71-B24-C1; | A71-B24-C2; | A71-B24-C3; |

-continued

| | | | | | |
|---|---|---|---|---|---|
| A71-B24-C4; | A71-B24-C5; | A71-B24-C6; | A71-B24-C7; | A71-B24-C8; | A71-B24-C9; |
| A1-B25-C1; | A1-B25-C2; | A1-B25-C3; | A1-B25-C4; | A1-B25-C5; | A1-B25-C6; |
| A1-B25-C7; | A1-B25-C8; | A1-B25-C9; | A2-B25-C1; | A2-B25-C2; | A2-B25-C3; |
| A2-B25-C4; | A2-B25-C5; | A2-B25-C6; | A2-B25-C7; | A2-B25-C8; | A2-B25-C9; |
| A3-B25-C1; | A3-B25-C2; | A3-B25-C3; | A3-B25-C4; | A3-B25-C5; | A3-B25-C6; |
| A3-B25-C7; | A3-B25-C8; | A3-B25-C9; | A4-B25-C1; | A4-B25-C2; | A4-B25-C3; |
| A4-B25-C4; | A4-B25-C5; | A4-B25-C6; | A4-B25-C7; | A4-B25-C8; | A4-B25-C9; |
| A5-B25-C1; | A5-B25-C2; | A5-B25-C3; | A5-B25-C4; | A5-B25-C5; | A5-B25-C6; |
| A5-B25-C7; | A5-B25-C8; | A5-B25-C9; | A6-B25-C1; | A6-B25-C2; | A6-B25-C3; |
| A6-B25-C4; | A6-B25-C5; | A6-B25-C6; | A6-B25-C7; | A6-B25-C8; | A6-B25-C9; |
| A7-B25-C1; | A7-B25-C2; | A7-B25-C3; | A7-B25-C4; | A7-B25-C5; | A7-B25-C6; |
| A7-B25-C7; | A7-B25-C8; | A7-B25-C9; | A8-B25-C1; | A8-B25-C2; | A8-B25-C3; |
| A8-B25-C4; | A8-B25-C5; | A8-B25-C6; | A8-B25-C7; | A8-B25-C8; | A8-B25-C9; |
| A9-B25-C1; | A9-B25-C2; | A9-B25-C3; | A9-B25-C4; | A9-B25-C5; | A9-B25-C6; |
| A9-B25-C7; | A9-B25-C8; | A9-B25-C9; | A10-B25-C1; | A10-B25-C2; | A10-B25-C3; |
| A10-B25-C4; | A10-B25-C5; | A10-B25-C6; | A10-B25-C7; | A10-B25-C8; | A10-B25-C9; |
| A11-B25-C1; | A11-B25-C2; | A11-B25-C3; | A11-B25-C4; | A11-B25-C5; | A11-B25-C6; |
| A11-B25-C7; | A11-B25-C8; | A11-B25-C9; | A12-B25-C1; | A12-B25-C2; | A12-B25-C3; |
| A12-B25-C4; | A12-B25-C5; | A12-B25-C6; | A12-B25-C7; | A12-B25-C8; | A12-B25-C9; |
| A13-B25-C1; | A13-B25-C2; | A13-B25-C3; | A13-B25-C4; | A13-B25-C5; | A13-B25-C6; |
| A13-B25-C7; | A13-B25-C8; | A13-B25-C9; | A14-B25-C1; | A14-B25-C2; | A14-B25-C3; |
| A14-B25-C4; | A14-B25-C5; | A14-B25-C6; | A14-B25-C7; | A14-B25-C8; | A14-B25-C9; |
| A15-B25-C1; | A15-B25-C2; | A15-B25-C3; | A15-B25-C4; | A15-B25-C5; | A15-B25-C6; |
| A15-B25-C7; | A15-B25-C8; | A15-B25-C9; | A16-B25-C1; | A16-B25-C2; | A16-B25-C3; |
| A16-B25-C4; | A16-B25-C5; | A16-B25-C6; | A16-B25-C7; | A16-B25-C8; | A16-B25-C9; |
| A17-B25-C1; | A17-B25-C2; | A17-B25-C3; | A17-B25-C4; | A17-B25-C5; | A17-B25-C6; |
| A17-B25-C7; | A17-B25-C8; | A17-B25-C9; | A18-B25-C1; | A18-B25-C2; | A18-B25-C3; |
| A18-B25-C4; | A18-B25-C5; | A18-B25-C6; | A18-B25-C7; | A18-B25-C8; | A18-B25-C9; |
| A19-B25-C1; | A19-B25-C2; | A19-B25-C3; | A19-B25-C4; | A19-B25-C5; | A19-B25-C6; |
| A19-B25-C7; | A19-B25-C8; | A19-B25-C9; | A20-B25-C1; | A20-B25-C2; | A20-B25-C3; |
| A20-B25-C4; | A20-B25-C5; | A20-B25-C6; | A20-B25-C7; | A20-B25-C8; | A20-B25-C9; |
| A21-B25-C1; | A21-B25-C2; | A21-B25-C3; | A21-B25-C4; | A21-B25-C5; | A21-B25-C6; |
| A21-B25-C7; | A21-B25-C8; | A21-B25-C9; | A22-B25-C1; | A22-B25-C2; | A22-B25-C3; |
| A22-B25-C4; | A22-B25-C5; | A22-B25-C6; | A22-B25-C7; | A22-B25-C8; | A22-B25-C9; |
| A23-B25-C1; | A23-B25-C2; | A23-B25-C3; | A23-B25-C4; | A23-B25-C5; | A23-B25-C6; |
| A23-B25-C7; | A23-B25-C8; | A23-B25-C9; | A24-B25-C1; | A24-B25-C2; | A24-B25-C3; |
| A24-B25-C4; | A24-B25-C5; | A24-B25-C6; | A24-B25-C7; | A24-B25-C8; | A24-B25-C9; |
| A25-B25-C1; | A25-B25-C2; | A25-B25-C3; | A25-B25-C4; | A25-B25-C5; | A25-B25-C6; |
| A25-B25-C7; | A25-B25-C8; | A25-B25-C9; | A26-B25-C1; | A26-B25-C2; | A26-B25-C3; |
| A26-B25-C4; | A26-B25-C5; | A26-B25-C6; | A26-B25-C7; | A26-B25-C8; | A26-B25-C9; |
| A27-B25-C1; | A27-B25-C2; | A27-B25-C3; | A27-B25-C4; | A27-B25-C5; | A27-B25-C6; |
| A27-B25-C7; | A27-B25-C8; | A27-B25-C9; | A28-B25-C1; | A28-B25-C2; | A28-B25-C3; |
| A28-B25-C4; | A28-B25-C5; | A28-B25-C6; | A28-B25-C7; | A28-B25-C8; | A28-B25-C9; |
| A29-B25-C1; | A29-B25-C2; | A29-B25-C3; | A29-B25-C4; | A29-B25-C5; | A29-B25-C6; |
| A29-B25-C7; | A29-B25-C8; | A29-B25-C9; | A30-B25-C1; | A30-B25-C2; | A30-B25-C3; |
| A30-B25-C4; | A30-B25-C5; | A30-B25-C6; | A30-B25-C7; | A30-B25-C8; | A30-B25-C9; |
| A31-B25-C1; | A31-B25-C2; | A31-B25-C3; | A31-B25-C4; | A31-B25-C5; | A31-B25-C6; |
| A31-B25-C7; | A31-B25-C8; | A31-B25-C9; | A32-B25-C1; | A32-B25-C2; | A32-B25-C3; |
| A32-B25-C4; | A32-B25-C5; | A32-B25-C6; | A32-B25-C7; | A32-B25-C8; | A32-B25-C9; |
| A33-B25-C1; | A33-B25-C2; | A33-B25-C3; | A33-B25-C4; | A33-B25-C5; | A33-B25-C6; |
| A33-B25-C7; | A33-B25-C8; | A33-B25-C9; | A34-B25-C1; | A34-B25-C2; | A34-B25-C3; |
| A34-B25-C4; | A34-B25-C5; | A34-B25-C6; | A34-B25-C7; | A34-B25-C8; | A34-B25-C9; |
| A35-B25-C1; | A35-B25-C2; | A35-B25-C3; | A35-B25-C4; | A35-B25-C5; | A35-B25-C6; |
| A35-B25-C7; | A35-B25-C8; | A35-B25-C9; | A36-B25-C1; | A36-B25-C2; | A36-B25-C3; |
| A36-B25-C4; | A36-B25-C5; | A36-B25-C6; | A36-B25-C7; | A36-B25-C8; | A36-B25-C9; |
| A37-B25-C1; | A37-B25-C2; | A37-B25-C3; | A37-B25-C4; | A37-B25-C5; | A37-B25-C6; |
| A37-B25-C7; | A37-B25-C8; | A37-B25-C9; | A38-B25-C1; | A38-B25-C2; | A38-B25-C3; |
| A38-B25-C4; | A38-B25-C5; | A38-B25-C6; | A38-B25-C7; | A38-B25-C8; | A38-B25-C9; |
| A39-B25-C1; | A39-B25-C2; | A39-B25-C3; | A39-B25-C4; | A39-B25-C5; | A39-B25-C6; |
| A39-B25-C7; | A39-B25-C8; | A39-B25-C9; | A40-B25-C1; | A40-B25-C2; | A40-B25-C3; |
| A40-B25-C4; | A40-B25-C5; | A40-B25-C6; | A40-B25-C7; | A40-B25-C8; | A40-B25-C9; |
| A41-B25-C1; | A41-B25-C2; | A41-B25-C3; | A41-B25-C4; | A41-B25-C5; | A41-B25-C6; |
| A41-B25-C7; | A41-B25-C8; | A41-B25-C9; | A42-B25-C1; | A42-B25-C2; | A42-B25-C3; |
| A42-B25-C4; | A42-B25-C5; | A42-B25-C6; | A42-B25-C7; | A42-B25-C8; | A42-B25-C9; |
| A43-B25-C1; | A43-B25-C2; | A43-B25-C3; | A43-B25-C4; | A43-B25-C5; | A43-B25-C6; |
| A43-B25-C7; | A43-B25-C8; | A43-B25-C9; | A44-B25-C1; | A44-B25-C2; | A44-B25-C3; |
| A44-B25-C4; | A44-B25-C5; | A44-B25-C6; | A44-B25-C7; | A44-B25-C8; | A44-B25-C9; |
| A45-B25-C1; | A45-B25-C2; | A45-B25-C3; | A45-B25-C4; | A45-B25-C5; | A45-B25-C6; |
| A45-B25-C7; | A45-B25-C8; | A45-B25-C9; | A46-B25-C1; | A46-B25-C2; | A46-B25-C3; |
| A46-B25-C4; | A46-B25-C5; | A46-B25-C6; | A46-B25-C7; | A46-B25-C8; | A46-B25-C9; |
| A47-B25-C1; | A47-B25-C2; | A47-B25-C3; | A47-B25-C4; | A47-B25-C5; | A47-B25-C6; |
| A47-B25-C7; | A47-B25-C8; | A47-B25-C9; | A48-B25-C1; | A48-B25-C2; | A48-B25-C3; |
| A48-B25-C4; | A48-B25-C5; | A48-B25-C6; | A48-B25-C7; | A48-B25-C8; | A48-B25-C9; |
| A49-B25-C1; | A49-B25-C2; | A49-B25-C3; | A49-B25-C4; | A49-B25-C5; | A49-B25-C6; |
| A49-B25-C7; | A49-B25-C8; | A49-B25-C9; | A50-B25-C1; | A50-B25-C2; | A50-B25-C3; |
| A50-B25-C4; | A50-B25-C5; | A50-B25-C6; | A50-B25-C7; | A50-B25-C8; | A50-B25-C9; |
| A51-B25-C1; | A51-B25-C2; | A51-B25-C3; | A51-B25-C4; | A51-B25-C5; | A51-B25-C6; |
| A51-B25-C7; | A51-B25-C8; | A51-B25-C9; | A52-B25-C1; | A52-B25-C2; | A52-B25-C3; |
| A52-B25-C4; | A52-B25-C5; | A52-B25-C6; | A52-B25-C7; | A52-B25-C8; | A52-B25-C9; |

-continued

| | | | | | |
|---|---|---|---|---|---|
| A53-B25-C1; | A53-B25-C2; | A53-B25-C3; | A53-B25-C4; | A53-B25-C5; | A53-B25-C6; |
| A53-B25-C7; | A53-B25-C8; | A53-B25-C9; | A54-B25-C1; | A54-B25-C2; | A54-B25-C3; |
| A54-B25-C4; | A54-B25-C5; | A54-B25-C6; | A54-B25-C7; | A54-B25-C8; | A54-B25-C9; |
| A55-B25-C1; | A55-B25-C2; | A55-B25-C3; | A55-B25-C4; | A55-B25-C5; | A55-B25-C6; |
| A55-B25-C7; | A55-B25-C8; | A55-B25-C9; | A56-B25-C1; | A56-B25-C2; | A56-B25-C3; |
| A56-B25-C4; | A56-B25-C5; | A56-B25-C6; | A56-B25-C7; | A56-B25-C8; | A56-B25-C9; |
| A57-B25-C1; | A57-B25-C2; | A57-B25-C3; | A57-B25-C4; | A57-B25-C5; | A57-B25-C6; |
| A57-B25-C7; | A57-B25-C8; | A57-B25-C9; | A58-B25-C1; | A58-B25-C2; | A58-B25-C3; |
| A58-B25-C4; | A58-B25-C5; | A58-B25-C6; | A58-B25-C7; | A58-B25-C8; | A58-B25-C9; |
| A59-B25-C1; | A59-B25-C2; | A59-B25-C3; | A59-B25-C4; | A59-B25-C5; | A59-B25-C6; |
| A59-B25-C7; | A59-B25-C8; | A59-B25-C9; | A60-B25-C1; | A60-B25-C2; | A60-B25-C3; |
| A60-B25-C4; | A60-B25-C5; | A60-B25-C6; | A60-B25-C7; | A60-B25-C8; | A60-B25-C9; |
| A61-B25-C1; | A61-B25-C2; | A61-B25-C3; | A61-B25-C4; | A61-B25-C5; | A61-B25-C6; |
| A61-B25-C7; | A61-B25-C8; | A61-B25-C9; | A62-B25-C1; | A62-B25-C2; | A62-B25-C3; |
| A62-B25-C4; | A62-B25-C5; | A62-B25-C6; | A62-B25-C7; | A62-B25-C8; | A62-B25-C9; |
| A63-B25-C1; | A63-B25-C2; | A63-B25-C3; | A63-B25-C4; | A63-B25-C5; | A63-B25-C6; |
| A63-B25-C7; | A63-B25-C8; | A63-B25-C9; | A64-B25-C1; | A64-B25-C2; | A64-B25-C3; |
| A64-B25-C4; | A64-B25-C5; | A64-B25-C6; | A64-B25-C7; | A64-B25-C8; | A64-B25-C9; |
| A65-B25-C1; | A65-B25-C2; | A65-B25-C3; | A65-B25-C4; | A65-B25-C5; | A65-B25-C6; |
| A65-B25-C7; | A65-B25-C8; | A65-B25-C9; | A66-B25-C1; | A66-B25-C2; | A66-B25-C3; |
| A66-B25-C4; | A66-B25-C5; | A66-B25-C6; | A66-B25-C7; | A66-B25-C8; | A66-B25-C9; |
| A67-B25-C1; | A67-B25-C2; | A67-B25-C3; | A67-B25-C4; | A67-B25-C5; | A67-B25-C6; |
| A67-B25-C7; | A67-B25-C8; | A67-B25-C9; | A68-B25-C1; | A68-B25-C2; | A68-B25-C3; |
| A68-B25-C4; | A68-B25-C5; | A68-B25-C6; | A68-B25-C7; | A68-B25-C8; | A68-B25-C9; |
| A69-B25-C1; | A69-B25-C2; | A69-B25-C3; | A69-B25-C4; | A69-B25-C5; | A69-B25-C6; |
| A69-B25-C7; | A69-B25-C8; | A69-B25-C9; | A70-B25-C1; | A70-B25-C2; | A70-B25-C3; |
| A70-B25-C4; | A70-B25-C5; | A70-B25-C6; | A70-B25-C7; | A70-B25-C8; | A70-B25-C9; |
| A71-B25-C1; | A71-B25-C2; | A71-B25-C3; | A71-B25-C4; | A71-B25-C5; | A71-B25-C6; |
| A71-B25-C7; | A71-B25-C8; | A71-B25-C9; | A1-B26-C1; | A1-B26-C2; | A1-B26-C3; |
| A1-B26-C4; | A1-B26-C5; | A1-B26-C6; | A1-B26-C7; | A1-B26-C8; | A1-B26-C9; |
| A2-B26-C1; | A2-B26-C2; | A2-B26-C3; | A2-B26-C4; | A2-B26-C5; | A2-B26-C6; |
| A2-B26-C7; | A2-B26-C8; | A2-B26-C9; | A3-B26-C1; | A3-B26-C2; | A3-B26-C3; |
| A3-B26-C4; | A3-B26-C5; | A3-B26-C6; | A3-B26-C7; | A3-B26-C8; | A3-B26-C9; |
| A4-B26-C1; | A4-B26-C2; | A4-B26-C3; | A4-B26-C4; | A4-B26-C5; | A4-B26-C6; |
| A4-B26-C7; | A4-B26-C8; | A4-B26-C9; | A5-B26-C1; | A5-B26-C2; | A5-B26-C3; |
| A5-B26-C4; | A5-B26-C5; | A5-B26-C6; | A5-B26-C7; | A5-B26-C8; | A5-B26-C9; |
| A6-B26-C1; | A6-B26-C2; | A6-B26-C3; | A6-B26-C4; | A6-B26-C5; | A6-B26-C6; |
| A6-B26-C7; | A6-B26-C8; | A6-B26-C9; | A7-B26-C1; | A7-B26-C2; | A7-B26-C3; |
| A7-B26-C4; | A7-B26-C5; | A7-B26-C6; | A7-B26-C7; | A7-B26-C8; | A7-B26-C9; |
| A8-B26-C1; | A8-B26-C2; | A8-B26-C3; | A8-B26-C4; | A8-B26-C5; | A8-B26-C6; |
| A8-B26-C7; | A8-B26-C8; | A8-B26-C9; | A9-B26-C1; | A9-B26-C2; | A9-B26-C3; |
| A9-B26-C4; | A9-B26-C5; | A9-B26-C6; | A9-B26-C7; | A9-B26-C8; | A9-B26-C9; |
| A10-B26-C1; | A10-B26-C2; | A10-B26-C3; | A10-B26-C4; | A10-B26-C5; | A10-B26-C6; |
| A10-B26-C7; | A10-B26-C8; | A10-B26-C9; | A11-B26-C1; | A11-B26-C2; | A11-B26-C3; |
| A11-B26-C4; | A11-B26-C5; | A11-B26-C6; | A11-B26-C7; | A11-B26-C8; | A11-B26-C9; |
| A12-B26-C1; | A12-B26-C2; | A12-B26-C3; | A12-B26-C4; | A12-B26-C5; | A12-B26-C6; |
| A12-B26-C7; | A12-B26-C8; | A12-B26-C9; | A13-B26-C1; | A13-B26-C2; | A13-B26-C3; |
| A13-B26-C4; | A13-B26-C5; | A13-B26-C6; | A13-B26-C7; | A13-B26-C8; | A13-B26-C9; |
| A14-B26-C1; | A14-B26-C2; | A14-B26-C3; | A14-B26-C4; | A14-B26-C5; | A14-B26-C6; |
| A14-B26-C7; | A14-B26-C8; | A14-B26-C9; | A15-B26-C1; | A15-B26-C2; | A15-B26-C3; |
| A15-B26-C4; | A15-B26-C5; | A15-B26-C6; | A15-B26-C7; | A15-B26-C8; | A15-B26-C9; |
| A16-B26-C1; | A16-B26-C2; | A16-B26-C3; | A16-B26-C4; | A16-B26-C5; | A16-B26-C6; |
| A16-B26-C7; | A16-B26-C8; | A16-B26-C9; | A17-B26-C1; | A17-B26-C2; | A17-B26-C3; |
| A17-B26-C4; | A17-B26-C5; | A17-B26-C6; | A17-B26-C7; | A17-B26-C8; | A17-B26-C9; |
| A18-B26-C1; | A18-B26-C2; | A18-B26-C3; | A18-B26-C4; | A18-B26-C5; | A18-B26-C6; |
| A18-B26-C7; | A18-B26-C8; | A18-B26-C9; | A19-B26-C1; | A19-B26-C2; | A19-B26-C3; |
| A19-B26-C4; | A19-B26-C5; | A19-B26-C6; | A19-B26-C7; | A19-B26-C8; | A19-B26-C9; |
| A20-B26-C1; | A20-B26-C2; | A20-B26-C3; | A20-B26-C4; | A20-B26-C5; | A20-B26-C6; |
| A20-B26-C7; | A20-B26-C8; | A20-B26-C9; | A21-B26-C1; | A21-B26-C2; | A21-B26-C3; |
| A21-B26-C4; | A21-B26-C5; | A21-B26-C6; | A21-B26-C7; | A21-B26-C8; | A21-B26-C9; |
| A22-B26-C1; | A22-B26-C2; | A22-B26-C3; | A22-B26-C4; | A22-B26-C5; | A22-B26-C6; |
| A22-B26-C7; | A22-B26-C8; | A22-B26-C9; | A23-B26-C1; | A23-B26-C2; | A23-B26-C3; |
| A23-B26-C4; | A23-B26-C5; | A23-B26-C6; | A23-B26-C7; | A23-B26-C8; | A23-B26-C9; |
| A24-B26-C1; | A24-B26-C2; | A24-B26-C3; | A24-B26-C4; | A24-B26-C5; | A24-B26-C6; |
| A24-B26-C7; | A24-B26-C8; | A24-B26-C9; | A25-B26-C1; | A25-B26-C2; | A25-B26-C3; |
| A25-B26-C4; | A25-B26-C5; | A25-B26-C6; | A25-B26-C7; | A25-B26-C8; | A25-B26-C9; |
| A26-B26-C1; | A26-B26-C2; | A26-B26-C3; | A26-B26-C4; | A26-B26-C5; | A26-B26-C6; |
| A26-B26-C7; | A26-B26-C8; | A26-B26-C9; | A27-B26-C1; | A27-B26-C2; | A27-B26-C3; |
| A27-B26-C4; | A27-B26-C5; | A27-B26-C6; | A27-B26-C7; | A27-B26-C8; | A27-B26-C9; |
| A28-B26-C1; | A28-B26-C2; | A28-B26-C3; | A28-B26-C4; | A28-B26-C5; | A28-B26-C6; |
| A28-B26-C7; | A28-B26-C8; | A28-B26-C9; | A29-B26-C1; | A29-B26-C2; | A29-B26-C3; |
| A29-B26-C4; | A29-B26-C5; | A29-B26-C6; | A29-B26-C7; | A29-B26-C8; | A29-B26-C9; |
| A30-B26-C1; | A30-B26-C2; | A30-B26-C3; | A30-B26-C4; | A30-B26-C5; | A30-B26-C6; |
| A30-B26-C7; | A30-B26-C8; | A30-B26-C9; | A31-B26-C1; | A31-B26-C2; | A31-B26-C3; |
| A31-B26-C4; | A31-B26-C5; | A31-B26-C6; | A31-B26-C7; | A31-B26-C8; | A31-B26-C9; |
| A32-B26-C1; | A32-B26-C2; | A32-B26-C3; | A32-B26-C4; | A32-B26-C5; | A32-B26-C6; |
| A32-B26-C7; | A32-B26-C8; | A32-B26-C9; | A33-B26-C1; | A33-B26-C2; | A33-B26-C3; |
| A33-B26-C4; | A33-B26-C5; | A33-B26-C6; | A33-B26-C7; | A33-B26-C8; | A33-B26-C9; |
| A34-B26-C1; | A34-B26-C2; | A34-B26-C3; | A34-B26-C4; | A34-B26-C5; | A34-B26-C6; |

-continued

| | | | | | |
|---|---|---|---|---|---|
| A34-B26-C7; | A34-B26-C8; | A34-B26-C9; | A35-B26-C1; | A35-B26-C2; | A35-B26-C3; |
| A35-B26-C4; | A35-B26-C5; | A35-B26-C6; | A35-B26-C7; | A35-B26-C8; | A35-B26-C9; |
| A36-B26-C1; | A36-B26-C2; | A36-B26-C3; | A36-B26-C4; | A36-B26-C5; | A36-B26-C6; |
| A36-B26-C7; | A36-B26-C8; | A36-B26-C9; | A37-B26-C1; | A37-B26-C2; | A37-B26-C3; |
| A37-B26-C4; | A37-B26-C5; | A37-B26-C6; | A37-B26-C7; | A37-B26-C8; | A37-B26-C9; |
| A38-B26-C1; | A38-B26-C2; | A38-B26-C3; | A38-B26-C4; | A38-B26-C5; | A38-B26-C6; |
| A38-B26-C7; | A38-B26-C8; | A38-B26-C9; | A39-B26-C1; | A39-B26-C2; | A39-B26-C3; |
| A39-B26-C4; | A39-B26-C5; | A39-B26-C6; | A39-B26-C7; | A39-B26-C8; | A39-B26-C9; |
| A40-B26-C1; | A40-B26-C2; | A40-B26-C3; | A40-B26-C4; | A40-B26-C5; | A40-B26-C6; |
| A40-B26-C7; | A40-B26-C8; | A40-B26-C9; | A41-B26-C1; | A41-B26-C2; | A41-B26-C3; |
| A41-B26-C4; | A41-B26-C5; | A41-B26-C6; | A41-B26-C7; | A41-B26-C8; | A41-B26-C9; |
| A42-B26-C1; | A42-B26-C2; | A42-B26-C3; | A42-B26-C4; | A42-B26-C5; | A42-B26-C6; |
| A42-B26-C7; | A42-B26-C8; | A42-B26-C9; | A43-B26-C1; | A43-B26-C2; | A43-B26-C3; |
| A43-B26-C4; | A43-B26-C5; | A43-B26-C6; | A43-B26-C7; | A43-B26-C8; | A43-B26-C9; |
| A44-B26-C1; | A44-B26-C2; | A44-B26-C3; | A44-B26-C4; | A44-B26-C5; | A44-B26-C6; |
| A44-B26-C7; | A44-B26-C8; | A44-B26-C9; | A45-B26-C1; | A45-B26-C2; | A45-B26-C3; |
| A45-B26-C4; | A45-B26-C5; | A45-B26-C6; | A45-B26-C7; | A45-B26-C8; | A45-B26-C9; |
| A46-B26-C1; | A46-B26-C2; | A46-B26-C3; | A46-B26-C4; | A46-B26-C5; | A46-B26-C6; |
| A46-B26-C7; | A46-B26-C8; | A46-B26-C9; | A47-B26-C1; | A47-B26-C2; | A47-B26-C3; |
| A47-B26-C4; | A47-B26-C5; | A47-B26-C6; | A47-B26-C7; | A47-B26-C8; | A47-B26-C9; |
| A48-B26-C1; | A48-B26-C2; | A48-B26-C3; | A48-B26-C4; | A48-B26-C5; | A48-B26-C6; |
| A48-B26-C7; | A48-B26-C8; | A48-B26-C9; | A49-B26-C1; | A49-B26-C2; | A49-B26-C3; |
| A49-B26-C4; | A49-B26-C5; | A49-B26-C6; | A49-B26-C7; | A49-B26-C8; | A49-B26-C9; |
| A50-B26-C1; | A50-B26-C2; | A50-B26-C3; | A50-B26-C4; | A50-B26-C5; | A50-B26-C6; |
| A50-B26-C7; | A50-B26-C8; | A50-B26-C9; | A51-B26-C1; | A51-B26-C2; | A51-B26-C3; |
| A51-B26-C4; | A51-B26-C5; | A51-B26-C6; | A51-B26-C7; | A51-B26-C8; | A51-B26-C9; |
| A52-B26-C1; | A52-B26-C2; | A52-B26-C3; | A52-B26-C4; | A52-B26-C5; | A52-B26-C6; |
| A52-B26-C7; | A52-B26-C8; | A52-B26-C9; | A53-B26-C1; | A53-B26-C2; | A53-B26-C3; |
| A53-B26-C4; | A53-B26-C5; | A53-B26-C6; | A53-B26-C7; | A53-B26-C8; | A53-B26-C9; |
| A54-B26-C1; | A54-B26-C2; | A54-B26-C3; | A54-B26-C4; | A54-B26-C5; | A54-B26-C6; |
| A54-B26-C7; | A54-B26-C8; | A54-B26-C9; | A55-B26-C1; | A55-B26-C2; | A55-B26-C3; |
| A55-B26-C4; | A55-B26-C5; | A55-B26-C6; | A55-B26-C7; | A55-B26-C8; | A55-B26-C9; |
| A56-B26-C1; | A56-B26-C2; | A56-B26-C3; | A56-B26-C4; | A56-B26-C5; | A56-B26-C6; |
| A56-B26-C7; | A56-B26-C8; | A56-B26-C9; | A57-B26-C1; | A57-B26-C2; | A57-B26-C3; |
| A57-B26-C4; | A57-B26-C5; | A57-B26-C6; | A57-B26-C7; | A57-B26-C8; | A57-B26-C9; |
| A58-B26-C1; | A58-B26-C2; | A58-B26-C3; | A58-B26-C4; | A58-B26-C5; | A58-B26-C6; |
| A58-B26-C7; | A58-B26-C8; | A58-B26-C9; | A59-B26-C1; | A59-B26-C2; | A59-B26-C3; |
| A59-B26-C4; | A59-B26-C5; | A59-B26-C6; | A59-B26-C7; | A59-B26-C8; | A59-B26-C9; |
| A60-B26-C1; | A60-B26-C2; | A60-B26-C3; | A60-B26-C4; | A60-B26-C5; | A60-B26-C6; |
| A60-B26-C7; | A60-B26-C8; | A60-B26-C9; | A61-B26-C1; | A61-B26-C2; | A61-B26-C3; |
| A61-B26-C4; | A61-B26-C5; | A61-B26-C6; | A61-B26-C7; | A61-B26-C8; | A61-B26-C9; |
| A62-B26-C1; | A62-B26-C2; | A62-B26-C3; | A62-B26-C4; | A62-B26-C5; | A62-B26-C6; |
| A62-B26-C7; | A62-B26-C8; | A62-B26-C9; | A63-B26-C1; | A63-B26-C2; | A63-B26-C3; |
| A63-B26-C4; | A63-B26-C5; | A63-B26-C6; | A63-B26-C7; | A63-B26-C8; | A63-B26-C9; |
| A64-B26-C1; | A64-B26-C2; | A64-B26-C3; | A64-B26-C4; | A64-B26-C5; | A64-B26-C6; |
| A64-B26-C7; | A64-B26-C8; | A64-B26-C9; | A65-B26-C1; | A65-B26-C2; | A65-B26-C3; |
| A65-B26-C4; | A65-B26-C5; | A65-B26-C6; | A65-B26-C7; | A65-B26-C8; | A65-B26-C9; |
| A66-B26-C1; | A66-B26-C2; | A66-B26-C3; | A66-B26-C4; | A66-B26-C5; | A66-B26-C6; |
| A66-B26-C7; | A66-B26-C8; | A66-B26-C9; | A67-B26-C1; | A67-B26-C2; | A67-B26-C3; |
| A67-B26-C4; | A67-B26-C5; | A67-B26-C6; | A67-B26-C7; | A67-B26-C8; | A67-B26-C9; |
| A68-B26-C1; | A68-B26-C2; | A68-B26-C3; | A68-B26-C4; | A68-B26-C5; | A68-B26-C6; |
| A68-B26-C7; | A68-B26-C8; | A68-B26-C9; | A69-B26-C1; | A69-B26-C2; | A69-B26-C3; |
| A69-B26-C4; | A69-B26-C5; | A69-B26-C6; | A69-B26-C7; | A69-B26-C8; | A69-B26-C9; |
| A70-B26-C1; | A70-B26-C2; | A70-B26-C3; | A70-B26-C4; | A70-B26-C5; | A70-B26-C6; |
| A70-B26-C7; | A70-B26-C8; | A70-B26-C9; | A71-B26-C1; | A71-B26-C2; | A71-B26-C3; |
| A71-B26-C4; | A71-B26-C5; | A71-B26-C6; | A71-B26-C7; | A71-B26-C8; | A71-B26-C9; |
| A1-B27-C1; | A1-B27-C2; | A1-B27-C3; | A1-B27-C4; | A1-B27-C5; | A1-B27-C6; |
| A1-B27-C7; | A1-B27-C8; | A1-B27-C9; | A2-B27-C1; | A2-B27-C2; | A2-B27-C3; |
| A2-B27-C4; | A2-B27-C5; | A2-B27-C6; | A2-B27-C7; | A2-B27-C8; | A2-B27-C9; |
| A3-B27-C1; | A3-B27-C2; | A3-B27-C3; | A3-B27-C4; | A3-B27-C5; | A3-B27-C6; |
| A3-B27-C7; | A3-B27-C8; | A3-B27-C9; | A4-B27-C1; | A4-B27-C2; | A4-B27-C3; |
| A4-B27-C4; | A4-B27-C5; | A4-B27-C6; | A4-B27-C7; | A4-B27-C8; | A4-B27-C9; |
| A5-B27-C1; | A5-B27-C2; | A5-B27-C3; | A5-B27-C4; | A5-B27-C5; | A5-B27-C6; |
| A5-B27-C7; | A5-B27-C8; | A5-B27-C9; | A6-B27-C1; | A6-B27-C2; | A6-B27-C3; |
| A6-B27-C4; | A6-B27-C5; | A6-B27-C6; | A6-B27-C7; | A6-B27-C8; | A6-B27-C9; |
| A7-B27-C1; | A7-B27-C2; | A7-B27-C3; | A7-B27-C4; | A7-B27-C5; | A7-B27-C6; |
| A7-B27-C7; | A7-B27-C8; | A7-B27-C9; | A8-B27-C1; | A8-B27-C2; | A8-B27-C3; |
| A8-B27-C4; | A8-B27-C5; | A8-B27-C6; | A8-B27-C7; | A8-B27-C8; | A8-B27-C9; |
| A9-B27-C1; | A9-B27-C2; | A9-B27-C3; | A9-B27-C4; | A9-B27-C5; | A9-B27-C6; |
| A9-B27-C7; | A9-B27-C8; | A9-B27-C9; | A10-B27-C1; | A10-B27-C2; | A10-B27-C3; |
| A10-B27-C4; | A10-B27-C5; | A10-B27-C6; | A10-B27-C7; | A10-B27-C8; | A10-B27-C9; |
| A11-B27-C1; | A11-B27-C2; | A11-B27-C3; | A11-B27-C4; | A11-B27-C5; | A11-B27-C6; |
| A11-B27-C7; | A11-B27-C8; | A11-B27-C9; | A12-B27-C1; | A12-B27-C2; | A12-B27-C3; |
| A12-B27-C4; | A12-B27-C5; | A12-B27-C6; | A12-B27-C7; | A12-B27-C8; | A12-B27-C9; |
| A13-B27-C1; | A13-B27-C2; | A13-B27-C3; | A13-B27-C4; | A13-B27-C5; | A13-B27-C6; |
| A13-B27-C7; | A13-B27-C8; | A13-B27-C9; | A14-B27-C1; | A14-B27-C2; | A14-B27-C3; |
| A14-B27-C4; | A14-B27-C5; | A14-B27-C6; | A14-B27-C7; | A14-B27-C8; | A14-B27-C9; |
| A15-B27-C1; | A15-B27-C2; | A15-B27-C3; | A15-B27-C4; | A15-B27-C5; | A15-B27-C6; |
| A15-B27-C7; | A15-B27-C8; | A15-B27-C9; | A16-B27-C1; | A16-B27-C2; | A16-B27-C3; |

-continued

| | | | | | |
|---|---|---|---|---|---|
| A16-B27-C4; | A16-B27-C5; | A16-B27-C6; | A16-B27-C7; | A16-B27-C8; | A16-B27-C9; |
| A17-B27-C1; | A17-B27-C2; | A17-B27-C3; | A17-B27-C4; | A17-B27-C5; | A17-B27-C6; |
| A17-B27-C7; | A17-B27-C8; | A17-B27-C9; | A18-B27-C1; | A18-B27-C2; | A18-B27-C3; |
| A18-B27-C4; | A18-B27-C5; | A18-B27-C6; | A18-B27-C7; | A18-B27-C8; | A18-B27-C9; |
| A19-B27-C1; | A19-B27-C2; | A19-B27-C3; | A19-B27-C4; | A19-B27-C5; | A19-B27-C6; |
| A19-B27-C7; | A19-B27-C8; | A19-B27-C9; | A20-B27-C1; | A20-B27-C2; | A20-B27-C3; |
| A20-B27-C4; | A20-B27-C5; | A20-B27-C6; | A20-B27-C7; | A20-B27-C8; | A20-B27-C9; |
| A21-B27-C1; | A21-B27-C2; | A21-B27-C3; | A21-B27-C4; | A21-B27-C5; | A21-B27-C6; |
| A21-B27-C7; | A21-B27-C8; | A21-B27-C9; | A22-B27-C1; | A22-B27-C2; | A22-B27-C3; |
| A22-B27-C4; | A22-B27-C5; | A22-B27-C6; | A22-B27-C7; | A22-B27-C8; | A22-B27-C9; |
| A23-B27-C1; | A23-B27-C2; | A23-B27-C3; | A23-B27-C4; | A23-B27-C5; | A23-B27-C6; |
| A23-B27-C7; | A23-B27-C8; | A23-B27-C9; | A24-B27-C1; | A24-B27-C2; | A24-B27-C3; |
| A24-B27-C4; | A24-B27-C5; | A24-B27-C6; | A24-B27-C7; | A24-B27-C8; | A24-B27-C9; |
| A25-B27-C1; | A25-B27-C2; | A25-B27-C3; | A25-B27-C4; | A25-B27-C5; | A25-B27-C6; |
| A25-B27-C7; | A25-B27-C8; | A25-B27-C9; | A26-B27-C1; | A26-B27-C2; | A26-B27-C3; |
| A26-B27-C4; | A26-B27-C5; | A26-B27-C6; | A26-B27-C7; | A26-B27-C8; | A26-B27-C9; |
| A27-B27-C1; | A27-B27-C2; | A27-B27-C3; | A27-B27-C4; | A27-B27-C5; | A27-B27-C6; |
| A27-B27-C7; | A27-B27-C8; | A27-B27-C9; | A28-B27-C1; | A28-B27-C2; | A28-B27-C3; |
| A28-B27-C4; | A28-B27-C5; | A28-B27-C6; | A28-B27-C7; | A28-B27-C8; | A28-B27-C9; |
| A29-B27-C1; | A29-B27-C2; | A29-B27-C3; | A29-B27-C4; | A29-B27-C5; | A29-B27-C6; |
| A29-B27-C7; | A29-B27-C8; | A29-B27-C9; | A30-B27-C1; | A30-B27-C2; | A30-B27-C3; |
| A30-B27-C4; | A30-B27-C5; | A30-B27-C6; | A30-B27-C7; | A30-B27-C8; | A30-B27-C9; |
| A31-B27-C1; | A31-B27-C2; | A31-B27-C3; | A31-B27-C4; | A31-B27-C5; | A31-B27-C6; |
| A31-B27-C7; | A31-B27-C8; | A31-B27-C9; | A32-B27-C1; | A32-B27-C2; | A32-B27-C3; |
| A32-B27-C4; | A32-B27-C5; | A32-B27-C6; | A32-B27-C7; | A32-B27-C8; | A32-B27-C9; |
| A33-B27-C1; | A33-B27-C2; | A33-B27-C3; | A33-B27-C4; | A33-B27-C5; | A33-B27-C6; |
| A33-B27-C7; | A33-B27-C8; | A33-B27-C9; | A34-B27-C1; | A34-B27-C2; | A34-B27-C3; |
| A34-B27-C4; | A34-B27-C5; | A34-B27-C6; | A34-B27-C7; | A34-B27-C8; | A34-B27-C9; |
| A35-B27-C1; | A35-B27-C2; | A35-B27-C3; | A35-B27-C4; | A35-B27-C5; | A35-B27-C6; |
| A35-B27-C7; | A35-B27-C8; | A35-B27-C9; | A36-B27-C1; | A36-B27-C2; | A36-B27-C3; |
| A36-B27-C4; | A36-B27-C5; | A36-B27-C6; | A36-B27-C7; | A36-B27-C8; | A36-B27-C9; |
| A37-B27-C1; | A37-B27-C2; | A37-B27-C3; | A37-B27-C4; | A37-B27-C5; | A37-B27-C6; |
| A37-B27-C7; | A37-B27-C8; | A37-B27-C9; | A38-B27-C1; | A38-B27-C2; | A38-B27-C3; |
| A38-B27-C4; | A38-B27-C5; | A38-B27-C6; | A38-B27-C7; | A38-B27-C8; | A38-B27-C9; |
| A39-B27-C1; | A39-B27-C2; | A39-B27-C3; | A39-B27-C4; | A39-B27-C5; | A39-B27-C6; |
| A39-B27-C7; | A39-B27-C8; | A39-B27-C9; | A40-B27-C1; | A40-B27-C2; | A40-B27-C3; |
| A40-B27-C4; | A40-B27-C5; | A40-B27-C6; | A40-B27-C7; | A40-B27-C8; | A40-B27-C9; |
| A41-B27-C1; | A41-B27-C2; | A41-B27-C3; | A41-B27-C4; | A41-B27-C5; | A41-B27-C6; |
| A41-B27-C7; | A41-B27-C8; | A41-B27-C9; | A42-B27-C1; | A42-B27-C2; | A42-B27-C3; |
| A42-B27-C4; | A42-B27-C5; | A42-B27-C6; | A42-B27-C7; | A42-B27-C8; | A42-B27-C9; |
| A43-B27-C1; | A43-B27-C2; | A43-B27-C3; | A43-B27-C4; | A43-B27-C5; | A43-B27-C6; |
| A43-B27-C7; | A43-B27-C8; | A43-B27-C9; | A44-B27-C1; | A44-B27-C2; | A44-B27-C3; |
| A44-B27-C4; | A44-B27-C5; | A44-B27-C6; | A44-B27-C7; | A44-B27-C8; | A44-B27-C9; |
| A45-B27-C1; | A45-B27-C2; | A45-B27-C3; | A45-B27-C4; | A45-B27-C5; | A45-B27-C6; |
| A45-B27-C7; | A45-B27-C8; | A45-B27-C9; | A46-B27-C1; | A46-B27-C2; | A46-B27-C3; |
| A46-B27-C4; | A46-B27-C5; | A46-B27-C6; | A46-B27-C7; | A46-B27-C8; | A46-B27-C9; |
| A47-B27-C1; | A47-B27-C2; | A47-B27-C3; | A47-B27-C4; | A47-B27-C5; | A47-B27-C6; |
| A47-B27-C7; | A47-B27-C8; | A47-B27-C9; | A48-B27-C1; | A48-B27-C2; | A48-B27-C3; |
| A48-B27-C4; | A48-B27-C5; | A48-B27-C6; | A48-B27-C7; | A48-B27-C8; | A48-B27-C9; |
| A49-B27-C1; | A49-B27-C2; | A49-B27-C3; | A49-B27-C4; | A49-B27-C5; | A49-B27-C6; |
| A49-B27-C7; | A49-B27-C8; | A49-B27-C9; | A50-B27-C1; | A50-B27-C2; | A50-B27-C3; |
| A50-B27-C4; | A50-B27-C5; | A50-B27-C6; | A50-B27-C7; | A50-B27-C8; | A50-B27-C9; |
| A51-B27-C1; | A51-B27-C2; | A51-B27-C3; | A51-B27-C4; | A51-B27-C5; | A51-B27-C6; |
| A51-B27-C7; | A51-B27-C8; | A51-B27-C9; | A52-B27-C1; | A52-B27-C2; | A52-B27-C3; |
| A52-B27-C4; | A52-B27-C5; | A52-B27-C6; | A52-B27-C7; | A52-B27-C8; | A52-B27-C9; |
| A53-B27-C1; | A53-B27-C2; | A53-B27-C3; | A53-B27-C4; | A53-B27-C5; | A53-B27-C6; |
| A53-B27-C7; | A53-B27-C8; | A53-B27-C9; | A54-B27-C1; | A54-B27-C2; | A54-B27-C3; |
| A54-B27-C4; | A54-B27-C5; | A54-B27-C6; | A54-B27-C7; | A54-B27-C8; | A54-B27-C9; |
| A55-B27-C1; | A55-B27-C2; | A55-B27-C3; | A55-B27-C4; | A55-B27-C5; | A55-B27-C6; |
| A55-B27-C7; | A55-B27-C8; | A55-B27-C9; | A56-B27-C1; | A56-B27-C2; | A56-B27-C3; |
| A56-B27-C4; | A56-B27-C5; | A56-B27-C6; | A56-B27-C7; | A56-B27-C8; | A56-B27-C9; |
| A57-B27-C1; | A57-B27-C2; | A57-B27-C3; | A57-B27-C4; | A57-B27-C5; | A57-B27-C6; |
| A57-B27-C7; | A57-B27-C8; | A57-B27-C9; | A58-B27-C1; | A58-B27-C2; | A58-B27-C3; |
| A58-B27-C4; | A58-B27-C5; | A58-B27-C6; | A58-B27-C7; | A58-B27-C8; | A58-B27-C9; |
| A59-B27-C1; | A59-B27-C2; | A59-B27-C3; | A59-B27-C4; | A59-B27-C5; | A59-B27-C6; |
| A59-B27-C7; | A59-B27-C8; | A59-B27-C9; | A60-B27-C1; | A60-B27-C2; | A60-B27-C3; |
| A60-B27-C4; | A60-B27-C5; | A60-B27-C6; | A60-B27-C7; | A60-B27-C8; | A60-B27-C9; |
| A61-B27-C1; | A61-B27-C2; | A61-B27-C3; | A61-B27-C4; | A61-B27-C5; | A61-B27-C6; |
| A61-B27-C7; | A61-B27-C8; | A61-B27-C9; | A62-B27-C1; | A62-B27-C2; | A62-B27-C3; |
| A62-B27-C4; | A62-B27-C5; | A62-B27-C6; | A62-B27-C7; | A62-B27-C8; | A62-B27-C9; |
| A63-B27-C1; | A63-B27-C2; | A63-B27-C3; | A63-B27-C4; | A63-B27-C5; | A63-B27-C6; |
| A63-B27-C7; | A63-B27-C8; | A63-B27-C9; | A64-B27-C1; | A64-B27-C2; | A64-B27-C3; |
| A64-B27-C4; | A64-B27-C5; | A64-B27-C6; | A64-B27-C7; | A64-B27-C8; | A64-B27-C9; |
| A65-B27-C1; | A65-B27-C2; | A65-B27-C3; | A65-B27-C4; | A65-B27-C5; | A65-B27-C6; |
| A65-B27-C7; | A65-B27-C8; | A65-B27-C9; | A66-B27-C1; | A66-B27-C2; | A66-B27-C3; |
| A66-B27-C4; | A66-B27-C5; | A66-B27-C6; | A66-B27-C7; | A66-B27-C8; | A66-B27-C9; |
| A67-B27-C1; | A67-B27-C2; | A67-B27-C3; | A67-B27-C4; | A67-B27-C5; | A67-B27-C6; |
| A67-B27-C7; | A67-B27-C8; | A67-B27-C9; | A68-B27-C1; | A68-B27-C2; | A68-B27-C3; |
| A68-B27-C4; | A68-B27-C5; | A68-B27-C6; | A68-B27-C7; | A68-B27-C8; | A68-B27-C9; |

-continued

| | | | | | |
|---|---|---|---|---|---|
| A69-B27-C1; | A69-B27-C2; | A69-B27-C3; | A69-B27-C4; | A69-B27-C5; | A69-B27-C6; |
| A69-B27-C7; | A69-B27-C8; | A69-B27-C9; | A70-B27-C1; | A70-B27-C2; | A70-B27-C3; |
| A70-B27-C4; | A70-B27-C5; | A70-B27-C6; | A70-B27-C7; | A70-B27-C8; | A70-B27-C9; |
| A71-B27-C1; | A71-B27-C2; | A71-B27-C3; | A71-B27-C4; | A71-B27-C5; | A71-B27-C6; |
| A71-B27-C7; | A71-B27-C8; | A71-B27-C9; | A1-B28-C1; | A1-B28-C2; | A1-B28-C3; |
| A1-B28-C4; | A1-B28-C5; | A1-B28-C6; | A1-B28-C7; | A1-B28-C8; | A1-B28-C9; |
| A2-B28-C1; | A2-B28-C2; | A2-B28-C3; | A2-B28-C4; | A2-B28-C5; | A2-B28-C6; |
| A2-B28-C7; | A2-B28-C8; | A2-B28-C9; | A3-B28-C1; | A3-B28-C2; | A3-B28-C3; |
| A3-B28-C4; | A3-B28-C5; | A3-B28-C6; | A3-B28-C7; | A3-B28-C8; | A3-B28-C9; |
| A4-B28-C1; | A4-B28-C2; | A4-B28-C3; | A4-B28-C4; | A4-B28-C5; | A4-B28-C6; |
| A4-B28-C7; | A4-B28-C8; | A4-B28-C9; | A5-B28-C1; | A5-B28-C2; | A5-B28-C3; |
| A5-B28-C4; | A5-B28-C5; | A5-B28-C6; | A5-B28-C7; | A5-B28-C8; | A5-B28-C9; |
| A6-B28-C1; | A6-B28-C2; | A6-B28-C3; | A6-B28-C4; | A6-B28-C5; | A6-B28-C6; |
| A6-B28-C7; | A6-B28-C8; | A6-B28-C9; | A7-B28-C1; | A7-B28-C2; | A7-B28-C3; |
| A7-B28-C4; | A7-B28-C5; | A7-B28-C6; | A7-B28-C7; | A7-B28-C8; | A7-B28-C9; |
| A8-B28-C1; | A8-B28-C2; | A8-B28-C3; | A8-B28-C4; | A8-B28-C5; | A8-B28-C6; |
| A8-B28-C7; | A8-B28-C8; | A8-B28-C9; | A9-B28-C1; | A9-B28-C2; | A9-B28-C3; |
| A9-B28-C4; | A9-B28-C5; | A9-B28-C6; | A9-B28-C7; | A9-B28-C8; | A9-B28-C9; |
| A10-B28-C1; | A10-B28-C2; | A10-B28-C3; | A10-B28-C4; | A10-B28-C5; | A10-B28-C6; |
| A10-B28-C7; | A10-B28-C8; | A10-B28-C9; | A11-B28-C1; | A11-B28-C2; | A11-B28-C3; |
| A11-B28-C4; | A11-B28-C5; | A11-B28-C6; | A11-B28-C7; | A11-B28-C8; | A11-B28-C9; |
| A12-B28-C1; | A12-B28-C2; | A12-B28-C3; | A12-B28-C4; | A12-B28-C5; | A12-B28-C6; |
| A12-B28-C7; | A12-B28-C8; | A12-B28-C9; | A13-B28-C1; | A13-B28-C2; | A13-B28-C3; |
| A13-B28-C4; | A13-B28-C5; | A13-B28-C6; | A13-B28-C7; | A13-B28-C8; | A13-B28-C9; |
| A14-B28-C1; | A14-B28-C2; | A14-B28-C3; | A14-B28-C4; | A14-B28-C5; | A14-B28-C6; |
| A14-B28-C7; | A14-B28-C8; | A14-B28-C9; | A15-B28-C1; | A15-B28-C2; | A15-B28-C3; |
| A15-B28-C4; | A15-B28-C5; | A15-B28-C6; | A15-B28-C7; | A15-B28-C8; | A15-B28-C9; |
| A16-B28-C1; | A16-B28-C2; | A16-B28-C3; | A16-B28-C4; | A16-B28-C5; | A16-B28-C6; |
| A16-B28-C7; | A16-B28-C8; | A16-B28-C9; | A17-B28-C1; | A17-B28-C2; | A17-B28-C3; |
| A17-B28-C4; | A17-B28-C5; | A17-B28-C6; | A17-B28-C7; | A17-B28-C8; | A17-B28-C9; |
| A18-B28-C1; | A18-B28-C2; | A18-B28-C3; | A18-B28-C4; | A18-B28-C5; | A18-B28-C6; |
| A18-B28-C7; | A18-B28-C8; | A18-B28-C9; | A19-B28-C1; | A19-B28-C2; | A19-B28-C3; |
| A19-B28-C4; | A19-B28-C5; | A19-B28-C6; | A19-B28-C7; | A19-B28-C8; | A19-B28-C9; |
| A20-B28-C1; | A20-B28-C2; | A20-B28-C3; | A20-B28-C4; | A20-B28-C5; | A20-B28-C6; |
| A20-B28-C7; | A20-B28-C8; | A20-B28-C9; | A21-B28-C1; | A21-B28-C2; | A21-B28-C3; |
| A21-B28-C4; | A21-B28-C5; | A21-B28-C6; | A21-B28-C7; | A21-B28-C8; | A21-B28-C9; |
| A22-B28-C1; | A22-B28-C2; | A22-B28-C3; | A22-B28-C4; | A22-B28-C5; | A22-B28-C6; |
| A22-B28-C7; | A22-B28-C8; | A22-B28-C9; | A23-B28-C1; | A23-B28-C2; | A23-B28-C3; |
| A23-B28-C4; | A23-B28-C5; | A23-B28-C6; | A23-B28-C7; | A23-B28-C8; | A23-B28-C9; |
| A24-B28-C1; | A24-B28-C2; | A24-B28-C3; | A24-B28-C4; | A24-B28-C5; | A24-B28-C6; |
| A24-B28-C7; | A24-B28-C8; | A24-B28-C9; | A25-B28-C1; | A25-B28-C2; | A25-B28-C3; |
| A25-B28-C4; | A25-B28-C5; | A25-B28-C6; | A25-B28-C7; | A25-B28-C8; | A25-B28-C9; |
| A26-B28-C1; | A26-B28-C2; | A26-B28-C3; | A26-B28-C4; | A26-B28-C5; | A26-B28-C6; |
| A26-B28-C7; | A26-B28-C8; | A26-B28-C9; | A27-B28-C1; | A27-B28-C2; | A27-B28-C3; |
| A27-B28-C4; | A27-B28-C5; | A27-B28-C6; | A27-B28-C7; | A27-B28-C8; | A27-B28-C9; |
| A28-B28-C1; | A28-B28-C2; | A28-B28-C3; | A28-B28-C4; | A28-B28-C5; | A28-B28-C6; |
| A28-B28-C7; | A28-B28-C8; | A28-B28-C9; | A29-B28-C1; | A29-B28-C2; | A29-B28-C3; |
| A29-B28-C4; | A29-B28-C5; | A29-B28-C6; | A29-B28-C7; | A29-B28-C8; | A29-B28-C9; |
| A30-B28-C1; | A30-B28-C2; | A30-B28-C3; | A30-B28-C4; | A30-B28-C5; | A30-B28-C6; |
| A30-B28-C7; | A30-B28-C8; | A30-B28-C9; | A31-B28-C1; | A31-B28-C2; | A31-B28-C3; |
| A31-B28-C4; | A31-B28-C5; | A31-B28-C6; | A31-B28-C7; | A31-B28-C8; | A31-B28-C9; |
| A32-B28-C1; | A32-B28-C2; | A32-B28-C3; | A32-B28-C4; | A32-B28-C5; | A32-B28-C6; |
| A32-B28-C7; | A32-B28-C8; | A32-B28-C9; | A33-B28-C1; | A33-B28-C2; | A33-B28-C3; |
| A33-B28-C4; | A33-B28-C5; | A33-B28-C6; | A33-B28-C7; | A33-B28-C8; | A33-B28-C9; |
| A34-B28-C1; | A34-B28-C2; | A34-B28-C3; | A34-B28-C4; | A34-B28-C5; | A34-B28-C6; |
| A34-B28-C7; | A34-B28-C8; | A34-B28-C9; | A35-B28-C1; | A35-B28-C2; | A35-B28-C3; |
| A35-B28-C4; | A35-B28-C5; | A35-B28-C6; | A35-B28-C7; | A35-B28-C8; | A35-B28-C9; |
| A36-B28-C1; | A36-B28-C2; | A36-B28-C3; | A36-B28-C4; | A36-B28-C5; | A36-B28-C6; |
| A36-B28-C7; | A36-B28-C8; | A36-B28-C9; | A37-B28-C1; | A37-B28-C2; | A37-B28-C3; |
| A37-B28-C4; | A37-B28-C5; | A37-B28-C6; | A37-B28-C7; | A37-B28-C8; | A37-B28-C9; |
| A38-B28-C1; | A38-B28-C2; | A38-B28-C3; | A38-B28-C4; | A38-B28-C5; | A38-B28-C6; |
| A38-B28-C7; | A38-B28-C8; | A38-B28-C9; | A39-B28-C1; | A39-B28-C2; | A39-B28-C3; |
| A39-B28-C4; | A39-B28-C5; | A39-B28-C6; | A39-B28-C7; | A39-B28-C8; | A39-B28-C9; |
| A40-B28-C1; | A40-B28-C2; | A40-B28-C3; | A40-B28-C4; | A40-B28-C5; | A40-B28-C6; |
| A40-B28-C7; | A40-B28-C8; | A40-B28-C9; | A41-B28-C1; | A41-B28-C2; | A41-B28-C3; |
| A41-B28-C4; | A41-B28-C5; | A41-B28-C6; | A41-B28-C7; | A41-B28-C8; | A41-B28-C9; |
| A42-B28-C1; | A42-B28-C2; | A42-B28-C3; | A42-B28-C4; | A42-B28-C5; | A42-B28-C6; |
| A42-B28-C7; | A42-B28-C8; | A42-B28-C9; | A43-B28-C1; | A43-B28-C2; | A43-B28-C3; |
| A43-B28-C4; | A43-B28-C5; | A43-B28-C6; | A43-B28-C7; | A43-B28-C8; | A43-B28-C9; |
| A44-B28-C1; | A44-B28-C2; | A44-B28-C3; | A44-B28-C4; | A44-B28-C5; | A44-B28-C6; |
| A44-B28-C7; | A44-B28-C8; | A44-B28-C9; | A45-B28-C1; | A45-B28-C2; | A45-B28-C3; |
| A45-B28-C4; | A45-B28-C5; | A45-B28-C6; | A45-B28-C7; | A45-B28-C8; | A45-B28-C9; |
| A46-B28-C1; | A46-B28-C2; | A46-B28-C3; | A46-B28-C4; | A46-B28-C5; | A46-B28-C6; |
| A46-B28-C7; | A46-B28-C8; | A46-B28-C9; | A47-B28-C1; | A47-B28-C2; | A47-B28-C3; |
| A47-B28-C4; | A47-B28-C5; | A47-B28-C6; | A47-B28-C7; | A47-B28-C8; | A47-B28-C9; |
| A48-B28-C1; | A48-B28-C2; | A48-B28-C3; | A48-B28-C4; | A48-B28-C5; | A48-B28-C6; |
| A48-B28-C7; | A48-B28-C8; | A48-B28-C9; | A49-B28-C1; | A49-B28-C2; | A49-B28-C3; |
| A49-B28-C4; | A49-B28-C5; | A49-B28-C6; | A49-B28-C7; | A49-B28-C8; | A49-B28-C9; |
| A50-B28-C1; | A50-B28-C2; | A50-B28-C3; | A50-B28-C4; | A50-B28-C5; | A50-B28-C6; |

-continued

| | | | | | |
|---|---|---|---|---|---|
| A50-B28-C7; | A50-B28-C8; | A50-B28-C9; | A51-B28-C1; | A51-B28-C2; | A51-B28-C3; |
| A51-B28-C4; | A51-B28-C5; | A51-B28-C6; | A51-B28-C7; | A51-B28-C8; | A51-B28-C9; |
| A52-B28-C1; | A52-B28-C2; | A52-B28-C3; | A52-B28-C4; | A52-B28-C5; | A52-B28-C6; |
| A52-B28-C7; | A52-B28-C8; | A52-B28-C9; | A53-B28-C1; | A53-B28-C2; | A53-B28-C3; |
| A53-B28-C4; | A53-B28-C5; | A53-B28-C6; | A53-B28-C7; | A53-B28-C8; | A53-B28-C9; |
| A54-B28-C1; | A54-B28-C2; | A54-B28-C3; | A54-B28-C4; | A54-B28-C5; | A54-B28-C6; |
| A54-B28-C7; | A54-B28-C8; | A54-B28-C9; | A55-B28-C1; | A55-B28-C2; | A55-B28-C3; |
| A55-B28-C4; | A55-B28-C5; | A55-B28-C6; | A55-B28-C7; | A55-B28-C8; | A55-B28-C9; |
| A56-B28-C1; | A56-B28-C2; | A56-B28-C3; | A56-B28-C4; | A56-B28-C5; | A56-B28-C6; |
| A56-B28-C7; | A56-B28-C8; | A56-B28-C9; | A57-B28-C1; | A57-B28-C2; | A57-B28-C3; |
| A57-B28-C4; | A57-B28-C5; | A57-B28-C6; | A57-B28-C7; | A57-B28-C8; | A57-B28-C9; |
| A58-B28-C1; | A58-B28-C2; | A58-B28-C3; | A58-B28-C4; | A58-B28-C5; | A58-B28-C6; |
| A58-B28-C7; | A58-B28-C8; | A58-B28-C9; | A59-B28-C1; | A59-B28-C2; | A59-B28-C3; |
| A59-B28-C4; | A59-B28-C5; | A59-B28-C6; | A59-B28-C7; | A59-B28-C8; | A59-B28-C9; |
| A60-B28-C1; | A60-B28-C2; | A60-B28-C3; | A60-B28-C4; | A60-B28-C5; | A60-B28-C6; |
| A60-B28-C7; | A60-B28-C8; | A60-B28-C9; | A61-B28-C1; | A61-B28-C2; | A61-B28-C3; |
| A61-B28-C4; | A61-B28-C5; | A61-B28-C6; | A61-B28-C7; | A61-B28-C8; | A61-B28-C9; |
| A62-B28-C1; | A62-B28-C2; | A62-B28-C3; | A62-B28-C4; | A62-B28-C5; | A62-B28-C6; |
| A62-B28-C7; | A62-B28-C8; | A62-B28-C9; | A63-B28-C1; | A63-B28-C2; | A63-B28-C3; |
| A63-B28-C4; | A63-B28-C5; | A63-B28-C6; | A63-B28-C7; | A63-B28-C8; | A63-B28-C9; |
| A64-B28-C1; | A64-B28-C2; | A64-B28-C3; | A64-B28-C4; | A64-B28-C5; | A64-B28-C6; |
| A64-B28-C7; | A64-B28-C8; | A64-B28-C9; | A65-B28-C1; | A65-B28-C2; | A65-B28-C3; |
| A65-B28-C4; | A65-B28-C5; | A65-B28-C6; | A65-B28-C7; | A65-B28-C8; | A65-B28-C9; |
| A66-B28-C1; | A66-B28-C2; | A66-B28-C3; | A66-B28-C4; | A66-B28-C5; | A66-B28-C6; |
| A66-B28-C7; | A66-B28-C8; | A66-B28-C9; | A67-B28-C1; | A67-B28-C2; | A67-B28-C3; |
| A67-B28-C4; | A67-B28-C5; | A67-B28-C6; | A67-B28-C7; | A67-B28-C8; | A67-B28-C9; |
| A68-B28-C1; | A68-B28-C2; | A68-B28-C3; | A68-B28-C4; | A68-B28-C5; | A68-B28-C6; |
| A68-B28-C7; | A68-B28-C8; | A68-B28-C9; | A69-B28-C1; | A69-B28-C2; | A69-B28-C3; |
| A69-B28-C4; | A69-B28-C5; | A69-B28-C6; | A69-B28-C7; | A69-B28-C8; | A69-B28-C9; |
| A70-B28-C1; | A70-B28-C2; | A70-B28-C3; | A70-B28-C4; | A70-B28-C5; | A70-B28-C6; |
| A70-B28-C7; | A70-B28-C8; | A70-B28-C9; | A71-B28-C1; | A71-B28-C2; | A71-B28-C3; |
| A71-B28-C4; | A71-B28-C5; | A71-B28-C6; | A71-B28-C7; | A71-B28-C8; | A71-B28-C9; |
| A1-B29-C1; | A1-B29-C2; | A1-B29-C3; | A1-B29-C4; | A1-B29-C5; | A1-B29-C6; |
| A1-B29-C7; | A1-B29-C8; | A1-B29-C9; | A2-B29-C1; | A2-B29-C2; | A2-B29-C3; |
| A2-B29-C4; | A2-B29-C5; | A2-B29-C6; | A2-B29-C7; | A2-B29-C8; | A2-B29-C9; |
| A3-B29-C1; | A3-B29-C2; | A3-B29-C3; | A3-B29-C4; | A3-B29-C5; | A3-B29-C6; |
| A3-B29-C7; | A3-B29-C8; | A3-B29-C9; | A4-B29-C1; | A4-B29-C2; | A4-B29-C3; |
| A4-B29-C4; | A4-B29-C5; | A4-B29-C6; | A4-B29-C7; | A4-B29-C8; | A4-B29-C9; |
| A5-B29-C1; | A5-B29-C2; | A5-B29-C3; | A5-B29-C4; | A5-B29-C5; | A5-B29-C6; |
| A5-B29-C7; | A5-B29-C8; | A5-B29-C9; | A6-B29-C1; | A6-B29-C2; | A6-B29-C3; |
| A6-B29-C4; | A6-B29-C5; | A6-B29-C6; | A6-B29-C7; | A6-B29-C8; | A6-B29-C9; |
| A7-B29-C1; | A7-B29-C2; | A7-B29-C3; | A7-B29-C4; | A7-B29-C5; | A7-B29-C6; |
| A7-B29-C7; | A7-B29-C8; | A7-B29-C9; | A8-B29-C1; | A8-B29-C2; | A8-B29-C3; |
| A8-B29-C4; | A8-B29-C5; | A8-B29-C6; | A8-B29-C7; | A8-B29-C8; | A8-B29-C9; |
| A9-B29-C1; | A9-B29-C2; | A9-B29-C3; | A9-B29-C4; | A9-B29-C5; | A9-B29-C6; |
| A9-B29-C7; | A9-B29-C8; | A9-B29-C9; | A10-B29-C1; | A10-B29-C2; | A10-B29-C3; |
| A10-B29-C4; | A10-B29-C5; | A10-B29-C6; | A10-B29-C7; | A10-B29-C8; | A10-B29-C9; |
| A11-B29-C1; | A11-B29-C2; | A11-B29-C3; | A11-B29-C4; | A11-B29-C5; | A11-B29-C6; |
| A11-B29-C7; | A11-B29-C8; | A11-B29-C9; | A12-B29-C1; | A12-B29-C2; | A12-B29-C3; |
| A12-B29-C4; | A12-B29-C5; | A12-B29-C6; | A12-B29-C7; | A12-B29-C8; | A12-B29-C9; |
| A13-B29-C1; | A13-B29-C2; | A13-B29-C3; | A13-B29-C4; | A13-B29-C5; | A13-B29-C6; |
| A13-B29-C7; | A13-B29-C8; | A13-B29-C9; | A14-B29-C1; | A14-B29-C2; | A14-B29-C3; |
| A14-B29-C4; | A14-B29-C5; | A14-B29-C6; | A14-B29-C7; | A14-B29-C8; | A14-B29-C9; |
| A15-B29-C1; | A15-B29-C2; | A15-B29-C3; | A15-B29-C4; | A15-B29-C5; | A15-B29-C6; |
| A15-B29-C7; | A15-B29-C8; | A15-B29-C9; | A16-B29-C1; | A16-B29-C2; | A16-B29-C3; |
| A16-B29-C4; | A16-B29-C5; | A16-B29-C6; | A16-B29-C7; | A16-B29-C8; | A16-B29-C9; |
| A17-B29-C1; | A17-B29-C2; | A17-B29-C3; | A17-B29-C4; | A17-B29-C5; | A17-B29-C6; |
| A17-B29-C7; | A17-B29-C8; | A17-B29-C9; | A18-B29-C1; | A18-B29-C2; | A18-B29-C3; |
| A18-B29-C4; | A18-B29-C5; | A18-B29-C6; | A18-B29-C7; | A18-B29-C8; | A18-B29-C9; |
| A19-B29-C1; | A19-B29-C2; | A19-B29-C3; | A19-B29-C4; | A19-B29-C5; | A19-B29-C6; |
| A19-B29-C7; | A19-B29-C8; | A19-B29-C9; | A20-B29-C1; | A20-B29-C2; | A20-B29-C3; |
| A20-B29-C4; | A20-B29-C5; | A20-B29-C6; | A20-B29-C7; | A20-B29-C8; | A20-B29-C9; |
| A21-B29-C1; | A21-B29-C2; | A21-B29-C3; | A21-B29-C4; | A21-B29-C5; | A21-B29-C6; |
| A21-B29-C7; | A21-B29-C8; | A21-B29-C9; | A22-B29-C1; | A22-B29-C2; | A22-B29-C3; |
| A22-B29-C4; | A22-B29-C5; | A22-B29-C6; | A22-B29-C7; | A22-B29-C8; | A22-B29-C9; |
| A23-B29-C1; | A23-B29-C2; | A23-B29-C3; | A23-B29-C4; | A23-B29-C5; | A23-B29-C6; |
| A23-B29-C7; | A23-B29-C8; | A23-B29-C9; | A24-B29-C1; | A24-B29-C2; | A24-B29-C3; |
| A24-B29-C4; | A24-B29-C5; | A24-B29-C6; | A24-B29-C7; | A24-B29-C8; | A24-B29-C9; |
| A25-B29-C1; | A25-B29-C2; | A25-B29-C3; | A25-B29-C4; | A25-B29-C5; | A25-B29-C6; |
| A25-B29-C7; | A25-B29-C8; | A25-B29-C9; | A26-B29-C1; | A26-B29-C2; | A26-B29-C3; |
| A26-B29-C4; | A26-B29-C5; | A26-B29-C6; | A26-B29-C7; | A26-B29-C8; | A26-B29-C9; |
| A27-B29-C1; | A27-B29-C2; | A27-B29-C3; | A27-B29-C4; | A27-B29-C5; | A27-B29-C6; |
| A27-B29-C7; | A27-B29-C8; | A27-B29-C9; | A28-B29-C1; | A28-B29-C2; | A28-B29-C3; |
| A28-B29-C4; | A28-B29-C5; | A28-B29-C6; | A28-B29-C7; | A28-B29-C8; | A28-B29-C9; |
| A29-B29-C1; | A29-B29-C2; | A29-B29-C3; | A29-B29-C4; | A29-B29-C5; | A29-B29-C6; |
| A29-B29-C7; | A29-B29-C8; | A29-B29-C9; | A30-B29-C1; | A30-B29-C2; | A30-B29-C3; |
| A30-B29-C4; | A30-B29-C5; | A30-B29-C6; | A30-B29-C7; | A30-B29-C8; | A30-B29-C9; |
| A31-B29-C1; | A31-B29-C2; | A31-B29-C3; | A31-B29-C4; | A31-B29-C5; | A31-B29-C6; |
| A31-B29-C7; | A31-B29-C8; | A31-B29-C9; | A32-B29-C1; | A32-B29-C2; | A32-B29-C3; |

-continued

| | | | | | |
|---|---|---|---|---|---|
| A32-B29-C4; | A32-B29-C5; | A32-B29-C6; | A32-B29-C7; | A32-B29-C8; | A32-B29-C9; |
| A33-B29-C1; | A33-B29-C2; | A33-B29-C3; | A33-B29-C4; | A33-B29-C5; | A33-B29-C6; |
| A33-B29-C7; | A33-B29-C8; | A33-B29-C9; | A34-B29-C1; | A34-B29-C2; | A34-B29-C3; |
| A34-B29-C4; | A34-B29-C5; | A34-B29-C6; | A34-B29-C7; | A34-B29-C8; | A34-B29-C9; |
| A35-B29-C1; | A35-B29-C2; | A35-B29-C3; | A35-B29-C4; | A35-B29-C5; | A35-B29-C6; |
| A35-B29-C7; | A35-B29-C8; | A35-B29-C9; | A36-B29-C1; | A36-B29-C2; | A36-B29-C3; |
| A36-B29-C4; | A36-B29-C5; | A36-B29-C6; | A36-B29-C7; | A36-B29-C8; | A36-B29-C9; |
| A37-B29-C1; | A37-B29-C2; | A37-B29-C3; | A37-B29-C4; | A37-B29-C5; | A37-B29-C6; |
| A37-B29-C7; | A37-B29-C8; | A37-B29-C9; | A38-B29-C1; | A38-B29-C2; | A38-B29-C3; |
| A38-B29-C4; | A38-B29-C5; | A38-B29-C6; | A38-B29-C7; | A38-B29-C8; | A38-B29-C9; |
| A39-B29-C1; | A39-B29-C2; | A39-B29-C3; | A39-B29-C4; | A39-B29-C5; | A39-B29-C6; |
| A39-B29-C7; | A39-B29-C8; | A39-B29-C9; | A40-B29-C1; | A40-B29-C2; | A40-B29-C3; |
| A40-B29-C4; | A40-B29-C5; | A40-B29-C6; | A40-B29-C7; | A40-B29-C8; | A40-B29-C9; |
| A41-B29-C1; | A41-B29-C2; | A41-B29-C3; | A41-B29-C4; | A41-B29-C5; | A41-B29-C6; |
| A41-B29-C7; | A41-B29-C8; | A41-B29-C9; | A42-B29-C1; | A42-B29-C2; | A42-B29-C3; |
| A42-B29-C4; | A42-B29-C5; | A42-B29-C6; | A42-B29-C7; | A42-B29-C8; | A42-B29-C9; |
| A43-B29-C1; | A43-B29-C2; | A43-B29-C3; | A43-B29-C4; | A43-B29-C5; | A43-B29-C6; |
| A43-B29-C7; | A43-B29-C8; | A43-B29-C9; | A44-B29-C1; | A44-B29-C2; | A44-B29-C3; |
| A44-B29-C4; | A44-B29-C5; | A44-B29-C6; | A44-B29-C7; | A44-B29-C8; | A44-B29-C9; |
| A45-B29-C1; | A45-B29-C2; | A45-B29-C3; | A45-B29-C4; | A45-B29-C5; | A45-B29-C6; |
| A45-B29-C7; | A45-B29-C8; | A45-B29-C9; | A46-B29-C1; | A46-B29-C2; | A46-B29-C3; |
| A46-B29-C4; | A46-B29-C5; | A46-B29-C6; | A46-B29-C7; | A46-B29-C8; | A46-B29-C9; |
| A47-B29-C1; | A47-B29-C2; | A47-B29-C3; | A47-B29-C4; | A47-B29-C5; | A47-B29-C6; |
| A47-B29-C7; | A47-B29-C8; | A47-B29-C9; | A48-B29-C1; | A48-B29-C2; | A48-B29-C3; |
| A48-B29-C4; | A48-B29-C5; | A48-B29-C6; | A48-B29-C7; | A48-B29-C8; | A48-B29-C9; |
| A49-B29-C1; | A49-B29-C2; | A49-B29-C3; | A49-B29-C4; | A49-B29-C5; | A49-B29-C6; |
| A49-B29-C7; | A49-B29-C8; | A49-B29-C9; | A50-B29-C1; | A50-B29-C2; | A50-B29-C3; |
| A50-B29-C4; | A50-B29-C5; | A50-B29-C6; | A50-B29-C7; | A50-B29-C8; | A50-B29-C9; |
| A51-B29-C1; | A51-B29-C2; | A51-B29-C3; | A51-B29-C4; | A51-B29-C5; | A51-B29-C6; |
| A51-B29-C7; | A51-B29-C8; | A51-B29-C9; | A52-B29-C1; | A52-B29-C2; | A52-B29-C3; |
| A52-B29-C4; | A52-B29-C5; | A52-B29-C6; | A52-B29-C7; | A52-B29-C8; | A52-B29-C9; |
| A53-B29-C1; | A53-B29-C2; | A53-B29-C3; | A53-B29-C4; | A53-B29-C5; | A53-B29-C6; |
| A53-B29-C7; | A53-B29-C8; | A53-B29-C9; | A54-B29-C1; | A54-B29-C2; | A54-B29-C3; |
| A54-B29-C4; | A54-B29-C5; | A54-B29-C6; | A54-B29-C7; | A54-B29-C8; | A54-B29-C9; |
| A55-B29-C1; | A55-B29-C2; | A55-B29-C3; | A55-B29-C4; | A55-B29-C5; | A55-B29-C6; |
| A55-B29-C7; | A55-B29-C8; | A55-B29-C9; | A56-B29-C1; | A56-B29-C2; | A56-B29-C3; |
| A56-B29-C4; | A56-B29-C5; | A56-B29-C6; | A56-B29-C7; | A56-B29-C8; | A56-B29-C9; |
| A57-B29-C1; | A57-B29-C2; | A57-B29-C3; | A57-B29-C4; | A57-B29-C5; | A57-B29-C6; |
| A57-B29-C7; | A57-B29-C8; | A57-B29-C9; | A58-B29-C1; | A58-B29-C2; | A58-B29-C3; |
| A58-B29-C4; | A58-B29-C5; | A58-B29-C6; | A58-B29-C7; | A58-B29-C8; | A58-B29-C9; |
| A59-B29-C1; | A59-B29-C2; | A59-B29-C3; | A59-B29-C4; | A59-B29-C5; | A59-B29-C6; |
| A59-B29-C7; | A59-B29-C8; | A59-B29-C9; | A60-B29-C1; | A60-B29-C2; | A60-B29-C3; |
| A60-B29-C4; | A60-B29-C5; | A60-B29-C6; | A60-B29-C7; | A60-B29-C8; | A60-B29-C9; |
| A61-B29-C1; | A61-B29-C2; | A61-B29-C3; | A61-B29-C4; | A61-B29-C5; | A61-B29-C6; |
| A61-B29-C7; | A61-B29-C8; | A61-B29-C9; | A62-B29-C1; | A62-B29-C2; | A62-B29-C3; |
| A62-B29-C4; | A62-B29-C5; | A62-B29-C6; | A62-B29-C7; | A62-B29-C8; | A62-B29-C9; |
| A63-B29-C1; | A63-B29-C2; | A63-B29-C3; | A63-B29-C4; | A63-B29-C5; | A63-B29-C6; |
| A63-B29-C7; | A63-B29-C8; | A63-B29-C9; | A64-B29-C1; | A64-B29-C2; | A64-B29-C3; |
| A64-B29-C4; | A64-B29-C5; | A64-B29-C6; | A64-B29-C7; | A64-B29-C8; | A64-B29-C9; |
| A65-B29-C1; | A65-B29-C2; | A65-B29-C3; | A65-B29-C4; | A65-B29-C5; | A65-B29-C6; |
| A65-B29-C7; | A65-B29-C8; | A65-B29-C9; | A66-B29-C1; | A66-B29-C2; | A66-B29-C3; |
| A66-B29-C4; | A66-B29-C5; | A66-B29-C6; | A66-B29-C7; | A66-B29-C8; | A66-B29-C9; |
| A67-B29-C1; | A67-B29-C2; | A67-B29-C3; | A67-B29-C4; | A67-B29-C5; | A67-B29-C6; |
| A67-B29-C7; | A67-B29-C8; | A67-B29-C9; | A68-B29-C1; | A68-B29-C2; | A68-B29-C3; |
| A68-B29-C4; | A68-B29-C5; | A68-B29-C6; | A68-B29-C7; | A68-B29-C8; | A68-B29-C9; |
| A69-B29-C1; | A69-B29-C2; | A69-B29-C3; | A69-B29-C4; | A69-B29-C5; | A69-B29-C6; |
| A69-B29-C7; | A69-B29-C8; | A69-B29-C9; | A70-B29-C1; | A70-B29-C2; | A70-B29-C3; |
| A70-B29-C4; | A70-B29-C5; | A70-B29-C6; | A70-B29-C7; | A70-B29-C8; | A70-B29-C9; |
| A71-B29-C1; | A71-B29-C2; | A71-B29-C3; | A71-B29-C4; | A71-B29-C5; | A71-B29-C6; |
| A71-B29-C7; | A71-B29-C8; | A71-B29-C9; | A1-B30-C1; | A1-B30-C2; | A1-B30-C3; |
| A1-B30-C4; | A1-B30-C5; | A1-B30-C6; | A1-B30-C7; | A1-B30-C8; | A1-B30-C9; |
| A2-B30-C1; | A2-B30-C2; | A2-B30-C3; | A2-B30-C4; | A2-B30-C5; | A2-B30-C6; |
| A2-B30-C7; | A2-B30-C8; | A2-B30-C9; | A3-B30-C1; | A3-B30-C2; | A3-B30-C3; |
| A3-B30-C4; | A3-B30-C5; | A3-B30-C6; | A3-B30-C7; | A3-B30-C8; | A3-B30-C9; |
| A4-B30-C1; | A4-B30-C2; | A4-B30-C3; | A4-B30-C4; | A4-B30-C5; | A4-B30-C6; |
| A4-B30-C7; | A4-B30-C8; | A4-B30-C9; | A5-B30-C1; | A5-B30-C2; | A5-B30-C3; |
| A5-B30-C4; | A5-B30-C5; | A5-B30-C6; | A5-B30-C7; | A5-B30-C8; | A5-B30-C9; |
| A6-B30-C1; | A6-B30-C2; | A6-B30-C3; | A6-B30-C4; | A6-B30-C5; | A6-B30-C6; |
| A6-B30-C7; | A6-B30-C8; | A6-B30-C9; | A7-B30-C1; | A7-B30-C2; | A7-B30-C3; |
| A7-B30-C4; | A7-B30-C5; | A7-B30-C6; | A7-B30-C7; | A7-B30-C8; | A7-B30-C9; |
| A8-B30-C1; | A8-B30-C2; | A8-B30-C3; | A8-B30-C4; | A8-B30-C5; | A8-B30-C6; |
| A8-B30-C7; | A8-B30-C8; | A8-B30-C9; | A9-B30-C1; | A9-B30-C2; | A9-B30-C3; |
| A9-B30-C4; | A9-B30-C5; | A9-B30-C6; | A9-B30-C7; | A9-B30-C8; | A9-B30-C9; |
| A10-B30-C1; | A10-B30-C2; | A10-B30-C3; | A10-B30-C4; | A10-B30-C5; | A10-B30-C6; |
| A10-B30-C7; | A10-B30-C8; | A10-B30-C9; | A11-B30-C1; | A11-B30-C2; | A11-B30-C3; |
| A11-B30-C4; | A11-B30-C5; | A11-B30-C6; | A11-B30-C7; | A11-B30-C8; | A11-B30-C9; |
| A12-B30-C1; | A12-B30-C2; | A12-B30-C3; | A12-B30-C4; | A12-B30-C5; | A12-B30-C6; |
| A12-B30-C7; | A12-B30-C8; | A12-B30-C9; | A13-B30-C1; | A13-B30-C2; | A13-B30-C3; |
| A13-B30-C4; | A13-B30-C5; | A13-B30-C6; | A13-B30-C7; | A13-B30-C8; | A13-B30-C9; |

-continued

| | | | | | |
|---|---|---|---|---|---|
| A14-B30-C1; | A14-B30-C2; | A14-B30-C3; | A14-B30-C4; | A14-B30-C5; | A14-B30-C6; |
| A14-B30-C7; | A14-B30-C8; | A14-B30-C9; | A15-B30-C1; | A15-B30-C2; | A15-B30-C3; |
| A15-B30-C4; | A15-B30-C5; | A15-B30-C6; | A15-B30-C7; | A15-B30-C8; | A15-B30-C9; |
| A16-B30-C1; | A16-B30-C2; | A16-B30-C3; | A16-B30-C4; | A16-B30-C5; | A16-B30-C6; |
| A16-B30-C7; | A16-B30-C8; | A16-B30-C9; | A17-B30-C1; | A17-B30-C2; | A17-B30-C3; |
| A17-B30-C4; | A17-B30-C5; | A17-B30-C6; | A17-B30-C7; | A17-B30-C8; | A17-B30-C9; |
| A18-B30-C1; | A18-B30-C2; | A18-B30-C3; | A18-B30-C4; | A18-B30-C5; | A18-B30-C6; |
| A18-B30-C7; | A18-B30-C8; | A18-B30-C9; | A19-B30-C1; | A19-B30-C2; | A19-B30-C3; |
| A19-B30-C4; | A19-B30-C5; | A19-B30-C6; | A19-B30-C7; | A19-B30-C8; | A19-B30-C9; |
| A20-B30-C1; | A20-B30-C2; | A20-B30-C3; | A20-B30-C4; | A20-B30-C5; | A20-B30-C6; |
| A20-B30-C7; | A20-B30-C8; | A20-B30-C9; | A21-B30-C1; | A21-B30-C2; | A21-B30-C3; |
| A21-B30-C4; | A21-B30-C5; | A21-B30-C6; | A21-B30-C7; | A21-B30-C8; | A21-B30-C9; |
| A22-B30-C1; | A22-B30-C2; | A22-B30-C3; | A22-B30-C4; | A22-B30-C5; | A22-B30-C6; |
| A22-B30-C7; | A22-B30-C8; | A22-B30-C9; | A23-B30-C1; | A23-B30-C2; | A23-B30-C3; |
| A23-B30-C4; | A23-B30-C5; | A23-B30-C6; | A23-B30-C7; | A23-B30-C8; | A23-B30-C9; |
| A24-B30-C1; | A24-B30-C2; | A24-B30-C3; | A24-B30-C4; | A24-B30-C5; | A24-B30-C6; |
| A24-B30-C7; | A24-B30-C8; | A24-B30-C9; | A25-B30-C1; | A25-B30-C2; | A25-B30-C3; |
| A25-B30-C4; | A25-B30-C5; | A25-B30-C6; | A25-B30-C7; | A25-B30-C8; | A25-B30-C9; |
| A26-B30-C1; | A26-B30-C2; | A26-B30-C3; | A26-B30-C4; | A26-B30-C5; | A26-B30-C6; |
| A26-B30-C7; | A26-B30-C8; | A26-B30-C9; | A27-B30-C1; | A27-B30-C2; | A27-B30-C3; |
| A27-B30-C4; | A27-B30-C5; | A27-B30-C6; | A27-B30-C7; | A27-B30-C8; | A27-B30-C9; |
| A28-B30-C1; | A28-B30-C2; | A28-B30-C3; | A28-B30-C4; | A28-B30-C5; | A28-B30-C6; |
| A28-B30-C7; | A28-B30-C8; | A28-B30-C9; | A29-B30-C1; | A29-B30-C2; | A29-B30-C3; |
| A29-B30-C4; | A29-B30-C5; | A29-B30-C6; | A29-B30-C7; | A29-B30-C8; | A29-B30-C9; |
| A30-B30-C1; | A30-B30-C2; | A30-B30-C3; | A30-B30-C4; | A30-B30-C5; | A30-B30-C6; |
| A30-B30-C7; | A30-B30-C8; | A30-B30-C9; | A31-B30-C1; | A31-B30-C2; | A31-B30-C3; |
| A31-B30-C4; | A31-B30-C5; | A31-B30-C6; | A31-B30-C7; | A31-B30-C8; | A31-B30-C9; |
| A32-B30-C1; | A32-B30-C2; | A32-B30-C3; | A32-B30-C4; | A32-B30-C5; | A32-B30-C6; |
| A32-B30-C7; | A32-B30-C8; | A32-B30-C9; | A33-B30-C1; | A33-B30-C2; | A33-B30-C3; |
| A33-B30-C4; | A33-B30-C5; | A33-B30-C6; | A33-B30-C7; | A33-B30-C8; | A33-B30-C9; |
| A34-B30-C1; | A34-B30-C2; | A34-B30-C3; | A34-B30-C4; | A34-B30-C5; | A34-B30-C6; |
| A34-B30-C7; | A34-B30-C8; | A34-B30-C9; | A35-B30-C1; | A35-B30-C2; | A35-B30-C3; |
| A35-B30-C4; | A35-B30-C5; | A35-B30-C6; | A35-B30-C7; | A35-B30-C8; | A35-B30-C9; |
| A36-B30-C1; | A36-B30-C2; | A36-B30-C3; | A36-B30-C4; | A36-B30-C5; | A36-B30-C6; |
| A36-B30-C7; | A36-B30-C8; | A36-B30-C9; | A37-B30-C1; | A37-B30-C2; | A37-B30-C3; |
| A37-B30-C4; | A37-B30-C5; | A37-B30-C6; | A37-B30-C7; | A37-B30-C8; | A37-B30-C9; |
| A38-B30-C1; | A38-B30-C2; | A38-B30-C3; | A38-B30-C4; | A38-B30-C5; | A38-B30-C6; |
| A38-B30-C7; | A38-B30-C8; | A38-B30-C9; | A39-B30-C1; | A39-B30-C2; | A39-B30-C3; |
| A39-B30-C4; | A39-B30-C5; | A39-B30-C6; | A39-B30-C7; | A39-B30-C8; | A39-B30-C9; |
| A40-B30-C1; | A40-B30-C2; | A40-B30-C3; | A40-B30-C4; | A40-B30-C5; | A40-B30-C6; |
| A40-B30-C7; | A40-B30-C8; | A40-B30-C9; | A41-B30-C1; | A41-B30-C2; | A41-B30-C3; |
| A41-B30-C4; | A41-B30-C5; | A41-B30-C6; | A41-B30-C7; | A41-B30-C8; | A41-B30-C9; |
| A42-B30-C1; | A42-B30-C2; | A42-B30-C3; | A42-B30-C4; | A42-B30-C5; | A42-B30-C6; |
| A42-B30-C7; | A42-B30-C8; | A42-B30-C9; | A43-B30-C1; | A43-B30-C2; | A43-B30-C3; |
| A43-B30-C4; | A43-B30-C5; | A43-B30-C6; | A43-B30-C7; | A43-B30-C8; | A43-B30-C9; |
| A44-B30-C1; | A44-B30-C2; | A44-B30-C3; | A44-B30-C4; | A44-B30-C5; | A44-B30-C6; |
| A44-B30-C7; | A44-B30-C8; | A44-B30-C9; | A45-B30-C1; | A45-B30-C2; | A45-B30-C3; |
| A45-B30-C4; | A45-B30-C5; | A45-B30-C6; | A45-B30-C7; | A45-B30-C8; | A45-B30-C9; |
| A46-B30-C1; | A46-B30-C2; | A46-B30-C3; | A46-B30-C4; | A46-B30-C5; | A46-B30-C6; |
| A46-B30-C7; | A46-B30-C8; | A46-B30-C9; | A47-B30-C1; | A47-B30-C2; | A47-B30-C3; |
| A47-B30-C4; | A47-B30-C5; | A47-B30-C6; | A47-B30-C7; | A47-B30-C8; | A47-B30-C9; |
| A48-B30-C1; | A48-B30-C2; | A48-B30-C3; | A48-B30-C4; | A48-B30-C5; | A48-B30-C6; |
| A48-B30-C7; | A48-B30-C8; | A48-B30-C9; | A49-B30-C1; | A49-B30-C2; | A49-B30-C3; |
| A49-B30-C4; | A49-B30-C5; | A49-B30-C6; | A49-B30-C7; | A49-B30-C8; | A49-B30-C9; |
| A50-B30-C1; | A50-B30-C2; | A50-B30-C3; | A50-B30-C4; | A50-B30-C5; | A50-B30-C6; |
| A50-B30-C7; | A50-B30-C8; | A50-B30-C9; | A51-B30-C1; | A51-B30-C2; | A51-B30-C3; |
| A51-B30-C4; | A51-B30-C5; | A51-B30-C6; | A51-B30-C7; | A51-B30-C8; | A51-B30-C9; |
| A52-B30-C1; | A52-B30-C2; | A52-B30-C3; | A52-B30-C4; | A52-B30-C5; | A52-B30-C6; |
| A52-B30-C7; | A52-B30-C8; | A52-B30-C9; | A53-B30-C1; | A53-B30-C2; | A53-B30-C3; |
| A53-B30-C4; | A53-B30-C5; | A53-B30-C6; | A53-B30-C7; | A53-B30-C8; | A53-B30-C9; |
| A54-B30-C1; | A54-B30-C2; | A54-B30-C3; | A54-B30-C4; | A54-B30-C5; | A54-B30-C6; |
| A54-B30-C7; | A54-B30-C8; | A54-B30-C9; | A55-B30-C1; | A55-B30-C2; | A55-B30-C3; |
| A55-B30-C4; | A55-B30-C5; | A55-B30-C6; | A55-B30-C7; | A55-B30-C8; | A55-B30-C9; |
| A56-B30-C1; | A56-B30-C2; | A56-B30-C3; | A56-B30-C4; | A56-B30-C5; | A56-B30-C6; |
| A56-B30-C7; | A56-B30-C8; | A56-B30-C9; | A57-B30-C1; | A57-B30-C2; | A57-B30-C3; |
| A57-B30-C4; | A57-B30-C5; | A57-B30-C6; | A57-B30-C7; | A57-B30-C8; | A57-B30-C9; |
| A58-B30-C1; | A58-B30-C2; | A58-B30-C3; | A58-B30-C4; | A58-B30-C5; | A58-B30-C6; |
| A58-B30-C7; | A58-B30-C8; | A58-B30-C9; | A59-B30-C1; | A59-B30-C2; | A59-B30-C3; |
| A59-B30-C4; | A59-B30-C5; | A59-B30-C6; | A59-B30-C7; | A59-B30-C8; | A59-B30-C9; |
| A60-B30-C1; | A60-B30-C2; | A60-B30-C3; | A60-B30-C4; | A60-B30-C5; | A60-B30-C6; |
| A60-B30-C7; | A60-B30-C8; | A60-B30-C9; | A61-B30-C1; | A61-B30-C2; | A61-B30-C3; |
| A61-B30-C4; | A61-B30-C5; | A61-B30-C6; | A61-B30-C7; | A61-B30-C8; | A61-B30-C9; |
| A62-B30-C1; | A62-B30-C2; | A62-B30-C3; | A62-B30-C4; | A62-B30-C5; | A62-B30-C6; |
| A62-B30-C7; | A62-B30-C8; | A62-B30-C9; | A63-B30-C1; | A63-B30-C2; | A63-B30-C3; |
| A63-B30-C4; | A63-B30-C5; | A63-B30-C6; | A63-B30-C7; | A63-B30-C8; | A63-B30-C9; |
| A64-B30-C1; | A64-B30-C2; | A64-B30-C3; | A64-B30-C4; | A64-B30-C5; | A64-B30-C6; |
| A64-B30-C7; | A64-B30-C8; | A64-B30-C9; | A65-B30-C1; | A65-B30-C2; | A65-B30-C3; |
| A65-B30-C4; | A65-B30-C5; | A65-B30-C6; | A65-B30-C7; | A65-B30-C8; | A65-B30-C9; |
| A66-B30-C1; | A66-B30-C2; | A66-B30-C3; | A66-B30-C4; | A66-B30-C5; | A66-B30-C6; |

-continued

| | | | | | |
|---|---|---|---|---|---|
| A66-B30-C7; | A66-B30-C8; | A66-B30-C9; | A67-B30-C1; | A67-B30-C2; | A67-B30-C3; |
| A67-B30-C4; | A67-B30-C5; | A67-B30-C6; | A67-B30-C7; | A67-B30-C8; | A67-B30-C9; |
| A68-B30-C1; | A68-B30-C2; | A68-B30-C3; | A68-B30-C4; | A68-B30-C5; | A68-B30-C6; |
| A68-B30-C7; | A68-B30-C8; | A68-B30-C9; | A69-B30-C1; | A69-B30-C2; | A69-B30-C3; |
| A69-B30-C4; | A69-B30-C5; | A69-B30-C6; | A69-B30-C7; | A69-B30-C8; | A69-B30-C9; |
| A70-B30-C1; | A70-B30-C2; | A70-B30-C3; | A70-B30-C4; | A70-B30-C5; | A70-B30-C6; |
| A70-B30-C7; | A70-B30-C8; | A70-B30-C9; | A71-B30-C1; | A71-B30-C2; | A71-B30-C3; |
| A71-B30-C4; | A71-B30-C5; | A71-B30-C6; | A71-B30-C7; | A71-B30-C8; | A71-B30-C9; |
| A1-B31-C1; | A1-B31-C2; | A1-B31-C3; | A1-B31-C4; | A1-B31-C5; | A1-B31-C6; |
| A1-B31-C7; | A1-B31-C8; | A1-B31-C9; | A2-B31-C1; | A2-B31-C2; | A2-B31-C3; |
| A2-B31-C4; | A2-B31-C5; | A2-B31-C6; | A2-B31-C7; | A2-B31-C8; | A2-B31-C9; |
| A3-B31-C1; | A3-B31-C2; | A3-B31-C3; | A3-B31-C4; | A3-B31-C5; | A3-B31-C6; |
| A3-B31-C7; | A3-B31-C8; | A3-B31-C9; | A4-B31-C1; | A4-B31-C2; | A4-B31-C3; |
| A4-B31-C4; | A4-B31-C5; | A4-B31-C6; | A4-B31-C7; | A4-B31-C8; | A4-B31-C9; |
| A5-B31-C1; | A5-B31-C2; | A5-B31-C3; | A5-B31-C4; | A5-B31-C5; | A5-B31-C6; |
| A5-B31-C7; | A5-B31-C8; | A5-B31-C9; | A6-B31-C1; | A6-B31-C2; | A6-B31-C3; |
| A6-B31-C4; | A6-B31-C5; | A6-B31-C6; | A6-B31-C7; | A6-B31-C8; | A6-B31-C9; |
| A7-B31-C1; | A7-B31-C2; | A7-B31-C3; | A7-B31-C4; | A7-B31-C5; | A7-B31-C6; |
| A7-B31-C7; | A7-B31-C8; | A7-B31-C9; | A8-B31-C1; | A8-B31-C2; | A8-B31-C3; |
| A8-B31-C4; | A8-B31-C5; | A8-B31-C6; | A8-B31-C7; | A8-B31-C8; | A8-B31-C9; |
| A9-B31-C1; | A9-B31-C2; | A9-B31-C3; | A9-B31-C4; | A9-B31-C5; | A9-B31-C6; |
| A9-B31-C7; | A9-B31-C8; | A9-B31-C9; | A10-B31-C1; | A10-B31-C2; | A10-B31-C3; |
| A10-B31-C4; | A10-B31-C5; | A10-B31-C6; | A10-B31-C7; | A10-B31-C8; | A10-B31-C9; |
| A11-B31-C1; | A11-B31-C2; | A11-B31-C3; | A11-B31-C4; | A11-B31-C5; | A11-B31-C6; |
| A11-B31-C7; | A11-B31-C8; | A11-B31-C9; | A12-B31-C1; | A12-B31-C2; | A12-B31-C3; |
| A12-B31-C4; | A12-B31-C5; | A12-B31-C6; | A12-B31-C7; | A12-B31-C8; | A12-B31-C9; |
| A13-B31-C1; | A13-B31-C2; | A13-B31-C3; | A13-B31-C4; | A13-B31-C5; | A13-B31-C6; |
| A13-B31-C7; | A13-B31-C8; | A13-B31-C9; | A14-B31-C1; | A14-B31-C2; | A14-B31-C3; |
| A14-B31-C4; | A14-B31-C5; | A14-B31-C6; | A14-B31-C7; | A14-B31-C8; | A14-B31-C9; |
| A15-B31-C1; | A15-B31-C2; | A15-B31-C3; | A15-B31-C4; | A15-B31-C5; | A15-B31-C6; |
| A15-B31-C7; | A15-B31-C8; | A15-B31-C9; | A16-B31-C1; | A16-B31-C2; | A16-B31-C3; |
| A16-B31-C4; | A16-B31-C5; | A16-B31-C6; | A16-B31-C7; | A16-B31-C8; | A16-B31-C9; |
| A17-B31-C1; | A17-B31-C2; | A17-B31-C3; | A17-B31-C4; | A17-B31-C5; | A17-B31-C6; |
| A17-B31-C7; | A17-B31-C8; | A17-B31-C9; | A18-B31-C1; | A18-B31-C2; | A18-B31-C3; |
| A18-B31-C4; | A18-B31-C5; | A18-B31-C6; | A18-B31-C7; | A18-B31-C8; | A18-B31-C9; |
| A19-B31-C1; | A19-B31-C2; | A19-B31-C3; | A19-B31-C4; | A19-B31-C5; | A19-B31-C6; |
| A19-B31-C7; | A19-B31-C8; | A19-B31-C9; | A20-B31-C1; | A20-B31-C2; | A20-B31-C3; |
| A20-B31-C4; | A20-B31-C5; | A20-B31-C6; | A20-B31-C7; | A20-B31-C8; | A20-B31-C9; |
| A21-B31-C1; | A21-B31-C2; | A21-B31-C3; | A21-B31-C4; | A21-B31-C5; | A21-B31-C6; |
| A21-B31-C7; | A21-B31-C8; | A21-B31-C9; | A22-B31-C1; | A22-B31-C2; | A22-B31-C3; |
| A22-B31-C4; | A22-B31-C5; | A22-B31-C6; | A22-B31-C7; | A22-B31-C8; | A22-B31-C9; |
| A23-B31-C1; | A23-B31-C2; | A23-B31-C3; | A23-B31-C4; | A23-B31-C5; | A23-B31-C6; |
| A23-B31-C7; | A23-B31-C8; | A23-B31-C9; | A24-B31-C1; | A24-B31-C2; | A24-B31-C3; |
| A24-B31-C4; | A24-B31-C5; | A24-B31-C6; | A24-B31-C7; | A24-B31-C8; | A24-B31-C9; |
| A25-B31-C1; | A25-B31-C2; | A25-B31-C3; | A25-B31-C4; | A25-B31-C5; | A25-B31-C6; |
| A25-B31-C7; | A25-B31-C8; | A25-B31-C9; | A26-B31-C1; | A26-B31-C2; | A26-B31-C3; |
| A26-B31-C4; | A26-B31-C5; | A26-B31-C6; | A26-B31-C7; | A26-B31-C8; | A26-B31-C9; |
| A27-B31-C1; | A27-B31-C2; | A27-B31-C3; | A27-B31-C4; | A27-B31-C5; | A27-B31-C6; |
| A27-B31-C7; | A27-B31-C8; | A27-B31-C9; | A28-B31-C1; | A28-B31-C2; | A28-B31-C3; |
| A28-B31-C4; | A28-B31-C5; | A28-B31-C6; | A28-B31-C7; | A28-B31-C8; | A28-B31-C9; |
| A29-B31-C1; | A29-B31-C2; | A29-B31-C3; | A29-B31-C4; | A29-B31-C5; | A29-B31-C6; |
| A29-B31-C7; | A29-B31-C8; | A29-B31-C9; | A30-B31-C1; | A30-B31-C2; | A30-B31-C3; |
| A30-B31-C4; | A30-B31-C5; | A30-B31-C6; | A30-B31-C7; | A30-B31-C8; | A30-B31-C9; |
| A31-B31-C1; | A31-B31-C2; | A31-B31-C3; | A31-B31-C4; | A31-B31-C5; | A31-B31-C6; |
| A31-B31-C7; | A31-B31-C8; | A31-B31-C9; | A32-B31-C1; | A32-B31-C2; | A32-B31-C3; |
| A32-B31-C4; | A32-B31-C5; | A32-B31-C6; | A32-B31-C7; | A32-B31-C8; | A32-B31-C9; |
| A33-B31-C1; | A33-B31-C2; | A33-B31-C3; | A33-B31-C4; | A33-B31-C5; | A33-B31-C6; |
| A33-B31-C7; | A33-B31-C8; | A33-B31-C9; | A34-B31-C1; | A34-B31-C2; | A34-B31-C3; |
| A34-B31-C4; | A34-B31-C5; | A34-B31-C6; | A34-B31-C7; | A34-B31-C8; | A34-B31-C9; |
| A35-B31-C1; | A35-B31-C2; | A35-B31-C3; | A35-B31-C4; | A35-B31-C5; | A35-B31-C6; |
| A35-B31-C7; | A35-B31-C8; | A35-B31-C9; | A36-B31-C1; | A36-B31-C2; | A36-B31-C3; |
| A36-B31-C4; | A36-B31-C5; | A36-B31-C6; | A36-B31-C7; | A36-B31-C8; | A36-B31-C9; |
| A37-B31-C1; | A37-B31-C2; | A37-B31-C3; | A37-B31-C4; | A37-B31-C5; | A37-B31-C6; |
| A37-B31-C7; | A37-B31-C8; | A37-B31-C9; | A38-B31-C1; | A38-B31-C2; | A38-B31-C3; |
| A38-B31-C4; | A38-B31-C5; | A38-B31-C6; | A38-B31-C7; | A38-B31-C8; | A38-B31-C9; |
| A39-B31-C1; | A39-B31-C2; | A39-B31-C3; | A39-B31-C4; | A39-B31-C5; | A39-B31-C6; |
| A39-B31-C7; | A39-B31-C8; | A39-B31-C9; | A40-B31-C1; | A40-B31-C2; | A40-B31-C3; |
| A40-B31-C4; | A40-B31-C5; | A40-B31-C6; | A40-B31-C7; | A40-B31-C8; | A40-B31-C9; |
| A41-B31-C1; | A41-B31-C2; | A41-B31-C3; | A41-B31-C4; | A41-B31-C5; | A41-B31-C6; |
| A41-B31-C7; | A41-B31-C8; | A41-B31-C9; | A42-B31-C1; | A42-B31-C2; | A42-B31-C3; |
| A42-B31-C4; | A42-B31-C5; | A42-B31-C6; | A42-B31-C7; | A42-B31-C8; | A42-B31-C9; |
| A43-B31-C1; | A43-B31-C2; | A43-B31-C3; | A43-B31-C4; | A43-B31-C5; | A43-B31-C6; |
| A43-B31-C7; | A43-B31-C8; | A43-B31-C9; | A44-B31-C1; | A44-B31-C2; | A44-B31-C3; |
| A44-B31-C4; | A44-B31-C5; | A44-B31-C6; | A44-B31-C7; | A44-B31-C8; | A44-B31-C9; |
| A45-B31-C1; | A45-B31-C2; | A45-B31-C3; | A45-B31-C4; | A45-B31-C5; | A45-B31-C6; |
| A45-B31-C7; | A45-B31-C8; | A45-B31-C9; | A46-B31-C1; | A46-B31-C2; | A46-B31-C3; |
| A46-B31-C4; | A46-B31-C5; | A46-B31-C6; | A46-B31-C7; | A46-B31-C8; | A46-B31-C9; |
| A47-B31-C1; | A47-B31-C2; | A47-B31-C3; | A47-B31-C4; | A47-B31-C5; | A47-B31-C6; |
| A47-B31-C7; | A47-B31-C8; | A47-B31-C9; | A48-B31-C1; | A48-B31-C2; | A48-B31-C3; |

-continued

| | | | | | |
|---|---|---|---|---|---|
| A48-B31-C4; | A48-B31-C5; | A48-B31-C6; | A48-B31-C7; | A48-B31-C8; | A48-B31-C9; |
| A49-B31-C1; | A49-B31-C2; | A49-B31-C3; | A49-B31-C4; | A49-B31-C5; | A49-B31-C6; |
| A49-B31-C7; | A49-B31-C8; | A49-B31-C9; | A50-B31-C1; | A50-B31-C2; | A50-B31-C3; |
| A50-B31-C4; | A50-B31-C5; | A50-B31-C6; | A50-B31-C7; | A50-B31-C8; | A50-B31-C9; |
| A51-B31-C1; | A51-B31-C2; | A51-B31-C3; | A51-B31-C4; | A51-B31-C5; | A51-B31-C6; |
| A51-B31-C7; | A51-B31-C8; | A51-B31-C9; | A52-B31-C1; | A52-B31-C2; | A52-B31-C3; |
| A52-B31-C4; | A52-B31-C5; | A52-B31-C6; | A52-B31-C7; | A52-B31-C8; | A52-B31-C9; |
| A53-B31-C1; | A53-B31-C2; | A53-B31-C3; | A53-B31-C4; | A53-B31-C5; | A53-B31-C6; |
| A53-B31-C7; | A53-B31-C8; | A53-B31-C9; | A54-B31-C1; | A54-B31-C2; | A54-B31-C3; |
| A54-B31-C4; | A54-B31-C5; | A54-B31-C6; | A54-B31-C7; | A54-B31-C8; | A54-B31-C9; |
| A55-B31-C1; | A55-B31-C2; | A55-B31-C3; | A55-B31-C4; | A55-B31-C5; | A55-B31-C6; |
| A55-B31-C7; | A55-B31-C8; | A55-B31-C9; | A56-B31-C1; | A56-B31-C2; | A56-B31-C3; |
| A56-B31-C4; | A56-B31-C5; | A56-B31-C6; | A56-B31-C7; | A56-B31-C8; | A56-B31-C9; |
| A57-B31-C1; | A57-B31-C2; | A57-B31-C3; | A57-B31-C4; | A57-B31-C5; | A57-B31-C6; |
| A57-B31-C7; | A57-B31-C8; | A57-B31-C9; | A58-B31-C1; | A58-B31-C2; | A58-B31-C3; |
| A58-B31-C4; | A58-B31-C5; | A58-B31-C6; | A58-B31-C7; | A58-B31-C8; | A58-B31-C9; |
| A59-B31-C1; | A59-B31-C2; | A59-B31-C3; | A59-B31-C4; | A59-B31-C5; | A59-B31-C6; |
| A59-B31-C7; | A59-B31-C8; | A59-B31-C9; | A60-B31-C1; | A60-B31-C2; | A60-B31-C3; |
| A60-B31-C4; | A60-B31-C5; | A60-B31-C6; | A60-B31-C7; | A60-B31-C8; | A60-B31-C9; |
| A61-B31-C1; | A61-B31-C2; | A61-B31-C3; | A61-B31-C4; | A61-B31-C5; | A61-B31-C6; |
| A61-B31-C7; | A61-B31-C8; | A61-B31-C9; | A62-B31-C1; | A62-B31-C2; | A62-B31-C3; |
| A62-B31-C4; | A62-B31-C5; | A62-B31-C6; | A62-B31-C7; | A62-B31-C8; | A62-B31-C9; |
| A63-B31-C1; | A63-B31-C2; | A63-B31-C3; | A63-B31-C4; | A63-B31-C5; | A63-B31-C6; |
| A63-B31-C7; | A63-B31-C8; | A63-B31-C9; | A64-B31-C1; | A64-B31-C2; | A64-B31-C3; |
| A64-B31-C4; | A64-B31-C5; | A64-B31-C6; | A64-B31-C7; | A64-B31-C8; | A64-B31-C9; |
| A65-B31-C1; | A65-B31-C2; | A65-B31-C3; | A65-B31-C4; | A65-B31-C5; | A65-B31-C6; |
| A65-B31-C7; | A65-B31-C8; | A65-B31-C9; | A66-B31-C1; | A66-B31-C2; | A66-B31-C3; |
| A66-B31-C4; | A66-B31-C5; | A66-B31-C6; | A66-B31-C7; | A66-B31-C8; | A66-B31-C9; |
| A67-B31-C1; | A67-B31-C2; | A67-B31-C3; | A67-B31-C4; | A67-B31-C5; | A67-B31-C6; |
| A67-B31-C7; | A67-B31-C8; | A67-B31-C9; | A68-B31-C1; | A68-B31-C2; | A68-B31-C3; |
| A68-B31-C4; | A68-B31-C5; | A68-B31-C6; | A68-B31-C7; | A68-B31-C8; | A68-B31-C9; |
| A69-B31-C1; | A69-B31-C2; | A69-B31-C3; | A69-B31-C4; | A69-B31-C5; | A69-B31-C6; |
| A69-B31-C7; | A69-B31-C8; | A69-B31-C9; | A70-B31-C1; | A70-B31-C2; | A70-B31-C3; |
| A70-B31-C4; | A70-B31-C5; | A70-B31-C6; | A70-B31-C7; | A70-B31-C8; | A70-B31-C9; |
| A71-B31-C1; | A71-B31-C2; | A71-B31-C3; | A71-B31-C4; | A71-B31-C5; | A71-B31-C6; |
| A71-B31-C7; | A71-B31-C8; | A71-B31-C9; | A1-B32-C1; | A1-B32-C2; | A1-B32-C3; |
| A1-B32-C4; | A1-B32-C5; | A1-B32-C6; | A1-B32-C7; | A1-B32-C8; | A1-B32-C9; |
| A2-B32-C1; | A2-B32-C2; | A2-B32-C3; | A2-B32-C4; | A2-B32-C5; | A2-B32-C6; |
| A2-B32-C7; | A2-B32-C8; | A2-B32-C9; | A3-B32-C1; | A3-B32-C2; | A3-B32-C3; |
| A3-B32-C4; | A3-B32-C5; | A3-B32-C6; | A3-B32-C7; | A3-B32-C8; | A3-B32-C9; |
| A4-B32-C1; | A4-B32-C2; | A4-B32-C3; | A4-B32-C4; | A4-B32-C5; | A4-B32-C6; |
| A4-B32-C7; | A4-B32-C8; | A4-B32-C9; | A5-B32-C1; | A5-B32-C2; | A5-B32-C3; |
| A5-B32-C4; | A5-B32-C5; | A5-B32-C6; | A5-B32-C7; | A5-B32-C8; | A5-B32-C9; |
| A6-B32-C1; | A6-B32-C2; | A6-B32-C3; | A6-B32-C4; | A6-B32-C5; | A6-B32-C6; |
| A6-B32-C7; | A6-B32-C8; | A6-B32-C9; | A7-B32-C1; | A7-B32-C2; | A7-B32-C3; |
| A7-B32-C4; | A7-B32-C5; | A7-B32-C6; | A7-B32-C7; | A7-B32-C8; | A7-B32-C9; |
| A8-B32-C1; | A8-B32-C2; | A8-B32-C3; | A8-B32-C4; | A8-B32-C5; | A8-B32-C6; |
| A8-B32-C7; | A8-B32-C8; | A8-B32-C9; | A9-B32-C1; | A9-B32-C2; | A9-B32-C3; |
| A9-B32-C4; | A9-B32-C5; | A9-B32-C6; | A9-B32-C7; | A9-B32-C8; | A9-B32-C9; |
| A10-B32-C1; | A10-B32-C2; | A10-B32-C3; | A10-B32-C4; | A10-B32-C5; | A10-B32-C6; |
| A10-B32-C7; | A10-B32-C8; | A10-B32-C9; | A11-B32-C1; | A11-B32-C2; | A11-B32-C3; |
| A11-B32-C4; | A11-B32-C5; | A11-B32-C6; | A11-B32-C7; | A11-B32-C8; | A11-B32-C9; |
| A12-B32-C1; | A12-B32-C2; | A12-B32-C3; | A12-B32-C4; | A12-B32-C5; | A12-B32-C6; |
| A12-B32-C7; | A12-B32-C8; | A12-B32-C9; | A13-B32-C1; | A13-B32-C2; | A13-B32-C3; |
| A13-B32-C4; | A13-B32-C5; | A13-B32-C6; | A13-B32-C7; | A13-B32-C8; | A13-B32-C9; |
| A14-B32-C1; | A14-B32-C2; | A14-B32-C3; | A14-B32-C4; | A14-B32-C5; | A14-B32-C6; |
| A14-B32-C7; | A14-B32-C8; | A14-B32-C9; | A15-B32-C1; | A15-B32-C2; | A15-B32-C3; |
| A15-B32-C4; | A15-B32-C5; | A15-B32-C6; | A15-B32-C7; | A15-B32-C8; | A15-B32-C9; |
| A16-B32-C1; | A16-B32-C2; | A16-B32-C3; | A16-B32-C4; | A16-B32-C5; | A16-B32-C6; |
| A16-B32-C7; | A16-B32-C8; | A16-B32-C9; | A17-B32-C1; | A17-B32-C2; | A17-B32-C3; |
| A17-B32-C4; | A17-B32-C5; | A17-B32-C6; | A17-B32-C7; | A17-B32-C8; | A17-B32-C9; |
| A18-B32-C1; | A18-B32-C2; | A18-B32-C3; | A18-B32-C4; | A18-B32-C5; | A18-B32-C6; |
| A18-B32-C7; | A18-B32-C8; | A18-B32-C9; | A19-B32-C1; | A19-B32-C2; | A19-B32-C3; |
| A19-B32-C4; | A19-B32-C5; | A19-B32-C6; | A19-B32-C7; | A19-B32-C8; | A19-B32-C9; |
| A20-B32-C1; | A20-B32-C2; | A20-B32-C3; | A20-B32-C4; | A20-B32-C5; | A20-B32-C6; |
| A20-B32-C7; | A20-B32-C8; | A20-B32-C9; | A21-B32-C1; | A21-B32-C2; | A21-B32-C3; |
| A21-B32-C4; | A21-B32-C5; | A21-B32-C6; | A21-B32-C7; | A21-B32-C8; | A21-B32-C9; |
| A22-B32-C1; | A22-B32-C2; | A22-B32-C3; | A22-B32-C4; | A22-B32-C5; | A22-B32-C6; |
| A22-B32-C7; | A22-B32-C8; | A22-B32-C9; | A23-B32-C1; | A23-B32-C2; | A23-B32-C3; |
| A23-B32-C4; | A23-B32-C5; | A23-B32-C6; | A23-B32-C7; | A23-B32-C8; | A23-B32-C9; |
| A24-B32-C1; | A24-B32-C2; | A24-B32-C3; | A24-B32-C4; | A24-B32-C5; | A24-B32-C6; |
| A24-B32-C7; | A24-B32-C8; | A24-B32-C9; | A25-B32-C1; | A25-B32-C2; | A25-B32-C3; |
| A25-B32-C4; | A25-B32-C5; | A25-B32-C6; | A25-B32-C7; | A25-B32-C8; | A25-B32-C9; |
| A26-B32-C1; | A26-B32-C2; | A26-B32-C3; | A26-B32-C4; | A26-B32-C5; | A26-B32-C6; |
| A26-B32-C7; | A26-B32-C8; | A26-B32-C9; | A27-B32-C1; | A27-B32-C2; | A27-B32-C3; |
| A27-B32-C4; | A27-B32-C5; | A27-B32-C6; | A27-B32-C7; | A27-B32-C8; | A27-B32-C9; |
| A28-B32-C1; | A28-B32-C2; | A28-B32-C3; | A28-B32-C4; | A28-B32-C5; | A28-B32-C6; |
| A28-B32-C7; | A28-B32-C8; | A28-B32-C9; | A29-B32-C1; | A29-B32-C2; | A29-B32-C3; |
| A29-B32-C4; | A29-B32-C5; | A29-B32-C6; | A29-B32-C7; | A29-B32-C8; | A29-B32-C9; |

-continued

| | | | | | |
|---|---|---|---|---|---|
| A30-B32-C1; | A30-B32-C2; | A30-B32-C3; | A30-B32-C4; | A30-B32-C5; | A30-B32-C6; |
| A30-B32-C7; | A30-B32-C8; | A30-B32-C9; | A31-B32-C1; | A31-B32-C2; | A31-B32-C3; |
| A31-B32-C4; | A31-B32-C5; | A31-B32-C6; | A31-B32-C7; | A31-B32-C8; | A31-B32-C9; |
| A32-B32-C1; | A32-B32-C2; | A32-B32-C3; | A32-B32-C4; | A32-B32-C5; | A32-B32-C6; |
| A32-B32-C7; | A32-B32-C8; | A32-B32-C9; | A33-B32-C1; | A33-B32-C2; | A33-B32-C3; |
| A33-B32-C4; | A33-B32-C5; | A33-B32-C6; | A33-B32-C7; | A33-B32-C8; | A33-B32-C9; |
| A34-B32-C1; | A34-B32-C2; | A34-B32-C3; | A34-B32-C4; | A34-B32-C5; | A34-B32-C6; |
| A34-B32-C7; | A34-B32-C8; | A34-B32-C9; | A35-B32-C1; | A35-B32-C2; | A35-B32-C3; |
| A35-B32-C4; | A35-B32-C5; | A35-B32-C6; | A35-B32-C7; | A35-B32-C8; | A35-B32-C9; |
| A36-B32-C1; | A36-B32-C2; | A36-B32-C3; | A36-B32-C4; | A36-B32-C5; | A36-B32-C6; |
| A36-B32-C7; | A36-B32-C8; | A36-B32-C9; | A37-B32-C1; | A37-B32-C2; | A37-B32-C3; |
| A37-B32-C4; | A37-B32-C5; | A37-B32-C6; | A37-B32-C7; | A37-B32-C8; | A37-B32-C9; |
| A38-B32-C1; | A38-B32-C2; | A38-B32-C3; | A38-B32-C4; | A38-B32-C5; | A38-B32-C6; |
| A38-B32-C7; | A38-B32-C8; | A38-B32-C9; | A39-B32-C1; | A39-B32-C2; | A39-B32-C3; |
| A39-B32-C4; | A39-B32-C5; | A39-B32-C6; | A39-B32-C7; | A39-B32-C8; | A39-B32-C9; |
| A40-B32-C1; | A40-B32-C2; | A40-B32-C3; | A40-B32-C4; | A40-B32-C5; | A40-B32-C6; |
| A40-B32-C7; | A40-B32-C8; | A40-B32-C9; | A41-B32-C1; | A41-B32-C2; | A41-B32-C3; |
| A41-B32-C4; | A41-B32-C5; | A41-B32-C6; | A41-B32-C7; | A41-B32-C8; | A41-B32-C9; |
| A42-B32-C1; | A42-B32-C2; | A42-B32-C3; | A42-B32-C4; | A42-B32-C5; | A42-B32-C6; |
| A42-B32-C7; | A42-B32-C8; | A42-B32-C9; | A43-B32-C1; | A43-B32-C2; | A43-B32-C3; |
| A43-B32-C4; | A43-B32-C5; | A43-B32-C6; | A43-B32-C7; | A43-B32-C8; | A43-B32-C9; |
| A44-B32-C1; | A44-B32-C2; | A44-B32-C3; | A44-B32-C4; | A44-B32-C5; | A44-B32-C6; |
| A44-B32-C7; | A44-B32-C8; | A44-B32-C9; | A45-B32-C1; | A45-B32-C2; | A45-B32-C3; |
| A45-B32-C4; | A45-B32-C5; | A45-B32-C6; | A45-B32-C7; | A45-B32-C8; | A45-B32-C9; |
| A46-B32-C1; | A46-B32-C2; | A46-B32-C3; | A46-B32-C4; | A46-B32-C5; | A46-B32-C6; |
| A46-B32-C7; | A46-B32-C8; | A46-B32-C9; | A47-B32-C1; | A47-B32-C2; | A47-B32-C3; |
| A47-B32-C4; | A47-B32-C5; | A47-B32-C6; | A47-B32-C7; | A47-B32-C8; | A47-B32-C9; |
| A48-B32-C1; | A48-B32-C2; | A48-B32-C3; | A48-B32-C4; | A48-B32-C5; | A48-B32-C6; |
| A48-B32-C7; | A48-B32-C8; | A48-B32-C9; | A49-B32-C1; | A49-B32-C2; | A49-B32-C3; |
| A49-B32-C4; | A49-B32-C5; | A49-B32-C6; | A49-B32-C7; | A49-B32-C8; | A49-B32-C9; |
| A50-B32-C1; | A50-B32-C2; | A50-B32-C3; | A50-B32-C4; | A50-B32-C5; | A50-B32-C6; |
| A50-B32-C7; | A50-B32-C8; | A50-B32-C9; | A51-B32-C1; | A51-B32-C2; | A51-B32-C3; |
| A51-B32-C4; | A51-B32-C5; | A51-B32-C6; | A51-B32-C7; | A51-B32-C8; | A51-B32-C9; |
| A52-B32-C1; | A52-B32-C2; | A52-B32-C3; | A52-B32-C4; | A52-B32-C5; | A52-B32-C6; |
| A52-B32-C7; | A52-B32-C8; | A52-B32-C9; | A53-B32-C1; | A53-B32-C2; | A53-B32-C3; |
| A53-B32-C4; | A53-B32-C5; | A53-B32-C6; | A53-B32-C7; | A53-B32-C8; | A53-B32-C9; |
| A54-B32-C1; | A54-B32-C2; | A54-B32-C3; | A54-B32-C4; | A54-B32-C5; | A54-B32-C6; |
| A54-B32-C7; | A54-B32-C8; | A54-B32-C9; | A55-B32-C1; | A55-B32-C2; | A55-B32-C3; |
| A55-B32-C4; | A55-B32-C5; | A55-B32-C6; | A55-B32-C7; | A55-B32-C8; | A55-B32-C9; |
| A56-B32-C1; | A56-B32-C2; | A56-B32-C3; | A56-B32-C4; | A56-B32-C5; | A56-B32-C6; |
| A56-B32-C7; | A56-B32-C8; | A56-B32-C9; | A57-B32-C1; | A57-B32-C2; | A57-B32-C3; |
| A57-B32-C4; | A57-B32-C5; | A57-B32-C6; | A57-B32-C7; | A57-B32-C8; | A57-B32-C9; |
| A58-B32-C1; | A58-B32-C2; | A58-B32-C3; | A58-B32-C4; | A58-B32-C5; | A58-B32-C6; |
| A58-B32-C7; | A58-B32-C8; | A58-B32-C9; | A59-B32-C1; | A59-B32-C2; | A59-B32-C3; |
| A59-B32-C4; | A59-B32-C5; | A59-B32-C6; | A59-B32-C7; | A59-B32-C8; | A59-B32-C9; |
| A60-B32-C1; | A60-B32-C2; | A60-B32-C3; | A60-B32-C4; | A60-B32-C5; | A60-B32-C6; |
| A60-B32-C7; | A60-B32-C8; | A60-B32-C9; | A61-B32-C1; | A61-B32-C2; | A61-B32-C3; |
| A61-B32-C4; | A61-B32-C5; | A61-B32-C6; | A61-B32-C7; | A61-B32-C8; | A61-B32-C9; |
| A62-B32-C1; | A62-B32-C2; | A62-B32-C3; | A62-B32-C4; | A62-B32-C5; | A62-B32-C6; |
| A62-B32-C7; | A62-B32-C8; | A62-B32-C9; | A63-B32-C1; | A63-B32-C2; | A63-B32-C3; |
| A63-B32-C4; | A63-B32-C5; | A63-B32-C6; | A63-B32-C7; | A63-B32-C8; | A63-B32-C9; |
| A64-B32-C1; | A64-B32-C2; | A64-B32-C3; | A64-B32-C4; | A64-B32-C5; | A64-B32-C6; |
| A64-B32-C7; | A64-B32-C8; | A64-B32-C9; | A65-B32-C1; | A65-B32-C2; | A65-B32-C3; |
| A65-B32-C4; | A65-B32-C5; | A65-B32-C6; | A65-B32-C7; | A65-B32-C8; | A65-B32-C9; |
| A66-B32-C1; | A66-B32-C2; | A66-B32-C3; | A66-B32-C4; | A66-B32-C5; | A66-B32-C6; |
| A66-B32-C7; | A66-B32-C8; | A66-B32-C9; | A67-B32-C1; | A67-B32-C2; | A67-B32-C3; |
| A67-B32-C4; | A67-B32-C5; | A67-B32-C6; | A67-B32-C7; | A67-B32-C8; | A67-B32-C9; |
| A68-B32-C1; | A68-B32-C2; | A68-B32-C3; | A68-B32-C4; | A68-B32-C5; | A68-B32-C6; |
| A68-B32-C7; | A68-B32-C8; | A68-B32-C9; | A69-B32-C1; | A69-B32-C2; | A69-B32-C3; |
| A69-B32-C4; | A69-B32-C5; | A69-B32-C6; | A69-B32-C7; | A69-B32-C8; | A69-B32-C9; |
| A70-B32-C1; | A70-B32-C2; | A70-B32-C3; | A70-B32-C4; | A70-B32-C5; | A70-B32-C6; |
| A70-B32-C7; | A70-B32-C8; | A70-B32-C9; | A71-B32-C1; | A71-B32-C2; | A71-B32-C3; |
| A71-B32-C4; | A71-B32-C5; | A71-B32-C6; | A71-B32-C7; | A71-B32-C8; | A71-B32-C9; |
| A1-B33-C1; | A1-B33-C2; | A1-B33-C3; | A1-B33-C4; | A1-B33-C5; | A1-B33-C6; |
| A1-B33-C7; | A1-B33-C8; | A1-B33-C9; | A2-B33-C1; | A2-B33-C2; | A2-B33-C3; |
| A2-B33-C4; | A2-B33-C5; | A2-B33-C6; | A2-B33-C7; | A2-B33-C8; | A2-B33-C9; |
| A3-B33-C1; | A3-B33-C2; | A3-B33-C3; | A3-B33-C4; | A3-B33-C5; | A3-B33-C6; |
| A3-B33-C7; | A3-B33-C8; | A3-B33-C9; | A4-B33-C1; | A4-B33-C2; | A4-B33-C3; |
| A4-B33-C4; | A4-B33-C5; | A4-B33-C6; | A4-B33-C7; | A4-B33-C8; | A4-B33-C9; |
| A5-B33-C1; | A5-B33-C2; | A5-B33-C3; | A5-B33-C4; | A5-B33-C5; | A5-B33-C6; |
| A5-B33-C7; | A5-B33-C8; | A5-B33-C9; | A6-B33-C1; | A6-B33-C2; | A6-B33-C3; |
| A6-B33-C4; | A6-B33-C5; | A6-B33-C6; | A6-B33-C7; | A6-B33-C8; | A6-B33-C9; |
| A7-B33-C1; | A7-B33-C2; | A7-B33-C3; | A7-B33-C4; | A7-B33-C5; | A7-B33-C6; |
| A7-B33-C7; | A7-B33-C8; | A7-B33-C9; | A8-B33-C1; | A8-B33-C2; | A8-B33-C3; |
| A8-B33-C4; | A8-B33-C5; | A8-B33-C6; | A8-B33-C7; | A8-B33-C8; | A8-B33-C9; |
| A9-B33-C1; | A9-B33-C2; | A9-B33-C3; | A9-B33-C4; | A9-B33-C5; | A9-B33-C6; |
| A9-B33-C7; | A9-B33-C8; | A9-B33-C9; | A10-B33-C1; | A10-B33-C2; | A10-B33-C3; |
| A10-B33-C4; | A10-B33-C5; | A10-B33-C6; | A10-B33-C7; | A10-B33-C8; | A10-B33-C9; |
| A11-B33-C1; | A11-B33-C2; | A11-B33-C3; | A11-B33-C4; | A11-B33-C5; | A11-B33-C6; |

-continued

A11-B33-C7; A11-B33-C8; A11-B33-C9; A12-B33-C1; A12-B33-C2; A12-B33-C3;
A12-B33-C4; A12-B33-C5; A12-B33-C6; A12-B33-C7; A12-B33-C8; A12-B33-C9;
A13-B33-C1; A13-B33-C2; A13-B33-C3; A13-B33-C4; A13-B33-C5; A13-B33-C6;
A13-B33-C7; A13-B33-C8; A13-B33-C9; A14-B33-C1; A14-B33-C2; A14-B33-C3;
A14-B33-C4; A14-B33-C5; A14-B33-C6; A14-B33-C7; A14-B33-C8; A14-B33-C9;
A15-B33-C1; A15-B33-C2; A15-B33-C3; A15-B33-C4; A15-B33-C5; A15-B33-C6;
A15-B33-C7; A15-B33-C8; A15-B33-C9; A16-B33-C1; A16-B33-C2; A16-B33-C3;
A16-B33-C4; A16-B33-C5; A16-B33-C6; A16-B33-C7; A16-B33-C8; A16-B33-C9;
A17-B33-C1; A17-B33-C2; A17-B33-C3; A17-B33-C4; A17-B33-C5; A17-B33-C6;
A17-B33-C7; A17-B33-C8; A17-B33-C9; A18-B33-C1; A18-B33-C2; A18-B33-C3;
A18-B33-C4; A18-B33-C5; A18-B33-C6; A18-B33-C7; A18-B33-C8; A18-B33-C9;
A19-B33-C1; A19-B33-C2; A19-B33-C3; A19-B33-C4; A19-B33-C5; A19-B33-C6;
A19-B33-C7; A19-B33-C8; A19-B33-C9; A20-B33-C1; A20-B33-C2; A20-B33-C3;
A20-B33-C4; A20-B33-C5; A20-B33-C6; A20-B33-C7; A20-B33-C8; A20-B33-C9;
A21-B33-C1; A21-B33-C2; A21-B33-C3; A21-B33-C4; A21-B33-C5; A21-B33-C6;
A21-B33-C7; A21-B33-C8; A21-B33-C9; A22-B33-C1; A22-B33-C2; A22-B33-C3;
A22-B33-C4; A22-B33-C5; A22-B33-C6; A22-B33-C7; A22-B33-C8; A22-B33-C9;
A23-B33-C1; A23-B33-C2; A23-B33-C3; A23-B33-C4; A23-B33-C5; A23-B33-C6;
A23-B33-C7; A23-B33-C8; A23-B33-C9; A24-B33-C1; A24-B33-C2; A24-B33-C3;
A24-B33-C4; A24-B33-C5; A24-B33-C6; A24-B33-C7; A24-B33-C8; A24-B33-C9;
A25-B33-C1; A25-B33-C2; A25-B33-C3; A25-B33-C4; A25-B33-C5; A25-B33-C6;
A25-B33-C7; A25-B33-C8; A25-B33-C9; A26-B33-C1; A26-B33-C2; A26-B33-C3;
A26-B33-C4; A26-B33-C5; A26-B33-C6; A26-B33-C7; A26-B33-C8; A26-B33-C9;
A27-B33-C1; A27-B33-C2; A27-B33-C3; A27-B33-C4; A27-B33-C5; A27-B33-C6;
A27-B33-C7; A27-B33-C8; A27-B33-C9; A28-B33-C1; A28-B33-C2; A28-B33-C3;
A28-B33-C4; A28-B33-C5; A28-B33-C6; A28-B33-C7; A28-B33-C8; A28-B33-C9;
A29-B33-C1; A29-B33-C2; A29-B33-C3; A29-B33-C4; A29-B33-C5; A29-B33-C6;
A29-B33-C7; A29-B33-C8; A29-B33-C9; A30-B33-C1; A30-B33-C2; A30-B33-C3;
A30-B33-C4; A30-B33-C5; A30-B33-C6; A30-B33-C7; A30-B33-C8; A30-B33-C9;
A31-B33-C1; A31-B33-C2; A31-B33-C3; A31-B33-C4; A31-B33-C5; A31-B33-C6;
A31-B33-C7; A31-B33-C8; A31-B33-C9; A32-B33-C1; A32-B33-C2; A32-B33-C3;
A32-B33-C4; A32-B33-C5; A32-B33-C6; A32-B33-C7; A32-B33-C8; A32-B33-C9;
A33-B33-C1; A33-B33-C2; A33-B33-C3; A33-B33-C4; A33-B33-C5; A33-B33-C6;
A33-B33-C7; A33-B33-C8; A33-B33-C9; A34-B33-C1; A34-B33-C2; A34-B33-C3;
A34-B33-C4; A34-B33-C5; A34-B33-C6; A34-B33-C7; A34-B33-C8; A34-B33-C9;
A35-B33-C1; A35-B33-C2; A35-B33-C3; A35-B33-C4; A35-B33-C5; A35-B33-C6;
A35-B33-C7; A35-B33-C8; A35-B33-C9; A36-B33-C1; A36-B33-C2; A36-B33-C3;
A36-B33-C4; A36-B33-C5; A36-B33-C6; A36-B33-C7; A36-B33-C8; A36-B33-C9;
A37-B33-C1; A37-B33-C2; A37-B33-C3; A37-B33-C4; A37-B33-C5; A37-B33-C6;
A37-B33-C7; A37-B33-C8; A37-B33-C9; A38-B33-C1; A38-B33-C2; A38-B33-C3;
A38-B33-C4; A38-B33-C5; A38-B33-C6; A38-B33-C7; A38-B33-C8; A38-B33-C9;
A39-B33-C1; A39-B33-C2; A39-B33-C3; A39-B33-C4; A39-B33-C5; A39-B33-C6;
A39-B33-C7; A39-B33-C8; A39-B33-C9; A40-B33-C1; A40-B33-C2; A40-B33-C3;
A40-B33-C4; A40-B33-C5; A40-B33-C6; A40-B33-C7; A40-B33-C8; A40-B33-C9;
A41-B33-C1; A41-B33-C2; A41-B33-C3; A41-B33-C4; A41-B33-C5; A41-B33-C6;
A41-B33-C7; A41-B33-C8; A41-B33-C9; A42-B33-C1; A42-B33-C2; A42-B33-C3;
A42-B33-C4; A42-B33-C5; A42-B33-C6; A42-B33-C7; A42-B33-C8; A42-B33-C9;
A43-B33-C1; A43-B33-C2; A43-B33-C3; A43-B33-C4; A43-B33-C5; A43-B33-C6;
A43-B33-C7; A43-B33-C8; A43-B33-C9; A44-B33-C1; A44-B33-C2; A44-B33-C3;
A44-B33-C4; A44-B33-C5; A44-B33-C6; A44-B33-C7; A44-B33-C8; A44-B33-C9;
A45-B33-C1; A45-B33-C2; A45-B33-C3; A45-B33-C4; A45-B33-C5; A45-B33-C6;
A45-B33-C7; A45-B33-C8; A45-B33-C9; A46-B33-C1; A46-B33-C2; A46-B33-C3;
A46-B33-C4; A46-B33-C5; A46-B33-C6; A46-B33-C7; A46-B33-C8; A46-B33-C9;
A47-B33-C1; A47-B33-C2; A47-B33-C3; A47-B33-C4; A47-B33-C5; A47-B33-C6;
A47-B33-C7; A47-B33-C8; A47-B33-C9; A48-B33-C1; A48-B33-C2; A48-B33-C3;
A48-B33-C4; A48-B33-C5; A48-B33-C6; A48-B33-C7; A48-B33-C8; A48-B33-C9;
A49-B33-C1; A49-B33-C2; A49-B33-C3; A49-B33-C4; A49-B33-C5; A49-B33-C6;
A49-B33-C7; A49-B33-C8; A49-B33-C9; A50-B33-C1; A50-B33-C2; A50-B33-C3;
A50-B33-C4; A50-B33-C5; A50-B33-C6; A50-B33-C7; A50-B33-C8; A50-B33-C9;
A51-B33-C1; A51-B33-C2; A51-B33-C3; A51-B33-C4; A51-B33-C5; A51-B33-C6;
A51-B33-C7; A51-B33-C8; A51-B33-C9; A52-B33-C1; A52-B33-C2; A52-B33-C3;
A52-B33-C4; A52-B33-C5; A52-B33-C6; A52-B33-C7; A52-B33-C8; A52-B33-C9;
A53-B33-C1; A53-B33-C2; A53-B33-C3; A53-B33-C4; A53-B33-C5; A53-B33-C6;
A53-B33-C7; A53-B33-C8; A53-B33-C9; A54-B33-C1; A54-B33-C2; A54-B33-C3;
A54-B33-C4; A54-B33-C5; A54-B33-C6; A54-B33-C7; A54-B33-C8; A54-B33-C9;
A55-B33-C1; A55-B33-C2; A55-B33-C3; A55-B33-C4; A55-B33-C5; A55-B33-C6;
A55-B33-C7; A55-B33-C8; A55-B33-C9; A56-B33-C1; A56-B33-C2; A56-B33-C3;
A56-B33-C4; A56-B33-C5; A56-B33-C6; A56-B33-C7; A56-B33-C8; A56-B33-C9;
A57-B33-C1; A57-B33-C2; A57-B33-C3; A57-B33-C4; A57-B33-C5; A57-B33-C6;
A57-B33-C7; A57-B33-C8; A57-B33-C9; A58-B33-C1; A58-B33-C2; A58-B33-C3;
A58-B33-C4; A58-B33-C5; A58-B33-C6; A58-B33-C7; A58-B33-C8; A58-B33-C9;
A59-B33-C1; A59-B33-C2; A59-B33-C3; A59-B33-C4; A59-B33-C5; A59-B33-C6;
A59-B33-C7; A59-B33-C8; A59-B33-C9; A60-B33-C1; A60-B33-C2; A60-B33-C3;
A60-B33-C4; A60-B33-C5; A60-B33-C6; A60-B33-C7; A60-B33-C8; A60-B33-C9;
A61-B33-C1; A61-B33-C2; A61-B33-C3; A61-B33-C4; A61-B33-C5; A61-B33-C6;
A61-B33-C7; A61-B33-C8; A61-B33-C9; A62-B33-C1; A62-B33-C2; A62-B33-C3;
A62-B33-C4; A62-B33-C5; A62-B33-C6; A62-B33-C7; A62-B33-C8; A62-B33-C9;
A63-B33-C1; A63-B33-C2; A63-B33-C3; A63-B33-C4; A63-B33-C5; A63-B33-C6;
A63-B33-C7; A63-B33-C8; A63-B33-C9; A64-B33-C1; A64-B33-C2; A64-B33-C3;

-continued

| | | | | | |
|---|---|---|---|---|---|
| A64-B33-C4; | A64-B33-C5; | A64-B33-C6; | A64-B33-C7; | A64-B33-C8; | A64-B33-C9; |
| A65-B33-C1; | A65-B33-C2; | A65-B33-C3; | A65-B33-C4; | A65-B33-C5; | A65-B33-C6; |
| A65-B33-C7; | A65-B33-C8; | A65-B33-C9; | A66-B33-C1; | A66-B33-C2; | A66-B33-C3; |
| A66-B33-C4; | A66-B33-C5; | A66-B33-C6; | A66-B33-C7; | A66-B33-C8; | A66-B33-C9; |
| A67-B33-C1; | A67-B33-C2; | A67-B33-C3; | A67-B33-C4; | A67-B33-C5; | A67-B33-C6; |
| A67-B33-C7; | A67-B33-C8; | A67-B33-C9; | A68-B33-C1; | A68-B33-C2; | A68-B33-C3; |
| A68-B33-C4; | A68-B33-C5; | A68-B33-C6; | A68-B33-C7; | A68-B33-C8; | A68-B33-C9; |
| A69-B33-C1; | A69-B33-C2; | A69-B33-C3; | A69-B33-C4; | A69-B33-C5; | A69-B33-C6; |
| A69-B33-C7; | A69-B33-C8; | A69-B33-C9; | A70-B33-C1; | A70-B33-C2; | A70-B33-C3; |
| A70-B33-C4; | A70-B33-C5; | A70-B33-C6; | A70-B33-C7; | A70-B33-C8; | A70-B33-C9; |
| A71-B33-C1; | A71-B33-C2; | A71-B33-C3; | A71-B33-C4; | A71-B33-C5; | A71-B33-C6; |
| A71-B33-C7; | A71-B33-C8; | A71-B33-C9; | A1-B34-C1; | A1-B34-C2; | A1-B34-C3; |
| A1-B34-C4; | A1-B34-C5; | A1-B34-C6; | A1-B34-C7; | A1-B34-C8; | A1-B34-C9; |
| A2-B34-C1; | A2-B34-C2; | A2-B34-C3; | A2-B34-C4; | A2-B34-C5; | A2-B34-C6; |
| A2-B34-C7; | A2-B34-C8; | A2-B34-C9; | A3-B34-C1; | A3-B34-C2; | A3-B34-C3; |
| A3-B34-C4; | A3-B34-C5; | A3-B34-C6; | A3-B34-C7; | A3-B34-C8; | A3-B34-C9; |
| A4-B34-C1; | A4-B34-C2; | A4-B34-C3; | A4-B34-C4; | A4-B34-C5; | A4-B34-C6; |
| A4-B34-C7; | A4-B34-C8; | A4-B34-C9; | A5-B34-C1; | A5-B34-C2; | A5-B34-C3; |
| A5-B34-C4; | A5-B34-C5; | A5-B34-C6; | A5-B34-C7; | A5-B34-C8; | A5-B34-C9; |
| A6-B34-C1; | A6-B34-C2; | A6-B34-C3; | A6-B34-C4; | A6-B34-C5; | A6-B34-C6; |
| A6-B34-C7; | A6-B34-C8; | A6-B34-C9; | A7-B34-C1; | A7-B34-C2; | A7-B34-C3; |
| A7-B34-C4; | A7-B34-C5; | A7-B34-C6; | A7-B34-C7; | A7-B34-C8; | A7-B34-C9; |
| A8-B34-C1; | A8-B34-C2; | A8-B34-C3; | A8-B34-C4; | A8-B34-C5; | A8-B34-C6; |
| A8-B34-C7; | A8-B34-C8; | A8-B34-C9; | A9-B34-C1; | A9-B34-C2; | A9-B34-C3; |
| A9-B34-C4; | A9-B34-C5; | A9-B34-C6; | A9-B34-C7; | A9-B34-C8; | A9-B34-C9; |
| A10-B34-C1; | A10-B34-C2; | A10-B34-C3; | A10-B34-C4; | A10-B34-C5; | A10-B34-C6; |
| A10-B34-C7; | A10-B34-C8; | A10-B34-C9; | A11-B34-C1; | A11-B34-C2; | A11-B34-C3; |
| A11-B34-C4; | A11-B34-C5; | A11-B34-C6; | A11-B34-C7; | A11-B34-C8; | A11-B34-C9; |
| A12-B34-C1; | A12-B34-C2; | A12-B34-C3; | A12-B34-C4; | A12-B34-C5; | A12-B34-C6; |
| A12-B34-C7; | A12-B34-C8; | A12-B34-C9; | A13-B34-C1; | A13-B34-C2; | A13-B34-C3; |
| A13-B34-C4; | A13-B34-C5; | A13-B34-C6; | A13-B34-C7; | A13-B34-C8; | A13-B34-C9; |
| A14-B34-C1; | A14-B34-C2; | A14-B34-C3; | A14-B34-C4; | A14-B34-C5; | A14-B34-C6; |
| A14-B34-C7; | A14-B34-C8; | A14-B34-C9; | A15-B34-C1; | A15-B34-C2; | A15-B34-C3; |
| A15-B34-C4; | A15-B34-C5; | A15-B34-C6; | A15-B34-C7; | A15-B34-C8; | A15-B34-C9; |
| A16-B34-C1; | A16-B34-C2; | A16-B34-C3; | A16-B34-C4; | A16-B34-C5; | A16-B34-C6; |
| A16-B34-C7; | A16-B34-C8; | A16-B34-C9; | A17-B34-C1; | A17-B34-C2; | A17-B34-C3; |
| A17-B34-C4; | A17-B34-C5; | A17-B34-C6; | A17-B34-C7; | A17-B34-C8; | A17-B34-C9; |
| A18-B34-C1; | A18-B34-C2; | A18-B34-C3; | A18-B34-C4; | A18-B34-C5; | A18-B34-C6; |
| A18-B34-C7; | A18-B34-C8; | A18-B34-C9; | A19-B34-C1; | A19-B34-C2; | A19-B34-C3; |
| A19-B34-C4; | A19-B34-C5; | A19-B34-C6; | A19-B34-C7; | A19-B34-C8; | A19-B34-C9; |
| A20-B34-C1; | A20-B34-C2; | A20-B34-C3; | A20-B34-C4; | A20-B34-C5; | A20-B34-C6; |
| A20-B34-C7; | A20-B34-C8; | A20-B34-C9; | A21-B34-C1; | A21-B34-C2; | A21-B34-C3; |
| A21-B34-C4; | A21-B34-C5; | A21-B34-C6; | A21-B34-C7; | A21-B34-C8; | A21-B34-C9; |
| A22-B34-C1; | A22-B34-C2; | A22-B34-C3; | A22-B34-C4; | A22-B34-C5; | A22-B34-C6; |
| A22-B34-C7; | A22-B34-C8; | A22-B34-C9; | A23-B34-C1; | A23-B34-C2; | A23-B34-C3; |
| A23-B34-C4; | A23-B34-C5; | A23-B34-C6; | A23-B34-C7; | A23-B34-C8; | A23-B34-C9; |
| A24-B34-C1; | A24-B34-C2; | A24-B34-C3; | A24-B34-C4; | A24-B34-C5; | A24-B34-C6; |
| A24-B34-C7; | A24-B34-C8; | A24-B34-C9; | A25-B34-C1; | A25-B34-C2; | A25-B34-C3; |
| A25-B34-C4; | A25-B34-C5; | A25-B34-C6; | A25-B34-C7; | A25-B34-C8; | A25-B34-C9; |
| A26-B34-C1; | A26-B34-C2; | A26-B34-C3; | A26-B34-C4; | A26-B34-C5; | A26-B34-C6; |
| A26-B34-C7; | A26-B34-C8; | A26-B34-C9; | A27-B34-C1; | A27-B34-C2; | A27-B34-C3; |
| A27-B34-C4; | A27-B34-C5; | A27-B34-C6; | A27-B34-C7; | A27-B34-C8; | A27-B34-C9; |
| A28-B34-C1; | A28-B34-C2; | A28-B34-C3; | A28-B34-C4; | A28-B34-C5; | A28-B34-C6; |
| A28-B34-C7; | A28-B34-C8; | A28-B34-C9; | A29-B34-C1; | A29-B34-C2; | A29-B34-C3; |
| A29-B34-C4; | A29-B34-C5; | A29-B34-C6; | A29-B34-C7; | A29-B34-C8; | A29-B34-C9; |
| A30-B34-C1; | A30-B34-C2; | A30-B34-C3; | A30-B34-C4; | A30-B34-C5; | A30-B34-C6; |
| A30-B34-C7; | A30-B34-C8; | A30-B34-C9; | A31-B34-C1; | A31-B34-C2; | A31-B34-C3; |
| A31-B34-C4; | A31-B34-C5; | A31-B34-C6; | A31-B34-C7; | A31-B34-C8; | A31-B34-C9; |
| A32-B34-C1; | A32-B34-C2; | A32-B34-C3; | A32-B34-C4; | A32-B34-C5; | A32-B34-C6; |
| A32-B34-C7; | A32-B34-C8; | A32-B34-C9; | A33-B34-C1; | A33-B34-C2; | A33-B34-C3; |
| A33-B34-C4; | A33-B34-C5; | A33-B34-C6; | A33-B34-C7; | A33-B34-C8; | A33-B34-C9; |
| A34-B34-C1; | A34-B34-C2; | A34-B34-C3; | A34-B34-C4; | A34-B34-C5; | A34-B34-C6; |
| A34-B34-C7; | A34-B34-C8; | A34-B34-C9; | A35-B34-C1; | A35-B34-C2; | A35-B34-C3; |
| A35-B34-C4; | A35-B34-C5; | A35-B34-C6; | A35-B34-C7; | A35-B34-C8; | A35-B34-C9; |
| A36-B34-C1; | A36-B34-C2; | A36-B34-C3; | A36-B34-C4; | A36-B34-C5; | A36-B34-C6; |
| A36-B34-C7; | A36-B34-C8; | A36-B34-C9; | A37-B34-C1; | A37-B34-C2; | A37-B34-C3; |
| A37-B34-C4; | A37-B34-C5; | A37-B34-C6; | A37-B34-C7; | A37-B34-C8; | A37-B34-C9; |
| A38-B34-C1; | A38-B34-C2; | A38-B34-C3; | A38-B34-C4; | A38-B34-C5; | A38-B34-C6; |
| A38-B34-C7; | A38-B34-C8; | A38-B34-C9; | A39-B34-C1; | A39-B34-C2; | A39-B34-C3; |
| A39-B34-C4; | A39-B34-C5; | A39-B34-C6; | A39-B34-C7; | A39-B34-C8; | A39-B34-C9; |
| A40-B34-C1; | A40-B34-C2; | A40-B34-C3; | A40-B34-C4; | A40-B34-C5; | A40-B34-C6; |
| A40-B34-C7; | A40-B34-C8; | A40-B34-C9; | A41-B34-C1; | A41-B34-C2; | A41-B34-C3; |
| A41-B34-C4; | A41-B34-C5; | A41-B34-C6; | A41-B34-C7; | A41-B34-C8; | A41-B34-C9; |
| A42-B34-C1; | A42-B34-C2; | A42-B34-C3; | A42-B34-C4; | A42-B34-C5; | A42-B34-C6; |
| A42-B34-C7; | A42-B34-C8; | A42-B34-C9; | A43-B34-C1; | A43-B34-C2; | A43-B34-C3; |
| A43-B34-C4; | A43-B34-C5; | A43-B34-C6; | A43-B34-C7; | A43-B34-C8; | A43-B34-C9; |
| A44-B34-C1; | A44-B34-C2; | A44-B34-C3; | A44-B34-C4; | A44-B34-C5; | A44-B34-C6; |
| A44-B34-C7; | A44-B34-C8; | A44-B34-C9; | A45-B34-C1; | A45-B34-C2; | A45-B34-C3; |
| A45-B34-C4; | A45-B34-C5; | A45-B34-C6; | A45-B34-C7; | A45-B34-C8; | A45-B34-C9; |

-continued

| | | | | | |
|---|---|---|---|---|---|
| A46-B34-C1; | A46-B34-C2; | A46-B34-C3; | A46-B34-C4; | A46-B34-C5; | A46-B34-C6; |
| A46-B34-C7; | A46-B34-C8; | A46-B34-C9; | A47-B34-C1; | A47-B34-C2; | A47-B34-C3; |
| A47-B34-C4; | A47-B34-C5; | A47-B34-C6; | A47-B34-C7; | A47-B34-C8; | A47-B34-C9; |
| A48-B34-C1; | A48-B34-C2; | A48-B34-C3; | A48-B34-C4; | A48-B34-C5; | A48-B34-C6; |
| A48-B34-C7; | A48-B34-C8; | A48-B34-C9; | A49-B34-C1; | A49-B34-C2; | A49-B34-C3; |
| A49-B34-C4; | A49-B34-C5; | A49-B34-C6; | A49-B34-C7; | A49-B34-C8; | A49-B34-C9; |
| A50-B34-C1; | A50-B34-C2; | A50-B34-C3; | A50-B34-C4; | A50-B34-C5; | A50-B34-C6; |
| A50-B34-C7; | A50-B34-C8; | A50-B34-C9; | A51-B34-C1; | A51-B34-C2; | A51-B34-C3; |
| A51-B34-C4; | A51-B34-C5; | A51-B34-C6; | A51-B34-C7; | A51-B34-C8; | A51-B34-C9; |
| A52-B34-C1; | A52-B34-C2; | A52-B34-C3; | A52-B34-C4; | A52-B34-C5; | A52-B34-C6; |
| A52-B34-C7; | A52-B34-C8; | A52-B34-C9; | A53-B34-C1; | A53-B34-C2; | A53-B34-C3; |
| A53-B34-C4; | A53-B34-C5; | A53-B34-C6; | A53-B34-C7; | A53-B34-C8; | A53-B34-C9; |
| A54-B34-C1; | A54-B34-C2; | A54-B34-C3; | A54-B34-C4; | A54-B34-C5; | A54-B34-C6; |
| A54-B34-C7; | A54-B34-C8; | A54-B34-C9; | A55-B34-C1; | A55-B34-C2; | A55-B34-C3; |
| A55-B34-C4; | A55-B34-C5; | A55-B34-C6; | A55-B34-C7; | A55-B34-C8; | A55-B34-C9; |
| A56-B34-C1; | A56-B34-C2; | A56-B34-C3; | A56-B34-C4; | A56-B34-C5; | A56-B34-C6; |
| A56-B34-C7; | A56-B34-C8; | A56-B34-C9; | A57-B34-C1; | A57-B34-C2; | A57-B34-C3; |
| A57-B34-C4; | A57-B34-C5; | A57-B34-C6; | A57-B34-C7; | A57-B34-C8; | A57-B34-C9; |
| A58-B34-C1; | A58-B34-C2; | A58-B34-C3; | A58-B34-C4; | A58-B34-C5; | A58-B34-C6; |
| A58-B34-C7; | A58-B34-C8; | A58-B34-C9; | A59-B34-C1; | A59-B34-C2; | A59-B34-C3; |
| A59-B34-C4; | A59-B34-C5; | A59-B34-C6; | A59-B34-C7; | A59-B34-C8; | A59-B34-C9; |
| A60-B34-C1; | A60-B34-C2; | A60-B34-C3; | A60-B34-C4; | A60-B34-C5; | A60-B34-C6; |
| A60-B34-C7; | A60-B34-C8; | A60-B34-C9; | A61-B34-C1; | A61-B34-C2; | A61-B34-C3; |
| A61-B34-C4; | A61-B34-C5; | A61-B34-C6; | A61-B34-C7; | A61-B34-C8; | A61-B34-C9; |
| A62-B34-C1; | A62-B34-C2; | A62-B34-C3; | A62-B34-C4; | A62-B34-C5; | A62-B34-C6; |
| A62-B34-C7; | A62-B34-C8; | A62-B34-C9; | A63-B34-C1; | A63-B34-C2; | A63-B34-C3; |
| A63-B34-C4; | A63-B34-C5; | A63-B34-C6; | A63-B34-C7; | A63-B34-C8; | A63-B34-C9; |
| A64-B34-C1; | A64-B34-C2; | A64-B34-C3; | A64-B34-C4; | A64-B34-C5; | A64-B34-C6; |
| A64-B34-C7; | A64-B34-C8; | A64-B34-C9; | A65-B34-C1; | A65-B34-C2; | A65-B34-C3; |
| A65-B34-C4; | A65-B34-C5; | A65-B34-C6; | A65-B34-C7; | A65-B34-C8; | A65-B34-C9; |
| A66-B34-C1; | A66-B34-C2; | A66-B34-C3; | A66-B34-C4; | A66-B34-C5; | A66-B34-C6; |
| A66-B34-C7; | A66-B34-C8; | A66-B34-C9; | A67-B34-C1; | A67-B34-C2; | A67-B34-C3; |
| A67-B34-C4; | A67-B34-C5; | A67-B34-C6; | A67-B34-C7; | A67-B34-C8; | A67-B34-C9; |
| A68-B34-C1; | A68-B34-C2; | A68-B34-C3; | A68-B34-C4; | A68-B34-C5; | A68-B34-C6; |
| A68-B34-C7; | A68-B34-C8; | A68-B34-C9; | A69-B34-C1; | A69-B34-C2; | A69-B34-C3; |
| A69-B34-C4; | A69-B34-C5; | A69-B34-C6; | A69-B34-C7; | A69-B34-C8; | A69-B34-C9; |
| A70-B34-C1; | A70-B34-C2; | A70-B34-C3; | A70-B34-C4; | A70-B34-C5; | A70-B34-C6; |
| A70-B34-C7; | A70-B34-C8; | A70-B34-C9; | A71-B34-C1; | A71-B34-C2; | A71-B34-C3; |
| A71-B34-C4; | A71-B34-C5; | A71-B34-C6; | A71-B34-C7; | A71-B34-C8; | A71-B34-C9; |
| A1-B35-C1; | A1-B35-C2; | A1-B35-C3; | A1-B35-C4; | A1-B35-C5; | A1-B35-C6; |
| A1-B35-C7; | A1-B35-C8; | A1-B35-C9; | A2-B35-C1; | A2-B35-C2; | A2-B35-C3; |
| A2-B35-C4; | A2-B35-C5; | A2-B35-C6; | A2-B35-C7; | A2-B35-C8; | A2-B35-C9; |
| A3-B35-C1; | A3-B35-C2; | A3-B35-C3; | A3-B35-C4; | A3-B35-C5; | A3-B35-C6; |
| A3-B35-C7; | A3-B35-C8; | A3-B35-C9; | A4-B35-C1; | A4-B35-C2; | A4-B35-C3; |
| A4-B35-C4; | A4-B35-C5; | A4-B35-C6; | A4-B35-C7; | A4-B35-C8; | A4-B35-C9; |
| A5-B35-C1; | A5-B35-C2; | A5-B35-C3; | A5-B35-C4; | A5-B35-C5; | A5-B35-C6; |
| A5-B35-C7; | A5-B35-C8; | A5-B35-C9; | A6-B35-C1; | A6-B35-C2; | A6-B35-C3; |
| A6-B35-C4; | A6-B35-C5; | A6-B35-C6; | A6-B35-C7; | A6-B35-C8; | A6-B35-C9; |
| A7-B35-C1; | A7-B35-C2; | A7-B35-C3; | A7-B35-C4; | A7-B35-C5; | A7-B35-C6; |
| A7-B35-C7; | A7-B35-C8; | A7-B35-C9; | A8-B35-C1; | A8-B35-C2; | A8-B35-C3; |
| A8-B35-C4; | A8-B35-C5; | A8-B35-C6; | A8-B35-C7; | A8-B35-C8; | A8-B35-C9; |
| A9-B35-C1; | A9-B35-C2; | A9-B35-C3; | A9-B35-C4; | A9-B35-C5; | A9-B35-C6; |
| A9-B35-C7; | A9-B35-C8; | A9-B35-C9; | A10-B35-C1; | A10-B35-C2; | A10-B35-C3; |
| A10-B35-C4; | A10-B35-C5; | A10-B35-C6; | A10-B35-C7; | A10-B35-C8; | A10-B35-C9; |
| A11-B35-C1; | A11-B35-C2; | A11-B35-C3; | A11-B35-C4; | A11-B35-C5; | A11-B35-C6; |
| A11-B35-C7; | A11-B35-C8; | A11-B35-C9; | A12-B35-C1; | A12-B35-C2; | A12-B35-C3; |
| A12-B35-C4; | A12-B35-C5; | A12-B35-C6; | A12-B35-C7; | A12-B35-C8; | A12-B35-C9; |
| A13-B35-C1; | A13-B35-C2; | A13-B35-C3; | A13-B35-C4; | A13-B35-C5; | A13-B35-C6; |
| A13-B35-C7; | A13-B35-C8; | A13-B35-C9; | A14-B35-C1; | A14-B35-C2; | A14-B35-C3; |
| A14-B35-C4; | A14-B35-C5; | A14-B35-C6; | A14-B35-C7; | A14-B35-C8; | A14-B35-C9; |
| A15-B35-C1; | A15-B35-C2; | A15-B35-C3; | A15-B35-C4; | A15-B35-C5; | A15-B35-C6; |
| A15-B35-C7; | A15-B35-C8; | A15-B35-C9; | A16-B35-C1; | A16-B35-C2; | A16-B35-C3; |
| A16-B35-C4; | A16-B35-C5; | A16-B35-C6; | A16-B35-C7; | A16-B35-C8; | A16-B35-C9; |
| A17-B35-C1; | A17-B35-C2; | A17-B35-C3; | A17-B35-C4; | A17-B35-C5; | A17-B35-C6; |
| A17-B35-C7; | A17-B35-C8; | A17-B35-C9; | A18-B35-C1; | A18-B35-C2; | A18-B35-C3; |
| A18-B35-C4; | A18-B35-C5; | A18-B35-C6; | A18-B35-C7; | A18-B35-C8; | A18-B35-C9; |
| A19-B35-C1; | A19-B35-C2; | A19-B35-C3; | A19-B35-C4; | A19-B35-C5; | A19-B35-C6; |
| A19-B35-C7; | A19-B35-C8; | A19-B35-C9; | A20-B35-C1; | A20-B35-C2; | A20-B35-C3; |
| A20-B35-C4; | A20-B35-C5; | A20-B35-C6; | A20-B35-C7; | A20-B35-C8; | A20-B35-C9; |
| A21-B35-C1; | A21-B35-C2; | A21-B35-C3; | A21-B35-C4; | A21-B35-C5; | A21-B35-C6; |
| A21-B35-C7; | A21-B35-C8; | A21-B35-C9; | A22-B35-C1; | A22-B35-C2; | A22-B35-C3; |
| A22-B35-C4; | A22-B35-C5; | A22-B35-C6; | A22-B35-C7; | A22-B35-C8; | A22-B35-C9; |
| A23-B35-C1; | A23-B35-C2; | A23-B35-C3; | A23-B35-C4; | A23-B35-C5; | A23-B35-C6; |
| A23-B35-C7; | A23-B35-C8; | A23-B35-C9; | A24-B35-C1; | A24-B35-C2; | A24-B35-C3; |
| A24-B35-C4; | A24-B35-C5; | A24-B35-C6; | A24-B35-C7; | A24-B35-C8; | A24-B35-C9; |
| A25-B35-C1; | A25-B35-C2; | A25-B35-C3; | A25-B35-C4; | A25-B35-C5; | A25-B35-C6; |
| A25-B35-C7; | A25-B35-C8; | A25-B35-C9; | A26-B35-C1; | A26-B35-C2; | A26-B35-C3; |
| A26-B35-C4; | A26-B35-C5; | A26-B35-C6; | A26-B35-C7; | A26-B35-C8; | A26-B35-C9; |
| A27-B35-C1; | A27-B35-C2; | A27-B35-C3; | A27-B35-C4; | A27-B35-C5; | A27-B35-C6; |

-continued

| | | | | | |
|---|---|---|---|---|---|
| A27-B35-C7; | A27-B35-C8; | A27-B35-C9; | A28-B35-C1; | A28-B35-C2; | A28-B35-C3; |
| A28-B35-C4; | A28-B35-C5; | A28-B35-C6; | A28-B35-C7; | A28-B35-C8; | A28-B35-C9; |
| A29-B35-C1; | A29-B35-C2; | A29-B35-C3; | A29-B35-C4; | A29-B35-C5; | A29-B35-C6; |
| A29-B35-C7; | A29-B35-C8; | A29-B35-C9; | A30-B35-C1; | A30-B35-C2; | A30-B35-C3; |
| A30-B35-C4; | A30-B35-C5; | A30-B35-C6; | A30-B35-C7; | A30-B35-C8; | A30-B35-C9; |
| A31-B35-C1; | A31-B35-C2; | A31-B35-C3; | A31-B35-C4; | A31-B35-C5; | A31-B35-C6; |
| A31-B35-C7; | A31-B35-C8; | A31-B35-C9; | A32-B35-C1; | A32-B35-C2; | A32-B35-C3; |
| A32-B35-C4; | A32-B35-C5; | A32-B35-C6; | A32-B35-C7; | A32-B35-C8; | A32-B35-C9; |
| A33-B35-C1; | A33-B35-C2; | A33-B35-C3; | A33-B35-C4; | A33-B35-C5; | A33-B35-C6; |
| A33-B35-C7; | A33-B35-C8; | A33-B35-C9; | A34-B35-C1; | A34-B35-C2; | A34-B35-C3; |
| A34-B35-C4; | A34-B35-C5; | A34-B35-C6; | A34-B35-C7; | A34-B35-C8; | A34-B35-C9; |
| A35-B35-C1; | A35-B35-C2; | A35-B35-C3; | A35-B35-C4; | A35-B35-C5; | A35-B35-C6; |
| A35-B35-C7; | A35-B35-C8; | A35-B35-C9; | A36-B35-C1; | A36-B35-C2; | A36-B35-C3; |
| A36-B35-C4; | A36-B35-C5; | A36-B35-C6; | A36-B35-C7; | A36-B35-C8; | A36-B35-C9; |
| A37-B35-C1; | A37-B35-C2; | A37-B35-C3; | A37-B35-C4; | A37-B35-C5; | A37-B35-C6; |
| A37-B35-C7; | A37-B35-C8; | A37-B35-C9; | A38-B35-C1; | A38-B35-C2; | A38-B35-C3; |
| A38-B35-C4; | A38-B35-C5; | A38-B35-C6; | A38-B35-C7; | A38-B35-C8; | A38-B35-C9; |
| A39-B35-C1; | A39-B35-C2; | A39-B35-C3; | A39-B35-C4; | A39-B35-C5; | A39-B35-C6; |
| A39-B35-C7; | A39-B35-C8; | A39-B35-C9; | A40-B35-C1; | A40-B35-C2; | A40-B35-C3; |
| A40-B35-C4; | A40-B35-C5; | A40-B35-C6; | A40-B35-C7; | A40-B35-C8; | A40-B35-C9; |
| A41-B35-C1; | A41-B35-C2; | A41-B35-C3; | A41-B35-C4; | A41-B35-C5; | A41-B35-C6; |
| A41-B35-C7; | A41-B35-C8; | A41-B35-C9; | A42-B35-C1; | A42-B35-C2; | A42-B35-C3; |
| A42-B35-C4; | A42-B35-C5; | A42-B35-C6; | A42-B35-C7; | A42-B35-C8; | A42-B35-C9; |
| A43-B35-C1; | A43-B35-C2; | A43-B35-C3; | A43-B35-C4; | A43-B35-C5; | A43-B35-C6; |
| A43-B35-C7; | A43-B35-C8; | A43-B35-C9; | A44-B35-C1; | A44-B35-C2; | A44-B35-C3; |
| A44-B35-C4; | A44-B35-C5; | A44-B35-C6; | A44-B35-C7; | A44-B35-C8; | A44-B35-C9; |
| A45-B35-C1; | A45-B35-C2; | A45-B35-C3; | A45-B35-C4; | A45-B35-C5; | A45-B35-C6; |
| A45-B35-C7; | A45-B35-C8; | A45-B35-C9; | A46-B35-C1; | A46-B35-C2; | A46-B35-C3; |
| A46-B35-C4; | A46-B35-C5; | A46-B35-C6; | A46-B35-C7; | A46-B35-C8; | A46-B35-C9; |
| A47-B35-C1; | A47-B35-C2; | A47-B35-C3; | A47-B35-C4; | A47-B35-C5; | A47-B35-C6; |
| A47-B35-C7; | A47-B35-C8; | A47-B35-C9; | A48-B35-C1; | A48-B35-C2; | A48-B35-C3; |
| A48-B35-C4; | A48-B35-C5; | A48-B35-C6; | A48-B35-C7; | A48-B35-C8; | A48-B35-C9; |
| A49-B35-C1; | A49-B35-C2; | A49-B35-C3; | A49-B35-C4; | A49-B35-C5; | A49-B35-C6; |
| A49-B35-C7; | A49-B35-C8; | A49-B35-C9; | A50-B35-C1; | A50-B35-C2; | A50-B35-C3; |
| A50-B35-C4; | A50-B35-C5; | A50-B35-C6; | A50-B35-C7; | A50-B35-C8; | A50-B35-C9; |
| A51-B35-C1; | A51-B35-C2; | A51-B35-C3; | A51-B35-C4; | A51-B35-C5; | A51-B35-C6; |
| A51-B35-C7; | A51-B35-C8; | A51-B35-C9; | A52-B35-C1; | A52-B35-C2; | A52-B35-C3; |
| A52-B35-C4; | A52-B35-C5; | A52-B35-C6; | A52-B35-C7; | A52-B35-C8; | A52-B35-C9; |
| A53-B35-C1; | A53-B35-C2; | A53-B35-C3; | A53-B35-C4; | A53-B35-C5; | A53-B35-C6; |
| A53-B35-C7; | A53-B35-C8; | A53-B35-C9; | A54-B35-C1; | A54-B35-C2; | A54-B35-C3; |
| A54-B35-C4; | A54-B35-C5; | A54-B35-C6; | A54-B35-C7; | A54-B35-C8; | A54-B35-C9; |
| A55-B35-C1; | A55-B35-C2; | A55-B35-C3; | A55-B35-C4; | A55-B35-C5; | A55-B35-C6; |
| A55-B35-C7; | A55-B35-C8; | A55-B35-C9; | A56-B35-C1; | A56-B35-C2; | A56-B35-C3; |
| A56-B35-C4; | A56-B35-C5; | A56-B35-C6; | A56-B35-C7; | A56-B35-C8; | A56-B35-C9; |
| A57-B35-C1; | A57-B35-C2; | A57-B35-C3; | A57-B35-C4; | A57-B35-C5; | A57-B35-C6; |
| A57-B35-C7; | A57-B35-C8; | A57-B35-C9; | A58-B35-C1; | A58-B35-C2; | A58-B35-C3; |
| A58-B35-C4; | A58-B35-C5; | A58-B35-C6; | A58-B35-C7; | A58-B35-C8; | A58-B35-C9; |
| A59-B35-C1; | A59-B35-C2; | A59-B35-C3; | A59-B35-C4; | A59-B35-C5; | A59-B35-C6; |
| A59-B35-C7; | A59-B35-C8; | A59-B35-C9; | A60-B35-C1; | A60-B35-C2; | A60-B35-C3; |
| A60-B35-C4; | A60-B35-C5; | A60-B35-C6; | A60-B35-C7; | A60-B35-C8; | A60-B35-C9; |
| A61-B35-C1; | A61-B35-C2; | A61-B35-C3; | A61-B35-C4; | A61-B35-C5; | A61-B35-C6; |
| A61-B35-C7; | A61-B35-C8; | A61-B35-C9; | A62-B35-C1; | A62-B35-C2; | A62-B35-C3; |
| A62-B35-C4; | A62-B35-C5; | A62-B35-C6; | A62-B35-C7; | A62-B35-C8; | A62-B35-C9; |
| A63-B35-C1; | A63-B35-C2; | A63-B35-C3; | A63-B35-C4; | A63-B35-C5; | A63-B35-C6; |
| A63-B35-C7; | A63-B35-C8; | A63-B35-C9; | A64-B35-C1; | A64-B35-C2; | A64-B35-C3; |
| A64-B35-C4; | A64-B35-C5; | A64-B35-C6; | A64-B35-C7; | A64-B35-C8; | A64-B35-C9; |
| A65-B35-C1; | A65-B35-C2; | A65-B35-C3; | A65-B35-C4; | A65-B35-C5; | A65-B35-C6; |
| A65-B35-C7; | A65-B35-C8; | A65-B35-C9; | A66-B35-C1; | A66-B35-C2; | A66-B35-C3; |
| A66-B35-C4; | A66-B35-C5; | A66-B35-C6; | A66-B35-C7; | A66-B35-C8; | A66-B35-C9; |
| A67-B35-C1; | A67-B35-C2; | A67-B35-C3; | A67-B35-C4; | A67-B35-C5; | A67-B35-C6; |
| A67-B35-C7; | A67-B35-C8; | A67-B35-C9; | A68-B35-C1; | A68-B35-C2; | A68-B35-C3; |
| A68-B35-C4; | A68-B35-C5; | A68-B35-C6; | A68-B35-C7; | A68-B35-C8; | A68-B35-C9; |
| A69-B35-C1; | A69-B35-C2; | A69-B35-C3; | A69-B35-C4; | A69-B35-C5; | A69-B35-C6; |
| A69-B35-C7; | A69-B35-C8; | A69-B35-C9; | A70-B35-C1; | A70-B35-C2; | A70-B35-C3; |
| A70-B35-C4; | A70-B35-C5; | A70-B35-C6; | A70-B35-C7; | A70-B35-C8; | A70-B35-C9; |
| A71-B35-C1; | A71-B35-C2; | A71-B35-C3; | A71-B35-C4; | A71-B35-C5; | A71-B35-C6; |
| A71-B35-C7; | A71-B35-C8; | A71-B35-C9; | A1-B36-C1; | A1-B36-C2; | A1-B36-C3; |
| A1-B36-C4; | A1-B36-C5; | A1-B36-C6; | A1-B36-C7; | A1-B36-C8; | A1-B36-C9; |
| A2-B36-C1; | A2-B36-C2; | A2-B36-C3; | A2-B36-C4; | A2-B36-C5; | A2-B36-C6; |
| A2-B36-C7; | A2-B36-C8; | A2-B36-C9; | A3-B36-C1; | A3-B36-C2; | A3-B36-C3; |
| A3-B36-C4; | A3-B36-C5; | A3-B36-C6; | A3-B36-C7; | A3-B36-C8; | A3-B36-C9; |
| A4-B36-C1; | A4-B36-C2; | A4-B36-C3; | A4-B36-C4; | A4-B36-C5; | A4-B36-C6; |
| A4-B36-C7; | A4-B36-C8; | A4-B36-C9; | A5-B36-C1; | A5-B36-C2; | A5-B36-C3; |
| A5-B36-C4; | A5-B36-C5; | A5-B36-C6; | A5-B36-C7; | A5-B36-C8; | A5-B36-C9; |
| A6-B36-C1; | A6-B36-C2; | A6-B36-C3; | A6-B36-C4; | A6-B36-C5; | A6-B36-C6; |
| A6-B36-C7; | A6-B36-C8; | A6-B36-C9; | A7-B36-C1; | A7-B36-C2; | A7-B36-C3; |
| A7-B36-C4; | A7-B36-C5; | A7-B36-C6; | A7-B36-C7; | A7-B36-C8; | A7-B36-C9; |
| A8-B36-C1; | A8-B36-C2; | A8-B36-C3; | A8-B36-C4; | A8-B36-C5; | A8-B36-C6; |
| A8-B36-C7; | A8-B36-C8; | A8-B36-C9; | A9-B36-C1; | A9-B36-C2; | A9-B36-C3; |

-continued

| | | | | | |
|---|---|---|---|---|---|
| A9-B36-C4; | A9-B36-C5; | A9-B36-C6; | A9-B36-C7; | A9-B36-C8; | A9-B36-C9; |
| A10-B36-C1; | A10-B36-C2; | A10-B36-C3; | A10-B36-C4; | A10-B36-C5; | A10-B36-C6; |
| A10-B36-C7; | A10-B36-C8; | A10-B36-C9; | A11-B36-C1; | A11-B36-C2; | A11-B36-C3; |
| A11-B36-C4; | A11-B36-C5; | A11-B36-C6; | A11-B36-C7; | A11-B36-C8; | A11-B36-C9; |
| A12-B36-C1; | A12-B36-C2; | A12-B36-C3; | A12-B36-C4; | A12-B36-C5; | A12-B36-C6; |
| A12-B36-C7; | A12-B36-C8; | A12-B36-C9; | A13-B36-C1; | A13-B36-C2; | A13-B36-C3; |
| A13-B36-C4; | A13-B36-C5; | A13-B36-C6; | A13-B36-C7; | A13-B36-C8; | A13-B36-C9; |
| A14-B36-C1; | A14-B36-C2; | A14-B36-C3; | A14-B36-C4; | A14-B36-C5; | A14-B36-C6; |
| A14-B36-C7; | A14-B36-C8; | A14-B36-C9; | A15-B36-C1; | A15-B36-C2; | A15-B36-C3; |
| A15-B36-C4; | A15-B36-C5; | A15-B36-C6; | A15-B36-C7; | A15-B36-C8; | A15-B36-C9; |
| A16-B36-C1; | A16-B36-C2; | A16-B36-C3; | A16-B36-C4; | A16-B36-C5; | A16-B36-C6; |
| A16-B36-C7; | A16-B36-C8; | A16-B36-C9; | A17-B36-C1; | A17-B36-C2; | A17-B36-C3; |
| A17-B36-C4; | A17-B36-C5; | A17-B36-C6; | A17-B36-C7; | A17-B36-C8; | A17-B36-C9; |
| A18-B36-C1; | A18-B36-C2; | A18-B36-C3; | A18-B36-C4; | A18-B36-C5; | A18-B36-C6; |
| A18-B36-C7; | A18-B36-C8; | A18-B36-C9; | A19-B36-C1; | A19-B36-C2; | A19-B36-C3; |
| A19-B36-C4; | A19-B36-C5; | A19-B36-C6; | A19-B36-C7; | A19-B36-C8; | A19-B36-C9; |
| A20-B36-C1; | A20-B36-C2; | A20-B36-C3; | A20-B36-C4; | A20-B36-C5; | A20-B36-C6; |
| A20-B36-C7; | A20-B36-C8; | A20-B36-C9; | A21-B36-C1; | A21-B36-C2; | A21-B36-C3; |
| A21-B36-C4; | A21-B36-C5; | A21-B36-C6; | A21-B36-C7; | A21-B36-C8; | A21-B36-C9; |
| A22-B36-C1; | A22-B36-C2; | A22-B36-C3; | A22-B36-C4; | A22-B36-C5; | A22-B36-C6; |
| A22-B36-C7; | A22-B36-C8; | A22-B36-C9; | A23-B36-C1; | A23-B36-C2; | A23-B36-C3; |
| A23-B36-C4; | A23-B36-C5; | A23-B36-C6; | A23-B36-C7; | A23-B36-C8; | A23-B36-C9; |
| A24-B36-C1; | A24-B36-C2; | A24-B36-C3; | A24-B36-C4; | A24-B36-C5; | A24-B36-C6; |
| A24-B36-C7; | A24-B36-C8; | A24-B36-C9; | A25-B36-C1; | A25-B36-C2; | A25-B36-C3; |
| A25-B36-C4; | A25-B36-C5; | A25-B36-C6; | A25-B36-C7; | A25-B36-C8; | A25-B36-C9; |
| A26-B36-C1; | A26-B36-C2; | A26-B36-C3; | A26-B36-C4; | A26-B36-C5; | A26-B36-C6; |
| A26-B36-C7; | A26-B36-C8; | A26-B36-C9; | A27-B36-C1; | A27-B36-C2; | A27-B36-C3; |
| A27-B36-C4; | A27-B36-C5; | A27-B36-C6; | A27-B36-C7; | A27-B36-C8; | A27-B36-C9; |
| A28-B36-C1; | A28-B36-C2; | A28-B36-C3; | A28-B36-C4; | A28-B36-C5; | A28-B36-C6; |
| A28-B36-C7; | A28-B36-C8; | A28-B36-C9; | A29-B36-C1; | A29-B36-C2; | A29-B36-C3; |
| A29-B36-C4; | A29-B36-C5; | A29-B36-C6; | A29-B36-C7; | A29-B36-C8; | A29-B36-C9; |
| A30-B36-C1; | A30-B36-C2; | A30-B36-C3; | A30-B36-C4; | A30-B36-C5; | A30-B36-C6; |
| A30-B36-C7; | A30-B36-C8; | A30-B36-C9; | A31-B36-C1; | A31-B36-C2; | A31-B36-C3; |
| A31-B36-C4; | A31-B36-C5; | A31-B36-C6; | A31-B36-C7; | A31-B36-C8; | A31-B36-C9; |
| A32-B36-C1; | A32-B36-C2; | A32-B36-C3; | A32-B36-C4; | A32-B36-C5; | A32-B36-C6; |
| A32-B36-C7; | A32-B36-C8; | A32-B36-C9; | A33-B36-C1; | A33-B36-C2; | A33-B36-C3; |
| A33-B36-C4; | A33-B36-C5; | A33-B36-C6; | A33-B36-C7; | A33-B36-C8; | A33-B36-C9; |
| A34-B36-C1; | A34-B36-C2; | A34-B36-C3; | A34-B36-C4; | A34-B36-C5; | A34-B36-C6; |
| A34-B36-C7; | A34-B36-C8; | A34-B36-C9; | A35-B36-C1; | A35-B36-C2; | A35-B36-C3; |
| A35-B36-C4; | A35-B36-C5; | A35-B36-C6; | A35-B36-C7; | A35-B36-C8; | A35-B36-C9; |
| A36-B36-C1; | A36-B36-C2; | A36-B36-C3; | A36-B36-C4; | A36-B36-C5; | A36-B36-C6; |
| A36-B36-C7; | A36-B36-C8; | A36-B36-C9; | A37-B36-C1; | A37-B36-C2; | A37-B36-C3; |
| A37-B36-C4; | A37-B36-C5; | A37-B36-C6; | A37-B36-C7; | A37-B36-C8; | A37-B36-C9; |
| A38-B36-C1; | A38-B36-C2; | A38-B36-C3; | A38-B36-C4; | A38-B36-C5; | A38-B36-C6; |
| A38-B36-C7; | A38-B36-C8; | A38-B36-C9; | A39-B36-C1; | A39-B36-C2; | A39-B36-C3; |
| A39-B36-C4; | A39-B36-C5; | A39-B36-C6; | A39-B36-C7; | A39-B36-C8; | A39-B36-C9; |
| A40-B36-C1; | A40-B36-C2; | A40-B36-C3; | A40-B36-C4; | A40-B36-C5; | A40-B36-C6; |
| A40-B36-C7; | A40-B36-C8; | A40-B36-C9; | A41-B36-C1; | A41-B36-C2; | A41-B36-C3; |
| A41-B36-C4; | A41-B36-C5; | A41-B36-C6; | A41-B36-C7; | A41-B36-C8; | A41-B36-C9; |
| A42-B36-C1; | A42-B36-C2; | A42-B36-C3; | A42-B36-C4; | A42-B36-C5; | A42-B36-C6; |
| A42-B36-C7; | A42-B36-C8; | A42-B36-C9; | A43-B36-C1; | A43-B36-C2; | A43-B36-C3; |
| A43-B36-C4; | A43-B36-C5; | A43-B36-C6; | A43-B36-C7; | A43-B36-C8; | A43-B36-C9; |
| A44-B36-C1; | A44-B36-C2; | A44-B36-C3; | A44-B36-C4; | A44-B36-C5; | A44-B36-C6; |
| A44-B36-C7; | A44-B36-C8; | A44-B36-C9; | A45-B36-C1; | A45-B36-C2; | A45-B36-C3; |
| A45-B36-C4; | A45-B36-C5; | A45-B36-C6; | A45-B36-C7; | A45-B36-C8; | A45-B36-C9; |
| A46-B36-C1; | A46-B36-C2; | A46-B36-C3; | A46-B36-C4; | A46-B36-C5; | A46-B36-C6; |
| A46-B36-C7; | A46-B36-C8; | A46-B36-C9; | A47-B36-C1; | A47-B36-C2; | A47-B36-C3; |
| A47-B36-C4; | A47-B36-C5; | A47-B36-C6; | A47-B36-C7; | A47-B36-C8; | A47-B36-C9; |
| A48-B36-C1; | A48-B36-C2; | A48-B36-C3; | A48-B36-C4; | A48-B36-C5; | A48-B36-C6; |
| A48-B36-C7; | A48-B36-C8; | A48-B36-C9; | A49-B36-C1; | A49-B36-C2; | A49-B36-C3; |
| A49-B36-C4; | A49-B36-C5; | A49-B36-C6; | A49-B36-C7; | A49-B36-C8; | A49-B36-C9; |
| A50-B36-C1; | A50-B36-C2; | A50-B36-C3; | A50-B36-C4; | A50-B36-C5; | A50-B36-C6; |
| A50-B36-C7; | A50-B36-C8; | A50-B36-C9; | A51-B36-C1; | A51-B36-C2; | A51-B36-C3; |
| A51-B36-C4; | A51-B36-C5; | A51-B36-C6; | A51-B36-C7; | A51-B36-C8; | A51-B36-C9; |
| A52-B36-C1; | A52-B36-C2; | A52-B36-C3; | A52-B36-C4; | A52-B36-C5; | A52-B36-C6; |
| A52-B36-C7; | A52-B36-C8; | A52-B36-C9; | A53-B36-C1; | A53-B36-C2; | A53-B36-C3; |
| A53-B36-C4; | A53-B36-C5; | A53-B36-C6; | A53-B36-C7; | A53-B36-C8; | A53-B36-C9; |
| A54-B36-C1; | A54-B36-C2; | A54-B36-C3; | A54-B36-C4; | A54-B36-C5; | A54-B36-C6; |
| A54-B36-C7; | A54-B36-C8; | A54-B36-C9; | A55-B36-C1; | A55-B36-C2; | A55-B36-C3; |
| A55-B36-C4; | A55-B36-C5; | A55-B36-C6; | A55-B36-C7; | A55-B36-C8; | A55-B36-C9; |
| A56-B36-C1; | A56-B36-C2; | A56-B36-C3; | A56-B36-C4; | A56-B36-C5; | A56-B36-C6; |
| A56-B36-C7; | A56-B36-C8; | A56-B36-C9; | A57-B36-C1; | A57-B36-C2; | A57-B36-C3; |
| A57-B36-C4; | A57-B36-C5; | A57-B36-C6; | A57-B36-C7; | A57-B36-C8; | A57-B36-C9; |
| A58-B36-C1; | A58-B36-C2; | A58-B36-C3; | A58-B36-C4; | A58-B36-C5; | A58-B36-C6; |
| A58-B36-C7; | A58-B36-C8; | A58-B36-C9; | A59-B36-C1; | A59-B36-C2; | A59-B36-C3; |
| A59-B36-C4; | A59-B36-C5; | A59-B36-C6; | A59-B36-C7; | A59-B36-C8; | A59-B36-C9; |
| A60-B36-C1; | A60-B36-C2; | A60-B36-C3; | A60-B36-C4; | A60-B36-C5; | A60-B36-C6; |
| A60-B36-C7; | A60-B36-C8; | A60-B36-C9; | A61-B36-C1; | A61-B36-C2; | A61-B36-C3; |
| A61-B36-C4; | A61-B36-C5; | A61-B36-C6; | A61-B36-C7; | A61-B36-C8; | A61-B36-C9; |

-continued

| | | | | | |
|---|---|---|---|---|---|
| A62-B36-C1; | A62-B36-C2; | A62-B36-C3; | A62-B36-C4; | A62-B36-C5; | A62-B36-C6; |
| A62-B36-C7; | A62-B36-C8; | A62-B36-C9; | A63-B36-C1; | A63-B36-C2; | A63-B36-C3; |
| A63-B36-C4; | A63-B36-C5; | A63-B36-C6; | A63-B36-C7; | A63-B36-C8; | A63-B36-C9; |
| A64-B36-C1; | A64-B36-C2; | A64-B36-C3; | A64-B36-C4; | A64-B36-C5; | A64-B36-C6; |
| A64-B36-C7; | A64-B36-C8; | A64-B36-C9; | A65-B36-C1; | A65-B36-C2; | A65-B36-C3; |
| A65-B36-C4; | A65-B36-C5; | A65-B36-C6; | A65-B36-C7; | A65-B36-C8; | A65-B36-C9; |
| A66-B36-C1; | A66-B36-C2; | A66-B36-C3; | A66-B36-C4; | A66-B36-C5; | A66-B36-C6; |
| A66-B36-C7; | A66-B36-C8; | A66-B36-C9; | A67-B36-C1; | A67-B36-C2; | A67-B36-C3; |
| A67-B36-C4; | A67-B36-C5; | A67-B36-C6; | A67-B36-C7; | A67-B36-C8; | A67-B36-C9; |
| A68-B36-C1; | A68-B36-C2; | A68-B36-C3; | A68-B36-C4; | A68-B36-C5; | A68-B36-C6; |
| A68-B36-C7; | A68-B36-C8; | A68-B36-C9; | A69-B36-C1; | A69-B36-C2; | A69-B36-C3; |
| A69-B36-C4; | A69-B36-C5; | A69-B36-C6; | A69-B36-C7; | A69-B36-C8; | A69-B36-C9; |
| A70-B36-C1; | A70-B36-C2; | A70-B36-C3; | A70-B36-C4; | A70-B36-C5; | A70-B36-C6; |
| A70-B36-C7; | A70-B36-C8; | A70-B36-C9; | A71-B36-C1; | A71-B36-C2; | A71-B36-C3; |
| A71-B36-C4; | A71-B36-C5; | A71-B36-C6; | A71-B36-C7; | A71-B36-C8; | A71-B36-C9; |
| A1-B37-C1; | A1-B37-C2; | A1-B37-C3; | A1-B37-C4; | A1-B37-C5; | A1-B37-C6; |
| A1-B37-C7; | A1-B37-C8; | A1-B37-C9; | A2-B37-C1; | A2-B37-C2; | A2-B37-C3; |
| A2-B37-C4; | A2-B37-C5; | A2-B37-C6; | A2-B37-C7; | A2-B37-C8; | A2-B37-C9; |
| A3-B37-C1; | A3-B37-C2; | A3-B37-C3; | A3-B37-C4; | A3-B37-C5; | A3-B37-C6; |
| A3-B37-C7; | A3-B37-C8; | A3-B37-C9; | A4-B37-C1; | A4-B37-C2; | A4-B37-C3; |
| A4-B37-C4; | A4-B37-C5; | A4-B37-C6; | A4-B37-C7; | A4-B37-C8; | A4-B37-C9; |
| A5-B37-C1; | A5-B37-C2; | A5-B37-C3; | A5-B37-C4; | A5-B37-C5; | A5-B37-C6; |
| A5-B37-C7; | A5-B37-C8; | A5-B37-C9; | A6-B37-C1; | A6-B37-C2; | A6-B37-C3; |
| A6-B37-C4; | A6-B37-C5; | A6-B37-C6; | A6-B37-C7; | A6-B37-C8; | A6-B37-C9; |
| A7-B37-C1; | A7-B37-C2; | A7-B37-C3; | A7-B37-C4; | A7-B37-C5; | A7-B37-C6; |
| A7-B37-C7; | A7-B37-C8; | A7-B37-C9; | A8-B37-C1; | A8-B37-C2; | A8-B37-C3; |
| A8-B37-C4; | A8-B37-C5; | A8-B37-C6; | A8-B37-C7; | A8-B37-C8; | A8-B37-C9; |
| A9-B37-C1; | A9-B37-C2; | A9-B37-C3; | A9-B37-C4; | A9-B37-C5; | A9-B37-C6; |
| A9-B37-C7; | A9-B37-C8; | A9-B37-C9; | A10-B37-C1; | A10-B37-C2; | A10-B37-C3; |
| A10-B37-C4; | A10-B37-C5; | A10-B37-C6; | A10-B37-C7; | A10-B37-C8; | A10-B37-C9; |
| A11-B37-C1; | A11-B37-C2; | A11-B37-C3; | A11-B37-C4; | A11-B37-C5; | A11-B37-C6; |
| A11-B37-C7; | A11-B37-C8; | A11-B37-C9; | A12-B37-C1; | A12-B37-C2; | A12-B37-C3; |
| A12-B37-C4; | A12-B37-C5; | A12-B37-C6; | A12-B37-C7; | A12-B37-C8; | A12-B37-C9; |
| A13-B37-C1; | A13-B37-C2; | A13-B37-C3; | A13-B37-C4; | A13-B37-C5; | A13-B37-C6; |
| A13-B37-C7; | A13-B37-C8; | A13-B37-C9; | A14-B37-C1; | A14-B37-C2; | A14-B37-C3; |
| A14-B37-C4; | A14-B37-C5; | A14-B37-C6; | A14-B37-C7; | A14-B37-C8; | A14-B37-C9; |
| A15-B37-C1; | A15-B37-C2; | A15-B37-C3; | A15-B37-C4; | A15-B37-C5; | A15-B37-C6; |
| A15-B37-C7; | A15-B37-C8; | A15-B37-C9; | A16-B37-C1; | A16-B37-C2; | A16-B37-C3; |
| A16-B37-C4; | A16-B37-C5; | A16-B37-C6; | A16-B37-C7; | A16-B37-C8; | A16-B37-C9; |
| A17-B37-C1; | A17-B37-C2; | A17-B37-C3; | A17-B37-C4; | A17-B37-C5; | A17-B37-C6; |
| A17-B37-C7; | A17-B37-C8; | A17-B37-C9; | A18-B37-C1; | A18-B37-C2; | A18-B37-C3; |
| A18-B37-C4; | A18-B37-C5; | A18-B37-C6; | A18-B37-C7; | A18-B37-C8; | A18-B37-C9; |
| A19-B37-C1; | A19-B37-C2; | A19-B37-C3; | A19-B37-C4; | A19-B37-C5; | A19-B37-C6; |
| A19-B37-C7; | A19-B37-C8; | A19-B37-C9; | A20-B37-C1; | A20-B37-C2; | A20-B37-C3; |
| A20-B37-C4; | A20-B37-C5; | A20-B37-C6; | A20-B37-C7; | A20-B37-C8; | A20-B37-C9; |
| A21-B37-C1; | A21-B37-C2; | A21-B37-C3; | A21-B37-C4; | A21-B37-C5; | A21-B37-C6; |
| A21-B37-C7; | A21-B37-C8; | A21-B37-C9; | A22-B37-C1; | A22-B37-C2; | A22-B37-C3; |
| A22-B37-C4; | A22-B37-C5; | A22-B37-C6; | A22-B37-C7; | A22-B37-C8; | A22-B37-C9; |
| A23-B37-C1; | A23-B37-C2; | A23-B37-C3; | A23-B37-C4; | A23-B37-C5; | A23-B37-C6; |
| A23-B37-C7; | A23-B37-C8; | A23-B37-C9; | A24-B37-C1; | A24-B37-C2; | A24-B37-C3; |
| A24-B37-C4; | A24-B37-C5; | A24-B37-C6; | A24-B37-C7; | A24-B37-C8; | A24-B37-C9; |
| A25-B37-C1; | A25-B37-C2; | A25-B37-C3; | A25-B37-C4; | A25-B37-C5; | A25-B37-C6; |
| A25-B37-C7; | A25-B37-C8; | A25-B37-C9; | A26-B37-C1; | A26-B37-C2; | A26-B37-C3; |
| A26-B37-C4; | A26-B37-C5; | A26-B37-C6; | A26-B37-C7; | A26-B37-C8; | A26-B37-C9; |
| A27-B37-C1; | A27-B37-C2; | A27-B37-C3; | A27-B37-C4; | A27-B37-C5; | A27-B37-C6; |
| A27-B37-C7; | A27-B37-C8; | A27-B37-C9; | A28-B37-C1; | A28-B37-C2; | A28-B37-C3; |
| A28-B37-C4; | A28-B37-C5; | A28-B37-C6; | A28-B37-C7; | A28-B37-C8; | A28-B37-C9; |
| A29-B37-C1; | A29-B37-C2; | A29-B37-C3; | A29-B37-C4; | A29-B37-C5; | A29-B37-C6; |
| A29-B37-C7; | A29-B37-C8; | A29-B37-C9; | A30-B37-C1; | A30-B37-C2; | A30-B37-C3; |
| A30-B37-C4; | A30-B37-C5; | A30-B37-C6; | A30-B37-C7; | A30-B37-C8; | A30-B37-C9; |
| A31-B37-C1; | A31-B37-C2; | A31-B37-C3; | A31-B37-C4; | A31-B37-C5; | A31-B37-C6; |
| A31-B37-C7; | A31-B37-C8; | A31-B37-C9; | A32-B37-C1; | A32-B37-C2; | A32-B37-C3; |
| A32-B37-C4; | A32-B37-C5; | A32-B37-C6; | A32-B37-C7; | A32-B37-C8; | A32-B37-C9; |
| A33-B37-C1; | A33-B37-C2; | A33-B37-C3; | A33-B37-C4; | A33-B37-C5; | A33-B37-C6; |
| A33-B37-C7; | A33-B37-C8; | A33-B37-C9; | A34-B37-C1; | A34-B37-C2; | A34-B37-C3; |
| A34-B37-C4; | A34-B37-C5; | A34-B37-C6; | A34-B37-C7; | A34-B37-C8; | A34-B37-C9; |
| A35-B37-C1; | A35-B37-C2; | A35-B37-C3; | A35-B37-C4; | A35-B37-C5; | A35-B37-C6; |
| A35-B37-C7; | A35-B37-C8; | A35-B37-C9; | A36-B37-C1; | A36-B37-C2; | A36-B37-C3; |
| A36-B37-C4; | A36-B37-C5; | A36-B37-C6; | A36-B37-C7; | A36-B37-C8; | A36-B37-C9; |
| A37-B37-C1; | A37-B37-C2; | A37-B37-C3; | A37-B37-C4; | A37-B37-C5; | A37-B37-C6; |
| A37-B37-C7; | A37-B37-C8; | A37-B37-C9; | A38-B37-C1; | A38-B37-C2; | A38-B37-C3; |
| A38-B37-C4; | A38-B37-C5; | A38-B37-C6; | A38-B37-C7; | A38-B37-C8; | A38-B37-C9; |
| A39-B37-C1; | A39-B37-C2; | A39-B37-C3; | A39-B37-C4; | A39-B37-C5; | A39-B37-C6; |
| A39-B37-C7; | A39-B37-C8; | A39-B37-C9; | A40-B37-C1; | A40-B37-C2; | A40-B37-C3; |
| A40-B37-C4; | A40-B37-C5; | A40-B37-C6; | A40-B37-C7; | A40-B37-C8; | A40-B37-C9; |
| A41-B37-C1; | A41-B37-C2; | A41-B37-C3; | A41-B37-C4; | A41-B37-C5; | A41-B37-C6; |
| A41-B37-C7; | A41-B37-C8; | A41-B37-C9; | A42-B37-C1; | A42-B37-C2; | A42-B37-C3; |
| A42-B37-C4; | A42-B37-C5; | A42-B37-C6; | A42-B37-C7; | A42-B37-C8; | A42-B37-C9; |
| A43-B37-C1; | A43-B37-C2; | A43-B37-C3; | A43-B37-C4; | A43-B37-C5; | A43-B37-C6; |

-continued

A43-B37-C7; A43-B37-C8; A43-B37-C9; A44-B37-C1; A44-B37-C2; A44-B37-C3;
A44-B37-C4; A44-B37-C5; A44-B37-C6; A44-B37-C7; A44-B37-C8; A44-B37-C9;
A45-B37-C1; A45-B37-C2; A45-B37-C3; A45-B37-C4; A45-B37-C5; A45-B37-C6;
A45-B37-C7; A45-B37-C8; A45-B37-C9; A46-B37-C1; A46-B37-C2; A46-B37-C3;
A46-B37-C4; A46-B37-C5; A46-B37-C6; A46-B37-C7; A46-B37-C8; A46-B37-C9;
A47-B37-C1; A47-B37-C2; A47-B37-C3; A47-B37-C4; A47-B37-C5; A47-B37-C6;
A47-B37-C7; A47-B37-C8; A47-B37-C9; A48-B37-C1; A48-B37-C2; A48-B37-C3;
A48-B37-C4; A48-B37-C5; A48-B37-C6; A48-B37-C7; A48-B37-C8; A48-B37-C9;
A49-B37-C1; A49-B37-C2; A49-B37-C3; A49-B37-C4; A49-B37-C5; A49-B37-C6;
A49-B37-C7; A49-B37-C8; A49-B37-C9; A50-B37-C1; A50-B37-C2; A50-B37-C3;
A50-B37-C4; A50-B37-C5; A50-B37-C6; A50-B37-C7; A50-B37-C8; A50-B37-C9;
A51-B37-C1; A51-B37-C2; A51-B37-C3; A51-B37-C4; A51-B37-C5; A51-B37-C6;
A51-B37-C7; A51-B37-C8; A51-B37-C9; A52-B37-C1; A52-B37-C2; A52-B37-C3;
A52-B37-C4; A52-B37-C5; A52-B37-C6; A52-B37-C7; A52-B37-C8; A52-B37-C9;
A53-B37-C1; A53-B37-C2; A53-B37-C3; A53-B37-C4; A53-B37-C5; A53-B37-C6;
A53-B37-C7; A53-B37-C8; A53-B37-C9; A54-B37-C1; A54-B37-C2; A54-B37-C3;
A54-B37-C4; A54-B37-C5; A54-B37-C6; A54-B37-C7; A54-B37-C8; A54-B37-C9;
A55-B37-C1; A55-B37-C2; A55-B37-C3; A55-B37-C4; A55-B37-C5; A55-B37-C6;
A55-B37-C7; A55-B37-C8; A55-B37-C9; A56-B37-C1; A56-B37-C2; A56-B37-C3;
A56-B37-C4; A56-B37-C5; A56-B37-C6; A56-B37-C7; A56-B37-C8; A56-B37-C9;
A57-B37-C1; A57-B37-C2; A57-B37-C3; A57-B37-C4; A57-B37-C5; A57-B37-C6;
A57-B37-C7; A57-B37-C8; A57-B37-C9; A58-B37-C1; A58-B37-C2; A58-B37-C3;
A58-B37-C4; A58-B37-C5; A58-B37-C6; A58-B37-C7; A58-B37-C8; A58-B37-C9;
A59-B37-C1; A59-B37-C2; A59-B37-C3; A59-B37-C4; A59-B37-C5; A59-B37-C6;
A59-B37-C7; A59-B37-C8; A59-B37-C9; A60-B37-C1; A60-B37-C2; A60-B37-C3;
A60-B37-C4; A60-B37-C5; A60-B37-C6; A60-B37-C7; A60-B37-C8; A60-B37-C9;
A61-B37-C1; A61-B37-C2; A61-B37-C3; A61-B37-C4; A61-B37-C5; A61-B37-C6;
A61-B37-C7; A61-B37-C8; A61-B37-C9; A62-B37-C1; A62-B37-C2; A62-B37-C3;
A62-B37-C4; A62-B37-C5; A62-B37-C6; A62-B37-C7; A62-B37-C8; A62-B37-C9;
A63-B37-C1; A63-B37-C2; A63-B37-C3; A63-B37-C4; A63-B37-C5; A63-B37-C6;
A63-B37-C7; A63-B37-C8; A63-B37-C9; A64-B37-C1; A64-B37-C2; A64-B37-C3;
A64-B37-C4; A64-B37-C5; A64-B37-C6; A64-B37-C7; A64-B37-C8; A64-B37-C9;
A65-B37-C1; A65-B37-C2; A65-B37-C3; A65-B37-C4; A65-B37-C5; A65-B37-C6;
A65-B37-C7; A65-B37-C8; A65-B37-C9; A66-B37-C1; A66-B37-C2; A66-B37-C3;
A66-B37-C4; A66-B37-C5; A66-B37-C6; A66-B37-C7; A66-B37-C8; A66-B37-C9;
A67-B37-C1; A67-B37-C2; A67-B37-C3; A67-B37-C4; A67-B37-C5; A67-B37-C6;
A67-B37-C7; A67-B37-C8; A67-B37-C9; A68-B37-C1; A68-B37-C2; A68-B37-C3;
A68-B37-C4; A68-B37-C5; A68-B37-C6; A68-B37-C7; A68-B37-C8; A68-B37-C9;
A69-B37-C1; A69-B37-C2; A69-B37-C3; A69-B37-C4; A69-B37-C5; A69-B37-C6;
A69-B37-C7; A69-B37-C8; A69-B37-C9; A70-B37-C1; A70-B37-C2; A70-B37-C3;
A70-B37-C4; A70-B37-C5; A70-B37-C6; A70-B37-C7; A70-B37-C8; A70-B37-C9;
A71-B37-C1; A71-B37-C2; A71-B37-C3; A71-B37-C4; A71-B37-C5; A71-B37-C6;
A71-B37-C7; A71-B37-C8; A71-B37-C9; A1-B38-C1; A1-B38-C2; A1-B38-C3;
A1-B38-C4; A1-B38-C5; A1-B38-C6; A1-B38-C7; A1-B38-C8; A1-B38-C9;
A2-B38-C1; A2-B38-C2; A2-B38-C3; A2-B38-C4; A2-B38-C5; A2-B38-C6;
A2-B38-C7; A2-B38-C8; A2-B38-C9; A3-B38-C1; A3-B38-C2; A3-B38-C3;
A3-B38-C4; A3-B38-C5; A3-B38-C6; A3-B38-C7; A3-B38-C8; A3-B38-C9;
A4-B38-C1; A4-B38-C2; A4-B38-C3; A4-B38-C4; A4-B38-C5; A4-B38-C6;
A4-B38-C7; A4-B38-C8; A4-B38-C9; A5-B38-C1; A5-B38-C2; A5-B38-C3;
A5-B38-C4; A5-B38-C5; A5-B38-C6; A5-B38-C7; A5-B38-C8; A5-B38-C9;
A6-B38-C1; A6-B38-C2; A6-B38-C3; A6-B38-C4; A6-B38-C5; A6-B38-C6;
A6-B38-C7; A6-B38-C8; A6-B38-C9; A7-B38-C1; A7-B38-C2; A7-B38-C3;
A7-B38-C4; A7-B38-C5; A7-B38-C6; A7-B38-C7; A7-B38-C8; A7-B38-C9;
A8-B38-C1; A8-B38-C2; A8-B38-C3; A8-B38-C4; A8-B38-C5; A8-B38-C6;
A8-B38-C7; A8-B38-C8; A8-B38-C9; A9-B38-C1; A9-B38-C2; A9-B38-C3;
A9-B38-C4; A9-B38-C5; A9-B38-C6; A9-B38-C7; A9-B38-C8; A9-B38-C9;
A10-B38-C1; A10-B38-C2; A10-B38-C3; A10-B38-C4; A10-B38-C5; A10-B38-C6;
A10-B38-C7; A10-B38-C8; A10-B38-C9; A11-B38-C1; A11-B38-C2; A11-B38-C3;
A11-B38-C4; A11-B38-C5; A11-B38-C6; A11-B38-C7; A11-B38-C8; A11-B38-C9;
A12-B38-C1; A12-B38-C2; A12-B38-C3; A12-B38-C4; A12-B38-C5; A12-B38-C6;
A12-B38-C7; A12-B38-C8; A12-B38-C9; A13-B38-C1; A13-B38-C2; A13-B38-C3;
A13-B38-C4; A13-B38-C5; A13-B38-C6; A13-B38-C7; A13-B38-C8; A13-B38-C9;
A14-B38-C1; A14-B38-C2; A14-B38-C3; A14-B38-C4; A14-B38-C5; A14-B38-C6;
A14-B38-C7; A14-B38-C8; A14-B38-C9; A15-B38-C1; A15-B38-C2; A15-B38-C3;
A15-B38-C4; A15-B38-C5; A15-B38-C6; A15-B38-C7; A15-B38-C8; A15-B38-C9;
A16-B38-C1; A16-B38-C2; A16-B38-C3; A16-B38-C4; A16-B38-C5; A16-B38-C6;
A16-B38-C7; A16-B38-C8; A16-B38-C9; A17-B38-C1; A17-B38-C2; A17-B38-C3;
A17-B38-C4; A17-B38-C5; A17-B38-C6; A17-B38-C7; A17-B38-C8; A17-B38-C9;
A18-B38-C1; A18-B38-C2; A18-B38-C3; A18-B38-C4; A18-B38-C5; A18-B38-C6;
A18-B38-C7; A18-B38-C8; A18-B38-C9; A19-B38-C1; A19-B38-C2; A19-B38-C3;
A19-B38-C4; A19-B38-C5; A19-B38-C6; A19-B38-C7; A19-B38-C8; A19-B38-C9;
A20-B38-C1; A20-B38-C2; A20-B38-C3; A20-B38-C4; A20-B38-C5; A20-B38-C6;
A20-B38-C7; A20-B38-C8; A20-B38-C9; A21-B38-C1; A21-B38-C2; A21-B38-C3;
A21-B38-C4; A21-B38-C5; A21-B38-C6; A21-B38-C7; A21-B38-C8; A21-B38-C9;
A22-B38-C1; A22-B38-C2; A22-B38-C3; A22-B38-C4; A22-B38-C5; A22-B38-C6;
A22-B38-C7; A22-B38-C8; A22-B38-C9; A23-B38-C1; A23-B38-C2; A23-B38-C3;
A23-B38-C4; A23-B38-C5; A23-B38-C6; A23-B38-C7; A23-B38-C8; A23-B38-C9;
A24-B38-C1; A24-B38-C2; A24-B38-C3; A24-B38-C4; A24-B38-C5; A24-B38-C6;
A24-B38-C7; A24-B38-C8; A24-B38-C9; A25-B38-C1; A25-B38-C2; A25-B38-C3;

-continued

| | | | | | |
|---|---|---|---|---|---|
| A25-B38-C4; | A25-B38-C5; | A25-B38-C6; | A25-B38-C7; | A25-B38-C8; | A25-B38-C9; |
| A26-B38-C1; | A26-B38-C2; | A26-B38-C3; | A26-B38-C4; | A26-B38-C5; | A26-B38-C6; |
| A26-B38-C7; | A26-B38-C8; | A26-B38-C9; | A27-B38-C1; | A27-B38-C2; | A27-B38-C3; |
| A27-B38-C4; | A27-B38-C5; | A27-B38-C6; | A27-B38-C7; | A27-B38-C8; | A27-B38-C9; |
| A28-B38-C1; | A28-B38-C2; | A28-B38-C3; | A28-B38-C4; | A28-B38-C5; | A28-B38-C6; |
| A28-B38-C7; | A28-B38-C8; | A28-B38-C9; | A29-B38-C1; | A29-B38-C2; | A29-B38-C3; |
| A29-B38-C4; | A29-B38-C5; | A29-B38-C6; | A29-B38-C7; | A29-B38-C8; | A29-B38-C9; |
| A30-B38-C1; | A30-B38-C2; | A30-B38-C3; | A30-B38-C4; | A30-B38-C5; | A30-B38-C6; |
| A30-B38-C7; | A30-B38-C8; | A30-B38-C9; | A31-B38-C1; | A31-B38-C2; | A31-B38-C3; |
| A31-B38-C4; | A31-B38-C5; | A31-B38-C6; | A31-B38-C7; | A31-B38-C8; | A31-B38-C9; |
| A32-B38-C1; | A32-B38-C2; | A32-B38-C3; | A32-B38-C4; | A32-B38-C5; | A32-B38-C6; |
| A32-B38-C7; | A32-B38-C8; | A32-B38-C9; | A33-B38-C1; | A33-B38-C2; | A33-B38-C3; |
| A33-B38-C4; | A33-B38-C5; | A33-B38-C6; | A33-B38-C7; | A33-B38-C8; | A33-B38-C9; |
| A34-B38-C1; | A34-B38-C2; | A34-B38-C3; | A34-B38-C4; | A34-B38-C5; | A34-B38-C6; |
| A34-B38-C7; | A34-B38-C8; | A34-B38-C9; | A35-B38-C1; | A35-B38-C2; | A35-B38-C3; |
| A35-B38-C4; | A35-B38-C5; | A35-B38-C6; | A35-B38-C7; | A35-B38-C8; | A35-B38-C9; |
| A36-B38-C1; | A36-B38-C2; | A36-B38-C3; | A36-B38-C4; | A36-B38-C5; | A36-B38-C6; |
| A36-B38-C7; | A36-B38-C8; | A36-B38-C9; | A37-B38-C1; | A37-B38-C2; | A37-B38-C3; |
| A37-B38-C4; | A37-B38-C5; | A37-B38-C6; | A37-B38-C7; | A37-B38-C8; | A37-B38-C9; |
| A38-B38-C1; | A38-B38-C2; | A38-B38-C3; | A38-B38-C4; | A38-B38-C5; | A38-B38-C6; |
| A38-B38-C7; | A38-B38-C8; | A38-B38-C9; | A39-B38-C1; | A39-B38-C2; | A39-B38-C3; |
| A39-B38-C4; | A39-B38-C5; | A39-B38-C6; | A39-B38-C7; | A39-B38-C8; | A39-B38-C9; |
| A40-B38-C1; | A40-B38-C2; | A40-B38-C3; | A40-B38-C4; | A40-B38-C5; | A40-B38-C6; |
| A40-B38-C7; | A40-B38-C8; | A40-B38-C9; | A41-B38-C1; | A41-B38-C2; | A41-B38-C3; |
| A41-B38-C4; | A41-B38-C5; | A41-B38-C6; | A41-B38-C7; | A41-B38-C8; | A41-B38-C9; |
| A42-B38-C1; | A42-B38-C2; | A42-B38-C3; | A42-B38-C4; | A42-B38-C5; | A42-B38-C6; |
| A42-B38-C7; | A42-B38-C8; | A42-B38-C9; | A43-B38-C1; | A43-B38-C2; | A43-B38-C3; |
| A43-B38-C4; | A43-B38-C5; | A43-B38-C6; | A43-B38-C7; | A43-B38-C8; | A43-B38-C9; |
| A44-B38-C1; | A44-B38-C2; | A44-B38-C3; | A44-B38-C4; | A44-B38-C5; | A44-B38-C6; |
| A44-B38-C7; | A44-B38-C8; | A44-B38-C9; | A45-B38-C1; | A45-B38-C2; | A45-B38-C3; |
| A45-B38-C4; | A45-B38-C5; | A45-B38-C6; | A45-B38-C7; | A45-B38-C8; | A45-B38-C9; |
| A46-B38-C1; | A46-B38-C2; | A46-B38-C3; | A46-B38-C4; | A46-B38-C5; | A46-B38-C6; |
| A46-B38-C7; | A46-B38-C8; | A46-B38-C9; | A47-B38-C1; | A47-B38-C2; | A47-B38-C3; |
| A47-B38-C4; | A47-B38-C5; | A47-B38-C6; | A47-B38-C7; | A47-B38-C8; | A47-B38-C9; |
| A48-B38-C1; | A48-B38-C2; | A48-B38-C3; | A48-B38-C4; | A48-B38-C5; | A48-B38-C6; |
| A48-B38-C7; | A48-B38-C8; | A48-B38-C9; | A49-B38-C1; | A49-B38-C2; | A49-B38-C3; |
| A49-B38-C4; | A49-B38-C5; | A49-B38-C6; | A49-B38-C7; | A49-B38-C8; | A49-B38-C9; |
| A50-B38-C1; | A50-B38-C2; | A50-B38-C3; | A50-B38-C4; | A50-B38-C5; | A50-B38-C6; |
| A50-B38-C7; | A50-B38-C8; | A50-B38-C9; | A51-B38-C1; | A51-B38-C2; | A51-B38-C3; |
| A51-B38-C4; | A51-B38-C5; | A51-B38-C6; | A51-B38-C7; | A51-B38-C8; | A51-B38-C9; |
| A52-B38-C1; | A52-B38-C2; | A52-B38-C3; | A52-B38-C4; | A52-B38-C5; | A52-B38-C6; |
| A52-B38-C7; | A52-B38-C8; | A52-B38-C9; | A53-B38-C1; | A53-B38-C2; | A53-B38-C3; |
| A53-B38-C4; | A53-B38-C5; | A53-B38-C6; | A53-B38-C7; | A53-B38-C8; | A53-B38-C9; |
| A54-B38-C1; | A54-B38-C2; | A54-B38-C3; | A54-B38-C4; | A54-B38-C5; | A54-B38-C6; |
| A54-B38-C7; | A54-B38-C8; | A54-B38-C9; | A55-B38-C1; | A55-B38-C2; | A55-B38-C3; |
| A55-B38-C4; | A55-B38-C5; | A55-B38-C6; | A55-B38-C7; | A55-B38-C8; | A55-B38-C9; |
| A56-B38-C1; | A56-B38-C2; | A56-B38-C3; | A56-B38-C4; | A56-B38-C5; | A56-B38-C6; |
| A56-B38-C7; | A56-B38-C8; | A56-B38-C9; | A57-B38-C1; | A57-B38-C2; | A57-B38-C3; |
| A57-B38-C4; | A57-B38-C5; | A57-B38-C6; | A57-B38-C7; | A57-B38-C8; | A57-B38-C9; |
| A58-B38-C1; | A58-B38-C2; | A58-B38-C3; | A58-B38-C4; | A58-B38-C5; | A58-B38-C6; |
| A58-B38-C7; | A58-B38-C8; | A58-B38-C9; | A59-B38-C1; | A59-B38-C2; | A59-B38-C3; |
| A59-B38-C4; | A59-B38-C5; | A59-B38-C6; | A59-B38-C7; | A59-B38-C8; | A59-B38-C9; |
| A60-B38-C1; | A60-B38-C2; | A60-B38-C3; | A60-B38-C4; | A60-B38-C5; | A60-B38-C6; |
| A60-B38-C7; | A60-B38-C8; | A60-B38-C9; | A61-B38-C1; | A61-B38-C2; | A61-B38-C3; |
| A61-B38-C4; | A61-B38-C5; | A61-B38-C6; | A61-B38-C7; | A61-B38-C8; | A61-B38-C9; |
| A62-B38-C1; | A62-B38-C2; | A62-B38-C3; | A62-B38-C4; | A62-B38-C5; | A62-B38-C6; |
| A62-B38-C7; | A62-B38-C8; | A62-B38-C9; | A63-B38-C1; | A63-B38-C2; | A63-B38-C3; |
| A63-B38-C4; | A63-B38-C5; | A63-B38-C6; | A63-B38-C7; | A63-B38-C8; | A63-B38-C9; |
| A64-B38-C1; | A64-B38-C2; | A64-B38-C3; | A64-B38-C4; | A64-B38-C5; | A64-B38-C6; |
| A64-B38-C7; | A64-B38-C8; | A64-B38-C9; | A65-B38-C1; | A65-B38-C2; | A65-B38-C3; |
| A65-B38-C4; | A65-B38-C5; | A65-B38-C6; | A65-B38-C7; | A65-B38-C8; | A65-B38-C9; |
| A66-B38-C1; | A66-B38-C2; | A66-B38-C3; | A66-B38-C4; | A66-B38-C5; | A66-B38-C6; |
| A66-B38-C7; | A66-B38-C8; | A66-B38-C9; | A67-B38-C1; | A67-B38-C2; | A67-B38-C3; |
| A67-B38-C4; | A67-B38-C5; | A67-B38-C6; | A67-B38-C7; | A67-B38-C8; | A67-B38-C9; |
| A68-B38-C1; | A68-B38-C2; | A68-B38-C3; | A68-B38-C4; | A68-B38-C5; | A68-B38-C6; |
| A68-B38-C7; | A68-B38-C8; | A68-B38-C9; | A69-B38-C1; | A69-B38-C2; | A69-B38-C3; |
| A69-B38-C4; | A69-B38-C5; | A69-B38-C6; | A69-B38-C7; | A69-B38-C8; | A69-B38-C9; |
| A70-B38-C1; | A70-B38-C2; | A70-B38-C3; | A70-B38-C4; | A70-B38-C5; | A70-B38-C6; |
| A70-B38-C7; | A70-B38-C8; | A70-B38-C9; | A71-B38-C1; | A71-B38-C2; | A71-B38-C3; |
| A71-B38-C4; | A71-B38-C5; | A71-B38-C6; | A71-B38-C7; | A71-B38-C8; | A71-B38-C9; |
| A1-B39-C1; | A1-B39-C2; | A1-B39-C3; | A1-B39-C4; | A1-B39-C5; | A1-B39-C6; |
| A1-B39-C7; | A1-B39-C8; | A1-B39-C9; | A2-B39-C1; | A2-B39-C2; | A2-B39-C3; |
| A2-B39-C4; | A2-B39-C5; | A2-B39-C6; | A2-B39-C7; | A2-B39-C8; | A2-B39-C9; |
| A3-B39-C1; | A3-B39-C2; | A3-B39-C3; | A3-B39-C4; | A3-B39-C5; | A3-B39-C6; |
| A3-B39-C7; | A3-B39-C8; | A3-B39-C9; | A4-B39-C1; | A4-B39-C2; | A4-B39-C3; |
| A4-B39-C4; | A4-B39-C5; | A4-B39-C6; | A4-B39-C7; | A4-B39-C8; | A4-B39-C9; |
| A5-B39-C1; | A5-B39-C2; | A5-B39-C3; | A5-B39-C4; | A5-B39-C5; | A5-B39-C6; |
| A5-B39-C7; | A5-B39-C8; | A5-B39-C9; | A6-B39-C1; | A6-B39-C2; | A6-B39-C3; |
| A6-B39-C4; | A6-B39-C5; | A6-B39-C6; | A6-B39-C7; | A6-B39-C8; | A6-B39-C9; |

-continued

| | | | | | |
|---|---|---|---|---|---|
| A7-B39-C1; | A7-B39-C2; | A7-B39-C3; | A7-B39-C4; | A7-B39-C5; | A7-B39-C6; |
| A7-B39-C7; | A7-B39-C8; | A7-B39-C9; | A8-B39-C1; | A8-B39-C2; | A8-B39-C3; |
| A8-B39-C4; | A8-B39-C5; | A8-B39-C6; | A8-B39-C7; | A8-B39-C8; | A8-B39-C9; |
| A9-B39-C1; | A9-B39-C2; | A9-B39-C3; | A9-B39-C4; | A9-B39-C5; | A9-B39-C6; |
| A9-B39-C7; | A9-B39-C8; | A9-B39-C9; | A10-B39-C1; | A10-B39-C2; | A10-B39-C3; |
| A10-B39-C4; | A10-B39-C5; | A10-B39-C6; | A10-B39-C7; | A10-B39-C8; | A10-B39-C9; |
| A11-B39-C1; | A11-B39-C2; | A11-B39-C3; | A11-B39-C4; | A11-B39-C5; | A11-B39-C6; |
| A11-B39-C7; | A11-B39-C8; | A11-B39-C9; | A12-B39-C1; | A12-B39-C2; | A12-B39-C3; |
| A12-B39-C4; | A12-B39-C5; | A12-B39-C6; | A12-B39-C7; | A12-B39-C8; | A12-B39-C9; |
| A13-B39-C1; | A13-B39-C2; | A13-B39-C3; | A13-B39-C4; | A13-B39-C5; | A13-B39-C6; |
| A13-B39-C7; | A13-B39-C8; | A13-B39-C9; | A14-B39-C1; | A14-B39-C2; | A14-B39-C3; |
| A14-B39-C4; | A14-B39-C5; | A14-B39-C6; | A14-B39-C7; | A14-B39-C8; | A14-B39-C9; |
| A15-B39-C1; | A15-B39-C2; | A15-B39-C3; | A15-B39-C4; | A15-B39-C5; | A15-B39-C6; |
| A15-B39-C7; | A15-B39-C8; | A15-B39-C9; | A16-B39-C1; | A16-B39-C2; | A16-B39-C3; |
| A16-B39-C4; | A16-B39-C5; | A16-B39-C6; | A16-B39-C7; | A16-B39-C8; | A16-B39-C9; |
| A17-B39-C1; | A17-B39-C2; | A17-B39-C3; | A17-B39-C4; | A17-B39-C5; | A17-B39-C6; |
| A17-B39-C7; | A17-B39-C8; | A17-B39-C9; | A18-B39-C1; | A18-B39-C2; | A18-B39-C3; |
| A18-B39-C4; | A18-B39-C5; | A18-B39-C6; | A18-B39-C7; | A18-B39-C8; | A18-B39-C9; |
| A19-B39-C1; | A19-B39-C2; | A19-B39-C3; | A19-B39-C4; | A19-B39-C5; | A19-B39-C6; |
| A19-B39-C7; | A19-B39-C8; | A19-B39-C9; | A20-B39-C1; | A20-B39-C2; | A20-B39-C3; |
| A20-B39-C4; | A20-B39-C5; | A20-B39-C6; | A20-B39-C7; | A20-B39-C8; | A20-B39-C9; |
| A21-B39-C1; | A21-B39-C2; | A21-B39-C3; | A21-B39-C4; | A21-B39-C5; | A21-B39-C6; |
| A21-B39-C7; | A21-B39-C8; | A21-B39-C9; | A22-B39-C1; | A22-B39-C2; | A22-B39-C3; |
| A22-B39-C4; | A22-B39-C5; | A22-B39-C6; | A22-B39-C7; | A22-B39-C8; | A22-B39-C9; |
| A23-B39-C1; | A23-B39-C2; | A23-B39-C3; | A23-B39-C4; | A23-B39-C5; | A23-B39-C6; |
| A23-B39-C7; | A23-B39-C8; | A23-B39-C9; | A24-B39-C1; | A24-B39-C2; | A24-B39-C3; |
| A24-B39-C4; | A24-B39-C5; | A24-B39-C6; | A24-B39-C7; | A24-B39-C8; | A24-B39-C9; |
| A25-B39-C1; | A25-B39-C2; | A25-B39-C3; | A25-B39-C4; | A25-B39-C5; | A25-B39-C6; |
| A25-B39-C7; | A25-B39-C8; | A25-B39-C9; | A26-B39-C1; | A26-B39-C2; | A26-B39-C3; |
| A26-B39-C4; | A26-B39-C5; | A26-B39-C6; | A26-B39-C7; | A26-B39-C8; | A26-B39-C9; |
| A27-B39-C1; | A27-B39-C2; | A27-B39-C3; | A27-B39-C4; | A27-B39-C5; | A27-B39-C6; |
| A27-B39-C7; | A27-B39-C8; | A27-B39-C9; | A28-B39-C1; | A28-B39-C2; | A28-B39-C3; |
| A28-B39-C4; | A28-B39-C5; | A28-B39-C6; | A28-B39-C7; | A28-B39-C8; | A28-B39-C9; |
| A29-B39-C1; | A29-B39-C2; | A29-B39-C3; | A29-B39-C4; | A29-B39-C5; | A29-B39-C6; |
| A29-B39-C7; | A29-B39-C8; | A29-B39-C9; | A30-B39-C1; | A30-B39-C2; | A30-B39-C3; |
| A30-B39-C4; | A30-B39-C5; | A30-B39-C6; | A30-B39-C7; | A30-B39-C8; | A30-B39-C9; |
| A31-B39-C1; | A31-B39-C2; | A31-B39-C3; | A31-B39-C4; | A31-B39-C5; | A31-B39-C6; |
| A31-B39-C7; | A31-B39-C8; | A31-B39-C9; | A32-B39-C1; | A32-B39-C2; | A32-B39-C3; |
| A32-B39-C4; | A32-B39-C5; | A32-B39-C6; | A32-B39-C7; | A32-B39-C8; | A32-B39-C9; |
| A33-B39-C1; | A33-B39-C2; | A33-B39-C3; | A33-B39-C4; | A33-B39-C5; | A33-B39-C6; |
| A33-B39-C7; | A33-B39-C8; | A33-B39-C9; | A34-B39-C1; | A34-B39-C2; | A34-B39-C3; |
| A34-B39-C4; | A34-B39-C5; | A34-B39-C6; | A34-B39-C7; | A34-B39-C8; | A34-B39-C9; |
| A35-B39-C1; | A35-B39-C2; | A35-B39-C3; | A35-B39-C4; | A35-B39-C5; | A35-B39-C6; |
| A35-B39-C7; | A35-B39-C8; | A35-B39-C9; | A36-B39-C1; | A36-B39-C2; | A36-B39-C3; |
| A36-B39-C4; | A36-B39-C5; | A36-B39-C6; | A36-B39-C7; | A36-B39-C8; | A36-B39-C9; |
| A37-B39-C1; | A37-B39-C2; | A37-B39-C3; | A37-B39-C4; | A37-B39-C5; | A37-B39-C6; |
| A37-B39-C7; | A37-B39-C8; | A37-B39-C9; | A38-B39-C1; | A38-B39-C2; | A38-B39-C3; |
| A38-B39-C4; | A38-B39-C5; | A38-B39-C6; | A38-B39-C7; | A38-B39-C8; | A38-B39-C9; |
| A39-B39-C1; | A39-B39-C2; | A39-B39-C3; | A39-B39-C4; | A39-B39-C5; | A39-B39-C6; |
| A39-B39-C7; | A39-B39-C8; | A39-B39-C9; | A40-B39-C1; | A40-B39-C2; | A40-B39-C3; |
| A40-B39-C4; | A40-B39-C5; | A40-B39-C6; | A40-B39-C7; | A40-B39-C8; | A40-B39-C9; |
| A41-B39-C1; | A41-B39-C2; | A41-B39-C3; | A41-B39-C4; | A41-B39-C5; | A41-B39-C6; |
| A41-B39-C7; | A41-B39-C8; | A41-B39-C9; | A42-B39-C1; | A42-B39-C2; | A42-B39-C3; |
| A42-B39-C4; | A42-B39-C5; | A42-B39-C6; | A42-B39-C7; | A42-B39-C8; | A42-B39-C9; |
| A43-B39-C1; | A43-B39-C2; | A43-B39-C3; | A43-B39-C4; | A43-B39-C5; | A43-B39-C6; |
| A43-B39-C7; | A43-B39-C8; | A43-B39-C9; | A44-B39-C1; | A44-B39-C2; | A44-B39-C3; |
| A44-B39-C4; | A44-B39-C5; | A44-B39-C6; | A44-B39-C7; | A44-B39-C8; | A44-B39-C9; |
| A45-B39-C1; | A45-B39-C2; | A45-B39-C3; | A45-B39-C4; | A45-B39-C5; | A45-B39-C6; |
| A45-B39-C7; | A45-B39-C8; | A45-B39-C9; | A46-B39-C1; | A46-B39-C2; | A46-B39-C3; |
| A46-B39-C4; | A46-B39-C5; | A46-B39-C6; | A46-B39-C7; | A46-B39-C8; | A46-B39-C9; |
| A47-B39-C1; | A47-B39-C2; | A47-B39-C3; | A47-B39-C4; | A47-B39-C5; | A47-B39-C6; |
| A47-B39-C7; | A47-B39-C8; | A47-B39-C9; | A48-B39-C1; | A48-B39-C2; | A48-B39-C3; |
| A48-B39-C4; | A48-B39-C5; | A48-B39-C6; | A48-B39-C7; | A48-B39-C8; | A48-B39-C9; |
| A49-B39-C1; | A49-B39-C2; | A49-B39-C3; | A49-B39-C4; | A49-B39-C5; | A49-B39-C6; |
| A49-B39-C7; | A49-B39-C8; | A49-B39-C9; | A50-B39-C1; | A50-B39-C2; | A50-B39-C3; |
| A50-B39-C4; | A50-B39-C5; | A50-B39-C6; | A50-B39-C7; | A50-B39-C8; | A50-B39-C9; |
| A51-B39-C1; | A51-B39-C2; | A51-B39-C3; | A51-B39-C4; | A51-B39-C5; | A51-B39-C6; |
| A51-B39-C7; | A51-B39-C8; | A51-B39-C9; | A52-B39-C1; | A52-B39-C2; | A52-B39-C3; |
| A52-B39-C4; | A52-B39-C5; | A52-B39-C6; | A52-B39-C7; | A52-B39-C8; | A52-B39-C9; |
| A53-B39-C1; | A53-B39-C2; | A53-B39-C3; | A53-B39-C4; | A53-B39-C5; | A53-B39-C6; |
| A53-B39-C7; | A53-B39-C8; | A53-B39-C9; | A54-B39-C1; | A54-B39-C2; | A54-B39-C3; |
| A54-B39-C4; | A54-B39-C5; | A54-B39-C6; | A54-B39-C7; | A54-B39-C8; | A54-B39-C9; |
| A55-B39-C1; | A55-B39-C2; | A55-B39-C3; | A55-B39-C4; | A55-B39-C5; | A55-B39-C6; |
| A55-B39-C7; | A55-B39-C8; | A55-B39-C9; | A56-B39-C1; | A56-B39-C2; | A56-B39-C3; |
| A56-B39-C4; | A56-B39-C5; | A56-B39-C6; | A56-B39-C7; | A56-B39-C8; | A56-B39-C9; |
| A57-B39-C1; | A57-B39-C2; | A57-B39-C3; | A57-B39-C4; | A57-B39-C5; | A57-B39-C6; |
| A57-B39-C7; | A57-B39-C8; | A57-B39-C9; | A58-B39-C1; | A58-B39-C2; | A58-B39-C3; |
| A58-B39-C4; | A58-B39-C5; | A58-B39-C6; | A58-B39-C7; | A58-B39-C8; | A58-B39-C9; |
| A59-B39-C1; | A59-B39-C2; | A59-B39-C3; | A59-B39-C4; | A59-B39-C5; | A59-B39-C6; |

-continued

| | | | | | |
|---|---|---|---|---|---|
| A59-B39-C7; | A59-B39-C8; | A59-B39-C9; | A60-B39-C1; | A60-B39-C2; | A60-B39-C3; |
| A60-B39-C4; | A60-B39-C5; | A60-B39-C6; | A60-B39-C7; | A60-B39-C8; | A60-B39-C9; |
| A61-B39-C1; | A61-B39-C2; | A61-B39-C3; | A61-B39-C4; | A61-B39-C5; | A61-B39-C6; |
| A61-B39-C7; | A61-B39-C8; | A61-B39-C9; | A62-B39-C1; | A62-B39-C2; | A62-B39-C3; |
| A62-B39-C4; | A62-B39-C5; | A62-B39-C6; | A62-B39-C7; | A62-B39-C8; | A62-B39-C9; |
| A63-B39-C1; | A63-B39-C2; | A63-B39-C3; | A63-B39-C4; | A63-B39-C5; | A63-B39-C6; |
| A63-B39-C7; | A63-B39-C8; | A63-B39-C9; | A64-B39-C1; | A64-B39-C2; | A64-B39-C3; |
| A64-B39-C4; | A64-B39-C5; | A64-B39-C6; | A64-B39-C7; | A64-B39-C8; | A64-B39-C9; |
| A65-B39-C1; | A65-B39-C2; | A65-B39-C3; | A65-B39-C4; | A65-B39-C5; | A65-B39-C6; |
| A65-B39-C7; | A65-B39-C8; | A65-B39-C9; | A66-B39-C1; | A66-B39-C2; | A66-B39-C3; |
| A66-B39-C4; | A66-B39-C5; | A66-B39-C6; | A66-B39-C7; | A66-B39-C8; | A66-B39-C9; |
| A67-B39-C1; | A67-B39-C2; | A67-B39-C3; | A67-B39-C4; | A67-B39-C5; | A67-B39-C6; |
| A67-B39-C7; | A67-B39-C8; | A67-B39-C9; | A68-B39-C1; | A68-B39-C2; | A68-B39-C3; |
| A68-B39-C4; | A68-B39-C5; | A68-B39-C6; | A68-B39-C7; | A68-B39-C8; | A68-B39-C9; |
| A69-B39-C1; | A69-B39-C2; | A69-B39-C3; | A69-B39-C4; | A69-B39-C5; | A69-B39-C6; |
| A69-B39-C7; | A69-B39-C8; | A69-B39-C9; | A70-B39-C1; | A70-B39-C2; | A70-B39-C3; |
| A70-B39-C4; | A70-B39-C5; | A70-B39-C6; | A70-B39-C7; | A70-B39-C8; | A70-B39-C9; |
| A71-B39-C1; | A71-B39-C2; | A71-B39-C3; | A71-B39-C4; | A71-B39-C5; | A71-B39-C6; |
| A71-B39-C7; | A71-B39-C8; | A71-B39-C9; | A1-B40-C1; | A1-B40-C2; | A1-B40-C3; |
| A1-B40-C4; | A1-B40-C5; | A1-B40-C6; | A1-B40-C7; | A1-B40-C8; | A1-B40-C9; |
| A2-B40-C1; | A2-B40-C2; | A2-B40-C3; | A2-B40-C4; | A2-B40-C5; | A2-B40-C6; |
| A2-B40-C7; | A2-B40-C8; | A2-B40-C9; | A3-B40-C1; | A3-B40-C2; | A3-B40-C3; |
| A3-B40-C4; | A3-B40-C5; | A3-B40-C6; | A3-B40-C7; | A3-B40-C8; | A3-B40-C9; |
| A4-B40-C1; | A4-B40-C2; | A4-B40-C3; | A4-B40-C4; | A4-B40-C5; | A4-B40-C6; |
| A4-B40-C7; | A4-B40-C8; | A4-B40-C9; | A5-B40-C1; | A5-B40-C2; | A5-B40-C3; |
| A5-B40-C4; | A5-B40-C5; | A5-B40-C6; | A5-B40-C7; | A5-B40-C8; | A5-B40-C9; |
| A6-B40-C1; | A6-B40-C2; | A6-B40-C3; | A6-B40-C4; | A6-B40-C5; | A6-B40-C6; |
| A6-B40-C7; | A6-B40-C8; | A6-B40-C9; | A7-B40-C1; | A7-B40-C2; | A7-B40-C3; |
| A7-B40-C4; | A7-B40-C5; | A7-B40-C6; | A7-B40-C7; | A7-B40-C8; | A7-B40-C9; |
| A8-B40-C1; | A8-B40-C2; | A8-B40-C3; | A8-B40-C4; | A8-B40-C5; | A8-B40-C6; |
| A8-B40-C7; | A8-B40-C8; | A8-B40-C9; | A9-B40-C1; | A9-B40-C2; | A9-B40-C3; |
| A9-B40-C4; | A9-B40-C5; | A9-B40-C6; | A9-B40-C7; | A9-B40-C8; | A9-B40-C9; |
| A10-B40-C1; | A10-B40-C2; | A10-B40-C3; | A10-B40-C4; | A10-B40-C5; | A10-B40-C6; |
| A10-B40-C7; | A10-B40-C8; | A10-B40-C9; | A11-B40-C1; | A11-B40-C2; | A11-B40-C3; |
| A11-B40-C4; | A11-B40-C5; | A11-B40-C6; | A11-B40-C7; | A11-B40-C8; | A11-B40-C9; |
| A12-B40-C1; | A12-B40-C2; | A12-B40-C3; | A12-B40-C4; | A12-B40-C5; | A12-B40-C6; |
| A12-B40-C7; | A12-B40-C8; | A12-B40-C9; | A13-B40-C1; | A13-B40-C2; | A13-B40-C3; |
| A13-B40-C4; | A13-B40-C5; | A13-B40-C6; | A13-B40-C7; | A13-B40-C8; | A13-B40-C9; |
| A14-B40-C1; | A14-B40-C2; | A14-B40-C3; | A14-B40-C4; | A14-B40-C5; | A14-B40-C6; |
| A14-B40-C7; | A14-B40-C8; | A14-B40-C9; | A15-B40-C1; | A15-B40-C2; | A15-B40-C3; |
| A15-B40-C4; | A15-B40-C5; | A15-B40-C6; | A15-B40-C7; | A15-B40-C8; | A15-B40-C9; |
| A16-B40-C1; | A16-B40-C2; | A16-B40-C3; | A16-B40-C4; | A16-B40-C5; | A16-B40-C6; |
| A16-B40-C7; | A16-B40-C8; | A16-B40-C9; | A17-B40-C1; | A17-B40-C2; | A17-B40-C3; |
| A17-B40-C4; | A17-B40-C5; | A17-B40-C6; | A17-B40-C7; | A17-B40-C8; | A17-B40-C9; |
| A18-B40-C1; | A18-B40-C2; | A18-B40-C3; | A18-B40-C4; | A18-B40-C5; | A18-B40-C6; |
| A18-B40-C7; | A18-B40-C8; | A18-B40-C9; | A19-B40-C1; | A19-B40-C2; | A19-B40-C3; |
| A19-B40-C4; | A19-B40-C5; | A19-B40-C6; | A19-B40-C7; | A19-B40-C8; | A19-B40-C9; |
| A20-B40-C1; | A20-B40-C2; | A20-B40-C3; | A20-B40-C4; | A20-B40-C5; | A20-B40-C6; |
| A20-B40-C7; | A20-B40-C8; | A20-B40-C9; | A21-B40-C1; | A21-B40-C2; | A21-B40-C3; |
| A21-B40-C4; | A21-B40-C5; | A21-B40-C6; | A21-B40-C7; | A21-B40-C8; | A21-B40-C9; |
| A22-B40-C1; | A22-B40-C2; | A22-B40-C3; | A22-B40-C4; | A22-B40-C5; | A22-B40-C6; |
| A22-B40-C7; | A22-B40-C8; | A22-B40-C9; | A23-B40-C1; | A23-B40-C2; | A23-B40-C3; |
| A23-B40-C4; | A23-B40-C5; | A23-B40-C6; | A23-B40-C7; | A23-B40-C8; | A23-B40-C9; |
| A24-B40-C1; | A24-B40-C2; | A24-B40-C3; | A24-B40-C4; | A24-B40-C5; | A24-B40-C6; |
| A24-B40-C7; | A24-B40-C8; | A24-B40-C9; | A25-B40-C1; | A25-B40-C2; | A25-B40-C3; |
| A25-B40-C4; | A25-B40-C5; | A25-B40-C6; | A25-B40-C7; | A25-B40-C8; | A25-B40-C9; |
| A26-B40-C1; | A26-B40-C2; | A26-B40-C3; | A26-B40-C4; | A26-B40-C5; | A26-B40-C6; |
| A26-B40-C7; | A26-B40-C8; | A26-B40-C9; | A27-B40-C1; | A27-B40-C2; | A27-B40-C3; |
| A27-B40-C4; | A27-B40-C5; | A27-B40-C6; | A27-B40-C7; | A27-B40-C8; | A27-B40-C9; |
| A28-B40-C1; | A28-B40-C2; | A28-B40-C3; | A28-B40-C4; | A28-B40-C5; | A28-B40-C6; |
| A28-B40-C7; | A28-B40-C8; | A28-B40-C9; | A29-B40-C1; | A29-B40-C2; | A29-B40-C3; |
| A29-B40-C4; | A29-B40-C5; | A29-B40-C6; | A29-B40-C7; | A29-B40-C8; | A29-B40-C9; |
| A30-B40-C1; | A30-B40-C2; | A30-B40-C3; | A30-B40-C4; | A30-B40-C5; | A30-B40-C6; |
| A30-B40-C7; | A30-B40-C8; | A30-B40-C9; | A31-B40-C1; | A31-B40-C2; | A31-B40-C3; |
| A31-B40-C4; | A31-B40-C5; | A31-B40-C6; | A31-B40-C7; | A31-B40-C8; | A31-B40-C9; |
| A32-B40-C1; | A32-B40-C2; | A32-B40-C3; | A32-B40-C4; | A32-B40-C5; | A32-B40-C6; |
| A32-B40-C7; | A32-B40-C8; | A32-B40-C9; | A33-B40-C1; | A33-B40-C2; | A33-B40-C3; |
| A33-B40-C4; | A33-B40-C5; | A33-B40-C6; | A33-B40-C7; | A33-B40-C8; | A33-B40-C9; |
| A34-B40-C1; | A34-B40-C2; | A34-B40-C3; | A34-B40-C4; | A34-B40-C5; | A34-B40-C6; |
| A34-B40-C7; | A34-B40-C8; | A34-B40-C9; | A35-B40-C1; | A35-B40-C2; | A35-B40-C3; |
| A35-B40-C4; | A35-B40-C5; | A35-B40-C6; | A35-B40-C7; | A35-B40-C8; | A35-B40-C9; |
| A36-B40-C1; | A36-B40-C2; | A36-B40-C3; | A36-B40-C4; | A36-B40-C5; | A36-B40-C6; |
| A36-B40-C7; | A36-B40-C8; | A36-B40-C9; | A37-B40-C1; | A37-B40-C2; | A37-B40-C3; |
| A37-B40-C4; | A37-B40-C5; | A37-B40-C6; | A37-B40-C7; | A37-B40-C8; | A37-B40-C9; |
| A38-B40-C1; | A38-B40-C2; | A38-B40-C3; | A38-B40-C4; | A38-B40-C5; | A38-B40-C6; |
| A38-B40-C7; | A38-B40-C8; | A38-B40-C9; | A39-B40-C1; | A39-B40-C2; | A39-B40-C3; |
| A39-B40-C4; | A39-B40-C5; | A39-B40-C6; | A39-B40-C7; | A39-B40-C8; | A39-B40-C9; |
| A40-B40-C1; | A40-B40-C2; | A40-B40-C3; | A40-B40-C4; | A40-B40-C5; | A40-B40-C6; |
| A40-B40-C7; | A40-B40-C8; | A40-B40-C9; | A41-B40-C1; | A41-B40-C2; | A41-B40-C3; |

-continued

| | | | | | |
|---|---|---|---|---|---|
| A41-B40-C4; | A41-B40-C5; | A41-B40-C6; | A41-B40-C7; | A41-B40-C8; | A41-B40-C9; |
| A42-B40-C1; | A42-B40-C2; | A42-B40-C3; | A42-B40-C4; | A42-B40-C5; | A42-B40-C6; |
| A42-B40-C7; | A42-B40-C8; | A42-B40-C9; | A43-B40-C1; | A43-B40-C2; | A43-B40-C3; |
| A43-B40-C4; | A43-B40-C5; | A43-B40-C6; | A43-B40-C7; | A43-B40-C8; | A43-B40-C9; |
| A44-B40-C1; | A44-B40-C2; | A44-B40-C3; | A44-B40-C4; | A44-B40-C5; | A44-B40-C6; |
| A44-B40-C7; | A44-B40-C8; | A44-B40-C9; | A45-B40-C1; | A45-B40-C2; | A45-B40-C3; |
| A45-B40-C4; | A45-B40-C5; | A45-B40-C6; | A45-B40-C7; | A45-B40-C8; | A45-B40-C9; |
| A46-B40-C1; | A46-B40-C2; | A46-B40-C3; | A46-B40-C4; | A46-B40-C5; | A46-B40-C6; |
| A46-B40-C7; | A46-B40-C8; | A46-B40-C9; | A47-B40-C1; | A47-B40-C2; | A47-B40-C3; |
| A47-B40-C4; | A47-B40-C5; | A47-B40-C6; | A47-B40-C7; | A47-B40-C8; | A47-B40-C9; |
| A48-B40-C1; | A48-B40-C2; | A48-B40-C3; | A48-B40-C4; | A48-B40-C5; | A48-B40-C6; |
| A48-B40-C7; | A48-B40-C8; | A48-B40-C9; | A49-B40-C1; | A49-B40-C2; | A49-B40-C3; |
| A49-B40-C4; | A49-B40-C5; | A49-B40-C6; | A49-B40-C7; | A49-B40-C8; | A49-B40-C9; |
| A50-B40-C1; | A50-B40-C2; | A50-B40-C3; | A50-B40-C4; | A50-B40-C5; | A50-B40-C6; |
| A50-B40-C7; | A50-B40-C8; | A50-B40-C9; | A51-B40-C1; | A51-B40-C2; | A51-B40-C3; |
| A51-B40-C4; | A51-B40-C5; | A51-B40-C6; | A51-B40-C7; | A51-B40-C8; | A51-B40-C9; |
| A52-B40-C1; | A52-B40-C2; | A52-B40-C3; | A52-B40-C4; | A52-B40-C5; | A52-B40-C6; |
| A52-B40-C7; | A52-B40-C8; | A52-B40-C9; | A53-B40-C1; | A53-B40-C2; | A53-B40-C3; |
| A53-B40-C4; | A53-B40-C5; | A53-B40-C6; | A53-B40-C7; | A53-B40-C8; | A53-B40-C9; |
| A54-B40-C1; | A54-B40-C2; | A54-B40-C3; | A54-B40-C4; | A54-B40-C5; | A54-B40-C6; |
| A54-B40-C7; | A54-B40-C8; | A54-B40-C9; | A55-B40-C1; | A55-B40-C2; | A55-B40-C3; |
| A55-B40-C4; | A55-B40-C5; | A55-B40-C6; | A55-B40-C7; | A55-B40-C8; | A55-B40-C9; |
| A56-B40-C1; | A56-B40-C2; | A56-B40-C3; | A56-B40-C4; | A56-B40-C5; | A56-B40-C6; |
| A56-B40-C7; | A56-B40-C8; | A56-B40-C9; | A57-B40-C1; | A57-B40-C2; | A57-B40-C3; |
| A57-B40-C4; | A57-B40-C5; | A57-B40-C6; | A57-B40-C7; | A57-B40-C8; | A57-B40-C9; |
| A58-B40-C1; | A58-B40-C2; | A58-B40-C3; | A58-B40-C4; | A58-B40-C5; | A58-B40-C6; |
| A58-B40-C7; | A58-B40-C8; | A58-B40-C9; | A59-B40-C1; | A59-B40-C2; | A59-B40-C3; |
| A59-B40-C4; | A59-B40-C5; | A59-B40-C6; | A59-B40-C7; | A59-B40-C8; | A59-B40-C9; |
| A60-B40-C1; | A60-B40-C2; | A60-B40-C3; | A60-B40-C4; | A60-B40-C5; | A60-B40-C6; |
| A60-B40-C7; | A60-B40-C8; | A60-B40-C9; | A61-B40-C1; | A61-B40-C2; | A61-B40-C3; |
| A61-B40-C4; | A61-B40-C5; | A61-B40-C6; | A61-B40-C7; | A61-B40-C8; | A61-B40-C9; |
| A62-B40-C1; | A62-B40-C2; | A62-B40-C3; | A62-B40-C4; | A62-B40-C5; | A62-B40-C6; |
| A62-B40-C7; | A62-B40-C8; | A62-B40-C9; | A63-B40-C1; | A63-B40-C2; | A63-B40-C3; |
| A63-B40-C4; | A63-B40-C5; | A63-B40-C6; | A63-B40-C7; | A63-B40-C8; | A63-B40-C9; |
| A64-B40-C1; | A64-B40-C2; | A64-B40-C3; | A64-B40-C4; | A64-B40-C5; | A64-B40-C6; |
| A64-B40-C7; | A64-B40-C8; | A64-B40-C9; | A65-B40-C1; | A65-B40-C2; | A65-B40-C3; |
| A65-B40-C4; | A65-B40-C5; | A65-B40-C6; | A65-B40-C7; | A65-B40-C8; | A65-B40-C9; |
| A66-B40-C1; | A66-B40-C2; | A66-B40-C3; | A66-B40-C4; | A66-B40-C5; | A66-B40-C6; |
| A66-B40-C7; | A66-B40-C8; | A66-B40-C9; | A67-B40-C1; | A67-B40-C2; | A67-B40-C3; |
| A67-B40-C4; | A67-B40-C5; | A67-B40-C6; | A67-B40-C7; | A67-B40-C8; | A67-B40-C9; |
| A68-B40-C1; | A68-B40-C2; | A68-B40-C3; | A68-B40-C4; | A68-B40-C5; | A68-B40-C6; |
| A68-B40-C7; | A68-B40-C8; | A68-B40-C9; | A69-B40-C1; | A69-B40-C2; | A69-B40-C3; |
| A69-B40-C4; | A69-B40-C5; | A69-B40-C6; | A69-B40-C7; | A69-B40-C8; | A69-B40-C9; |
| A70-B40-C1; | A70-B40-C2; | A70-B40-C3; | A70-B40-C4; | A70-B40-C5; | A70-B40-C6; |
| A70-B40-C7; | A70-B40-C8; | A70-B40-C9; | A71-B40-C1; | A71-B40-C2; | A71-B40-C3; |
| A71-B40-C4; | A71-B40-C5; | A71-B40-C6; | A71-B40-C7; | A71-B40-C8; | A71-B40-C9; |
| A1-B41-C1; | A1-B41-C2; | A1-B41-C3; | A1-B41-C4; | A1-B41-C5; | A1-B41-C6; |
| A1-B41-C7; | A1-B41-C8; | A1-B41-C9; | A2-B41-C1; | A2-B41-C2; | A2-B41-C3; |
| A2-B41-C4; | A2-B41-C5; | A2-B41-C6; | A2-B41-C7; | A2-B41-C8; | A2-B41-C9; |
| A3-B41-C1; | A3-B41-C2; | A3-B41-C3; | A3-B41-C4; | A3-B41-C5; | A3-B41-C6; |
| A3-B41-C7; | A3-B41-C8; | A3-B41-C9; | A4-B41-C1; | A4-B41-C2; | A4-B41-C3; |
| A4-B41-C4; | A4-B41-C5; | A4-B41-C6; | A4-B41-C7; | A4-B41-C8; | A4-B41-C9; |
| A5-B41-C1; | A5-B41-C2; | A5-B41-C3; | A5-B41-C4; | A5-B41-C5; | A5-B41-C6; |
| A5-B41-C7; | A5-B41-C8; | A5-B41-C9; | A6-B41-C1; | A6-B41-C2; | A6-B41-C3; |
| A6-B41-C4; | A6-B41-C5; | A6-B41-C6; | A6-B41-C7; | A6-B41-C8; | A6-B41-C9; |
| A7-B41-C1; | A7-B41-C2; | A7-B41-C3; | A7-B41-C4; | A7-B41-C5; | A7-B41-C6; |
| A7-B41-C7; | A7-B41-C8; | A7-B41-C9; | A8-B41-C1; | A8-B41-C2; | A8-B41-C3; |
| A8-B41-C4; | A8-B41-C5; | A8-B41-C6; | A8-B41-C7; | A8-B41-C8; | A8-B41-C9; |
| A9-B41-C1; | A9-B41-C2; | A9-B41-C3; | A9-B41-C4; | A9-B41-C5; | A9-B41-C6; |
| A9-B41-C7; | A9-B41-C8; | A9-B41-C9; | A10-B41-C1; | A10-B41-C2; | A10-B41-C3; |
| A10-B41-C4; | A10-B41-C5; | A10-B41-C6; | A10-B41-C7; | A10-B41-C8; | A10-B41-C9; |
| A11-B41-C1; | A11-B41-C2; | A11-B41-C3; | A11-B41-C4; | A11-B41-C5; | A11-B41-C6; |
| A11-B41-C7; | A11-B41-C8; | A11-B41-C9; | A12-B41-C1; | A12-B41-C2; | A12-B41-C3; |
| A12-B41-C4; | A12-B41-C5; | A12-B41-C6; | A12-B41-C7; | A12-B41-C8; | A12-B41-C9; |
| A13-B41-C1; | A13-B41-C2; | A13-B41-C3; | A13-B41-C4; | A13-B41-C5; | A13-B41-C6; |
| A13-B41-C7; | A13-B41-C8; | A13-B41-C9; | A14-B41-C1; | A14-B41-C2; | A14-B41-C3; |
| A14-B41-C4; | A14-B41-C5; | A14-B41-C6; | A14-B41-C7; | A14-B41-C8; | A14-B41-C9; |
| A15-B41-C1; | A15-B41-C2; | A15-B41-C3; | A15-B41-C4; | A15-B41-C5; | A15-B41-C6; |
| A15-B41-C7; | A15-B41-C8; | A15-B41-C9; | A16-B41-C1; | A16-B41-C2; | A16-B41-C3; |
| A16-B41-C4; | A16-B41-C5; | A16-B41-C6; | A16-B41-C7; | A16-B41-C8; | A16-B41-C9; |
| A17-B41-C1; | A17-B41-C2; | A17-B41-C3; | A17-B41-C4; | A17-B41-C5; | A17-B41-C6; |
| A17-B41-C7; | A17-B41-C8; | A17-B41-C9; | A18-B41-C1; | A18-B41-C2; | A18-B41-C3; |
| A18-B41-C4; | A18-B41-C5; | A18-B41-C6; | A18-B41-C7; | A18-B41-C8; | A18-B41-C9; |
| A19-B41-C1; | A19-B41-C2; | A19-B41-C3; | A19-B41-C4; | A19-B41-C5; | A19-B41-C6; |
| A19-B41-C7; | A19-B41-C8; | A19-B41-C9; | A20-B41-C1; | A20-B41-C2; | A20-B41-C3; |
| A20-B41-C4; | A20-B41-C5; | A20-B41-C6; | A20-B41-C7; | A20-B41-C8; | A20-B41-C9; |
| A21-B41-C1; | A21-B41-C2; | A21-B41-C3; | A21-B41-C4; | A21-B41-C5; | A21-B41-C6; |
| A21-B41-C7; | A21-B41-C8; | A21-B41-C9; | A22-B41-C1; | A22-B41-C2; | A22-B41-C3; |
| A22-B41-C4; | A22-B41-C5; | A22-B41-C6; | A22-B41-C7; | A22-B41-C8; | A22-B41-C9; |

-continued

| | | | | | |
|---|---|---|---|---|---|
| A23-B41-C1; | A23-B41-C2; | A23-B41-C3; | A23-B41-C4; | A23-B41-C5; | A23-B41-C6; |
| A23-B41-C7; | A23-B41-C8; | A23-B41-C9; | A24-B41-C1; | A24-B41-C2; | A24-B41-C3; |
| A24-B41-C4; | A24-B41-C5; | A24-B41-C6; | A24-B41-C7; | A24-B41-C8; | A24-B41-C9; |
| A25-B41-C1; | A25-B41-C2; | A25-B41-C3; | A25-B41-C4; | A25-B41-C5; | A25-B41-C6; |
| A25-B41-C7; | A25-B41-C8; | A25-B41-C9; | A26-B41-C1; | A26-B41-C2; | A26-B41-C3; |
| A26-B41-C4; | A26-B41-C5; | A26-B41-C6; | A26-B41-C7; | A26-B41-C8; | A26-B41-C9; |
| A27-B41-C1; | A27-B41-C2; | A27-B41-C3; | A27-B41-C4; | A27-B41-C5; | A27-B41-C6; |
| A27-B41-C7; | A27-B41-C8; | A27-B41-C9; | A28-B41-C1; | A28-B41-C2; | A28-B41-C3; |
| A28-B41-C4; | A28-B41-C5; | A28-B41-C6; | A28-B41-C7; | A28-B41-C8; | A28-B41-C9; |
| A29-B41-C1; | A29-B41-C2; | A29-B41-C3; | A29-B41-C4; | A29-B41-C5; | A29-B41-C6; |
| A29-B41-C7; | A29-B41-C8; | A29-B41-C9; | A30-B41-C1; | A30-B41-C2; | A30-B41-C3; |
| A30-B41-C4; | A30-B41-C5; | A30-B41-C6; | A30-B41-C7; | A30-B41-C8; | A30-B41-C9; |
| A31-B41-C1; | A31-B41-C2; | A31-B41-C3; | A31-B41-C4; | A31-B41-C5; | A31-B41-C6; |
| A31-B41-C7; | A31-B41-C8; | A31-B41-C9; | A32-B41-C1; | A32-B41-C2; | A32-B41-C3; |
| A32-B41-C4; | A32-B41-C5; | A32-B41-C6; | A32-B41-C7; | A32-B41-C8; | A32-B41-C9; |
| A33-B41-C1; | A33-B41-C2; | A33-B41-C3; | A33-B41-C4; | A33-B41-C5; | A33-B41-C6; |
| A33-B41-C7; | A33-B41-C8; | A33-B41-C9; | A34-B41-C1; | A34-B41-C2; | A34-B41-C3; |
| A34-B41-C4; | A34-B41-C5; | A34-B41-C6; | A34-B41-C7; | A34-B41-C8; | A34-B41-C9; |
| A35-B41-C1; | A35-B41-C2; | A35-B41-C3; | A35-B41-C4; | A35-B41-C5; | A35-B41-C6; |
| A35-B41-C7; | A35-B41-C8; | A35-B41-C9; | A36-B41-C1; | A36-B41-C2; | A36-B41-C3; |
| A36-B41-C4; | A36-B41-C5; | A36-B41-C6; | A36-B41-C7; | A36-B41-C8; | A36-B41-C9; |
| A37-B41-C1; | A37-B41-C2; | A37-B41-C3; | A37-B41-C4; | A37-B41-C5; | A37-B41-C6; |
| A37-B41-C7; | A37-B41-C8; | A37-B41-C9; | A38-B41-C1; | A38-B41-C2; | A38-B41-C3; |
| A38-B41-C4; | A38-B41-C5; | A38-B41-C6; | A38-B41-C7; | A38-B41-C8; | A38-B41-C9; |
| A39-B41-C1; | A39-B41-C2; | A39-B41-C3; | A39-B41-C4; | A39-B41-C5; | A39-B41-C6; |
| A39-B41-C7; | A39-B41-C8; | A39-B41-C9; | A40-B41-C1; | A40-B41-C2; | A40-B41-C3; |
| A40-B41-C4; | A40-B41-C5; | A40-B41-C6; | A40-B41-C7; | A40-B41-C8; | A40-B41-C9; |
| A41-B41-C1; | A41-B41-C2; | A41-B41-C3; | A41-B41-C4; | A41-B41-C5; | A41-B41-C6; |
| A41-B41-C7; | A41-B41-C8; | A41-B41-C9; | A42-B41-C1; | A42-B41-C2; | A42-B41-C3; |
| A42-B41-C4; | A42-B41-C5; | A42-B41-C6; | A42-B41-C7; | A42-B41-C8; | A42-B41-C9; |
| A43-B41-C1; | A43-B41-C2; | A43-B41-C3; | A43-B41-C4; | A43-B41-C5; | A43-B41-C6; |
| A43-B41-C7; | A43-B41-C8; | A43-B41-C9; | A44-B41-C1; | A44-B41-C2; | A44-B41-C3; |
| A44-B41-C4; | A44-B41-C5; | A44-B41-C6; | A44-B41-C7; | A44-B41-C8; | A44-B41-C9; |
| A45-B41-C1; | A45-B41-C2; | A45-B41-C3; | A45-B41-C4; | A45-B41-C5; | A45-B41-C6; |
| A45-B41-C7; | A45-B41-C8; | A45-B41-C9; | A46-B41-C1; | A46-B41-C2; | A46-B41-C3; |
| A46-B41-C4; | A46-B41-C5; | A46-B41-C6; | A46-B41-C7; | A46-B41-C8; | A46-B41-C9; |
| A47-B41-C1; | A47-B41-C2; | A47-B41-C3; | A47-B41-C4; | A47-B41-C5; | A47-B41-C6; |
| A47-B41-C7; | A47-B41-C8; | A47-B41-C9; | A48-B41-C1; | A48-B41-C2; | A48-B41-C3; |
| A48-B41-C4; | A48-B41-C5; | A48-B41-C6; | A48-B41-C7; | A48-B41-C8; | A48-B41-C9; |
| A49-B41-C1; | A49-B41-C2; | A49-B41-C3; | A49-B41-C4; | A49-B41-C5; | A49-B41-C6; |
| A49-B41-C7; | A49-B41-C8; | A49-B41-C9; | A50-B41-C1; | A50-B41-C2; | A50-B41-C3; |
| A50-B41-C4; | A50-B41-C5; | A50-B41-C6; | A50-B41-C7; | A50-B41-C8; | A50-B41-C9; |
| A51-B41-C1; | A51-B41-C2; | A51-B41-C3; | A51-B41-C4; | A51-B41-C5; | A51-B41-C6; |
| A51-B41-C7; | A51-B41-C8; | A51-B41-C9; | A52-B41-C1; | A52-B41-C2; | A52-B41-C3; |
| A52-B41-C4; | A52-B41-C5; | A52-B41-C6; | A52-B41-C7; | A52-B41-C8; | A52-B41-C9; |
| A53-B41-C1; | A53-B41-C2; | A53-B41-C3; | A53-B41-C4; | A53-B41-C5; | A53-B41-C6; |
| A53-B41-C7; | A53-B41-C8; | A53-B41-C9; | A54-B41-C1; | A54-B41-C2; | A54-B41-C3; |
| A54-B41-C4; | A54-B41-C5; | A54-B41-C6; | A54-B41-C7; | A54-B41-C8; | A54-B41-C9; |
| A55-B41-C1; | A55-B41-C2; | A55-B41-C3; | A55-B41-C4; | A55-B41-C5; | A55-B41-C6; |
| A55-B41-C7; | A55-B41-C8; | A55-B41-C9; | A56-B41-C1; | A56-B41-C2; | A56-B41-C3; |
| A56-B41-C4; | A56-B41-C5; | A56-B41-C6; | A56-B41-C7; | A56-B41-C8; | A56-B41-C9; |
| A57-B41-C1; | A57-B41-C2; | A57-B41-C3; | A57-B41-C4; | A57-B41-C5; | A57-B41-C6; |
| A57-B41-C7; | A57-B41-C8; | A57-B41-C9; | A58-B41-C1; | A58-B41-C2; | A58-B41-C3; |
| A58-B41-C4; | A58-B41-C5; | A58-B41-C6; | A58-B41-C7; | A58-B41-C8; | A58-B41-C9; |
| A59-B41-C1; | A59-B41-C2; | A59-B41-C3; | A59-B41-C4; | A59-B41-C5; | A59-B41-C6; |
| A59-B41-C7; | A59-B41-C8; | A59-B41-C9; | A60-B41-C1; | A60-B41-C2; | A60-B41-C3; |
| A60-B41-C4; | A60-B41-C5; | A60-B41-C6; | A60-B41-C7; | A60-B41-C8; | A60-B41-C9; |
| A61-B41-C1; | A61-B41-C2; | A61-B41-C3; | A61-B41-C4; | A61-B41-C5; | A61-B41-C6; |
| A61-B41-C7; | A61-B41-C8; | A61-B41-C9; | A62-B41-C1; | A62-B41-C2; | A62-B41-C3; |
| A62-B41-C4; | A62-B41-C5; | A62-B41-C6; | A62-B41-C7; | A62-B41-C8; | A62-B41-C9; |
| A63-B41-C1; | A63-B41-C2; | A63-B41-C3; | A63-B41-C4; | A63-B41-C5; | A63-B41-C6; |
| A63-B41-C7; | A63-B41-C8; | A63-B41-C9; | A64-B41-C1; | A64-B41-C2; | A64-B41-C3; |
| A64-B41-C4; | A64-B41-C5; | A64-B41-C6; | A64-B41-C7; | A64-B41-C8; | A64-B41-C9; |
| A65-B41-C1; | A65-B41-C2; | A65-B41-C3; | A65-B41-C4; | A65-B41-C5; | A65-B41-C6; |
| A65-B41-C7; | A65-B41-C8; | A65-B41-C9; | A66-B41-C1; | A66-B41-C2; | A66-B41-C3; |
| A66-B41-C4; | A66-B41-C5; | A66-B41-C6; | A66-B41-C7; | A66-B41-C8; | A66-B41-C9; |
| A67-B41-C1; | A67-B41-C2; | A67-B41-C3; | A67-B41-C4; | A67-B41-C5; | A67-B41-C6; |
| A67-B41-C7; | A67-B41-C8; | A67-B41-C9; | A68-B41-C1; | A68-B41-C2; | A68-B41-C3; |
| A68-B41-C4; | A68-B41-C5; | A68-B41-C6; | A68-B41-C7; | A68-B41-C8; | A68-B41-C9; |
| A69-B41-C1; | A69-B41-C2; | A69-B41-C3; | A69-B41-C4; | A69-B41-C5; | A69-B41-C6; |
| A69-B41-C7; | A69-B41-C8; | A69-B41-C9; | A70-B41-C1; | A70-B41-C2; | A70-B41-C3; |
| A70-B41-C4; | A70-B41-C5; | A70-B41-C6; | A70-B41-C7; | A70-B41-C8; | A70-B41-C9; |
| A71-B41-C1; | A71-B41-C2; | A71-B41-C3; | A71-B41-C4; | A71-B41-C5; | A71-B41-C6; |
| A71-B41-C7; | A71-B41-C8; | A71-B41-C9; | A1-B42-C1; | A1-B42-C2; | A1-B42-C3; |
| A1-B42-C4; | A1-B42-C5; | A1-B42-C6; | A1-B42-C7; | A1-B42-C8; | A1-B42-C9; |
| A2-B42-C1; | A2-B42-C2; | A2-B42-C3; | A2-B42-C4; | A2-B42-C5; | A2-B42-C6; |
| A2-B42-C7; | A2-B42-C8; | A2-B42-C9; | A3-B42-C1; | A3-B42-C2; | A3-B42-C3; |
| A3-B42-C4; | A3-B42-C5; | A3-B42-C6; | A3-B42-C7; | A3-B42-C8; | A3-B42-C9; |
| A4-B42-C1; | A4-B42-C2; | A4-B42-C3; | A4-B42-C4; | A4-B42-C5; | A4-B42-C6; |

-continued

| | | | | | |
|---|---|---|---|---|---|
| A4-B42-C7; | A4-B42-C8; | A4-B42-C9; | A5-B42-C1; | A5-B42-C2; | A5-B42-C3; |
| A5-B42-C4; | A5-B42-C5; | A5-B42-C6; | A5-B42-C7; | A5-B42-C8; | A5-B42-C9; |
| A6-B42-C1; | A6-B42-C2; | A6-B42-C3; | A6-B42-C4; | A6-B42-C5; | A6-B42-C6; |
| A6-B42-C7; | A6-B42-C8; | A6-B42-C9; | A7-B42-C1; | A7-B42-C2; | A7-B42-C3; |
| A7-B42-C4; | A7-B42-C5; | A7-B42-C6; | A7-B42-C7; | A7-B42-C8; | A7-B42-C9; |
| A8-B42-C1; | A8-B42-C2; | A8-B42-C3; | A8-B42-C4; | A8-B42-C5; | A8-B42-C6; |
| A8-B42-C7; | A8-B42-C8; | A8-B42-C9; | A9-B42-C1; | A9-B42-C2; | A9-B42-C3; |
| A9-B42-C4; | A9-B42-C5; | A9-B42-C6; | A9-B42-C7; | A9-B42-C8; | A9-B42-C9; |
| A10-B42-C1; | A10-B42-C2; | A10-B42-C3; | A10-B42-C4; | A10-B42-C5; | A10-B42-C6; |
| A10-B42-C7; | A10-B42-C8; | A10-B42-C9; | A11-B42-C1; | A11-B42-C2; | A11-B42-C3; |
| A11-B42-C4; | A11-B42-C5; | A11-B42-C6; | A11-B42-C7; | A11-B42-C8; | A11-B42-C9; |
| A12-B42-C1; | A12-B42-C2; | A12-B42-C3; | A12-B42-C4; | A12-B42-C5; | A12-B42-C6; |
| A12-B42-C7; | A12-B42-C8; | A12-B42-C9; | A13-B42-C1; | A13-B42-C2; | A13-B42-C3; |
| A13-B42-C4; | A13-B42-C5; | A13-B42-C6; | A13-B42-C7; | A13-B42-C8; | A13-B42-C9; |
| A14-B42-C1; | A14-B42-C2; | A14-B42-C3; | A14-B42-C4; | A14-B42-C5; | A14-B42-C6; |
| A14-B42-C7; | A14-B42-C8; | A14-B42-C9; | A15-B42-C1; | A15-B42-C2; | A15-B42-C3; |
| A15-B42-C4; | A15-B42-C5; | A15-B42-C6; | A15-B42-C7; | A15-B42-C8; | A15-B42-C9; |
| A16-B42-C1; | A16-B42-C2; | A16-B42-C3; | A16-B42-C4; | A16-B42-C5; | A16-B42-C6; |
| A16-B42-C7; | A16-B42-C8; | A16-B42-C9; | A17-B42-C1; | A17-B42-C2; | A17-B42-C3; |
| A17-B42-C4; | A17-B42-C5; | A17-B42-C6; | A17-B42-C7; | A17-B42-C8; | A17-B42-C9; |
| A18-B42-C1; | A18-B42-C2; | A18-B42-C3; | A18-B42-C4; | A18-B42-C5; | A18-B42-C6; |
| A18-B42-C7; | A18-B42-C8; | A18-B42-C9; | A19-B42-C1; | A19-B42-C2; | A19-B42-C3; |
| A19-B42-C4; | A19-B42-C5; | A19-B42-C6; | A19-B42-C7; | A19-B42-C8; | A19-B42-C9; |
| A20-B42-C1; | A20-B42-C2; | A20-B42-C3; | A20-B42-C4; | A20-B42-C5; | A20-B42-C6; |
| A20-B42-C7; | A20-B42-C8; | A20-B42-C9; | A21-B42-C1; | A21-B42-C2; | A21-B42-C3; |
| A21-B42-C4; | A21-B42-C5; | A21-B42-C6; | A21-B42-C7; | A21-B42-C8; | A21-B42-C9; |
| A22-B42-C1; | A22-B42-C2; | A22-B42-C3; | A22-B42-C4; | A22-B42-C5; | A22-B42-C6; |
| A22-B42-C7; | A22-B42-C8; | A22-B42-C9; | A23-B42-C1; | A23-B42-C2; | A23-B42-C3; |
| A23-B42-C4; | A23-B42-C5; | A23-B42-C6; | A23-B42-C7; | A23-B42-C8; | A23-B42-C9; |
| A24-B42-C1; | A24-B42-C2; | A24-B42-C3; | A24-B42-C4; | A24-B42-C5; | A24-B42-C6; |
| A24-B42-C7; | A24-B42-C8; | A24-B42-C9; | A25-B42-C1; | A25-B42-C2; | A25-B42-C3; |
| A25-B42-C4; | A25-B42-C5; | A25-B42-C6; | A25-B42-C7; | A25-B42-C8; | A25-B42-C9; |
| A26-B42-C1; | A26-B42-C2; | A26-B42-C3; | A26-B42-C4; | A26-B42-C5; | A26-B42-C6; |
| A26-B42-C7; | A26-B42-C8; | A26-B42-C9; | A27-B42-C1; | A27-B42-C2; | A27-B42-C3; |
| A27-B42-C4; | A27-B42-C5; | A27-B42-C6; | A27-B42-C7; | A27-B42-C8; | A27-B42-C9; |
| A28-B42-C1; | A28-B42-C2; | A28-B42-C3; | A28-B42-C4; | A28-B42-C5; | A28-B42-C6; |
| A28-B42-C7; | A28-B42-C8; | A28-B42-C9; | A29-B42-C1; | A29-B42-C2; | A29-B42-C3; |
| A29-B42-C4; | A29-B42-C5; | A29-B42-C6; | A29-B42-C7; | A29-B42-C8; | A29-B42-C9; |
| A30-B42-C1; | A30-B42-C2; | A30-B42-C3; | A30-B42-C4; | A30-B42-C5; | A30-B42-C6; |
| A30-B42-C7; | A30-B42-C8; | A30-B42-C9; | A31-B42-C1; | A31-B42-C2; | A31-B42-C3; |
| A31-B42-C4; | A31-B42-C5; | A31-B42-C6; | A31-B42-C7; | A31-B42-C8; | A31-B42-C9; |
| A32-B42-C1; | A32-B42-C2; | A32-B42-C3; | A32-B42-C4; | A32-B42-C5; | A32-B42-C6; |
| A32-B42-C7; | A32-B42-C8; | A32-B42-C9; | A33-B42-C1; | A33-B42-C2; | A33-B42-C3; |
| A33-B42-C4; | A33-B42-C5; | A33-B42-C6; | A33-B42-C7; | A33-B42-C8; | A33-B42-C9; |
| A34-B42-C1; | A34-B42-C2; | A34-B42-C3; | A34-B42-C4; | A34-B42-C5; | A34-B42-C6; |
| A34-B42-C7; | A34-B42-C8; | A34-B42-C9; | A35-B42-C1; | A35-B42-C2; | A35-B42-C3; |
| A35-B42-C4; | A35-B42-C5; | A35-B42-C6; | A35-B42-C7; | A35-B42-C8; | A35-B42-C9; |
| A36-B42-C1; | A36-B42-C2; | A36-B42-C3; | A36-B42-C4; | A36-B42-C5; | A36-B42-C6; |
| A36-B42-C7; | A36-B42-C8; | A36-B42-C9; | A37-B42-C1; | A37-B42-C2; | A37-B42-C3; |
| A37-B42-C4; | A37-B42-C5; | A37-B42-C6; | A37-B42-C7; | A37-B42-C8; | A37-B42-C9; |
| A38-B42-C1; | A38-B42-C2; | A38-B42-C3; | A38-B42-C4; | A38-B42-C5; | A38-B42-C6; |
| A38-B42-C7; | A38-B42-C8; | A38-B42-C9; | A39-B42-C1; | A39-B42-C2; | A39-B42-C3; |
| A39-B42-C4; | A39-B42-C5; | A39-B42-C6; | A39-B42-C7; | A39-B42-C8; | A39-B42-C9; |
| A40-B42-C1; | A40-B42-C2; | A40-B42-C3; | A40-B42-C4; | A40-B42-C5; | A40-B42-C6; |
| A40-B42-C7; | A40-B42-C8; | A40-B42-C9; | A41-B42-C1; | A41-B42-C2; | A41-B42-C3; |
| A41-B42-C4; | A41-B42-C5; | A41-B42-C6; | A41-B42-C7; | A41-B42-C8; | A41-B42-C9; |
| A42-B42-C1; | A42-B42-C2; | A42-B42-C3; | A42-B42-C4; | A42-B42-C5; | A42-B42-C6; |
| A42-B42-C7; | A42-B42-C8; | A42-B42-C9; | A43-B42-C1; | A43-B42-C2; | A43-B42-C3; |
| A43-B42-C4; | A43-B42-C5; | A43-B42-C6; | A43-B42-C7; | A43-B42-C8; | A43-B42-C9; |
| A44-B42-C1; | A44-B42-C2; | A44-B42-C3; | A44-B42-C4; | A44-B42-C5; | A44-B42-C6; |
| A44-B42-C7; | A44-B42-C8; | A44-B42-C9; | A45-B42-C1; | A45-B42-C2; | A45-B42-C3; |
| A45-B42-C4; | A45-B42-C5; | A45-B42-C6; | A45-B42-C7; | A45-B42-C8; | A45-B42-C9; |
| A46-B42-C1; | A46-B42-C2; | A46-B42-C3; | A46-B42-C4; | A46-B42-C5; | A46-B42-C6; |
| A46-B42-C7; | A46-B42-C8; | A46-B42-C9; | A47-B42-C1; | A47-B42-C2; | A47-B42-C3; |
| A47-B42-C4; | A47-B42-C5; | A47-B42-C6; | A47-B42-C7; | A47-B42-C8; | A47-B42-C9; |
| A48-B42-C1; | A48-B42-C2; | A48-B42-C3; | A48-B42-C4; | A48-B42-C5; | A48-B42-C6; |
| A48-B42-C7; | A48-B42-C8; | A48-B42-C9; | A49-B42-C1; | A49-B42-C2; | A49-B42-C3; |
| A49-B42-C4; | A49-B42-C5; | A49-B42-C6; | A49-B42-C7; | A49-B42-C8; | A49-B42-C9; |
| A50-B42-C1; | A50-B42-C2; | A50-B42-C3; | A50-B42-C4; | A50-B42-C5; | A50-B42-C6; |
| A50-B42-C7; | A50-B42-C8; | A50-B42-C9; | A51-B42-C1; | A51-B42-C2; | A51-B42-C3; |
| A51-B42-C4; | A51-B42-C5; | A51-B42-C6; | A51-B42-C7; | A51-B42-C8; | A51-B42-C9; |
| A52-B42-C1; | A52-B42-C2; | A52-B42-C3; | A52-B42-C4; | A52-B42-C5; | A52-B42-C6; |
| A52-B42-C7; | A52-B42-C8; | A52-B42-C9; | A53-B42-C1; | A53-B42-C2; | A53-B42-C3; |
| A53-B42-C4; | A53-B42-C5; | A53-B42-C6; | A53-B42-C7; | A53-B42-C8; | A53-B42-C9; |
| A54-B42-C1; | A54-B42-C2; | A54-B42-C3; | A54-B42-C4; | A54-B42-C5; | A54-B42-C6; |
| A54-B42-C7; | A54-B42-C8; | A54-B42-C9; | A55-B42-C1; | A55-B42-C2; | A55-B42-C3; |
| A55-B42-C4; | A55-B42-C5; | A55-B42-C6; | A55-B42-C7; | A55-B42-C8; | A55-B42-C9; |
| A56-B42-C1; | A56-B42-C2; | A56-B42-C3; | A56-B42-C4; | A56-B42-C5; | A56-B42-C6; |
| A56-B42-C7; | A56-B42-C8; | A56-B42-C9; | A57-B42-C1; | A57-B42-C2; | A57-B42-C3; |

-continued

| | | | | | |
|---|---|---|---|---|---|
| A57-B42-C4; | A57-B42-C5; | A57-B42-C6; | A57-B42-C7; | A57-B42-C8; | A57-B42-C9; |
| A58-B42-C1; | A58-B42-C2; | A58-B42-C3; | A58-B42-C4; | A58-B42-C5; | A58-B42-C6; |
| A58-B42-C7; | A58-B42-C8; | A58-B42-C9; | A59-B42-C1; | A59-B42-C2; | A59-B42-C3; |
| A59-B42-C4; | A59-B42-C5; | A59-B42-C6; | A59-B42-C7; | A59-B42-C8; | A59-B42-C9; |
| A60-B42-C1; | A60-B42-C2; | A60-B42-C3; | A60-B42-C4; | A60-B42-C5; | A60-B42-C6; |
| A60-B42-C7; | A60-B42-C8; | A60-B42-C9; | A61-B42-C1; | A61-B42-C2; | A61-B42-C3; |
| A61-B42-C4; | A61-B42-C5; | A61-B42-C6; | A61-B42-C7; | A61-B42-C8; | A61-B42-C9; |
| A62-B42-C1; | A62-B42-C2; | A62-B42-C3; | A62-B42-C4; | A62-B42-C5; | A62-B42-C6; |
| A62-B42-C7; | A62-B42-C8; | A62-B42-C9; | A63-B42-C1; | A63-B42-C2; | A63-B42-C3; |
| A63-B42-C4; | A63-B42-C5; | A63-B42-C6; | A63-B42-C7; | A63-B42-C8; | A63-B42-C9; |
| A64-B42-C1; | A64-B42-C2; | A64-B42-C3; | A64-B42-C4; | A64-B42-C5; | A64-B42-C6; |
| A64-B42-C7; | A64-B42-C8; | A64-B42-C9; | A65-B42-C1; | A65-B42-C2; | A65-B42-C3; |
| A65-B42-C4; | A65-B42-C5; | A65-B42-C6; | A65-B42-C7; | A65-B42-C8; | A65-B42-C9; |
| A66-B42-C1; | A66-B42-C2; | A66-B42-C3; | A66-B42-C4; | A66-B42-C5; | A66-B42-C6; |
| A66-B42-C7; | A66-B42-C8; | A66-B42-C9; | A67-B42-C1; | A67-B42-C2; | A67-B42-C3; |
| A67-B42-C4; | A67-B42-C5; | A67-B42-C6; | A67-B42-C7; | A67-B42-C8; | A67-B42-C9; |
| A68-B42-C1; | A68-B42-C2; | A68-B42-C3; | A68-B42-C4; | A68-B42-C5; | A68-B42-C6; |
| A68-B42-C7; | A68-B42-C8; | A68-B42-C9; | A69-B42-C1; | A69-B42-C2; | A69-B42-C3; |
| A69-B42-C4; | A69-B42-C5; | A69-B42-C6; | A69-B42-C7; | A69-B42-C8; | A69-B42-C9; |
| A70-B42-C1; | A70-B42-C2; | A70-B42-C3; | A70-B42-C4; | A70-B42-C5; | A70-B42-C6; |
| A70-B42-C7; | A70-B42-C8; | A70-B42-C9; | A71-B42-C1; | A71-B42-C2; | A71-B42-C3; |
| A71-B42-C4; | A71-B42-C5; | A71-B42-C6; | A71-B42-C7; | A71-B42-C8; | A71-B42-C9; |
| A1-B43-C1; | A1-B43-C2; | A1-B43-C3; | A1-B43-C4; | A1-B43-C5; | A1-B43-C6; |
| A1-B43-C7; | A1-B43-C8; | A1-B43-C9; | A2-B43-C1; | A2-B43-C2; | A2-B43-C3; |
| A2-B43-C4; | A2-B43-C5; | A2-B43-C6; | A2-B43-C7; | A2-B43-C8; | A2-B43-C9; |
| A3-B43-C1; | A3-B43-C2; | A3-B43-C3; | A3-B43-C4; | A3-B43-C5; | A3-B43-C6; |
| A3-B43-C7; | A3-B43-C8; | A3-B43-C9; | A4-B43-C1; | A4-B43-C2; | A4-B43-C3; |
| A4-B43-C4; | A4-B43-C5; | A4-B43-C6; | A4-B43-C7; | A4-B43-C8; | A4-B43-C9; |
| A5-B43-C1; | A5-B43-C2; | A5-B43-C3; | A5-B43-C4; | A5-B43-C5; | A5-B43-C6; |
| A5-B43-C7; | A5-B43-C8; | A5-B43-C9; | A6-B43-C1; | A6-B43-C2; | A6-B43-C3; |
| A6-B43-C4; | A6-B43-C5; | A6-B43-C6; | A6-B43-C7; | A6-B43-C8; | A6-B43-C9; |
| A7-B43-C1; | A7-B43-C2; | A7-B43-C3; | A7-B43-C4; | A7-B43-C5; | A7-B43-C6; |
| A7-B43-C7; | A7-B43-C8; | A7-B43-C9; | A8-B43-C1; | A8-B43-C2; | A8-B43-C3; |
| A8-B43-C4; | A8-B43-C5; | A8-B43-C6; | A8-B43-C7; | A8-B43-C8; | A8-B43-C9; |
| A9-B43-C1; | A9-B43-C2; | A9-B43-C3; | A9-B43-C4; | A9-B43-C5; | A9-B43-C6; |
| A9-B43-C7; | A9-B43-C8; | A9-B43-C9; | A10-B43-C1; | A10-B43-C2; | A10-B43-C3; |
| A10-B43-C4; | A10-B43-C5; | A10-B43-C6; | A10-B43-C7; | A10-B43-C8; | A10-B43-C9; |
| A11-B43-C1; | A11-B43-C2; | A11-B43-C3; | A11-B43-C4; | A11-B43-C5; | A11-B43-C6; |
| A11-B43-C7; | A11-B43-C8; | A11-B43-C9; | A12-B43-C1; | A12-B43-C2; | A12-B43-C3; |
| A12-B43-C4; | A12-B43-C5; | A12-B43-C6; | A12-B43-C7; | A12-B43-C8; | A12-B43-C9; |
| A13-B43-C1; | A13-B43-C2; | A13-B43-C3; | A13-B43-C4; | A13-B43-C5; | A13-B43-C6; |
| A13-B43-C7; | A13-B43-C8; | A13-B43-C9; | A14-B43-C1; | A14-B43-C2; | A14-B43-C3; |
| A14-B43-C4; | A14-B43-C5; | A14-B43-C6; | A14-B43-C7; | A14-B43-C8; | A14-B43-C9; |
| A15-B43-C1; | A15-B43-C2; | A15-B43-C3; | A15-B43-C4; | A15-B43-C5; | A15-B43-C6; |
| A15-B43-C7; | A15-B43-C8; | A15-B43-C9; | A16-B43-C1; | A16-B43-C2; | A16-B43-C3; |
| A16-B43-C4; | A16-B43-C5; | A16-B43-C6; | A16-B43-C7; | A16-B43-C8; | A16-B43-C9; |
| A17-B43-C1; | A17-B43-C2; | A17-B43-C3; | A17-B43-C4; | A17-B43-C5; | A17-B43-C6; |
| A17-B43-C7; | A17-B43-C8; | A17-B43-C9; | A18-B43-C1; | A18-B43-C2; | A18-B43-C3; |
| A18-B43-C4; | A18-B43-C5; | A18-B43-C6; | A18-B43-C7; | A18-B43-C8; | A18-B43-C9; |
| A19-B43-C1; | A19-B43-C2; | A19-B43-C3; | A19-B43-C4; | A19-B43-C5; | A19-B43-C6; |
| A19-B43-C7; | A19-B43-C8; | A19-B43-C9; | A20-B43-C1; | A20-B43-C2; | A20-B43-C3; |
| A20-B43-C4; | A20-B43-C5; | A20-B43-C6; | A20-B43-C7; | A20-B43-C8; | A20-B43-C9; |
| A21-B43-C1; | A21-B43-C2; | A21-B43-C3; | A21-B43-C4; | A21-B43-C5; | A21-B43-C6; |
| A21-B43-C7; | A21-B43-C8; | A21-B43-C9; | A22-B43-C1; | A22-B43-C2; | A22-B43-C3; |
| A22-B43-C4; | A22-B43-C5; | A22-B43-C6; | A22-B43-C7; | A22-B43-C8; | A22-B43-C9; |
| A23-B43-C1; | A23-B43-C2; | A23-B43-C3; | A23-B43-C4; | A23-B43-C5; | A23-B43-C6; |
| A23-B43-C7; | A23-B43-C8; | A23-B43-C9; | A24-B43-C1; | A24-B43-C2; | A24-B43-C3; |
| A24-B43-C4; | A24-B43-C5; | A24-B43-C6; | A24-B43-C7; | A24-B43-C8; | A24-B43-C9; |
| A25-B43-C1; | A25-B43-C2; | A25-B43-C3; | A25-B43-C4; | A25-B43-C5; | A25-B43-C6; |
| A25-B43-C7; | A25-B43-C8; | A25-B43-C9; | A26-B43-C1; | A26-B43-C2; | A26-B43-C3; |
| A26-B43-C4; | A26-B43-C5; | A26-B43-C6; | A26-B43-C7; | A26-B43-C8; | A26-B43-C9; |
| A27-B43-C1; | A27-B43-C2; | A27-B43-C3; | A27-B43-C4; | A27-B43-C5; | A27-B43-C6; |
| A27-B43-C7; | A27-B43-C8; | A27-B43-C9; | A28-B43-C1; | A28-B43-C2; | A28-B43-C3; |
| A28-B43-C4; | A28-B43-C5; | A28-B43-C6; | A28-B43-C7; | A28-B43-C8; | A28-B43-C9; |
| A29-B43-C1; | A29-B43-C2; | A29-B43-C3; | A29-B43-C4; | A29-B43-C5; | A29-B43-C6; |
| A29-B43-C7; | A29-B43-C8; | A29-B43-C9; | A30-B43-C1; | A30-B43-C2; | A30-B43-C3; |
| A30-B43-C4; | A30-B43-C5; | A30-B43-C6; | A30-B43-C7; | A30-B43-C8; | A30-B43-C9; |
| A31-B43-C1; | A31-B43-C2; | A31-B43-C3; | A31-B43-C4; | A31-B43-C5; | A31-B43-C6; |
| A31-B43-C7; | A31-B43-C8; | A31-B43-C9; | A32-B43-C1; | A32-B43-C2; | A32-B43-C3; |
| A32-B43-C4; | A32-B43-C5; | A32-B43-C6; | A32-B43-C7; | A32-B43-C8; | A32-B43-C9; |
| A33-B43-C1; | A33-B43-C2; | A33-B43-C3; | A33-B43-C4; | A33-B43-C5; | A33-B43-C6; |
| A33-B43-C7; | A33-B43-C8; | A33-B43-C9; | A34-B43-C1; | A34-B43-C2; | A34-B43-C3; |
| A34-B43-C4; | A34-B43-C5; | A34-B43-C6; | A34-B43-C7; | A34-B43-C8; | A34-B43-C9; |
| A35-B43-C1; | A35-B43-C2; | A35-B43-C3; | A35-B43-C4; | A35-B43-C5; | A35-B43-C6; |
| A35-B43-C7; | A35-B43-C8; | A35-B43-C9; | A36-B43-C1; | A36-B43-C2; | A36-B43-C3; |
| A36-B43-C4; | A36-B43-C5; | A36-B43-C6; | A36-B43-C7; | A36-B43-C8; | A36-B43-C9; |
| A37-B43-C1; | A37-B43-C2; | A37-B43-C3; | A37-B43-C4; | A37-B43-C5; | A37-B43-C6; |
| A37-B43-C7; | A37-B43-C8; | A37-B43-C9; | A38-B43-C1; | A38-B43-C2; | A38-B43-C3; |
| A38-B43-C4; | A38-B43-C5; | A38-B43-C6; | A38-B43-C7; | A38-B43-C8; | A38-B43-C9; |

-continued

| | | | | | |
|---|---|---|---|---|---|
| A39-B43-C1; | A39-B43-C2; | A39-B43-C3; | A39-B43-C4; | A39-B43-C5; | A39-B43-C6; |
| A39-B43-C7; | A39-B43-C8; | A39-B43-C9; | A40-B43-C1; | A40-B43-C2; | A40-B43-C3; |
| A40-B43-C4; | A40-B43-C5; | A40-B43-C6; | A40-B43-C7; | A40-B43-C8; | A40-B43-C9; |
| A41-B43-C1; | A41-B43-C2; | A41-B43-C3; | A41-B43-C4; | A41-B43-C5; | A41-B43-C6; |
| A41-B43-C7; | A41-B43-C8; | A41-B43-C9; | A42-B43-C1; | A42-B43-C2; | A42-B43-C3; |
| A42-B43-C4; | A42-B43-C5; | A42-B43-C6; | A42-B43-C7; | A42-B43-C8; | A42-B43-C9; |
| A43-B43-C1; | A43-B43-C2; | A43-B43-C3; | A43-B43-C4; | A43-B43-C5; | A43-B43-C6; |
| A43-B43-C7; | A43-B43-C8; | A43-B43-C9; | A44-B43-C1; | A44-B43-C2; | A44-B43-C3; |
| A44-B43-C4; | A44-B43-C5; | A44-B43-C6; | A44-B43-C7; | A44-B43-C8; | A44-B43-C9; |
| A45-B43-C1; | A45-B43-C2; | A45-B43-C3; | A45-B43-C4; | A45-B43-C5; | A45-B43-C6; |
| A45-B43-C7; | A45-B43-C8; | A45-B43-C9; | A46-B43-C1; | A46-B43-C2; | A46-B43-C3; |
| A46-B43-C4; | A46-B43-C5; | A46-B43-C6; | A46-B43-C7; | A46-B43-C8; | A46-B43-C9; |
| A47-B43-C1; | A47-B43-C2; | A47-B43-C3; | A47-B43-C4; | A47-B43-C5; | A47-B43-C6; |
| A47-B43-C7; | A47-B43-C8; | A47-B43-C9; | A48-B43-C1; | A48-B43-C2; | A48-B43-C3; |
| A48-B43-C4; | A48-B43-C5; | A48-B43-C6; | A48-B43-C7; | A48-B43-C8; | A48-B43-C9; |
| A49-B43-C1; | A49-B43-C2; | A49-B43-C3; | A49-B43-C4; | A49-B43-C5; | A49-B43-C6; |
| A49-B43-C7; | A49-B43-C8; | A49-B43-C9; | A50-B43-C1; | A50-B43-C2; | A50-B43-C3; |
| A50-B43-C4; | A50-B43-C5; | A50-B43-C6; | A50-B43-C7; | A50-B43-C8; | A50-B43-C9; |
| A51-B43-C1; | A51-B43-C2; | A51-B43-C3; | A51-B43-C4; | A51-B43-C5; | A51-B43-C6; |
| A51-B43-C7; | A51-B43-C8; | A51-B43-C9; | A52-B43-C1; | A52-B43-C2; | A52-B43-C3; |
| A52-B43-C4; | A52-B43-C5; | A52-B43-C6; | A52-B43-C7; | A52-B43-C8; | A52-B43-C9; |
| A53-B43-C1; | A53-B43-C2; | A53-B43-C3; | A53-B43-C4; | A53-B43-C5; | A53-B43-C6; |
| A53-B43-C7; | A53-B43-C8; | A53-B43-C9; | A54-B43-C1; | A54-B43-C2; | A54-B43-C3; |
| A54-B43-C4; | A54-B43-C5; | A54-B43-C6; | A54-B43-C7; | A54-B43-C8; | A54-B43-C9; |
| A55-B43-C1; | A55-B43-C2; | A55-B43-C3; | A55-B43-C4; | A55-B43-C5; | A55-B43-C6; |
| A55-B43-C7; | A55-B43-C8; | A55-B43-C9; | A56-B43-C1; | A56-B43-C2; | A56-B43-C3; |
| A56-B43-C4; | A56-B43-C5; | A56-B43-C6; | A56-B43-C7; | A56-B43-C8; | A56-B43-C9; |
| A57-B43-C1; | A57-B43-C2; | A57-B43-C3; | A57-B43-C4; | A57-B43-C5; | A57-B43-C6; |
| A57-B43-C7; | A57-B43-C8; | A57-B43-C9; | A58-B43-C1; | A58-B43-C2; | A58-B43-C3; |
| A58-B43-C4; | A58-B43-C5; | A58-B43-C6; | A58-B43-C7; | A58-B43-C8; | A58-B43-C9; |
| A59-B43-C1; | A59-B43-C2; | A59-B43-C3; | A59-B43-C4; | A59-B43-C5; | A59-B43-C6; |
| A59-B43-C7; | A59-B43-C8; | A59-B43-C9; | A60-B43-C1; | A60-B43-C2; | A60-B43-C3; |
| A60-B43-C4; | A60-B43-C5; | A60-B43-C6; | A60-B43-C7; | A60-B43-C8; | A60-B43-C9; |
| A61-B43-C1; | A61-B43-C2; | A61-B43-C3; | A61-B43-C4; | A61-B43-C5; | A61-B43-C6; |
| A61-B43-C7; | A61-B43-C8; | A61-B43-C9; | A62-B43-C1; | A62-B43-C2; | A62-B43-C3; |
| A62-B43-C4; | A62-B43-C5; | A62-B43-C6; | A62-B43-C7; | A62-B43-C8; | A62-B43-C9; |
| A63-B43-C1; | A63-B43-C2; | A63-B43-C3; | A63-B43-C4; | A63-B43-C5; | A63-B43-C6; |
| A63-B43-C7; | A63-B43-C8; | A63-B43-C9; | A64-B43-C1; | A64-B43-C2; | A64-B43-C3; |
| A64-B43-C4; | A64-B43-C5; | A64-B43-C6; | A64-B43-C7; | A64-B43-C8; | A64-B43-C9; |
| A65-B43-C1; | A65-B43-C2; | A65-B43-C3; | A65-B43-C4; | A65-B43-C5; | A65-B43-C6; |
| A65-B43-C7; | A65-B43-C8; | A65-B43-C9; | A66-B43-C1; | A66-B43-C2; | A66-B43-C3; |
| A66-B43-C4; | A66-B43-C5; | A66-B43-C6; | A66-B43-C7; | A66-B43-C8; | A66-B43-C9; |
| A67-B43-C1; | A67-B43-C2; | A67-B43-C3; | A67-B43-C4; | A67-B43-C5; | A67-B43-C6; |
| A67-B43-C7; | A67-B43-C8; | A67-B43-C9; | A68-B43-C1; | A68-B43-C2; | A68-B43-C3; |
| A68-B43-C4; | A68-B43-C5; | A68-B43-C6; | A68-B43-C7; | A68-B43-C8; | A68-B43-C9; |
| A69-B43-C1; | A69-B43-C2; | A69-B43-C3; | A69-B43-C4; | A69-B43-C5; | A69-B43-C6; |
| A69-B43-C7; | A69-B43-C8; | A69-B43-C9; | A70-B43-C1; | A70-B43-C2; | A70-B43-C3; |
| A70-B43-C4; | A70-B43-C5; | A70-B43-C6; | A70-B43-C7; | A70-B43-C8; | A70-B43-C9; |
| A71-B43-C1; | A71-B43-C2; | A71-B43-C3; | A71-B43-C4; | A71-B43-C5; | A71-B43-C6; |
| A71-B43-C7; | A71-B43-C8; | A71-B43-C9; | A1-B44-C1; | A1-B44-C2; | A1-B44-C3; |
| A1-B44-C4; | A1-B44-C5; | A1-B44-C6; | A1-B44-C7; | A1-B44-C8; | A1-B44-C9; |
| A2-B44-C1; | A2-B44-C2; | A2-B44-C3; | A2-B44-C4; | A2-B44-C5; | A2-B44-C6; |
| A2-B44-C7; | A2-B44-C8; | A2-B44-C9; | A3-B44-C1; | A3-B44-C2; | A3-B44-C3; |
| A3-B44-C4; | A3-B44-C5; | A3-B44-C6; | A3-B44-C7; | A3-B44-C8; | A3-B44-C9; |
| A4-B44-C1; | A4-B44-C2; | A4-B44-C3; | A4-B44-C4; | A4-B44-C5; | A4-B44-C6; |
| A4-B44-C7; | A4-B44-C8; | A4-B44-C9; | A5-B44-C1; | A5-B44-C2; | A5-B44-C3; |
| A5-B44-C4; | A5-B44-C5; | A5-B44-C6; | A5-B44-C7; | A5-B44-C8; | A5-B44-C9; |
| A6-B44-C1; | A6-B44-C2; | A6-B44-C3; | A6-B44-C4; | A6-B44-C5; | A6-B44-C6; |
| A6-B44-C7; | A6-B44-C8; | A6-B44-C9; | A7-B44-C1; | A7-B44-C2; | A7-B44-C3; |
| A7-B44-C4; | A7-B44-C5; | A7-B44-C6; | A7-B44-C7; | A7-B44-C8; | A7-B44-C9; |
| A8-B44-C1; | A8-B44-C2; | A8-B44-C3; | A8-B44-C4; | A8-B44-C5; | A8-B44-C6; |
| A8-B44-C7; | A8-B44-C8; | A8-B44-C9; | A9-B44-C1; | A9-B44-C2; | A9-B44-C3; |
| A9-B44-C4; | A9-B44-C5; | A9-B44-C6; | A9-B44-C7; | A9-B44-C8; | A9-B44-C9; |
| A10-B44-C1; | A10-B44-C2; | A10-B44-C3; | A10-B44-C4; | A10-B44-C5; | A10-B44-C6; |
| A10-B44-C7; | A10-B44-C8; | A10-B44-C9; | A11-B44-C1; | A11-B44-C2; | A11-B44-C3; |
| A11-B44-C4; | A11-B44-C5; | A11-B44-C6; | A11-B44-C7; | A11-B44-C8; | A11-B44-C9; |
| A12-B44-C1; | A12-B44-C2; | A12-B44-C3; | A12-B44-C4; | A12-B44-C5; | A12-B44-C6; |
| A12-B44-C7; | A12-B44-C8; | A12-B44-C9; | A13-B44-C1; | A13-B44-C2; | A13-B44-C3; |
| A13-B44-C4; | A13-B44-C5; | A13-B44-C6; | A13-B44-C7; | A13-B44-C8; | A13-B44-C9; |
| A14-B44-C1; | A14-B44-C2; | A14-B44-C3; | A14-B44-C4; | A14-B44-C5; | A14-B44-C6; |
| A14-B44-C7; | A14-B44-C8; | A14-B44-C9; | A15-B44-C1; | A15-B44-C2; | A15-B44-C3; |
| A15-B44-C4; | A15-B44-C5; | A15-B44-C6; | A15-B44-C7; | A15-B44-C8; | A15-B44-C9; |
| A16-B44-C1; | A16-B44-C2; | A16-B44-C3; | A16-B44-C4; | A16-B44-C5; | A16-B44-C6; |
| A16-B44-C7; | A16-B44-C8; | A16-B44-C9; | A17-B44-C1; | A17-B44-C2; | A17-B44-C3; |
| A17-B44-C4; | A17-B44-C5; | A17-B44-C6; | A17-B44-C7; | A17-B44-C8; | A17-B44-C9; |
| A18-B44-C1; | A18-B44-C2; | A18-B44-C3; | A18-B44-C4; | A18-B44-C5; | A18-B44-C6; |
| A18-B44-C7; | A18-B44-C8; | A18-B44-C9; | A19-B44-C1; | A19-B44-C2; | A19-B44-C3; |
| A19-B44-C4; | A19-B44-C5; | A19-B44-C6; | A19-B44-C7; | A19-B44-C8; | A19-B44-C9; |
| A20-B44-C1; | A20-B44-C2; | A20-B44-C3; | A20-B44-C4; | A20-B44-C5; | A20-B44-C6; |

-continued

| | | | | | |
|---|---|---|---|---|---|
| A20-B44-C7; | A20-B44-C8; | A20-B44-C9; | A21-B44-C1; | A21-B44-C2; | A21-B44-C3; |
| A21-B44-C4; | A21-B44-C5; | A21-B44-C6; | A21-B44-C7; | A21-B44-C8; | A21-B44-C9; |
| A22-B44-C1; | A22-B44-C2; | A22-B44-C3; | A22-B44-C4; | A22-B44-C5; | A22-B44-C6; |
| A22-B44-C7; | A22-B44-C8; | A22-B44-C9; | A23-B44-C1; | A23-B44-C2; | A23-B44-C3; |
| A23-B44-C4; | A23-B44-C5; | A23-B44-C6; | A23-B44-C7; | A23-B44-C8; | A23-B44-C9; |
| A24-B44-C1; | A24-B44-C2; | A24-B44-C3; | A24-B44-C4; | A24-B44-C5; | A24-B44-C6; |
| A24-B44-C7; | A24-B44-C8; | A24-B44-C9; | A25-B44-C1; | A25-B44-C2; | A25-B44-C3; |
| A25-B44-C4; | A25-B44-C5; | A25-B44-C6; | A25-B44-C7; | A25-B44-C8; | A25-B44-C9; |
| A26-B44-C1; | A26-B44-C2; | A26-B44-C3; | A26-B44-C4; | A26-B44-C5; | A26-B44-C6; |
| A26-B44-C7; | A26-B44-C8; | A26-B44-C9; | A27-B44-C1; | A27-B44-C2; | A27-B44-C3; |
| A27-B44-C4; | A27-B44-C5; | A27-B44-C6; | A27-B44-C7; | A27-B44-C8; | A27-B44-C9; |
| A28-B44-C1; | A28-B44-C2; | A28-B44-C3; | A28-B44-C4; | A28-B44-C5; | A28-B44-C6; |
| A28-B44-C7; | A28-B44-C8; | A28-B44-C9; | A29-B44-C1; | A29-B44-C2; | A29-B44-C3; |
| A29-B44-C4; | A29-B44-C5; | A29-B44-C6; | A29-B44-C7; | A29-B44-C8; | A29-B44-C9; |
| A30-B44-C1; | A30-B44-C2; | A30-B44-C3; | A30-B44-C4; | A30-B44-C5; | A30-B44-C6; |
| A30-B44-C7; | A30-B44-C8; | A30-B44-C9; | A31-B44-C1; | A31-B44-C2; | A31-B44-C3; |
| A31-B44-C4; | A31-B44-C5; | A31-B44-C6; | A31-B44-C7; | A31-B44-C8; | A31-B44-C9; |
| A32-B44-C1; | A32-B44-C2; | A32-B44-C3; | A32-B44-C4; | A32-B44-C5; | A32-B44-C6; |
| A32-B44-C7; | A32-B44-C8; | A32-B44-C9; | A33-B44-C1; | A33-B44-C2; | A33-B44-C3; |
| A33-B44-C4; | A33-B44-C5; | A33-B44-C6; | A33-B44-C7; | A33-B44-C8; | A33-B44-C9; |
| A34-B44-C1; | A34-B44-C2; | A34-B44-C3; | A34-B44-C4; | A34-B44-C5; | A34-B44-C6; |
| A34-B44-C7; | A34-B44-C8; | A34-B44-C9; | A35-B44-C1; | A35-B44-C2; | A35-B44-C3; |
| A35-B44-C4; | A35-B44-C5; | A35-B44-C6; | A35-B44-C7; | A35-B44-C8; | A35-B44-C9; |
| A36-B44-C1; | A36-B44-C2; | A36-B44-C3; | A36-B44-C4; | A36-B44-C5; | A36-B44-C6; |
| A36-B44-C7; | A36-B44-C8; | A36-B44-C9; | A37-B44-C1; | A37-B44-C2; | A37-B44-C3; |
| A37-B44-C4; | A37-B44-C5; | A37-B44-C6; | A37-B44-C7; | A37-B44-C8; | A37-B44-C9; |
| A38-B44-C1; | A38-B44-C2; | A38-B44-C3; | A38-B44-C4; | A38-B44-C5; | A38-B44-C6; |
| A38-B44-C7; | A38-B44-C8; | A38-B44-C9; | A39-B44-C1; | A39-B44-C2; | A39-B44-C3; |
| A39-B44-C4; | A39-B44-C5; | A39-B44-C6; | A39-B44-C7; | A39-B44-C8; | A39-B44-C9; |
| A40-B44-C1; | A40-B44-C2; | A40-B44-C3; | A40-B44-C4; | A40-B44-C5; | A40-B44-C6; |
| A40-B44-C7; | A40-B44-C8; | A40-B44-C9; | A41-B44-C1; | A41-B44-C2; | A41-B44-C3; |
| A41-B44-C4; | A41-B44-C5; | A41-B44-C6; | A41-B44-C7; | A41-B44-C8; | A41-B44-C9; |
| A42-B44-C1; | A42-B44-C2; | A42-B44-C3; | A42-B44-C4; | A42-B44-C5; | A42-B44-C6; |
| A42-B44-C7; | A42-B44-C8; | A42-B44-C9; | A43-B44-C1; | A43-B44-C2; | A43-B44-C3; |
| A43-B44-C4; | A43-B44-C5; | A43-B44-C6; | A43-B44-C7; | A43-B44-C8; | A43-B44-C9; |
| A44-B44-C1; | A44-B44-C2; | A44-B44-C3; | A44-B44-C4; | A44-B44-C5; | A44-B44-C6; |
| A44-B44-C7; | A44-B44-C8; | A44-B44-C9; | A45-B44-C1; | A45-B44-C2; | A45-B44-C3; |
| A45-B44-C4; | A45-B44-C5; | A45-B44-C6; | A45-B44-C7; | A45-B44-C8; | A45-B44-C9; |
| A46-B44-C1; | A46-B44-C2; | A46-B44-C3; | A46-B44-C4; | A46-B44-C5; | A46-B44-C6; |
| A46-B44-C7; | A46-B44-C8; | A46-B44-C9; | A47-B44-C1; | A47-B44-C2; | A47-B44-C3; |
| A47-B44-C4; | A47-B44-C5; | A47-B44-C6; | A47-B44-C7; | A47-B44-C8; | A47-B44-C9; |
| A48-B44-C1; | A48-B44-C2; | A48-B44-C3; | A48-B44-C4; | A48-B44-C5; | A48-B44-C6; |
| A48-B44-C7; | A48-B44-C8; | A48-B44-C9; | A49-B44-C1; | A49-B44-C2; | A49-B44-C3; |
| A49-B44-C4; | A49-B44-C5; | A49-B44-C6; | A49-B44-C7; | A49-B44-C8; | A49-B44-C9; |
| A50-B44-C1; | A50-B44-C2; | A50-B44-C3; | A50-B44-C4; | A50-B44-C5; | A50-B44-C6; |
| A50-B44-C7; | A50-B44-C8; | A50-B44-C9; | A51-B44-C1; | A51-B44-C2; | A51-B44-C3; |
| A51-B44-C4; | A51-B44-C5; | A51-B44-C6; | A51-B44-C7; | A51-B44-C8; | A51-B44-C9; |
| A52-B44-C1; | A52-B44-C2; | A52-B44-C3; | A52-B44-C4; | A52-B44-C5; | A52-B44-C6; |
| A52-B44-C7; | A52-B44-C8; | A52-B44-C9; | A53-B44-C1; | A53-B44-C2; | A53-B44-C3; |
| A53-B44-C4; | A53-B44-C5; | A53-B44-C6; | A53-B44-C7; | A53-B44-C8; | A53-B44-C9; |
| A54-B44-C1; | A54-B44-C2; | A54-B44-C3; | A54-B44-C4; | A54-B44-C5; | A54-B44-C6; |
| A54-B44-C7; | A54-B44-C8; | A54-B44-C9; | A55-B44-C1; | A55-B44-C2; | A55-B44-C3; |
| A55-B44-C4; | A55-B44-C5; | A55-B44-C6; | A55-B44-C7; | A55-B44-C8; | A55-B44-C9; |
| A56-B44-C1; | A56-B44-C2; | A56-B44-C3; | A56-B44-C4; | A56-B44-C5; | A56-B44-C6; |
| A56-B44-C7; | A56-B44-C8; | A56-B44-C9; | A57-B44-C1; | A57-B44-C2; | A57-B44-C3; |
| A57-B44-C4; | A57-B44-C5; | A57-B44-C6; | A57-B44-C7; | A57-B44-C8; | A57-B44-C9; |
| A58-B44-C1; | A58-B44-C2; | A58-B44-C3; | A58-B44-C4; | A58-B44-C5; | A58-B44-C6; |
| A58-B44-C7; | A58-B44-C8; | A58-B44-C9; | A59-B44-C1; | A59-B44-C2; | A59-B44-C3; |
| A59-B44-C4; | A59-B44-C5; | A59-B44-C6; | A59-B44-C7; | A59-B44-C8; | A59-B44-C9; |
| A60-B44-C1; | A60-B44-C2; | A60-B44-C3; | A60-B44-C4; | A60-B44-C5; | A60-B44-C6; |
| A60-B44-C7; | A60-B44-C8; | A60-B44-C9; | A61-B44-C1; | A61-B44-C2; | A61-B44-C3; |
| A61-B44-C4; | A61-B44-C5; | A61-B44-C6; | A61-B44-C7; | A61-B44-C8; | A61-B44-C9; |
| A62-B44-C1; | A62-B44-C2; | A62-B44-C3; | A62-B44-C4; | A62-B44-C5; | A62-B44-C6; |
| A62-B44-C7; | A62-B44-C8; | A62-B44-C9; | A63-B44-C1; | A63-B44-C2; | A63-B44-C3; |
| A63-B44-C4; | A63-B44-C5; | A63-B44-C6; | A63-B44-C7; | A63-B44-C8; | A63-B44-C9; |
| A64-B44-C1; | A64-B44-C2; | A64-B44-C3; | A64-B44-C4; | A64-B44-C5; | A64-B44-C6; |
| A64-B44-C7; | A64-B44-C8; | A64-B44-C9; | A65-B44-C1; | A65-B44-C2; | A65-B44-C3; |
| A65-B44-C4; | A65-B44-C5; | A65-B44-C6; | A65-B44-C7; | A65-B44-C8; | A65-B44-C9; |
| A66-B44-C1; | A66-B44-C2; | A66-B44-C3; | A66-B44-C4; | A66-B44-C5; | A66-B44-C6; |
| A66-B44-C7; | A66-B44-C8; | A66-B44-C9; | A67-B44-C1; | A67-B44-C2; | A67-B44-C3; |
| A67-B44-C4; | A67-B44-C5; | A67-B44-C6; | A67-B44-C7; | A67-B44-C8; | A67-B44-C9; |
| A68-B44-C1; | A68-B44-C2; | A68-B44-C3; | A68-B44-C4; | A68-B44-C5; | A68-B44-C6; |
| A68-B44-C7; | A68-B44-C8; | A68-B44-C9; | A69-B44-C1; | A69-B44-C2; | A69-B44-C3; |
| A69-B44-C4; | A69-B44-C5; | A69-B44-C6; | A69-B44-C7; | A69-B44-C8; | A69-B44-C9; |
| A70-B44-C1; | A70-B44-C2; | A70-B44-C3; | A70-B44-C4; | A70-B44-C5; | A70-B44-C6; |
| A70-B44-C7; | A70-B44-C8; | A70-B44-C9; | A71-B44-C1; | A71-B44-C2; | A71-B44-C3; |
| A71-B44-C4; | A71-B44-C5; | A71-B44-C6; | A71-B44-C7; | A71-B44-C8; | A71-B44-C9; |
| A1-B45-C1; | A1-B45-C2; | A1-B45-C3; | A1-B45-C4; | A1-B45-C5; | A1-B45-C6; |
| A1-B45-C7; | A1-B45-C8; | A1-B45-C9; | A2-B45-C1; | A2-B45-C2; | A2-B45-C3; |

-continued

| | | | | | |
|---|---|---|---|---|---|
| A2-B45-C4; | A2-B45-C5; | A2-B45-C6; | A2-B45-C7; | A2-B45-C8; | A2-B45-C9; |
| A3-B45-C1; | A3-B45-C2; | A3-B45-C3; | A3-B45-C4; | A3-B45-C5; | A3-B45-C6; |
| A3-B45-C7; | A3-B45-C8; | A3-B45-C9; | A4-B45-C1; | A4-B45-C2; | A4-B45-C3; |
| A4-B45-C4; | A4-B45-C5; | A4-B45-C6; | A4-B45-C7; | A4-B45-C8; | A4-B45-C9; |
| A5-B45-C1; | A5-B45-C2; | A5-B45-C3; | A5-B45-C4; | A5-B45-C5; | A5-B45-C6; |
| A5-B45-C7; | A5-B45-C8; | A5-B45-C9; | A6-B45-C1; | A6-B45-C2; | A6-B45-C3; |
| A6-B45-C4; | A6-B45-C5; | A6-B45-C6; | A6-B45-C7; | A6-B45-C8; | A6-B45-C9; |
| A7-B45-C1; | A7-B45-C2; | A7-B45-C3; | A7-B45-C4; | A7-B45-C5; | A7-B45-C6; |
| A7-B45-C7; | A7-B45-C8; | A7-B45-C9; | A8-B45-C1; | A8-B45-C2; | A8-B45-C3; |
| A8-B45-C4; | A8-B45-C5; | A8-B45-C6; | A8-B45-C7; | A8-B45-C8; | A8-B45-C9; |
| A9-B45-C1; | A9-B45-C2; | A9-B45-C3; | A9-B45-C4; | A9-B45-C5; | A9-B45-C6; |
| A9-B45-C7; | A9-B45-C8; | A9-B45-C9; | A10-B45-C1; | A10-B45-C2; | A10-B45-C3; |
| A10-B45-C4; | A10-B45-C5; | A10-B45-C6; | A10-B45-C7; | A10-B45-C8; | A10-B45-C9; |
| A11-B45-C1; | A11-B45-C2; | A11-B45-C3; | A11-B45-C4; | A11-B45-C5; | A11-B45-C6; |
| A11-B45-C7; | A11-B45-C8; | A11-B45-C9; | A12-B45-C1; | A12-B45-C2; | A12-B45-C3; |
| A12-B45-C4; | A12-B45-C5; | A12-B45-C6; | A12-B45-C7; | A12-B45-C8; | A12-B45-C9; |
| A13-B45-C1; | A13-B45-C2; | A13-B45-C3; | A13-B45-C4; | A13-B45-C5; | A13-B45-C6; |
| A13-B45-C7; | A13-B45-C8; | A13-B45-C9; | A14-B45-C1; | A14-B45-C2; | A14-B45-C3; |
| A14-B45-C4; | A14-B45-C5; | A14-B45-C6; | A14-B45-C7; | A14-B45-C8; | A14-B45-C9; |
| A15-B45-C1; | A15-B45-C2; | A15-B45-C3; | A15-B45-C4; | A15-B45-C5; | A15-B45-C6; |
| A15-B45-C7; | A15-B45-C8; | A15-B45-C9; | A16-B45-C1; | A16-B45-C2; | A16-B45-C3; |
| A16-B45-C4; | A16-B45-C5; | A16-B45-C6; | A16-B45-C7; | A16-B45-C8; | A16-B45-C9; |
| A17-B45-C1; | A17-B45-C2; | A17-B45-C3; | A17-B45-C4; | A17-B45-C5; | A17-B45-C6; |
| A17-B45-C7; | A17-B45-C8; | A17-B45-C9; | A18-B45-C1; | A18-B45-C2; | A18-B45-C3; |
| A18-B45-C4; | A18-B45-C5; | A18-B45-C6; | A18-B45-C7; | A18-B45-C8; | A18-B45-C9; |
| A19-B45-C1; | A19-B45-C2; | A19-B45-C3; | A19-B45-C4; | A19-B45-C5; | A19-B45-C6; |
| A19-B45-C7; | A19-B45-C8; | A19-B45-C9; | A20-B45-C1; | A20-B45-C2; | A20-B45-C3; |
| A20-B45-C4; | A20-B45-C5; | A20-B45-C6; | A20-B45-C7; | A20-B45-C8; | A20-B45-C9; |
| A21-B45-C1; | A21-B45-C2; | A21-B45-C3; | A21-B45-C4; | A21-B45-C5; | A21-B45-C6; |
| A21-B45-C7; | A21-B45-C8; | A21-B45-C9; | A22-B45-C1; | A22-B45-C2; | A22-B45-C3; |
| A22-B45-C4; | A22-B45-C5; | A22-B45-C6; | A22-B45-C7; | A22-B45-C8; | A22-B45-C9; |
| A23-B45-C1; | A23-B45-C2; | A23-B45-C3; | A23-B45-C4; | A23-B45-C5; | A23-B45-C6; |
| A23-B45-C7; | A23-B45-C8; | A23-B45-C9; | A24-B45-C1; | A24-B45-C2; | A24-B45-C3; |
| A24-B45-C4; | A24-B45-C5; | A24-B45-C6; | A24-B45-C7; | A24-B45-C8; | A24-B45-C9; |
| A25-B45-C1; | A25-B45-C2; | A25-B45-C3; | A25-B45-C4; | A25-B45-C5; | A25-B45-C6; |
| A25-B45-C7; | A25-B45-C8; | A25-B45-C9; | A26-B45-C1; | A26-B45-C2; | A26-B45-C3; |
| A26-B45-C4; | A26-B45-C5; | A26-B45-C6; | A26-B45-C7; | A26-B45-C8; | A26-B45-C9; |
| A27-B45-C1; | A27-B45-C2; | A27-B45-C3; | A27-B45-C4; | A27-B45-C5; | A27-B45-C6; |
| A27-B45-C7; | A27-B45-C8; | A27-B45-C9; | A28-B45-C1; | A28-B45-C2; | A28-B45-C3; |
| A28-B45-C4; | A28-B45-C5; | A28-B45-C6; | A28-B45-C7; | A28-B45-C8; | A28-B45-C9; |
| A29-B45-C1; | A29-B45-C2; | A29-B45-C3; | A29-B45-C4; | A29-B45-C5; | A29-B45-C6; |
| A29-B45-C7; | A29-B45-C8; | A29-B45-C9; | A30-B45-C1; | A30-B45-C2; | A30-B45-C3; |
| A30-B45-C4; | A30-B45-C5; | A30-B45-C6; | A30-B45-C7; | A30-B45-C8; | A30-B45-C9; |
| A31-B45-C1; | A31-B45-C2; | A31-B45-C3; | A31-B45-C4; | A31-B45-C5; | A31-B45-C6; |
| A31-B45-C7; | A31-B45-C8; | A31-B45-C9; | A32-B45-C1; | A32-B45-C2; | A32-B45-C3; |
| A32-B45-C4; | A32-B45-C5; | A32-B45-C6; | A32-B45-C7; | A32-B45-C8; | A32-B45-C9; |
| A33-B45-C1; | A33-B45-C2; | A33-B45-C3; | A33-B45-C4; | A33-B45-C5; | A33-B45-C6; |
| A33-B45-C7; | A33-B45-C8; | A33-B45-C9; | A34-B45-C1; | A34-B45-C2; | A34-B45-C3; |
| A34-B45-C4; | A34-B45-C5; | A34-B45-C6; | A34-B45-C7; | A34-B45-C8; | A34-B45-C9; |
| A35-B45-C1; | A35-B45-C2; | A35-B45-C3; | A35-B45-C4; | A35-B45-C5; | A35-B45-C6; |
| A35-B45-C7; | A35-B45-C8; | A35-B45-C9; | A36-B45-C1; | A36-B45-C2; | A36-B45-C3; |
| A36-B45-C4; | A36-B45-C5; | A36-B45-C6; | A36-B45-C7; | A36-B45-C8; | A36-B45-C9; |
| A37-B45-C1; | A37-B45-C2; | A37-B45-C3; | A37-B45-C4; | A37-B45-C5; | A37-B45-C6; |
| A37-B45-C7; | A37-B45-C8; | A37-B45-C9; | A38-B45-C1; | A38-B45-C2; | A38-B45-C3; |
| A38-B45-C4; | A38-B45-C5; | A38-B45-C6; | A38-B45-C7; | A38-B45-C8; | A38-B45-C9; |
| A39-B45-C1; | A39-B45-C2; | A39-B45-C3; | A39-B45-C4; | A39-B45-C5; | A39-B45-C6; |
| A39-B45-C7; | A39-B45-C8; | A39-B45-C9; | A40-B45-C1; | A40-B45-C2; | A40-B45-C3; |
| A40-B45-C4; | A40-B45-C5; | A40-B45-C6; | A40-B45-C7; | A40-B45-C8; | A40-B45-C9; |
| A41-B45-C1; | A41-B45-C2; | A41-B45-C3; | A41-B45-C4; | A41-B45-C5; | A41-B45-C6; |
| A41-B45-C7; | A41-B45-C8; | A41-B45-C9; | A42-B45-C1; | A42-B45-C2; | A42-B45-C3; |
| A42-B45-C4; | A42-B45-C5; | A42-B45-C6; | A42-B45-C7; | A42-B45-C8; | A42-B45-C9; |
| A43-B45-C1; | A43-B45-C2; | A43-B45-C3; | A43-B45-C4; | A43-B45-C5; | A43-B45-C6; |
| A43-B45-C7; | A43-B45-C8; | A43-B45-C9; | A44-B45-C1; | A44-B45-C2; | A44-B45-C3; |
| A44-B45-C4; | A44-B45-C5; | A44-B45-C6; | A44-B45-C7; | A44-B45-C8; | A44-B45-C9; |
| A45-B45-C1; | A45-B45-C2; | A45-B45-C3; | A45-B45-C4; | A45-B45-C5; | A45-B45-C6; |
| A45-B45-C7; | A45-B45-C8; | A45-B45-C9; | A46-B45-C1; | A46-B45-C2; | A46-B45-C3; |
| A46-B45-C4; | A46-B45-C5; | A46-B45-C6; | A46-B45-C7; | A46-B45-C8; | A46-B45-C9; |
| A47-B45-C1; | A47-B45-C2; | A47-B45-C3; | A47-B45-C4; | A47-B45-C5; | A47-B45-C6; |
| A47-B45-C7; | A47-B45-C8; | A47-B45-C9; | A48-B45-C1; | A48-B45-C2; | A48-B45-C3; |
| A48-B45-C4; | A48-B45-C5; | A48-B45-C6; | A48-B45-C7; | A48-B45-C8; | A48-B45-C9; |
| A49-B45-C1; | A49-B45-C2; | A49-B45-C3; | A49-B45-C4; | A49-B45-C5; | A49-B45-C6; |
| A49-B45-C7; | A49-B45-C8; | A49-B45-C9; | A50-B45-C1; | A50-B45-C2; | A50-B45-C3; |
| A50-B45-C4; | A50-B45-C5; | A50-B45-C6; | A50-B45-C7; | A50-B45-C8; | A50-B45-C9; |
| A51-B45-C1; | A51-B45-C2; | A51-B45-C3; | A51-B45-C4; | A51-B45-C5; | A51-B45-C6; |
| A51-B45-C7; | A51-B45-C8; | A51-B45-C9; | A52-B45-C1; | A52-B45-C2; | A52-B45-C3; |
| A52-B45-C4; | A52-B45-C5; | A52-B45-C6; | A52-B45-C7; | A52-B45-C8; | A52-B45-C9; |
| A53-B45-C1; | A53-B45-C2; | A53-B45-C3; | A53-B45-C4; | A53-B45-C5; | A53-B45-C6; |
| A53-B45-C7; | A53-B45-C8; | A53-B45-C9; | A54-B45-C1; | A54-B45-C2; | A54-B45-C3; |
| A54-B45-C4; | A54-B45-C5; | A54-B45-C6; | A54-B45-C7; | A54-B45-C8; | A54-B45-C9; |

-continued

| | | | | | |
|---|---|---|---|---|---|
| A55-B45-C1; | A55-B45-C2; | A55-B45-C3; | A55-B45-C4; | A55-B45-C5; | A55-B45-C6; |
| A55-B45-C7; | A55-B45-C8; | A55-B45-C9; | A56-B45-C1; | A56-B45-C2; | A56-B45-C3; |
| A56-B45-C4; | A56-B45-C5; | A56-B45-C6; | A56-B45-C7; | A56-B45-C8; | A56-B45-C9; |
| A57-B45-C1; | A57-B45-C2; | A57-B45-C3; | A57-B45-C4; | A57-B45-C5; | A57-B45-C6; |
| A57-B45-C7; | A57-B45-C8; | A57-B45-C9; | A58-B45-C1; | A58-B45-C2; | A58-B45-C3; |
| A58-B45-C4; | A58-B45-C5; | A58-B45-C6; | A58-B45-C7; | A58-B45-C8; | A58-B45-C9; |
| A59-B45-C1; | A59-B45-C2; | A59-B45-C3; | A59-B45-C4; | A59-B45-C5; | A59-B45-C6; |
| A59-B45-C7; | A59-B45-C8; | A59-B45-C9; | A60-B45-C1; | A60-B45-C2; | A60-B45-C3; |
| A60-B45-C4; | A60-B45-C5; | A60-B45-C6; | A60-B45-C7; | A60-B45-C8; | A60-B45-C9; |
| A61-B45-C1; | A61-B45-C2; | A61-B45-C3; | A61-B45-C4; | A61-B45-C5; | A61-B45-C6; |
| A61-B45-C7; | A61-B45-C8; | A61-B45-C9; | A62-B45-C1; | A62-B45-C2; | A62-B45-C3; |
| A62-B45-C4; | A62-B45-C5; | A62-B45-C6; | A62-B45-C7; | A62-B45-C8; | A62-B45-C9; |
| A63-B45-C1; | A63-B45-C2; | A63-B45-C3; | A63-B45-C4; | A63-B45-C5; | A63-B45-C6; |
| A63-B45-C7; | A63-B45-C8; | A63-B45-C9; | A64-B45-C1; | A64-B45-C2; | A64-B45-C3; |
| A64-B45-C4; | A64-B45-C5; | A64-B45-C6; | A64-B45-C7; | A64-B45-C8; | A64-B45-C9; |
| A65-B45-C1; | A65-B45-C2; | A65-B45-C3; | A65-B45-C4; | A65-B45-C5; | A65-B45-C6; |
| A65-B45-C7; | A65-B45-C8; | A65-B45-C9; | A66-B45-C1; | A66-B45-C2; | A66-B45-C3; |
| A66-B45-C4; | A66-B45-C5; | A66-B45-C6; | A66-B45-C7; | A66-B45-C8; | A66-B45-C9; |
| A67-B45-C1; | A67-B45-C2; | A67-B45-C3; | A67-B45-C4; | A67-B45-C5; | A67-B45-C6; |
| A67-B45-C7; | A67-B45-C8; | A67-B45-C9; | A68-B45-C1; | A68-B45-C2; | A68-B45-C3; |
| A68-B45-C4; | A68-B45-C5; | A68-B45-C6; | A68-B45-C7; | A68-B45-C8; | A68-B45-C9; |
| A69-B45-C1; | A69-B45-C2; | A69-B45-C3; | A69-B45-C4; | A69-B45-C5; | A69-B45-C6; |
| A69-B45-C7; | A69-B45-C8; | A69-B45-C9; | A70-B45-C1; | A70-B45-C2; | A70-B45-C3; |
| A70-B45-C4; | A70-B45-C5; | A70-B45-C6; | A70-B45-C7; | A70-B45-C8; | A70-B45-C9; |
| A71-B45-C1; | A71-B45-C2; | A71-B45-C3; | A71-B45-C4; | A71-B45-C5; | A71-B45-C6; |
| A71-B45-C7; | A71-B45-C8; | A71-B45-C9; | A1-B46-C1; | A1-B46-C2; | A1-B46-C3; |
| A1-B46-C4; | A1-B46-C5; | A1-B46-C6; | A1-B46-C7; | A1-B46-C8; | A1-B46-C9 |
| A2-B46-C1; | A2-B46-C2; | A2-B46-C3; | A2-B46-C4; | A2-B46-C5; | A2-B46-C6; |
| A2-B46-C7; | A2-B46-C8; | A2-B46-C9; | A3-B46-C1; | A3-B46-C2; | A3-B46-C3; |
| A3-B46-C4; | A3-B46-C5; | A3-B46-C6; | A3-B46-C7; | A3-B46-C8; | A3-B46-C9; |
| A4-B46-C1; | A4-B46-C2; | A4-B46-C3; | A4-B46-C4; | A4-B46-C5; | A4-B46-C6; |
| A4-B46-C7; | A4-B46-C8; | A4-B46-C9; | A5-B46-C1; | A5-B46-C2; | A5-B46-C3; |
| A5-B46-C4; | A5-B46-C5; | A5-B46-C6; | A5-B46-C7; | A5-B46-C8; | A5-B46-C9; |
| A6-B46-C1; | A6-B46-C2; | A6-B46-C3; | A6-B46-C4; | A6-B46-C5; | A6-B46-C6; |
| A6-B46-C7; | A6-B46-C8; | A6-B46-C9; | A7-B46-C1; | A7-B46-C2; | A7-B46-C3; |
| A7-B46-C4; | A7-B46-C5; | A7-B46-C6; | A7-B46-C7; | A7-B46-C8; | A7-B46-C9; |
| A8-B46-C1; | A8-B46-C2; | A8-B46-C3; | A8-B46-C4; | A8-B46-C5; | A8-B46-C6; |
| A8-B46-C7; | A8-B46-C8; | A8-B46-C9; | A9-B46-C1; | A9-B46-C2; | A9-B46-C3; |
| A9-B46-C4; | A9-B46-C5; | A9-B46-C6; | A9-B46-C7; | A9-B46-C8; | A9-B46-C9; |
| A10-B46-C2; | A10-B46-C3; | A10-B46-C4; | A10-B46-C5; | A10-B46-C6; | |
| A10-B46-C7; | A10-B46-C8; | A10-B46-C9; | A11-B46-C1; | A11-B46-C2; | A11-B46-C3; |
| A11-B46-C4; | A11-B46-C5; | A11-B46-C6; | A11-B46-C7; | A11-B46-C8; | A11-B46-C9; |
| A12-B46-C1; | A12-B46-C2; | A12-B46-C3; | A12-B46-C4; | A12-B46-C5; | A12-B46-C6; |
| A12-B46-C7; | A12-B46-C8; | A12-B46-C9; | A13-B46-C1; | A13-B46-C2; | A13-B46-C3; |
| A13-B46-C4; | A13-B46-C5; | A13-B46-C6; | A13-B46-C7; | A13-B46-C8; | A13-B46-C9; |
| A14-B46-C1; | A14-B46-C2; | A14-B46-C3; | A14-B46-C4; | A14-B46-C5; | A14-B46-C6; |
| A14-B46-C7; | A14-B46-C8; | A14-B46-C9; | A15-B46-C1; | A15-B46-C2; | A15-B46-C3; |
| A15-B46-C4; | A15-B46-C5; | A15-B46-C6; | A15-B46-C7; | A15-B46-C8; | A15-B46-C9; |
| A16-B46-C1; | A16-B46-C2; | A16-B46-C3; | A16-B46-C4; | A16-B46-C5; | A16-B46-C6; |
| A16-B46-C7; | A16-B46-C8; | A16-B46-C9; | A17-B46-C1; | A17-B46-C2; | A17-B46-C3; |
| A17-B46-C4; | A17-B46-C5; | A17-B46-C6; | A17-B46-C7; | A17-B46-C8; | A17-B46-C9; |
| A18-B46-C1; | A18-B46-C2; | A18-B46-C3; | A18-B46-C4; | A18-B46-C5; | A18-B46-C6; |
| A18-B46-C7; | A18-B46-C8; | A18-B46-C9; | A19-B46-C1; | A19-B46-C2; | A19-B46-C3; |
| A19-B46-C4; | A19-B46-C5; | A19-B46-C6; | A19-B46-C7; | A19-B46-C8; | A19-B46-C9; |
| A20-B46-C1; | A20-B46-C2; | A20-B46-C3; | A20-B46-C4; | A20-B46-C5; | A20-B46-C6; |
| A20-B46-C7; | A20-B46-C8; | A20-B46-C9; | A21-B46-C1; | A21-B46-C2; | A21-B46-C3; |
| A21-B46-C4; | A21-B46-C5; | A21-B46-C6; | A21-B46-C7; | A21-B46-C8; | A21-B46-C9; |
| A22-B46-C1; | A22-B46-C2; | A22-B46-C3; | A22-B46-C4; | A22-B46-C5; | A22-B46-C6; |
| A22-B46-C7; | A22-B46-C8; | A22-B46-C9; | A23-B46-C1; | A23-B46-C2; | A23-B46-C3; |
| A23-B46-C4; | A23-B46-C5; | A23-B46-C6; | A23-B46-C7; | A23-B46-C8; | A23-B46-C9; |
| A24-B46-C1; | A24-B46-C2; | A24-B46-C3; | A24-B46-C4; | A24-B46-C5; | A24-B46-C6; |
| A24-B46-C7; | A24-B46-C8; | A24-B46-C9; | A25-B46-C1; | A25-B46-C2; | A25-B46-C3; |
| A25-B46-C4; | A25-B46-C5; | A25-B46-C6; | A25-B46-C7; | A25-B46-C8; | A25-B46-C9; |
| A26-B46-C1; | A26-B46-C2; | A26-B46-C3; | A26-B46-C4; | A26-B46-C5; | A26-B46-C6; |
| A26-B46-C7; | A26-B46-C8; | A26-B46-C9; | A27-B46-C1; | A27-B46-C2; | A27-B46-C3; |
| A27-B46-C4; | A27-B46-C5; | A27-B46-C6; | A27-B46-C7; | A27-B46-C8; | A27-B46-C9; |
| A28-B46-C1; | A28-B46-C2; | A28-B46-C3; | A28-B46-C4; | A28-B46-C5; | A28-B46-C6; |
| A28-B46-C7; | A28-B46-C8; | A28-B46-C9; | A29-B46-C1; | A29-B46-C2; | A29-B46-C3; |
| A29-B46-C4; | A29-B46-C5; | A29-B46-C6; | A29-B46-C7; | A29-B46-C8; | A29-B46-C9; |
| A30-B46-C1; | A30-B46-C2; | A30-B46-C3; | A30-B46-C4; | A30-B46-C5; | A30-B46-C6; |
| A30-B46-C7; | A30-B46-C8; | A30-B46-C9; | A31-B46-C1; | A31-B46-C2; | A31-B46-C3; |
| A31-B46-C4; | A31-B46-C5; | A31-B46-C6; | A31-B46-C7; | A31-B46-C8; | A31-B46-C9; |
| A32-B46-C1; | A32-B46-C2; | A32-B46-C3; | A32-B46-C4; | A32-B46-C5; | A32-B46-C6; |
| A32-B46-C7; | A32-B46-C8; | A32-B46-C9; | A33-B46-C1; | A33-B46-C2; | A33-B46-C3; |
| A33-B46-C4; | A33-B46-C5; | A33-B46-C6; | A33-B46-C7; | A33-B46-C8; | A33-B46-C9; |
| A34-B46-C1; | A34-B46-C2; | A34-B46-C3; | A34-B46-C4; | A34-B46-C5; | A34-B46-C6; |
| A34-B46-C7; | A34-B46-C8; | A34-B46-C9; | A35-B46-C1; | A35-B46-C2; | A35-B46-C3; |
| A35-B46-C4; | A35-B46-C5; | A35-B46-C6; | A35-B46-C7; | A35-B46-C8; | A35-B46-C9; |
| A36-B46-C1; | A36-B46-C2; | A36-B46-C3; | A36-B46-C4; | A36-B46-C5; | A36-B46-C6; |

-continued

| | | | | | |
|---|---|---|---|---|---|
| A36-B46-C7; | A36-B46-C8; | A36-B46-C9; | A37-B46-C1; | A37-B46-C2; | A37-B46-C3; |
| A37-B46-C4; | A37-B46-C5; | A37-B46-C6; | A37-B46-C7; | A37-B46-C8; | A37-B46-C9; |
| A38-B46-C1; | A38-B46-C2; | A38-B46-C3; | A38-B46-C4; | A38-B46-C5; | A38-B46-C6; |
| A38-B46-C7; | A38-B46-C8; | A38-B46-C9; | A39-B46-C1; | A39-B46-C2; | A39-B46-C3; |
| A39-B46-C4; | A39-B46-C5; | A39-B46-C6; | A39-B46-C7; | A39-B46-C8; | A39-B46-C9; |
| A40-B46-C1; | A40-B46-C2; | A40-B46-C3; | A40-B46-C4; | A40-B46-C5; | A40-B46-C6; |
| A40-B46-C7; | A40-B46-C8; | A40-B46-C9; | A41-B46-C1; | A41-B46-C2; | A41-B46-C3; |
| A41-B46-C4; | A41-B46-C5; | A41-B46-C6; | A41-B46-C7; | A41-B46-C8; | A41-B46-C9; |
| A42-B46-C1; | A42-B46-C2; | A42-B46-C3; | A42-B46-C4; | A42-B46-C5; | A42-B46-C6; |
| A42-B46-C7; | A42-B46-C8; | A42-B46-C9; | A43-B46-C1; | A43-B46-C2; | A43-B46-C3; |
| A43-B46-C4; | A43-B46-C5; | A43-B46-C6; | A43-B46-C7; | A43-B46-C8; | A43-B46-C9; |
| A44-B46-C1; | A44-B46-C2; | A44-B46-C3; | A44-B46-C4; | A44-B46-C5; | A44-B46-C6; |
| A44-B46-C7; | A44-B46-C8; | A44-B46-C9; | A45-B46-C1; | A45-B46-C2; | A45-B46-C3; |
| A45-B46-C4; | A45-B46-C5; | A45-B46-C6; | A45-B46-C7; | A45-B46-C8; | A45-B46-C9; |
| A46-B46-C1; | A46-B46-C2; | A46-B46-C3; | A46-B46-C4; | A46-B46-C5; | A46-B46-C6; |
| A46-B46-C7; | A46-B46-C8; | A46-B46-C9; | A47-B46-C1; | A47-B46-C2; | A47-B46-C3; |
| A47-B46-C4; | A47-B46-C5; | A47-B46-C6; | A47-B46-C7; | A47-B46-C8; | A47-B46-C9; |
| A48-B46-C1; | A48-B46-C2; | A48-B46-C3; | A48-B46-C4; | A48-B46-C5; | A48-B46-C6; |
| A48-B46-C7; | A48-B46-C8; | A48-B46-C9; | A49-B46-C1; | A49-B46-C2; | A49-B46-C3; |
| A49-B46-C4; | A49-B46-C5; | A49-B46-C6; | A49-B46-C7; | A49-B46-C8; | A49-B46-C9; |
| A50-B46-C1; | A50-B46-C2; | A50-B46-C3; | A50-B46-C4; | A50-B46-C5; | A50-B46-C6; |
| A50-B46-C7; | A50-B46-C8; | A50-B46-C9; | A51-B46-C1; | A51-B46-C2; | A51-B46-C3; |
| A51-B46-C4; | A51-B46-C5; | A51-B46-C6; | A51-B46-C7; | A51-B46-C8; | A51-B46-C9; |
| A52-B46-C1; | A52-B46-C2; | A52-B46-C3; | A52-B46-C4; | A52-B46-C5; | A52-B46-C6; |
| A52-B46-C7; | A52-B46-C8; | A52-B46-C9; | A53-B46-C1; | A53-B46-C2; | A53-B46-C3; |
| A53-B46-C4; | A53-B46-C5; | A53-B46-C6; | A53-B46-C7; | A53-B46-C8; | A53-B46-C9; |
| A54-B46-C1; | A54-B46-C2; | A54-B46-C3; | A54-B46-C4; | A54-B46-C5; | A54-B46-C6; |
| A54-B46-C7; | A54-B46-C8; | A54-B46-C9; | A55-B46-C1; | A55-B46-C2; | A55-B46-C3; |
| A55-B46-C4; | A55-B46-C5; | A55-B46-C6; | A55-B46-C7; | A55-B46-C8; | A55-B46-C9; |
| A56-B46-C1; | A56-B46-C2; | A56-B46-C3; | A56-B46-C4; | A56-B46-C5; | A56-B46-C6; |
| A56-B46-C7; | A56-B46-C8; | A56-B46-C9; | A57-B46-C1; | A57-B46-C2; | A57-B46-C3; |
| A57-B46-C4; | A57-B46-C5; | A57-B46-C6; | A57-B46-C7; | A57-B46-C8; | A57-B46-C9; |
| A58-B46-C1; | A58-B46-C2; | A58-B46-C3; | A58-B46-C4; | A58-B46-C5; | A58-B46-C6; |
| A58-B46-C7; | A58-B46-C8; | A58-B46-C9; | A59-B46-C1; | A59-B46-C2; | A59-B46-C3; |
| A59-B46-C4; | A59-B46-C5; | A59-B46-C6; | A59-B46-C7; | A59-B46-C8; | A59-B46-C9; |
| A60-B46-C1; | A60-B46-C2; | A60-B46-C3; | A60-B46-C4; | A60-B46-C5; | A60-B46-C6; |
| A60-B46-C7; | A60-B46-C8; | A60-B46-C9; | A61-B46-C1; | A61-B46-C2; | A61-B46-C3; |
| A61-B46-C4; | A61-B46-C5; | A61-B46-C6; | A61-B46-C7; | A61-B46-C8; | A61-B46-C9; |
| A62-B46-C1; | A62-B46-C2; | A62-B46-C3; | A62-B46-C4; | A62-B46-C5; | A62-B46-C6; |
| A62-B46-C7; | A62-B46-C8; | A62-B46-C9; | A63-B46-C1; | A63-B46-C2; | A63-B46-C3; |
| A63-B46-C4; | A63-B46-C5; | A63-B46-C6; | A63-B46-C7; | A63-B46-C8; | A63-B46-C9; |
| A64-B46-C1; | A64-B46-C2; | A64-B46-C3; | A64-B46-C4; | A64-B46-C5; | A64-B46-C6; |
| A64-B46-C7; | A64-B46-C8; | A64-B46-C9; | A65-B46-C1; | A65-B46-C2; | A65-B46-C3; |
| A65-B46-C4; | A65-B46-C5; | A65-B46-C6; | A65-B46-C7; | A65-B46-C8; | A65-B46-C9; |
| A66-B46-C1; | A66-B46-C2; | A66-B46-C3; | A66-B46-C4; | A66-B46-C5; | A66-B46-C6; |
| A66-B46-C7; | A66-B46-C8; | A66-B46-C9; | A67-B46-C1; | A67-B46-C2; | A67-B46-C3; |
| A67-B46-C4; | A67-B46-C5; | A67-B46-C6; | A67-B46-C7; | A67-B46-C8; | A67-B46-C9; |
| A68-B46-C1; | A68-B46-C2; | A68-B46-C3; | A68-B46-C4; | A68-B46-C5; | A68-B46-C6; |
| A68-B46-C7; | A68-B46-C8; | A68-B46-C9; | A69-B46-C1; | A69-B46-C2; | A69-B46-C3; |
| A69-B46-C4; | A69-B46-C5; | A69-B46-C6; | A69-B46-C7; | A69-B46-C8; | A69-B46-C9; |
| A70-B46-C1; | A70-B46-C2; | A70-B46-C3; | A70-B46-C4; | A70-B46-C5; | A70-B46-C6; |
| A70-B46-C7; | A70-B46-C8; | A70-B46-C9; | A71-B46-C1; | A71-B46-C2; | A71-B46-C3; |
| A71-B46-C4; | A71-B46-C5; | A71-B46-C6; | A71-B46-C7; | A71-B46-C8; | A71-B46-C9; |
| A1-B47-C1; | A1-B47-C2; | A1-B47-C3; | A1-B47-C4; | A1-B47-C5; | A1-B47-C6; |
| A1-B47-C7; | A1-B47-C8; | A1-B47-C9; | A2-B47-C1; | A2-B47-C2; | A2-B47-C3; |
| A2-B47-C4; | A2-B47-C5; | A2-B47-C6; | A2-B47-C7; | A2-B47-C8; | A2-B47-C9; |
| A3-B47-C1; | A3-B47-C2; | A3-B47-C3; | A3-B47-C4; | A3-B47-C5; | A3-B47-C6; |
| A3-B47-C7; | A3-B47-C8; | A3-B47-C9; | A4-B47-C1; | A4-B47-C2; | A4-B47-C3; |
| A4-B47-C4; | A4-B47-C5; | A4-B47-C6; | A4-B47-C7; | A4-B47-C8; | A4-B47-C9; |
| A5-B47-C1; | A5-B47-C2; | A5-B47-C3; | A5-B47-C4; | A5-B47-C5; | A5-B47-C6; |
| A5-B47-C7; | A5-B47-C8; | A5-B47-C9; | A6-B47-C1; | A6-B47-C2; | A6-B47-C3; |
| A6-B47-C4; | A6-B47-C5; | A6-B47-C6; | A6-B47-C7; | A6-B47-C8; | A6-B47-C9; |
| A7-B47-C1; | A7-B47-C2; | A7-B47-C3; | A7-B47-C4; | A7-B47-C5; | A7-B47-C6; |
| A7-B47-C7; | A7-B47-C8; | A7-B47-C9; | A8-B47-C1; | A8-B47-C2; | A8-B47-C3; |
| A8-B47-C4; | A8-B47-C5; | A8-B47-C6; | A8-B47-C7; | A8-B47-C8; | A8-B47-C9; |
| A9-B47-C1; | A9-B47-C2; | A9-B47-C3; | A9-B47-C4; | A9-B47-C5; | A9-B47-C6; |
| A9-B47-C7; | A9-B47-C8; | A9-B47-C9; | A10-B47-C1; | A10-B47-C2; | A10-B47-C3; |
| A10-B47-C4; | A10-B47-C5; | A10-B47-C6; | A10-B47-C7; | A10-B47-C8; | A10-B47-C9; |
| A11-B47-C1; | A11-B47-C2; | A11-B47-C3; | A11-B47-C4; | A11-B47-C5; | A11-B47-C6; |
| A11-B47-C7; | A11-B47-C8; | A11-B47-C9; | A12-B47-C1; | A12-B47-C2; | A12-B47-C3; |
| A12-B47-C4; | A12-B47-C5; | A12-B47-C6; | A12-B47-C7; | A12-B47-C8; | A12-B47-C9; |
| A13-B47-C1; | A13-B47-C2; | A13-B47-C3; | A13-B47-C4; | A13-B47-C5; | A13-B47-C6; |
| A13-B47-C7; | A13-B47-C8; | A13-B47-C9; | A14-B47-C1; | A14-B47-C2; | A14-B47-C3; |
| A14-B47-C4; | A14-B47-C5; | A14-B47-C6; | A14-B47-C7; | A14-B47-C8; | A14-B47-C9; |
| A15-B47-C1; | A15-B47-C2; | A15-B47-C3; | A15-B47-C4; | A15-B47-C5; | A15-B47-C6; |
| A15-B47-C7; | A15-B47-C8; | A15-B47-C9; | A16-B47-C1; | A16-B47-C2; | A16-B47-C3; |
| A16-B47-C4; | A16-B47-C5; | A16-B47-C6; | A16-B47-C7; | A16-B47-C8; | A16-B47-C9; |
| A17-B47-C1; | A17-B47-C2; | A17-B47-C3; | A17-B47-C4; | A17-B47-C5; | A17-B47-C6; |
| A17-B47-C7; | A17-B47-C8; | A17-B47-C9; | A18-B47-C1; | A18-B47-C2; | A18-B47-C3; |

-continued

| | | | | | |
|---|---|---|---|---|---|
| A18-B47-C4; | A18-B47-C5; | A18-B47-C6; | A18-B47-C7; | A18-B47-C8; | A18-B47-C9; |
| A19-B47-C1; | A19-B47-C2; | A19-B47-C3; | A19-B47-C4; | A19-B47-C5; | A19-B47-C6; |
| A19-B47-C7; | A19-B47-C8; | A19-B47-C9; | A20-B47-C1; | A20-B47-C2; | A20-B47-C3; |
| A20-B47-C4; | A20-B47-C5; | A20-B47-C6; | A20-B47-C7; | A20-B47-C8; | A20-B47-C9; |
| A21-B47-C1; | A21-B47-C2; | A21-B47-C3; | A21-B47-C4; | A21-B47-C5; | A21-B47-C6; |
| A21-B47-C7; | A21-B47-C8; | A21-B47-C9; | A22-B47-C1; | A22-B47-C2; | A22-B47-C3; |
| A22-B47-C4; | A22-B47-C5; | A22-B47-C6; | A22-B47-C7; | A22-B47-C8; | A22-B47-C9; |
| A23-B47-C1; | A23-B47-C2; | A23-B47-C3; | A23-B47-C4; | A23-B47-C5; | A23-B47-C6; |
| A23-B47-C7; | A23-B47-C8; | A23-B47-C9; | A24-B47-C1; | A24-B47-C2; | A24-B47-C3; |
| A24-B47-C4; | A24-B47-C5; | A24-B47-C6; | A24-B47-C7; | A24-B47-C8; | A24-B47-C9; |
| A25-B47-C1; | A25-B47-C2; | A25-B47-C3; | A25-B47-C4; | A25-B47-C5; | A25-B47-C6; |
| A25-B47-C7; | A25-B47-C8; | A25-B47-C9; | A26-B47-C1; | A26-B47-C2; | A26-B47-C3; |
| A26-B47-C4; | A26-B47-C5; | A26-B47-C6; | A26-B47-C7; | A26-B47-C8; | A26-B47-C9; |
| A27-B47-C1; | A27-B47-C2; | A27-B47-C3; | A27-B47-C4; | A27-B47-C5; | A27-B47-C6; |
| A27-B47-C7; | A27-B47-C8; | A27-B47-C9; | A28-B47-C1; | A28-B47-C2; | A28-B47-C3; |
| A28-B47-C4; | A28-B47-C5; | A28-B47-C6; | A28-B47-C7; | A28-B47-C8; | A28-B47-C9; |
| A29-B47-C1; | A29-B47-C2; | A29-B47-C3; | A29-B47-C4; | A29-B47-C5; | A29-B47-C6; |
| A29-B47-C7; | A29-B47-C8; | A29-B47-C9; | A30-B47-C1; | A30-B47-C2; | A30-B47-C3; |
| A30-B47-C4; | A30-B47-C5; | A30-B47-C6; | A30-B47-C7; | A30-B47-C8; | A30-B47-C9; |
| A31-B47-C1; | A31-B47-C2; | A31-B47-C3; | A31-B47-C4; | A31-B47-C5; | A31-B47-C6; |
| A31-B47-C7; | A31-B47-C8; | A31-B47-C9; | A32-B47-C1; | A32-B47-C2; | A32-B47-C3; |
| A32-B47-C4; | A32-B47-C5; | A32-B47-C6; | A32-B47-C7; | A32-B47-C8; | A32-B47-C9; |
| A33-B47-C1; | A33-B47-C2; | A33-B47-C3; | A33-B47-C4; | A33-B47-C5; | A33-B47-C6; |
| A33-B47-C7; | A33-B47-C8; | A33-B47-C9; | A34-B47-C1; | A34-B47-C2; | A34-B47-C3; |
| A34-B47-C4; | A34-B47-C5; | A34-B47-C6; | A34-B47-C7; | A34-B47-C8; | A34-B47-C9; |
| A35-B47-C1; | A35-B47-C2; | A35-B47-C3; | A35-B47-C4; | A35-B47-C5; | A35-B47-C6; |
| A35-B47-C7; | A35-B47-C8; | A35-B47-C9; | A36-B47-C1; | A36-B47-C2; | A36-B47-C3; |
| A36-B47-C4; | A36-B47-C5; | A36-B47-C6; | A36-B47-C7; | A36-B47-C8; | A36-B47-C9; |
| A37-B47-C1; | A37-B47-C2; | A37-B47-C3; | A37-B47-C4; | A37-B47-C5; | A37-B47-C6; |
| A37-B47-C7; | A37-B47-C8; | A37-B47-C9; | A38-B47-C1; | A38-B47-C2; | A38-B47-C3; |
| A38-B47-C4; | A38-B47-C5; | A38-B47-C6; | A38-B47-C7; | A38-B47-C8; | A38-B47-C9; |
| A39-B47-C1; | A39-B47-C2; | A39-B47-C3; | A39-B47-C4; | A39-B47-C5; | A39-B47-C6; |
| A39-B47-C7; | A39-B47-C8; | A39-B47-C9; | A40-B47-C1; | A40-B47-C2; | A40-B47-C3; |
| A40-B47-C4; | A40-B47-C5; | A40-B47-C6; | A40-B47-C7; | A40-B47-C8; | A40-B47-C9; |
| A41-B47-C1; | A41-B47-C2; | A41-B47-C3; | A41-B47-C4; | A41-B47-C5; | A41-B47-C6; |
| A41-B47-C7; | A41-B47-C8; | A41-B47-C9; | A42-B47-C1; | A42-B47-C2; | A42-B47-C3; |
| A42-B47-C4; | A42-B47-C5; | A42-B47-C6; | A42-B47-C7; | A42-B47-C8; | A42-B47-C9; |
| A43-B47-C1; | A43-B47-C2; | A43-B47-C3; | A43-B47-C4; | A43-B47-C5; | A43-B47-C6; |
| A43-B47-C7; | A43-B47-C8; | A43-B47-C9; | A44-B47-C1; | A44-B47-C2; | A44-B47-C3; |
| A44-B47-C4; | A44-B47-C5; | A44-B47-C6; | A44-B47-C7; | A44-B47-C8; | A44-B47-C9; |
| A45-B47-C1; | A45-B47-C2; | A45-B47-C3; | A45-B47-C4; | A45-B47-C5; | A45-B47-C6; |
| A45-B47-C7; | A45-B47-C8; | A45-B47-C9; | A46-B47-C1; | A46-B47-C2; | A46-B47-C3; |
| A46-B47-C4; | A46-B47-C5; | A46-B47-C6; | A46-B47-C7; | A46-B47-C8; | A46-B47-C9; |
| A47-B47-C1; | A47-B47-C2; | A47-B47-C3; | A47-B47-C4; | A47-B47-C5; | A47-B47-C6; |
| A47-B47-C7; | A47-B47-C8; | A47-B47-C9; | A48-B47-C1; | A48-B47-C2; | A48-B47-C3; |
| A48-B47-C4; | A48-B47-C5; | A48-B47-C6; | A48-B47-C7; | A48-B47-C8; | A48-B47-C9; |
| A49-B47-C1; | A49-B47-C2; | A49-B47-C3; | A49-B47-C4; | A49-B47-C5; | A49-B47-C6; |
| A49-B47-C7; | A49-B47-C8; | A49-B47-C9; | A50-B47-C1; | A50-B47-C2; | A50-B47-C3; |
| A50-B47-C4; | A50-B47-C5; | A50-B47-C6; | A50-B47-C7; | A50-B47-C8; | A50-B47-C9; |
| A51-B47-C1; | A51-B47-C2; | A51-B47-C3; | A51-B47-C4; | A51-B47-C5; | A51-B47-C6; |
| A51-B47-C7; | A51-B47-C8; | A51-B47-C9; | A52-B47-C1; | A52-B47-C2; | A52-B47-C3; |
| A52-B47-C4; | A52-B47-C5; | A52-B47-C6; | A52-B47-C7; | A52-B47-C8; | A52-B47-C9; |
| A53-B47-C1; | A53-B47-C2; | A53-B47-C3; | A53-B47-C4; | A53-B47-C5; | A53-B47-C6; |
| A53-B47-C7; | A53-B47-C8; | A53-B47-C9; | A54-B47-C1; | A54-B47-C2; | A54-B47-C3; |
| A54-B47-C4; | A54-B47-C5; | A54-B47-C6; | A54-B47-C7; | A54-B47-C8; | A54-B47-C9; |
| A55-B47-C1; | A55-B47-C2; | A55-B47-C3; | A55-B47-C4; | A55-B47-C5; | A55-B47-C6; |
| A55-B47-C7; | A55-B47-C8; | A55-B47-C9; | A56-B47-C1; | A56-B47-C2; | A56-B47-C3; |
| A56-B47-C4; | A56-B47-C5; | A56-B47-C6; | A56-B47-C7; | A56-B47-C8; | A56-B47-C9; |
| A57-B47-C1; | A57-B47-C2; | A57-B47-C3; | A57-B47-C4; | A57-B47-C5; | A57-B47-C6; |
| A57-B47-C7; | A57-B47-C8; | A57-B47-C9; | A58-B47-C1; | A58-B47-C2; | A58-B47-C3; |
| A58-B47-C4; | A58-B47-C5; | A58-B47-C6; | A58-B47-C7; | A58-B47-C8; | A58-B47-C9; |
| A59-B47-C1; | A59-B47-C2; | A59-B47-C3; | A59-B47-C4; | A59-B47-C5; | A59-B47-C6; |
| A59-B47-C7; | A59-B47-C8; | A59-B47-C9; | A60-B47-C1; | A60-B47-C2; | A60-B47-C3; |
| A60-B47-C4; | A60-B47-C5; | A60-B47-C6; | A60-B47-C7; | A60-B47-C8; | A60-B47-C9; |
| A61-B47-C1; | A61-B47-C2; | A61-B47-C3; | A61-B47-C4; | A61-B47-C5; | A61-B47-C6; |
| A61-B47-C7; | A61-B47-C8; | A61-B47-C9; | A62-B47-C1; | A62-B47-C2; | A62-B47-C3; |
| A62-B47-C4; | A62-B47-C5; | A62-B47-C6; | A62-B47-C7; | A62-B47-C8; | A62-B47-C9; |
| A63-B47-C1; | A63-B47-C2; | A63-B47-C3; | A63-B47-C4; | A63-B47-C5; | A63-B47-C6; |
| A63-B47-C7; | A63-B47-C8; | A63-B47-C9; | A64-B47-C1; | A64-B47-C2; | A64-B47-C3; |
| A64-B47-C4; | A64-B47-C5; | A64-B47-C6; | A64-B47-C7; | A64-B47-C8; | A64-B47-C9; |
| A65-B47-C1; | A65-B47-C2; | A65-B47-C3; | A65-B47-C4; | A65-B47-C5; | A65-B47-C6; |
| A65-B47-C7; | A65-B47-C8; | A65-B47-C9; | A66-B47-C1; | A66-B47-C2; | A66-B47-C3; |
| A66-B47-C4; | A66-B47-C5; | A66-B47-C6; | A66-B47-C7; | A66-B47-C8; | A66-B47-C9; |
| A67-B47-C1; | A67-B47-C2; | A67-B47-C3; | A67-B47-C4; | A67-B47-C5; | A67-B47-C6; |
| A67-B47-C7; | A67-B47-C8; | A67-B47-C9; | A68-B47-C1; | A68-B47-C2; | A68-B47-C3; |
| A68-B47-C4; | A68-B47-C5; | A68-B47-C6; | A68-B47-C7; | A68-B47-C8; | A68-B47-C9; |
| A69-B47-C1; | A69-B47-C2; | A69-B47-C3; | A69-B47-C4; | A69-B47-C5; | A69-B47-C6; |
| A69-B47-C7; | A69-B47-C8; | A69-B47-C9; | A70-B47-C1; | A70-B47-C2; | A70-B47-C3; |
| A70-B47-C4; | A70-B47-C5; | A70-B47-C6; | A70-B47-C7; | A70-B47-C8; | A70-B47-C9; |

-continued

| | | | | | |
|---|---|---|---|---|---|
| A71-B47-C1; | A71-B47-C2; | A71-B47-C3; | A71-B47-C4; | A71-B47-C5; | A71-B47-C6; |
| A71-B47-C7; | A71-B47-C8; | A71-B47-C9; | A1-B48-C1; | A1-B48-C2; | A1-B48-C3; |
| A1-B48-C4; | A1-B48-C5; | A1-B48-C6; | A1-B48-C7; | A1-B48-C8; | A1-B48-C9; |
| A2-B48-C1; | A2-B48-C2; | A2-B48-C3; | A2-B48-C4; | A2-B48-C5; | A2-B48-C6; |
| A2-B48-C7; | A2-B48-C8; | A2-B48-C9; | A3-B48-C1; | A3-B48-C2; | A3-B48-C3; |
| A3-B48-C4; | A3-B48-C5; | A3-B48-C6; | A3-B48-C7; | A3-B48-C8; | A3-B48-C9; |
| A4-B48-C1; | A4-B48-C2; | A4-B48-C3; | A4-B48-C4; | A4-B48-C5; | A4-B48-C6; |
| A4-B48-C7; | A4-B48-C8; | A4-B48-C9; | A5-B48-C1; | A5-B48-C2; | A5-B48-C3; |
| A5-B48-C4; | A5-B48-C5; | A5-B48-C6; | A5-B48-C7; | A5-B48-C8; | A5-B48-C9; |
| A6-B48-C1; | A6-B48-C2; | A6-B48-C3; | A6-B48-C4; | A6-B48-C5; | A6-B48-C6; |
| A6-B48-C7; | A6-B48-C8; | A6-B48-C9; | A7-B48-C1; | A7-B48-C2; | A7-B48-C3; |
| A7-B48-C4; | A7-B48-C5; | A7-B48-C6; | A7-B48-C7; | A7-B48-C8; | A7-B48-C9; |
| A8-B48-C1; | A8-B48-C2; | A8-B48-C3; | A8-B48-C4; | A8-B48-C5; | A8-B48-C6; |
| A8-B48-C7; | A8-B48-C8; | A8-B48-C9; | A9-B48-C1; | A9-B48-C2; | A9-B48-C3; |
| A9-B48-C4; | A9-B48-C5; | A9-B48-C6; | A9-B48-C7; | A9-B48-C8; | A9-B48-C9; |
| A10-B48-C1; | A10-B48-C2; | A10-B48-C3; | A10-B48-C4; | A10-B48-C5; | A10-B48-C6; |
| A10-B48-C7; | A10-B48-C8; | A10-B48-C9; | A11-B48-C1; | A11-B48-C2; | A11-B48-C3; |
| A11-B48-C4; | A11-B48-C5; | A11-B48-C6; | A11-B48-C7; | A11-B48-C8; | A11-B48-C9; |
| A12-B48-C1; | A12-B48-C2; | A12-B48-C3; | A12-B48-C4; | A12-B48-C5; | A12-B48-C6; |
| A12-B48-C7; | A12-B48-C8; | A12-B48-C9; | A13-B48-C1; | A13-B48-C2; | A13-B48-C3; |
| A13-B48-C4; | A13-B48-C5; | A13-B48-C6; | A13-B48-C7; | A13-B48-C8; | A13-B48-C9; |
| A14-B48-C1; | A14-B48-C2; | A14-B48-C3; | A14-B48-C4; | A14-B48-C5; | A14-B48-C6; |
| A14-B48-C7; | A14-B48-C8; | A14-B48-C9; | A15-B48-C1; | A15-B48-C2; | A15-B48-C3; |
| A15-B48-C4; | A15-B48-C5; | A15-B48-C6; | A15-B48-C7; | A15-B48-C8; | A15-B48-C9; |
| A16-B48-C1; | A16-B48-C2; | A16-B48-C3; | A16-B48-C4; | A16-B48-C5; | A16-B48-C6; |
| A16-B48-C7; | A16-B48-C8; | A16-B48-C9; | A17-B48-C1; | A17-B48-C2; | A17-B48-C3; |
| A17-B48-C4; | A17-B48-C5; | A17-B48-C6; | A17-B48-C7; | A17-B48-C8; | A17-B48-C9; |
| A18-B48-C1; | A18-B48-C2; | A18-B48-C3; | A18-B48-C4; | A18-B48-C5; | A18-B48-C6; |
| A18-B48-C7; | A18-B48-C8; | A18-B48-C9; | A19-B48-C1; | A19-B48-C2; | A19-B48-C3; |
| A19-B48-C4; | A19-B48-C5; | A19-B48-C6; | A19-B48-C7; | A19-B48-C8; | A19-B48-C9; |
| A20-B48-C1; | A20-B48-C2; | A20-B48-C3; | A20-B48-C4; | A20-B48-C5; | A20-B48-C6; |
| A20-B48-C7; | A20-B48-C8; | A20-B48-C9; | A21-B48-C1; | A21-B48-C2; | A21-B48-C3; |
| A21-B48-C4; | A21-B48-C5; | A21-B48-C6; | A21-B48-C7; | A21-B48-C8; | A21-B48-C9; |
| A22-B48-C1; | A22-B48-C2; | A22-B48-C3; | A22-B48-C4; | A22-B48-C5; | A22-B48-C6; |
| A22-B48-C7; | A22-B48-C8; | A22-B48-C9; | A23-B48-C1; | A23-B48-C2; | A23-B48-C3; |
| A23-B48-C4; | A23-B48-C5; | A23-B48-C6; | A23-B48-C7; | A23-B48-C8; | A23-B48-C9; |
| A24-B48-C1; | A24-B48-C2; | A24-B48-C3; | A24-B48-C4; | A24-B48-C5; | A24-B48-C6; |
| A24-B48-C7; | A24-B48-C8; | A24-B48-C9; | A25-B48-C1; | A25-B48-C2; | A25-B48-C3; |
| A25-B48-C4; | A25-B48-C5; | A25-B48-C6; | A25-B48-C7; | A25-B48-C8; | A25-B48-C9; |
| A26-B48-C1; | A26-B48-C2; | A26-B48-C3; | A26-B48-C4; | A26-B48-C5; | A26-B48-C6; |
| A26-B48-C7; | A26-B48-C8; | A26-B48-C9; | A27-B48-C1; | A27-B48-C2; | A27-B48-C3; |
| A27-B48-C4; | A27-B48-C5; | A27-B48-C6; | A27-B48-C7; | A27-B48-C8; | A27-B48-C9; |
| A28-B48-C1; | A28-B48-C2; | A28-B48-C3; | A28-B48-C4; | A28-B48-C5; | A28-B48-C6; |
| A28-B48-C7; | A28-B48-C8; | A28-B48-C9; | A29-B48-C1; | A29-B48-C2; | A29-B48-C3; |
| A29-B48-C4; | A29-B48-C5; | A29-B48-C6; | A29-B48-C7; | A29-B48-C8; | A29-B48-C9; |
| A30-B48-C1; | A30-B48-C2; | A30-B48-C3; | A30-B48-C4; | A30-B48-C5; | A30-B48-C6; |
| A30-B48-C7; | A30-B48-C8; | A30-B48-C9; | A31-B48-C1; | A31-B48-C2; | A31-B48-C3; |
| A31-B48-C4; | A31-B48-C5; | A31-B48-C6; | A31-B48-C7; | A31-B48-C8; | A31-B48-C9; |
| A32-B48-C1; | A32-B48-C2; | A32-B48-C3; | A32-B48-C4; | A32-B48-C5; | A32-B48-C6; |
| A32-B48-C7; | A32-B48-C8; | A32-B48-C9; | A33-B48-C1; | A33-B48-C2; | A33-B48-C3; |
| A33-B48-C4; | A33-B48-C5; | A33-B48-C6; | A33-B48-C7; | A33-B48-C8; | A33-B48-C9; |
| A34-B48-C1; | A34-B48-C2; | A34-B48-C3; | A34-B48-C4; | A34-B48-C5; | A34-B48-C6; |
| A34-B48-C7; | A34-B48-C8; | A34-B48-C9; | A35-B48-C1; | A35-B48-C2; | A35-B48-C3; |
| A35-B48-C4; | A35-B48-C5; | A35-B48-C6; | A35-B48-C7; | A35-B48-C8; | A35-B48-C9; |
| A36-B48-C1; | A36-B48-C2; | A36-B48-C3; | A36-B48-C4; | A36-B48-C5; | A36-B48-C6; |
| A36-B48-C7; | A36-B48-C8; | A36-B48-C9; | A37-B48-C1; | A37-B48-C2; | A37-B48-C3; |
| A37-B48-C4; | A37-B48-C5; | A37-B48-C6; | A37-B48-C7; | A37-B48-C8; | A37-B48-C9; |
| A38-B48-C1; | A38-B48-C2; | A38-B48-C3; | A38-B48-C4; | A38-B48-C5; | A38-B48-C6; |
| A38-B48-C7; | A38-B48-C8; | A38-B48-C9; | A39-B48-C1; | A39-B48-C2; | A39-B48-C3; |
| A39-B48-C4; | A39-B48-C5; | A39-B48-C6; | A39-B48-C7; | A39-B48-C8; | A39-B48-C9; |
| A40-B48-C1; | A40-B48-C2; | A40-B48-C3; | A40-B48-C4; | A40-B48-C5; | A40-B48-C6; |
| A40-B48-C7; | A40-B48-C8; | A40-B48-C9; | A41-B48-C1; | A41-B48-C2; | A41-B48-C3; |
| A41-B48-C4; | A41-B48-C5; | A41-B48-C6; | A41-B48-C7; | A41-B48-C8; | A41-B48-C9; |
| A42-B48-C1; | A42-B48-C2; | A42-B48-C3; | A42-B48-C4; | A42-B48-C5; | A42-B48-C6; |
| A42-B48-C7; | A42-B48-C8; | A42-B48-C9; | A43-B48-C1; | A43-B48-C2; | A43-B48-C3; |
| A43-B48-C4; | A43-B48-C5; | A43-B48-C6; | A43-B48-C7; | A43-B48-C8; | A43-B48-C9; |
| A44-B48-C1; | A44-B48-C2; | A44-B48-C3; | A44-B48-C4; | A44-B48-C5; | A44-B48-C6; |
| A44-B48-C7; | A44-B48-C8; | A44-B48-C9; | A45-B48-C1; | A45-B48-C2; | A45-B48-C3; |
| A45-B48-C4; | A45-B48-C5; | A45-B48-C6; | A45-B48-C7; | A45-B48-C8; | A45-B48-C9; |
| A46-B48-C1; | A46-B48-C2; | A46-B48-C3; | A46-B48-C4; | A46-B48-C5; | A46-B48-C6; |
| A46-B48-C7; | A46-B48-C8; | A46-B48-C9; | A47-B48-C1; | A47-B48-C2; | A47-B48-C3; |
| A47-B48-C4; | A47-B48-C5; | A47-B48-C6; | A47-B48-C7; | A47-B48-C8; | A47-B48-C9; |
| A48-B48-C1; | A48-B48-C2; | A48-B48-C3; | A48-B48-C4; | A48-B48-C5; | A48-B48-C6; |
| A48-B48-C7; | A48-B48-C8; | A48-B48-C9; | A49-B48-C1; | A49-B48-C2; | A49-B48-C3; |
| A49-B48-C4; | A49-B48-C5; | A49-B48-C6; | A49-B48-C7; | A49-B48-C8; | A49-B48-C9; |
| A50-B48-C1; | A50-B48-C2; | A50-B48-C3; | A50-B48-C4; | A50-B48-C5; | A50-B48-C6; |
| A50-B48-C7; | A50-B48-C8; | A50-B48-C9; | A51-B48-C1; | A51-B48-C2; | A51-B48-C3; |
| A51-B48-C4; | A51-B48-C5; | A51-B48-C6; | A51-B48-C7; | A51-B48-C8; | A51-B48-C9; |
| A52-B48-C1; | A52-B48-C2; | A52-B48-C3; | A52-B48-C4; | A52-B48-C5; | A52-B48-C6; |

| | | | | | |
|---|---|---|---|---|---|
| A52-B48-C7; | A52-B48-C8; | A52-B48-C9; | A53-B48-C1; | A53-B48-C2; | A53-B48-C3; |
| A53-B48-C4; | A53-B48-C5; | A53-B48-C6; | A53-B48-C7; | A53-B48-C8; | A53-B48-C9; |
| A54-B48-C1; | A54-B48-C2; | A54-B48-C3; | A54-B48-C4; | A54-B48-C5; | A54-B48-C6; |
| A54-B48-C7; | A54-B48-C8; | A54-B48-C9; | A55-B48-C1; | A55-B48-C2; | A55-B48-C3; |
| A55-B48-C4; | A55-B48-C5; | A55-B48-C6; | A55-B48-C7; | A55-B48-C8; | A55-B48-C9; |
| A56-B48-C1; | A56-B48-C2; | A56-B48-C3; | A56-B48-C4; | A56-B48-C5; | A56-B48-C6; |
| A56-B48-C7; | A56-B48-C8; | A56-B48-C9; | A57-B48-C1; | A57-B48-C2; | A57-B48-C3; |
| A57-B48-C4; | A57-B48-C5; | A57-B48-C6; | A57-B48-C7; | A57-B48-C8; | A57-B48-C9; |
| A58-B48-C1; | A58-B48-C2; | A58-B48-C3; | A58-B48-C4; | A58-B48-C5; | A58-B48-C6; |
| A58-B48-C7; | A58-B48-C8; | A58-B48-C9; | A59-B48-C1; | A59-B48-C2; | A59-B48-C3; |
| A59-B48-C4; | A59-B48-C5; | A59-B48-C6; | A59-B48-C7; | A59-B48-C8; | A59-B48-C9; |
| A60-B48-C1; | A60-B48-C2; | A60-B48-C3; | A60-B48-C4; | A60-B48-C5; | A60-B48-C6; |
| A60-B48-C7; | A60-B48-C8; | A60-B48-C9; | A61-B48-C1; | A61-B48-C2; | A61-B48-C3; |
| A61-B48-C4; | A61-B48-C5; | A61-B48-C6; | A61-B48-C7; | A61-B48-C8; | A61-B48-C9; |
| A62-B48-C1; | A62-B48-C2; | A62-B48-C3; | A62-B48-C4; | A62-B48-C5; | A62-B48-C6; |
| A62-B48-C7; | A62-B48-C8; | A62-B48-C9; | A63-B48-C1; | A63-B48-C2; | A63-B48-C3; |
| A63-B48-C4; | A63-B48-C5; | A63-B48-C6; | A63-B48-C7; | A63-B48-C8; | A63-B48-C9; |
| A64-B48-C1; | A64-B48-C2; | A64-B48-C3; | A64-B48-C4; | A64-B48-C5; | A64-B48-C6; |
| A64-B48-C7; | A64-B48-C8; | A64-B48-C9; | A65-B48-C1; | A65-B48-C2; | A65-B48-C3; |
| A65-B48-C4; | A65-B48-C5; | A65-B48-C6; | A65-B48-C7; | A65-B48-C8; | A65-B48-C9; |
| A66-B48-C1; | A66-B48-C2; | A66-B48-C3; | A66-B48-C4; | A66-B48-C5; | A66-B48-C6; |
| A66-B48-C7; | A66-B48-C8; | A66-B48-C9; | A67-B48-C1; | A67-B48-C2; | A67-B48-C3; |
| A67-B48-C4; | A67-B48-C5; | A67-B48-C6; | A67-B48-C7; | A67-B48-C8; | A67-B48-C9; |
| A68-B48-C1; | A68-B48-C2; | A68-B48-C3; | A68-B48-C4; | A68-B48-C5; | A68-B48-C6; |
| A68-B48-C7; | A68-B48-C8; | A68-B48-C9; | A69-B48-C1; | A69-B48-C2; | A69-B48-C3; |
| A69-B48-C4; | A69-B48-C5; | A69-B48-C6; | A69-B48-C7; | A69-B48-C8; | A69-B48-C9; |
| A70-B48-C1; | A70-B48-C2; | A70-B48-C3; | A70-B48-C4; | A70-B48-C5; | A70-B48-C6; |
| A70-B48-C7; | A70-B48-C8; | A70-B48-C9; | A71-B48-C1; | A71-B48-C2; | A71-B48-C3; |
| A71-B48-C4; | A71-B48-C5; | A71-B48-C6; | A71-B48-C7; | A71-B48-C8; | A71-B48-C9; |
| A1-B49-C1; | A1-B49-C2; | A1-B49-C3; | A1-B49-C4; | A1-B49-C5; | A1-B49-C6; |
| A1-B49-C7; | A1-B49-C8; | A1-B49-C9; | A2-B49-C1; | A2-B49-C2; | A2-B49-C3; |
| A2-B49-C4; | A2-B49-C5; | A2-B49-C6; | A2-B49-C7; | A2-B49-C8; | A2-B49-C9; |
| A3-B49-C1; | A3-B49-C2; | A3-B49-C3; | A3-B49-C4; | A3-B49-C5; | A3-B49-C6; |
| A3-B49-C7; | A3-B49-C8; | A3-B49-C9; | A4-B49-C1; | A4-B49-C2; | A4-B49-C3; |
| A4-B49-C4; | A4-B49-C5; | A4-B49-C6; | A4-B49-C7; | A4-B49-C8; | A4-B49-C9; |
| A5-B49-C1; | A5-B49-C2; | A5-B49-C3; | A5-B49-C4; | A5-B49-C5; | A5-B49-C6; |
| A5-B49-C7; | A5-B49-C8; | A5-B49-C9; | A6-B49-C1; | A6-B49-C2; | A6-B49-C3; |
| A6-B49-C4; | A6-B49-C5; | A6-B49-C6; | A6-B49-C7; | A6-B49-C8; | A6-B49-C9; |
| A7-B49-C1; | A7-B49-C2; | A7-B49-C3; | A7-B49-C4; | A7-B49-C5; | A7-B49-C6; |
| A7-B49-C7; | A7-B49-C8; | A7-B49-C9; | A8-B49-C1; | A8-B49-C2; | A8-B49-C3; |
| A8-B49-C4; | A8-B49-C5; | A8-B49-C6; | A8-B49-C7; | A8-B49-C8; | A8-B49-C9; |
| A9-B49-C1; | A9-B49-C2; | A9-B49-C3; | A9-B49-C4; | A9-B49-C5; | A9-B49-C6; |
| A9-B49-C7; | A9-B49-C8; | A9-B49-C9; | A10-B49-C1; | A10-B49-C2; | A10-B49-C3; |
| A10-B49-C4; | A10-B49-C5; | A10-B49-C6; | A10-B49-C7; | A10-B49-C8; | A10-B49-C9; |
| A11-B49-C1; | A11-B49-C2; | A11-B49-C3; | A11-B49-C4; | A11-B49-C5; | A11-B49-C6; |
| A11-B49-C7; | A11-B49-C8; | A11-B49-C9; | A12-B49-C1; | A12-B49-C2; | A12-B49-C3; |
| A12-B49-C4; | A12-B49-C5; | A12-B49-C6; | A12-B49-C7; | A12-B49-C8; | A12-B49-C9; |
| A13-B49-C1; | A13-B49-C2; | A13-B49-C3; | A13-B49-C4; | A13-B49-C5; | A13-B49-C6; |
| A13-B49-C7; | A13-B49-C8; | A13-B49-C9; | A14-B49-C1; | A14-B49-C2; | A14-B49-C3; |
| A14-B49-C4; | A14-B49-C5; | A14-B49-C6; | A14-B49-C7; | A14-B49-C8; | A14-B49-C9; |
| A15-B49-C1; | A15-B49-C2; | A15-B49-C3; | A15-B49-C4; | A15-B49-C5; | A15-B49-C6; |
| A15-B49-C7; | A15-B49-C8; | A15-B49-C9; | A16-B49-C1; | A16-B49-C2; | A16-B49-C3; |
| A16-B49-C4; | A16-B49-C5; | A16-B49-C6; | A16-B49-C7; | A16-B49-C8; | A16-B49-C9; |
| A17-B49-C1; | A17-B49-C2; | A17-B49-C3; | A17-B49-C4; | A17-B49-C5; | A17-B49-C6; |
| A17-B49-C7; | A17-B49-C8; | A17-B49-C9; | A18-B49-C1; | A18-B49-C2; | A18-B49-C3; |
| A18-B49-C4; | A18-B49-C5; | A18-B49-C6; | A18-B49-C7; | A18-B49-C8; | A18-B49-C9; |
| A19-B49-C1; | A19-B49-C2; | A19-B49-C3; | A19-B49-C4; | A19-B49-C5; | A19-B49-C6; |
| A19-B49-C7; | A19-B49-C8; | A19-B49-C9; | A20-B49-C1; | A20-B49-C2; | A20-B49-C3; |
| A20-B49-C4; | A20-B49-C5; | A20-B49-C6; | A20-B49-C7; | A20-B49-C8; | A20-B49-C9; |
| A21-B49-C1; | A21-B49-C2; | A21-B49-C3; | A21-B49-C4; | A21-B49-C5; | A21-B49-C6; |
| A21-B49-C7; | A21-B49-C8; | A21-B49-C9; | A22-B49-C1; | A22-B49-C2; | A22-B49-C3; |
| A22-B49-C4; | A22-B49-C5; | A22-B49-C6; | A22-B49-C7; | A22-B49-C8; | A22-B49-C9; |
| A23-B49-C1; | A23-B49-C2; | A23-B49-C3; | A23-B49-C4; | A23-B49-C5; | A23-B49-C6; |
| A23-B49-C7; | A23-B49-C8; | A23-B49-C9; | A24-B49-C1; | A24-B49-C2; | A24-B49-C3; |
| A24-B49-C4; | A24-B49-C5; | A24-B49-C6; | A24-B49-C7; | A24-B49-C8; | A24-B49-C9; |
| A25-B49-C1; | A25-B49-C2; | A25-B49-C3; | A25-B49-C4; | A25-B49-C5; | A25-B49-C6; |
| A25-B49-C7; | A25-B49-C8; | A25-B49-C9; | A26-B49-C1; | A26-B49-C2; | A26-B49-C3; |
| A26-B49-C4; | A26-B49-C5; | A26-B49-C6; | A26-B49-C7; | A26-B49-C8; | A26-B49-C9; |
| A27-B49-C1; | A27-B49-C2; | A27-B49-C3; | A27-B49-C4; | A27-B49-C5; | A27-B49-C6; |
| A27-B49-C7; | A27-B49-C8; | A27-B49-C9; | A28-B49-C1; | A28-B49-C2; | A28-B49-C3; |
| A28-B49-C4; | A28-B49-C5; | A28-B49-C6; | A28-B49-C7; | A28-B49-C8; | A28-B49-C9; |
| A29-B49-C1; | A29-B49-C2; | A29-B49-C3; | A29-B49-C4; | A29-B49-C5; | A29-B49-C6; |
| A29-B49-C7; | A29-B49-C8; | A29-B49-C9; | A30-B49-C1; | A30-B49-C2; | A30-B49-C3; |
| A30-B49-C4; | A30-B49-C5; | A30-B49-C6; | A30-B49-C7; | A30-B49-C8; | A30-B49-C9; |
| A31-B49-C1; | A31-B49-C2; | A31-B49-C3; | A31-B49-C4; | A31-B49-C5; | A31-B49-C6; |
| A31-B49-C7; | A31-B49-C8; | A31-B49-C9; | A32-B49-C1; | A32-B49-C2; | A32-B49-C3; |
| A32-B49-C4; | A32-B49-C5; | A32-B49-C6; | A32-B49-C7; | A32-B49-C8; | A32-B49-C9; |
| A33-B49-C1; | A33-B49-C2; | A33-B49-C3; | A33-B49-C4; | A33-B49-C5; | A33-B49-C6; |
| A33-B49-C7; | A33-B49-C8; | A33-B49-C9; | A34-B49-C1; | A34-B49-C2; | A34-B49-C3; |

-continued

| | | | | | |
|---|---|---|---|---|---|
| A34-B49-C4; | A34-B49-C5; | A34-B49-C6; | A34-B49-C7; | A34-B49-C8; | A34-B49-C9; |
| A35-B49-C1; | A35-B49-C2; | A35-B49-C3; | A35-B49-C4; | A35-B49-C5; | A35-B49-C6; |
| A35-B49-C7; | A35-B49-C8; | A35-B49-C9; | A36-B49-C1; | A36-B49-C2; | A36-B49-C3; |
| A36-B49-C4; | A36-B49-C5; | A36-B49-C6; | A36-B49-C7; | A36-B49-C8; | A36-B49-C9; |
| A37-B49-C1; | A37-B49-C2; | A37-B49-C3; | A37-B49-C4; | A37-B49-C5; | A37-B49-C6; |
| A37-B49-C7; | A37-B49-C8; | A37-B49-C9; | A38-B49-C1; | A38-B49-C2; | A38-B49-C3; |
| A38-B49-C4; | A38-B49-C5; | A38-B49-C6; | A38-B49-C7; | A38-B49-C8; | A38-B49-C9; |
| A39-B49-C1; | A39-B49-C2; | A39-B49-C3; | A39-B49-C4; | A39-B49-C5; | A39-B49-C6; |
| A39-B49-C7; | A39-B49-C8; | A39-B49-C9; | A40-B49-C1; | A40-B49-C2; | A40-B49-C3; |
| A40-B49-C4; | A40-B49-C5; | A40-B49-C6; | A40-B49-C7; | A40-B49-C8; | A40-B49-C9; |
| A41-B49-C1; | A41-B49-C2; | A41-B49-C3; | A41-B49-C4; | A41-B49-C5; | A41-B49-C6; |
| A41-B49-C7; | A41-B49-C8; | A41-B49-C9; | A42-B49-C1; | A42-B49-C2; | A42-B49-C3; |
| A42-B49-C4; | A42-B49-C5; | A42-B49-C6; | A42-B49-C7; | A42-B49-C8; | A42-B49-C9; |
| A43-B49-C1; | A43-B49-C2; | A43-B49-C3; | A43-B49-C4; | A43-B49-C5; | A43-B49-C6; |
| A43-B49-C7; | A43-B49-C8; | A43-B49-C9; | A44-B49-C1; | A44-B49-C2; | A44-B49-C3; |
| A44-B49-C4; | A44-B49-C5; | A44-B49-C6; | A44-B49-C7; | A44-B49-C8; | A44-B49-C9; |
| A45-B49-C1; | A45-B49-C2; | A45-B49-C3; | A45-B49-C4; | A45-B49-C5; | A45-B49-C6; |
| A45-B49-C7; | A45-B49-C8; | A45-B49-C9; | A46-B49-C1; | A46-B49-C2; | A46-B49-C3; |
| A46-B49-C4; | A46-B49-C5; | A46-B49-C6; | A46-B49-C7; | A46-B49-C8; | A46-B49-C9; |
| A47-B49-C1; | A47-B49-C2; | A47-B49-C3; | A47-B49-C4; | A47-B49-C5; | A47-B49-C6; |
| A47-B49-C7; | A47-B49-C8; | A47-B49-C9; | A48-B49-C1; | A48-B49-C2; | A48-B49-C3; |
| A48-B49-C4; | A48-B49-C5; | A48-B49-C6; | A48-B49-C7; | A48-B49-C8; | A48-B49-C9; |
| A49-B49-C1; | A49-B49-C2; | A49-B49-C3; | A49-B49-C4; | A49-B49-C5; | A49-B49-C6; |
| A49-B49-C7; | A49-B49-C8; | A49-B49-C9; | A50-B49-C1; | A50-B49-C2; | A50-B49-C3; |
| A50-B49-C4; | A50-B49-C5; | A50-B49-C6; | A50-B49-C7; | A50-B49-C8; | A50-B49-C9; |
| A51-B49-C1; | A51-B49-C2; | A51-B49-C3; | A51-B49-C4; | A51-B49-C5; | A51-B49-C6; |
| A51-B49-C7; | A51-B49-C8; | A51-B49-C9; | A52-B49-C1; | A52-B49-C2; | A52-B49-C3; |
| A52-B49-C4; | A52-B49-C5; | A52-B49-C6; | A52-B49-C7; | A52-B49-C8; | A52-B49-C9; |
| A53-B49-C1; | A53-B49-C2; | A53-B49-C3; | A53-B49-C4; | A53-B49-C5; | A53-B49-C6; |
| A53-B49-C7; | A53-B49-C8; | A53-B49-C9; | A54-B49-C1; | A54-B49-C2; | A54-B49-C3; |
| A54-B49-C4; | A54-B49-C5; | A54-B49-C6; | A54-B49-C7; | A54-B49-C8; | A54-B49-C9; |
| A55-B49-C1; | A55-B49-C2; | A55-B49-C3; | A55-B49-C4; | A55-B49-C5; | A55-B49-C6; |
| A55-B49-C7; | A55-B49-C8; | A55-B49-C9; | A56-B49-C1; | A56-B49-C2; | A56-B49-C3; |
| A56-B49-C4; | A56-B49-C5; | A56-B49-C6; | A56-B49-C7; | A56-B49-C8; | A56-B49-C9; |
| A57-B49-C1; | A57-B49-C2; | A57-B49-C3; | A57-B49-C4; | A57-B49-C5; | A57-B49-C6; |
| A57-B49-C7; | A57-B49-C8; | A57-B49-C9; | A58-B49-C1; | A58-B49-C2; | A58-B49-C3; |
| A58-B49-C4; | A58-B49-C5; | A58-B49-C6; | A58-B49-C7; | A58-B49-C8; | A58-B49-C9; |
| A59-B49-C1; | A59-B49-C2; | A59-B49-C3; | A59-B49-C4; | A59-B49-C5; | A59-B49-C6; |
| A59-B49-C7; | A59-B49-C8; | A59-B49-C9; | A60-B49-C1; | A60-B49-C2; | A60-B49-C3; |
| A60-B49-C4; | A60-B49-C5; | A60-B49-C6; | A60-B49-C7; | A60-B49-C8; | A60-B49-C9; |
| A61-B49-C1; | A61-B49-C2; | A61-B49-C3; | A61-B49-C4; | A61-B49-C5; | A61-B49-C6; |
| A61-B49-C7; | A61-B49-C8; | A61-B49-C9; | A62-B49-C1; | A62-B49-C2; | A62-B49-C3; |
| A62-B49-C4; | A62-B49-C5; | A62-B49-C6; | A62-B49-C7; | A62-B49-C8; | A62-B49-C9; |
| A63-B49-C1; | A63-B49-C2; | A63-B49-C3; | A63-B49-C4; | A63-B49-C5; | A63-B49-C6; |
| A63-B49-C7; | A63-B49-C8; | A63-B49-C9; | A64-B49-C1; | A64-B49-C2; | A64-B49-C3; |
| A64-B49-C4; | A64-B49-C5; | A64-B49-C6; | A64-B49-C7; | A64-B49-C8; | A64-B49-C9; |
| A65-B49-C1; | A65-B49-C2; | A65-B49-C3; | A65-B49-C4; | A65-B49-C5; | A65-B49-C6; |
| A65-B49-C7; | A65-B49-C8; | A65-B49-C9; | A66-B49-C1; | A66-B49-C2; | A66-B49-C3; |
| A66-B49-C4; | A66-B49-C5; | A66-B49-C6; | A66-B49-C7; | A66-B49-C8; | A66-B49-C9; |
| A67-B49-C1; | A67-B49-C2; | A67-B49-C3; | A67-B49-C4; | A67-B49-C5; | A67-B49-C6; |
| A67-B49-C7; | A67-B49-C8; | A67-B49-C9; | A68-B49-C1; | A68-B49-C2; | A68-B49-C3; |
| A68-B49-C4; | A68-B49-C5; | A68-B49-C6; | A68-B49-C7; | A68-B49-C8; | A68-B49-C9; |
| A69-B49-C1; | A69-B49-C2; | A69-B49-C3; | A69-B49-C4; | A69-B49-C5; | A69-B49-C6; |
| A69-B49-C7; | A69-B49-C8; | A69-B49-C9; | A70-B49-C1; | A70-B49-C2; | A70-B49-C3; |
| A70-B49-C4; | A70-B49-C5; | A70-B49-C6; | A70-B49-C7; | A70-B49-C8; | A70-B49-C9; |
| A71-B49-C1; | A71-B49-C2; | A71-B49-C3; | A71-B49-C4; | A71-B49-C5; | A71-B49-C6; |
| A71-B49-C7; | A71-B49-C8; | A71-B49-C9; | A1-B50-C1; | A1-B50-C2; | A1-B50-C3; |
| A1-B50-C4; | A1-B50-C5; | A1-B50-C6; | A1-B50-C7; | A1-B50-C8; | A1-B50-C9; |
| A2-B50-C1; | A2-B50-C2; | A2-B50-C3; | A2-B50-C4; | A2-B50-C5; | A2-B50-C6; |
| A2-B50-C7; | A2-B50-C8; | A2-B50-C9; | A3-B50-C1; | A3-B50-C2; | A3-B50-C3; |
| A3-B50-C4; | A3-B50-C5; | A3-B50-C6; | A3-B50-C7; | A3-B50-C8; | A3-B50-C9; |
| A4-B50-C1; | A4-B50-C2; | A4-B50-C3; | A4-B50-C4; | A4-B50-C5; | A4-B50-C6; |
| A4-B50-C7; | A4-B50-C8; | A4-B50-C9; | A5-B50-C1; | A5-B50-C2; | A5-B50-C3; |
| A5-B50-C4; | A5-B50-C5; | A5-B50-C6; | A5-B50-C7; | A5-B50-C8; | A5-B50-C9; |
| A6-B50-C1; | A6-B50-C2; | A6-B50-C3; | A6-B50-C4; | A6-B50-C5; | A6-B50-C6; |
| A6-B50-C7; | A6-B50-C8; | A6-B50-C9; | A7-B50-C1; | A7-B50-C2; | A7-B50-C3; |
| A7-B50-C4; | A7-B50-C5; | A7-B50-C6; | A7-B50-C7; | A7-B50-C8; | A7-B50-C9; |
| A8-B50-C1; | A8-B50-C2; | A8-B50-C3; | A8-B50-C4; | A8-B50-C5; | A8-B50-C6; |
| A8-B50-C7; | A8-B50-C8; | A8-B50-C9; | A9-B50-C1; | A9-B50-C2; | A9-B50-C3; |
| A9-B50-C4; | A9-B50-C5; | A9-B50-C6; | A9-B50-C7; | A9-B50-C8; | A9-B50-C9; |
| A10-B50-C1; | A10-B50-C2; | A10-B50-C3; | A10-B50-C4; | A10-B50-C5; | A10-B50-C6; |
| A10-B50-C7; | A10-B50-C8; | A10-B50-C9; | A11-B50-C1; | A11-B50-C2; | A11-B50-C3; |
| A11-B50-C4; | A11-B50-C5; | A11-B50-C6; | A11-B50-C7; | A11-B50-C8; | A11-B50-C9; |
| A12-B50-C1; | A12-B50-C2; | A12-B50-C3; | A12-B50-C4; | A12-B50-C5; | A12-B50-C6; |
| A12-B50-C7; | A12-B50-C8; | A12-B50-C9; | A13-B50-C1; | A13-B50-C2; | A13-B50-C3; |
| A13-B50-C4; | A13-B50-C5; | A13-B50-C6; | A13-B50-C7; | A13-B50-C8; | A13-B50-C9; |
| A14-B50-C1; | A14-B50-C2; | A14-B50-C3; | A14-B50-C4; | A14-B50-C5; | A14-B50-C6; |
| A14-B50-C7; | A14-B50-C8; | A14-B50-C9; | A15-B50-C1; | A15-B50-C2; | A15-B50-C3; |
| A15-B50-C4; | A15-B50-C5; | A15-B50-C6; | A15-B50-C7; | A15-B50-C8; | A15-B50-C9; |

-continued

A16-B50-C1; A16-B50-C2; A16-B50-C3; A16-B50-C4; A16-B50-C5; A16-B50-C6;
A16-B50-C7; A16-B50-C8; A16-B50-C9; A17-B50-C1; A17-B50-C2; A17-B50-C3;
A17-B50-C4; A17-B50-C5; A17-B50-C6; A17-B50-C7; A17-B50-C8; A17-B50-C9;
A18-B50-C1; A18-B50-C2; A18-B50-C3; A18-B50-C4; A18-B50-C5; A18-B50-C6;
A18-B50-C7; A18-B50-C8; A18-B50-C9; A19-B50-C1; A19-B50-C2; A19-B50-C3;
A19-B50-C4; A19-B50-C5; A19-B50-C6; A19-B50-C7; A19-B50-C8; A19-B50-C9;
A20-B50-C1; A20-B50-C2; A20-B50-C3; A20-B50-C4; A20-B50-C5; A20-B50-C6;
A20-B50-C7; A20-B50-C8; A20-B50-C9; A21-B50-C1; A21-B50-C2; A21-B50-C3;
A21-B50-C4; A21-B50-C5; A21-B50-C6; A21-B50-C7; A21-B50-C8; A21-B50-C9;
A22-B50-C1; A22-B50-C2; A22-B50-C3; A22-B50-C4; A22-B50-C5; A22-B50-C6;
A22-B50-C7; A22-B50-C8; A22-B50-C9; A23-B50-C1; A23-B50-C2; A23-B50-C3;
A23-B50-C4; A23-B50-C5; A23-B50-C6; A23-B50-C7; A23-B50-C8; A23-B50-C9;
A24-B50-C1; A24-B50-C2; A24-B50-C3; A24-B50-C4; A24-B50-C5; A24-B50-C6;
A24-B50-C7; A24-B50-C8; A24-B50-C9; A25-B50-C1; A25-B50-C2; A25-B50-C3;
A25-B50-C4; A25-B50-C5; A25-B50-C6; A25-B50-C7; A25-B50-C8; A25-B50-C9;
A26-B50-C1; A26-B50-C2; A26-B50-C3; A26-B50-C4; A26-B50-C5; A26-B50-C6;
A26-B50-C7; A26-B50-C8; A26-B50-C9; A27-B50-C1; A27-B50-C2; A27-B50-C3;
A27-B50-C4; A27-B50-C5; A27-B50-C6; A27-B50-C7; A27-B50-C8; A27-B50-C9;
A28-B50-C1; A28-B50-C2; A28-B50-C3; A28-B50-C4; A28-B50-C5; A28-B50-C6;
A28-B50-C7; A28-B50-C8; A28-B50-C9; A29-B50-C1; A29-B50-C2; A29-B50-C3;
A29-B50-C4; A29-B50-C5; A29-B50-C6; A29-B50-C7; A29-B50-C8; A29-B50-C9;
A30-B50-C1; A30-B50-C2; A30-B50-C3; A30-B50-C4; A30-B50-C5; A30-B50-C6;
A30-B50-C7; A30-B50-C8; A30-B50-C9; A31-B50-C1; A31-B50-C2; A31-B50-C3;
A31-B50-C4; A31-B50-C5; A31-B50-C6; A31-B50-C7; A31-B50-C8; A31-B50-C9;
A32-B50-C1; A32-B50-C2; A32-B50-C3; A32-B50-C4; A32-B50-C5; A32-B50-C6;
A32-B50-C7; A32-B50-C8; A32-B50-C9; A33-B50-C1; A33-B50-C2; A33-B50-C3;
A33-B50-C4; A33-B50-C5; A33-B50-C6; A33-B50-C7; A33-B50-C8; A33-B50-C9;
A34-B50-C1; A34-B50-C2; A34-B50-C3; A34-B50-C4; A34-B50-C5; A34-B50-C6;
A34-B50-C7; A34-B50-C8; A34-B50-C9; A35-B50-C1; A35-B50-C2; A35-B50-C3;
A35-B50-C4; A35-B50-C5; A35-B50-C6; A35-B50-C7; A35-B50-C8; A35-B50-C9;
A36-B50-C1; A36-B50-C2; A36-B50-C3; A36-B50-C4; A36-B50-C5; A36-B50-C6;
A36-B50-C7; A36-B50-C8; A36-B50-C9; A37-B50-C1; A37-B50-C2; A37-B50-C3;
A37-B50-C4; A37-B50-C5; A37-B50-C6; A37-B50-C7; A37-B50-C8; A37-B50-C9;
A38-B50-C1; A38-B50-C2; A38-B50-C3; A38-B50-C4; A38-B50-C5; A38-B50-C6;
A38-B50-C7; A38-B50-C8; A38-B50-C9; A39-B50-C1; A39-B50-C2; A39-B50-C3;
A39-B50-C4; A39-B50-C5; A39-B50-C6; A39-B50-C7; A39-B50-C8; A39-B50-C9;
A40-B50-C1; A40-B50-C2; A40-B50-C3; A40-B50-C4; A40-B50-C5; A40-B50-C6;
A40-B50-C7; A40-B50-C8; A40-B50-C9; A41-B50-C1; A41-B50-C2; A41-B50-C3;
A41-B50-C4; A41-B50-C5; A41-B50-C6; A41-B50-C7; A41-B50-C8; A41-B50-C9;
A42-B50-C1; A42-B50-C2; A42-B50-C3; A42-B50-C4; A42-B50-C5; A42-B50-C6;
A42-B50-C7; A42-B50-C8; A42-B50-C9; A43-B50-C1; A43-B50-C2; A43-B50-C3;
A43-B50-C4; A43-B50-C5; A43-B50-C6; A43-B50-C7; A43-B50-C8; A43-B50-C9;
A44-B50-C1; A44-B50-C2; A44-B50-C3; A44-B50-C4; A44-B50-C5; A44-B50-C6;
A44-B50-C7; A44-B50-C8; A44-B50-C9; A45-B50-C1; A45-B50-C2; A45-B50-C3;
A45-B50-C4; A45-B50-C5; A45-B50-C6; A45-B50-C7; A45-B50-C8; A45-B50-C9;
A46-B50-C1; A46-B50-C2; A46-B50-C3; A46-B50-C4; A46-B50-C5; A46-B50-C6;
A46-B50-C7; A46-B50-C8; A46-B50-C9; A47-B50-C1; A47-B50-C2; A47-B50-C3;
A47-B50-C4; A47-B50-C5; A47-B50-C6; A47-B50-C7; A47-B50-C8; A47-B50-C9;
A48-B50-C1; A48-B50-C2; A48-B50-C3; A48-B50-C4; A48-B50-C5; A48-B50-C6;
A48-B50-C7; A48-B50-C8; A48-B50-C9; A49-B50-C1; A49-B50-C2; A49-B50-C3;
A49-B50-C4; A49-B50-C5; A49-B50-C6; A49-B50-C7; A49-B50-C8; A49-B50-C9;
A50-B50-C1; A50-B50-C2; A50-B50-C3; A50-B50-C4; A50-B50-C5; A50-B50-C6;
A50-B50-C7; A50-B50-C8; A50-B50-C9; A51-B50-C1; A51-B50-C2; A51-B50-C3;
A51-B50-C4; A51-B50-C5; A51-B50-C6; A51-B50-C7; A51-B50-C8; A51-B50-C9;
A52-B50-C1; A52-B50-C2; A52-B50-C3; A52-B50-C4; A52-B50-C5; A52-B50-C6;
A52-B50-C7; A52-B50-C8; A52-B50-C9; A53-B50-C1; A53-B50-C2; A53-B50-C3;
A53-B50-C4; A53-B50-C5; A53-B50-C6; A53-B50-C7; A53-B50-C8; A53-B50-C9;
A54-B50-C1; A54-B50-C2; A54-B50-C3; A54-B50-C4; A54-B50-C5; A54-B50-C6;
A54-B50-C7; A54-B50-C8; A54-B50-C9; A55-B50-C1; A55-B50-C2; A55-B50-C3;
A55-B50-C4; A55-B50-C5; A55-B50-C6; A55-B50-C7; A55-B50-C8; A55-B50-C9;
A56-B50-C1; A56-B50-C2; A56-B50-C3; A56-B50-C4; A56-B50-C5; A56-B50-C6;
A56-B50-C7; A56-B50-C8; A56-B50-C9; A57-B50-C1; A57-B50-C2; A57-B50-C3;
A57-B50-C4; A57-B50-C5; A57-B50-C6; A57-B50-C7; A57-B50-C8; A57-B50-C9;
A58-B50-C1; A58-B50-C2; A58-B50-C3; A58-B50-C4; A58-B50-C5; A58-B50-C6;
A58-B50-C7; A58-B50-C8; A58-B50-C9; A59-B50-C1; A59-B50-C2; A59-B50-C3;
A59-B50-C4; A59-B50-C5; A59-B50-C6; A59-B50-C7; A59-B50-C8; A59-B50-C9;
A60-B50-C1; A60-B50-C2; A60-B50-C3; A60-B50-C4; A60-B50-C5; A60-B50-C6;
A60-B50-C7; A60-B50-C8; A60-B50-C9; A61-B50-C1; A61-B50-C2; A61-B50-C3;
A61-B50-C4; A61-B50-C5; A61-B50-C6; A61-B50-C7; A61-B50-C8; A61-B50-C9;
A62-B50-C1; A62-B50-C2; A62-B50-C3; A62-B50-C4; A62-B50-C5; A62-B50-C6;
A62-B50-C7; A62-B50-C8; A62-B50-C9; A63-B50-C1; A63-B50-C2; A63-B50-C3;
A63-B50-C4; A63-B50-C5; A63-B50-C6; A63-B50-C7; A63-B50-C8; A63-B50-C9;
A64-B50-C1; A64-B50-C2; A64-B50-C3; A64-B50-C4; A64-B50-C5; A64-B50-C6;
A64-B50-C7; A64-B50-C8; A64-B50-C9; A65-B50-C1; A65-B50-C2; A65-B50-C3;
A65-B50-C4; A65-B50-C5; A65-B50-C6; A65-B50-C7; A65-B50-C8; A65-B50-C9;
A66-B50-C1; A66-B50-C2; A66-B50-C3; A66-B50-C4; A66-B50-C5; A66-B50-C6;
A66-B50-C7; A66-B50-C8; A66-B50-C9; A67-B50-C1; A67-B50-C2; A67-B50-C3;
A67-B50-C4; A67-B50-C5; A67-B50-C6; A67-B50-C7; A67-B50-C8; A67-B50-C9;
A68-B50-C1; A68-B50-C2; A68-B50-C3; A68-B50-C4; A68-B50-C5; A68-B50-C6;

-continued

| | | | | | |
|---|---|---|---|---|---|
| A68-B50-C7; | A68-B50-C8; | A68-B50-C9; | A69-B50-C1; | A69-B50-C2; | A69-B50-C3; |
| A69-B50-C4; | A69-B50-C5; | A69-B50-C6; | A69-B50-C7; | A69-B50-C8; | A69-B50-C9; |
| A70-B50-C1; | A70-B50-C2; | A70-B50-C3; | A70-B50-C4; | A70-B50-C5; | A70-B50-C6; |
| A70-B50-C7; | A70-B50-C8; | A70-B50-C9; | A71-B50-C1; | A71-B50-C2; | A71-B50-C3; |
| A71-B50-C4; | A71-B50-C5; | A71-B50-C6; | A71-B50-C7; | A71-B50-C8; | A71-B50-C9; |
| A1-B51-C1; | A1-B51-C2; | A1-B51-C3; | A1-B51-C4; | A1-B51-C5; | A1-B51-C6; |
| A1-B51-C7; | A1-B51-C8; | A1-B51-C9; | A2-B51-C1; | A2-B51-C2; | A2-B51-C3; |
| A2-B51-C4; | A2-B51-C5; | A2-B51-C6; | A2-B51-C7; | A2-B51-C8; | A2-B51-C9; |
| A3-B51-C1; | A3-B51-C2; | A3-B51-C3; | A3-B51-C4; | A3-B51-C5; | A3-B51-C6; |
| A3-B51-C7; | A3-B51-C8; | A3-B51-C9; | A4-B51-C1; | A4-B51-C2; | A4-B51-C3; |
| A4-B51-C4; | A4-B51-C5; | A4-B51-C6; | A4-B51-C7; | A4-B51-C8; | A4-B51-C9; |
| A5-B51-C1; | A5-B51-C2; | A5-B51-C3; | A5-B51-C4; | A5-B51-C5; | A5-B51-C6; |
| A5-B51-C7; | A5-B51-C8; | A5-B51-C9; | A6-B51-C1; | A6-B51-C2; | A6-B51-C3; |
| A6-B51-C4; | A6-B51-C5; | A6-B51-C6; | A6-B51-C7; | A6-B51-C8; | A6-B51-C9; |
| A7-B51-C1; | A7-B51-C2; | A7-B51-C3; | A7-B51-C4; | A7-B51-C5; | A7-B51-C6; |
| A7-B51-C7; | A7-B51-C8; | A7-B51-C9; | A8-B51-C1; | A8-B51-C2; | A8-B51-C3; |
| A8-B51-C4; | A8-B51-C5; | A8-B51-C6; | A8-B51-C7; | A8-B51-C8; | A8-B51-C9; |
| A9-B51-C1; | A9-B51-C2; | A9-B51-C3; | A9-B51-C4; | A9-B51-C5; | A9-B51-C6; |
| A9-B51-C7; | A9-B51-C8; | A9-B51-C9; | A10-B51-C1; | A10-B51-C2; | A10-B51-C3; |
| A10-B51-C4; | A10-B51-C5; | A10-B51-C6; | A10-B51-C7; | A10-B51-C8; | A10-B51-C9; |
| A11-B51-C1; | A11-B51-C2; | A11-B51-C3; | A11-B51-C4; | A11-B51-C5; | A11-B51-C6; |
| A11-B51-C7; | A11-B51-C8; | A11-B51-C9; | A12-B51-C1; | A12-B51-C2; | A12-B51-C3; |
| A12-B51-C4; | A12-B51-C5; | A12-B51-C6; | A12-B51-C7; | A12-B51-C8; | A12-B51-C9; |
| A13-B51-C1; | A13-B51-C2; | A13-B51-C3; | A13-B51-C4; | A13-B51-C5; | A13-B51-C6; |
| A13-B51-C7; | A13-B51-C8; | A13-B51-C9; | A14-B51-C1; | A14-B51-C2; | A14-B51-C3; |
| A14-B51-C4; | A14-B51-C5; | A14-B51-C6; | A14-B51-C7; | A14-B51-C8; | A14-B51-C9; |
| A15-B51-C1; | A15-B51-C2; | A15-B51-C3; | A15-B51-C4; | A15-B51-C5; | A15-B51-C6; |
| A15-B51-C7; | A15-B51-C8; | A15-B51-C9; | A16-B51-C1; | A16-B51-C2; | A16-B51-C3; |
| A16-B51-C4; | A16-B51-C5; | A16-B51-C6; | A16-B51-C7; | A16-B51-C8; | A16-B51-C9; |
| A17-B51-C1; | A17-B51-C2; | A17-B51-C3; | A17-B51-C4; | A17-B51-C5; | A17-B51-C6; |
| A17-B51-C7; | A17-B51-C8; | A17-B51-C9; | A18-B51-C1; | A18-B51-C2; | A18-B51-C3; |
| A18-B51-C4; | A18-B51-C5; | A18-B51-C6; | A18-B51-C7; | A18-B51-C8; | A18-B51-C9; |
| A19-B51-C1; | A19-B51-C2; | A19-B51-C3; | A19-B51-C4; | A19-B51-C5; | A19-B51-C6; |
| A19-B51-C7; | A19-B51-C8; | A19-B51-C9; | A20-B51-C1; | A20-B51-C2; | A20-B51-C3; |
| A20-B51-C4; | A20-B51-C5; | A20-B51-C6; | A20-B51-C7; | A20-B51-C8; | A20-B51-C9; |
| A21-B51-C1; | A21-B51-C2; | A21-B51-C3; | A21-B51-C4; | A21-B51-C5; | A21-B51-C6; |
| A21-B51-C7; | A21-B51-C8; | A21-B51-C9; | A22-B51-C1; | A22-B51-C2; | A22-B51-C3; |
| A22-B51-C4; | A22-B51-C5; | A22-B51-C6; | A22-B51-C7; | A22-B51-C8; | A22-B51-C9; |
| A23-B51-C1; | A23-B51-C2; | A23-B51-C3; | A23-B51-C4; | A23-B51-C5; | A23-B51-C6; |
| A23-B51-C7; | A23-B51-C8; | A23-B51-C9; | A24-B51-C1; | A24-B51-C2; | A24-B51-C3; |
| A24-B51-C4; | A24-B51-C5; | A24-B51-C6; | A24-B51-C7; | A24-B51-C8; | A24-B51-C9; |
| A25-B51-C1; | A25-B51-C2; | A25-B51-C3; | A25-B51-C4; | A25-B51-C5; | A25-B51-C6; |
| A25-B51-C7; | A25-B51-C8; | A25-B51-C9; | A26-B51-C1; | A26-B51-C2; | A26-B51-C3; |
| A26-B51-C4; | A26-B51-C5; | A26-B51-C6; | A26-B51-C7; | A26-B51-C8; | A26-B51-C9; |
| A27-B51-C1; | A27-B51-C2; | A27-B51-C3; | A27-B51-C4; | A27-B51-C5; | A27-B51-C6; |
| A27-B51-C7; | A27-B51-C8; | A27-B51-C9; | A28-B51-C1; | A28-B51-C2; | A28-B51-C3; |
| A28-B51-C4; | A28-B51-C5; | A28-B51-C6; | A28-B51-C7; | A28-B51-C8; | A28-B51-C9; |
| A29-B51-C1; | A29-B51-C2; | A29-B51-C3; | A29-B51-C4; | A29-B51-C5; | A29-B51-C6; |
| A29-B51-C7; | A29-B51-C8; | A29-B51-C9; | A30-B51-C1; | A30-B51-C2; | A30-B51-C3; |
| A30-B51-C4; | A30-B51-C5; | A30-B51-C6; | A30-B51-C7; | A30-B51-C8; | A30-B51-C9; |
| A31-B51-C1; | A31-B51-C2; | A31-B51-C3; | A31-B51-C4; | A31-B51-C5; | A31-B51-C6; |
| A31-B51-C7; | A31-B51-C8; | A31-B51-C9; | A32-B51-C1; | A32-B51-C2; | A32-B51-C3; |
| A32-B51-C4; | A32-B51-C5; | A32-B51-C6; | A32-B51-C7; | A32-B51-C8; | A32-B51-C9; |
| A33-B51-C1; | A33-B51-C2; | A33-B51-C3; | A33-B51-C4; | A33-B51-C5; | A33-B51-C6; |
| A33-B51-C7; | A33-B51-C8; | A33-B51-C9; | A34-B51-C1; | A34-B51-C2; | A34-B51-C3; |
| A34-B51-C4; | A34-B51-C5; | A34-B51-C6; | A34-B51-C7; | A34-B51-C8; | A34-B51-C9; |
| A35-B51-C1; | A35-B51-C2; | A35-B51-C3; | A35-B51-C4; | A35-B51-C5; | A35-B51-C6; |
| A35-B51-C7; | A35-B51-C8; | A35-B51-C9; | A36-B51-C1; | A36-B51-C2; | A36-B51-C3; |
| A36-B51-C4; | A36-B51-C5; | A36-B51-C6; | A36-B51-C7; | A36-B51-C8; | A36-B51-C9; |
| A37-B51-C1; | A37-B51-C2; | A37-B51-C3; | A37-B51-C4; | A37-B51-C5; | A37-B51-C6; |
| A37-B51-C7; | A37-B51-C8; | A37-B51-C9; | A38-B51-C1; | A38-B51-C2; | A38-B51-C3; |
| A38-B51-C4; | A38-B51-C5; | A38-B51-C6; | A38-B51-C7; | A38-B51-C8; | A38-B51-C9; |
| A39-B51-C1; | A39-B51-C2; | A39-B51-C3; | A39-B51-C4; | A39-B51-C5; | A39-B51-C6; |
| A39-B51-C7; | A39-B51-C8; | A39-B51-C9; | A40-B51-C1; | A40-B51-C2; | A40-B51-C3; |
| A40-B51-C4; | A40-B51-C5; | A40-B51-C6; | A40-B51-C7; | A40-B51-C8; | A40-B51-C9; |
| A41-B51-C1; | A41-B51-C2; | A41-B51-C3; | A41-B51-C4; | A41-B51-C5; | A41-B51-C6; |
| A41-B51-C7; | A41-B51-C8; | A41-B51-C9; | A42-B51-C1; | A42-B51-C2; | A42-B51-C3; |
| A42-B51-C4; | A42-B51-C5; | A42-B51-C6; | A42-B51-C7; | A42-B51-C8; | A42-B51-C9; |
| A43-B51-C1; | A43-B51-C2; | A43-B51-C3; | A43-B51-C4; | A43-B51-C5; | A43-B51-C6; |
| A43-B51-C7; | A43-B51-C8; | A43-B51-C9; | A44-B51-C1; | A44-B51-C2; | A44-B51-C3; |
| A44-B51-C4; | A44-B51-C5; | A44-B51-C6; | A44-B51-C7; | A44-B51-C8; | A44-B51-C9; |
| A45-B51-C1; | A45-B51-C2; | A45-B51-C3; | A45-B51-C4; | A45-B51-C5; | A45-B51-C6; |
| A45-B51-C7; | A45-B51-C8; | A45-B51-C9; | A46-B51-C1; | A46-B51-C2; | A46-B51-C3; |
| A46-B51-C4; | A46-B51-C5; | A46-B51-C6; | A46-B51-C7; | A46-B51-C8; | A46-B51-C9; |
| A47-B51-C1; | A47-B51-C2; | A47-B51-C3; | A47-B51-C4; | A47-B51-C5; | A47-B51-C6; |
| A47-B51-C7; | A47-B51-C8; | A47-B51-C9; | A48-B51-C1; | A48-B51-C2; | A48-B51-C3; |
| A48-B51-C4; | A48-B51-C5; | A48-B51-C6; | A48-B51-C7; | A48-B51-C8; | A48-B51-C9; |
| A49-B51-C1; | A49-B51-C2; | A49-B51-C3; | A49-B51-C4; | A49-B51-C5; | A49-B51-C6; |
| A49-B51-C7; | A49-B51-C8; | A49-B51-C9; | A50-B51-C1; | A50-B51-C2; | A50-B51-C3; |

-continued

| | | | | | |
|---|---|---|---|---|---|
| A50-B51-C4; | A50-B51-C5; | A50-B51-C6; | A50-B51-C7; | A50-B51-C8; | A50-B51-C9; |
| A51-B51-C1; | A51-B51-C2; | A51-B51-C3; | A51-B51-C4; | A51-B51-C5; | A51-B51-C6; |
| A51-B51-C7; | A51-B51-C8; | A51-B51-C9; | A52-B51-C1; | A52-B51-C2; | A52-B51-C3; |
| A52-B51-C4; | A52-B51-C5; | A52-B51-C6; | A52-B51-C7; | A52-B51-C8; | A52-B51-C9; |
| A53-B51-C1; | A53-B51-C2; | A53-B51-C3; | A53-B51-C4; | A53-B51-C5; | A53-B51-C6; |
| A53-B51-C7; | A53-B51-C8; | A53-B51-C9; | A54-B51-C1; | A54-B51-C2; | A54-B51-C3; |
| A54-B51-C4; | A54-B51-C5; | A54-B51-C6; | A54-B51-C7; | A54-B51-C8; | A54-B51-C9; |
| A55-B51-C1; | A55-B51-C2; | A55-B51-C3; | A55-B51-C4; | A55-B51-C5; | A55-B51-C6; |
| A55-B51-C7; | A55-B51-C8; | A55-B51-C9; | A56-B51-C1; | A56-B51-C2; | A56-B51-C3; |
| A56-B51-C4; | A56-B51-C5; | A56-B51-C6; | A56-B51-C7; | A56-B51-C8; | A56-B51-C9; |
| A57-B51-C1; | A57-B51-C2; | A57-B51-C3; | A57-B51-C4; | A57-B51-C5; | A57-B51-C6; |
| A57-B51-C7; | A57-B51-C8; | A57-B51-C9; | A58-B51-C1; | A58-B51-C2; | A58-B51-C3; |
| A58-B51-C4; | A58-B51-C5; | A58-B51-C6; | A58-B51-C7; | A58-B51-C8; | A58-B51-C9; |
| A59-B51-C1; | A59-B51-C2; | A59-B51-C3; | A59-B51-C4; | A59-B51-C5; | A59-B51-C6; |
| A59-B51-C7; | A59-B51-C8; | A59-B51-C9; | A60-B51-C1; | A60-B51-C2; | A60-B51-C3; |
| A60-B51-C4; | A60-B51-C5; | A60-B51-C6; | A60-B51-C7; | A60-B51-C8; | A60-B51-C9; |
| A61-B51-C1; | A61-B51-C2; | A61-B51-C3; | A61-B51-C4; | A61-B51-C5; | A61-B51-C6; |
| A61-B51-C7; | A61-B51-C8; | A61-B51-C9; | A62-B51-C1; | A62-B51-C2; | A62-B51-C3; |
| A62-B51-C4; | A62-B51-C5; | A62-B51-C6; | A62-B51-C7; | A62-B51-C8; | A62-B51-C9; |
| A63-B51-C1; | A63-B51-C2; | A63-B51-C3; | A63-B51-C4; | A63-B51-C5; | A63-B51-C6; |
| A63-B51-C7; | A63-B51-C8; | A63-B51-C9; | A64-B51-C1; | A64-B51-C2; | A64-B51-C3; |
| A64-B51-C4; | A64-B51-C5; | A64-B51-C6; | A64-B51-C7; | A64-B51-C8; | A64-B51-C9; |
| A65-B51-C1; | A65-B51-C2; | A65-B51-C3; | A65-B51-C4; | A65-B51-C5; | A65-B51-C6; |
| A65-B51-C7; | A65-B51-C8; | A65-B51-C9; | A66-B51-C1; | A66-B51-C2; | A66-B51-C3; |
| A66-B51-C4; | A66-B51-C5; | A66-B51-C6; | A66-B51-C7; | A66-B51-C8; | A66-B51-C9; |
| A67-B51-C1; | A67-B51-C2; | A67-B51-C3; | A67-B51-C4; | A67-B51-C5; | A67-B51-C6; |
| A67-B51-C7; | A67-B51-C8; | A67-B51-C9; | A68-B51-C1; | A68-B51-C2; | A68-B51-C3; |
| A68-B51-C4; | A68-B51-C5; | A68-B51-C6; | A68-B51-C7; | A68-B51-C8; | A68-B51-C9; |
| A69-B51-C1; | A69-B51-C2; | A69-B51-C3; | A69-B51-C4; | A69-B51-C5; | A69-B51-C6; |
| A69-B51-C7; | A69-B51-C8; | A69-B51-C9; | A70-B51-C1; | A70-B51-C2; | A70-B51-C3; |
| A70-B51-C4; | A70-B51-C5; | A70-B51-C6; | A70-B51-C7; | A70-B51-C8; | A70-B51-C9; |
| A71-B51-C1; | A71-B51-C2; | A71-B51-C3; | A71-B51-C4; | A71-B51-C5; | A71-B51-C6; |
| A71-B51-C7; | A71-B51-C8; | A71-B51-C9; | A1-B52-C1; | A1-B52-C2; | A1-B52-C3; |
| A1-B52-C4; | A1-B52-C5; | A1-B52-C6; | A1-B52-C7; | A1-B52-C8; | A1-B52-C9; |
| A2-B52-C1; | A2-B52-C2; | A2-B52-C3; | A2-B52-C4; | A2-B52-C5; | A2-B52-C6; |
| A2-B52-C7; | A2-B52-C8; | A2-B52-C9; | A3-B52-C1; | A3-B52-C2; | A3-B52-C3; |
| A3-B52-C4; | A3-B52-C5; | A3-B52-C6; | A3-B52-C7; | A3-B52-C8; | A3-B52-C9; |
| A4-B52-C1; | A4-B52-C2; | A4-B52-C3; | A4-B52-C4; | A4-B52-C5; | A4-B52-C6; |
| A4-B52-C7; | A4-B52-C8; | A4-B52-C9; | A5-B52-C1; | A5-B52-C2; | A5-B52-C3; |
| A5-B52-C4; | A5-B52-C5; | A5-B52-C6; | A5-B52-C7; | A5-B52-C8; | A5-B52-C9; |
| A6-B52-C1; | A6-B52-C2; | A6-B52-C3; | A6-B52-C4; | A6-B52-C5; | A6-B52-C6; |
| A6-B52-C7; | A6-B52-C8; | A6-B52-C9; | A7-B52-C1; | A7-B52-C2; | A7-B52-C3; |
| A7-B52-C4; | A7-B52-C5; | A7-B52-C6; | A7-B52-C7; | A7-B52-C8; | A7-B52-C9; |
| A8-B52-C1; | A8-B52-C2; | A8-B52-C3; | A8-B52-C4; | A8-B52-C5; | A8-B52-C6; |
| A8-B52-C7; | A8-B52-C8; | A8-B52-C9; | A9-B52-C1; | A9-B52-C2; | A9-B52-C3; |
| A9-B52-C4; | A9-B52-C5; | A9-B52-C6; | A9-B52-C7; | A9-B52-C8; | A9-B52-C9; |
| A10-B52-C1; | A10-B52-C2; | A10-B52-C3; | A10-B52-C4; | A10-B52-C5; | A10-B52-C6; |
| A10-B52-C7; | A10-B52-C8; | A10-B52-C9; | A11-B52-C1; | A11-B52-C2; | A11-B52-C3; |
| A11-B52-C4; | A11-B52-C5; | A11-B52-C6; | A11-B52-C7; | A11-B52-C8; | A11-B52-C9; |
| A12-B52-C1; | A12-B52-C2; | A12-B52-C3; | A12-B52-C4; | A12-B52-C5; | A12-B52-C6; |
| A12-B52-C7; | A12-B52-C8; | A12-B52-C9; | A13-B52-C1; | A13-B52-C2; | A13-B52-C3; |
| A13-B52-C4; | A13-B52-C5; | A13-B52-C6; | A13-B52-C7; | A13-B52-C8; | A13-B52-C9; |
| A14-B52-C1; | A14-B52-C2; | A14-B52-C3; | A14-B52-C4; | A14-B52-C5; | A14-B52-C6; |
| A14-B52-C7; | A14-B52-C8; | A14-B52-C9; | A15-B52-C1; | A15-B52-C2; | A15-B52-C3; |
| A15-B52-C4; | A15-B52-C5; | A15-B52-C6; | A15-B52-C7; | A15-B52-C8; | A15-B52-C9; |
| A16-B52-C1; | A16-B52-C2; | A16-B52-C3; | A16-B52-C4; | A16-B52-C5; | A16-B52-C6; |
| A16-B52-C7; | A16-B52-C8; | A16-B52-C9; | A17-B52-C1; | A17-B52-C2; | A17-B52-C3; |
| A17-B52-C4; | A17-B52-C5; | A17-B52-C6; | A17-B52-C7; | A17-B52-C8; | A17-B52-C9; |
| A18-B52-C1; | A18-B52-C2; | A18-B52-C3; | A18-B52-C4; | A18-B52-C5; | A18-B52-C6; |
| A18-B52-C7; | A18-B52-C8; | A18-B52-C9; | A19-B52-C1; | A19-B52-C2; | A19-B52-C3; |
| A19-B52-C4; | A19-B52-C5; | A19-B52-C6; | A19-B52-C7; | A19-B52-C8; | A19-B52-C9; |
| A20-B52-C1; | A20-B52-C2; | A20-B52-C3; | A20-B52-C4; | A20-B52-C5; | A20-B52-C6; |
| A20-B52-C7; | A20-B52-C8; | A20-B52-C9; | A21-B52-C1; | A21-B52-C2; | A21-B52-C3; |
| A21-B52-C4; | A21-B52-C5; | A21-B52-C6; | A21-B52-C7; | A21-B52-C8; | A21-B52-C9; |
| A22-B52-C1; | A22-B52-C2; | A22-B52-C3; | A22-B52-C4; | A22-B52-C5; | A22-B52-C6; |
| A22-B52-C7; | A22-B52-C8; | A22-B52-C9; | A23-B52-C1; | A23-B52-C2; | A23-B52-C3; |
| A23-B52-C4; | A23-B52-C5; | A23-B52-C6; | A23-B52-C7; | A23-B52-C8; | A23-B52-C9; |
| A24-B52-C1; | A24-B52-C2; | A24-B52-C3; | A24-B52-C4; | A24-B52-C5; | A24-B52-C6; |
| A24-B52-C7; | A24-B52-C8; | A24-B52-C9; | A25-B52-C1; | A25-B52-C2; | A25-B52-C3; |
| A25-B52-C4; | A25-B52-C5; | A25-B52-C6; | A25-B52-C7; | A25-B52-C8; | A25-B52-C9; |
| A26-B52-C1; | A26-B52-C2; | A26-B52-C3; | A26-B52-C4; | A26-B52-C5; | A26-B52-C6; |
| A26-B52-C7; | A26-B52-C8; | A26-B52-C9; | A27-B52-C1; | A27-B52-C2; | A27-B52-C3; |
| A27-B52-C4; | A27-B52-C5; | A27-B52-C6; | A27-B52-C7; | A27-B52-C8; | A27-B52-C9; |
| A28-B52-C1; | A28-B52-C2; | A28-B52-C3; | A28-B52-C4; | A28-B52-C5; | A28-B52-C6; |
| A28-B52-C7; | A28-B52-C8; | A28-B52-C9; | A29-B52-C1; | A29-B52-C2; | A29-B52-C3; |
| A29-B52-C4; | A29-B52-C5; | A29-B52-C6; | A29-B52-C7; | A29-B52-C8; | A29-B52-C9; |
| A30-B52-C1; | A30-B52-C2; | A30-B52-C3; | A30-B52-C4; | A30-B52-C5; | A30-B52-C6; |
| A30-B52-C7; | A30-B52-C8; | A30-B52-C9; | A31-B52-C1; | A31-B52-C2; | A31-B52-C3; |
| A31-B52-C4; | A31-B52-C5; | A31-B52-C6; | A31-B52-C7; | A31-B52-C8; | A31-B52-C9; |

-continued

| | | | | | |
|---|---|---|---|---|---|
| A32-B52-C1; | A32-B52-C2; | A32-B52-C3; | A32-B52-C4; | A32-B52-C5; | A32-B52-C6; |
| A32-B52-C7; | A32-B52-C8; | A32-B52-C9; | A33-B52-C1; | A33-B52-C2; | A33-B52-C3; |
| A33-B52-C4; | A33-B52-C5; | A33-B52-C6; | A33-B52-C7; | A33-B52-C8; | A33-B52-C9; |
| A34-B52-C1; | A34-B52-C2; | A34-B52-C3; | A34-B52-C4; | A34-B52-C5; | A34-B52-C6; |
| A34-B52-C7; | A34-B52-C8; | A34-B52-C9; | A35-B52-C1; | A35-B52-C2; | A35-B52-C3; |
| A35-B52-C4; | A35-B52-C5; | A35-B52-C6; | A35-B52-C7; | A35-B52-C8; | A35-B52-C9; |
| A36-B52-C1; | A36-B52-C2; | A36-B52-C3; | A36-B52-C4; | A36-B52-C5; | A36-B52-C6; |
| A36-B52-C7; | A36-B52-C8; | A36-B52-C9; | A37-B52-C1; | A37-B52-C2; | A37-B52-C3; |
| A37-B52-C4; | A37-B52-C5; | A37-B52-C6; | A37-B52-C7; | A37-B52-C8; | A37-B52-C9; |
| A38-B52-C1; | A38-B52-C2; | A38-B52-C3; | A38-B52-C4; | A38-B52-C5; | A38-B52-C6; |
| A38-B52-C7; | A38-B52-C8; | A38-B52-C9; | A39-B52-C1; | A39-B52-C2; | A39-B52-C3; |
| A39-B52-C4; | A39-B52-C5; | A39-B52-C6; | A39-B52-C7; | A39-B52-C8; | A39-B52-C9; |
| A40-B52-C1; | A40-B52-C2; | A40-B52-C3; | A40-B52-C4; | A40-B52-C5; | A40-B52-C6; |
| A40-B52-C7; | A40-B52-C8; | A40-B52-C9; | A41-B52-C1; | A41-B52-C2; | A41-B52-C3; |
| A41-B52-C4; | A41-B52-C5; | A41-B52-C6; | A41-B52-C7; | A41-B52-C8; | A41-B52-C9; |
| A42-B52-C1; | A42-B52-C2; | A42-B52-C3; | A42-B52-C4; | A42-B52-C5; | A42-B52-C6; |
| A42-B52-C7; | A42-B52-C8; | A42-B52-C9; | A43-B52-C1; | A43-B52-C2; | A43-B52-C3; |
| A43-B52-C4; | A43-B52-C5; | A43-B52-C6; | A43-B52-C7; | A43-B52-C8; | A43-B52-C9; |
| A44-B52-C1; | A44-B52-C2; | A44-B52-C3; | A44-B52-C4; | A44-B52-C5; | A44-B52-C6; |
| A44-B52-C7; | A44-B52-C8; | A44-B52-C9; | A45-B52-C1; | A45-B52-C2; | A45-B52-C3; |
| A45-B52-C4; | A45-B52-C5; | A45-B52-C6; | A45-B52-C7; | A45-B52-C8; | A45-B52-C9; |
| A46-B52-C1; | A46-B52-C2; | A46-B52-C3; | A46-B52-C4; | A46-B52-C5; | A46-B52-C6; |
| A46-B52-C7; | A46-B52-C8; | A46-B52-C9; | A47-B52-C1; | A47-B52-C2; | A47-B52-C3; |
| A47-B52-C4; | A47-B52-C5; | A47-B52-C6; | A47-B52-C7; | A47-B52-C8; | A47-B52-C9; |
| A48-B52-C1; | A48-B52-C2; | A48-B52-C3; | A48-B52-C4; | A48-B52-C5; | A48-B52-C6; |
| A48-B52-C7; | A48-B52-C8; | A48-B52-C9; | A49-B52-C1; | A49-B52-C2; | A49-B52-C3; |
| A49-B52-C4; | A49-B52-C5; | A49-B52-C6; | A49-B52-C7; | A49-B52-C8; | A49-B52-C9; |
| A50-B52-C1; | A50-B52-C2; | A50-B52-C3; | A50-B52-C4; | A50-B52-C5; | A50-B52-C6; |
| A50-B52-C7; | A50-B52-C8; | A50-B52-C9; | A51-B52-C1; | A51-B52-C2; | A51-B52-C3; |
| A51-B52-C4; | A51-B52-C5; | A51-B52-C6; | A51-B52-C7; | A51-B52-C8; | A51-B52-C9; |
| A52-B52-C1; | A52-B52-C2; | A52-B52-C3; | A52-B52-C4; | A52-B52-C5; | A52-B52-C6; |
| A52-B52-C7; | A52-B52-C8; | A52-B52-C9; | A53-B52-C1; | A53-B52-C2; | A53-B52-C3; |
| A53-B52-C4; | A53-B52-C5; | A53-B52-C6; | A53-B52-C7; | A53-B52-C8; | A53-B52-C9; |
| A54-B52-C1; | A54-B52-C2; | A54-B52-C3; | A54-B52-C4; | A54-B52-C5; | A54-B52-C6; |
| A54-B52-C7; | A54-B52-C8; | A54-B52-C9; | A55-B52-C1; | A55-B52-C2; | A55-B52-C3; |
| A55-B52-C4; | A55-B52-C5; | A55-B52-C6; | A55-B52-C7; | A55-B52-C8; | A55-B52-C9; |
| A56-B52-C1; | A56-B52-C2; | A56-B52-C3; | A56-B52-C4; | A56-B52-C5; | A56-B52-C6; |
| A56-B52-C7; | A56-B52-C8; | A56-B52-C9; | A57-B52-C1; | A57-B52-C2; | A57-B52-C3; |
| A57-B52-C4; | A57-B52-C5; | A57-B52-C6; | A57-B52-C7; | A57-B52-C8; | A57-B52-C9; |
| A58-B52-C1; | A58-B52-C2; | A58-B52-C3; | A58-B52-C4; | A58-B52-C5; | A58-B52-C6; |
| A58-B52-C7; | A58-B52-C8; | A58-B52-C9; | A59-B52-C1; | A59-B52-C2; | A59-B52-C3; |
| A59-B52-C4; | A59-B52-C5; | A59-B52-C6; | A59-B52-C7; | A59-B52-C8; | A59-B52-C9; |
| A60-B52-C1; | A60-B52-C2; | A60-B52-C3; | A60-B52-C4; | A60-B52-C5; | A60-B52-C6; |
| A60-B52-C7; | A60-B52-C8; | A60-B52-C9; | A61-B52-C1; | A61-B52-C2; | A61-B52-C3; |
| A61-B52-C4; | A61-B52-C5; | A61-B52-C6; | A61-B52-C7; | A61-B52-C8; | A61-B52-C9; |
| A62-B52-C1; | A62-B52-C2; | A62-B52-C3; | A62-B52-C4; | A62-B52-C5; | A62-B52-C6; |
| A62-B52-C7; | A62-B52-C8; | A62-B52-C9; | A63-B52-C1; | A63-B52-C2; | A63-B52-C3; |
| A63-B52-C4; | A63-B52-C5; | A63-B52-C6; | A63-B52-C7; | A63-B52-C8; | A63-B52-C9; |
| A64-B52-C1; | A64-B52-C2; | A64-B52-C3; | A64-B52-C4; | A64-B52-C5; | A64-B52-C6; |
| A64-B52-C7; | A64-B52-C8; | A64-B52-C9; | A65-B52-C1; | A65-B52-C2; | A65-B52-C3; |
| A65-B52-C4; | A65-B52-C5; | A65-B52-C6; | A65-B52-C7; | A65-B52-C8; | A65-B52-C9; |
| A66-B52-C1; | A66-B52-C2; | A66-B52-C3; | A66-B52-C4; | A66-B52-C5; | A66-B52-C6; |
| A66-B52-C7; | A66-B52-C8; | A66-B52-C9; | A67-B52-C1; | A67-B52-C2; | A67-B52-C3; |
| A67-B52-C4; | A67-B52-C5; | A67-B52-C6; | A67-B52-C7; | A67-B52-C8; | A67-B52-C9; |
| A68-B52-C1; | A68-B52-C2; | A68-B52-C3; | A68-B52-C4; | A68-B52-C5; | A68-B52-C6; |
| A68-B52-C7; | A68-B52-C8; | A68-B52-C9; | A69-B52-C1; | A69-B52-C2; | A69-B52-C3; |
| A69-B52-C4; | A69-B52-C5; | A69-B52-C6; | A69-B52-C7; | A69-B52-C8; | A69-B52-C9; |
| A70-B52-C1; | A70-B52-C2; | A70-B52-C3; | A70-B52-C4; | A70-B52-C5; | A70-B52-C6; |
| A70-B52-C7; | A70-B52-C8; | A70-B52-C9; | A71-B52-C1; | A71-B52-C2; | A71-B52-C3; |
| A71-B52-C4; | A71-B52-C5; | A71-B52-C6; | A71-B52-C7; | A71-B52-C8; | A71-B52-C9; |
| A1-B53-C1; | A1-B53-C2; | A1-B53-C3; | A1-B53-C5; | A1-B53-C5; | A1-B53-C6; |
| A1-B53-C7; | A1-B53-C8; | A1-B53-C9; | A2-B53-C1; | A2-B53-C2; | A2-B53-C3; |
| A2-B53-C4; | A2-B53-C5; | A2-B53-C6; | A2-B53-C7; | A2-B53-C8; | A2-B53-C9; |
| A3-B53-C1; | A3-B53-C2; | A3-B53-C3; | A3-B53-C4; | A3-B53-C5; | A3-B53-C6; |
| A3-B53-C7; | A3-B53-C8; | A3-B53-C9; | A4-B53-C1; | A4-B53-C2; | A4-B53-C3; |
| A4-B53-C4; | A4-B53-C5; | A4-B53-C6; | A4-B53-C7; | A4-B53-C8; | A4-B53-C9; |
| A5-B53-C1; | A5-B53-C2; | A5-B53-C3; | A5-B53-C4; | A5-B53-C5; | A5-B53-C6; |
| A5-B53-C7; | A5-B53-C8; | A5-B53-C9; | A6-B53-C1; | A6-B53-C2; | A6-B53-C3; |
| A6-B53-C4; | A6-B53-C5; | A6-B53-C6; | A6-B53-C7; | A6-B53-C8; | A6-B53-C9; |
| A7-B53-C1; | A7-B53-C2; | A7-B53-C3; | A7-B53-C4; | A7-B53-C5; | A7-B53-C6; |
| A7-B53-C7; | A7-B53-C8; | A7-B53-C9; | A8-B53-C1; | A8-B53-C2; | A8-B53-C3; |
| A8-B53-C4; | A8-B53-C5; | A8-B53-C6; | A8-B53-C7; | A8-B53-C8; | A8-B53-C9; |
| A9-B53-C1; | A9-B53-C2; | A9-B53-C3; | A9-B53-C4; | A9-B53-C5; | A9-B53-C6; |
| A9-B53-C7; | A9-B53-C8; | A9-B53-C9; | A10-B53-C1; | A10-B53-C2; | A10-B53-C3; |
| A10-B53-C4; | A10-B53-C5; | A10-B53-C6; | A10-B53-C7; | A10-B53-C8; | A10-B53-C9; |
| A11-B53-C1; | A11-B53-C2; | A11-B53-C3; | A11-B53-C4; | A11-B53-C5; | A11-B53-C6; |
| A11-B53-C7; | A11-B53-C8; | A11-B53-C9; | A12-B53-C1; | A12-B53-C2; | A12-B53-C3; |
| A12-B53-C4; | A12-B53-C5; | A12-B53-C6; | A12-B53-C7; | A12-B53-C8; | A12-B53-C9; |
| A13-B53-C1; | A13-B53-C2; | A13-B53-C3; | A13-B53-C4; | A13-B53-C5; | A13-B53-C6; |

-continued

| | | | | | |
|---|---|---|---|---|---|
| A13-B53-C7; | A13-B53-C8; | A13-B53-C9; | A14-B53-C1; | A14-B53-C2; | A14-B53-C3; |
| A14-B53-C4; | A14-B53-C5; | A14-B53-C6; | A14-B53-C7; | A14-B53-C8; | A14-B53-C9; |
| A15-B53-C1; | A15-B53-C2; | A15-B53-C3; | A15-B53-C4; | A15-B53-C5; | A15-B53-C6; |
| A15-B53-C7; | A15-B53-C8; | A15-B53-C9; | A16-B53-C1; | A16-B53-C2; | A16-B53-C3; |
| A16-B53-C4; | A16-B53-C5; | A16-B53-C6; | A16-B53-C7; | A16-B53-C8; | A16-B53-C9; |
| A17-B53-C1; | A17-B53-C2; | A17-B53-C3; | A17-B53-C4; | A17-B53-C5; | A17-B53-C6; |
| A17-B53-C7; | A17-B53-C8; | A17-B53-C9; | A18-B53-C1; | A18-B53-C2; | A18-B53-C3; |
| A18-B53-C4; | A18-B53-C5; | A18-B53-C6; | A18-B53-C7; | A18-B53-C8; | A18-B53-C9; |
| A19-B53-C1; | A19-B53-C2; | A19-B53-C3; | A19-B53-C4; | A19-B53-C5; | A19-B53-C6; |
| A19-B53-C7; | A19-B53-C8; | A19-B53-C9; | A20-B53-C1; | A20-B53-C2; | A20-B53-C3; |
| A20-B53-C4; | A20-B53-C5; | A20-B53-C6; | A20-B53-C7; | A20-B53-C8; | A20-B53-C9; |
| A21-B53-C1; | A21-B53-C2; | A21-B53-C3; | A21-B53-C4; | A21-B53-C5; | A21-B53-C6; |
| A21-B53-C7; | A21-B53-C8; | A21-B53-C9; | A22-B53-C1; | A22-B53-C2; | A22-B53-C3; |
| A22-B53-C4; | A22-B53-C5; | A22-B53-C6; | A22-B53-C7; | A22-B53-C8; | A22-B53-C9; |
| A23-B53-C1; | A23-B53-C2; | A23-B53-C3; | A23-B53-C4; | A23-B53-C5; | A23-B53-C6; |
| A23-B53-C7; | A23-B53-C8; | A23-B53-C9; | A24-B53-C1; | A24-B53-C2; | A24-B53-C3; |
| A24-B53-C4; | A24-B53-C5; | A24-B53-C6; | A24-B53-C7; | A24-B53-C8; | A24-B53-C9; |
| A25-B53-C1; | A25-B53-C2; | A25-B53-C3; | A25-B53-C4; | A25-B53-C5; | A25-B53-C6; |
| A25-B53-C7; | A25-B53-C8; | A25-B53-C9; | A26-B53-C1; | A26-B53-C2; | A26-B53-C3; |
| A26-B53-C4; | A26-B53-C5; | A26-B53-C6; | A26-B53-C7; | A26-B53-C8; | A26-B53-C9; |
| A27-B53-C1; | A27-B53-C2; | A27-B53-C3; | A27-B53-C4; | A27-B53-C5; | A27-B53-C6; |
| A27-B53-C7; | A27-B53-C8; | A27-B53-C9; | A28-B53-C1; | A28-B53-C2; | A28-B53-C3; |
| A28-B53-C4; | A28-B53-C5; | A28-B53-C6; | A28-B53-C7; | A28-B53-C8; | A28-B53-C9; |
| A29-B53-C1; | A29-B53-C2; | A29-B53-C3; | A29-B53-C4; | A29-B53-C5; | A29-B53-C6; |
| A29-B53-C7; | A29-B53-C8; | A29-B53-C9; | A30-B53-C1; | A30-B53-C2; | A30-B53-C3; |
| A30-B53-C4; | A30-B53-C5; | A30-B53-C6; | A30-B53-C7; | A30-B53-C8; | A30-B53-C9; |
| A31-B53-C1; | A31-B53-C2; | A31-B53-C3; | A31-B53-C4; | A31-B53-C5; | A31-B53-C6; |
| A31-B53-C7; | A31-B53-C8; | A31-B53-C9; | A32-B53-C1; | A32-B53-C2; | A32-B53-C3; |
| A32-B53-C4; | A32-B53-C5; | A32-B53-C6; | A32-B53-C7; | A32-B53-C8; | A32-B53-C9; |
| A33-B53-C1; | A33-B53-C2; | A33-B53-C3; | A33-B53-C4; | A33-B53-C5; | A33-B53-C6; |
| A33-B53-C7; | A33-B53-C8; | A33-B53-C9; | A34-B53-C1; | A34-B53-C2; | A34-B53-C3; |
| A34-B53-C4; | A34-B53-C5; | A34-B53-C6; | A34-B53-C7; | A34-B53-C8; | A34-B53-C9; |
| A35-B53-C1; | A35-B53-C2; | A35-B53-C3; | A35-B53-C4; | A35-B53-C5; | A35-B53-C6; |
| A35-B53-C7; | A35-B53-C8; | A35-B53-C9; | A36-B53-C1; | A36-B53-C2; | A36-B53-C3; |
| A36-B53-C4; | A36-B53-C5; | A36-B53-C6; | A36-B53-C7; | A36-B53-C8; | A36-B53-C9; |
| A37-B53-C1; | A37-B53-C2; | A37-B53-C3; | A37-B53-C4; | A37-B53-C5; | A37-B53-C6; |
| A37-B53-C7; | A37-B53-C8; | A37-B53-C9; | A38-B53-C1; | A38-B53-C2; | A38-B53-C3; |
| A38-B53-C4; | A38-B53-C5; | A38-B53-C6; | A38-B53-C7; | A38-B53-C8; | A38-B53-C9; |
| A39-B53-C1; | A39-B53-C2; | A39-B53-C3; | A39-B53-C4; | A39-B53-C5; | A39-B53-C6; |
| A39-B53-C7; | A39-B53-C8; | A39-B53-C9; | A40-B53-C1; | A40-B53-C2; | A40-B53-C3; |
| A40-B53-C4; | A40-B53-C5; | A40-B53-C6; | A40-B53-C7; | A40-B53-C8; | A40-B53-C9; |
| A41-B53-C1; | A41-B53-C2; | A41-B53-C3; | A41-B53-C4; | A41-B53-C5; | A41-B53-C6; |
| A41-B53-C7; | A41-B53-C8; | A41-B53-C9; | A42-B53-C1; | A42-B53-C2; | A42-B53-C3; |
| A42-B53-C4; | A42-B53-C5; | A42-B53-C6; | A42-B53-C7; | A42-B53-C8; | A42-B53-C9; |
| A43-B53-C1; | A43-B53-C2; | A43-B53-C3; | A43-B53-C4; | A43-B53-C5; | A43-B53-C6; |
| A43-B53-C7; | A43-B53-C8; | A43-B53-C9; | A44-B53-C1; | A44-B53-C2; | A44-B53-C3; |
| A44-B53-C4; | A44-B53-C5; | A44-B53-C6; | A44-B53-C7; | A44-B53-C8; | A44-B53-C9; |
| A45-B53-C1; | A45-B53-C2; | A45-B53-C3; | A45-B53-C4; | A45-B53-C5; | A45-B53-C6; |
| A45-B53-C7; | A45-B53-C8; | A45-B53-C9; | A46-B53-C1; | A46-B53-C2; | A46-B53-C3; |
| A46-B53-C4; | A46-B53-C5; | A46-B53-C6; | A46-B53-C7; | A46-B53-C8; | A46-B53-C9; |
| A47-B53-C1; | A47-B53-C2; | A47-B53-C3; | A47-B53-C4; | A47-B53-C5; | A47-B53-C6; |
| A47-B53-C7; | A47-B53-C8; | A47-B53-C9; | A48-B53-C1; | A48-B53-C2; | A48-B53-C3; |
| A48-B53-C4; | A48-B53-C5; | A48-B53-C6; | A48-B53-C7; | A48-B53-C8; | A48-B53-C9; |
| A49-B53-C1; | A49-B53-C2; | A49-B53-C3; | A49-B53-C4; | A49-B53-C5; | A49-B53-C6; |
| A49-B53-C7; | A49-B53-C8; | A49-B53-C9; | A50-B53-C1; | A50-B53-C2; | A50-B53-C3; |
| A50-B53-C4; | A50-B53-C5; | A50-B53-C6; | A50-B53-C7; | A50-B53-C8; | A50-B53-C9; |
| A51-B53-C1; | A51-B53-C2; | A51-B53-C3; | A51-B53-C4; | A51-B53-C5; | A51-B53-C6; |
| A51-B53-C7; | A51-B53-C8; | A51-B53-C9; | A52-B53-C1; | A52-B53-C2; | A52-B53-C3; |
| A52-B53-C4; | A52-B53-C5; | A52-B53-C6; | A52-B53-C7; | A52-B53-C8; | A52-B53-C9; |
| A53-B53-C1; | A53-B53-C2; | A53-B53-C3; | A53-B53-C4; | A53-B53-C5; | A53-B53-C6; |
| A53-B53-C7; | A53-B53-C8; | A53-B53-C9; | A54-B53-C1; | A54-B53-C2; | A54-B53-C3; |
| A54-B53-C4; | A54-B53-C5; | A54-B53-C6; | A54-B53-C7; | A54-B53-C8; | A54-B53-C9; |
| A55-B53-C1; | A55-B53-C2; | A55-B53-C3; | A55-B53-C4; | A55-B53-C5; | A55-B53-C6; |
| A55-B53-C7; | A55-B53-C8; | A55-B53-C9; | A56-B53-C1; | A56-B53-C2; | A56-B53-C3; |
| A56-B53-C4; | A56-B53-C5; | A56-B53-C6; | A56-B53-C7; | A56-B53-C8; | A56-B53-C9; |
| A57-B53-C1; | A57-B53-C2; | A57-B53-C3; | A57-B53-C4; | A57-B53-C5; | A57-B53-C6; |
| A57-B53-C7; | A57-B53-C8; | A57-B53-C9; | A58-B53-C1; | A58-B53-C2; | A58-B53-C3; |
| A58-B53-C4; | A58-B53-C5; | A58-B53-C6; | A58-B53-C7; | A58-B53-C8; | A58-B53-C9; |
| A59-B53-C1; | A59-B53-C2; | A59-B53-C3; | A59-B53-C4; | A59-B53-C5; | A59-B53-C6; |
| A59-B53-C7; | A59-B53-C8; | A59-B53-C9; | A60-B53-C1; | A60-B53-C2; | A60-B53-C3; |
| A60-B53-C4; | A60-B53-C5; | A60-B53-C6; | A60-B53-C7; | A60-B53-C8; | A60-B53-C9; |
| A61-B53-C1; | A61-B53-C2; | A61-B53-C3; | A61-B53-C4; | A61-B53-C5; | A61-B53-C6; |
| A61-B53-C7; | A61-B53-C8; | A61-B53-C9; | A62-B53-C1; | A62-B53-C2; | A62-B53-C3; |
| A62-B53-C4; | A62-B53-C5; | A62-B53-C6; | A62-B53-C7; | A62-B53-C8; | A62-B53-C9; |
| A63-B53-C1; | A63-B53-C2; | A63-B53-C3; | A63-B53-C4; | A63-B53-C5; | A63-B53-C6; |
| A63-B53-C7; | A63-B53-C8; | A63-B53-C9; | A64-B53-C1; | A64-B53-C2; | A64-B53-C3; |
| A64-B53-C4; | A64-B53-C5; | A64-B53-C6; | A64-B53-C7; | A64-B53-C8; | A64-B53-C9; |
| A65-B53-C1; | A65-B53-C2; | A65-B53-C3; | A65-B53-C4; | A65-B53-C5; | A65-B53-C6; |
| A65-B53-C7; | A65-B53-C8; | A65-B53-C9; | A66-B53-C1; | A66-B53-C2; | A66-B53-C3; |

-continued

| | | | | | |
|---|---|---|---|---|---|
| A66-B53-C4; | A66-B53-C5; | A66-B53-C6; | A66-B53-C7; | A66-B53-C8; | A66-B53-C9; |
| A67-B53-C1; | A67-B53-C2; | A67-B53-C3; | A67-B53-C4; | A67-B53-C5; | A67-B53-C6; |
| A67-B53-C7; | A67-B53-C8; | A67-B53-C9; | A68-B53-C1; | A68-B53-C2; | A68-B53-C3; |
| A68-B53-C4; | A68-B53-C5; | A68-B53-C6; | A68-B53-C7; | A68-B53-C8; | A68-B53-C9; |
| A69-B53-C1; | A69-B53-C2; | A69-B53-C3; | A69-B53-C4; | A69-B53-C5; | A69-B53-C6; |
| A69-B53-C7; | A69-B53-C8; | A69-B53-C9; | A70-B53-C1; | A70-B53-C2; | A70-B53-C3; |
| A70-B53-C4; | A70-B53-C5; | A70-B53-C6; | A70-B53-C7; | A70-B53-C8; | A70-B53-C9; |
| A71-B53-C1; | A71-B53-C2; | A71-B53-C3; | A71-B53-C4; | A71-B53-C5; | A71-B53-C6; |
| A71-B53-C7; | A71-B53-C8; | A71-B53-C9; | A1-B54-C1; | A1-B54-C2; | A1-B54-C3; |
| A1-B54-C4; | A1-B54-C5; | A1-B54-C6; | A1-B54-C7; | A1-B54-C8; | A1-B54-C9; |
| A2-B54-C1; | A2-B54-C2; | A2-B54-C3; | A2-B54-C4; | A2-B54-C5; | A2-B54-C6; |
| A2-B54-C7; | A2-B54-C8; | A2-B54-C9; | A3-B54-C1; | A3-B54-C2; | A3-B54-C3; |
| A3-B54-C4; | A3-B54-C5; | A3-B54-C6; | A3-B54-C7; | A3-B54-C8; | A3-B54-C9; |
| A4-B54-C1; | A4-B54-C2; | A4-B54-C3; | A4-B54-C4; | A4-B54-C5; | A4-B54-C6; |
| A4-B54-C7; | A4-B54-C8; | A4-B54-C9; | A5-B54-C1; | A5-B54-C2; | A5-B54-C3; |
| A5-B54-C4; | A5-B54-C5; | A5-B54-C6; | A5-B54-C7; | A5-B54-C8; | A5-B54-C9; |
| A6-B54-C1; | A6-B54-C2; | A6-B54-C3; | A6-B54-C4; | A6-B54-C5; | A6-B54-C6; |
| A6-B54-C7; | A6-B54-C8; | A6-B54-C9; | A7-B54-C1; | A7-B54-C2; | A7-B54-C3; |
| A7-B54-C4; | A7-B54-C5; | A7-B54-C6; | A7-B54-C7; | A7-B54-C8; | A7-B54-C9; |
| A8-B54-C1; | A8-B54-C2; | A8-B54-C3; | A8-B54-C4; | A8-B54-C5; | A8-B54-C6; |
| A8-B54-C7; | A8-B54-C8; | A8-B54-C9; | A9-B54-C1; | A9-B54-C2; | A9-B54-C3; |
| A9-B54-C4; | A9-B54-C5; | A9-B54-C6; | A9-B54-C7; | A9-B54-C8; | A9-B54-C9; |
| A10-B54-C1; | A10-B54-C2; | A10-B54-C3; | A10-B54-C4; | A10-B54-C5; | A10-B54-C6; |
| A10-B54-C7; | A10-B54-C8; | A10-B54-C9; | A11-B54-C1; | A11-B54-C2; | A11-B54-C3; |
| A11-B54-C4; | A11-B54-C5; | A11-B54-C6; | A11-B54-C7; | A11-B54-C8; | A11-B54-C9; |
| A12-B54-C1; | A12-B54-C2; | A12-B54-C3; | A12-B54-C4; | A12-B54-C5; | A12-B54-C6; |
| A12-B54-C7; | A12-B54-C8; | A12-B54-C9; | A13-B54-C1; | A13-B54-C2; | A13-B54-C3; |
| A13-B54-C4; | A13-B54-C5; | A13-B54-C6; | A13-B54-C7; | A13-B54-C8; | A13-B54-C9; |
| A14-B54-C1; | A14-B54-C2; | A14-B54-C3; | A14-B54-C4; | A14-B54-C5; | A14-B54-C6; |
| A14-B54-C7; | A14-B54-C8; | A14-B54-C9; | A15-B54-C1; | A15-B54-C2; | A15-B54-C3; |
| A15-B54-C4; | A15-B54-C5; | A15-B54-C6; | A15-B54-C7; | A15-B54-C8; | A15-B54-C9; |
| A16-B54-C1; | A16-B54-C2; | A16-B54-C3; | A16-B54-C4; | A16-B54-C5; | A16-B54-C6; |
| A16-B54-C7; | A16-B54-C8; | A16-B54-C9; | A17-B54-C1; | A17-B54-C2; | A17-B54-C3; |
| A17-B54-C4; | A17-B54-C5; | A17-B54-C6; | A17-B54-C7; | A17-B54-C8; | A17-B54-C9; |
| A18-B54-C1; | A18-B54-C2; | A18-B54-C3; | A18-B54-C4; | A18-B54-C5; | A18-B54-C6; |
| A18-B54-C7; | A18-B54-C8; | A18-B54-C9; | A19-B54-C1; | A19-B54-C2; | A19-B54-C3; |
| A19-B54-C4; | A19-B54-C5; | A19-B54-C6; | A19-B54-C7; | A19-B54-C8; | A19-B54-C9; |
| A20-B54-C1; | A20-B54-C2; | A20-B54-C3; | A20-B54-C4; | A20-B54-C5; | A20-B54-C6; |
| A20-B54-C7; | A20-B54-C8; | A20-B54-C9; | A21-B54-C1; | A21-B54-C2; | A21-B54-C3; |
| A21-B54-C4; | A21-B54-C5; | A21-B54-C6; | A21-B54-C7; | A21-B54-C8; | A21-B54-C9; |
| A22-B54-C1; | A22-B54-C2; | A22-B54-C3; | A22-B54-C4; | A22-B54-C5; | A22-B54-C6; |
| A22-B54-C7; | A22-B54-C8; | A22-B54-C9; | A23-B54-C1; | A23-B54-C2; | A23-B54-C3; |
| A23-B54-C4; | A23-B54-C5; | A23-B54-C6; | A23-B54-C7; | A23-B54-C8; | A23-B54-C9; |
| A24-B54-C1; | A24-B54-C2; | A24-B54-C3; | A24-B54-C4; | A24-B54-C5; | A24-B54-C6; |
| A24-B54-C7; | A24-B54-C8; | A24-B54-C9; | A25-B54-C1; | A25-B54-C2; | A25-B54-C3; |
| A25-B54-C4; | A25-B54-C5; | A25-B54-C6; | A25-B54-C7; | A25-B54-C8; | A25-B54-C9; |
| A26-B54-C1; | A26-B54-C2; | A26-B54-C3; | A26-B54-C4; | A26-B54-C5; | A26-B54-C6; |
| A26-B54-C7; | A26-B54-C8; | A26-B54-C9; | A27-B54-C1; | A27-B54-C2; | A27-B54-C3; |
| A27-B54-C4; | A27-B54-C5; | A27-B54-C6; | A27-B54-C7; | A27-B54-C8; | A27-B54-C9; |
| A28-B54-C1; | A28-B54-C2; | A28-B54-C3; | A28-B54-C4; | A28-B54-C5; | A28-B54-C6; |
| A28-B54-C7; | A28-B54-C8; | A28-B54-C9; | A29-B54-C1; | A29-B54-C2; | A29-B54-C3; |
| A29-B54-C4; | A29-B54-C5; | A29-B54-C6; | A29-B54-C7; | A29-B54-C8; | A29-B54-C9; |
| A30-B54-C1; | A30-B54-C2; | A30-B54-C3; | A30-B54-C4; | A30-B54-C5; | A30-B54-C6; |
| A30-B54-C7; | A30-B54-C8; | A30-B54-C9; | A31-B54-C1; | A31-B54-C2; | A31-B54-C3; |
| A31-B54-C4; | A31-B54-C5; | A31-B54-C6; | A31-B54-C7; | A31-B54-C8; | A31-B54-C9; |
| A32-B54-C1; | A32-B54-C2; | A32-B54-C3; | A32-B54-C4; | A32-B54-C5; | A32-B54-C6; |
| A32-B54-C7; | A32-B54-C8; | A32-B54-C9; | A33-B54-C1; | A33-B54-C2; | A33-B54-C3; |
| A33-B54-C4; | A33-B54-C5; | A33-B54-C6; | A33-B54-C7; | A33-B54-C8; | A33-B54-C9; |
| A34-B54-C1; | A34-B54-C2; | A34-B54-C3; | A34-B54-C4; | A34-B54-C5; | A34-B54-C6; |
| A34-B54-C7; | A34-B54-C8; | A34-B54-C9; | A35-B54-C1; | A35-B54-C2; | A35-B54-C3; |
| A35-B54-C4; | A35-B54-C5; | A35-B54-C6; | A35-B54-C7; | A35-B54-C8; | A35-B54-C9; |
| A36-B54-C1; | A36-B54-C2; | A36-B54-C3; | A36-B54-C4; | A36-B54-C5; | A36-B54-C6; |
| A36-B54-C7; | A36-B54-C8; | A36-B54-C9; | A37-B54-C1; | A37-B54-C2; | A37-B54-C3; |
| A37-B54-C4; | A37-B54-C5; | A37-B54-C6; | A37-B54-C7; | A37-B54-C8; | A37-B54-C9; |
| A38-B54-C1; | A38-B54-C2; | A38-B54-C3; | A38-B54-C4; | A38-B54-C5; | A38-B54-C6; |
| A38-B54-C7; | A38-B54-C8; | A38-B54-C9; | A39-B54-C1; | A39-B54-C2; | A39-B54-C3; |
| A39-B54-C4; | A39-B54-C5; | A39-B54-C6; | A39-B54-C7; | A39-B54-C8; | A39-B54-C9; |
| A40-B54-C1; | A40-B54-C2; | A40-B54-C3; | A40-B54-C4; | A40-B54-C5; | A40-B54-C6; |
| A40-B54-C7; | A40-B54-C8; | A40-B54-C9; | A41-B54-C1; | A41-B54-C2; | A41-B54-C3; |
| A41-B54-C4; | A41-B54-C5; | A41-B54-C6; | A41-B54-C7; | A41-B54-C8; | A41-B54-C9; |
| A42-B54-C1; | A42-B54-C2; | A42-B54-C3; | A42-B54-C4; | A42-B54-C5; | A42-B54-C6; |
| A42-B54-C7; | A42-B54-C8; | A42-B54-C9; | A43-B54-C1; | A43-B54-C2; | A43-B54-C3; |
| A43-B54-C4; | A43-B54-C5; | A43-B54-C6; | A43-B54-C7; | A43-B54-C8; | A43-B54-C9; |
| A44-B54-C1; | A44-B54-C2; | A44-B54-C3; | A44-B54-C4; | A44-B54-C5; | A44-B54-C6; |
| A44-B54-C7; | A44-B54-C8; | A44-B54-C9; | A45-B54-C1; | A45-B54-C2; | A45-B54-C3; |
| A45-B54-C4; | A45-B54-C5; | A45-B54-C6; | A45-B54-C7; | A45-B54-C8; | A45-B54-C9; |
| A46-B54-C1; | A46-B54-C2; | A46-B54-C3; | A46-B54-C4; | A46-B54-C5; | A46-B54-C6; |
| A46-B54-C7; | A46-B54-C8; | A46-B54-C9; | A47-B54-C1; | A47-B54-C2; | A47-B54-C3; |
| A47-B54-C4; | A47-B54-C5; | A47-B54-C6; | A47-B54-C7; | A47-B54-C8; | A47-B54-C9; |

-continued

| | | | | | |
|---|---|---|---|---|---|
| A48-B54-C1; | A48-B54-C2; | A48-B54-C3; | A48-B54-C4; | A48-B54-C5; | A48-B54-C6; |
| A48-B54-C7; | A48-B54-C8; | A48-B54-C9; | A49-B54-C1; | A49-B54-C2; | A49-B54-C3; |
| A49-B54-C4; | A49-B54-C5; | A49-B54-C6; | A49-B54-C7; | A49-B54-C8; | A49-B54-C9; |
| A50-B54-C1; | A50-B54-C2; | A50-B54-C3; | A50-B54-C4; | A50-B54-C5; | A50-B54-C6; |
| A50-B54-C7; | A50-B54-C8; | A50-B54-C9; | A51-B54-C1; | A51-B54-C2; | A51-B54-C3; |
| A51-B54-C4; | A51-B54-C5; | A51-B54-C6; | A51-B54-C7; | A51-B54-C8; | A51-B54-C9; |
| A52-B54-C1; | A52-B54-C2; | A52-B54-C3; | A52-B54-C4; | A52-B54-C5; | A52-B54-C6; |
| A52-B54-C7; | A52-B54-C8; | A52-B54-C9; | A53-B54-C1; | A53-B54-C2; | A53-B54-C3; |
| A53-B54-C4; | A53-B54-C5; | A53-B54-C6; | A53-B54-C7; | A53-B54-C8; | A53-B54-C9; |
| A54-B54-C1; | A54-B54-C2; | A54-B54-C3; | A54-B54-C4; | A54-B54-C5; | A54-B54-C6; |
| A54-B54-C7; | A54-B54-C8; | A54-B54-C9; | A55-B54-C1; | A55-B54-C2; | A55-B54-C3; |
| A55-B54-C4; | A55-B54-C5; | A55-B54-C6; | A55-B54-C7; | A55-B54-C8; | A55-B54-C9; |
| A56-B54-C1; | A56-B54-C2; | A56-B54-C3; | A56-B54-C4; | A56-B54-C5; | A56-B54-C6; |
| A56-B54-C7; | A56-B54-C8; | A56-B54-C9; | A57-B54-C1; | A57-B54-C2; | A57-B54-C3; |
| A57-B54-C4; | A57-B54-C5; | A57-B54-C6; | A57-B54-C7; | A57-B54-C8; | A57-B54-C9; |
| A58-B54-C1; | A58-B54-C2; | A58-B54-C3; | A58-B54-C4; | A58-B54-C5; | A58-B54-C6; |
| A58-B54-C7; | A58-B54-C8; | A58-B54-C9; | A59-B54-C1; | A59-B54-C2; | A59-B54-C3; |
| A59-B54-C4; | A59-B54-C5; | A59-B54-C6; | A59-B54-C7; | A59-B54-C8; | A59-B54-C9; |
| A60-B54-C1; | A60-B54-C2; | A60-B54-C3; | A60-B54-C4; | A60-B54-C5; | A60-B54-C6; |
| A60-B54-C7; | A60-B54-C8; | A60-B54-C9; | A61-B54-C1; | A61-B54-C2; | A61-B54-C3; |
| A61-B54-C4; | A61-B54-C5; | A61-B54-C6; | A61-B54-C7; | A61-B54-C8; | A61-B54-C9; |
| A62-B54-C1; | A62-B54-C2; | A62-B54-C3; | A62-B54-C4; | A62-B54-C5; | A62-B54-C6; |
| A62-B54-C7; | A62-B54-C8; | A62-B54-C9; | A63-B54-C1; | A63-B54-C2; | A63-B54-C3; |
| A63-B54-C4; | A63-B54-C5; | A63-B54-C6; | A63-B54-C7; | A63-B54-C8; | A63-B54-C9; |
| A64-B54-C1; | A64-B54-C2; | A64-B54-C3; | A64-B54-C4; | A64-B54-C5; | A64-B54-C6; |
| A64-B54-C7; | A64-B54-C8; | A64-B54-C9; | A65-B54-C1; | A65-B54-C2; | A65-B54-C3; |
| A65-B54-C4; | A65-B54-C5; | A65-B54-C6; | A65-B54-C7; | A65-B54-C8; | A65-B54-C9; |
| A66-B54-C1; | A66-B54-C2; | A66-B54-C3; | A66-B54-C4; | A66-B54-C5; | A66-B54-C6; |
| A66-B54-C7; | A66-B54-C8; | A66-B54-C9; | A67-B54-C1; | A67-B54-C2; | A67-B54-C3; |
| A67-B54-C4; | A67-B54-C5; | A67-B54-C6; | A67-B54-C7; | A67-B54-C8; | A67-B54-C9; |
| A68-B54-C1; | A68-B54-C2; | A68-B54-C3; | A68-B54-C4; | A68-B54-C5; | A68-B54-C6; |
| A68-B54-C7; | A68-B54-C8; | A68-B54-C9; | A69-B54-C1; | A69-B54-C2; | A69-B54-C3; |
| A69-B54-C4; | A69-B54-C5; | A69-B54-C6; | A69-B54-C7; | A69-B54-C8; | A69-B54-C9; |
| A70-B54-C1; | A70-B54-C2; | A70-B54-C3; | A70-B54-C4; | A70-B54-C5; | A70-B54-C6; |
| A70-B54-C7; | A70-B54-C8; | A70-B54-C9; | A71-B54-C1; | A71-B54-C2; | A71-B54-C3; |
| A71-B54-C4; | A71-B54-C5; | A71-B54-C6; | A71-B54-C7; | A71-B54-C8; | A71-B54-C9; |
| A1-B55-C1; | A1-B55-C2; | A1-B55-C3; | A1-B55-C4; | A1-B55-C5; | A1-B55-C6; |
| A1-B55-C7; | A1-B55-C8; | A1-B55-C9; | A2-B55-C1; | A2-B55-C2; | A2-B55-C3; |
| A2-B55-C4; | A2-B55-C5; | A2-B55-C6; | A2-B55-C7; | A2-B55-C8; | A2-B55-C9; |
| A3-B55-C1; | A3-B55-C2; | A3-B55-C3; | A3-B55-C4; | A3-B55-C5; | A3-B55-C6; |
| A3-B55-C7; | A3-B55-C8; | A3-B55-C9; | A4-B55-C1; | A4-B55-C2; | A4-B55-C3; |
| A4-B55-C4; | A4-B55-C5; | A4-B55-C6; | A4-B55-C7; | A4-B55-C8; | A4-B55-C9; |
| A5-B55-C1; | A5-B55-C2; | A5-B55-C3; | A5-B55-C4; | A5-B55-C5; | A5-B55-C6; |
| A5-B55-C7; | A5-B55-C8; | A5-B55-C9; | A6-B55-C1; | A6-B55-C2; | A6-B55-C3; |
| A6-B55-C4; | A6-B55-C5; | A6-B55-C6; | A6-B55-C7; | A6-B55-C8; | A6-B55-C9; |
| A7-B55-C1; | A7-B55-C2; | A7-B55-C3; | A7-B55-C4; | A7-B55-C5; | A7-B55-C6; |
| A7-B55-C7; | A7-B55-C8; | A7-B55-C9; | A8-B55-C1; | A8-B55-C2; | A8-B55-C3; |
| A8-B55-C4; | A8-B55-C5; | A8-B55-C6; | A8-B55-C7; | A8-B55-C8; | A8-B55-C9; |
| A9-B55-C1; | A9-B55-C2; | A9-B55-C3; | A9-B55-C4; | A9-B55-C5; | A9-B55-C6; |
| A9-B55-C7; | A9-B55-C8; | A9-B55-C9; | A10-B55-C1; | A10-B55-C2; | A10-B55-C3; |
| A10-B55-C4; | A10-B55-C5; | A10-B55-C6; | A10-B55-C7; | A10-B55-C8; | A10-B55-C9; |
| A11-B55-C1; | A11-B55-C2; | A11-B55-C3; | A11-B55-C4; | A11-B55-C5; | A11-B55-C6; |
| A11-B55-C7; | A11-B55-C8; | A11-B55-C9; | A12-B55-C1; | A12-B55-C2; | A12-B55-C3; |
| A12-B55-C4; | A12-B55-C5; | A12-B55-C6; | A12-B55-C7; | A12-B55-C8; | A12-B55-C9; |
| A13-B55-C1; | A13-B55-C2; | A13-B55-C3; | A13-B55-C4; | A13-B55-C5; | A13-B55-C6; |
| A13-B55-C7; | A13-B55-C8; | A13-B55-C9; | A14-B55-C1; | A14-B55-C2; | A14-B55-C3; |
| A14-B55-C4; | A14-B55-C5; | A14-B55-C6; | A14-B55-C7; | A14-B55-C8; | A14-B55-C9; |
| A15-B55-C1; | A15-B55-C2; | A15-B55-C3; | A15-B55-C4; | A15-B55-C5; | A15-B55-C6; |
| A15-B55-C7; | A15-B55-C8; | A15-B55-C9; | A16-B55-C1; | A16-B55-C2; | A16-B55-C3; |
| A16-B55-C4; | A16-B55-C5; | A16-B55-C6; | A16-B55-C7; | A16-B55-C8; | A16-B55-C9; |
| A17-B55-C1; | A17-B55-C2; | A17-B55-C3; | A17-B55-C4; | A17-B55-C5; | A17-B55-C6; |
| A17-B55-C7; | A17-B55-C8; | A17-B55-C9; | A18-B55-C1; | A18-B55-C2; | A18-B55-C3; |
| A18-B55-C4; | A18-B55-C5; | A18-B55-C6; | A18-B55-C7; | A18-B55-C8; | A18-B55-C9; |
| A19-B55-C1; | A19-B55-C2; | A19-B55-C3; | A19-B55-C4; | A19-B55-C5; | A19-B55-C6; |
| A19-B55-C7; | A19-B55-C8; | A19-B55-C9; | A20-B55-C1; | A20-B55-C2; | A20-B55-C3; |
| A20-B55-C4; | A20-B55-C5; | A20-B55-C6; | A20-B55-C7; | A20-B55-C8; | A20-B55-C9; |
| A21-B55-C1; | A21-B55-C2; | A21-B55-C3; | A21-B55-C4; | A21-B55-C5; | A21-B55-C6; |
| A21-B55-C7; | A21-B55-C8; | A21-B55-C9; | A22-B55-C1; | A22-B55-C2; | A22-B55-C3; |
| A22-B55-C4; | A22-B55-C5; | A22-B55-C6; | A22-B55-C7; | A22-B55-C8; | A22-B55-C9; |
| A23-B55-C1; | A23-B55-C2; | A23-B55-C3; | A23-B55-C4; | A23-B55-C5; | A23-B55-C6; |
| A23-B55-C7; | A23-B55-C8; | A23-B55-C9; | A24-B55-C1; | A24-B55-C2; | A24-B55-C3; |
| A24-B55-C4; | A24-B55-C5; | A24-B55-C6; | A24-B55-C7; | A24-B55-C8; | A24-B55-C9; |
| A25-B55-C1; | A25-B55-C2; | A25-B55-C3; | A25-B55-C4; | A25-B55-C5; | A25-B55-C6; |
| A25-B55-C7; | A25-B55-C8; | A25-B55-C9; | A26-B55-C1; | A26-B55-C2; | A26-B55-C3; |
| A26-B55-C4; | A26-B55-C5; | A26-B55-C6; | A26-B55-C7; | A26-B55-C8; | A26-B55-C9; |
| A27-B55-C1; | A27-B55-C2; | A27-B55-C3; | A27-B55-C4; | A27-B55-C5; | A27-B55-C6; |
| A27-B55-C7; | A27-B55-C8; | A27-B55-C9; | A28-B55-C1; | A28-B55-C2; | A28-B55-C3; |
| A28-B55-C4; | A28-B55-C5; | A28-B55-C6; | A28-B55-C7; | A28-B55-C8; | A28-B55-C9; |
| A29-B55-C1; | A29-B55-C2; | A29-B55-C3; | A29-B55-C4; | A29-B55-C5; | A29-B55-C6; |

-continued

A29-B55-C7; A29-B55-C8; A29-B55-C9; A30-B55-C1; A30-B55-C2; A30-B55-C3;
A30-B55-C4; A30-B55-C5; A30-B55-C6; A30-B55-C7; A30-B55-C8; A30-B55-C9;
A31-B55-C1; A31-B55-C2; A31-B55-C3; A31-B55-C4; A31-B55-C5; A31-B55-C6;
A31-B55-C7; A31-B55-C8; A31-B55-C9; A32-B55-C1; A32-B55-C2; A32-B55-C3;
A32-B55-C4; A32-B55-C5; A32-B55-C6; A32-B55-C7; A32-B55-C8; A32-B55-C9;
A33-B55-C1; A33-B55-C2; A33-B55-C3; A33-B55-C4; A33-B55-C5; A33-B55-C6;
A33-B55-C7; A33-B55-C8; A33-B55-C9; A34-B55-C1; A34-B55-C2; A34-B55-C3;
A34-B55-C4; A34-B55-C5; A34-B55-C6; A34-B55-C7; A34-B55-C8; A34-B55-C9;
A35-B55-C1; A35-B55-C2; A35-B55-C3; A35-B55-C4; A35-B55-C5; A35-B55-C6;
A35-B55-C7; A35-B55-C8; A35-B55-C9; A36-B55-C1; A36-B55-C2; A36-B55-C3;
A36-B55-C4; A36-B55-C5; A36-B55-C6; A36-B55-C7; A36-B55-C8; A36-B55-C9;
A37-B55-C1; A37-B55-C2; A37-B55-C3; A37-B55-C4; A37-B55-C5; A37-B55-C6;
A37-B55-C7; A37-B55-C8; A37-B55-C9; A38-B55-C1; A38-B55-C2; A38-B55-C3;
A38-B55-C4; A38-B55-C5; A38-B55-C6; A38-B55-C7; A38-B55-C8; A38-B55-C9;
A39-B55-C1; A39-B55-C2; A39-B55-C3; A39-B55-C4; A39-B55-C5; A39-B55-C6;
A39-B55-C7; A39-B55-C8; A39-B55-C9; A40-B55-C1; A40-B55-C2; A40-B55-C3;
A40-B55-C4; A40-B55-C5; A40-B55-C6; A40-B55-C7; A40-B55-C8; A40-B55-C9;
A41-B55-C1; A41-B55-C2; A41-B55-C3; A41-B55-C4; A41-B55-C5; A41-B55-C6;
A41-B55-C7; A41-B55-C8; A41-B55-C9; A42-B55-C1; A42-B55-C2; A42-B55-C3;
A42-B55-C4; A42-B55-C5; A42-B55-C6; A42-B55-C7; A42-B55-C8; A42-B55-C9;
A43-B55-C1; A43-B55-C2; A43-B55-C3; A43-B55-C4; A43-B55-C5; A43-B55-C6;
A43-B55-C7; A43-B55-C8; A43-B55-C9; A44-B55-C1; A44-B55-C2; A44-B55-C3;
A44-B55-C4; A44-B55-C5; A44-B55-C6; A44-B55-C7; A44-B55-C8; A44-B55-C9;
A45-B55-C1; A45-B55-C2; A45-B55-C3; A45-B55-C4; A45-B55-C5; A45-B55-C6;
A45-B55-C7; A45-B55-C8; A45-B55-C9; A46-B55-C1; A46-B55-C2; A46-B55-C3;
A46-B55-C4; A46-B55-C5; A46-B55-C6; A46-B55-C7; A46-B55-C8; A46-B55-C9;
A47-B55-C1; A47-B55-C2; A47-B55-C3; A47-B55-C4; A47-B55-C5; A47-B55-C6;
A47-B55-C7; A47-B55-C8; A47-B55-C9; A48-B55-C1; A48-B55-C2; A48-B55-C3;
A48-B55-C4; A48-B55-C5; A48-B55-C6; A48-B55-C7; A48-B55-C8; A48-B55-C9;
A49-B55-C1; A49-B55-C2; A49-B55-C3; A49-B55-C4; A49-B55-C5; A49-B55-C6;
A49-B55-C7; A49-B55-C8; A49-B55-C9; A50-B55-C1; A50-B55-C2; A50-B55-C3;
A50-B55-C4; A50-B55-C5; A50-B55-C6; A50-B55-C7; A50-B55-C8; A50-B55-C9;
A51-B55-C1; A51-B55-C2; A51-B55-C3; A51-B55-C4; A51-B55-C5; A51-B55-C6;
A51-B55-C7; A51-B55-C8; A51-B55-C9; A52-B55-C1; A52-B55-C2; A52-B55-C3;
A52-B55-C4; A52-B55-C5; A52-B55-C6; A52-B55-C7; A52-B55-C8; A52-B55-C9;
A53-B55-C1; A53-B55-C2; A53-B55-C3; A53-B55-C4; A53-B55-C5; A53-B55-C6;
A53-B55-C7; A53-B55-C8; A53-B55-C9; A54-B55-C1; A54-B55-C2; A54-B55-C3;
A54-B55-C4; A54-B55-C5; A54-B55-C6; A54-B55-C7; A54-B55-C8; A54-B55-C9;
A55-B55-C1; A55-B55-C2; A55-B55-C3; A55-B55-C4; A55-B55-C5; A55-B55-C6;
A55-B55-C7; A55-B55-C8; A55-B55-C9; A56-B55-C1; A56-B55-C2; A56-B55-C3;
A56-B55-C4; A56-B55-C5; A56-B55-C6; A56-B55-C7; A56-B55-C8; A56-B55-C9;
A57-B55-C1; A57-B55-C2; A57-B55-C3; A57-B55-C4; A57-B55-C5; A57-B55-C6;
A57-B55-C7; A57-B55-C8; A57-B55-C9; A58-B55-C1; A58-B55-C2; A58-B55-C3;
A58-B55-C4; A58-B55-C5; A58-B55-C6; A58-B55-C7; A58-B55-C8; A58-B55-C9;
A59-B55-C1; A59-B55-C2; A59-B55-C3; A59-B55-C4; A59-B55-C5; A59-B55-C6;
A59-B55-C7; A59-B55-C8; A59-B55-C9; A60-B55-C1; A60-B55-C2; A60-B55-C3;
A60-B55-C4; A60-B55-C5; A60-B55-C6; A60-B55-C7; A60-B55-C8; A60-B55-C9;
A61-B55-C1; A61-B55-C2; A61-B55-C3; A61-B55-C4; A61-B55-C5; A61-B55-C6;
A61-B55-C7; A61-B55-C8; A61-B55-C9; A62-B55-C1; A62-B55-C2; A62-B55-C3;
A62-B55-C4; A62-B55-C5; A62-B55-C6; A62-B55-C7; A62-B55-C8; A62-B55-C9;
A63-B55-C1; A63-B55-C2; A63-B55-C3; A63-B55-C4; A63-B55-C5; A63-B55-C6;
A63-B55-C7; A63-B55-C8; A63-B55-C9; A64-B55-C1; A64-B55-C2; A64-B55-C3;
A64-B55-C4; A64-B55-C5; A64-B55-C6; A64-B55-C7; A64-B55-C8; A64-B55-C9;
A65-B55-C1; A65-B55-C2; A65-B55-C3; A65-B55-C4; A65-B55-C5; A65-B55-C6;
A65-B55-C7; A65-B55-C8; A65-B55-C9; A66-B55-C1; A66-B55-C2; A66-B55-C3;
A66-B55-C4; A66-B55-C5; A66-B55-C6; A66-B55-C7; A66-B55-C8; A66-B55-C9;
A67-B55-C1; A67-B55-C2; A67-B55-C3; A67-B55-C4; A67-B55-C5; A67-B55-C6;
A67-B55-C7; A67-B55-C8; A67-B55-C9; A68-B55-C1; A68-B55-C2; A68-B55-C3;
A68-B55-C4; A68-B55-C5; A68-B55-C6; A68-B55-C7; A68-B55-C8; A68-B55-C9;
A69-B55-C1; A69-B55-C2; A69-B55-C3; A69-B55-C4; A69-B55-C5; A69-B55-C6;
A69-B55-C7; A69-B55-C8; A69-B55-C9; A70-B55-C1; A70-B55-C2; A70-B55-C3;
A70-B55-C4; A70-B55-C5; A70-B55-C6; A70-B55-C7; A70-B55-C8; A70-B55-C9;
A71-B55-C1; A71-B55-C2; A71-B55-C3; A71-B55-C4; A71-B55-C5; A71-B55-C6;
A71-B55-C7; A71-B55-C8; A71-B55-C9; A1-B56-C1; A1-B56-C2; A1-B56-C3;
A1-B56-C4; A1-B56-C5; A1-B56-C6; A1-B56-C7; A1-B56-C8; A1-B56-C9;
A2-B56-C1; A2-B56-C2; A2-B56-C3; A2-B56-C4; A2-B56-C5; A2-B56-C6;
A2-B56-C7; A2-B56-C8; A2-B56-C9; A3-B56-C1; A3-B56-C2; A3-B56-C3;
A3-B56-C4; A3-B56-C5; A3-B56-C6; A3-B56-C7; A3-B56-C8; A3-B56-C9;
A4-B56-C1; A4-B56-C2; A4-B56-C3; A4-B56-C4; A4-B56-C5; A4-B56-C6;
A4-B56-C7; A4-B56-C8; A4-B56-C9; A5-B56-C1; A5-B56-C2; A5-B56-C3;
A5-B56-C4; A5-B56-C5; A5-B56-C6; A5-B56-C7; A5-B56-C8; A5-B56-C9;
A6-B56-C1; A6-B56-C2; A6-B56-C3; A6-B56-C4; A6-B56-C5; A6-B56-C6;
A6-B56-C7; A6-B56-C8; A6-B56-C9; A7-B56-C1; A7-B56-C2; A7-B56-C3;
A7-B56-C4; A7-B56-C5; A7-B56-C6; A7-B56-C7; A7-B56-C8; A7-B56-C9;
A8-B56-C1; A8-B56-C2; A8-B56-C3; A8-B56-C4; A8-B56-C5; A8-B56-C6;
A8-B56-C7; A8-B56-C8; A8-B56-C9; A9-B56-C1; A9-B56-C2; A9-B56-C3;
A9-B56-C4; A9-B56-C5; A9-B56-C6; A9-B56-C7; A9-B56-C8; A9-B56-C9;
A10-B56-C1; A10-B56-C2; A10-B56-C3; A10-B56-C4; A10-B56-C5; A10-B56-C6;
A10-B56-C7; A10-B56-C8; A10-B56-C9; A11-B56-C1; A11-B56-C2; A11-B56-C3;

-continued

| | | | | | |
|---|---|---|---|---|---|
| A11-B56-C4; | A11-B56-C5; | A11-B56-C6; | A11-B56-C7; | A11-B56-C8; | A11-B56-C9; |
| A12-B56-C1; | A12-B56-C2; | A12-B56-C3; | A12-B56-C4; | A12-B56-C5; | A12-B56-C6; |
| A12-B56-C7; | A12-B56-C8; | A12-B56-C9; | A13-B56-C1; | A13-B56-C2; | A13-B56-C3; |
| A13-B56-C4; | A13-B56-C5; | A13-B56-C6; | A13-B56-C7; | A13-B56-C8; | A13-B56-C9; |
| A14-B56-C1; | A14-B56-C2; | A14-B56-C3; | A14-B56-C4; | A14-B56-C5; | A14-B56-C6; |
| A14-B56-C7; | A14-B56-C8; | A14-B56-C9; | A15-B56-C1; | A15-B56-C2; | A15-B56-C3; |
| A15-B56-C4; | A15-B56-C5; | A15-B56-C6; | A15-B56-C7; | A15-B56-C8; | A15-B56-C9; |
| A16-B56-C1; | A16-B56-C2; | A16-B56-C3; | A16-B56-C4; | A16-B56-C5; | A16-B56-C6; |
| A16-B56-C7; | A16-B56-C8; | A16-B56-C9; | A17-B56-C1; | A17-B56-C2; | A17-B56-C3; |
| A17-B56-C4; | A17-B56-C5; | A17-B56-C6; | A17-B56-C7; | A17-B56-C8; | A17-B56-C9; |
| A18-B56-C1; | A18-B56-C2; | A18-B56-C3; | A18-B56-C4; | A18-B56-C5; | A18-B56-C6; |
| A18-B56-C7; | A18-B56-C8; | A18-B56-C9; | A19-B56-C1; | A19-B56-C2; | A19-B56-C3; |
| A19-B56-C4; | A19-B56-C5; | A19-B56-C6; | A19-B56-C7; | A19-B56-C8; | A19-B56-C9; |
| A20-B56-C1; | A20-B56-C2; | A20-B56-C3; | A20-B56-C4; | A20-B56-C5; | A20-B56-C6; |
| A20-B56-C7; | A20-B56-C8; | A20-B56-C9; | A21-B56-C1; | A21-B56-C2; | A21-B56-C3; |
| A21-B56-C4; | A21-B56-C5; | A21-B56-C6; | A21-B56-C7; | A21-B56-C8; | A21-B56-C9; |
| A22-B56-C1; | A22-B56-C2; | A22-B56-C3; | A22-B56-C4; | A22-B56-C5; | A22-B56-C6; |
| A22-B56-C7; | A22-B56-C8; | A22-B56-C9; | A23-B56-C1; | A23-B56-C2; | A23-B56-C3; |
| A23-B56-C4; | A23-B56-C5; | A23-B56-C6; | A23-B56-C7; | A23-B56-C8; | A23-B56-C9; |
| A24-B56-C1; | A24-B56-C2; | A24-B56-C3; | A24-B56-C4; | A24-B56-C5; | A24-B56-C6; |
| A24-B56-C7; | A24-B56-C8; | A24-B56-C9; | A25-B56-C1; | A25-B56-C2; | A25-B56-C3; |
| A25-B56-C4; | A25-B56-C5; | A25-B56-C6; | A25-B56-C7; | A25-B56-C8; | A25-B56-C9; |
| A26-B56-C1; | A26-B56-C2; | A26-B56-C3; | A26-B56-C4; | A26-B56-C5; | A26-B56-C6; |
| A26-B56-C7; | A26-B56-C8; | A26-B56-C9; | A27-B56-C1; | A27-B56-C2; | A27-B56-C3; |
| A27-B56-C4; | A27-B56-C5; | A27-B56-C6; | A27-B56-C7; | A27-B56-C8; | A27-B56-C9; |
| A28-B56-C1; | A28-B56-C2; | A28-B56-C3; | A28-B56-C4; | A28-B56-C5; | A28-B56-C6; |
| A28-B56-C7; | A28-B56-C8; | A28-B56-C9; | A29-B56-C1; | A29-B56-C2; | A29-B56-C3; |
| A29-B56-C4; | A29-B56-C5; | A29-B56-C6; | A29-B56-C7; | A29-B56-C8; | A29-B56-C9; |
| A30-B56-C1; | A30-B56-C2; | A30-B56-C3; | A30-B56-C4; | A30-B56-C5; | A30-B56-C6; |
| A30-B56-C7; | A30-B56-C8; | A30-B56-C9; | A31-B56-C1; | A31-B56-C2; | A31-B56-C3; |
| A31-B56-C4; | A31-B56-C5; | A31-B56-C6; | A31-B56-C7; | A31-B56-C8; | A31-B56-C9; |
| A32-B56-C1; | A32-B56-C2; | A32-B56-C3; | A32-B56-C4; | A32-B56-C5; | A32-B56-C6; |
| A32-B56-C7; | A32-B56-C8; | A32-B56-C9; | A33-B56-C1; | A33-B56-C2; | A33-B56-C3; |
| A33-B56-C4; | A33-B56-C5; | A33-B56-C6; | A33-B56-C7; | A33-B56-C8; | A33-B56-C9; |
| A34-B56-C1; | A34-B56-C2; | A34-B56-C3; | A34-B56-C4; | A34-B56-C5; | A34-B56-C6; |
| A34-B56-C7; | A34-B56-C8; | A34-B56-C9; | A35-B56-C1; | A35-B56-C2; | A35-B56-C3; |
| A35-B56-C4; | A35-B56-C5; | A35-B56-C6; | A35-B56-C7; | A35-B56-C8; | A35-B56-C9; |
| A36-B56-C1; | A36-B56-C2; | A36-B56-C3; | A36-B56-C4; | A36-B56-C5; | A36-B56-C6; |
| A36-B56-C7; | A36-B56-C8; | A36-B56-C9; | A37-B56-C1; | A37-B56-C2; | A37-B56-C3; |
| A37-B56-C4; | A37-B56-C5; | A37-B56-C6; | A37-B56-C7; | A37-B56-C8; | A37-B56-C9; |
| A38-B56-C1; | A38-B56-C2; | A38-B56-C3; | A38-B56-C4; | A38-B56-C5; | A38-B56-C6; |
| A38-B56-C7; | A38-B56-C8; | A38-B56-C9; | A39-B56-C1; | A39-B56-C2; | A39-B56-C3; |
| A39-B56-C4; | A39-B56-C5; | A39-B56-C6; | A39-B56-C7; | A39-B56-C8; | A39-B56-C9; |
| A40-B56-C1; | A40-B56-C2; | A40-B56-C3; | A40-B56-C4; | A40-B56-C5; | A40-B56-C6; |
| A40-B56-C7; | A40-B56-C8; | A40-B56-C9; | A41-B56-C1; | A41-B56-C2; | A41-B56-C3; |
| A41-B56-C4; | A41-B56-C5; | A41-B56-C6; | A41-B56-C7; | A41-B56-C8; | A41-B56-C9; |
| A42-B56-C1; | A42-B56-C2; | A42-B56-C3; | A42-B56-C4; | A42-B56-C5; | A42-B56-C6; |
| A42-B56-C7; | A42-B56-C8; | A42-B56-C9; | A43-B56-C1; | A43-B56-C2; | A43-B56-C3; |
| A43-B56-C4; | A43-B56-C5; | A43-B56-C6; | A43-B56-C7; | A43-B56-C8; | A43-B56-C9; |
| A44-B56-C1; | A44-B56-C2; | A44-B56-C3; | A44-B56-C4; | A44-B56-C5; | A44-B56-C6; |
| A44-B56-C7; | A44-B56-C8; | A44-B56-C9; | A45-B56-C1; | A45-B56-C2; | A45-B56-C3; |
| A45-B56-C4; | A45-B56-C5; | A45-B56-C6; | A45-B56-C7; | A45-B56-C8; | A45-B56-C9; |
| A46-B56-C1; | A46-B56-C2; | A46-B56-C3; | A46-B56-C4; | A46-B56-C5; | A46-B56-C6; |
| A46-B56-C7; | A46-B56-C8; | A46-B56-C9; | A47-B56-C1; | A47-B56-C2; | A47-B56-C3; |
| A47-B56-C4; | A47-B56-C5; | A47-B56-C6; | A47-B56-C7; | A47-B56-C8; | A47-B56-C9; |
| A48-B56-C1; | A48-B56-C2; | A48-B56-C3; | A48-B56-C4; | A48-B56-C5; | A48-B56-C6; |
| A48-B56-C7; | A48-B56-C8; | A48-B56-C9; | A49-B56-C1; | A49-B56-C2; | A49-B56-C3; |
| A49-B56-C4; | A49-B56-C5; | A49-B56-C6; | A49-B56-C7; | A49-B56-C8; | A49-B56-C9; |
| A50-B56-C1; | A50-B56-C2; | A50-B56-C3; | A50-B56-C4; | A50-B56-C5; | A50-B56-C6; |
| A50-B56-C7; | A50-B56-C8; | A50-B56-C9; | A51-B56-C1; | A51-B56-C2; | A51-B56-C3; |
| A51-B56-C4; | A51-B56-C5; | A51-B56-C6; | A51-B56-C7; | A51-B56-C8; | A51-B56-C9; |
| A52-B56-C1; | A52-B56-C2; | A52-B56-C3; | A52-B56-C4; | A52-B56-C5; | A52-B56-C6; |
| A52-B56-C7; | A52-B56-C8; | A52-B56-C9; | A53-B56-C1; | A53-B56-C2; | A53-B56-C3; |
| A53-B56-C4; | A53-B56-C5; | A53-B56-C6; | A53-B56-C7; | A53-B56-C8; | A53-B56-C9; |
| A54-B56-C1; | A54-B56-C2; | A54-B56-C3; | A54-B56-C4; | A54-B56-C5; | A54-B56-C6; |
| A54-B56-C7; | A54-B56-C8; | A54-B56-C9; | A55-B56-C1; | A55-B56-C2; | A55-B56-C3; |
| A55-B56-C4; | A55-B56-C5; | A55-B56-C6; | A55-B56-C7; | A55-B56-C8; | A55-B56-C9; |
| A56-B56-C1; | A56-B56-C2; | A56-B56-C3; | A56-B56-C4; | A56-B56-C5; | A56-B56-C6; |
| A56-B56-C7; | A56-B56-C8; | A56-B56-C9; | A57-B56-C1; | A57-B56-C2; | A57-B56-C3; |
| A57-B56-C4; | A57-B56-C5; | A57-B56-C6; | A57-B56-C7; | A57-B56-C8; | A57-B56-C9; |
| A58-B56-C1; | A58-B56-C2; | A58-B56-C3; | A58-B56-C4; | A58-B56-C5; | A58-B56-C6; |
| A58-B56-C7; | A58-B56-C8; | A58-B56-C9; | A59-B56-C1; | A59-B56-C2; | A59-B56-C3; |
| A59-B56-C4; | A59-B56-C5; | A59-B56-C6; | A59-B56-C7; | A59-B56-C8; | A59-B56-C9; |
| A60-B56-C1; | A60-B56-C2; | A60-B56-C3; | A60-B56-C4; | A60-B56-C5; | A60-B56-C6; |
| A60-B56-C7; | A60-B56-C8; | A60-B56-C9; | A61-B56-C1; | A61-B56-C2; | A61-B56-C3; |
| A61-B56-C4; | A61-B56-C5; | A61-B56-C6; | A61-B56-C7; | A61-B56-C8; | A61-B56-C9; |
| A62-B56-C1; | A62-B56-C2; | A62-B56-C3; | A62-B56-C4; | A62-B56-C5; | A62-B56-C6; |
| A62-B56-C7; | A62-B56-C8; | A62-B56-C9; | A63-B56-C1; | A63-B56-C2; | A63-B56-C3; |
| A63-B56-C4; | A63-B56-C5; | A63-B56-C6; | A63-B56-C7; | A63-B56-C8; | A63-B56-C9; |

-continued

| | | | | | |
|---|---|---|---|---|---|
| A64-B56-C1; | A64-B56-C2; | A64-B56-C3; | A64-B56-C4; | A64-B56-C5; | A64-B56-C6; |
| A64-B56-C7; | A64-B56-C8; | A64-B56-C9; | A65-B56-C1; | A65-B56-C2; | A65-B56-C3; |
| A65-B56-C4; | A65-B56-C5; | A65-B56-C6; | A65-B56-C7; | A65-B56-C8; | A65-B56-C9; |
| A66-B56-C1; | A66-B56-C2; | A66-B56-C3; | A66-B56-C4; | A66-B56-C5; | A66-B56-C6; |
| A66-B56-C7; | A66-B56-C8; | A66-B56-C9; | A67-B56-C1; | A67-B56-C2; | A67-B56-C3; |
| A67-B56-C4; | A67-B56-C5; | A67-B56-C6; | A67-B56-C7; | A67-B56-C8; | A67-B56-C9; |
| A68-B56-C1; | A68-B56-C2; | A68-B56-C3; | A68-B56-C4; | A68-B56-C5; | A68-B56-C6; |
| A68-B56-C7; | A68-B56-C8; | A68-B56-C9; | A69-B56-C1; | A69-B56-C2; | A69-B56-C3; |
| A69-B56-C4; | A69-B56-C5; | A69-B56-C6; | A69-B56-C7; | A69-B56-C8; | A69-B56-C9; |
| A70-B56-C1; | A70-B56-C2; | A70-B56-C3; | A70-B56-C4; | A70-B56-C5; | A70-B56-C6; |
| A70-B56-C7; | A70-B56-C8; | A70-B56-C9; | A71-B56-C1; | A71-B56-C2; | A71-B56-C3; |
| A71-B56-C4; | A71-B56-C5; | A71-B56-C6; | A71-B56-C7; | A71-B56-C8; | A71-B56-C9; |
| A1-B57-C1; | A1-B57-C2; | A1-B57-C3; | A1-B57-C4; | A1-B57-C5; | A1-B57-C6; |
| A1-B57-C7; | A1-B57-C8; | A1-B57-C9; | A2-B57-C1; | A2-B57-C2; | A2-B57-C3; |
| A2-B57-C4; | A2-B57-C5; | A2-B57-C6; | A2-B57-C7; | A2-B57-C8; | A2-B57-C9; |
| A3-B57-C1; | A3-B57-C2; | A3-B57-C3; | A3-B57-C4; | A3-B57-C5; | A3-B57-C6; |
| A3-B57-C7; | A3-B57-C8; | A3-B57-C9; | A4-B57-C1; | A4-B57-C2; | A4-B57-C3; |
| A4-B57-C4; | A4-B57-C5; | A4-B57-C6; | A4-B57-C7; | A4-B57-C8; | A4-B57-C9; |
| A5-B57-C1; | A5-B57-C2; | A5-B57-C3; | A5-B57-C4; | A5-B57-C5; | A5-B57-C6; |
| A5-B57-C7; | A5-B57-C8; | A5-B57-C9; | A6-B57-C1; | A6-B57-C2; | A6-B57-C3; |
| A6-B57-C4; | A6-B57-C5; | A6-B57-C6; | A6-B57-C7; | A6-B57-C8; | A6-B57-C9; |
| A7-B57-C1; | A7-B57-C2; | A7-B57-C3; | A7-B57-C4; | A7-B57-C5; | A7-B57-C6; |
| A7-B57-C7; | A7-B57-C8; | A7-B57-C9; | A8-B57-C1; | A8-B57-C2; | A8-B57-C3; |
| A8-B57-C4; | A8-B57-C5; | A8-B57-C6; | A8-B57-C7; | A8-B57-C8; | A8-B57-C9; |
| A9-B57-C1; | A9-B57-C2; | A9-B57-C3; | A9-B57-C4; | A9-B57-C5; | A9-B57-C6; |
| A9-B57-C7; | A9-B57-C8; | A9-B57-C9; | A10-B57-C1; | A10-B57-C2; | A10-B57-C3; |
| A10-B57-C4; | A10-B57-C5; | A10-B57-C6; | A10-B57-C7; | A10-B57-C8; | A10-B57-C9; |
| A11-B57-C1; | A11-B57-C2; | A11-B57-C3; | A11-B57-C4; | A11-B57-C5; | A11-B57-C6; |
| A11-B57-C7; | A11-B57-C8; | A11-B57-C9; | A12-B57-C1; | A12-B57-C2; | A12-B57-C3; |
| A12-B57-C4; | A12-B57-C5; | A12-B57-C6; | A12-B57-C7; | A12-B57-C8; | A12-B57-C9; |
| A13-B57-C1; | A13-B57-C2; | A13-B57-C3; | A13-B57-C4; | A13-B57-C5; | A13-B57-C6; |
| A13-B57-C7; | A13-B57-C8; | A13-B57-C9; | A14-B57-C1; | A14-B57-C2; | A14-B57-C3; |
| A14-B57-C4; | A14-B57-C5; | A14-B57-C6; | A14-B57-C7; | A14-B57-C8; | A14-B57-C9; |
| A15-B57-C1; | A15-B57-C2; | A15-B57-C3; | A15-B57-C4; | A15-B57-C5; | A15-B57-C6; |
| A15-B57-C7; | A15-B57-C8; | A15-B57-C9; | A16-B57-C1; | A16-B57-C2; | A16-B57-C3; |
| A16-B57-C4; | A16-B57-C5; | A16-B57-C6; | A16-B57-C7; | A16-B57-C8; | A16-B57-C9; |
| A17-B57-C1; | A17-B57-C2; | A17-B57-C3; | A17-B57-C4; | A17-B57-C5; | A17-B57-C6; |
| A17-B57-C7; | A17-B57-C8; | A17-B57-C9; | A18-B57-C1; | A18-B57-C2; | A18-B57-C3; |
| A18-B57-C4; | A18-B57-C5; | A18-B57-C6; | A18-B57-C7; | A18-B57-C8; | A18-B57-C9; |
| A19-B57-C1; | A19-B57-C2; | A19-B57-C3; | A19-B57-C4; | A19-B57-C5; | A19-B57-C6; |
| A19-B57-C7; | A19-B57-C8; | A19-B57-C9; | A20-B57-C1; | A20-B57-C2; | A20-B57-C3; |
| A20-B57-C4; | A20-B57-C5; | A20-B57-C6; | A20-B57-C7; | A20-B57-C8; | A20-B57-C9; |
| A21-B57-C1; | A21-B57-C2; | A21-B57-C3; | A21-B57-C4; | A21-B57-C5; | A21-B57-C6; |
| A21-B57-C7; | A21-B57-C8; | A21-B57-C9; | A22-B57-C1; | A22-B57-C2; | A22-B57-C3; |
| A22-B57-C4; | A22-B57-C5; | A22-B57-C6; | A22-B57-C7; | A22-B57-C8; | A22-B57-C9; |
| A23-B57-C1; | A23-B57-C2; | A23-B57-C3; | A23-B57-C4; | A23-B57-C5; | A23-B57-C6; |
| A23-B57-C7; | A23-B57-C8; | A23-B57-C9; | A24-B57-C1; | A24-B57-C2; | A24-B57-C3; |
| A24-B57-C4; | A24-B57-C5; | A24-B57-C6; | A24-B57-C7; | A24-B57-C8; | A24-B57-C9; |
| A25-B57-C1; | A25-B57-C2; | A25-B57-C3; | A25-B57-C4; | A25-B57-C5; | A25-B57-C6; |
| A25-B57-C7; | A25-B57-C8; | A25-B57-C9; | A26-B57-C1; | A26-B57-C2; | A26-B57-C3; |
| A26-B57-C4; | A26-B57-C5; | A26-B57-C6; | A26-B57-C7; | A26-B57-C8; | A26-B57-C9; |
| A27-B57-C1; | A27-B57-C2; | A27-B57-C3; | A27-B57-C4; | A27-B57-C5; | A27-B57-C6; |
| A27-B57-C7; | A27-B57-C8; | A27-B57-C9; | A28-B57-C1; | A28-B57-C2; | A28-B57-C3; |
| A28-B57-C4; | A28-B57-C5; | A28-B57-C6; | A28-B57-C7; | A28-B57-C8; | A28-B57-C9; |
| A29-B57-C1; | A29-B57-C2; | A29-B57-C3; | A29-B57-C4; | A29-B57-C5; | A29-B57-C6; |
| A29-B57-C7; | A29-B57-C8; | A29-B57-C9; | A30-B57-C1; | A30-B57-C2; | A30-B57-C3; |
| A30-B57-C4; | A30-B57-C5; | A30-B57-C6; | A30-B57-C7; | A30-B57-C8; | A30-B57-C9; |
| A31-B57-C1; | A31-B57-C2; | A31-B57-C3; | A31-B57-C4; | A31-B57-C5; | A31-B57-C6; |
| A31-B57-C7; | A31-B57-C8; | A31-B57-C9; | A32-B57-C1; | A32-B57-C2; | A32-B57-C3; |
| A32-B57-C4; | A32-B57-C5; | A32-B57-C6; | A32-B57-C7; | A32-B57-C8; | A32-B57-C9; |
| A33-B57-C1; | A33-B57-C2; | A33-B57-C3; | A33-B57-C4; | A33-B57-C5; | A33-B57-C6; |
| A33-B57-C7; | A33-B57-C8; | A33-B57-C9; | A34-B57-C1; | A34-B57-C2; | A34-B57-C3; |
| A34-B57-C4; | A34-B57-C5; | A34-B57-C6; | A34-B57-C7; | A34-B57-C8; | A34-B57-C9; |
| A35-B57-C1; | A35-B57-C2; | A35-B57-C3; | A35-B57-C4; | A35-B57-C5; | A35-B57-C6; |
| A35-B57-C7; | A35-B57-C8; | A35-B57-C9; | A36-B57-C1; | A36-B57-C2; | A36-B57-C3; |
| A36-B57-C4; | A36-B57-C5; | A36-B57-C6; | A36-B57-C7; | A36-B57-C8; | A36-B57-C9; |
| A37-B57-C1; | A37-B57-C2; | A37-B57-C3; | A37-B57-C4; | A37-B57-C5; | A37-B57-C6; |
| A37-B57-C7; | A37-B57-C8; | A37-B57-C9; | A38-B57-C1; | A38-B57-C2; | A38-B57-C3; |
| A38-B57-C4; | A38-B57-C5; | A38-B57-C6; | A38-B57-C7; | A38-B57-C8; | A38-B57-C9; |
| A39-B57-C1; | A39-B57-C2; | A39-B57-C3; | A39-B57-C4; | A39-B57-C5; | A39-B57-C6; |
| A39-B57-C7; | A39-B57-C8; | A39-B57-C9; | A40-B57-C1; | A40-B57-C2; | A40-B57-C3; |
| A40-B57-C4; | A40-B57-C5; | A40-B57-C6; | A40-B57-C7; | A40-B57-C8; | A40-B57-C9; |
| A41-B57-C1; | A41-B57-C2; | A41-B57-C3; | A41-B57-C4; | A41-B57-C5; | A41-B57-C6; |
| A41-B57-C7; | A41-B57-C8; | A41-B57-C9; | A42-B57-C1; | A42-B57-C2; | A42-B57-C3; |
| A42-B57-C4; | A42-B57-C5; | A42-B57-C6; | A42-B57-C7; | A42-B57-C8; | A42-B57-C9; |
| A43-B57-C1; | A43-B57-C2; | A43-B57-C3; | A43-B57-C4; | A43-B57-C5; | A43-B57-C6; |
| A43-B57-C7; | A43-B57-C8; | A43-B57-C9; | A44-B57-C1; | A44-B57-C2; | A44-B57-C3; |
| A44-B57-C4; | A44-B57-C5; | A44-B57-C6; | A44-B57-C7; | A44-B57-C8; | A44-B57-C9; |
| A45-B57-C1; | A45-B57-C2; | A45-B57-C3; | A45-B57-C4; | A45-B57-C5; | A45-B57-C6; |

-continued

| | | | | | |
|---|---|---|---|---|---|
| A45-B57-C7; | A45-B57-C8; | A45-B57-C9; | A46-B57-C1; | A46-B57-C2; | A46-B57-C3; |
| A46-B57-C4; | A46-B57-C5; | A46-B57-C6; | A46-B57-C7; | A46-B57-C8; | A46-B57-C9; |
| A47-B57-C1; | A47-B57-C2; | A47-B57-C3; | A47-B57-C4; | A47-B57-C5; | A47-B57-C6; |
| A47-B57-C7; | A47-B57-C8; | A47-B57-C9; | A48-B57-C1; | A48-B57-C2; | A48-B57-C3; |
| A48-B57-C4; | A48-B57-C5; | A48-B57-C6; | A48-B57-C7; | A48-B57-C8; | A48-B57-C9; |
| A49-B57-C1; | A49-B57-C2; | A49-B57-C3; | A49-B57-C4; | A49-B57-C5; | A49-B57-C6; |
| A49-B57-C7; | A49-B57-C8; | A49-B57-C9; | A50-B57-C1; | A50-B57-C2; | A50-B57-C3; |
| A50-B57-C4; | A50-B57-C5; | A50-B57-C6; | A50-B57-C7; | A50-B57-C8; | A50-B57-C9; |
| A51-B57-C1; | A51-B57-C2; | A51-B57-C3; | A51-B57-C4; | A51-B57-C5; | A51-B57-C6; |
| A51-B57-C7; | A51-B57-C8; | A51-B57-C9; | A52-B57-C1; | A52-B57-C2; | A52-B57-C3; |
| A52-B57-C4; | A52-B57-C5; | A52-B57-C6; | A52-B57-C7; | A52-B57-C8; | A52-B57-C9; |
| A53-B57-C1; | A53-B57-C2; | A53-B57-C3; | A53-B57-C4; | A53-B57-C5; | A53-B57-C6; |
| A53-B57-C7; | A53-B57-C8; | A53-B57-C9; | A54-B57-C1; | A54-B57-C2; | A54-B57-C3; |
| A54-B57-C4; | A54-B57-C5; | A54-B57-C6; | A54-B57-C7; | A54-B57-C8; | A54-B57-C9; |
| A55-B57-C1; | A55-B57-C2; | A55-B57-C3; | A55-B57-C4; | A55-B57-C5; | A55-B57-C6; |
| A55-B57-C7; | A55-B57-C8; | A55-B57-C9; | A56-B57-C1; | A56-B57-C2; | A56-B57-C3; |
| A56-B57-C4; | A56-B57-C5; | A56-B57-C6; | A56-B57-C7; | A56-B57-C8; | A56-B57-C9; |
| A57-B57-C1; | A57-B57-C2; | A57-B57-C3; | A57-B57-C4; | A57-B57-C5; | A57-B57-C6; |
| A57-B57-C7; | A57-B57-C8; | A57-B57-C9; | A58-B57-C1; | A58-B57-C2; | A58-B57-C3; |
| A58-B57-C4; | A58-B57-C5; | A58-B57-C6; | A58-B57-C7; | A58-B57-C8; | A58-B57-C9; |
| A59-B57-C1; | A59-B57-C2; | A59-B57-C3; | A59-B57-C4; | A59-B57-C5; | A59-B57-C6; |
| A59-B57-C7; | A59-B57-C8; | A59-B57-C9; | A60-B57-C1; | A60-B57-C2; | A60-B57-C3; |
| A60-B57-C4; | A60-B57-C5; | A60-B57-C6; | A60-B57-C7; | A60-B57-C8; | A60-B57-C9; |
| A61-B57-C1; | A61-B57-C2; | A61-B57-C3; | A61-B57-C4; | A61-B57-C5; | A61-B57-C6; |
| A61-B57-C7; | A61-B57-C8; | A61-B57-C9; | A62-B57-C1; | A62-B57-C2; | A62-B57-C3; |
| A62-B57-C4; | A62-B57-C5; | A62-B57-C6; | A62-B57-C7; | A62-B57-C8; | A62-B57-C9; |
| A63-B57-C1; | A63-B57-C2; | A63-B57-C3; | A63-B57-C4; | A63-B57-C5; | A63-B57-C6; |
| A63-B57-C7; | A63-B57-C8; | A63-B57-C9; | A64-B57-C1; | A64-B57-C2; | A64-B57-C3; |
| A64-B57-C4; | A64-B57-C5; | A64-B57-C6; | A64-B57-C7; | A64-B57-C8; | A64-B57-C9; |
| A65-B57-C1; | A65-B57-C2; | A65-B57-C3; | A65-B57-C4; | A65-B57-C5; | A65-B57-C6; |
| A65-B57-C7; | A65-B57-C8; | A65-B57-C9; | A66-B57-C1; | A66-B57-C2; | A66-B57-C3; |
| A66-B57-C4; | A66-B57-C5; | A66-B57-C6; | A66-B57-C7; | A66-B57-C8; | A66-B57-C9; |
| A67-B57-C1; | A67-B57-C2; | A67-B57-C3; | A67-B57-C4; | A67-B57-C5; | A67-B57-C6; |
| A67-B57-C7; | A67-B57-C8; | A67-B57-C9; | A68-B57-C1; | A68-B57-C2; | A68-B57-C3; |
| A68-B57-C4; | A68-B57-C5; | A68-B57-C6; | A68-B57-C7; | A68-B57-C8; | A68-B57-C9; |
| A69-B57-C1; | A69-B57-C2; | A69-B57-C3; | A69-B57-C4; | A69-B57-C5; | A69-B57-C6; |
| A69-B57-C7; | A69-B57-C8; | A69-B57-C9; | A70-B57-C1; | A70-B57-C2; | A70-B57-C3; |
| A70-B57-C4; | A70-B57-C5; | A70-B57-C6; | A70-B57-C7; | A70-B57-C8; | A70-B57-C9; |
| A71-B57-C1; | A71-B57-C2; | A71-B57-C3; | A71-B57-C4; | A71-B57-C5; | A71-B57-C6; |
| A71-B57-C7; | A71-B57-C8; | A71-B57-C9; | A1-B58-C1; | A1-B58-C2; | A1-B58-C3; |
| A1-B58-C4; | A1-B58-C5; | A1-B58-C6; | A1-B58-C7; | A1-B58-C8; | A1-B58-C9; |
| A2-B58-C1; | A2-B58-C2; | A2-B58-C3; | A2-B58-C4; | A2-B58-C5; | A2-B58-C6; |
| A2-B58-C7; | A2-B58-C8; | A2-B58-C9; | A3-B58-C1; | A3-B58-C2; | A3-B58-C3; |
| A3-B58-C4; | A3-B58-C5; | A3-B58-C6; | A3-B58-C7; | A3-B58-C8; | A3-B58-C9; |
| A4-B58-C1; | A4-B58-C2; | A4-B58-C3; | A4-B58-C4; | A4-B58-C5; | A4-B58-C6; |
| A4-B58-C7; | A4-B58-C8; | A4-B58-C9; | A5-B58-C1; | A5-B58-C2; | A5-B58-C3; |
| A5-B58-C4; | A5-B58-C5; | A5-B58-C6; | A5-B58-C7; | A5-B58-C8; | A5-B58-C9; |
| A6-B58-C1; | A6-B58-C2; | A6-B58-C3; | A6-B58-C4; | A6-B58-C5; | A6-B58-C6; |
| A6-B58-C7; | A6-B58-C8; | A6-B58-C9; | A7-B58-C1; | A7-B58-C2; | A7-B58-C3; |
| A7-B58-C4; | A7-B58-C5; | A7-B58-C6; | A7-B58-C7; | A7-B58-C8; | A7-B58-C9; |
| A8-B58-C1; | A8-B58-C2; | A8-B58-C3; | A8-B58-C4; | A8-B58-C5; | A8-B58-C6; |
| A8-B58-C7; | A8-B58-C8; | A8-B58-C9; | A9-B58-C1; | A9-B58-C2; | A9-B58-C3; |
| A9-B58-C4; | A9-B58-C5; | A9-B58-C6; | A9-B58-C7; | A9-B58-C8; | A9-B58-C9; |
| A10-B58-C1; | A10-B58-C2; | A10-B58-C3; | A10-B58-C4; | A10-B58-C5; | A10-B58-C6; |
| A10-B58-C7; | A10-B58-C8; | A10-B58-C9; | A11-B58-C1; | A11-B58-C2; | A11-B58-C3; |
| A11-B58-C4; | A11-B58-C5; | A11-B58-C6; | A11-B58-C7; | A11-B58-C8; | A11-B58-C9; |
| A12-B58-C1; | A12-B58-C2; | A12-B58-C3; | A12-B58-C4; | A12-B58-C5; | A12-B58-C6; |
| A12-B58-C7; | A12-B58-C8; | A12-B58-C9; | A13-B58-C1; | A13-B58-C2; | A13-B58-C3; |
| A13-B58-C4; | A13-B58-C5; | A13-B58-C6; | A13-B58-C7; | A13-B58-C8; | A13-B58-C9; |
| A14-B58-C1; | A14-B58-C2; | A14-B58-C3; | A14-B58-C4; | A14-B58-C5; | A14-B58-C6; |
| A14-B58-C7; | A14-B58-C8; | A14-B58-C9; | A15-B58-C1; | A15-B58-C2; | A15-B58-C3; |
| A15-B58-C4; | A15-B58-C5; | A15-B58-C6; | A15-B58-C7; | A15-B58-C8; | A15-B58-C9; |
| A16-B58-C1; | A16-B58-C2; | A16-B58-C3; | A16-B58-C4; | A16-B58-C5; | A16-B58-C6; |
| A16-B58-C7; | A16-B58-C8; | A16-B58-C9; | A17-B58-C1; | A17-B58-C2; | A17-B58-C3; |
| A17-B58-C4; | A17-B58-C5; | A17-B58-C6; | A17-B58-C7; | A17-B58-C8; | A17-B58-C9; |
| A18-B58-C1; | A18-B58-C2; | A18-B58-C3; | A18-B58-C4; | A18-B58-C5; | A18-B58-C6; |
| A18-B58-C7; | A18-B58-C8; | A18-B58-C9; | A19-B58-C1; | A19-B58-C2; | A19-B58-C3; |
| A19-B58-C4; | A19-B58-C5; | A19-B58-C6; | A19-B58-C7; | A19-B58-C8; | A19-B58-C9; |
| A20-B58-C1; | A20-B58-C2; | A20-B58-C3; | A20-B58-C4; | A20-B58-C5; | A20-B58-C6; |
| A20-B58-C7; | A20-B58-C8; | A20-B58-C9; | A21-B58-C1; | A21-B58-C2; | A21-B58-C3; |
| A21-B58-C4; | A21-B58-C5; | A21-B58-C6; | A21-B58-C7; | A21-B58-C8; | A21-B58-C9; |
| A22-B58-C1; | A22-B58-C2; | A22-B58-C3; | A22-B58-C4; | A22-B58-C5; | A22-B58-C6; |
| A22-B58-C7; | A22-B58-C8; | A22-B58-C9; | A23-B58-C1; | A23-B58-C2; | A23-B58-C3; |
| A23-B58-C4; | A23-B58-C5; | A23-B58-C6; | A23-B58-C7; | A23-B58-C8; | A23-B58-C9; |
| A24-B58-C1; | A24-B58-C2; | A24-B58-C3; | A24-B58-C4; | A24-B58-C5; | A24-B58-C6; |
| A24-B58-C7; | A24-B58-C8; | A24-B58-C9; | A25-B58-C1; | A25-B58-C2; | A25-B58-C3; |
| A25-B58-C4; | A25-B58-C5; | A25-B58-C6; | A25-B58-C7; | A25-B58-C8; | A25-B58-C9; |
| A26-B58-C1; | A26-B58-C2; | A26-B58-C3; | A26-B58-C4; | A26-B58-C5; | A26-B58-C6; |
| A26-B58-C7; | A26-B58-C8; | A26-B58-C9; | A27-B58-C1; | A27-B58-C2; | A27-B58-C3; |

| | | | | | |
|---|---|---|---|---|---|
| A27-B58-C4; | A27-B58-C5; | A27-B58-C6; | A27-B58-C7; | A27-B58-C8; | A27-B58-C9; |
| A28-B58-C1; | A28-B58-C2; | A28-B58-C3; | A28-B58-C4; | A28-B58-C5; | A28-B58-C6; |
| A28-B58-C7; | A28-B58-C8; | A28-B58-C9; | A29-B58-C1; | A29-B58-C2; | A29-B58-C3; |
| A29-B58-C4; | A29-B58-C5; | A29-B58-C6; | A29-B58-C7; | A29-B58-C8; | A29-B58-C9; |
| A30-B58-C1; | A30-B58-C2; | A30-B58-C3; | A30-B58-C4; | A30-B58-C5; | A30-B58-C6; |
| A30-B58-C7; | A30-B58-C8; | A30-B58-C9; | A31-B58-C1; | A31-B58-C2; | A31-B58-C3; |
| A31-B58-C4; | A31-B58-C5; | A31-B58-C6; | A31-B58-C7; | A31-B58-C8; | A31-B58-C9; |
| A32-B58-C1; | A32-B58-C2; | A32-B58-C3; | A32-B58-C4; | A32-B58-C5; | A32-B58-C6; |
| A32-B58-C7; | A32-B58-C8; | A32-B58-C9; | A33-B58-C1; | A33-B58-C2; | A33-B58-C3; |
| A33-B58-C4; | A33-B58-C5; | A33-B58-C6; | A33-B58-C7; | A33-B58-C8; | A33-B58-C9; |
| A34-B58-C1; | A34-B58-C2; | A34-B58-C3; | A34-B58-C4; | A34-B58-C5; | A34-B58-C6; |
| A34-B58-C7; | A34-B58-C8; | A34-B58-C9; | A35-B58-C1; | A35-B58-C2; | A35-B58-C3; |
| A35-B58-C4; | A35-B58-C5; | A35-B58-C6; | A35-B58-C7; | A35-B58-C8; | A35-B58-C9; |
| A36-B58-C1; | A36-B58-C2; | A36-B58-C3; | A36-B58-C4; | A36-B58-C5; | A36-B58-C6; |
| A36-B58-C7; | A36-B58-C8; | A36-B58-C9; | A37-B58-C1; | A37-B58-C2; | A37-B58-C3; |
| A37-B58-C4; | A37-B58-C5; | A37-B58-C6; | A37-B58-C7; | A37-B58-C8; | A37-B58-C9; |
| A38-B58-C1; | A38-B58-C2; | A38-B58-C3; | A38-B58-C4; | A38-B58-C5; | A38-B58-C6; |
| A38-B58-C7; | A38-B58-C8; | A38-B58-C9; | A39-B58-C1; | A39-B58-C2; | A39-B58-C3; |
| A39-B58-C4; | A39-B58-C5; | A39-B58-C6; | A39-B58-C7; | A39-B58-C8; | A39-B58-C9; |
| A40-B58-C1; | A40-B58-C2; | A40-B58-C3; | A40-B58-C4; | A40-B58-C5; | A40-B58-C6; |
| A40-B58-C7; | A40-B58-C8; | A40-B58-C9; | A41-B58-C1; | A41-B58-C2; | A41-B58-C3; |
| A41-B58-C4; | A41-B58-C5; | A41-B58-C6; | A41-B58-C7; | A41-B58-C8; | A41-B58-C9; |
| A42-B58-C1; | A42-B58-C2; | A42-B58-C3; | A42-B58-C4; | A42-B58-C5; | A42-B58-C6; |
| A42-B58-C7; | A42-B58-C8; | A42-B58-C9; | A43-B58-C1; | A43-B58-C2; | A43-B58-C3; |
| A43-B58-C4; | A43-B58-C5; | A43-B58-C6; | A43-B58-C7; | A43-B58-C8; | A43-B58-C9; |
| A44-B58-C1; | A44-B58-C2; | A44-B58-C3; | A44-B58-C4; | A44-B58-C5; | A44-B58-C6; |
| A44-B58-C7; | A44-B58-C8; | A44-B58-C9; | A45-B58-C1; | A45-B58-C2; | A45-B58-C3; |
| A45-B58-C4; | A45-B58-C5; | A45-B58-C6; | A45-B58-C7; | A45-B58-C8; | A45-B58-C9; |
| A46-B58-C1; | A46-B58-C2; | A46-B58-C3; | A46-B58-C4; | A46-B58-C5; | A46-B58-C6; |
| A46-B58-C7; | A46-B58-C8; | A46-B58-C9; | A47-B58-C1; | A47-B58-C2; | A47-B58-C3; |
| A47-B58-C4; | A47-B58-C5; | A47-B58-C6; | A47-B58-C7; | A47-B58-C8; | A47-B58-C9; |
| A48-B58-C1; | A48-B58-C2; | A48-B58-C3; | A48-B58-C4; | A48-B58-C5; | A48-B58-C6; |
| A48-B58-C7; | A48-B58-C8; | A48-B58-C9; | A49-B58-C1; | A49-B58-C2; | A49-B58-C3; |
| A49-B58-C4; | A49-B58-C5; | A49-B58-C6; | A49-B58-C7; | A49-B58-C8; | A49-B58-C9; |
| A50-B58-C1; | A50-B58-C2; | A50-B58-C3; | A50-B58-C4; | A50-B58-C5; | A50-B58-C6; |
| A50-B58-C7; | A50-B58-C8; | A50-B58-C9; | A51-B58-C1; | A51-B58-C2; | A51-B58-C3; |
| A51-B58-C4; | A51-B58-C5; | A51-B58-C6; | A51-B58-C7; | A51-B58-C8; | A51-B58-C9; |
| A52-B58-C1; | A52-B58-C2; | A52-B58-C3; | A52-B58-C4; | A52-B58-C5; | A52-B58-C6; |
| A52-B58-C7; | A52-B58-C8; | A52-B58-C9; | A53-B58-C1; | A53-B58-C2; | A53-B58-C3; |
| A53-B58-C4; | A53-B58-C5; | A53-B58-C6; | A53-B58-C7; | A53-B58-C8; | A53-B58-C9; |
| A54-B58-C1; | A54-B58-C2; | A54-B58-C3; | A54-B58-C4; | A54-B58-C5; | A54-B58-C6; |
| A54-B58-C7; | A54-B58-C8; | A54-B58-C9; | A55-B58-C1; | A55-B58-C2; | A55-B58-C3; |
| A55-B58-C4; | A55-B58-C5; | A55-B58-C6; | A55-B58-C7; | A55-B58-C8; | A55-B58-C9; |
| A56-B58-C1; | A56-B58-C2; | A56-B58-C3; | A56-B58-C4; | A56-B58-C5; | A56-B58-C6; |
| A56-B58-C7; | A56-B58-C8; | A56-B58-C9; | A57-B58-C1; | A57-B58-C2; | A57-B58-C3; |
| A57-B58-C4; | A57-B58-C5; | A57-B58-C6; | A57-B58-C7; | A57-B58-C8; | A57-B58-C9; |
| A58-B58-C1; | A58-B58-C2; | A58-B58-C3; | A58-B58-C4; | A58-B58-C5; | A58-B58-C6; |
| A58-B58-C7; | A58-B58-C8; | A58-B58-C9; | A59-B58-C1; | A59-B58-C2; | A59-B58-C3; |
| A59-B58-C4; | A59-B58-C5; | A59-B58-C6; | A59-B58-C7; | A59-B58-C8; | A59-B58-C9; |
| A60-B58-C1; | A60-B58-C2; | A60-B58-C3; | A60-B58-C4; | A60-B58-C5; | A60-B58-C6; |
| A60-B58-C7; | A60-B58-C8; | A60-B58-C9; | A61-B58-C1; | A61-B58-C2; | A61-B58-C3; |
| A61-B58-C4; | A61-B58-C5; | A61-B58-C6; | A61-B58-C7; | A61-B58-C8; | A61-B58-C9; |
| A62-B58-C1; | A62-B58-C2; | A62-B58-C3; | A62-B58-C4; | A62-B58-C5; | A62-B58-C6; |
| A62-B58-C7; | A62-B58-C8; | A62-B58-C9; | A63-B58-C1; | A63-B58-C2; | A63-B58-C3; |
| A63-B58-C4; | A63-B58-C5; | A63-B58-C6; | A63-B58-C7; | A63-B58-C8; | A63-B58-C9; |
| A64-B58-C1; | A64-B58-C2; | A64-B58-C3; | A64-B58-C4; | A64-B58-C5; | A64-B58-C6; |
| A64-B58-C7; | A64-B58-C8; | A64-B58-C9; | A65-B58-C1; | A65-B58-C2; | A65-B58-C3; |
| A65-B58-C4; | A65-B58-C5; | A65-B58-C6; | A65-B58-C7; | A65-B58-C8; | A65-B58-C9; |
| A66-B58-C1; | A66-B58-C2; | A66-B58-C3; | A66-B58-C4; | A66-B58-C5; | A66-B58-C6; |
| A66-B58-C7; | A66-B58-C8; | A66-B58-C9; | A67-B58-C1; | A67-B58-C2; | A67-B58-C3; |
| A67-B58-C4; | A67-B58-C5; | A67-B58-C6; | A67-B58-C7; | A67-B58-C8; | A67-B58-C9; |
| A68-B58-C1; | A68-B58-C2; | A68-B58-C3; | A68-B58-C4; | A68-B58-C5; | A68-B58-C6; |
| A68-B58-C7; | A68-B58-C8; | A68-B58-C9; | A69-B58-C1; | A69-B58-C2; | A69-B58-C3; |
| A69-B58-C4; | A69-B58-C5; | A69-B58-C6; | A69-B58-C7; | A69-B58-C8; | A69-B58-C9; |
| A70-B58-C1; | A70-B58-C2; | A70-B58-C3; | A70-B58-C4; | A70-B58-C5; | A70-B58-C6; |
| A70-B58-C7; | A70-B58-C8; | A70-B58-C9; | A71-B58-C1; | A71-B58-C2; | A71-B58-C3; |
| A71-B58-C4; | A71-B58-C5; | A71-B58-C6; | A71-B58-C7; | A71-B58-C8; | A71-B58-C9; |
| A1-B59-C1; | A1-B59-C2; | A1-B59-C3; | A1-B59-C4; | A1-B59-C5; | A1-B59-C6; |
| A1-B59-C7; | A1-B59-C8; | A1-B59-C9; | A2-B59-C1; | A2-B59-C2; | A2-B59-C3; |
| A2-B59-C4; | A2-B59-C5; | A2-B59-C6; | A2-B59-C7; | A2-B59-C8; | A2-B59-C9; |
| A3-B59-C1; | A3-B59-C2; | A3-B59-C3; | A3-B59-C4; | A3-B59-C5; | A3-B59-C6; |
| A3-B59-C7; | A3-B59-C8; | A3-B59-C9; | A4-B59-C1; | A4-B59-C2; | A4-B59-C3; |
| A4-B59-C4; | A4-B59-C5; | A4-B59-C6; | A4-B59-C7; | A4-B59-C8; | A4-B59-C9; |
| A5-B59-C1; | A5-B59-C2; | A5-B59-C3; | A5-B59-C4; | A5-B59-C5; | A5-B59-C6; |
| A5-B59-C7; | A5-B59-C8; | A5-B59-C9; | A6-B59-C1; | A6-B59-C2; | A6-B59-C3; |
| A6-B59-C4; | A6-B59-C5; | A6-B59-C6; | A6-B59-C7; | A6-B59-C8; | A6-B59-C9; |
| A7-B59-C1; | A7-B59-C2; | A7-B59-C3; | A7-B59-C4; | A7-B59-C5; | A7-B59-C6; |
| A7-B59-C7; | A7-B59-C8; | A7-B59-C9; | A8-B59-C1; | A8-B59-C2; | A8-B59-C3; |
| A8-B59-C4; | A8-B59-C5; | A8-B59-C6; | A8-B59-C7; | A8-B59-C8; | A8-B59-C9; |

-continued

| | | | | | |
|---|---|---|---|---|---|
| A9-B59-C1; | A9-B59-C2; | A9-B59-C3; | A9-B59-C4; | A9-B59-C5; | A9-B59-C6; |
| A9-B59-C7; | A9-B59-C8; | A9-B59-C9; | A10-B59-C1; | A10-B59-C2; | A10-B59-C3; |
| A10-B59-C4; | A10-B59-C5; | A10-B59-C6; | A10-B59-C7; | A10-B59-C8; | A10-B59-C9; |
| A11-B59-C1; | A11-B59-C2; | A11-B59-C3; | A11-B59-C4; | A11-B59-C5; | A11-B59-C6; |
| A11-B59-C7; | A11-B59-C8; | A11-B59-C9; | A12-B59-C1; | A12-B59-C2; | A12-B59-C3; |
| A12-B59-C4; | A12-B59-C5; | A12-B59-C6; | A12-B59-C7; | A12-B59-C8; | A12-B59-C9; |
| A13-B59-C1; | A13-B59-C2; | A13-B59-C3; | A13-B59-C4; | A13-B59-C5; | A13-B59-C6; |
| A13-B59-C7; | A13-B59-C8; | A13-B59-C9; | A14-B59-C1; | A14-B59-C2; | A14-B59-C3; |
| A14-B59-C4; | A14-B59-C5; | A14-B59-C6; | A14-B59-C7; | A14-B59-C8; | A14-B59-C9; |
| A15-B59-C1; | A15-B59-C2; | A15-B59-C3; | A15-B59-C4; | A15-B59-C5; | A15-B59-C6; |
| A15-B59-C7; | A15-B59-C8; | A15-B59-C9; | A16-B59-C1; | A16-B59-C2; | A16-B59-C3; |
| A16-B59-C4; | A16-B59-C5; | A16-B59-C6; | A16-B59-C7; | A16-B59-C8; | A16-B59-C9; |
| A17-B59-C1; | A17-B59-C2; | A17-B59-C3; | A17-B59-C4; | A17-B59-C5; | A17-B59-C6; |
| A17-B59-C7; | A17-B59-C8; | A17-B59-C9; | A18-B59-C1; | A18-B59-C2; | A18-B59-C3; |
| A18-B59-C4; | A18-B59-C5; | A18-B59-C6; | A18-B59-C7; | A18-B59-C8; | A18-B59-C9; |
| A19-B59-C1; | A19-B59-C2; | A19-B59-C3; | A19-B59-C4; | A19-B59-C5; | A19-B59-C6; |
| A19-B59-C7; | A19-B59-C8; | A19-B59-C9; | A20-B59-C1; | A20-B59-C2; | A20-B59-C3; |
| A20-B59-C4; | A20-B59-C5; | A20-B59-C6; | A20-B59-C7; | A20-B59-C8; | A20-B59-C9; |
| A21-B59-C1; | A21-B59-C2; | A21-B59-C3; | A21-B59-C4; | A21-B59-C5; | A21-B59-C6; |
| A21-B59-C7; | A21-B59-C8; | A21-B59-C9; | A22-B59-C1; | A22-B59-C2; | A22-B59-C3; |
| A22-B59-C4; | A22-B59-C5; | A22-B59-C6; | A22-B59-C7; | A22-B59-C8; | A22-B59-C9; |
| A23-B59-C1; | A23-B59-C2; | A23-B59-C3; | A23-B59-C4; | A23-B59-C5; | A23-B59-C6; |
| A23-B59-C7; | A23-B59-C8; | A23-B59-C9; | A24-B59-C1; | A24-B59-C2; | A24-B59-C3; |
| A24-B59-C4; | A24-B59-C5; | A24-B59-C6; | A24-B59-C7; | A24-B59-C8; | A24-B59-C9; |
| A25-B59-C1; | A25-B59-C2; | A25-B59-C3; | A25-B59-C4; | A25-B59-C5; | A25-B59-C6; |
| A25-B59-C7; | A25-B59-C8; | A25-B59-C9; | A26-B59-C1; | A26-B59-C2; | A26-B59-C3; |
| A26-B59-C4; | A26-B59-C5; | A26-B59-C6; | A26-B59-C7; | A26-B59-C8; | A26-B59-C9; |
| A27-B59-C1; | A27-B59-C2; | A27-B59-C3; | A27-B59-C4; | A27-B59-C5; | A27-B59-C6; |
| A27-B59-C7; | A27-B59-C8; | A27-B59-C9; | A28-B59-C1; | A28-B59-C2; | A28-B59-C3; |
| A28-B59-C4; | A28-B59-C5; | A28-B59-C6; | A28-B59-C7; | A28-B59-C8; | A28-B59-C9; |
| A29-B59-C1; | A29-B59-C2; | A29-B59-C3; | A29-B59-C4; | A29-B59-C5; | A29-B59-C6; |
| A29-B59-C7; | A29-B59-C8; | A29-B59-C9; | A30-B59-C1; | A30-B59-C2; | A30-B59-C3; |
| A30-B59-C4; | A30-B59-C5; | A30-B59-C6; | A30-B59-C7; | A30-B59-C8; | A30-B59-C9; |
| A31-B59-C1; | A31-B59-C2; | A31-B59-C3; | A31-B59-C4; | A31-B59-C5; | A31-B59-C6; |
| A31-B59-C7; | A31-B59-C8; | A31-B59-C9; | A32-B59-C1; | A32-B59-C2; | A32-B59-C3; |
| A32-B59-C4; | A32-B59-C5; | A32-B59-C6; | A32-B59-C7; | A32-B59-C8; | A32-B59-C9; |
| A33-B59-C1; | A33-B59-C2; | A33-B59-C3; | A33-B59-C4; | A33-B59-C5; | A33-B59-C6; |
| A33-B59-C7; | A33-B59-C8; | A33-B59-C9; | A34-B59-C1; | A34-B59-C2; | A34-B59-C3; |
| A34-B59-C4; | A34-B59-C5; | A34-B59-C6; | A34-B59-C7; | A34-B59-C8; | A34-B59-C9; |
| A35-B59-C1; | A35-B59-C2; | A35-B59-C3; | A35-B59-C4; | A35-B59-C5; | A35-B59-C6; |
| A35-B59-C7; | A35-B59-C8; | A35-B59-C9; | A36-B59-C1; | A36-B59-C2; | A36-B59-C3; |
| A36-B59-C4; | A36-B59-C5; | A36-B59-C6; | A36-B59-C7; | A36-B59-C8; | A36-B59-C9; |
| A37-B59-C1; | A37-B59-C2; | A37-B59-C3; | A37-B59-C4; | A37-B59-C5; | A37-B59-C6; |
| A37-B59-C7; | A37-B59-C8; | A37-B59-C9; | A38-B59-C1; | A38-B59-C2; | A38-B59-C3; |
| A38-B59-C4; | A38-B59-C5; | A38-B59-C6; | A38-B59-C7; | A38-B59-C8; | A38-B59-C9; |
| A39-B59-C1; | A39-B59-C2; | A39-B59-C3; | A39-B59-C4; | A39-B59-C5; | A39-B59-C6; |
| A39-B59-C7; | A39-B59-C8; | A39-B59-C9; | A40-B59-C1; | A40-B59-C2; | A40-B59-C3; |
| A40-B59-C4; | A40-B59-C5; | A40-B59-C6; | A40-B59-C7; | A40-B59-C8; | A40-B59-C9; |
| A41-B59-C1; | A41-B59-C2; | A41-B59-C3; | A41-B59-C4; | A41-B59-C5; | A41-B59-C6; |
| A41-B59-C7; | A41-B59-C8; | A41-B59-C9; | A42-B59-C1; | A42-B59-C2; | A42-B59-C3; |
| A42-B59-C4; | A42-B59-C5; | A42-B59-C6; | A42-B59-C7; | A42-B59-C8; | A42-B59-C9; |
| A43-B59-C1; | A43-B59-C2; | A43-B59-C3; | A43-B59-C4; | A43-B59-C5; | A43-B59-C6; |
| A43-B59-C7; | A43-B59-C8; | A43-B59-C9; | A44-B59-C1; | A44-B59-C2; | A44-B59-C3; |
| A44-B59-C4; | A44-B59-C5; | A44-B59-C6; | A44-B59-C7; | A44-B59-C8; | A44-B59-C9; |
| A45-B59-C1; | A45-B59-C2; | A45-B59-C3; | A45-B59-C4; | A45-B59-C5; | A45-B59-C6; |
| A45-B59-C7; | A45-B59-C8; | A45-B59-C9; | A46-B59-C1; | A46-B59-C2; | A46-B59-C3; |
| A46-B59-C4; | A46-B59-C5; | A46-B59-C6; | A46-B59-C7; | A46-B59-C8; | A46-B59-C9; |
| A47-B59-C1; | A47-B59-C2; | A47-B59-C3; | A47-B59-C4; | A47-B59-C5; | A47-B59-C6; |
| A47-B59-C7; | A47-B59-C8; | A47-B59-C9; | A48-B59-C1; | A48-B59-C2; | A48-B59-C3; |
| A48-B59-C4; | A48-B59-C5; | A48-B59-C6; | A48-B59-C7; | A48-B59-C8; | A48-B59-C9; |
| A49-B59-C1; | A49-B59-C2; | A49-B59-C3; | A49-B59-C4; | A49-B59-C5; | A49-B59-C6; |
| A49-B59-C7; | A49-B59-C8; | A49-B59-C9; | A50-B59-C1; | A50-B59-C2; | A50-B59-C3; |
| A50-B59-C4; | A50-B59-C5; | A50-B59-C6; | A50-B59-C7; | A50-B59-C8; | A50-B59-C9; |
| A51-B59-C1; | A51-B59-C2; | A51-B59-C3; | A51-B59-C4; | A51-B59-C5; | A51-B59-C6; |
| A51-B59-C7; | A51-B59-C8; | A51-B59-C9; | A52-B59-C1; | A52-B59-C2; | A52-B59-C3; |
| A52-B59-C4; | A52-B59-C5; | A52-B59-C6; | A52-B59-C7; | A52-B59-C8; | A52-B59-C9; |
| A53-B59-C1; | A53-B59-C2; | A53-B59-C3; | A53-B59-C4; | A53-B59-C5; | A53-B59-C6; |
| A53-B59-C7; | A53-B59-C8; | A53-B59-C9; | A54-B59-C1; | A54-B59-C2; | A54-B59-C3; |
| A54-B59-C4; | A54-B59-C5; | A54-B59-C6; | A54-B59-C7; | A54-B59-C8; | A54-B59-C9; |
| A55-B59-C1; | A55-B59-C2; | A55-B59-C3; | A55-B59-C4; | A55-B59-C5; | A55-B59-C6; |
| A55-B59-C7; | A55-B59-C8; | A55-B59-C9; | A56-B59-C1; | A56-B59-C2; | A56-B59-C3; |
| A56-B59-C4; | A56-B59-C5; | A56-B59-C6; | A56-B59-C7; | A56-B59-C8; | A56-B59-C9; |
| A57-B59-C1; | A57-B59-C2; | A57-B59-C3; | A57-B59-C4; | A57-B59-C5; | A57-B59-C6; |
| A57-B59-C7; | A57-B59-C8; | A57-B59-C9; | A58-B59-C1; | A58-B59-C2; | A58-B59-C3; |
| A58-B59-C4; | A58-B59-C5; | A58-B59-C6; | A58-B59-C7; | A58-B59-C8; | A58-B59-C9; |
| A59-B59-C1; | A59-B59-C2; | A59-B59-C3; | A59-B59-C4; | A59-B59-C5; | A59-B59-C6; |
| A59-B59-C7; | A59-B59-C8; | A59-B59-C9; | A60-B59-C1; | A60-B59-C2; | A60-B59-C3; |
| A60-B59-C4; | A60-B59-C5; | A60-B59-C6; | A60-B59-C7; | A60-B59-C8; | A60-B59-C9; |
| A61-B59-C1; | A61-B59-C2; | A61-B59-C3; | A61-B59-C4; | A61-B59-C5; | A61-B59-C6; |

-continued

| | | | | | |
|---|---|---|---|---|---|
| A61-B59-C7; | A61-B59-C8; | A61-B59-C9; | A62-B59-C1; | A62-B59-C2; | A62-B59-C3; |
| A62-B59-C4; | A62-B59-C5; | A62-B59-C6; | A62-B59-C7; | A62-B59-C8; | A62-B59-C9; |
| A63-B59-C1; | A63-B59-C2; | A63-B59-C3; | A63-B59-C4; | A63-B59-C5; | A63-B59-C6; |
| A63-B59-C7; | A63-B59-C8; | A63-B59-C9; | A64-B59-C1; | A64-B59-C2; | A64-B59-C3; |
| A64-B59-C4; | A64-B59-C5; | A64-B59-C6; | A64-B59-C7; | A64-B59-C8; | A64-B59-C9; |
| A65-B59-C1; | A65-B59-C2; | A65-B59-C3; | A65-B59-C4; | A65-B59-C5; | A65-B59-C6; |
| A65-B59-C7; | A65-B59-C8; | A65-B59-C9; | A66-B59-C1; | A66-B59-C2; | A66-B59-C3; |
| A66-B59-C4; | A66-B59-C5; | A66-B59-C6; | A66-B59-C7; | A66-B59-C8; | A66-B59-C9; |
| A67-B59-C1; | A67-B59-C2; | A67-B59-C3; | A67-B59-C4; | A67-B59-C5; | A67-B59-C6; |
| A67-B59-C7; | A67-B59-C8; | A67-B59-C9; | A68-B59-C1; | A68-B59-C2; | A68-B59-C3; |
| A68-B59-C4; | A68-B59-C5; | A68-B59-C6; | A68-B59-C7; | A68-B59-C8; | A68-B59-C9; |
| A69-B59-C1; | A69-B59-C2; | A69-B59-C3; | A69-B59-C4; | A69-B59-C5; | A69-B59-C6; |
| A69-B59-C7; | A69-B59-C8; | A69-B59-C9; | A70-B59-C1; | A70-B59-C2; | A70-B59-C3; |
| A70-B59-C4; | A70-B59-C5; | A70-B59-C6; | A70-B59-C7; | A70-B59-C8; | A70-B59-C9; |
| A71-B59-C1; | A71-B59-C2; | A71-B59-C3; | A71-B59-C4; | A71-B59-C5; | A71-B59-C6; |
| A71-B59-C7; | A71-B59-C8; | A71-B59-C9; | A1-B60-C1; | A1-B60-C2; | A1-B60-C3; |
| A1-B60-C4; | A1-B60-C5; | A1-B60-C6; | A1-B60-C7; | A1-B60-C8; | A1-B60-C9; |
| A2-B60-C1; | A2-B60-C2; | A2-B60-C3; | A2-B60-C4; | A2-B60-C5; | A2-B60-C6; |
| A2-B60-C7; | A2-B60-C8; | A2-B60-C9; | A3-B60-C1; | A3-B60-C2; | A3-B60-C3; |
| A3-B60-C4; | A3-B60-C5; | A3-B60-C6; | A3-B60-C7; | A3-B60-C8; | A3-B60-C9; |
| A4-B60-C1; | A4-B60-C2; | A4-B60-C3; | A4-B60-C4; | A4-B60-C5; | A4-B60-C6; |
| A4-B60-C7; | A4-B60-C8; | A4-B60-C9; | A5-B60-C1; | A5-B60-C2; | A5-B60-C3; |
| A5-B60-C4; | A5-B60-C5; | A5-B60-C6; | A5-B60-C7; | A5-B60-C8; | A5-B60-C9; |
| A6-B60-C1; | A6-B60-C2; | A6-B60-C3; | A6-B60-C4; | A6-B60-C5; | A6-B60-C6; |
| A6-B60-C7; | A6-B60-C8; | A6-B60-C9; | A7-B60-C1; | A7-B60-C2; | A7-B60-C3; |
| A7-B60-C4; | A7-B60-C5; | A7-B60-C6; | A7-B60-C7; | A7-B60-C8; | A7-B60-C9; |
| A8-B60-C1; | A8-B60-C2; | A8-B60-C3; | A8-B60-C4; | A8-B60-C5; | A8-B60-C6; |
| A8-B60-C7; | A8-B60-C8; | A8-B60-C9; | A9-B60-C1; | A9-B60-C2; | A9-B60-C3; |
| A9-B60-C4; | A9-B60-C5; | A9-B60-C6; | A9-B60-C7; | A9-B60-C8; | A9-B60-C9; |
| A10-B60-C1; | A10-B60-C2; | A10-B60-C3; | A10-B60-C4; | A10-B60-C5; | A10-B60-C6; |
| A10-B60-C7; | A10-B60-C8; | A10-B60-C9; | A11-B60-C1; | A11-B60-C2; | A11-B60-C3; |
| A11-B60-C4; | A11-B60-C5; | A11-B60-C6; | A11-B60-C7; | A11-B60-C8; | A11-B60-C9; |
| A12-B60-C1; | A12-B60-C2; | A12-B60-C3; | A12-B60-C4; | A12-B60-C5; | A12-B60-C6; |
| A12-B60-C7; | A12-B60-C8; | A12-B60-C9; | A13-B60-C1; | A13-B60-C2; | A13-B60-C3; |
| A13-B60-C4; | A13-B60-C5; | A13-B60-C6; | A13-B60-C7; | A13-B60-C8; | A13-B60-C9; |
| A14-B60-C1; | A14-B60-C2; | A14-B60-C3; | A14-B60-C4; | A14-B60-C5; | A14-B60-C6; |
| A14-B60-C7; | A14-B60-C8; | A14-B60-C9; | A15-B60-C1; | A15-B60-C2; | A15-B60-C3; |
| A15-B60-C4; | A15-B60-C5; | A15-B60-C6; | A15-B60-C7; | A15-B60-C8; | A15-B60-C9; |
| A16-B60-C1; | A16-B60-C2; | A16-B60-C3; | A16-B60-C4; | A16-B60-C5; | A16-B60-C6; |
| A16-B60-C7; | A16-B60-C8; | A16-B60-C9; | A17-B60-C1; | A17-B60-C2; | A17-B60-C3; |
| A17-B60-C4; | A17-B60-C5; | A17-B60-C6; | A17-B60-C7; | A17-B60-C8; | A17-B60-C9; |
| A18-B60-C1; | A18-B60-C2; | A18-B60-C3; | A18-B60-C4; | A18-B60-C5; | A18-B60-C6; |
| A18-B60-C7; | A18-B60-C8; | A18-B60-C9; | A19-B60-C1; | A19-B60-C2; | A19-B60-C3; |
| A19-B60-C4; | A19-B60-C5; | A19-B60-C6; | A19-B60-C7; | A19-B60-C8; | A19-B60-C9; |
| A20-B60-C1; | A20-B60-C2; | A20-B60-C3; | A20-B60-C4; | A20-B60-C5; | A20-B60-C6; |
| A20-B60-C7; | A20-B60-C8; | A20-B60-C9; | A21-B60-C1; | A21-B60-C2; | A21-B60-C3; |
| A21-B60-C4; | A21-B60-C5; | A21-B60-C6; | A21-B60-C7; | A21-B60-C8; | A21-B60-C9; |
| A22-B60-C1; | A22-B60-C2; | A22-B60-C3; | A22-B60-C4; | A22-B60-C5; | A22-B60-C6; |
| A22-B60-C7; | A22-B60-C8; | A22-B60-C9; | A23-B60-C1; | A23-B60-C2; | A23-B60-C3; |
| A23-B60-C4; | A23-B60-C5; | A23-B60-C6; | A23-B60-C7; | A23-B60-C8; | A23-B60-C9; |
| A24-B60-C1; | A24-B60-C2; | A24-B60-C3; | A24-B60-C4; | A24-B60-C5; | A24-B60-C6; |
| A24-B60-C7; | A24-B60-C8; | A24-B60-C9; | A25-B60-C1; | A25-B60-C2; | A25-B60-C3; |
| A25-B60-C4; | A25-B60-C5; | A25-B60-C6; | A25-B60-C7; | A25-B60-C8; | A25-B60-C9; |
| A26-B60-C1; | A26-B60-C2; | A26-B60-C3; | A26-B60-C4; | A26-B60-C5; | A26-B60-C6; |
| A26-B60-C7; | A26-B60-C8; | A26-B60-C9; | A27-B60-C1; | A27-B60-C2; | A27-B60-C3; |
| A27-B60-C4; | A27-B60-C5; | A27-B60-C6; | A27-B60-C7; | A27-B60-C8; | A27-B60-C9; |
| A28-B60-C1; | A28-B60-C2; | A28-B60-C3; | A28-B60-C4; | A28-B60-C5; | A28-B60-C6; |
| A28-B60-C7; | A28-B60-C8; | A28-B60-C9; | A29-B60-C1; | A29-B60-C2; | A29-B60-C3; |
| A29-B60-C4; | A29-B60-C5; | A29-B60-C6; | A29-B60-C7; | A29-B60-C8; | A29-B60-C9; |
| A30-B60-C1; | A30-B60-C2; | A30-B60-C3; | A30-B60-C4; | A30-B60-C5; | A30-B60-C6; |
| A30-B60-C7; | A30-B60-C8; | A30-B60-C9; | A31-B60-C1; | A31-B60-C2; | A31-B60-C3; |
| A31-B60-C4; | A31-B60-C5; | A31-B60-C6; | A31-B60-C7; | A31-B60-C8; | A31-B60-C9; |
| A32-B60-C1; | A32-B60-C2; | A32-B60-C3; | A32-B60-C4; | A32-B60-C5; | A32-B60-C6; |
| A32-B60-C7; | A32-B60-C8; | A32-B60-C9; | A33-B60-C1; | A33-B60-C2; | A33-B60-C3; |
| A33-B60-C4; | A33-B60-C5; | A33-B60-C6; | A33-B60-C7; | A33-B60-C8; | A33-B60-C9; |
| A34-B60-C1; | A34-B60-C2; | A34-B60-C3; | A34-B60-C4; | A34-B60-C5; | A34-B60-C6; |
| A34-B60-C7; | A34-B60-C8; | A34-B60-C9; | A35-B60-C1; | A35-B60-C2; | A35-B60-C3; |
| A35-B60-C4; | A35-B60-C5; | A35-B60-C6; | A35-B60-C7; | A35-B60-C8; | A35-B60-C9; |
| A36-B60-C1; | A36-B60-C2; | A36-B60-C3; | A36-B60-C4; | A36-B60-C5; | A36-B60-C6; |
| A36-B60-C7; | A36-B60-C8; | A36-B60-C9; | A37-B60-C1; | A37-B60-C2; | A37-B60-C3; |
| A37-B60-C4; | A37-B60-C5; | A37-B60-C6; | A37-B60-C7; | A37-B60-C8; | A37-B60-C9; |
| A38-B60-C1; | A38-B60-C2; | A38-B60-C3; | A38-B60-C4; | A38-B60-C5; | A38-B60-C6; |
| A38-B60-C7; | A38-B60-C8; | A38-B60-C9; | A39-B60-C1; | A39-B60-C2; | A39-B60-C3; |
| A39-B60-C4; | A39-B60-C5; | A39-B60-C6; | A39-B60-C7; | A39-B60-C8; | A39-B60-C9; |
| A40-B60-C1; | A40-B60-C2; | A40-B60-C3; | A40-B60-C4; | A40-B60-C5; | A40-B60-C6; |
| A40-B60-C7; | A40-B60-C8; | A40-B60-C9; | A41-B60-C1; | A41-B60-C2; | A41-B60-C3; |
| A41-B60-C4; | A41-B60-C5; | A41-B60-C6; | A41-B60-C7; | A41-B60-C8; | A41-B60-C9; |
| A42-B60-C1; | A42-B60-C2; | A42-B60-C3; | A42-B60-C4; | A42-B60-C5; | A42-B60-C6; |
| A42-B60-C7; | A42-B60-C8; | A42-B60-C9; | A43-B60-C1; | A43-B60-C2; | A43-B60-C3; |

-continued

| | | | | | |
|---|---|---|---|---|---|
| A43-B60-C4; | A43-B60-C5; | A43-B60-C6; | A43-B60-C7; | A43-B60-C8; | A43-B60-C9; |
| A44-B60-C1; | A44-B60-C2; | A44-B60-C3; | A44-B60-C4; | A44-B60-C5; | A44-B60-C6; |
| A44-B60-C7; | A44-B60-C8; | A44-B60-C9; | A45-B60-C1; | A45-B60-C2; | A45-B60-C3; |
| A45-B60-C4; | A45-B60-C5; | A45-B60-C6; | A45-B60-C7; | A45-B60-C8; | A45-B60-C9; |
| A46-B60-C1; | A46-B60-C2; | A46-B60-C3; | A46-B60-C4; | A46-B60-C5; | A46-B60-C6; |
| A46-B60-C7; | A46-B60-C8; | A46-B60-C9; | A47-B60-C1; | A47-B60-C2; | A47-B60-C3; |
| A47-B60-C4; | A47-B60-C5; | A47-B60-C6; | A47-B60-C7; | A47-B60-C8; | A47-B60-C9; |
| A48-B60-C1; | A48-B60-C2; | A48-B60-C3; | A48-B60-C4; | A48-B60-C5; | A48-B60-C6; |
| A48-B60-C7; | A48-B60-C8; | A48-B60-C9; | A49-B60-C1; | A49-B60-C2; | A49-B60-C3; |
| A49-B60-C4; | A49-B60-C5; | A49-B60-C6; | A49-B60-C7; | A49-B60-C8; | A49-B60-C9; |
| A50-B60-C1; | A50-B60-C2; | A50-B60-C3; | A50-B60-C4; | A50-B60-C5; | A50-B60-C6; |
| A50-B60-C7; | A50-B60-C8; | A50-B60-C9; | A51-B60-C1; | A51-B60-C2; | A51-B60-C3; |
| A51-B60-C4; | A51-B60-C5; | A51-B60-C6; | A51-B60-C7; | A51-B60-C8; | A51-B60-C9; |
| A52-B60-C1; | A52-B60-C2; | A52-B60-C3; | A52-B60-C4; | A52-B60-C5; | A52-B60-C6; |
| A52-B60-C7; | A52-B60-C8; | A52-B60-C9; | A53-B60-C1; | A53-B60-C2; | A53-B60-C3; |
| A53-B60-C4; | A53-B60-C5; | A53-B60-C6; | A53-B60-C7; | A53-B60-C8; | A53-B60-C9; |
| A54-B60-C1; | A54-B60-C2; | A54-B60-C3; | A54-B60-C4; | A54-B60-C5; | A54-B60-C6; |
| A54-B60-C7; | A54-B60-C8; | A54-B60-C9; | A55-B60-C1; | A55-B60-C2; | A55-B60-C3; |
| A55-B60-C4; | A55-B60-C5; | A55-B60-C6; | A55-B60-C7; | A55-B60-C8; | A55-B60-C9; |
| A56-B60-C1; | A56-B60-C2; | A56-B60-C3; | A56-B60-C4; | A56-B60-C5; | A56-B60-C6; |
| A56-B60-C7; | A56-B60-C8; | A56-B60-C9; | A57-B60-C1; | A57-B60-C2; | A57-B60-C3; |
| A57-B60-C4; | A57-B60-C5; | A57-B60-C6; | A57-B60-C7; | A57-B60-C8; | A57-B60-C9; |
| A58-B60-C1; | A58-B60-C2; | A58-B60-C3; | A58-B60-C4; | A58-B60-C5; | A58-B60-C6; |
| A58-B60-C7; | A58-B60-C8; | A58-B60-C9; | A59-B60-C1; | A59-B60-C2; | A59-B60-C3; |
| A59-B60-C4; | A59-B60-C5; | A59-B60-C6; | A59-B60-C7; | A59-B60-C8; | A59-B60-C9; |
| A60-B60-C1; | A60-B60-C2; | A60-B60-C3; | A60-B60-C4; | A60-B60-C5; | A60-B60-C6; |
| A60-B60-C7; | A60-B60-C8; | A60-B60-C9; | A61-B60-C1; | A61-B60-C2; | A61-B60-C3; |
| A61-B60-C4; | A61-B60-C5; | A61-B60-C6; | A61-B60-C7; | A61-B60-C8; | A61-B60-C9; |
| A62-B60-C1; | A62-B60-C2; | A62-B60-C3; | A62-B60-C4; | A62-B60-C5; | A62-B60-C6; |
| A62-B60-C7; | A62-B60-C8; | A62-B60-C9; | A63-B60-C1; | A63-B60-C2; | A63-B60-C3; |
| A63-B60-C4; | A63-B60-C5; | A63-B60-C6; | A63-B60-C7; | A63-B60-C8; | A63-B60-C9; |
| A64-B60-C1; | A64-B60-C2; | A64-B60-C3; | A64-B60-C4; | A64-B60-C5; | A64-B60-C6; |
| A64-B60-C7; | A64-B60-C8; | A64-B60-C9; | A65-B60-C1; | A65-B60-C2; | A65-B60-C3; |
| A65-B60-C4; | A65-B60-C5; | A65-B60-C6; | A65-B60-C7; | A65-B60-C8; | A65-B60-C9; |
| A66-B60-C1; | A66-B60-C2; | A66-B60-C3; | A66-B60-C4; | A66-B60-C5; | A66-B60-C6; |
| A66-B60-C7; | A66-B60-C8; | A66-B60-C9; | A67-B60-C1; | A67-B60-C2; | A67-B60-C3; |
| A67-B60-C4; | A67-B60-C5; | A67-B60-C6; | A67-B60-C7; | A67-B60-C8; | A67-B60-C9; |
| A68-B60-C1; | A68-B60-C2; | A68-B60-C3; | A68-B60-C4; | A68-B60-C5; | A68-B60-C6; |
| A68-B60-C7; | A68-B60-C8; | A68-B60-C9; | A69-B60-C1; | A69-B60-C2; | A69-B60-C3; |
| A69-B60-C4; | A69-B60-C5; | A69-B60-C6; | A69-B60-C7; | A69-B60-C8; | A69-B60-C9; |
| A70-B60-C1; | A70-B60-C2; | A70-B60-C3; | A70-B60-C4; | A70-B60-C5; | A70-B60-C6; |
| A70-B60-C7; | A70-B60-C8; | A70-B60-C9; | A71-B60-C1; | A71-B60-C2; | A71-B60-C3; |
| A71-B60-C4; | A71-B60-C5; | A71-B60-C6; | A71-B60-C7; | A71-B60-C8; | A71-B60-C9; |
| A1-B61-C1; | A1-B61-C2; | A1-B61-C3; | A1-B61-C4; | A1-B61-C5; | A1-B61-C6; |
| A1-B61-C7; | A1-B61-C8; | A1-B61-C9; | A2-B61-C1; | A2-B61-C2; | A2-B61-C3; |
| A2-B61-C4; | A2-B61-C5; | A2-B61-C6; | A2-B61-C7; | A2-B61-C8; | A2-B61-C9; |
| A3-B61-C1; | A3-B61-C2; | A3-B61-C3; | A3-B61-C4; | A3-B61-C5; | A3-B61-C6; |
| A3-B61-C7; | A3-B61-C8; | A3-B61-C9; | A4-B61-C1; | A4-B61-C2; | A4-B61-C3; |
| A4-B61-C4; | A4-B61-C5; | A4-B61-C6; | A4-B61-C7; | A4-B61-C8; | A4-B61-C9; |
| A5-B61-C1; | A5-B61-C2; | A5-B61-C3; | A5-B61-C4; | A5-B61-C5; | A5-B61-C6; |
| A5-B61-C7; | A5-B61-C8; | A5-B61-C9; | A6-B61-C1; | A6-B61-C2; | A6-B61-C3; |
| A6-B61-C4; | A6-B61-C5; | A6-B61-C6; | A6-B61-C7; | A6-B61-C8; | A6-B61-C9; |
| A7-B61-C1; | A7-B61-C2; | A7-B61-C3; | A7-B61-C4; | A7-B61-C5; | A7-B61-C6; |
| A7-B61-C7; | A7-B61-C8; | A7-B61-C9; | A8-B61-C1; | A8-B61-C2; | A8-B61-C3; |
| A8-B61-C4; | A8-B61-C5; | A8-B61-C6; | A8-B61-C7; | A8-B61-C8; | A8-B61-C9; |
| A9-B61-C1; | A9-B61-C2; | A9-B61-C3; | A9-B61-C4; | A9-B61-C5; | A9-B61-C6; |
| A9-B61-C7; | A9-B61-C8; | A9-B61-C9; | A10-B61-C1; | A10-B61-C2; | A10-B61-C3; |
| A10-B61-C4; | A10-B61-C5; | A10-B61-C6; | A10-B61-C7; | A10-B61-C8; | A10-B61-C9; |
| A11-B61-C1; | A11-B61-C2; | A11-B61-C3; | A11-B61-C4; | A11-B61-C5; | A11-B61-C6; |
| A11-B61-C7; | A11-B61-C8; | A11-B61-C9; | A12-B61-C1; | A12-B61-C2; | A12-B61-C3; |
| A12-B61-C4; | A12-B61-C5; | A12-B61-C6; | A12-B61-C7; | A12-B61-C8; | A12-B61-C9; |
| A13-B61-C1; | A13-B61-C2; | A13-B61-C3; | A13-B61-C4; | A13-B61-C5; | A13-B61-C6; |
| A13-B61-C7; | A13-B61-C8; | A13-B61-C9; | A14-B61-C1; | A14-B61-C2; | A14-B61-C3; |
| A14-B61-C4; | A14-B61-C5; | A14-B61-C6; | A14-B61-C7; | A14-B61-C8; | A14-B61-C9; |
| A15-B61-C1; | A15-B61-C2; | A15-B61-C3; | A15-B61-C4; | A15-B61-C5; | A15-B61-C6; |
| A15-B61-C7; | A15-B61-C8; | A15-B61-C9; | A16-B61-C1; | A16-B61-C2; | A16-B61-C3; |
| A16-B61-C4; | A16-B61-C5; | A16-B61-C6; | A16-B61-C7; | A16-B61-C8; | A16-B61-C9; |
| A17-B61-C1; | A17-B61-C2; | A17-B61-C3; | A17-B61-C4; | A17-B61-C5; | A17-B61-C6; |
| A17-B61-C7; | A17-B61-C8; | A17-B61-C9; | A18-B61-C1; | A18-B61-C2; | A18-B61-C3; |
| A18-B61-C4; | A18-B61-C5; | A18-B61-C6; | A18-B61-C7; | A18-B61-C8; | A18-B61-C9; |
| A19-B61-C1; | A19-B61-C2; | A19-B61-C3; | A19-B61-C4; | A19-B61-C5; | A19-B61-C6; |
| A19-B61-C7; | A19-B61-C8; | A19-B61-C9; | A20-B61-C1; | A20-B61-C2; | A20-B61-C3; |
| A20-B61-C4; | A20-B61-C5; | A20-B61-C6; | A20-B61-C7; | A20-B61-C8; | A20-B61-C9; |
| A21-B61-C1; | A21-B61-C2; | A21-B61-C3; | A21-B61-C4; | A21-B61-C5; | A21-B61-C6; |
| A21-B61-C7; | A21-B61-C8; | A21-B61-C9; | A22-B61-C1; | A22-B61-C2; | A22-B61-C3; |
| A22-B61-C4; | A22-B61-C5; | A22-B61-C6; | A22-B61-C7; | A22-B61-C8; | A22-B61-C9; |
| A23-B61-C1; | A23-B61-C2; | A23-B61-C3; | A23-B61-C4; | A23-B61-C5; | A23-B61-C6; |
| A23-B61-C7; | A23-B61-C8; | A23-B61-C9; | A24-B61-C1; | A24-B61-C2; | A24-B61-C3; |
| A24-B61-C4; | A24-B61-C5; | A24-B61-C6; | A24-B61-C7; | A24-B61-C8; | A24-B61-C9; |

-continued

| | | | | | |
|---|---|---|---|---|---|
| A25-B61-C1; | A25-B61-C2; | A25-B61-C3; | A25-B61-C4; | A25-B61-C5; | A25-B61-C6; |
| A25-B61-C7; | A25-B61-C8; | A25-B61-C9; | A26-B61-C1; | A26-B61-C2; | A26-B61-C3; |
| A26-B61-C4; | A26-B61-C5; | A26-B61-C6; | A26-B61-C7; | A26-B61-C8; | A26-B61-C9; |
| A27-B61-C1; | A27-B61-C2; | A27-B61-C3; | A27-B61-C4; | A27-B61-C5; | A27-B61-C6; |
| A27-B61-C7; | A27-B61-C8; | A27-B61-C9; | A28-B61-C1; | A28-B61-C2; | A28-B61-C3; |
| A28-B61-C4; | A28-B61-C5; | A28-B61-C6; | A28-B61-C7; | A28-B61-C8; | A28-B61-C9; |
| A29-B61-C1; | A29-B61-C2; | A29-B61-C3; | A29-B61-C4; | A29-B61-C5; | A29-B61-C6; |
| A29-B61-C7; | A29-B61-C8; | A29-B61-C9; | A30-B61-C1; | A30-B61-C2; | A30-B61-C3; |
| A30-B61-C4; | A30-B61-C5; | A30-B61-C6; | A30-B61-C7; | A30-B61-C8; | A30-B61-C9; |
| A31-B61-C1; | A31-B61-C2; | A31-B61-C3; | A31-B61-C4; | A31-B61-C5; | A31-B61-C6; |
| A31-B61-C7; | A31-B61-C8; | A31-B61-C9; | A32-B61-C1; | A32-B61-C2; | A32-B61-C3; |
| A32-B61-C4; | A32-B61-C5; | A32-B61-C6; | A32-B61-C7; | A32-B61-C8; | A32-B61-C9; |
| A33-B61-C1; | A33-B61-C2; | A33-B61-C3; | A33-B61-C4; | A33-B61-C5; | A33-B61-C6; |
| A33-B61-C7; | A33-B61-C8; | A33-B61-C9; | A34-B61-C1; | A34-B61-C2; | A34-B61-C3; |
| A34-B61-C4; | A34-B61-C5; | A34-B61-C6; | A34-B61-C7; | A34-B61-C8; | A34-B61-C9; |
| A35-B61-C1; | A35-B61-C2; | A35-B61-C3; | A35-B61-C4; | A35-B61-C5; | A35-B61-C6; |
| A35-B61-C7; | A35-B61-C8; | A35-B61-C9; | A36-B61-C1; | A36-B61-C2; | A36-B61-C3; |
| A36-B61-C4; | A36-B61-C5; | A36-B61-C6; | A36-B61-C7; | A36-B61-C8; | A36-B61-C9; |
| A37-B61-C1; | A37-B61-C2; | A37-B61-C3; | A37-B61-C4; | A37-B61-C5; | A37-B61-C6; |
| A37-B61-C7; | A37-B61-C8; | A37-B61-C9; | A38-B61-C1; | A38-B61-C2; | A38-B61-C3; |
| A38-B61-C4; | A38-B61-C5; | A38-B61-C6; | A38-B61-C7; | A38-B61-C8; | A38-B61-C9; |
| A39-B61-C1; | A39-B61-C2; | A39-B61-C3; | A39-B61-C4; | A39-B61-C5; | A39-B61-C6; |
| A39-B61-C7; | A39-B61-C8; | A39-B61-C9; | A40-B61-C1; | A40-B61-C2; | A40-B61-C3; |
| A40-B61-C4; | A40-B61-C5; | A40-B61-C6; | A40-B61-C7; | A40-B61-C8; | A40-B61-C9; |
| A41-B61-C1; | A41-B61-C2; | A41-B61-C3; | A41-B61-C4; | A41-B61-C5; | A41-B61-C6; |
| A41-B61-C7; | A41-B61-C8; | A41-B61-C9; | A42-B61-C1; | A42-B61-C2; | A42-B61-C3; |
| A42-B61-C4; | A42-B61-C5; | A42-B61-C6; | A42-B61-C7; | A42-B61-C8; | A42-B61-C9; |
| A43-B61-C1; | A43-B61-C2; | A43-B61-C3; | A43-B61-C4; | A43-B61-C5; | A43-B61-C6; |
| A43-B61-C7; | A43-B61-C8; | A43-B61-C9; | A44-B61-C1; | A44-B61-C2; | A44-B61-C3; |
| A44-B61-C4; | A44-B61-C5; | A44-B61-C6; | A44-B61-C7; | A44-B61-C8; | A44-B61-C9; |
| A45-B61-C1; | A45-B61-C2; | A45-B61-C3; | A45-B61-C4; | A45-B61-C5; | A45-B61-C6; |
| A45-B61-C7; | A45-B61-C8; | A45-B61-C9; | A46-B61-C1; | A46-B61-C2; | A46-B61-C3; |
| A46-B61-C4; | A46-B61-C5; | A46-B61-C6; | A46-B61-C7; | A46-B61-C8; | A46-B61-C9; |
| A47-B61-C1; | A47-B61-C2; | A47-B61-C3; | A47-B61-C4; | A47-B61-C5; | A47-B61-C6; |
| A47-B61-C7; | A47-B61-C8; | A47-B61-C9; | A48-B61-C1; | A48-B61-C2; | A48-B61-C3; |
| A48-B61-C4; | A48-B61-C5; | A48-B61-C6; | A48-B61-C7; | A48-B61-C8; | A48-B61-C9; |
| A49-B61-C1; | A49-B61-C2; | A49-B61-C3; | A49-B61-C4; | A49-B61-C5; | A49-B61-C6; |
| A49-B61-C7; | A49-B61-C8; | A49-B61-C9; | A50-B61-C1; | A50-B61-C2; | A50-B61-C3; |
| A50-B61-C4; | A50-B61-C5; | A50-B61-C6; | A50-B61-C7; | A50-B61-C8; | A50-B61-C9; |
| A51-B61-C1; | A51-B61-C2; | A51-B61-C3; | A51-B61-C4; | A51-B61-C5; | A51-B61-C6; |
| A51-B61-C7; | A51-B61-C8; | A51-B61-C9; | A52-B61-C1; | A52-B61-C2; | A52-B61-C3; |
| A52-B61-C4; | A52-B61-C5; | A52-B61-C6; | A52-B61-C7; | A52-B61-C8; | A52-B61-C9; |
| A53-B61-C1; | A53-B61-C2; | A53-B61-C3; | A53-B61-C4; | A53-B61-C5; | A53-B61-C6; |
| A53-B61-C7; | A53-B61-C8; | A53-B61-C9; | A54-B61-C1; | A54-B61-C2; | A54-B61-C3; |
| A54-B61-C4; | A54-B61-C5; | A54-B61-C6; | A54-B61-C7; | A54-B61-C8; | A54-B61-C9; |
| A55-B61-C1; | A55-B61-C2; | A55-B61-C3; | A55-B61-C4; | A55-B61-C5; | A55-B61-C6; |
| A55-B61-C7; | A55-B61-C8; | A55-B61-C9; | A56-B61-C1; | A56-B61-C2; | A56-B61-C3; |
| A56-B61-C4; | A56-B61-C5; | A56-B61-C6; | A56-B61-C7; | A56-B61-C8; | A56-B61-C9; |
| A57-B61-C1; | A57-B61-C2; | A57-B61-C3; | A57-B61-C4; | A57-B61-C5; | A57-B61-C6; |
| A57-B61-C7; | A57-B61-C8; | A57-B61-C9; | A58-B61-C1; | A58-B61-C2; | A58-B61-C3; |
| A58-B61-C4; | A58-B61-C5; | A58-B61-C6; | A58-B61-C7; | A58-B61-C8; | A58-B61-C9; |
| A59-B61-C1; | A59-B61-C2; | A59-B61-C3; | A59-B61-C4; | A59-B61-C5; | A59-B61-C6; |
| A59-B61-C7; | A59-B61-C8; | A59-B61-C9; | A60-B61-C1; | A60-B61-C2; | A60-B61-C3; |
| A60-B61-C4; | A60-B61-C5; | A60-B61-C6; | A60-B61-C7; | A60-B61-C8; | A60-B61-C9; |
| A61-B61-C1; | A61-B61-C2; | A61-B61-C3; | A61-B61-C4; | A61-B61-C5; | A61-B61-C6; |
| A61-B61-C7; | A61-B61-C8; | A61-B61-C9; | A62-B61-C1; | A62-B61-C2; | A62-B61-C3; |
| A62-B61-C4; | A62-B61-C5; | A62-B61-C6; | A62-B61-C7; | A62-B61-C8; | A62-B61-C9; |
| A63-B61-C1; | A63-B61-C2; | A63-B61-C3; | A63-B61-C4; | A63-B61-C5; | A63-B61-C6; |
| A63-B61-C7; | A63-B61-C8; | A63-B61-C9; | A64-B61-C1; | A64-B61-C2; | A64-B61-C3; |
| A64-B61-C4; | A64-B61-C5; | A64-B61-C6; | A64-B61-C7; | A64-B61-C8; | A64-B61-C9; |
| A65-B61-C1; | A65-B61-C2; | A65-B61-C3; | A65-B61-C4; | A65-B61-C5; | A65-B61-C6; |
| A65-B61-C7; | A65-B61-C8; | A65-B61-C9; | A66-B61-C1; | A66-B61-C2; | A66-B61-C3; |
| A66-B61-C4; | A66-B61-C5; | A66-B61-C6; | A66-B61-C7; | A66-B61-C8; | A66-B61-C9; |
| A67-B61-C1; | A67-B61-C2; | A67-B61-C3; | A67-B61-C4; | A67-B61-C5; | A67-B61-C6; |
| A67-B61-C7; | A67-B61-C8; | A67-B61-C9; | A68-B61-C1; | A68-B61-C2; | A68-B61-C3; |
| A68-B61-C4; | A68-B61-C5; | A68-B61-C6; | A68-B61-C7; | A68-B61-C8; | A68-B61-C9; |
| A69-B61-C1; | A69-B61-C2; | A69-B61-C3; | A69-B61-C4; | A69-B61-C5; | A69-B61-C6; |
| A69-B61-C7; | A69-B61-C8; | A69-B61-C9; | A70-B61-C1; | A70-B61-C2; | A70-B61-C3; |
| A70-B61-C4; | A70-B61-C5; | A70-B61-C6; | A70-B61-C7; | A70-B61-C8; | A70-B61-C9; |
| A71-B61-C1; | A71-B61-C2; | A71-B61-C3; | A71-B61-C4; | A71-B61-C5; | A71-B61-C6; |
| A71-B61-C7; | A71-B61-C8; | A71-B61-C9; | A1-B62-C1; | A1-B62-C2; | A1-B62-C3; |
| A1-B62-C4; | A1-B62-C5; | A1-B62-C6; | A1-B62-C7; | A1-B62-C8; | A1-B62-C9; |
| A2-B62-C1; | A2-B62-C2; | A2-B62-C3; | A2-B62-C4; | A2-B62-C5; | A2-B62-C6; |
| A2-B62-C7; | A2-B62-C8; | A2-B62-C9; | A3-B62-C1; | A3-B62-C2; | A3-B62-C3; |
| A3-B62-C4; | A3-B62-C5; | A3-B62-C6; | A3-B62-C7; | A3-B62-C8; | A3-B62-C9; |
| A4-B62-C1; | A4-B62-C2; | A4-B62-C3; | A4-B62-C4; | A4-B62-C5; | A4-B62-C6; |
| A4-B62-C7; | A4-B62-C8; | A4-B62-C9; | A5-B62-C1; | A5-B62-C2; | A5-B62-C3; |
| A5-B62-C4; | A5-B62-C5; | A5-B62-C6; | A5-B62-C7; | A5-B62-C8; | A5-B62-C9; |
| A6-B62-C1; | A6-B62-C2; | A6-B62-C3; | A6-B62-C4; | A6-B62-C5; | A6-B62-C6; |

-continued

| | | | | | |
|---|---|---|---|---|---|
| A6-B62-C7; | A6-B62-C8; | A6-B62-C9; | A7-B62-C1; | A7-B62-C2; | A7-B62-C3; |
| A7-B62-C4; | A7-B62-C5; | A7-B62-C6; | A7-B62-C7; | A7-B62-C8; | A7-B62-C9; |
| A8-B62-C1; | A8-B62-C2; | A8-B62-C3; | A8-B62-C4; | A8-B62-C5; | A8-B62-C6; |
| A8-B62-C7; | A8-B62-C8; | A8-B62-C9; | A9-B62-C1; | A9-B62-C2; | A9-B62-C3; |
| A9-B62-C4; | A9-B62-C5; | A9-B62-C6; | A9-B62-C7; | A9-B62-C8; | A9-B62-C9; |
| A10-B62-C1; | A10-B62-C2; | A10-B62-C3; | A10-B62-C4; | A10-B62-C5; | A10-B62-C6; |
| A10-B62-C7; | A10-B62-C8; | A10-B62-C9; | A11-B62-C1; | A11-B62-C2; | A11-B62-C3; |
| A11-B62-C4; | A11-B62-C5; | A11-B62-C6; | A11-B62-C7; | A11-B62-C8; | A11-B62-C9; |
| A12-B62-C1; | A12-B62-C2; | A12-B62-C3; | A12-B62-C4; | A12-B62-C5; | A12-B62-C6; |
| A12-B62-C7; | A12-B62-C8; | A12-B62-C9; | A13-B62-C1; | A13-B62-C2; | A13-B62-C3; |
| A13-B62-C4; | A13-B62-C5; | A13-B62-C6; | A13-B62-C7; | A13-B62-C8; | A13-B62-C9; |
| A14-B62-C1; | A14-B62-C2; | A14-B62-C3; | A14-B62-C4; | A14-B62-C5; | A14-B62-C6; |
| A14-B62-C7; | A14-B62-C8; | A14-B62-C9; | A15-B62-C1; | A15-B62-C2; | A15-B62-C3; |
| A15-B62-C4; | A15-B62-C5; | A15-B62-C6; | A15-B62-C7; | A15-B62-C8; | A15-B62-C9; |
| A16-B62-C1; | A16-B62-C2; | A16-B62-C3; | A16-B62-C4; | A16-B62-C5; | A16-B62-C6; |
| A16-B62-C7; | A16-B62-C8; | A16-B62-C9; | A17-B62-C1; | A17-B62-C2; | A17-B62-C3; |
| A17-B62-C4; | A17-B62-C5; | A17-B62-C6; | A17-B62-C7; | A17-B62-C8; | A17-B62-C9; |
| A18-B62-C1; | A18-B62-C2; | A18-B62-C3; | A18-B62-C4; | A18-B62-C5; | A18-B62-C6; |
| A18-B62-C7; | A18-B62-C8; | A18-B62-C9; | A19-B62-C1; | A19-B62-C2; | A19-B62-C3; |
| A19-B62-C4; | A19-B62-C5; | A19-B62-C6; | A19-B62-C7; | A19-B62-C8; | A19-B62-C9; |
| A20-B62-C1; | A20-B62-C2; | A20-B62-C3; | A20-B62-C4; | A20-B62-C5; | A20-B62-C6; |
| A20-B62-C7; | A20-B62-C8; | A20-B62-C9; | A21-B62-C1; | A21-B62-C2; | A21-B62-C3; |
| A21-B62-C4; | A21-B62-C5; | A21-B62-C6; | A21-B62-C7; | A21-B62-C8; | A21-B62-C9; |
| A22-B62-C1; | A22-B62-C2; | A22-B62-C3; | A22-B62-C4; | A22-B62-C5; | A22-B62-C6; |
| A22-B62-C7; | A22-B62-C8; | A22-B62-C9; | A23-B62-C1; | A23-B62-C2; | A23-B62-C3; |
| A23-B62-C4; | A23-B62-C5; | A23-B62-C6; | A23-B62-C7; | A23-B62-C8; | A23-B62-C9; |
| A24-B62-C1; | A24-B62-C2; | A24-B62-C3; | A24-B62-C4; | A24-B62-C5; | A24-B62-C6; |
| A24-B62-C7; | A24-B62-C8; | A24-B62-C9; | A25-B62-C1; | A25-B62-C2; | A25-B62-C3; |
| A25-B62-C4; | A25-B62-C5; | A25-B62-C6; | A25-B62-C7; | A25-B62-C8; | A25-B62-C9; |
| A26-B62-C1; | A26-B62-C2; | A26-B62-C3; | A26-B62-C4; | A26-B62-C5; | A26-B62-C6; |
| A26-B62-C7; | A26-B62-C8; | A26-B62-C9; | A27-B62-C1; | A27-B62-C2; | A27-B62-C3; |
| A27-B62-C4; | A27-B62-C5; | A27-B62-C6; | A27-B62-C7; | A27-B62-C8; | A27-B62-C9; |
| A28-B62-C1; | A28-B62-C2; | A28-B62-C3; | A28-B62-C4; | A28-B62-C5; | A28-B62-C6; |
| A28-B62-C7; | A28-B62-C8; | A28-B62-C9; | A29-B62-C1; | A29-B62-C2; | A29-B62-C3; |
| A29-B62-C4; | A29-B62-C5; | A29-B62-C6; | A29-B62-C7; | A29-B62-C8; | A29-B62-C9; |
| A30-B62-C4; | A30-B62-C2; | A30-B62-C3; | A30-B62-C4; | A30-B62-C5; | A30-B62-C6; |
| A30-B62-C7; | A30-B62-C8; | A30-B62-C9; | A31-B62-C1; | A31-B62-C2; | A31-B62-C3; |
| A31-B62-C4; | A31-B62-C5; | A31-B62-C6; | A31-B62-C7; | A31-B62-C8; | A31-B62-C9; |
| A32-B62-C1; | A32-B62-C2; | A32-B62-C3; | A32-B62-C4; | A32-B62-C5; | A32-B62-C6; |
| A32-B62-C7; | A32-B62-C8; | A32-B62-C9; | A33-B62-C1; | A33-B62-C2; | A33-B62-C3; |
| A33-B62-C4; | A33-B62-C5; | A33-B62-C6; | A33-B62-C7; | A33-B62-C8; | A33-B62-C9; |
| A34-B62-C1; | A34-B62-C2; | A34-B62-C3; | A34-B62-C4; | A34-B62-C5; | A34-B62-C6; |
| A34-B62-C7; | A34-B62-C8; | A34-B62-C9; | A35-B62-C1; | A35-B62-C2; | A35-B62-C3; |
| A35-B62-C4; | A35-B62-C5; | A35-B62-C6; | A35-B62-C7; | A35-B62-C8; | A35-B62-C9; |
| A36-B62-C1; | A36-B62-C2; | A36-B62-C3; | A36-B62-C4; | A36-B62-C5; | A36-B62-C6; |
| A36-B62-C7; | A36-B62-C8; | A36-B62-C9; | A37-B62-C1; | A37-B62-C2; | A37-B62-C3; |
| A37-B62-C4; | A37-B62-C5; | A37-B62-C6; | A37-B62-C7; | A37-B62-C8; | A37-B62-C9; |
| A38-B62-C1; | A38-B62-C2; | A38-B62-C3; | A38-B62-C4; | A38-B62-C5; | A38-B62-C6; |
| A38-B62-C7; | A38-B62-C8; | A38-B62-C9; | A39-B62-C1; | A39-B62-C2; | A39-B62-C3; |
| A39-B62-C4; | A39-B62-C5; | A39-B62-C6; | A39-B62-C7; | A39-B62-C8; | A39-B62-C9; |
| A40-B62-C1; | A40-B62-C2; | A40-B62-C3; | A40-B62-C4; | A40-B62-C5; | A40-B62-C6; |
| A40-B62-C7; | A40-B62-C8; | A40-B62-C9; | A41-B62-C1; | A41-B62-C2; | A41-B62-C3; |
| A41-B62-C4; | A41-B62-C5; | A41-B62-C6; | A41-B62-C7; | A41-B62-C8; | A41-B62-C9; |
| A42-B62-C1; | A42-B62-C2; | A42-B62-C3; | A42-B62-C4; | A42-B62-C5; | A42-B62-C6; |
| A42-B62-C7; | A42-B62-C8; | A42-B62-C9; | A43-B62-C1; | A43-B62-C2; | A43-B62-C3; |
| A43-B62-C4; | A43-B62-C5; | A43-B62-C6; | A43-B62-C7; | A43-B62-C8; | A43-B62-C9; |
| A44-B62-C1; | A44-B62-C2; | A44-B62-C3; | A44-B62-C4; | A44-B62-C5; | A44-B62-C6; |
| A44-B62-C7; | A44-B62-C8; | A44-B62-C9; | A45-B62-C1; | A45-B62-C2; | A45-B62-C3; |
| A45-B62-C4; | A45-B62-C5; | A45-B62-C6; | A45-B62-C7; | A45-B62-C8; | A45-B62-C9; |
| A46-B62-C1; | A46-B62-C2; | A46-B62-C3; | A46-B62-C4; | A46-B62-C5; | A46-B62-C6; |
| A46-B62-C7; | A46-B62-C8; | A46-B62-C9; | A47-B62-C1; | A47-B62-C2; | A47-B62-C3; |
| A47-B62-C4; | A47-B62-C5; | A47-B62-C6; | A47-B62-C7; | A47-B62-C8; | A47-B62-C9; |
| A48-B62-C1; | A48-B62-C2; | A48-B62-C3; | A48-B62-C4; | A48-B62-C5; | A48-B62-C6; |
| A48-B62-C7; | A48-B62-C8; | A48-B62-C9; | A49-B62-C1; | A49-B62-C2; | A49-B62-C3; |
| A49-B62-C4; | A49-B62-C5; | A49-B62-C6; | A49-B62-C7; | A49-B62-C8; | A49-B62-C9; |
| A50-B62-C1; | A50-B62-C2; | A50-B62-C3; | A50-B62-C4; | A50-B62-C5; | A50-B62-C6; |
| A50-B62-C7; | A50-B62-C8; | A50-B62-C9; | A51-B62-C1; | A51-B62-C2; | A51-B62-C3; |
| A51-B62-C4; | A51-B62-C5; | A51-B62-C6; | A51-B62-C7; | A51-B62-C8; | A51-B62-C9; |
| A52-B62-C1; | A52-B62-C2; | A52-B62-C3; | A52-B62-C4; | A52-B62-C5; | A52-B62-C6; |
| A52-B62-C7; | A52-B62-C8; | A52-B62-C9; | A53-B62-C1; | A53-B62-C2; | A53-B62-C3; |
| A53-B62-C4; | A53-B62-C5; | A53-B62-C6; | A53-B62-C7; | A53-B62-C8; | A53-B62-C9; |
| A54-B62-C1; | A54-B62-C2; | A54-B62-C3; | A54-B62-C4; | A54-B62-C5; | A54-B62-C6; |
| A54-B62-C7; | A54-B62-C8; | A54-B62-C9; | A55-B62-C1; | A55-B62-C2; | A55-B62-C3; |
| A55-B62-C4; | A55-B62-C5; | A55-B62-C6; | A55-B62-C7; | A55-B62-C8; | A55-B62-C9; |
| A56-B62-C1; | A56-B62-C2; | A56-B62-C3; | A56-B62-C4; | A56-B62-C5; | A56-B62-C6; |
| A56-B62-C7; | A56-B62-C8; | A56-B62-C9; | A57-B62-C1; | A57-B62-C2; | A57-B62-C3; |
| A57-B62-C4; | A57-B62-C5; | A57-B62-C6; | A57-B62-C7; | A57-B62-C8; | A57-B62-C9; |
| A58-B62-C1; | A58-B62-C2; | A58-B62-C3; | A58-B62-C4; | A58-B62-C5; | A58-B62-C6; |
| A58-B62-C7; | A58-B62-C8; | A58-B62-C9; | A59-B62-C1; | A59-B62-C2; | A59-B62-C3; |

-continued

| | | | | | |
|---|---|---|---|---|---|
| A59-B62-C4; | A59-B62-C5; | A59-B62-C6; | A59-B62-C7; | A59-B62-C8; | A59-B62-C9; |
| A60-B62-C1; | A60-B62-C2; | A60-B62-C3; | A60-B62-C4; | A60-B62-C5; | A60-B62-C6; |
| A60-B62-C7; | A60-B62-C8; | A60-B62-C9; | A61-B62-C1; | A61-B62-C2; | A61-B62-C3; |
| A61-B62-C4; | A61-B62-C5; | A61-B62-C6; | A61-B62-C7; | A61-B62-C8; | A61-B62-C9; |
| A62-B62-C1; | A62-B62-C2; | A62-B62-C3; | A62-B62-C4; | A62-B62-C5; | A62-B62-C6; |
| A62-B62-C7; | A62-B62-C8; | A62-B62-C9; | A63-B62-C1; | A63-B62-C2; | A63-B62-C3; |
| A63-B62-C4; | A63-B62-C5; | A63-B62-C6; | A63-B62-C7; | A63-B62-C8; | A63-B62-C9; |
| A64-B62-C1; | A64-B62-C2; | A64-B62-C3; | A64-B62-C4; | A64-B62-C5; | A64-B62-C6; |
| A64-B62-C7; | A64-B62-C8; | A64-B62-C9; | A65-B62-C1; | A65-B62-C2; | A65-B62-C3; |
| A65-B62-C4; | A65-B62-C5; | A65-B62-C6; | A65-B62-C7; | A65-B62-C8; | A65-B62-C9; |
| A66-B62-C1; | A66-B62-C2; | A66-B62-C3; | A66-B62-C4; | A66-B62-C5; | A66-B62-C6; |
| A66-B62-C7; | A66-B62-C8; | A66-B62-C9; | A67-B62-C1; | A67-B62-C2; | A67-B62-C3; |
| A67-B62-C4; | A67-B62-C5; | A67-B62-C6; | A67-B62-C7; | A67-B62-C8; | A67-B62-C9; |
| A68-B62-C1; | A68-B62-C2; | A68-B62-C3; | A68-B62-C4; | A68-B62-C5; | A68-B62-C6; |
| A68-B62-C7; | A68-B62-C8; | A68-B62-C9; | A69-B62-C1; | A69-B62-C2; | A69-B62-C3; |
| A69-B62-C4; | A69-B62-C5; | A69-B62-C6; | A69-B62-C7; | A69-B62-C8; | A69-B62-C9; |
| A70-B62-C1; | A70-B62-C2; | A70-B62-C3; | A70-B62-C4; | A70-B62-C5; | A70-B62-C6; |
| A70-B62-C7; | A70-B62-C8; | A70-B62-C9; | A71-B62-C1; | A71-B62-C2; | A71-B62-C3; |
| A71-B62-C4; | A71-B62-C5; | A71-B62-C6; | A71-B62-C7; | A71-B62-C8; | A71-B62-C9; |
| A1-B63-C1; | A1-B63-C2; | A1-B63-C3; | A1-B63-C4; | A1-B63-C5; | A1-B63-C6; |
| A1-B63-C7; | A1-B63-C8; | A1-B63-C9; | A2-B63-C1; | A2-B63-C2; | A2-B63-C3; |
| A2-B63-C4; | A2-B63-C5; | A2-B63-C6; | A2-B63-C7; | A2-B63-C8; | A2-B63-C9; |
| A3-B63-C1; | A3-B63-C2; | A3-B63-C3; | A3-B63-C4; | A3-B63-C5; | A3-B63-C6; |
| A3-B63-C7; | A3-B63-C8; | A3-B63-C9; | A4-B63-C1; | A4-B63-C2; | A4-B63-C3; |
| A4-B63-C4; | A4-B63-C5; | A4-B63-C6; | A4-B63-C7; | A4-B63-C8; | A4-B63-C9; |
| A5-B63-C1; | A5-B63-C2; | A5-B63-C3; | A5-B63-C4; | A5-B63-C5; | A5-B63-C6; |
| A5-B63-C7; | A5-B63-C8; | A5-B63-C9; | A6-B63-C1; | A6-B63-C2; | A6-B63-C3; |
| A6-B63-C4; | A6-B63-C5; | A6-B63-C6; | A6-B63-C7; | A6-B63-C8; | A6-B63-C9; |
| A7-B63-C1; | A7-B63-C2; | A7-B63-C3; | A7-B63-C4; | A7-B63-C5; | A7-B63-C6; |
| A7-B63-C7; | A7-B63-C8; | A7-B63-C9; | A8-B63-C1; | A8-B63-C2; | A8-B63-C3; |
| A8-B63-C4; | A8-B63-C5; | A8-B63-C6; | A8-B63-C7; | A8-B63-C8; | A8-B63-C9; |
| A9-B63-C1; | A9-B63-C2; | A9-B63-C3; | A9-B63-C4; | A9-B63-C5; | A9-B63-C6; |
| A9-B63-C7; | A9-B63-C8; | A9-B63-C9; | A10-B63-C1; | A10-B63-C2; | A10-B63-C3; |
| A10-B63-C4; | A10-B63-C5; | A10-B63-C6; | A10-B63-C7; | A10-B63-C8; | A10-B63-C9; |
| A11-B63-C1; | A11-B63-C2; | A11-B63-C3; | A11-B63-C4; | A11-B63-C5; | A11-B63-C6; |
| A11-B63-C7; | A11-B63-C8; | A11-B63-C9; | A12-B63-C1; | A12-B63-C2; | A12-B63-C3; |
| A12-B63-C4; | A12-B63-C5; | A12-B63-C6; | A12-B63-C7; | A12-B63-C8; | A12-B63-C9; |
| A13-B63-C1; | A13-B63-C2; | A13-B63-C3; | A13-B63-C4; | A13-B63-C5; | A13-B63-C6; |
| A13-B63-C7; | A13-B63-C8; | A13-B63-C9; | A14-B63-C1; | A14-B63-C2; | A14-B63-C3; |
| A14-B63-C4; | A14-B63-C5; | A14-B63-C6; | A14-B63-C7; | A14-B63-C8; | A14-B63-C9; |
| A15-B63-C1; | A15-B63-C2; | A15-B63-C3; | A15-B63-C4; | A15-B63-C5; | A15-B63-C6; |
| A15-B63-C7; | A15-B63-C8; | A15-B63-C9; | A16-B63-C1; | A16-B63-C2; | A16-B63-C3; |
| A16-B63-C4; | A16-B63-C5; | A16-B63-C6; | A16-B63-C7; | A16-B63-C8; | A16-B63-C9; |
| A17-B63-C1; | A17-B63-C2; | A17-B63-C3; | A17-B63-C4; | A17-B63-C5; | A17-B63-C6; |
| A17-B63-C7; | A17-B63-C8; | A17-B63-C9; | A18-B63-C1; | A18-B63-C2; | A18-B63-C3; |
| A18-B63-C4; | A18-B63-C5; | A18-B63-C6; | A18-B63-C7; | A18-B63-C8; | A18-B63-C9; |
| A19-B63-C1; | A19-B63-C2; | A19-B63-C3; | A19-B63-C4; | A19-B63-C5; | A19-B63-C6; |
| A19-B63-C7; | A19-B63-C8; | A19-B63-C9; | A20-B63-C1; | A20-B63-C2; | A20-B63-C3; |
| A20-B63-C4; | A20-B63-C5; | A20-B63-C6; | A20-B63-C7; | A20-B63-C8; | A20-B63-C9; |
| A21-B63-C1; | A21-B63-C2; | A21-B63-C3; | A21-B63-C4; | A21-B63-C5; | A21-B63-C6; |
| A21-B63-C7; | A21-B63-C8; | A21-B63-C9; | A22-B63-C1; | A22-B63-C2; | A22-B63-C3; |
| A22-B63-C4; | A22-B63-C5; | A22-B63-C6; | A22-B63-C7; | A22-B63-C8; | A22-B63-C9; |
| A23-B63-C1; | A23-B63-C2; | A23-B63-C3; | A23-B63-C4; | A23-B63-C5; | A23-B63-C6; |
| A23-B63-C7; | A23-B63-C8; | A23-B63-C9; | A24-B63-C1; | A24-B63-C2; | A24-B63-C3; |
| A24-B63-C4; | A24-B63-C5; | A24-B63-C6; | A24-B63-C7; | A24-B63-C8; | A24-B63-C9; |
| A25-B63-C1; | A25-B63-C2; | A25-B63-C3; | A25-B63-C4; | A25-B63-C5; | A25-B63-C6; |
| A25-B63-C7; | A25-B63-C8; | A25-B63-C9; | A26-B63-C1; | A26-B63-C2; | A26-B63-C3; |
| A26-B63-C4; | A26-B63-C5; | A26-B63-C6; | A26-B63-C7; | A26-B63-C8; | A26-B63-C9; |
| A27-B63-C1; | A27-B63-C2; | A27-B63-C3; | A27-B63-C4; | A27-B63-C5; | A27-B63-C6; |
| A27-B63-C7; | A27-B63-C8; | A27-B63-C9; | A28-B63-C1; | A28-B63-C2; | A28-B63-C3; |
| A28-B63-C4; | A28-B63-C5; | A28-B63-C6; | A28-B63-C7; | A28-B63-C8; | A28-B63-C9; |
| A29-B63-C1; | A29-B63-C2; | A29-B63-C3; | A29-B63-C4; | A29-B63-C5; | A29-B63-C6; |
| A29-B63-C7; | A29-B63-C8; | A29-B63-C9; | A30-B63-C1; | A30-B63-C2; | A30-B63-C3; |
| A30-B63-C4; | A30-B63-C5; | A30-B63-C6; | A30-B63-C7; | A30-B63-C8; | A30-B63-C9; |
| A31-B63-C1; | A31-B63-C2; | A31-B63-C3; | A31-B63-C4; | A31-B63-C5; | A31-B63-C6; |
| A31-B63-C7; | A31-B63-C8; | A31-B63-C9; | A32-B63-C1; | A32-B63-C2; | A32-B63-C3; |
| A32-B63-C4; | A32-B63-C5; | A32-B63-C6; | A32-B63-C7; | A32-B63-C8; | A32-B63-C9; |
| A33-B63-C1; | A33-B63-C2; | A33-B63-C3; | A33-B63-C4; | A33-B63-C5; | A33-B63-C6; |
| A33-B63-C7; | A33-B63-C8; | A33-B63-C9; | A34-B63-C1; | A34-B63-C2; | A34-B63-C3; |
| A34-B63-C4; | A34-B63-C5; | A34-B63-C6; | A34-B63-C7; | A34-B63-C8; | A34-B63-C9; |
| A35-B63-C1; | A35-B63-C2; | A35-B63-C3; | A35-B63-C4; | A35-B63-C5; | A35-B63-C6; |
| A35-B63-C7; | A35-B63-C8; | A35-B63-C9; | A36-B63-C1; | A36-B63-C2; | A36-B63-C3; |
| A36-B63-C4; | A36-B63-C5; | A36-B63-C6; | A36-B63-C7; | A36-B63-C8; | A36-B63-C9; |
| A37-B63-C1; | A37-B63-C2; | A37-B63-C3; | A37-B63-C4; | A37-B63-C5; | A37-B63-C6; |
| A37-B63-C7; | A37-B63-C8; | A37-B63-C9; | A38-B63-C1; | A38-B63-C2; | A38-B63-C3; |
| A38-B63-C4; | A38-B63-C5; | A38-B63-C6; | A38-B63-C7; | A38-B63-C8; | A38-B63-C9; |
| A39-B63-C1; | A39-B63-C2; | A39-B63-C3; | A39-B63-C4; | A39-B63-C5; | A39-B63-C6; |
| A39-B63-C7; | A39-B63-C8; | A39-B63-C9; | A40-B63-C1; | A40-B63-C2; | A40-B63-C3; |
| A40-B63-C4; | A40-B63-C5; | A40-B63-C6; | A40-B63-C7; | A40-B63-C8; | A40-B63-C9; |

| | | | | | |
|---|---|---|---|---|---|
| A41-B63-C1; | A41-B63-C2; | A41-B63-C3; | A41-B63-C4; | A41-B63-C5; | A41-B63-C6; |
| A41-B63-C7; | A41-B63-C8; | A41-B63-C9; | A42-B63-C1; | A42-B63-C2; | A42-B63-C3; |
| A42-B63-C4; | A42-B63-C5; | A42-B63-C6; | A42-B63-C7; | A42-B63-C8; | A42-B63-C9; |
| A43-B63-C1; | A43-B63-C2; | A43-B63-C3; | A43-B63-C4; | A43-B63-C5; | A43-B63-C6; |
| A43-B63-C7; | A43-B63-C8; | A43-B63-C9; | A44-B63-C1; | A44-B63-C2; | A44-B63-C3; |
| A44-B63-C4; | A44-B63-C5; | A44-B63-C6; | A44-B63-C7; | A44-B63-C8; | A44-B63-C9; |
| A45-B63-C1; | A45-B63-C2; | A45-B63-C3; | A45-B63-C4; | A45-B63-C5; | A45-B63-C6; |
| A45-B63-C7; | A45-B63-C8; | A45-B63-C9; | A46-B63-C1; | A46-B63-C2; | A46-B63-C3; |
| A46-B63-C4; | A46-B63-C5; | A46-B63-C6; | A46-B63-C7; | A46-B63-C8; | A46-B63-C9; |
| A47-B63-C1; | A47-B63-C2; | A47-B63-C3; | A47-B63-C4; | A47-B63-C5; | A47-B63-C6; |
| A47-B63-C7; | A47-B63-C8; | A47-B63-C9; | A48-B63-C1; | A48-B63-C2; | A48-B63-C3; |
| A48-B63-C4; | A48-B63-C5; | A48-B63-C6; | A48-B63-C7; | A48-B63-C8; | A48-B63-C9; |
| A49-B63-C1; | A49-B63-C2; | A49-B63-C3; | A49-B63-C4; | A49-B63-C5; | A49-B63-C6; |
| A49-B63-C7; | A49-B63-C8; | A49-B63-C9; | A50-B63-C1; | A50-B63-C2; | A50-B63-C3; |
| A50-B63-C4; | A50-B63-C5; | A50-B63-C6; | A50-B63-C7; | A50-B63-C8; | A50-B63-C9; |
| A51-B63-C1; | A51-B63-C2; | A51-B63-C3; | A51-B63-C4; | A51-B63-C5; | A51-B63-C6; |
| A51-B63-C7; | A51-B63-C8; | A51-B63-C9; | A52-B63-C1; | A52-B63-C2; | A52-B63-C3; |
| A52-B63-C4; | A52-B63-C5; | A52-B63-C6; | A52-B63-C7; | A52-B63-C8; | A52-B63-C9; |
| A53-B63-C1; | A53-B63-C2; | A53-B63-C3; | A53-B63-C4; | A53-B63-C5; | A53-B63-C6; |
| A53-B63-C7; | A53-B63-C8; | A53-B63-C9; | A54-B63-C1; | A54-B63-C2; | A54-B63-C3; |
| A54-B63-C4; | A54-B63-C5; | A54-B63-C6; | A54-B63-C7; | A54-B63-C8; | A54-B63-C9; |
| A55-B63-C1; | A55-B63-C2; | A55-B63-C3; | A55-B63-C4; | A55-B63-C5; | A55-B63-C6; |
| A55-B63-C7; | A55-B63-C8; | A55-B63-C9; | A56-B63-C1; | A56-B63-C2; | A56-B63-C3; |
| A56-B63-C4; | A56-B63-C5; | A56-B63-C6; | A56-B63-C7; | A56-B63-C8; | A56-B63-C9; |
| A57-B63-C1; | A57-B63-C2; | A57-B63-C3; | A57-B63-C4; | A57-B63-C5; | A57-B63-C6; |
| A57-B63-C7; | A57-B63-C8; | A57-B63-C9; | A58-B63-C1; | A58-B63-C2; | A58-B63-C3; |
| A58-B63-C4; | A58-B63-C5; | A58-B63-C6; | A58-B63-C7; | A58-B63-C8; | A58-B63-C9; |
| A59-B63-C1; | A59-B63-C2; | A59-B63-C3; | A59-B63-C4; | A59-B63-C5; | A59-B63-C6; |
| A59-B63-C7; | A59-B63-C8; | A59-B63-C9; | A60-B63-C1; | A60-B63-C2; | A60-B63-C3; |
| A60-B63-C4; | A60-B63-C5; | A60-B63-C6; | A60-B63-C7; | A60-B63-C8; | A60-B63-C9; |
| A61-B63-C1; | A61-B63-C2; | A61-B63-C3; | A61-B63-C4; | A61-B63-C5; | A61-B63-C6; |
| A61-B63-C7; | A61-B63-C8; | A61-B63-C9; | A62-B63-C1; | A62-B63-C2; | A62-B63-C3; |
| A62-B63-C4; | A62-B63-C5; | A62-B63-C6; | A62-B63-C7; | A62-B63-C8; | A62-B63-C9; |
| A63-B63-C1; | A63-B63-C2; | A63-B63-C3; | A63-B63-C4; | A63-B63-C5; | A63-B63-C6; |
| A63-B63-C7; | A63-B63-C8; | A63-B63-C9; | A64-B63-C1; | A64-B63-C2; | A64-B63-C3; |
| A64-B63-C4; | A64-B63-C5; | A64-B63-C6; | A64-B63-C7; | A64-B63-C8; | A64-B63-C9; |
| A65-B63-C1; | A65-B63-C2; | A65-B63-C3; | A65-B63-C4; | A65-B63-C5; | A65-B63-C6; |
| A65-B63-C7; | A65-B63-C8; | A65-B63-C9; | A66-B63-C1; | A66-B63-C2; | A66-B63-C3; |
| A66-B63-C4; | A66-B63-C5; | A66-B63-C6; | A66-B63-C7; | A66-B63-C8; | A66-B63-C9; |
| A67-B63-C1; | A67-B63-C2; | A67-B63-C3; | A67-B63-C4; | A67-B63-C5; | A67-B63-C6; |
| A67-B63-C7; | A67-B63-C8; | A67-B63-C9; | A68-B63-C1; | A68-B63-C2; | A68-B63-C3; |
| A68-B63-C4; | A68-B63-C5; | A68-B63-C6; | A68-B63-C7; | A68-B63-C8; | A68-B63-C9; |
| A69-B63-C1; | A69-B63-C2; | A69-B63-C3; | A69-B63-C4; | A69-B63-C5; | A69-B63-C6; |
| A69-B63-C7; | A69-B63-C8; | A69-B63-C9; | A70-B63-C1; | A70-B63-C2; | A70-B63-C3; |
| A70-B63-C4; | A70-B63-C5; | A70-B63-C6; | A70-B63-C7; | A70-B63-C8; | A70-B63-C9; |
| A71-B63-C1; | A71-B63-C2; | A71-B63-C3; | A71-B63-C4; | A71-B63-C5; | A71-B63-C6; |
| A71-B63-C7; | A71-B63-C8; | A71-B63-C9; | A1-B64-C1; | A1-B64-C2; | A1-B64-C3; |
| A1-B64-C4; | A1-B64-C5; | A1-B64-C6; | A1-B64-C7; | A1-B64-C8; | A1-B64-C9; |
| A2-B64-C1; | A2-B64-C2; | A2-B64-C3; | A2-B64-C4; | A2-B64-C5; | A2-B64-C6; |
| A2-B64-C7; | A2-B64-C8; | A2-B64-C9; | A3-B64-C1; | A3-B64-C2; | A3-B64-C3; |
| A3-B64-C4; | A3-B64-C5; | A3-B64-C6; | A3-B64-C7; | A3-B64-C8; | A3-B64-C9; |
| A4-B64-C1; | A4-B64-C2; | A4-B64-C3; | A4-B64-C4; | A4-B64-C5; | A4-B64-C6; |
| A4-B64-C7; | A4-B64-C8; | A4-B64-C9; | A5-B64-C1; | A5-B64-C2; | A5-B64-C3; |
| A5-B64-C4; | A5-B64-C5; | A5-B64-C6; | A5-B64-C7; | A5-B64-C8; | A5-B64-C9; |
| A6-B64-C1; | A6-B64-C2; | A6-B64-C3; | A6-B64-C4; | A6-B64-C5; | A6-B64-C6; |
| A6-B64-C7; | A6-B64-C8; | A6-B64-C9; | A7-B64-C1; | A7-B64-C2; | A7-B64-C3; |
| A7-B64-C4; | A7-B64-C5; | A7-B64-C6; | A7-B64-C7; | A7-B64-C8; | A7-B64-C9; |
| A8-B64-C1; | A8-B64-C2; | A8-B64-C3; | A8-B64-C4; | A8-B64-C5; | A8-B64-C6; |
| A8-B64-C7; | A8-B64-C8; | A8-B64-C9; | A9-B64-C1; | A9-B64-C2; | A9-B64-C3; |
| A9-B64-C4; | A9-B64-C5; | A9-B64-C6; | A9-B64-C7; | A9-B64-C8; | A9-B64-C9; |
| A10-B64-C1; | A10-B64-C2; | A10-B64-C3; | A10-B64-C4; | A10-B64-C5; | A10-B64-C6; |
| A10-B64-C7; | A10-B64-C8; | A10-B64-C9; | A11-B64-C1; | A11-B64-C2; | A11-B64-C3; |
| A11-B64-C4; | A11-B64-C5; | A11-B64-C6; | A11-B64-C7; | A11-B64-C8; | A11-B64-C9; |
| A12-B64-C1; | A12-B64-C2; | A12-B64-C3; | A12-B64-C4; | A12-B64-C5; | A12-B64-C6; |
| A12-B64-C7; | A12-B64-C8; | A12-B64-C9; | A13-B64-C1; | A13-B64-C2; | A13-B64-C3; |
| A13-B64-C4; | A13-B64-C5; | A13-B64-C6; | A13-B64-C7; | A13-B64-C8; | A13-B64-C9; |
| A14-B64-C1; | A14-B64-C2; | A14-B64-C3; | A14-B64-C4; | A14-B64-C5; | A14-B64-C6; |
| A14-B64-C7; | A14-B64-C8; | A14-B64-C9; | A15-B64-C1; | A15-B64-C2; | A15-B64-C3; |
| A15-B64-C4; | A15-B64-C5; | A15-B64-C6; | A15-B64-C7; | A15-B64-C8; | A15-B64-C9; |
| A16-B64-C1; | A16-B64-C2; | A16-B64-C3; | A16-B64-C4; | A16-B64-C5; | A16-B64-C6; |
| A16-B64-C7; | A16-B64-C8; | A16-B64-C9; | A17-B64-C1; | A17-B64-C2; | A17-B64-C3; |
| A17-B64-C4; | A17-B64-C5; | A17-B64-C6; | A17-B64-C7; | A17-B64-C8; | A17-B64-C9; |
| A18-B64-C1; | A18-B64-C2; | A18-B64-C3; | A18-B64-C4; | A18-B64-C5; | A18-B64-C6; |
| A18-B64-C7; | A18-B64-C8; | A18-B64-C9; | A19-B64-C1; | A19-B64-C2; | A19-B64-C3; |
| A19-B64-C4; | A19-B64-C5; | A19-B64-C6; | A19-B64-C7; | A19-B64-C8; | A19-B64-C9; |
| A20-B64-C1; | A20-B64-C2; | A20-B64-C3; | A20-B64-C4; | A20-B64-C5; | A20-B64-C6; |
| A20-B64-C7; | A20-B64-C8; | A20-B64-C9; | A21-B64-C1; | A21-B64-C2; | A21-B64-C3; |
| A21-B64-C4; | A21-B64-C5; | A21-B64-C6; | A21-B64-C7; | A21-B64-C8; | A21-B64-C9; |
| A22-B64-C1; | A22-B64-C2; | A22-B64-C3; | A22-B64-C4; | A22-B64-C5; | A22-B64-C6; |

-continued

| | | | | | |
|---|---|---|---|---|---|
| A22-B64-C7; | A22-B64-C8; | A22-B64-C9; | A23-B64-C1; | A23-B64-C2; | A23-B64-C3; |
| A23-B64-C4; | A23-B64-C5; | A23-B64-C6; | A23-B64-C7; | A23-B64-C8; | A23-B64-C9; |
| A24-B64-C1; | A24-B64-C2; | A24-B64-C3; | A24-B64-C4; | A24-B64-C5; | A24-B64-C6; |
| A24-B64-C7; | A24-B64-C8; | A24-B64-C9; | A25-B64-C1; | A25-B64-C2; | A25-B64-C3; |
| A25-B64-C4; | A25-B64-C5; | A25-B64-C6; | A25-B64-C7; | A25-B64-C8; | A25-B64-C9; |
| A26-B64-C1; | A26-B64-C2; | A26-B64-C3; | A26-B64-C4; | A26-B64-C5; | A26-B64-C6; |
| A26-B64-C7; | A26-B64-C8; | A26-B64-C9; | A27-B64-C1; | A27-B64-C2; | A27-B64-C3; |
| A27-B64-C4; | A27-B64-C5; | A27-B64-C6; | A27-B64-C7; | A27-B64-C8; | A27-B64-C9; |
| A28-B64-C1; | A28-B64-C2; | A28-B64-C3; | A28-B64-C4; | A28-B64-C5; | A28-B64-C6; |
| A28-B64-C7; | A28-B64-C8; | A28-B64-C9; | A29-B64-C1; | A29-B64-C2; | A29-B64-C3; |
| A29-B64-C4; | A29-B64-C5; | A29-B64-C6; | A29-B64-C7; | A29-B64-C8; | A29-B64-C9; |
| A30-B64-C1; | A30-B64-C2; | A30-B64-C3; | A30-B64-C4; | A30-B64-C5; | A30-B64-C6; |
| A30-B64-C7; | A30-B64-C8; | A30-B64-C9; | A31-B64-C1; | A31-B64-C2; | A31-B64-C3; |
| A31-B64-C4; | A31-B64-C5; | A31-B64-C6; | A31-B64-C7; | A31-B64-C8; | A31-B64-C9; |
| A32-B64-C1; | A32-B64-C2; | A32-B64-C3; | A32-B64-C4; | A32-B64-C5; | A32-B64-C6; |
| A32-B64-C7; | A32-B64-C8; | A32-B64-C9; | A33-B64-C1; | A33-B64-C2; | A33-B64-C3; |
| A33-B64-C4; | A33-B64-C5; | A33-B64-C6; | A33-B64-C7; | A33-B64-C8; | A33-B64-C9; |
| A34-B64-C1; | A34-B64-C2; | A34-B64-C3; | A34-B64-C4; | A34-B64-C5; | A34-B64-C6; |
| A34-B64-C7; | A34-B64-C8; | A34-B64-C9; | A35-B64-C1; | A35-B64-C2; | A35-B64-C3; |
| A35-B64-C4; | A35-B64-C5; | A35-B64-C6; | A35-B64-C7; | A35-B64-C8; | A35-B64-C9; |
| A36-B64-C1; | A36-B64-C2; | A36-B64-C3; | A36-B64-C4; | A36-B64-C5; | A36-B64-C6; |
| A36-B64-C7; | A36-B64-C8; | A36-B64-C9; | A37-B64-C1; | A37-B64-C2; | A37-B64-C3; |
| A37-B64-C4; | A37-B64-C5; | A37-B64-C6; | A37-B64-C7; | A37-B64-C8; | A37-B64-C9; |
| A38-B64-C1; | A38-B64-C2; | A38-B64-C3; | A38-B64-C4; | A38-B64-C5; | A38-B64-C6; |
| A38-B64-C7; | A38-B64-C8; | A38-B64-C9; | A39-B64-C1; | A39-B64-C2; | A39-B64-C3; |
| A39-B64-C4; | A39-B64-C5; | A39-B64-C6; | A39-B64-C7; | A39-B64-C8; | A39-B64-C9; |
| A40-B64-C1; | A40-B64-C2; | A40-B64-C3; | A40-B64-C4; | A40-B64-C5; | A40-B64-C6; |
| A40-B64-C7; | A40-B64-C8; | A40-B64-C9; | A41-B64-C1; | A41-B64-C2; | A41-B64-C3; |
| A41-B64-C4; | A41-B64-C5; | A41-B64-C6; | A41-B64-C7; | A41-B64-C8; | A41-B64-C9; |
| A42-B64-C1; | A42-B64-C2; | A42-B64-C3; | A42-B64-C4; | A42-B64-C5; | A42-B64-C6; |
| A42-B64-C7; | A42-B64-C8; | A42-B64-C9; | A43-B64-C1; | A43-B64-C2; | A43-B64-C3; |
| A43-B64-C4; | A43-B64-C5; | A43-B64-C6; | A43-B64-C7; | A43-B64-C8; | A43-B64-C9; |
| A44-B64-C1; | A44-B64-C2; | A44-B64-C3; | A44-B64-C4; | A44-B64-C5; | A44-B64-C6; |
| A44-B64-C7; | A44-B64-C8; | A44-B64-C9; | A45-B64-C1; | A45-B64-C2; | A45-B64-C3; |
| A45-B64-C4; | A45-B64-C5; | A45-B64-C6; | A45-B64-C7; | A45-B64-C8; | A45-B64-C9; |
| A46-B64-C1; | A46-B64-C2; | A46-B64-C3; | A46-B64-C4; | A46-B64-C5; | A46-B64-C6; |
| A46-B64-C7; | A46-B64-C8; | A46-B64-C9; | A47-B64-C1; | A47-B64-C2; | A47-B64-C3; |
| A47-B64-C4; | A47-B64-C5; | A47-B64-C6; | A47-B64-C7; | A47-B64-C8; | A47-B64-C9; |
| A48-B64-C1; | A48-B64-C2; | A48-B64-C3; | A48-B64-C4; | A48-B64-C5; | A48-B64-C6; |
| A48-B64-C7; | A48-B64-C8; | A48-B64-C9; | A49-B64-C1; | A49-B64-C2; | A49-B64-C3; |
| A49-B64-C4; | A49-B64-C5; | A49-B64-C6; | A49-B64-C7; | A49-B64-C8; | A49-B64-C9; |
| A50-B64-C1; | A50-B64-C2; | A50-B64-C3; | A50-B64-C4; | A50-B64-C5; | A50-B64-C6; |
| A50-B64-C7; | A50-B64-C8; | A50-B64-C9; | A51-B64-C1; | A51-B64-C2; | A51-B64-C3; |
| A51-B64-C4; | A51-B64-C5; | A51-B64-C6; | A51-B64-C7; | A51-B64-C8; | A51-B64-C9; |
| A52-B64-C1; | A52-B64-C2; | A52-B64-C3; | A52-B64-C4; | A52-B64-C5; | A52-B64-C6; |
| A52-B64-C7; | A52-B64-C8; | A52-B64-C9; | A53-B64-C1; | A53-B64-C2; | A53-B64-C3; |
| A53-B64-C4; | A53-B64-C5; | A53-B64-C6; | A53-B64-C7; | A53-B64-C8; | A53-B64-C9; |
| A54-B64-C1; | A54-B64-C2; | A54-B64-C3; | A54-B64-C4; | A54-B64-C5; | A54-B64-C6; |
| A54-B64-C7; | A54-B64-C8; | A54-B64-C9; | A55-B64-C1; | A55-B64-C2; | A55-B64-C3; |
| A55-B64-C4; | A55-B64-C5; | A55-B64-C6; | A55-B64-C7; | A55-B64-C8; | A55-B64-C9; |
| A56-B64-C1; | A56-B64-C2; | A56-B64-C3; | A56-B64-C4; | A56-B64-C5; | A56-B64-C6; |
| A56-B64-C7; | A56-B64-C8; | A56-B64-C9; | A57-B64-C1; | A57-B64-C2; | A57-B64-C3; |
| A57-B64-C4; | A57-B64-C5; | A57-B64-C6; | A57-B64-C7; | A57-B64-C8; | A57-B64-C9; |
| A58-B64-C1; | A58-B64-C2; | A58-B64-C3; | A58-B64-C4; | A58-B64-C5; | A58-B64-C6; |
| A58-B64-C7; | A58-B64-C8; | A58-B64-C9; | A59-B64-C1; | A59-B64-C2; | A59-B64-C3; |
| A59-B64-C4; | A59-B64-C5; | A59-B64-C6; | A59-B64-C7; | A59-B64-C8; | A59-B64-C9; |
| A60-B64-C1; | A60-B64-C2; | A60-B64-C3; | A60-B64-C4; | A60-B64-C5; | A60-B64-C6; |
| A60-B64-C7; | A60-B64-C8; | A60-B64-C9; | A61-B64-C1; | A61-B64-C2; | A61-B64-C3; |
| A61-B64-C4; | A61-B64-C5; | A61-B64-C6; | A61-B64-C7; | A61-B64-C8; | A61-B64-C9; |
| A62-B64-C1; | A62-B64-C2; | A62-B64-C3; | A62-B64-C4; | A62-B64-C5; | A62-B64-C6; |
| A62-B64-C7; | A62-B64-C8; | A62-B64-C9; | A63-B64-C1; | A63-B64-C2; | A63-B64-C3; |
| A63-B64-C4; | A63-B64-C5; | A63-B64-C6; | A63-B64-C7; | A63-B64-C8; | A63-B64-C9; |
| A64-B64-C1; | A64-B64-C2; | A64-B64-C3; | A64-B64-C4; | A64-B64-C5; | A64-B64-C6; |
| A64-B64-C7; | A64-B64-C8; | A64-B64-C9; | A65-B64-C1; | A65-B64-C2; | A65-B64-C3; |
| A65-B64-C4; | A65-B64-C5; | A65-B64-C6; | A65-B64-C7; | A65-B64-C8; | A65-B64-C9; |
| A66-B64-C1; | A66-B64-C2; | A66-B64-C3; | A66-B64-C4; | A66-B64-C5; | A66-B64-C6; |
| A66-B64-C7; | A66-B64-C8; | A66-B64-C9; | A67-B64-C1; | A67-B64-C2; | A67-B64-C3; |
| A67-B64-C4; | A67-B64-C5; | A67-B64-C6; | A67-B64-C7; | A67-B64-C8; | A67-B64-C9; |
| A68-B64-C1; | A68-B64-C2; | A68-B64-C3; | A68-B64-C4; | A68-B64-C5; | A68-B64-C6; |
| A68-B64-C7; | A68-B64-C8; | A68-B64-C9; | A69-B64-C1; | A69-B64-C2; | A69-B64-C3; |
| A69-B64-C4; | A69-B64-C5; | A69-B64-C6; | A69-B64-C7; | A69-B64-C8; | A69-B64-C9; |
| A70-B64-C1; | A70-B64-C2; | A70-B64-C3; | A70-B64-C4; | A70-B64-C5; | A70-B64-C6; |
| A70-B64-C7; | A70-B64-C8; | A70-B64-C9; | A71-B64-C1; | A71-B64-C2; | A71-B64-C3; |
| A71-B64-C4; | A71-B64-C5; | A71-B64-C6; | A71-B64-C7; | A71-B64-C8; | A71-B64-C9; |
| A1-B65-C1; | A1-B65-C2; | A1-B65-C3; | A1-B65-C4; | A1-B65-C5; | A1-B65-C6; |
| A1-B65-C7; | A1-B65-C8; | A1-B65-C9; | A2-B65-C1; | A2-B65-C2; | A2-B65-C3; |
| A2-B65-C4; | A2-B65-C5; | A2-B65-C6; | A2-B65-C7; | A2-B65-C8; | A2-B65-C9; |
| A3-B65-C1; | A3-B65-C2; | A3-B65-C3; | A3-B65-C4; | A3-B65-C5; | A3-B65-C6; |
| A3-B65-C7; | A3-B65-C8; | A3-B65-C9; | A4-B65-C1; | A4-B65-C2; | A4-B65-C3; |

-continued

| | | | | | |
|---|---|---|---|---|---|
| A4-B65-C4; | A4-B65-C5; | A4-B65-C6; | A4-B65-C7; | A4-B65-C8; | A4-B65-C9; |
| A5-B65-C1; | A5-B65-C2; | A5-B65-C3; | A5-B65-C4; | A5-B65-C5; | A5-B65-C6; |
| A5-B65-C7; | A5-B65-C8; | A5-B65-C9; | A6-B65-C1; | A6-B65-C2; | A6-B65-C3; |
| A6-B65-C4; | A6-B65-C5; | A6-B65-C6; | A6-B65-C7; | A6-B65-C8; | A6-B65-C9; |
| A7-B65-C1; | A7-B65-C2; | A7-B65-C3; | A7-B65-C4; | A7-B65-C5; | A7-B65-C6; |
| A7-B65-C7; | A7-B65-C8; | A7-B65-C9; | A8-B65-C1; | A8-B65-C2; | A8-B65-C3; |
| A8-B65-C4; | A8-B65-C5; | A8-B65-C6; | A8-B65-C7; | A8-B65-C8; | A8-B65-C9; |
| A9-B65-C1; | A9-B65-C2; | A9-B65-C3; | A9-B65-C4; | A9-B65-C5; | A9-B65-C6; |
| A9-B65-C7; | A9-B65-C8; | A9-B65-C9; | A10-B65-C1; | A10-B65-C2; | A10-B65-C3; |
| A10-B65-C4; | A10-B65-C5; | A10-B65-C6; | A10-B65-C7; | A10-B65-C8; | A10-B65-C9; |
| A11-B65-C1; | A11-B65-C2; | A11-B65-C3; | A11-B65-C4; | A11-B65-C5; | A11-B65-C6; |
| A11-B65-C7; | A11-B65-C8; | A11-B65-C9; | A12-B65-C1; | A12-B65-C2; | A12-B65-C3; |
| A12-B65-C4; | A12-B65-C5; | A12-B65-C6; | A12-B65-C7; | A12-B65-C8; | A12-B65-C9; |
| A13-B65-C1; | A13-B65-C2; | A13-B65-C3; | A13-B65-C4; | A13-B65-C5; | A13-B65-C6; |
| A13-B65-C7; | A13-B65-C8; | A13-B65-C9; | A14-B65-C1; | A14-B65-C2; | A14-B65-C3; |
| A14-B65-C4; | A14-B65-C5; | A14-B65-C6; | A14-B65-C7; | A14-B65-C8; | A14-B65-C9; |
| A15-B65-C1; | A15-B65-C2; | A15-B65-C3; | A15-B65-C4; | A15-B65-C5; | A15-B65-C6; |
| A15-B65-C7; | A15-B65-C8; | A15-B65-C9; | A16-B65-C1; | A16-B65-C2; | A16-B65-C3; |
| A16-B65-C4; | A16-B65-C5; | A16-B65-C6; | A16-B65-C7; | A16-B65-C8; | A16-B65-C9; |
| A17-B65-C1; | A17-B65-C2; | A17-B65-C3; | A17-B65-C4; | A17-B65-C5; | A17-B65-C6; |
| A17-B65-C7; | A17-B65-C8; | A17-B65-C9; | A18-B65-C1; | A18-B65-C2; | A18-B65-C3; |
| A18-B65-C4; | A18-B65-C5; | A18-B65-C6; | A18-B65-C7; | A18-B65-C8; | A18-B65-C9; |
| A19-B65-C1; | A19-B65-C2; | A19-B65-C3; | A19-B65-C4; | A19-B65-C5; | A19-B65-C6; |
| A19-B65-C7; | A19-B65-C8; | A19-B65-C9; | A20-B65-C1; | A20-B65-C2; | A20-B65-C3; |
| A20-B65-C4; | A20-B65-C5; | A20-B65-C6; | A20-B65-C7; | A20-B65-C8; | A20-B65-C9; |
| A21-B65-C1; | A21-B65-C2; | A21-B65-C3; | A21-B65-C4; | A21-B65-C5; | A21-B65-C6; |
| A21-B65-C7; | A21-B65-C8; | A21-B65-C9; | A22-B65-C1; | A22-B65-C2; | A22-B65-C3; |
| A22-B65-C4; | A22-B65-C5; | A22-B65-C6; | A22-B65-C7; | A22-B65-C8; | A22-B65-C9; |
| A23-B65-C1; | A23-B65-C2; | A23-B65-C3; | A23-B65-C4; | A23-B65-C5; | A23-B65-C6; |
| A23-B65-C7; | A23-B65-C8; | A23-B65-C9; | A24-B65-C1; | A24-B65-C2; | A24-B65-C3; |
| A24-B65-C4; | A24-B65-C5; | A24-B65-C6; | A24-B65-C7; | A24-B65-C8; | A24-B65-C9; |
| A25-B65-C1; | A25-B65-C2; | A25-B65-C3; | A25-B65-C4; | A25-B65-C5; | A25-B65-C6; |
| A25-B65-C7; | A25-B65-C8; | A25-B65-C9; | A26-B65-C1; | A26-B65-C2; | A26-B65-C3; |
| A26-B65-C4; | A26-B65-C5; | A26-B65-C6; | A26-B65-C7; | A26-B65-C8; | A26-B65-C9; |
| A27-B65-C1; | A27-B65-C2; | A27-B65-C3; | A27-B65-C4; | A27-B65-C5; | A27-B65-C6; |
| A27-B65-C7; | A27-B65-C8; | A27-B65-C9; | A28-B65-C1; | A28-B65-C2; | A28-B65-C3; |
| A28-B65-C4; | A28-B65-C5; | A28-B65-C6; | A28-B65-C7; | A28-B65-C8; | A28-B65-C9; |
| A29-B65-C1; | A29-B65-C2; | A29-B65-C3; | A29-B65-C4; | A29-B65-C5; | A29-B65-C6; |
| A29-B65-C7; | A29-B65-C8; | A29-B65-C9; | A30-B65-C1; | A30-B65-C2; | A30-B65-C3; |
| A30-B65-C4; | A30-B65-C5; | A30-B65-C6; | A30-B65-C7; | A30-B65-C8; | A30-B65-C9; |
| A31-B65-C1; | A31-B65-C2; | A31-B65-C3; | A31-B65-C4; | A31-B65-C5; | A31-B65-C6; |
| A31-B65-C7; | A31-B65-C8; | A31-B65-C9; | A32-B65-C1; | A32-B65-C2; | A32-B65-C3; |
| A32-B65-C4; | A32-B65-C5; | A32-B65-C6; | A32-B65-C7; | A32-B65-C8; | A32-B65-C9; |
| A33-B65-C1; | A33-B65-C2; | A33-B65-C3; | A33-B65-C4; | A33-B65-C5; | A33-B65-C6; |
| A33-B65-C7; | A33-B65-C8; | A33-B65-C9; | A34-B65-C1; | A34-B65-C2; | A34-B65-C3; |
| A34-B65-C4; | A34-B65-C5; | A34-B65-C6; | A34-B65-C7; | A34-B65-C8; | A34-B65-C9; |
| A35-B65-C1; | A35-B65-C2; | A35-B65-C3; | A35-B65-C4; | A35-B65-C5; | A35-B65-C6; |
| A35-B65-C7; | A35-B65-C8; | A35-B65-C9; | A36-B65-C1; | A36-B65-C2; | A36-B65-C3; |
| A36-B65-C4; | A36-B65-C5; | A36-B65-C6; | A36-B65-C7; | A36-B65-C8; | A36-B65-C9; |
| A37-B65-C1; | A37-B65-C2; | A37-B65-C3; | A37-B65-C4; | A37-B65-C5; | A37-B65-C6; |
| A37-B65-C7; | A37-B65-C8; | A37-B65-C9; | A38-B65-C1; | A38-B65-C2; | A38-B65-C3; |
| A38-B65-C4; | A38-B65-C5; | A38-B65-C6; | A38-B65-C7; | A38-B65-C8; | A38-B65-C9; |
| A39-B65-C1; | A39-B65-C2; | A39-B65-C3; | A39-B65-C4; | A39-B65-C5; | A39-B65-C6; |
| A39-B65-C7; | A39-B65-C8; | A39-B65-C9; | A40-B65-C1; | A40-B65-C2; | A40-B65-C3; |
| A40-B65-C4; | A40-B65-C5; | A40-B65-C6; | A40-B65-C7; | A40-B65-C8; | A40-B65-C9; |
| A41-B65-C1; | A41-B65-C2; | A41-B65-C3; | A41-B65-C4; | A41-B65-C5; | A41-B65-C6; |
| A41-B65-C7; | A41-B65-C8; | A41-B65-C9; | A42-B65-C1; | A42-B65-C2; | A42-B65-C3; |
| A42-B65-C4; | A42-B65-C5; | A42-B65-C6; | A42-B65-C7; | A42-B65-C8; | A42-B65-C9; |
| A43-B65-C1; | A43-B65-C2; | A43-B65-C3; | A43-B65-C4; | A43-B65-C5; | A43-B65-C6; |
| A43-B65-C7; | A43-B65-C8; | A43-B65-C9; | A44-B65-C1; | A44-B65-C2; | A44-B65-C3; |
| A44-B65-C4; | A44-B65-C5; | A44-B65-C6; | A44-B65-C7; | A44-B65-C8; | A44-B65-C9; |
| A45-B65-C1; | A45-B65-C2; | A45-B65-C3; | A45-B65-C4; | A45-B65-C5; | A45-B65-C6; |
| A45-B65-C7; | A45-B65-C8; | A45-B65-C9; | A46-B65-C1; | A46-B65-C2; | A46-B65-C3; |
| A46-B65-C4; | A46-B65-C5; | A46-B65-C6; | A46-B65-C7; | A46-B65-C8; | A46-B65-C9; |
| A47-B65-C1; | A47-B65-C2; | A47-B65-C3; | A47-B65-C4; | A47-B65-C5; | A47-B65-C6; |
| A47-B65-C7; | A47-B65-C8; | A47-B65-C9; | A48-B65-C1; | A48-B65-C2; | A48-B65-C3; |
| A48-B65-C4; | A48-B65-C5; | A48-B65-C6; | A48-B65-C7; | A48-B65-C8; | A48-B65-C9; |
| A49-B65-C1; | A49-B65-C2; | A49-B65-C3; | A49-B65-C4; | A49-B65-C5; | A49-B65-C6; |
| A49-B65-C7; | A49-B65-C8; | A49-B65-C9; | A50-B65-C1; | A50-B65-C2; | A50-B65-C3; |
| A50-B65-C4; | A50-B65-C5; | A50-B65-C6; | A50-B65-C7; | A50-B65-C8; | A50-B65-C9; |
| A51-B65-C1; | A51-B65-C2; | A51-B65-C3; | A51-B65-C4; | A51-B65-C5; | A51-B65-C6; |
| A51-B65-C7; | A51-B65-C8; | A51-B65-C9; | A52-B65-C1; | A52-B65-C2; | A52-B65-C3; |
| A52-B65-C4; | A52-B65-C5; | A52-B65-C6; | A52-B65-C7; | A52-B65-C8; | A52-B65-C9; |
| A53-B65-C1; | A53-B65-C2; | A53-B65-C3; | A53-B65-C4; | A53-B65-C5; | A53-B65-C6; |
| A53-B65-C7; | A53-B65-C8; | A53-B65-C9; | A54-B65-C1; | A54-B65-C2; | A54-B65-C3; |
| A54-B65-C4; | A54-B65-C5; | A54-B65-C6; | A54-B65-C7; | A54-B65-C8; | A54-B65-C9; |
| A55-B65-C1; | A55-B65-C2; | A55-B65-C3; | A55-B65-C4; | A55-B65-C5; | A55-B65-C6; |
| A55-B65-C7; | A55-B65-C8; | A55-B65-C9; | A56-B65-C1; | A56-B65-C2; | A56-B65-C3; |
| A56-B65-C4; | A56-B65-C5; | A56-B65-C6; | A56-B65-C7; | A56-B65-C8; | A56-B65-C9; |

-continued

| | | | | | |
|---|---|---|---|---|---|
| A57-B65-C1; | A57-B65-C2; | A57-B65-C3; | A57-B65-C4; | A57-B65-C5; | A57-B65-C6; |
| A57-B65-C7; | A57-B65-C8; | A57-B65-C9; | A58-B65-C1; | A58-B65-C2; | A58-B65-C3; |
| A58-B65-C4; | A58-B65-C5; | A58-B65-C6; | A58-B65-C7; | A58-B65-C8; | A58-B65-C9; |
| A59-B65-C1; | A59-B65-C2; | A59-B65-C3; | A59-B65-C4; | A59-B65-C5; | A59-B65-C6; |
| A59-B65-C7; | A59-B65-C8; | A59-B65-C9; | A60-B65-C1; | A60-B65-C2; | A60-B65-C3; |
| A60-B65-C4; | A60-B65-C5; | A60-B65-C6; | A60-B65-C7; | A60-B65-C8; | A60-B65-C9; |
| A61-B65-C1; | A61-B65-C2; | A61-B65-C3; | A61-B65-C4; | A61-B65-C5; | A61-B65-C6; |
| A61-B65-C7; | A61-B65-C8; | A61-B65-C9; | A62-B65-C1; | A62-B65-C2; | A62-B65-C3; |
| A62-B65-C4; | A62-B65-C5; | A62-B65-C6; | A62-B65-C7; | A62-B65-C8; | A62-B65-C9; |
| A63-B65-C1; | A63-B65-C2; | A63-B65-C3; | A63-B65-C4; | A63-B65-C5; | A63-B65-C6; |
| A63-B65-C7; | A63-B65-C8; | A63-B65-C9; | A64-B65-C1; | A64-B65-C2; | A64-B65-C3; |
| A64-B65-C4; | A64-B65-C5; | A64-B65-C6; | A64-B65-C7; | A64-B65-C8; | A64-B65-C9; |
| A65-B65-C1; | A65-B65-C2; | A65-B65-C3; | A65-B65-C4; | A65-B65-C5; | A65-B65-C6; |
| A65-B65-C7; | A65-B65-C8; | A65-B65-C9; | A66-B65-C1; | A66-B65-C2; | A66-B65-C3; |
| A66-B65-C4; | A66-B65-C5; | A66-B65-C6; | A66-B65-C7; | A66-B65-C8; | A66-B65-C9; |
| A67-B65-C1; | A67-B65-C2; | A67-B65-C3; | A67-B65-C4; | A67-B65-C5; | A67-B65-C6; |
| A67-B65-C7; | A67-B65-C8; | A67-B65-C9; | A68-B65-C1; | A68-B65-C2; | A68-B65-C3; |
| A68-B65-C4; | A68-B65-C5; | A68-B65-C6; | A68-B65-C7; | A68-B65-C8; | A68-B65-C9; |
| A69-B65-C1; | A69-B65-C2; | A69-B65-C3; | A69-B65-C4; | A69-B65-C5; | A69-B65-C6; |
| A69-B65-C7; | A69-B65-C8; | A69-B65-C9; | A70-B65-C1; | A70-B65-C2; | A70-B65-C3; |
| A70-B65-C4; | A70-B65-C5; | A70-B65-C6; | A70-B65-C7; | A70-B65-C8; | A70-B65-C9; |
| A71-B65-C1; | A71-B65-C2; | A71-B65-C3; | A71-B65-C4; | A71-B65-C5; | A71-B65-C6; |
| A71-B65-C7; | A71-B65-C8; | A71-B65-C9; | A1-B66-C1; | A1-B66-C2; | A1-B66-C3; |
| A1-B66-C4; | A1-B66-C5; | A1-B66-C6; | A1-B66-C7; | A1-B66-C8; | A1-B66-C9; |
| A2-B66-C1; | A2-B66-C2; | A2-B66-C3; | A2-B66-C4; | A2-B66-C5; | A2-B66-C6; |
| A2-B66-C7; | A2-B66-C8; | A2-B66-C9; | A3-B66-C1; | A3-B66-C2; | A3-B66-C3; |
| A3-B66-C4; | A3-B66-C5; | A3-B66-C6; | A3-B66-C7; | A3-B66-C8; | A3-B66-C9; |
| A4-B66-C1; | A4-B66-C2; | A4-B66-C3; | A4-B66-C4; | A4-B66-C5; | A4-B66-C6; |
| A4-B66-C7; | A4-B66-C8; | A4-B66-C9; | A5-B66-C1; | A5-B66-C2; | A5-B66-C3; |
| A5-B66-C4; | A5-B66-C5; | A5-B66-C6; | A5-B66-C7; | A5-B66-C8; | A5-B66-C9; |
| A6-B66-C1; | A6-B66-C2; | A6-B66-C3; | A6-B66-C4; | A6-B66-C5; | A6-B66-C6; |
| A6-B66-C7; | A6-B66-C8; | A6-B66-C9; | A7-B66-C1; | A7-B66-C2; | A7-B66-C3; |
| A7-B66-C4; | A7-B66-C5; | A7-B66-C6; | A7-B66-C7; | A7-B66-C8; | A7-B66-C9; |
| A8-B66-C1; | A8-B66-C2; | A8-B66-C3; | A8-B66-C4; | A8-B66-C5; | A8-B66-C6; |
| A8-B66-C7; | A8-B66-C8; | A8-B66-C9; | A9-B66-C1; | A9-B66-C2; | A9-B66-C3; |
| A9-B66-C4; | A9-B66-C5; | A9-B66-C6; | | | |
| A10-B66-C1; | A10-B66-C2; | A10-B66-C3; | A10-B66-C4; | A10-B66-C5; | A10-B66-C6; |
| A10-B66-C7; | A10-B66-C8; | A10-B66-C9; | A11-B66-C1; | A11-B66-C2; | A11-B66-C3; |
| A11-B66-C4; | A11-B66-C5; | A11-B66-C6; | A11-B66-C7; | A11-B66-C8; | A11-B66-C9; |
| A12-B66-C1; | A12-B66-C2; | A12-B66-C3; | A12-B66-C4; | A12-B66-C5; | A12-B66-C6; |
| A12-B66-C7; | A12-B66-C8; | A12-B66-C9; | A13-B66-C1; | A13-B66-C2; | A13-B66-C3; |
| A13-B66-C4; | A13-B66-C5; | A13-B66-C6; | A13-B66-C7; | A13-B66-C8; | A13-B66-C9; |
| A14-B66-C1; | A14-B66-C2; | A14-B66-C3; | A14-B66-C4; | A14-B66-C5; | A14-B66-C6; |
| A14-B66-C7; | A14-B66-C8; | A14-B66-C9; | A15-B66-C1; | A15-B66-C2; | A15-B66-C3; |
| A15-B66-C4; | A15-B66-C5; | A15-B66-C6; | A15-B66-C7; | A15-B66-C8; | A15-B66-C9; |
| A16-B66-C1; | A16-B66-C2; | A16-B66-C3; | A16-B66-C4; | A16-B66-C5; | A16-B66-C6; |
| A16-B66-C7; | A16-B66-C8; | A16-B66-C9; | A17-B66-C1; | A17-B66-C2; | A17-B66-C3; |
| A17-B66-C4; | A17-B66-C5; | A17-B66-C6; | A17-B66-C7; | A17-B66-C8; | A17-B66-C9; |
| A18-B66-C1; | A18-B66-C2; | A18-B66-C3; | A18-B66-C4; | A18-B66-C5; | A18-B66-C6; |
| A18-B66-C7; | A18-B66-C8; | A18-B66-C9; | A19-B66-C1; | A19-B66-C2; | A19-B66-C3; |
| A19-B66-C4; | A19-B66-C5; | A19-B66-C6; | A19-B66-C7; | A19-B66-C8; | A19-B66-C9; |
| A20-B66-C1; | A20-B66-C2; | A20-B66-C3; | A20-B66-C4; | A20-B66-C5; | A20-B66-C6; |
| A20-B66-C7; | A20-B66-C8; | A20-B66-C9; | A21-B66-C1; | A21-B66-C2; | A21-B66-C3; |
| A21-B66-C4; | A21-B66-C5; | A21-B66-C6; | A21-B66-C7; | A21-B66-C8; | A21-B66-C9; |
| A22-B66-C1; | A22-B66-C2; | A22-B66-C3; | A22-B66-C4; | A22-B66-C5; | A22-B66-C6; |
| A22-B66-C7; | A22-B66-C8; | A22-B66-C9; | A23-B66-C1; | A23-B66-C2; | A23-B66-C3; |
| A23-B66-C4; | A23-B66-C5; | A23-B66-C6; | A23-B66-C7; | A23-B66-C8; | A23-B66-C9; |
| A24-B66-C1; | A24-B66-C2; | A24-B66-C3; | A24-B66-C4; | A24-B66-C5; | A24-B66-C6; |
| A24-B66-C7; | A24-B66-C8; | A24-B66-C9; | A25-B66-C1; | A25-B66-C2; | A25-B66-C3; |
| A25-B66-C4; | A25-B66-C5; | A25-B66-C6; | A25-B66-C7; | A25-B66-C8; | A25-B66-C9; |
| A26-B66-C1; | A26-B66-C2; | A26-B66-C3; | A26-B66-C4; | A26-B66-C5; | A26-B66-C6; |
| A26-B66-C7; | A26-B66-C8; | A26-B66-C9; | A27-B66-C1; | A27-B66-C2; | A27-B66-C3; |
| A27-B66-C4; | A27-B66-C5; | A27-B66-C6; | A27-B66-C7; | A27-B66-C8; | A27-B66-C9; |
| A28-B66-C1; | A28-B66-C2; | A28-B66-C3; | A28-B66-C4; | A28-B66-C5; | A28-B66-C6; |
| A28-B66-C7; | A28-B66-C8; | A28-B66-C9; | A29-B66-C1; | A29-B66-C2; | A29-B66-C3; |
| A29-B66-C4; | A29-B66-C5; | A29-B66-C6; | A29-B66-C7; | A29-B66-C8; | A29-B66-C9; |
| A30-B66-C1; | A30-B66-C2; | A30-B66-C3; | A30-B66-C4; | A30-B66-C5; | A30-B66-C6; |
| A30-B66-C7; | A30-B66-C8; | A30-B66-C9; | A31-B66-C1; | A31-B66-C2; | A31-B66-C3; |
| A31-B66-C4; | A31-B66-C5; | A31-B66-C6; | A31-B66-C7; | A31-B66-C8; | A31-B66-C9; |
| A32-B66-C1; | A32-B66-C2; | A32-B66-C3; | A32-B66-C4; | A32-B66-C5; | A32-B66-C6; |
| A32-B66-C7; | A32-B66-C8; | A32-B66-C9; | A33-B66-C1; | A33-B66-C2; | A33-B66-C3; |
| A33-B66-C4; | A33-B66-C5; | A33-B66-C6; | A33-B66-C7; | A33-B66-C8; | A33-B66-C9; |
| A34-B66-C1; | A34-B66-C2; | A34-B66-C3; | A34-B66-C4; | A34-B66-C5; | A34-B66-C6; |
| A34-B66-C7; | A34-B66-C8; | A34-B66-C9; | A35-B66-C1; | A35-B66-C2; | A35-B66-C3; |
| A35-B66-C4; | A35-B66-C5; | A35-B66-C6; | A35-B66-C7; | A35-B66-C8; | A35-B66-C9; |
| A36-B66-C1; | A36-B66-C2; | A36-B66-C3; | A36-B66-C4; | A36-B66-C5; | A36-B66-C6; |
| A36-B66-C7; | A36-B66-C8; | A36-B66-C9; | A37-B66-C1; | A37-B66-C2; | A37-B66-C3; |
| A37-B66-C4; | A37-B66-C5; | A37-B66-C6; | A37-B66-C7; | A37-B66-C8; | A37-B66-C9; |
| A38-B66-C1; | A38-B66-C2; | A38-B66-C3; | A38-B66-C4; | A38-B66-C5; | A38-B66-C6; |

-continued

| | | | | | |
|---|---|---|---|---|---|
| A38-B66-C7; | A38-B66-C8; | A38-B66-C9; | A39-B66-C1; | A39-B66-C2; | A39-B66-C3; |
| A39-B66-C4; | A39-B66-C5; | A39-B66-C6; | A39-B66-C7; | A39-B66-C8; | A39-B66-C9; |
| A40-B66-C1; | A40-B66-C2; | A40-B66-C3; | A40-B66-C4; | A40-B66-C5; | A40-B66-C6; |
| A40-B66-C7; | A40-B66-C8; | A40-B66-C9; | A41-B66-C1; | A41-B66-C2; | A41-B66-C3; |
| A41-B66-C4; | A41-B66-C5; | A41-B66-C6; | A41-B66-C7; | A41-B66-C8; | A41-B66-C9; |
| A42-B66-C1; | A42-B66-C2; | A42-B66-C3; | A42-B66-C4; | A42-B66-C5; | A42-B66-C6; |
| A42-B66-C7; | A42-B66-C8; | A42-B66-C9; | A43-B66-C1; | A43-B66-C2; | A43-B66-C3; |
| A43-B66-C4; | A43-B66-C5; | A43-B66-C6; | A43-B66-C7; | A43-B66-C8; | A43-B66-C9; |
| A44-B66-C1; | A44-B66-C2; | A44-B66-C3; | A44-B66-C4; | A44-B66-C5; | A44-B66-C6; |
| A44-B66-C7; | A44-B66-C8; | A44-B66-C9; | A45-B66-C1; | A45-B66-C2; | A45-B66-C3; |
| A45-B66-C4; | A45-B66-C5; | A45-B66-C6; | A45-B66-C7; | A45-B66-C8; | A45-B66-C9; |
| A46-B66-C1; | A46-B66-C2; | A46-B66-C3; | A46-B66-C4; | A46-B66-C5; | A46-B66-C6; |
| A46-B66-C7; | A46-B66-C8; | A46-B66-C9; | A47-B66-C1; | A47-B66-C2; | A47-B66-C3; |
| A47-B66-C4; | A47-B66-C5; | A47-B66-C6; | A47-B66-C7; | A47-B66-C8; | A47-B66-C9; |
| A48-B66-C1; | A48-B66-C2; | A48-B66-C3; | A48-B66-C4; | A48-B66-C5; | A48-B66-C6; |
| A48-B66-C7; | A48-B66-C8; | A48-B66-C9; | A49-B66-C1; | A49-B66-C2; | A49-B66-C3; |
| A49-B66-C4; | A49-B66-C5; | A49-B66-C6; | A49-B66-C7; | A49-B66-C8; | A49-B66-C9; |
| A50-B66-C1; | A50-B66-C2; | A50-B66-C3; | A50-B66-C4; | A50-B66-C5; | A50-B66-C6; |
| A50-B66-C7; | A50-B66-C8; | A50-B66-C9; | A51-B66-C1; | A51-B66-C2; | A51-B66-C3; |
| A51-B66-C4; | A51-B66-C5; | A51-B66-C6; | A51-B66-C7; | A51-B66-C8; | A51-B66-C9; |
| A52-B66-C1; | A52-B66-C2; | A52-B66-C3; | A52-B66-C4; | A52-B66-C5; | A52-B66-C6; |
| A52-B66-C7; | A52-B66-C8; | A52-B66-C9; | A53-B66-C1; | A53-B66-C2; | A53-B66-C3; |
| A53-B66-C4; | A53-B66-C5; | A53-B66-C6; | A53-B66-C7; | A53-B66-C8; | A53-B66-C9; |
| A54-B66-C1; | A54-B66-C2; | A54-B66-C3; | A54-B66-C4; | A54-B66-C5; | A54-B66-C6; |
| A54-B66-C7; | A54-B66-C8; | A54-B66-C9; | A55-B66-C1; | A55-B66-C2; | A55-B66-C3; |
| A55-B66-C4; | A55-B66-C5; | A55-B66-C6; | A55-B66-C7; | A55-B66-C8; | A55-B66-C9; |
| A56-B66-C1; | A56-B66-C2; | A56-B66-C3; | A56-B66-C4; | A56-B66-C5; | A56-B66-C6; |
| A56-B66-C7; | A56-B66-C8; | A56-B66-C9; | A57-B66-C1; | A57-B66-C2; | A57-B66-C3; |
| A57-B66-C4; | A57-B66-C5; | A57-B66-C6; | A57-B66-C7; | A57-B66-C8; | A57-B66-C9; |
| A58-B66-C1; | A58-B66-C2; | A58-B66-C3; | A58-B66-C4; | A58-B66-C5; | A58-B66-C6; |
| A58-B66-C7; | A58-B66-C8; | A58-B66-C9; | A59-B66-C1; | A59-B66-C2; | A59-B66-C3; |
| A59-B66-C4; | A59-B66-C5; | A59-B66-C6; | A59-B66-C7; | A59-B66-C8; | A59-B66-C9; |
| A60-B66-C1; | A60-B66-C2; | A60-B66-C3; | A60-B66-C4; | A60-B66-C5; | A60-B66-C6; |
| A60-B66-C7; | A60-B66-C8; | A60-B66-C9; | A61-B66-C1; | A61-B66-C2; | A61-B66-C3; |
| A61-B66-C4; | A61-B66-C5; | A61-B66-C6; | A61-B66-C7; | A61-B66-C8; | A61-B66-C9; |
| A62-B66-C1; | A62-B66-C2; | A62-B66-C3; | A62-B66-C4; | A62-B66-C5; | A62-B66-C6; |
| A62-B66-C7; | A62-B66-C8; | A62-B66-C9; | A63-B66-C1; | A63-B66-C2; | A63-B66-C3; |
| A63-B66-C4; | A63-B66-C5; | A63-B66-C6; | A63-B66-C7; | A63-B66-C8; | A63-B66-C9; |
| A64-B66-C1; | A64-B66-C2; | A64-B66-C3; | A64-B66-C4; | A64-B66-C5; | A64-B66-C6; |
| A64-B66-C7; | A64-B66-C8; | A64-B66-C9; | A65-B66-C1; | A65-B66-C2; | A65-B66-C3; |
| A65-B66-C4; | A65-B66-C5; | A65-B66-C6; | A65-B66-C7; | A65-B66-C8; | A65-B66-C9; |
| A66-B66-C1; | A66-B66-C2; | A66-B66-C3; | A66-B66-C4; | A66-B66-C5; | A66-B66-C6; |
| A66-B66-C7; | A66-B66-C8; | A66-B66-C9; | A67-B66-C1; | A67-B66-C2; | A67-B66-C3; |
| A67-B66-C4; | A67-B66-C5; | A67-B66-C6; | A67-B66-C7; | A67-B66-C8; | A67-B66-C9; |
| A68-B66-C1; | A68-B66-C2; | A68-B66-C3; | A68-B66-C4; | A68-B66-C5; | A68-B66-C6; |
| A68-B66-C7; | A68-B66-C8; | A68-B66-C9; | A69-B66-C1; | A69-B66-C2; | A69-B66-C3; |
| A69-B66-C4; | A69-B66-C5; | A69-B66-C6; | A69-B66-C7; | A69-B66-C8; | A69-B66-C9; |
| A70-B66-C1; | A70-B66-C2; | A70-B66-C3; | A70-B66-C4; | A70-B66-C5; | A70-B66-C6; |
| A70-B66-C7; | A70-B66-C8; | A70-B66-C9; | A71-B66-C1; | A71-B66-C2; | A71-B66-C3; |
| A71-B66-C4; | A71-B66-C5; | A71-B66-C6; | A71-B66-C7; | A71-B66-C8; | A71-B66-C9; |
| A1-B67-C1; | A1-B67-C2; | A1-B67-C3; | A1-B67-C4; | A1-B67-C5; | A1-B67-C6; |
| A1-B67-C7; | A1-B67-C8; | A1-B67-C9; | A2-B67-C1; | A2-B67-C2; | A2-B67-C3; |
| A2-B67-C4; | A2-B67-C5; | A2-B67-C6; | A2-B67-C7; | A2-B67-C8; | A2-B67-C9; |
| A3-B67-C1; | A3-B67-C2; | A3-B67-C3; | A3-B67-C4; | A3-B67-C5; | A3-B67-C6; |
| A3-B67-C7; | A3-B67-C8; | A3-B67-C9; | A4-B67-C1; | A4-B67-C2; | A4-B67-C3; |
| A4-B67-C4; | A4-B67-C5; | A4-B67-C6; | A4-B67-C7; | A4-B67-C8; | A4-B67-C9; |
| A5-B67-C1; | A5-B67-C2; | A5-B67-C3; | A5-B67-C4; | A5-B67-C5; | A5-B67-C6; |
| A5-B67-C7; | A5-B67-C8; | A5-B67-C9; | A6-B67-C1; | A6-B67-C2; | A6-B67-C3; |
| A6-B67-C4; | A6-B67-C5; | A6-B67-C6; | A6-B67-C7; | A6-B67-C8; | A6-B67-C9; |
| A7-B67-C1; | A7-B67-C2; | A7-B67-C3; | A7-B67-C4; | A7-B67-C5; | A7-B67-C6; |
| A7-B67-C7; | A7-B67-C8; | A7-B67-C9; | A8-B67-C1; | A8-B67-C2; | A8-B67-C3; |
| A8-B67-C4; | A8-B67-C5; | A8-B67-C6; | A8-B67-C7; | A8-B67-C8; | A8-B67-C9; |
| A9-B67-C1; | A9-B67-C2; | A9-B67-C3; | A9-B67-C4; | A9-B67-C5; | A9-B67-C6; |
| A9-B67-C7; | A9-B67-C8; | A9-B67-C9; | A10-B67-C1; | A10-B67-C2; | A10-B67-C3; |
| A10-B67-C4; | A10-B67-C5; | A10-B67-C6; | A10-B67-C7; | A10-B67-C8; | A10-B67-C9; |
| A11-B67-C1; | A11-B67-C2; | A11-B67-C3; | A11-B67-C4; | A11-B67-C5; | A11-B67-C6; |
| A11-B67-C7; | A11-B67-C8; | A11-B67-C9; | A12-B67-C1; | A12-B67-C2; | A12-B67-C3; |
| A12-B67-C4; | A12-B67-C5; | A12-B67-C6; | A12-B67-C7; | A12-B67-C8; | A12-B67-C9; |
| A13-B67-C1; | A13-B67-C2; | A13-B67-C3; | A13-B67-C4; | A13-B67-C5; | A13-B67-C6; |
| A13-B67-C7; | A13-B67-C8; | A13-B67-C9; | A14-B67-C1; | A14-B67-C2; | A14-B67-C3; |
| A14-B67-C4; | A14-B67-C5; | A14-B67-C6; | A14-B67-C7; | A14-B67-C8; | A14-B67-C9; |
| A15-B67-C1; | A15-B67-C2; | A15-B67-C3; | A15-B67-C4; | A15-B67-C5; | A15-B67-C6; |
| A15-B67-C7; | A15-B67-C8; | A15-B67-C9; | A16-B67-C1; | A16-B67-C2; | A16-B67-C3; |
| A16-B67-C4; | A16-B67-C5; | A16-B67-C6; | A16-B67-C7; | A16-B67-C8; | A16-B67-C9; |
| A17-B67-C1; | A17-B67-C2; | A17-B67-C3; | A17-B67-C4; | A17-B67-C5; | A17-B67-C6; |
| A17-B67-C7; | A17-B67-C8; | A17-B67-C9; | A18-B67-C1; | A18-B67-C2; | A18-B67-C3; |
| A18-B67-C4; | A18-B67-C5; | A18-B67-C6; | A18-B67-C7; | A18-B67-C8; | A18-B67-C9; |
| A19-B67-C1; | A19-B67-C2; | A19-B67-C3; | A19-B67-C4; | A19-B67-C5; | A19-B67-C6; |
| A19-B67-C7; | A19-B67-C8; | A19-B67-C9; | A20-B67-C1; | A20-B67-C2; | A20-B67-C3; |

-continued

| | | | | | |
|---|---|---|---|---|---|
| A20-B67-C4; | A20-B67-C5; | A20-B67-C6; | A20-B67-C7; | A20-B67-C8; | A20-B67-C9; |
| A21-B67-C1; | A21-B67-C2; | A21-B67-C3; | A21-B67-C4; | A21-B67-C5; | A21-B67-C6; |
| A21-B67-C7; | A21-B67-C8; | A21-B67-C9; | A22-B67-C1; | A22-B67-C2; | A22-B67-C3; |
| A22-B67-C4; | A22-B67-C5; | A22-B67-C6; | A22-B67-C7; | A22-B67-C8; | A22-B67-C9; |
| A23-B67-C1; | A23-B67-C2; | A23-B67-C3; | A23-B67-C4; | A23-B67-C5; | A23-B67-C6; |
| A23-B67-C7; | A23-B67-C8; | A23-B67-C9; | A24-B67-C1; | A24-B67-C2; | A24-B67-C3; |
| A24-B67-C4; | A24-B67-C5; | A24-B67-C6; | A24-B67-C7; | A24-B67-C8; | A24-B67-C9; |
| A25-B67-C1; | A25-B67-C2; | A25-B67-C3; | A25-B67-C4; | A25-B67-C5; | A25-B67-C6; |
| A25-B67-C7; | A25-B67-C8; | A25-B67-C9; | A26-B67-C1; | A26-B67-C2; | A26-B67-C3; |
| A26-B67-C4; | A26-B67-C5; | A26-B67-C6; | A26-B67-C7; | A26-B67-C8; | A26-B67-C9; |
| A27-B67-C1; | A27-B67-C2; | A27-B67-C3; | A27-B67-C4; | A27-B67-C5; | A27-B67-C6; |
| A27-B67-C7; | A27-B67-C8; | A27-B67-C9; | A28-B67-C1; | A28-B67-C2; | A28-B67-C3; |
| A28-B67-C4; | A28-B67-C5; | A28-B67-C6; | A28-B67-C7; | A28-B67-C8; | A28-B67-C9; |
| A29-B67-C1; | A29-B67-C2; | A29-B67-C3; | A29-B67-C4; | A29-B67-C5; | A29-B67-C6; |
| A29-B67-C7; | A29-B67-C8; | A29-B67-C9; | A30-B67-C1; | A30-B67-C2; | A30-B67-C3; |
| A30-B67-C4; | A30-B67-C5; | A30-B67-C6; | A30-B67-C7; | A30-B67-C8; | A30-B67-C9; |
| A31-B67-C1; | A31-B67-C2; | A31-B67-C3; | A31-B67-C4; | A31-B67-C5; | A31-B67-C6; |
| A31-B67-C7; | A31-B67-C8; | A31-B67-C9; | A32-B67-C1; | A32-B67-C2; | A32-B67-C3; |
| A32-B67-C4; | A32-B67-C5; | A32-B67-C6; | A32-B67-C7; | A32-B67-C8; | A32-B67-C9; |
| A33-B67-C1; | A33-B67-C2; | A33-B67-C3; | A33-B67-C4; | A33-B67-C5; | A33-B67-C6; |
| A33-B67-C7; | A33-B67-C8; | A33-B67-C9; | A34-B67-C1; | A34-B67-C2; | A34-B67-C3; |
| A34-B67-C4; | A34-B67-C5; | A34-B67-C6; | A34-B67-C7; | A34-B67-C8; | A34-B67-C9; |
| A35-B67-C1; | A35-B67-C2; | A35-B67-C3; | A35-B67-C4; | A35-B67-C5; | A35-B67-C6; |
| A35-B67-C7; | A35-B67-C8; | A35-B67-C9; | A36-B67-C1; | A36-B67-C2; | A36-B67-C3; |
| A36-B67-C4; | A36-B67-C5; | A36-B67-C6; | A36-B67-C7; | A36-B67-C8; | A36-B67-C9; |
| A37-B67-C1; | A37-B67-C2; | A37-B67-C3; | A37-B67-C4; | A37-B67-C5; | A37-B67-C6; |
| A37-B67-C7; | A37-B67-C8; | A37-B67-C9; | A38-B67-C1; | A38-B67-C2; | A38-B67-C3; |
| A38-B67-C4; | A38-B67-C5; | A38-B67-C6; | A38-B67-C7; | A38-B67-C8; | A38-B67-C9; |
| A39-B67-C1; | A39-B67-C2; | A39-B67-C3; | A39-B67-C4; | A39-B67-C5; | A39-B67-C6; |
| A39-B67-C7; | A39-B67-C8; | A39-B67-C9; | A40-B67-C1; | A40-B67-C2; | A40-B67-C3; |
| A40-B67-C4; | A40-B67-C5; | A40-B67-C6; | A40-B67-C7; | A40-B67-C8; | A40-B67-C9; |
| A41-B67-C1; | A41-B67-C2; | A41-B67-C3; | A41-B67-C4; | A41-B67-C5; | A41-B67-C6; |
| A41-B67-C7; | A41-B67-C8; | A41-B67-C9; | A42-B67-C1; | A42-B67-C2; | A42-B67-C3; |
| A42-B67-C4; | A42-B67-C5; | A42-B67-C6; | A42-B67-C7; | A42-B67-C8; | A42-B67-C9; |
| A43-B67-C1; | A43-B67-C2; | A43-B67-C3; | A43-B67-C4; | A43-B67-C5; | A43-B67-C6; |
| A43-B67-C7; | A43-B67-C8; | A43-B67-C9; | A44-B67-C1; | A44-B67-C2; | A44-B67-C3; |
| A44-B67-C4; | A44-B67-C5; | A44-B67-C6; | A44-B67-C7; | A44-B67-C8; | A44-B67-C9; |
| A45-B67-C1; | A45-B67-C2; | A45-B67-C3; | A45-B67-C4; | A45-B67-C5; | A45-B67-C6; |
| A45-B67-C7; | A45-B67-C8; | A45-B67-C9; | A46-B67-C1; | A46-B67-C2; | A46-B67-C3; |
| A46-B67-C4; | A46-B67-C5; | A46-B67-C6; | A46-B67-C7; | A46-B67-C8; | A46-B67-C9; |
| A47-B67-C1; | A47-B67-C2; | A47-B67-C3; | A47-B67-C4; | A47-B67-C5; | A47-B67-C6; |
| A47-B67-C7; | A47-B67-C8; | A47-B67-C9; | A48-B67-C1; | A48-B67-C2; | A48-B67-C3; |
| A48-B67-C4; | A48-B67-C5; | A48-B67-C6; | A48-B67-C7; | A48-B67-C8; | A48-B67-C9; |
| A49-B67-C1; | A49-B67-C2; | A49-B67-C3; | A49-B67-C4; | A49-B67-C5; | A49-B67-C6; |
| A49-B67-C7; | A49-B67-C8; | A49-B67-C9; | A50-B67-C1; | A50-B67-C2; | A50-B67-C3; |
| A50-B67-C4; | A50-B67-C5; | A50-B67-C6; | A50-B67-C7; | A50-B67-C8; | A50-B67-C9; |
| A51-B67-C1; | A51-B67-C2; | A51-B67-C3; | A51-B67-C4; | A51-B67-C5; | A51-B67-C6; |
| A51-B67-C7; | A51-B67-C8; | A51-B67-C9; | A52-B67-C1; | A52-B67-C2; | A52-B67-C3; |
| A52-B67-C4; | A52-B67-C5; | A52-B67-C6; | A52-B67-C7; | A52-B67-C8; | A52-B67-C9; |
| A53-B67-C1; | A53-B67-C2; | A53-B67-C3; | A53-B67-C4; | A53-B67-C5; | A53-B67-C6; |
| A53-B67-C7; | A53-B67-C8; | A53-B67-C9; | A54-B67-C1; | A54-B67-C2; | A54-B67-C3; |
| A54-B67-C4; | A54-B67-C5; | A54-B67-C6; | A54-B67-C7; | A54-B67-C8; | A54-B67-C9; |
| A55-B67-C1; | A55-B67-C2; | A55-B67-C3; | A55-B67-C4; | A55-B67-C5; | A55-B67-C6; |
| A55-B67-C7; | A55-B67-C8; | A55-B67-C9; | A56-B67-C1; | A56-B67-C2; | A56-B67-C3; |
| A56-B67-C4; | A56-B67-C5; | A56-B67-C6; | A56-B67-C7; | A56-B67-C8; | A56-B67-C9; |
| A57-B67-C1; | A57-B67-C2; | A57-B67-C3; | A57-B67-C4; | A57-B67-C5; | A57-B67-C6; |
| A57-B67-C7; | A57-B67-C8; | A57-B67-C9; | A58-B67-C1; | A58-B67-C2; | A58-B67-C3; |
| A58-B67-C4; | A58-B67-C5; | A58-B67-C6; | A58-B67-C7; | A58-B67-C8; | A58-B67-C9; |
| A59-B67-C1; | A59-B67-C2; | A59-B67-C3; | A59-B67-C4; | A59-B67-C5; | A59-B67-C6; |
| A59-B67-C7; | A59-B67-C8; | A59-B67-C9; | A60-B67-C1; | A60-B67-C2; | A60-B67-C3; |
| A60-B67-C4; | A60-B67-C5; | A60-B67-C6; | A60-B67-C7; | A60-B67-C8; | A60-B67-C9; |
| A61-B67-C1; | A61-B67-C2; | A61-B67-C3; | A61-B67-C4; | A61-B67-C5; | A61-B67-C6; |
| A61-B67-C7; | A61-B67-C8; | A61-B67-C9; | A62-B67-C1; | A62-B67-C2; | A62-B67-C3; |
| A62-B67-C4; | A62-B67-C5; | A62-B67-C6; | A62-B67-C7; | A62-B67-C8; | A62-B67-C9; |
| A63-B67-C1; | A63-B67-C2; | A63-B67-C3; | A63-B67-C4; | A63-B67-C5; | A63-B67-C6; |
| A63-B67-C7; | A63-B67-C8; | A63-B67-C9; | A64-B67-C1; | A64-B67-C2; | A64-B67-C3; |
| A64-B67-C4; | A64-B67-C5; | A64-B67-C6; | A64-B67-C7; | A64-B67-C8; | A64-B67-C9; |
| A65-B67-C1; | A65-B67-C2; | A65-B67-C3; | A65-B67-C4; | A65-B67-C5; | A65-B67-C6; |
| A65-B67-C7; | A65-B67-C8; | A65-B67-C9; | A66-B67-C1; | A66-B67-C2; | A66-B67-C3; |
| A66-B67-C4; | A66-B67-C5; | A66-B67-C6; | A66-B67-C7; | A66-B67-C8; | A66-B67-C9; |
| A67-B67-C1; | A67-B67-C2; | A67-B67-C3; | A67-B67-C4; | A67-B67-C5; | A67-B67-C6; |
| A67-B67-C7; | A67-B67-C8; | A67-B67-C9; | A68-B67-C1; | A68-B67-C2; | A68-B67-C3; |
| A68-B67-C4; | A68-B67-C5; | A68-B67-C6; | A68-B67-C7; | A68-B67-C8; | A68-B67-C9; |
| A69-B67-C1; | A69-B67-C2; | A69-B67-C3; | A69-B67-C4; | A69-B67-C5; | A69-B67-C6; |
| A69-B67-C7; | A69-B67-C8; | A69-B67-C9; | A70-B67-C1; | A70-B67-C2; | A70-B67-C3; |
| A70-B67-C4; | A70-B67-C5; | A70-B67-C6; | A70-B67-C7; | A70-B67-C8; | A70-B67-C9; |
| A71-B67-C1; | A71-B67-C2; | A71-B67-C3; | A71-B67-C4; | A71-B67-C5; | A71-B67-C6; |
| A71-B67-C7; | A71-B67-C8; | A71-B67-C9; | A1-B68-C1; | A1-B68-C2; | A1-B68-C3; |
| A1-B68-C4; | A1-B68-C5; | A1-B68-C6; | A1-B68-C7; | A1-B68-C8; | A1-B68-C9; |

-continued

| | | | | | |
|---|---|---|---|---|---|
| A2-B68-C1; | A2-B68-C2; | A2-B68-C3; | A2-B68-C4; | A2-B68-C5; | A2-B68-C6; |
| A2-B68-C7; | A2-B68-C8; | A2-B68-C9; | A3-B68-C1; | A3-B68-C2; | A3-B68-C3; |
| A3-B68-C4; | A3-B68-C5; | A3-B68-C6; | A3-B68-C7; | A3-B68-C8; | A3-B68-C9; |
| A4-B68-C1; | A4-B68-C2; | A4-B68-C3; | A4-B68-C4; | A4-B68-C5; | A4-B68-C6; |
| A4-B68-C7; | A4-B68-C8; | A4-B68-C9; | A5-B68-C1; | A5-B68-C2; | A5-B68-C3; |
| A5-B68-C4; | A5-B68-C5; | A5-B68-C6; | A5-B68-C7; | A5-B68-C8; | A5-B68-C9; |
| A6-B68-C1; | A6-B68-C2; | A6-B68-C3; | A6-B68-C4; | A6-B68-C5; | A6-B68-C6; |
| A6-B68-C7; | A6-B68-C8; | A6-B68-C9; | A7-B68-C1; | A7-B68-C2; | A7-B68-C3; |
| A7-B68-C4; | A7-B68-C5; | A7-B68-C6; | A7-B68-C7; | A7-B68-C8; | A7-B68-C9; |
| A8-B68-C1; | A8-B68-C2; | A8-B68-C3; | A8-B68-C4; | A8-B68-C5; | A8-B68-C6; |
| A8-B68-C7; | A8-B68-C8; | A8-B68-C9; | A9-B68-C1; | A9-B68-C2; | A9-B68-C3; |
| A9-B68-C4; | A9-B68-C5; | A9-B68-C6; | A9-B68-C7; | A9-B68-C8; | A9-B68-C9; |
| A10-B68-C1; | A10-B68-C2; | A10-B68-C3; | A10-B68-C4; | A10-B68-C5; | A10-B68-C6; |
| A10-B68-C7; | A10-B68-C8; | A10-B68-C9; | A11-B68-C1; | A11-B68-C2; | A11-B68-C3; |
| A11-B68-C4; | A11-B68-C5; | A11-B68-C6; | A11-B68-C7; | A11-B68-C8; | A11-B68-C9; |
| A12-B68-C1; | A12-B68-C2; | A12-B68-C3; | A12-B68-C4; | A12-B68-C5; | A12-B68-C6; |
| A12-B68-C7; | A12-B68-C8; | A12-B68-C9; | A13-B68-C1; | A13-B68-C2; | A13-B68-C3; |
| A13-B68-C4; | A13-B68-C5; | A13-B68-C6; | A13-B68-C7; | A13-B68-C8; | A13-B68-C9; |
| A14-B68-C1; | A14-B68-C2; | A14-B68-C3; | A14-B68-C4; | A14-B68-C5; | A14-B68-C6; |
| A14-B68-C7; | A14-B68-C8; | A14-B68-C9; | A15-B68-C1; | A15-B68-C2; | A15-B68-C3; |
| A15-B68-C4; | A15-B68-C5; | A15-B68-C6; | A15-B68-C7; | A15-B68-C8; | A15-B68-C9; |
| A16-B68-C1; | A16-B68-C2; | A16-B68-C3; | A16-B68-C4; | A16-B68-C5; | A16-B68-C6; |
| A16-B68-C7; | A16-B68-C8; | A16-B68-C9; | A17-B68-C1; | A17-B68-C2; | A17-B68-C3; |
| A17-B68-C4; | A17-B68-C5; | A17-B68-C6; | A17-B68-C7; | A17-B68-C8; | A17-B68-C9; |
| A18-B68-C1; | A18-B68-C2; | A18-B68-C3; | A18-B68-C4; | A18-B68-C5; | A18-B68-C6; |
| A18-B68-C7; | A18-B68-C8; | A18-B68-C9; | A19-B68-C1; | A19-B68-C2; | A19-B68-C3; |
| A19-B68-C4; | A19-B68-C5; | A19-B68-C6; | A19-B68-C7; | A19-B68-C8; | A19-B68-C9; |
| A20-B68-C1; | A20-B68-C2; | A20-B68-C3; | A20-B68-C4; | A20-B68-C5; | A20-B68-C6; |
| A20-B68-C7; | A20-B68-C8; | A20-B68-C9; | A21-B68-C1; | A21-B68-C2; | A21-B68-C3; |
| A21-B68-C4; | A21-B68-C5; | A21-B68-C6; | A21-B68-C7; | A21-B68-C8; | A21-B68-C9; |
| A22-B68-C1; | A22-B68-C2; | A22-B68-C3; | A22-B68-C4; | A22-B68-C5; | A22-B68-C6; |
| A22-B68-C7; | A22-B68-C8; | A22-B68-C9; | A23-B68-C1; | A23-B68-C2; | A23-B68-C3; |
| A23-B68-C4; | A23-B68-C5; | A23-B68-C6; | A23-B68-C7; | A23-B68-C8; | A23-B68-C9; |
| A24-B68-C1; | A24-B68-C2; | A24-B68-C3; | A24-B68-C4; | A24-B68-C5; | A24-B68-C6; |
| A24-B68-C7; | A24-B68-C8; | A24-B68-C9; | A25-B68-C1; | A25-B68-C2; | A25-B68-C3; |
| A25-B68-C4; | A25-B68-C5; | A25-B68-C6; | A25-B68-C7; | A25-B68-C8; | A25-B68-C9; |
| A26-B68-C1; | A26-B68-C2; | A26-B68-C3; | A26-B68-C4; | A26-B68-C5; | A26-B68-C6; |
| A26-B68-C7; | A26-B68-C8; | A26-B68-C9; | A27-B68-C1; | A27-B68-C2; | A27-B68-C3; |
| A27-B68-C4; | A27-B68-C5; | A27-B68-C6; | A27-B68-C7; | A27-B68-C8; | A27-B68-C9; |
| A28-B68-C1; | A28-B68-C2; | A28-B68-C3; | A28-B68-C4; | A28-B68-C5; | A28-B68-C6; |
| A28-B68-C7; | A28-B68-C8; | A28-B68-C9; | A29-B68-C1; | A29-B68-C2; | A29-B68-C3; |
| A29-B68-C4; | A29-B68-C5; | A29-B68-C6; | A29-B68-C7; | A29-B68-C8; | A29-B68-C9; |
| A30-B68-C1; | A30-B68-C2; | A30-B68-C3; | A30-B68-C4; | A30-B68-C5; | A30-B68-C6; |
| A30-B68-C7; | A30-B68-C8; | A30-B68-C9; | A31-B68-C1; | A31-B68-C2; | A31-B68-C3; |
| A31-B68-C4; | A31-B68-C5; | A31-B68-C6; | A31-B68-C7; | A31-B68-C8; | A31-B68-C9; |
| A32-B68-C1; | A32-B68-C2; | A32-B68-C3; | A32-B68-C4; | A32-B68-C5; | A32-B68-C6; |
| A32-B68-C7; | A32-B68-C8; | A32-B68-C9; | A33-B68-C1; | A33-B68-C2; | A33-B68-C3; |
| A33-B68-C4; | A33-B68-C5; | A33-B68-C6; | A33-B68-C7; | A33-B68-C8; | A33-B68-C9; |
| A34-B68-C1; | A34-B68-C2; | A34-B68-C3; | A34-B68-C4; | A34-B68-C5; | A34-B68-C6; |
| A34-B68-C7; | A34-B68-C8; | A34-B68-C9; | A35-B68-C1; | A35-B68-C2; | A35-B68-C3; |
| A35-B68-C4; | A35-B68-C5; | A35-B68-C6; | A35-B68-C7; | A35-B68-C8; | A35-B68-C9; |
| A36-B68-C1; | A36-B68-C2; | A36-B68-C3; | A36-B68-C4; | A36-B68-C5; | A36-B68-C6; |
| A36-B68-C7; | A36-B68-C8; | A36-B68-C9; | A37-B68-C1; | A37-B68-C2; | A37-B68-C3; |
| A37-B68-C4; | A37-B68-C5; | A37-B68-C6; | A37-B68-C7; | A37-B68-C8; | A37-B68-C9; |
| A38-B68-C1; | A38-B68-C2; | A38-B68-C3; | A38-B68-C4; | A38-B68-C5; | A38-B68-C6; |
| A38-B68-C7; | A38-B68-C8; | A38-B68-C9; | A39-B68-C1; | A39-B68-C2; | A39-B68-C3; |
| A39-B68-C4; | A39-B68-C5; | A39-B68-C6; | A39-B68-C7; | A39-B68-C8; | A39-B68-C9; |
| A40-B68-C1; | A40-B68-C2; | A40-B68-C3; | A40-B68-C4; | A40-B68-C5; | A40-B68-C6; |
| A40-B68-C7; | A40-B68-C8; | A40-B68-C9; | A41-B68-C1; | A41-B68-C2; | A41-B68-C3; |
| A41-B68-C4; | A41-B68-C5; | A41-B68-C6; | A41-B68-C7; | A41-B68-C8; | A41-B68-C9; |
| A42-B68-C1; | A42-B68-C2; | A42-B68-C3; | A42-B68-C4; | A42-B68-C5; | A42-B68-C6; |
| A42-B68-C7; | A42-B68-C8; | A42-B68-C9; | A43-B68-C1; | A43-B68-C2; | A43-B68-C3; |
| A43-B68-C4; | A43-B68-C5; | A43-B68-C6; | A43-B68-C7; | A43-B68-C8; | A43-B68-C9; |
| A44-B68-C1; | A44-B68-C2; | A44-B68-C3; | A44-B68-C4; | A44-B68-C5; | A44-B68-C6; |
| A44-B68-C7; | A44-B68-C8; | A44-B68-C9; | A45-B68-C1; | A45-B68-C2; | A45-B68-C3; |
| A45-B68-C4; | A45-B68-C5; | A45-B68-C6; | A45-B68-C7; | A45-B68-C8; | A45-B68-C9; |
| A46-B68-C1; | A46-B68-C2; | A46-B68-C3; | A46-B68-C4; | A46-B68-C5; | A46-B68-C6; |
| A46-B68-C7; | A46-B68-C8; | A46-B68-C9; | A47-B68-C1; | A47-B68-C2; | A47-B68-C3; |
| A47-B68-C4; | A47-B68-C5; | A47-B68-C6; | A47-B68-C7; | A47-B68-C8; | A47-B68-C9; |
| A48-B68-C1; | A48-B68-C2; | A48-B68-C3; | A48-B68-C4; | A48-B68-C5; | A48-B68-C6; |
| A48-B68-C7; | A48-B68-C8; | A48-B68-C9; | A49-B68-C1; | A49-B68-C2; | A49-B68-C3; |
| A49-B68-C4; | A49-B68-C5; | A49-B68-C6; | A49-B68-C7; | A49-B68-C8; | A49-B68-C9; |
| A50-B68-C1; | A50-B68-C2; | A50-B68-C3; | A50-B68-C4; | A50-B68-C5; | A50-B68-C6; |
| A50-B68-C7; | A50-B68-C8; | A50-B68-C9; | A51-B68-C1; | A51-B68-C2; | A51-B68-C3; |
| A51-B68-C4; | A51-B68-C5; | A51-B68-C6; | A51-B68-C7; | A51-B68-C8; | A51-B68-C9; |
| A52-B68-C1; | A52-B68-C2; | A52-B68-C3; | A52-B68-C4; | A52-B68-C5; | A52-B68-C6; |
| A52-B68-C7; | A52-B68-C8; | A52-B68-C9; | A53-B68-C1; | A53-B68-C2; | A53-B68-C3; |
| A53-B68-C4; | A53-B68-C5; | A53-B68-C6; | A53-B68-C7; | A53-B68-C8; | A53-B68-C9; |
| A54-B68-C1; | A54-B68-C2; | A54-B68-C3; | A54-B68-C4; | A54-B68-C5; | A54-B68-C6; |

| | | | | | |
|---|---|---|---|---|---|
| A54-B68-C7; | A54-B68-C8; | A54-B68-C9; | A55-B68-C1; | A55-B68-C2; | A55-B68-C3; |
| A55-B68-C4; | A55-B68-C5; | A55-B68-C6; | A55-B68-C7; | A55-B68-C8; | A55-B68-C9; |
| A56-B68-C1; | A56-B68-C2; | A56-B68-C3; | A56-B68-C4; | A56-B68-C5; | A56-B68-C6; |
| A56-B68-C7; | A56-B68-C8; | A56-B68-C9; | A57-B68-C1; | A57-B68-C2; | A57-B68-C3; |
| A57-B68-C4; | A57-B68-C5; | A57-B68-C6; | A57-B68-C7; | A57-B68-C8; | A57-B68-C9; |
| A58-B68-C1; | A58-B68-C2; | A58-B68-C3; | A58-B68-C4; | A58-B68-C5; | A58-B68-C6; |
| A58-B68-C7; | A58-B68-C8; | A58-B68-C9; | A59-B68-C1; | A59-B68-C2; | A59-B68-C3; |
| A59-B68-C4; | A59-B68-C5; | A59-B68-C6; | A59-B68-C7; | A59-B68-C8; | A59-B68-C9; |
| A60-B68-C1; | A60-B68-C2; | A60-B68-C3; | A60-B68-C4; | A60-B68-C5; | A60-B68-C6; |
| A60-B68-C7; | A60-B68-C8; | A60-B68-C9; | A61-B68-C1; | A61-B68-C2; | A61-B68-C3; |
| A61-B68-C4; | A61-B68-C5; | A61-B68-C6; | A61-B68-C7; | A61-B68-C8; | A61-B68-C9; |
| A62-B68-C1; | A62-B68-C2; | A62-B68-C3; | A62-B68-C4; | A62-B68-C5; | A62-B68-C6; |
| A62-B68-C7; | A62-B68-C8; | A62-B68-C9; | A63-B68-C1; | A63-B68-C2; | A63-B68-C3; |
| A63-B68-C4; | A63-B68-C5; | A63-B68-C6; | A63-B68-C7; | A63-B68-C8; | A63-B68-C9; |
| A64-B68-C1; | A64-B68-C2; | A64-B68-C3; | A64-B68-C4; | A64-B68-C5; | A64-B68-C6; |
| A64-B68-C7; | A64-B68-C8; | A64-B68-C9; | A65-B68-C1; | A65-B68-C2; | A65-B68-C3; |
| A65-B68-C4; | A65-B68-C5; | A65-B68-C6; | A65-B68-C7; | A65-B68-C8; | A65-B68-C9; |
| A66-B68-C1; | A66-B68-C2; | A66-B68-C3; | A66-B68-C4; | A66-B68-C5; | A66-B68-C6; |
| A66-B68-C7; | A66-B68-C8; | A66-B68-C9; | A67-B68-C1; | A67-B68-C2; | A67-B68-C3; |
| A67-B68-C4; | A67-B68-C5; | A67-B68-C6; | A67-B68-C7; | A67-B68-C8; | A67-B68-C9; |
| A68-B68-C1; | A68-B68-C2; | A68-B68-C3; | A68-B68-C4; | A68-B68-C5; | A68-B68-C6; |
| A68-B68-C7; | A68-B68-C8; | A68-B68-C9; | A69-B68-C1; | A69-B68-C2; | A69-B68-C3; |
| A69-B68-C4; | A69-B68-C5; | A69-B68-C6; | A69-B68-C7; | A69-B68-C8; | A69-B68-C9; |
| A70-B68-C1; | A70-B68-C2; | A70-B68-C3; | A70-B68-C4; | A70-B68-C5; | A70-B68-C6; |
| A70-B68-C7; | A70-B68-C8; | A70-B68-C9; | A71-B68-C1; | A71-B68-C2; | A71-B68-C3; |
| A71-B68-C4; | A71-B68-C5; | A71-B68-C6; | A71-B68-C7; | A71-B68-C8; | A71-B68-C9; |
| A1-B69-C1; | A1-B69-C2; | A1-B69-C3; | A1-B69-C4; | A1-B69-C5; | A1-B69-C6; |
| A1-B69-C7; | A1-B69-C8; | A1-B69-C9; | A2-B69-C1; | A2-B69-C2; | A2-B69-C3; |
| A2-B69-C4; | A2-B69-C5; | A2-B69-C6; | A2-B69-C7; | A2-B69-C8; | A2-B69-C9; |
| A3-B69-C1; | A3-B69-C2; | A3-B69-C3; | A3-B69-C4; | A3-B69-C5; | A3-B69-C6; |
| A3-B69-C7; | A3-B69-C8; | A3-B69-C9; | A4-B69-C1; | A4-B69-C2; | A4-B69-C3; |
| A4-B69-C4; | A4-B69-C5; | A4-B69-C6; | A4-B69-C7; | A4-B69-C8; | A4-B69-C9; |
| A5-B69-C1; | A5-B69-C2; | A5-B69-C3; | A5-B69-C4; | A5-B69-C5; | A5-B69-C6; |
| A5-B69-C7; | A5-B69-C8; | A5-B69-C9; | A6-B69-C1; | A6-B69-C2; | A6-B69-C3; |
| A6-B69-C4; | A6-B69-C5; | A6-B69-C6; | A6-B69-C7; | A6-B69-C8; | A6-B69-C9; |
| A7-B69-C1; | A7-B69-C2; | A7-B69-C3; | A7-B69-C4; | A7-B69-C5; | A7-B69-C6; |
| A7-B69-C7; | A7-B69-C8; | A7-B69-C9; | A8-B69-C1; | A8-B69-C2; | A8-B69-C3; |
| A8-B69-C4; | A8-B69-C5; | A8-B69-C6; | A8-B69-C7; | A8-B69-C8; | A8-B69-C9; |
| A9-B69-C1; | A9-B69-C2; | A9-B69-C3; | A9-B69-C4; | A9-B69-C5; | A9-B69-C6; |
| A9-B69-C7; | A9-B69-C8; | A9-B69-C9; | A10-B69-C1; | A10-B69-C2; | A10-B69-C3; |
| A10-B69-C4; | A10-B69-C5; | A10-B69-C6; | A10-B69-C7; | A10-B69-C8; | A10-B69-C9; |
| A11-B69-C1; | A11-B69-C2; | A11-B69-C3; | A11-B69-C4; | A11-B69-C5; | A11-B69-C6; |
| A11-B69-C7; | A11-B69-C8; | A11-B69-C9; | A12-B69-C1; | A12-B69-C2; | A12-B69-C3; |
| A12-B69-C4; | A12-B69-C5; | A12-B69-C6; | A12-B69-C7; | A12-B69-C8; | A12-B69-C9; |
| A13-B69-C1; | A13-B69-C2; | A13-B69-C3; | A13-B69-C4; | A13-B69-C5; | A13-B69-C6; |
| A13-B69-C7; | A13-B69-C8; | A13-B69-C9; | A14-B69-C1; | A14-B69-C2; | A14-B69-C3; |
| A14-B69-C4; | A14-B69-C5; | A14-B69-C6; | A14-B69-C7; | A14-B69-C8; | A14-B69-C9; |
| A15-B69-C1; | A15-B69-C2; | A15-B69-C3; | A15-B69-C4; | A15-B69-C5; | A15-B69-C6; |
| A15-B69-C7; | A15-B69-C8; | A15-B69-C9; | A16-B69-C1; | A16-B69-C2; | A16-B69-C3; |
| A16-B69-C4; | A16-B69-C5; | A16-B69-C6; | A16-B69-C7; | A16-B69-C8; | A16-B69-C9; |
| A17-B69-C1; | A17-B69-C2; | A17-B69-C3; | A17-B69-C4; | A17-B69-C5; | A17-B69-C6; |
| A17-B69-C7; | A17-B69-C8; | A17-B69-C9; | A18-B69-C1; | A18-B69-C2; | A18-B69-C3; |
| A18-B69-C4; | A18-B69-C5; | A18-B69-C6; | A18-B69-C7; | A18-B69-C8; | A18-B69-C9; |
| A19-B69-C1; | A19-B69-C2; | A19-B69-C3; | A19-B69-C4; | A19-B69-C5; | A19-B69-C6; |
| A19-B69-C7; | A19-B69-C8; | A19-B69-C9; | A20-B69-C1; | A20-B69-C2; | A20-B69-C3; |
| A20-B69-C4; | A20-B69-C5; | A20-B69-C6; | A20-B69-C7; | A20-B69-C8; | A20-B69-C9; |
| A21-B69-C1; | A21-B69-C2; | A21-B69-C3; | A21-B69-C4; | A21-B69-C5; | A21-B69-C6; |
| A21-B69-C7; | A21-B69-C8; | A21-B69-C9; | A22-B69-C1; | A22-B69-C2; | A22-B69-C3; |
| A22-B69-C4; | A22-B69-C5; | A22-B69-C6; | A22-B69-C7; | A22-B69-C8; | A22-B69-C9; |
| A23-B69-C1; | A23-B69-C2; | A23-B69-C3; | A23-B69-C4; | A23-B69-C5; | A23-B69-C6; |
| A23-B69-C7; | A23-B69-C8; | A23-B69-C9; | A24-B69-C1; | A24-B69-C2; | A24-B69-C3; |
| A24-B69-C4; | A24-B69-C5; | A24-B69-C6; | A24-B69-C7; | A24-B69-C8; | A24-B69-C9; |
| A25-B69-C1; | A25-B69-C2; | A25-B69-C3; | A25-B69-C4; | A25-B69-C5; | A25-B69-C6; |
| A25-B69-C7; | A25-B69-C8; | A25-B69-C9; | A26-B69-C1; | A26-B69-C2; | A26-B69-C3; |
| A26-B69-C4; | A26-B69-C5; | A26-B69-C6; | A26-B69-C7; | A26-B69-C8; | A26-B69-C9; |
| A27-B69-C1; | A27-B69-C2; | A27-B69-C3; | A27-B69-C4; | A27-B69-C5; | A27-B69-C6; |
| A27-B69-C7; | A27-B69-C8; | A27-B69-C9; | A28-B69-C1; | A28-B69-C2; | A28-B69-C3; |
| A28-B69-C4; | A28-B69-C5; | A28-B69-C6; | A28-B69-C7; | A28-B69-C8; | A28-B69-C9; |
| A29-B69-C1; | A29-B69-C2; | A29-B69-C3; | A29-B69-C4; | A29-B69-C5; | A29-B69-C6; |
| A29-B69-C7; | A29-B69-C8; | A29-B69-C9; | A30-B69-C1; | A30-B69-C2; | A30-B69-C3; |
| A30-B69-C4; | A30-B69-C5; | A30-B69-C6; | A30-B69-C7; | A30-B69-C8; | A30-B69-C9; |
| A31-B69-C1; | A31-B69-C2; | A31-B69-C3; | A31-B69-C4; | A31-B69-C5; | A31-B69-C6; |
| A31-B69-C7; | A31-B69-C8; | A31-B69-C9; | A32-B69-C1; | A32-B69-C2; | A32-B69-C3; |
| A32-B69-C4; | A32-B69-C5; | A32-B69-C6; | A32-B69-C7; | A32-B69-C8; | A32-B69-C9; |
| A33-B69-C1; | A33-B69-C2; | A33-B69-C3; | A33-B69-C4; | A33-B69-C5; | A33-B69-C6; |
| A33-B69-C7; | A33-B69-C8; | A33-B69-C9; | A34-B69-C1; | A34-B69-C2; | A34-B69-C3; |
| A34-B69-C4; | A34-B69-C5; | A34-B69-C6; | A34-B69-C7; | A34-B69-C8; | A34-B69-C9; |
| A35-B69-C1; | A35-B69-C2; | A35-B69-C3; | A35-B69-C4; | A35-B69-C5; | A35-B69-C6; |
| A35-B69-C7; | A35-B69-C8; | A35-B69-C9; | A36-B69-C1; | A36-B69-C2; | A36-B69-C3; |

-continued

| | | | | | |
|---|---|---|---|---|---|
| A36-B69-C4; | A36-B69-C5; | A36-B69-C6; | A36-B69-C7; | A36-B69-C8; | A36-B69-C9; |
| A37-B69-C1; | A37-B69-C2; | A37-B69-C3; | A37-B69-C4; | A37-B69-C5; | A37-B69-C6; |
| A37-B69-C7; | A37-B69-C8; | A37-B69-C9; | A38-B69-C1; | A38-B69-C2; | A38-B69-C3; |
| A38-B69-C4; | A38-B69-C5; | A38-B69-C6; | A38-B69-C7; | A38-B69-C8; | A38-B69-C9; |
| A39-B69-C1; | A39-B69-C2; | A39-B69-C3; | A39-B69-C4; | A39-B69-C5; | A39-B69-C6; |
| A39-B69-C7; | A39-B69-C8; | A39-B69-C9; | A40-B69-C1; | A40-B69-C2; | A40-B69-C3; |
| A40-B69-C4; | A40-B69-C5; | A40-B69-C6; | A40-B69-C7; | A40-B69-C8; | A40-B69-C9; |
| A41-B69-C1; | A41-B69-C2; | A41-B69-C3; | A41-B69-C4; | A41-B69-C5; | A41-B69-C6; |
| A41-B69-C7; | A41-B69-C8; | A41-B69-C9; | A42-B69-C1; | A42-B69-C2; | A42-B69-C3; |
| A42-B69-C4; | A42-B69-C5; | A42-B69-C6; | A42-B69-C7; | A42-B69-C8; | A42-B69-C9; |
| A43-B69-C1; | A43-B69-C2; | A43-B69-C3; | A43-B69-C4; | A43-B69-C5; | A43-B69-C6; |
| A43-B69-C7; | A43-B69-C8; | A43-B69-C9; | A44-B69-C1; | A44-B69-C2; | A44-B69-C3; |
| A44-B69-C4; | A44-B69-C5; | A44-B69-C6; | A44-B69-C7; | A44-B69-C8; | A44-B69-C9; |
| A45-B69-C1; | A45-B69-C2; | A45-B69-C3; | A45-B69-C4; | A45-B69-C5; | A45-B69-C6; |
| A45-B69-C7; | A45-B69-C8; | A45-B69-C9; | A46-B69-C1; | A46-B69-C2; | A46-B69-C3; |
| A46-B69-C4; | A46-B69-C5; | A46-B69-C6; | A46-B69-C7; | A46-B69-C8; | A46-B69-C9; |
| A47-B69-C1; | A47-B69-C2; | A47-B69-C3; | A47-B69-C4; | A47-B69-C5; | A47-B69-C6; |
| A47-B69-C7; | A47-B69-C8; | A47-B69-C9; | A48-B69-C1; | A48-B69-C2; | A48-B69-C3; |
| A48-B69-C4; | A48-B69-C5; | A48-B69-C6; | A48-B69-C7; | A48-B69-C8; | A48-B69-C9; |
| A49-B69-C1; | A49-B69-C2; | A49-B69-C3; | A49-B69-C4; | A49-B69-C5; | A49-B69-C6; |
| A49-B69-C7; | A49-B69-C8; | A49-B69-C9; | A50-B69-C1; | A50-B69-C2; | A50-B69-C3; |
| A50-B69-C4; | A50-B69-C5; | A50-B69-C6; | A50-B69-C7; | A50-B69-C8; | A50-B69-C9; |
| A51-B69-C1; | A51-B69-C2; | A51-B69-C3; | A51-B69-C4; | A51-B69-C5; | A51-B69-C6; |
| A51-B69-C7; | A51-B69-C8; | A51-B69-C9; | A52-B69-C1; | A52-B69-C2; | A52-B69-C3; |
| A52-B69-C4; | A52-B69-C5; | A52-B69-C6; | A52-B69-C7; | A52-B69-C8; | A52-B69-C9; |
| A53-B69-C1; | A53-B69-C2; | A53-B69-C3; | A53-B69-C4; | A53-B69-C5; | A53-B69-C6; |
| A53-B69-C7; | A53-B69-C8; | A53-B69-C9; | A54-B69-C1; | A54-B69-C2; | A54-B69-C3; |
| A54-B69-C4; | A54-B69-C5; | A54-B69-C6; | A54-B69-C7; | A54-B69-C8; | A54-B69-C9; |
| A55-B69-C1; | A55-B69-C2; | A55-B69-C3; | A55-B69-C4; | A55-B69-C5; | A55-B69-C6; |
| A55-B69-C7; | A55-B69-C8; | A55-B69-C9; | A56-B69-C1; | A56-B69-C2; | A56-B69-C3; |
| A56-B69-C4; | A56-B69-C5; | A56-B69-C6; | A56-B69-C7; | A56-B69-C8; | A56-B69-C9; |
| A57-B69-C1; | A57-B69-C2; | A57-B69-C3; | A57-B69-C4; | A57-B69-C5; | A57-B69-C6; |
| A57-B69-C7; | A57-B69-C8; | A57-B69-C9; | A58-B69-C1; | A58-B69-C2; | A58-B69-C3; |
| A58-B69-C4; | A58-B69-C5; | A58-B69-C6; | A58-B69-C7; | A58-B69-C8; | A58-B69-C9; |
| A59-B69-C1; | A59-B69-C2; | A59-B69-C3; | A59-B69-C4; | A59-B69-C5; | A59-B69-C6; |
| A59-B69-C7; | A59-B69-C8; | A59-B69-C9; | A60-B69-C1; | A60-B69-C2; | A60-B69-C3; |
| A60-B69-C4; | A60-B69-C5; | A60-B69-C6; | A60-B69-C7; | A60-B69-C8; | A60-B69-C9; |
| A61-B69-C1; | A61-B69-C2; | A61-B69-C3; | A61-B69-C4; | A61-B69-C5; | A61-B69-C6; |
| A61-B69-C7; | A61-B69-C8; | A61-B69-C9; | A62-B69-C1; | A62-B69-C2; | A62-B69-C3; |
| A62-B69-C4; | A62-B69-C5; | A62-B69-C6; | A62-B69-C7; | A62-B69-C8; | A62-B69-C9; |
| A63-B69-C1; | A63-B69-C2; | A63-B69-C3; | A63-B69-C4; | A63-B69-C5; | A63-B69-C6; |
| A63-B69-C7; | A63-B69-C8; | A63-B69-C9; | A64-B69-C1; | A64-B69-C2; | A64-B69-C3; |
| A64-B69-C4; | A64-B69-C5; | A64-B69-C6; | A64-B69-C7; | A64-B69-C8; | A64-B69-C9; |
| A65-B69-C1; | A65-B69-C2; | A65-B69-C3; | A65-B69-C4; | A65-B69-C5; | A65-B69-C6; |
| A65-B69-C7; | A65-B69-C8; | A65-B69-C9; | A66-B69-C1; | A66-B69-C2; | A66-B69-C3; |
| A66-B69-C4; | A66-B69-C5; | A66-B69-C6; | A66-B69-C7; | A66-B69-C8; | A66-B69-C9; |
| A67-B69-C1; | A67-B69-C2; | A67-B69-C3; | A67-B69-C4; | A67-B69-C5; | A67-B69-C6; |
| A67-B69-C7; | A67-B69-C8; | A67-B69-C9; | A68-B69-C1; | A68-B69-C2; | A68-B69-C3; |
| A68-B69-C4; | A68-B69-C5; | A68-B69-C6; | A68-B69-C7; | A68-B69-C8; | A68-B69-C9; |
| A69-B69-C1; | A69-B69-C2; | A69-B69-C3; | A69-B69-C4; | A69-B69-C5; | A69-B69-C6; |
| A69-B69-C7; | A69-B69-C8; | A69-B69-C9; | A70-B69-C1; | A70-B69-C2; | A70-B69-C3; |
| A70-B69-C4; | A70-B69-C5; | A70-B69-C6; | A70-B69-C7; | A70-B69-C8; | A70-B69-C9; |
| A71-B69-C1; | A71-B69-C2; | A71-B69-C3; | A71-B69-C4; | A71-B69-C5; | A71-B69-C6; |
| A71-B69-C7; | A71-B69-C8; | A71-B69-C9; | A1-B70-C1; | A1-B70-C2; | A1-B70-C3; |
| A1-B70-C4; | A1-B70-C5; | A1-B70-C6; | A1-B70-C7; | A1-B70-C8; | A1-B70-C9; |
| A2-B70-C1; | A2-B70-C2; | A2-B70-C3; | A2-B70-C4; | A2-B70-C5; | A2-B70-C6; |
| A2-B70-C7; | A2-B70-C8; | A2-B70-C9; | A3-B70-C1; | A3-B70-C2; | A3-B70-C3; |
| A3-B70-C4; | A3-B70-C5; | A3-B70-C6; | A3-B70-C7; | A3-B70-C8; | A3-B70-C9; |
| A4-B70-C1; | A4-B70-C2; | A4-B70-C3; | A4-B70-C4; | A4-B70-C5; | A4-B70-C6; |
| A4-B70-C7; | A4-B70-C8; | A4-B70-C9; | A5-B70-C1; | A5-B70-C2; | A5-B70-C3; |
| A5-B70-C4; | A5-B70-C5; | A5-B70-C6; | A5-B70-C7; | A5-B70-C8; | A5-B70-C9; |
| A6-B70-C1; | A6-B70-C2; | A6-B70-C3; | A6-B70-C4; | A6-B70-C5; | A6-B70-C6; |
| A6-B70-C7; | A6-B70-C8; | A6-B70-C9; | A7-B70-C1; | A7-B70-C2; | A7-B70-C3; |
| A7-B70-C4; | A7-B70-C5; | A7-B70-C6; | A7-B70-C7; | A7-B70-C8; | A7-B70-C9; |
| A8-B70-C1; | A8-B70-C2; | A8-B70-C3; | A8-B70-C4; | A8-B70-C5; | A8-B70-C6; |
| A8-B70-C7; | A8-B70-C8; | A8-B70-C9; | A9-B70-C1; | A9-B70-C2; | A9-B70-C3; |
| A9-B70-C4; | A9-B70-C5; | A9-B70-C6; | A9-B70-C7; | A9-B70-C8; | A9-B70-C9; |
| A10-B70-C1; | A10-B70-C2; | A10-B70-C3; | A10-B70-C4; | A10-B70-C5; | A10-B70-C6; |
| A10-B70-C7; | A10-B70-C8; | A10-B70-C9; | A11-B70-C1; | A11-B70-C2; | A11-B70-C3; |
| A11-B70-C4; | A11-B70-C5; | A11-B70-C6; | A11-B70-C7; | A11-B70-C8; | A11-B70-C9; |
| A12-B70-C1; | A12-B70-C2; | A12-B70-C3; | A12-B70-C4; | A12-B70-C5; | A12-B70-C6; |
| A12-B70-C7; | A12-B70-C8; | A12-B70-C9; | A13-B70-C1; | A13-B70-C2; | A13-B70-C3; |
| A13-B70-C4; | A13-B70-C5; | A13-B70-C6; | A13-B70-C7; | A13-B70-C8; | A13-B70-C9; |
| A14-B70-C1; | A14-B70-C2; | A14-B70-C3; | A14-B70-C4; | A14-B70-C5; | A14-B70-C6; |
| A14-B70-C7; | A14-B70-C8; | A14-B70-C9; | A15-B70-C1; | A15-B70-C2; | A15-B70-C3; |
| A15-B70-C4; | A15-B70-C5; | A15-B70-C6; | A15-B70-C7; | A15-B70-C8; | A15-B70-C9; |
| A16-B70-C1; | A16-B70-C2; | A16-B70-C3; | A16-B70-C4; | A16-B70-C5; | A16-B70-C6; |
| A16-B70-C7; | A16-B70-C8; | A16-B70-C9; | A17-B70-C1; | A17-B70-C2; | A17-B70-C3; |
| A17-B70-C4; | A17-B70-C5; | A17-B70-C6; | A17-B70-C7; | A17-B70-C8; | A17-B70-C9; |

-continued

| | | | | | |
|---|---|---|---|---|---|
| A18-B70-C1; | A18-B70-C2; | A18-B70-C3; | A18-B70-C4; | A18-B70-C5; | A18-B70-C6; |
| A18-B70-C7; | A18-B70-C8; | A18-B70-C9; | A19-B70-C1; | A19-B70-C2; | A19-B70-C3; |
| A19-B70-C4; | A19-B70-C5; | A19-B70-C6; | A19-B70-C7; | A19-B70-C8; | A19-B70-C9; |
| A20-B70-C1; | A20-B70-C2; | A20-B70-C3; | A20-B70-C4; | A20-B70-C5; | A20-B70-C6; |
| A20-B70-C7; | A20-B70-C8; | A20-B70-C9; | A21-B70-C1; | A21-B70-C2; | A21-B70-C3; |
| A21-B70-C4; | A21-B70-C5; | A21-B70-C6; | A21-B70-C7; | A21-B70-C8; | A21-B70-C9; |
| A22-B70-C1; | A22-B70-C2; | A22-B70-C3; | A22-B70-C4; | A22-B70-C5; | A22-B70-C6; |
| A22-B70-C7; | A22-B70-C8; | A22-B70-C9; | A23-B70-C1; | A23-B70-C2; | A23-B70-C3; |
| A23-B70-C4; | A23-B70-C5; | A23-B70-C6; | A23-B70-C7; | A23-B70-C8; | A23-B70-C9; |
| A24-B70-C1; | A24-B70-C2; | A24-B70-C3; | A24-B70-C4; | A24-B70-C5; | A24-B70-C6; |
| A24-B70-C7; | A24-B70-C8; | A24-B70-C9; | A25-B70-C1; | A25-B70-C2; | A25-B70-C3; |
| A25-B70-C4; | A25-B70-C5; | A25-B70-C6; | A25-B70-C7; | A25-B70-C8; | A25-B70-C9; |
| A26-B70-C1; | A26-B70-C2; | A26-B70-C3; | A26-B70-C4; | A26-B70-C5; | A26-B70-C6; |
| A26-B70-C7; | A26-B70-C8; | A26-B70-C9; | A27-B70-C1; | A27-B70-C2; | A27-B70-C3; |
| A27-B70-C4; | A27-B70-C5; | A27-B70-C6; | A27-B70-C7; | A27-B70-C8; | A27-B70-C9; |
| A28-B70-C1; | A28-B70-C2; | A28-B70-C3; | A28-B70-C4; | A28-B70-C5; | A28-B70-C6; |
| A28-B70-C7; | A28-B70-C8; | A28-B70-C9; | A29-B70-C1; | A29-B70-C2; | A29-B70-C3; |
| A29-B70-C4; | A29-B70-C5; | A29-B70-C6; | A29-B70-C7; | A29-B70-C8; | A29-B70-C9; |
| A30-B70-C1; | A30-B70-C2; | A30-B70-C3; | A30-B70-C4; | A30-B70-C5; | A30-B70-C6; |
| A30-B70-C7; | A30-B70-C8; | A30-B70-C9; | A31-B70-C1; | A31-B70-C2; | A31-B70-C3; |
| A31-B70-C4; | A31-B70-C5; | A31-B70-C6; | A31-B70-C7; | A31-B70-C8; | A31-B70-C9; |
| A32-B70-C1; | A32-B70-C2; | A32-B70-C3; | A32-B70-C4; | A32-B70-C5; | A32-B70-C6; |
| A32-B70-C7; | A32-B70-C8; | A32-B70-C9; | A33-B70-C1; | A33-B70-C2; | A33-B70-C3; |
| A33-B70-C4; | A33-B70-C5; | A33-B70-C6; | A33-B70-C7; | A33-B70-C8; | A33-B70-C9; |
| A34-B70-C1; | A34-B70-C2; | A34-B70-C3; | A34-B70-C4; | A34-B70-C5; | A34-B70-C6; |
| A34-B70-C7; | A34-B70-C8; | A34-B70-C9; | A35-B70-C1; | A35-B70-C2; | A35-B70-C3; |
| A35-B70-C4; | A35-B70-C5; | A35-B70-C6; | A35-B70-C7; | A35-B70-C8; | A35-B70-C9; |
| A36-B70-C1; | A36-B70-C2; | A36-B70-C3; | A36-B70-C4; | A36-B70-C5; | A36-B70-C6; |
| A36-B70-C7; | A36-B70-C8; | A36-B70-C9; | A37-B70-C1; | A37-B70-C2; | A37-B70-C3; |
| A37-B70-C4; | A37-B70-C5; | A37-B70-C6; | A37-B70-C7; | A37-B70-C8; | A37-B70-C9; |
| A38-B70-C1; | A38-B70-C2; | A38-B70-C3; | A38-B70-C4; | A38-B70-C5; | A38-B70-C6; |
| A38-B70-C7; | A38-B70-C8; | A38-B70-C9; | A39-B70-C1; | A39-B70-C2; | A39-B70-C3; |
| A39-B70-C4; | A39-B70-C5; | A39-B70-C6; | A39-B70-C7; | A39-B70-C8; | A39-B70-C9; |
| A40-B70-C1; | A40-B70-C2; | A40-B70-C3; | A40-B70-C4; | A40-B70-C5; | A40-B70-C6; |
| A40-B70-C7; | A40-B70-C8; | A40-B70-C9; | A41-B70-C1; | A41-B70-C2; | A41-B70-C3; |
| A41-B70-C4; | A41-B70-C5; | A41-B70-C6; | A41-B70-C7; | A41-B70-C8; | A41-B70-C9; |
| A42-B70-C1; | A42-B70-C2; | A42-B70-C3; | A42-B70-C4; | A42-B70-C5; | A42-B70-C6; |
| A42-B70-C7; | A42-B70-C8; | A42-B70-C9; | A43-B70-C1; | A43-B70-C2; | A43-B70-C3; |
| A43-B70-C4; | A43-B70-C5; | A43-B70-C6; | A43-B70-C7; | A43-B70-C8; | A43-B70-C9; |
| A44-B70-C1; | A44-B70-C2; | A44-B70-C3; | A44-B70-C4; | A44-B70-C5; | A44-B70-C6; |
| A44-B70-C7; | A44-B70-C8; | A44-B70-C9; | A45-B70-C1; | A45-B70-C2; | A45-B70-C3; |
| A45-B70-C4; | A45-B70-C5; | A45-B70-C6; | A45-B70-C7; | A45-B70-C8; | A45-B70-C9; |
| A46-B70-C1; | A46-B70-C2; | A46-B70-C3; | A46-B70-C4; | A46-B70-C5; | A46-B70-C6; |
| A46-B70-C7; | A46-B70-C8; | A46-B70-C9; | A47-B70-C1; | A47-B70-C2; | A47-B70-C3; |
| A47-B70-C4; | A47-B70-C5; | A47-B70-C6; | A47-B70-C7; | A47-B70-C8; | A47-B70-C9; |
| A48-B70-C1; | A48-B70-C2; | A48-B70-C3; | A48-B70-C4; | A48-B70-C5; | A48-B70-C6; |
| A48-B70-C7; | A48-B70-C8; | A48-B70-C9; | A49-B70-C1; | A49-B70-C2; | A49-B70-C3; |
| A49-B70-C4; | A49-B70-C5; | A49-B70-C6; | A49-B70-C7; | A49-B70-C8; | A49-B70-C9; |
| A50-B70-C1; | A50-B70-C2; | A50-B70-C3; | A50-B70-C4; | A50-B70-C5; | A50-B70-C6; |
| A50-B70-C7; | A50-B70-C8; | A50-B70-C9; | A51-B70-C1; | A51-B70-C2; | A51-B70-C3; |
| A51-B70-C4; | A51-B70-C5; | A51-B70-C6; | A51-B70-C7; | A51-B70-C8; | A51-B70-C9; |
| A52-B70-C1; | A52-B70-C2; | A52-B70-C3; | A52-B70-C4; | A52-B70-C5; | A52-B70-C6; |
| A52-B70-C7; | A52-B70-C8; | A52-B70-C9; | A53-B70-C1; | A53-B70-C2; | A53-B70-C3; |
| A53-B70-C4; | A53-B70-C5; | A53-B70-C6; | A53-B70-C7; | A53-B70-C8; | A53-B70-C9; |
| A54-B70-C1; | A54-B70-C2; | A54-B70-C3; | A54-B70-C4; | A54-B70-C5; | A54-B70-C6; |
| A54-B70-C7; | A54-B70-C8; | A54-B70-C9; | A55-B70-C1; | A55-B70-C2; | A55-B70-C3; |
| A55-B70-C4; | A55-B70-C5; | A55-B70-C6; | A55-B70-C7; | A55-B70-C8; | A55-B70-C9; |
| A56-B70-C1; | A56-B70-C2; | A56-B70-C3; | A56-B70-C4; | A56-B70-C5; | A56-B70-C6; |
| A56-B70-C7; | A56-B70-C8; | A56-B70-C9; | A57-B70-C1; | A57-B70-C2; | A57-B70-C3; |
| A57-B70-C4; | A57-B70-C5; | A57-B70-C6; | A57-B70-C7; | A57-B70-C8; | A57-B70-C9; |
| A58-B70-C1; | A58-B70-C2; | A58-B70-C3; | A58-B70-C4; | A58-B70-C5; | A58-B70-C6; |
| A58-B70-C7; | A58-B70-C8; | A58-B70-C9; | A59-B70-C1; | A59-B70-C2; | A59-B70-C3; |
| A59-B70-C4; | A59-B70-C5; | A59-B70-C6; | A59-B70-C7; | A59-B70-C8; | A59-B70-C9; |
| A60-B70-C1; | A60-B70-C2; | A60-B70-C3; | A60-B70-C4; | A60-B70-C5; | A60-B70-C6; |
| A60-B70-C7; | A60-B70-C8; | A60-B70-C9; | A61-B70-C1; | A61-B70-C2; | A61-B70-C3; |
| A61-B70-C4; | A61-B70-C5; | A61-B70-C6; | A61-B70-C7; | A61-B70-C8; | A61-B70-C9; |
| A62-B70-C1; | A62-B70-C2; | A62-B70-C3; | A62-B70-C4; | A62-B70-C5; | A62-B70-C6; |
| A62-B70-C7; | A62-B70-C8; | A62-B70-C9; | A63-B70-C1; | A63-B70-C2; | A63-B70-C3; |
| A63-B70-C4; | A63-B70-C5; | A63-B70-C6; | A63-B70-C7; | A63-B70-C8; | A63-B70-C9; |
| A64-B70-C1; | A64-B70-C2; | A64-B70-C3; | A64-B70-C4; | A64-B70-C5; | A64-B70-C6; |
| A64-B70-C7; | A64-B70-C8; | A64-B70-C9; | A65-B70-C1; | A65-B70-C2; | A65-B70-C3; |
| A65-B70-C4; | A65-B70-C5; | A65-B70-C6; | A65-B70-C7; | A65-B70-C8; | A65-B70-C9; |
| A66-B70-C1; | A66-B70-C2; | A66-B70-C3; | A66-B70-C4; | A66-B70-C5; | A66-B70-C6; |
| A66-B70-C7; | A66-B70-C8; | A66-B70-C9; | A67-B70-C1; | A67-B70-C2; | A67-B70-C3; |
| A67-B70-C4; | A67-B70-C5; | A67-B70-C6; | A67-B70-C7; | A67-B70-C8; | A67-B70-C9; |
| A68-B70-C1; | A68-B70-C2; | A68-B70-C3; | A68-B70-C4; | A68-B70-C5; | A68-B70-C6; |
| A68-B70-C7; | A68-B70-C8; | A68-B70-C9; | A69-B70-C1; | A69-B70-C2; | A69-B70-C3; |
| A69-B70-C4; | A69-B70-C5; | A69-B70-C6; | A69-B70-C7; | A69-B70-C8; | A69-B70-C9; |
| A70-B70-C1; | A70-B70-C2; | A70-B70-C3; | A70-B70-C4; | A70-B70-C5; | A70-B70-C6; |

-continued

| | | | | | |
|---|---|---|---|---|---|
| A70-B70-C7; | A70-B70-C8; | A70-B70-C9; | A71-B70-C1; | A71-B70-C2; | A71-B70-C3; |
| A71-B70-C4; | A71-B70-C5; | A71-B70-C6; | A71-B70-C7; | A71-B70-C8; | A71-B70-C9; |
| A1-B71-C1; | A1-B71-C2; | A1-B71-C3; | A1-B71-C4; | A1-B71-C5; | A1-B71-C6; |
| A1-B71-C7; | A1-B71-C8; | A1-B71-C9; | A2-B71-C1; | A2-B71-C2; | A2-B71-C3; |
| A2-B71-C4; | A2-B71-C5; | A2-B71-C6; | A2-B71-C7; | A2-B71-C8; | A2-B71-C9; |
| A3-B71-C1; | A3-B71-C2; | A3-B71-C3; | A3-B71-C4; | A3-B71-C5; | A3-B71-C6; |
| A3-B71-C7; | A3-B71-C8; | A3-B71-C9; | A4-B71-C1; | A4-B71-C2; | A4-B71-C3; |
| A4-B71-C4; | A4-B71-C5; | A4-B71-C6; | A4-B71-C7; | A4-B71-C8; | A4-B71-C9; |
| A5-B71-C1; | A5-B71-C2; | A5-B71-C3; | A5-B71-C4; | A5-B71-C5; | A5-B71-C6; |
| A5-B71-C7; | A5-B71-C8; | A5-B71-C9; | A6-B71-C1; | A6-B71-C2; | A6-B71-C3; |
| A6-B71-C4; | A6-B71-C5; | A6-B71-C6; | A6-B71-C7; | A6-B71-C8; | A6-B71-C9; |
| A7-B71-C1; | A7-B71-C2; | A7-B71-C3; | A7-B71-C4; | A7-B71-C5; | A7-B71-C6; |
| A7-B71-C7; | A7-B71-C8; | A7-B71-C9; | A8-B71-C1; | A8-B71-C2; | A8-B71-C3; |
| A8-B71-C4; | A8-B71-C5; | A8-B71-C6; | A8-B71-C7; | A8-B71-C8; | A8-B71-C9; |
| A9-B71-C1; | A9-B71-C2; | A9-B71-C3; | A9-B71-C4; | A9-B71-C5; | A9-B71-C6; |
| A9-B71-C7; | A9-B71-C8; | A9-B71-C9; | A10-B71-C1; | A10-B71-C2; | A10-B71-C3; |
| A10-B71-C4; | A10-B71-C5; | A10-B71-C6; | A10-B71-C7; | A10-B71-C8; | A10-B71-C9; |
| A11-B71-C1; | A11-B71-C2; | A11-B71-C3; | A11-B71-C4; | A11-B71-C5; | A11-B71-C6; |
| A11-B71-C7; | A11-B71-C8; | A11-B71-C9; | A12-B71-C1; | A12-B71-C2; | A12-B71-C3; |
| A12-B71-C4; | A12-B71-C5; | A12-B71-C6; | A12-B71-C7; | A12-B71-C8; | A12-B71-C9; |
| A13-B71-C1; | A13-B71-C2; | A13-B71-C3; | A13-B71-C4; | A13-B71-C5; | A13-B71-C6; |
| A13-B71-C7; | A13-B71-C8; | A13-B71-C9; | A14-B71-C1; | A14-B71-C2; | A14-B71-C3; |
| A14-B71-C4; | A14-B71-C5; | A14-B71-C6; | A14-B71-C7; | A14-B71-C8; | A14-B71-C9; |
| A15-B71-C1; | A15-B71-C2; | A15-B71-C3; | A15-B71-C4; | A15-B71-C5; | A15-B71-C6; |
| A15-B71-C7; | A15-B71-C8; | A15-B71-C9; | A16-B71-C1; | A16-B71-C2; | A16-B71-C3; |
| A16-B71-C4; | A16-B71-C5; | A16-B71-C6; | A16-B71-C7; | A16-B71-C8; | A16-B71-C9; |
| A17-B71-C1; | A17-B71-C2; | A17-B71-C3; | A17-B71-C4; | A17-B71-C5; | A17-B71-C6; |
| A17-B71-C7; | A17-B71-C8; | A17-B71-C9; | A18-B71-C1; | A18-B71-C2; | A18-B71-C3; |
| A18-B71-C4; | A18-B71-C5; | A18-B71-C6; | A18-B71-C7; | A18-B71-C8; | A18-B71-C9; |
| A19-B71-C1; | A19-B71-C2; | A19-B71-C3; | A19-B71-C4; | A19-B71-C5; | A19-B71-C6; |
| A19-B71-C7; | A19-B71-C8; | A19-B71-C9; | A20-B71-C1; | A20-B71-C2; | A20-B71-C3; |
| A20-B71-C4; | A20-B71-C5; | A20-B71-C6; | A20-B71-C7; | A20-B71-C8; | A20-B71-C9; |
| A21-B71-C1; | A21-B71-C2; | A21-B71-C3; | A21-B71-C4; | A21-B71-C5; | A21-B71-C6; |
| A21-B71-C7; | A21-B71-C8; | A21-B71-C9; | A22-B71-C1; | A22-B71-C2; | A22-B71-C3; |
| A22-B71-C4; | A22-B71-C5; | A22-B71-C6; | A22-B71-C7; | A22-B71-C8; | A22-B71-C9; |
| A23-B71-C1; | A23-B71-C2; | A23-B71-C3; | A23-B71-C4; | A23-B71-C5; | A23-B71-C6; |
| A23-B71-C7; | A23-B71-C8; | A23-B71-C9; | A24-B71-C1; | A24-B71-C2; | A24-B71-C3; |
| A24-B71-C4; | A24-B71-C5; | A24-B71-C6; | A24-B71-C7; | A24-B71-C8; | A24-B71-C9; |
| A25-B71-C1; | A25-B71-C2; | A25-B71-C3; | A25-B71-C4; | A25-B71-C5; | A25-B71-C6; |
| A25-B71-C7; | A25-B71-C8; | A25-B71-C9; | A26-B71-C1; | A26-B71-C2; | A26-B71-C3; |
| A26-B71-C4; | A26-B71-C5; | A26-B71-C6; | A26-B71-C7; | A26-B71-C8; | A26-B71-C9; |
| A27-B71-C1; | A27-B71-C2; | A27-B71-C3; | A27-B71-C4; | A27-B71-C5; | A27-B71-C6; |
| A27-B71-C7; | A27-B71-C8; | A27-B71-C9; | A28-B71-C1; | A28-B71-C2; | A28-B71-C3; |
| A28-B71-C4; | A28-B71-C5; | A28-B71-C6; | A28-B71-C7; | A28-B71-C8; | A28-B71-C9; |
| A29-B71-C1; | A29-B71-C2; | A29-B71-C3; | A29-B71-C4; | A29-B71-C5; | A29-B71-C6; |
| A29-B71-C7; | A29-B71-C8; | A29-B71-C9; | A30-B71-C1; | A30-B71-C2; | A30-B71-C3; |
| A30-B71-C4; | A30-B71-C5; | A30-B71-C6; | A30-B71-C7; | A30-B71-C8; | A30-B71-C9; |
| A31-B71-C1; | A31-B71-C2; | A31-B71-C3; | A31-B71-C4; | A31-B71-C5; | A31-B71-C6; |
| A31-B71-C7; | A31-B71-C8; | A31-B71-C9; | A32-B71-C1; | A32-B71-C2; | A32-B71-C3; |
| A32-B71-C4; | A32-B71-C5; | A32-B71-C6; | A32-B71-C7; | A32-B71-C8; | A32-B71-C9; |
| A33-B71-C1; | A33-B71-C2; | A33-B71-C3; | A33-B71-C4; | A33-B71-C5; | A33-B71-C6; |
| A33-B71-C7; | A33-B71-C8; | A33-B71-C9; | A34-B71-C1; | A34-B71-C2; | A34-B71-C3; |
| A34-B71-C4; | A34-B71-C5; | A34-B71-C6; | A34-B71-C7; | A34-B71-C8; | A34-B71-C9; |
| A35-B71-C1; | A35-B71-C2; | A35-B71-C3; | A35-B71-C4; | A35-B71-C5; | A35-B71-C6; |
| A35-B71-C7; | A35-B71-C8; | A35-B71-C9; | A36-B71-C1; | A36-B71-C2; | A36-B71-C3; |
| A36-B71-C4; | A36-B71-C5; | A36-B71-C6; | A36-B71-C7; | A36-B71-C8; | A36-B71-C9; |
| A37-B71-C1; | A37-B71-C2; | A37-B71-C3; | A37-B71-C4; | A37-B71-C5; | A37-B71-C6; |
| A37-B71-C7; | A37-B71-C8; | A37-B71-C9; | A38-B71-C1; | A38-B71-C2; | A38-B71-C3; |
| A38-B71-C4; | A38-B71-C5; | A38-B71-C6; | A38-B71-C7; | A38-B71-C8; | A38-B71-C9; |
| A39-B71-C1; | A39-B71-C2; | A39-B71-C3; | A39-B71-C4; | A39-B71-C5; | A39-B71-C6; |
| A39-B71-C7; | A39-B71-C8; | A39-B71-C9; | A40-B71-C1; | A40-B71-C2; | A40-B71-C3; |
| A40-B71-C4; | A40-B71-C5; | A40-B71-C6; | A40-B71-C7; | A40-B71-C8; | A40-B71-C9; |
| A41-B71-C1; | A41-B71-C2; | A41-B71-C3; | A41-B71-C4; | A41-B71-C5; | A41-B71-C6; |
| A41-B71-C7; | A41-B71-C8; | A41-B71-C9; | A42-B71-C1; | A42-B71-C2; | A42-B71-C3; |
| A42-B71-C4; | A42-B71-C5; | A42-B71-C6; | A42-B71-C7; | A42-B71-C8; | A42-B71-C9; |
| A43-B71-C1; | A43-B71-C2; | A43-B71-C3; | A43-B71-C4; | A43-B71-C5; | A43-B71-C6; |
| A43-B71-C7; | A43-B71-C8; | A43-B71-C9; | A44-B71-C1; | A44-B71-C2; | A44-B71-C3; |
| A44-B71-C4; | A44-B71-C5; | A44-B71-C6; | A44-B71-C7; | A44-B71-C8; | A44-B71-C9; |
| A45-B71-C1; | A45-B71-C2; | A45-B71-C3; | A45-B71-C4; | A45-B71-C5; | A45-B71-C6; |
| A45-B71-C7; | A45-B71-C8; | A45-B71-C9; | A46-B71-C1; | A46-B71-C2; | A46-B71-C3; |
| A46-B71-C4; | A46-B71-C5; | A46-B71-C6; | A46-B71-C7; | A46-B71-C8; | A46-B71-C9; |
| A47-B71-C1; | A47-B71-C2; | A47-B71-C3; | A47-B71-C4; | A47-B71-C5; | A47-B71-C6; |
| A47-B71-C7; | A47-B71-C8; | A47-B71-C9; | A48-B71-C1; | A48-B71-C2; | A48-B71-C3; |
| A48-B71-C4; | A48-B71-C5; | A48-B71-C6; | A48-B71-C7; | A48-B71-C8; | A48-B71-C9; |
| A49-B71-C1; | A49-B71-C2; | A49-B71-C3; | A49-B71-C4; | A49-B71-C5; | A49-B71-C6; |
| A49-B71-C7; | A49-B71-C8; | A49-B71-C9; | A50-B71-C1; | A50-B71-C2; | A50-B71-C3; |
| A50-B71-C4; | A50-B71-C5; | A50-B71-C6; | A50-B71-C7; | A50-B71-C8; | A50-B71-C9; |
| A51-B71-C1; | A51-B71-C2; | A51-B71-C3; | A51-B71-C4; | A51-B71-C5; | A51-B71-C6; |
| A51-B71-C7; | A51-B71-C8; | A51-B71-C9; | A52-B71-C1; | A52-B71-C2; | A52-B71-C3; |

-continued

A52-B71-C4; A52-B71-C5; A52-B71-C6; A52-B71-C7; A52-B71-C8; A52-B71-C9;
A53-B71-C1; A53-B71-C2; A53-B71-C3; A53-B71-C4; A53-B71-C5; A53-B71-C6;
A53-B71-C7; A53-B71-C8; A53-B71-C9; A54-B71-C1; A54-B71-C2; A54-B71-C3;
A54-B71-C4; A54-B71-C5; A54-B71-C6; A54-B71-C7; A54-B71-C8; A54-B71-C9;
A55-B71-C1; A55-B71-C2; A55-B71-C3; A55-B71-C4; A55-B71-C5; A55-B71-C6;
A55-B71-C7; A55-B71-C8; A55-B71-C9; A56-B71-C1; A56-B71-C2; A56-B71-C3;
A56-B71-C4; A56-B71-C5; A56-B71-C6; A56-B71-C7; A56-B71-C8; A56-B71-C9;
A57-B71-C1; A57-B71-C2; A57-B71-C3; A57-B71-C4; A57-B71-C5; A57-B71-C6;
A57-B71-C7; A57-B71-C8; A57-B71-C9; A58-B71-C1; A58-B71-C2; A58-B71-C3;
A58-B71-C4; A58-B71-C5; A58-B71-C6; A58-B71-C7; A58-B71-C8; A58-B71-C9;
A59-B71-C1; A59-B71-C2; A59-B71-C3; A59-B71-C4; A59-B71-C5; A59-B71-C6;
A59-B71-C7; A59-B71-C8; A59-B71-C9; A60-B71-C1; A60-B71-C2; A60-B71-C3;
A60-B71-C4; A60-B71-C5; A60-B71-C6; A60-B71-C7; A60-B71-C8; A60-B71-C9;
A61-B71-C1; A61-B71-C2; A61-B71-C3; A61-B71-C4; A61-B71-C5; A61-B71-C6;
A61-B71-C7; A61-B71-C8; A61-B71-C9; A62-B71-C1; A62-B71-C2; A62-B71-C3;
A62-B71-C4; A62-B71-C5; A62-B71-C6; A62-B71-C7; A62-B71-C8; A62-B71-C9;
A63-B71-C1; A63-B71-C2; A63-B71-C3; A63-B71-C4; A63-B71-C5; A63-B71-C6;
A63-B71-C7; A63-B71-C8; A63-B71-C9; A64-B71-C1; A64-B71-C2; A64-B71-C3;
A64-B71-C4; A64-B71-C5; A64-B71-C6; A64-B71-C7; A64-B71-C8; A64-B71-C9;
A65-B71-C1; A65-B71-C2; A65-B71-C3; A65-B71-C4; A65-B71-C5; A65-B71-C6;
A65-B71-C7; A65-B71-C8; A65-B71-C9; A66-B71-C1; A66-B71-C2; A66-B71-C3;
A66-B71-C4; A66-B71-C5; A66-B71-C6; A66-B71-C7; A66-B71-C8; A66-B71-C9;
A67-B71-C1; A67-B71-C2; A67-B71-C3; A67-B71-C4; A67-B71-C5; A67-B71-C6;
A67-B71-C7; A67-B71-C8; A67-B71-C9; A68-B71-C1; A68-B71-C2; A68-B71-C3;
A68-B71-C4; A68-B71-C5; A68-B71-C6; A68-B71-C7; A68-B71-C8; A68-B71-C9;
A69-B71-C1; A69-B71-C2; A69-B71-C3; A69-B71-C4; A69-B71-C5; A69-B71-C6;
A69-B71-C7; A69-B71-C8; A69-B71-C9; A70-B71-C1; A70-B71-C2; A70-B71-C3;
A70-B71-C4; A70-B71-C5; A70-B71-C6; A70-B71-C7; A70-B71-C8; A70-B71-C9;
A71-B71-C1; A71-B71-C2; A71-B71-C3; A71-B71-C4; A71-B71-C5; A71-B71-C6;
A71-B71-C7; A71-B71-C8; A71-B71-C9; A1-B72-C1; A1-B72-C2; A1-B72-C3;
A1-B72-C4; A1-B72-C5; A1-B72-C6; A1-B72-C7; A1-B72-C8; A1-B72-C9;
A2-B72-C1; A2-B72-C2; A2-B72-C3; A2-B72-C4; A2-B72-C5; A2-B72-C6;
A2-B72-C7; A2-B72-C8; A2-B72-C9; A3-B72-C1; A3-B72-C2; A3-B72-C3;
A3-B72-C4; A3-B72-C5; A3-B72-C6; A3-B72-C7; A3-B72-C8; A3-B72-C9;
A4-B72-C1; A4-B72-C2; A4-B72-C3; A4-B72-C4; A4-B72-C5; A4-B72-C6;
A4-B72-C7; A4-B72-C8; A4-B72-C9; A5-B72-C1; A5-B72-C2; A5-B72-C3;
A5-B72-C4; A5-B72-C5; A5-B72-C6; A5-B72-C7; A5-B72-C8; A5-B72-C9;
A6-B72-C1; A6-B72-C2; A6-B72-C3; A6-B72-C4; A6-B72-C5; A6-B72-C6;
A6-B72-C7; A6-B72-C8; A6-B72-C9; A7-B72-C1; A7-B72-C2; A7-B72-C3;
A7-B72-C4; A7-B72-C5; A7-B72-C6; A7-B72-C7; A7-B72-C8; A7-B72-C9;
A8-B72-C1; A8-B72-C2; A8-B72-C3; A8-B72-C4; A8-B72-C5; A8-B72-C6;
A8-B72-C7; A8-B72-C8; A8-B72-C9; A9-B72-C1; A9-B72-C2; A9-B72-C3;
A9-B72-C4; A9-B72-C5; A9-B72-C6; A9-B72-C7; A9-B72-C8; A9-B72-C9;
A10-B72-C1; A10-B72-C2; A10-B72-C3; A10-B72-C5; A10-B72-C6;
A10-B72-C7; A10-B72-C8; A10-B72-C9; A11-B72-C1; A11-B72-C2; A11-B72-C3;
A11-B72-C4; A11-B72-C5; A11-B72-C6; A11-B72-C7; A11-B72-C8; A11-B72-C9;
A12-B72-C1; A12-B72-C2; A12-B72-C3; A12-B72-C4; A12-B72-C5; A12-B72-C6;
A12-B72-C7; A12-B72-C8; A12-B72-C9; A13-B72-C1; A13-B72-C2; A13-B72-C3;
A13-B72-C4; A13-B72-C5; A13-B72-C6; A13-B72-C7; A13-B72-C8; A13-B72-C9;
A14-B72-C1; A14-B72-C2; A14-B72-C3; A14-B72-C4; A14-B72-C5; A14-B72-C6;
A14-B72-C7; A14-B72-C8; A14-B72-C9; A15-B72-C1; A15-B72-C2; A15-B72-C3;
A15-B72-C4; A15-B72-C5; A15-B72-C6; A15-B72-C7; A15-B72-C8; A15-B72-C9;
A16-B72-C1; A16-B72-C2; A16-B72-C3; A16-B72-C4; A16-B72-C5; A16-B72-C6;
A16-B72-C7; A16-B72-C8; A16-B72-C9; A17-B72-C1; A17-B72-C2; A17-B72-C3;
A17-B72-C4; A17-B72-C5; A17-B72-C6; A17-B72-C7; A17-B72-C8; A17-B72-C9;
A18-B72-C1; A18-B72-C2; A18-B72-C3; A18-B72-C4; A18-B72-C5; A18-B72-C6;
A18-B72-C7; A18-B72-C8; A18-B72-C9; A19-B72-C1; A19-B72-C2; A19-B72-C3;
A19-B72-C4; A19-B72-C5; A19-B72-C6; A19-B72-C7; A19-B72-C8; A19-B72-C9;
A20-B72-C1; A20-B72-C2; A20-B72-C3; A20-B72-C4; A20-B72-C5; A20-B72-C6;
A20-B72-C7; A20-B72-C8; A20-B72-C9; A21-B72-C1; A21-B72-C2; A21-B72-C3;
A21-B72-C4; A21-B72-C5; A21-B72-C6; A21-B72-C7; A21-B72-C8; A21-B72-C9;
A22-B72-C1; A22-B72-C2; A22-B72-C3; A22-B72-C4; A22-B72-C5; A22-B72-C6;
A22-B72-C7; A22-B72-C8; A22-B72-C9; A23-B72-C1; A23-B72-C2; A23-B72-C3;
A23-B72-C4; A23-B72-C5; A23-B72-C6; A23-B72-C7; A23-B72-C8; A23-B72-C9;
A24-B72-C1; A24-B72-C2; A24-B72-C3; A24-B72-C4; A24-B72-C5; A24-B72-C6;
A24-B72-C7; A24-B72-C8; A24-B72-C9; A25-B72-C1; A25-B72-C2; A25-B72-C3;
A25-B72-C4; A25-B72-C5; A25-B72-C6; A25-B72-C7; A25-B72-C8; A25-B72-C9;
A26-B72-C1; A26-B72-C2; A26-B72-C3; A26-B72-C4; A26-B72-C5; A26-B72-C6;
A26-B72-C7; A26-B72-C8; A26-B72-C9; A27-B72-C1; A27-B72-C2; A27-B72-C3;
A27-B72-C4; A27-B72-C5; A27-B72-C6; A27-B72-C7; A27-B72-C8; A27-B72-C9;
A28-B72-C1; A28-B72-C2; A28-B72-C3; A28-B72-C4; A28-B72-C5; A28-B72-C6;
A28-B72-C7; A28-B72-C8; A28-B72-C9; A29-B72-C1; A29-B72-C2; A29-B72-C3;
A29-B72-C4; A29-B72-C5; A29-B72-C6; A29-B72-C7; A29-B72-C8; A29-B72-C9;
A30-B72-C1; A30-B72-C2; A30-B72-C3; A30-B72-C4; A30-B72-C5; A30-B72-C6;
A30-B72-C7; A30-B72-C8; A30-B72-C9; A31-B72-C1; A31-B72-C2; A31-B72-C3;
A31-B72-C4; A31-B72-C5; A31-B72-C6; A31-B72-C7; A31-B72-C8; A31-B72-C9;
A32-B72-C1; A32-B72-C2; A32-B72-C3; A32-B72-C4; A32-B72-C5; A32-B72-C6;
A32-B72-C7; A32-B72-C8; A32-B72-C9; A33-B72-C1; A33-B72-C2; A33-B72-C3;
A33-B72-C4; A33-B72-C5; A33-B72-C6; A33-B72-C7; A33-B72-C8; A33-B72-C9;

-continued

| | | | | | |
|---|---|---|---|---|---|
| A34-B72-C1; | A34-B72-C2; | A34-B72-C3; | A34-B72-C4; | A34-B72-C5; | A34-B72-C6; |
| A34-B72-C7; | A34-B72-C8; | A34-B72-C9; | A35-B72-C1; | A35-B72-C2; | A35-B72-C3; |
| A35-B72-C4; | A35-B72-C5; | A35-B72-C6; | A35-B72-C7; | A35-B72-C8; | A35-B72-C9; |
| A36-B72-C1; | A36-B72-C2; | A36-B72-C3; | A36-B72-C4; | A36-B72-C5; | A36-B72-C6; |
| A36-B72-C7; | A36-B72-C8; | A36-B72-C9; | A37-B72-C1; | A37-B72-C2; | A37-B72-C3; |
| A37-B72-C4; | A37-B72-C5; | A37-B72-C6; | A37-B72-C7; | A37-B72-C8; | A37-B72-C9; |
| A38-B72-C1; | A38-B72-C2; | A38-B72-C3; | A38-B72-C4; | A38-B72-C5; | A38-B72-C6; |
| A38-B72-C7; | A38-B72-C8; | A38-B72-C9; | A39-B72-C1; | A39-B72-C2; | A39-B72-C3; |
| A39-B72-C4; | A39-B72-C5; | A39-B72-C6; | A39-B72-C7; | A39-B72-C8; | A39-B72-C9; |
| A40-B72-C1; | A40-B72-C2; | A40-B72-C3; | A40-B72-C4; | A40-B72-C5; | A40-B72-C6; |
| A40-B72-C7; | A40-B72-C8; | A40-B72-C9; | A41-B72-C1; | A41-B72-C2; | A41-B72-C3; |
| A41-B72-C4; | A41-B72-C5; | A41-B72-C6; | A41-B72-C7; | A41-B72-C8; | A41-B72-C9; |
| A42-B72-C1; | A42-B72-C2; | A42-B72-C3; | A42-B72-C4; | A42-B72-C5; | A42-B72-C6; |
| A42-B72-C7; | A42-B72-C8; | A42-B72-C9; | A43-B72-C1; | A43-B72-C2; | A43-B72-C3; |
| A43-B72-C4; | A43-B72-C5; | A43-B72-C6; | A43-B72-C7; | A43-B72-C8; | A43-B72-C9; |
| A44-B72-C1; | A44-B72-C2; | A44-B72-C3; | A44-B72-C4; | A44-B72-C5; | A44-B72-C6; |
| A44-B72-C7; | A44-B72-C8; | A44-B72-C9; | A45-B72-C1; | A45-B72-C2; | A45-B72-C3; |
| A45-B72-C4; | A45-B72-C5; | A45-B72-C6; | A45-B72-C7; | A45-B72-C8; | A45-B72-C9; |
| A46-B72-C1; | A46-B72-C2; | A46-B72-C3; | A46-B72-C4; | A46-B72-C5; | A46-B72-C6; |
| A46-B72-C7; | A46-B72-C8; | A46-B72-C9; | A47-B72-C1; | A47-B72-C2; | A47-B72-C3; |
| A47-B72-C4; | A47-B72-C5; | A47-B72-C6; | A47-B72-C7; | A47-B72-C8; | A47-B72-C9; |
| A48-B72-C1; | A48-B72-C2; | A48-B72-C3; | A48-B72-C4; | A48-B72-C5; | A48-B72-C6; |
| A48-B72-C7; | A48-B72-C8; | A48-B72-C9; | A49-B72-C1; | A49-B72-C2; | A49-B72-C3; |
| A49-B72-C4; | A49-B72-C5; | A49-B72-C6; | A49-B72-C7; | A49-B72-C8; | A49-B72-C9; |
| A50-B72-C1; | A50-B72-C2; | A50-B72-C3; | A50-B72-C4; | A50-B72-C5; | A50-B72-C6; |
| A50-B72-C7; | A50-B72-C8; | A50-B72-C9; | A51-B72-C1; | A51-B72-C2; | A51-B72-C3; |
| A51-B72-C4; | A51-B72-C5; | A51-B72-C6; | A51-B72-C7; | A51-B72-C8; | A51-B72-C9; |
| A52-B72-C1; | A52-B72-C2; | A52-B72-C3; | A52-B72-C4; | A52-B72-C5; | A52-B72-C6; |
| A52-B72-C7; | A52-B72-C8; | A52-B72-C9; | A53-B72-C1; | A53-B72-C2; | A53-B72-C3; |
| A53-B72-C4; | A53-B72-C5; | A53-B72-C6; | A53-B72-C7; | A53-B72-C8; | A53-B72-C9; |
| A54-B72-C1; | A54-B72-C2; | A54-B72-C3; | A54-B72-C4; | A54-B72-C5; | A54-B72-C6; |
| A54-B72-C7; | A54-B72-C8; | A54-B72-C9; | A55-B72-C1; | A55-B72-C2; | A55-B72-C3; |
| A55-B72-C4; | A55-B72-C5; | A55-B72-C6; | A55-B72-C7; | A55-B72-C8; | A55-B72-C9; |
| A56-B72-C1; | A56-B72-C2; | A56-B72-C3; | A56-B72-C4; | A56-B72-C5; | A56-B72-C6; |
| A56-B72-C7; | A56-B72-C8; | A56-B72-C9; | A57-B72-C1; | A57-B72-C2; | A57-B72-C3; |
| A57-B72-C4; | A57-B72-C5; | A57-B72-C6; | A57-B72-C7; | A57-B72-C8; | A57-B72-C9; |
| A58-B72-C1; | A58-B72-C2; | A58-B72-C3; | A58-B72-C4; | A58-B72-C5; | A58-B72-C6; |
| A58-B72-C7; | A58-B72-C8; | A58-B72-C9; | A59-B72-C1; | A59-B72-C2; | A59-B72-C3; |
| A59-B72-C4; | A59-B72-C5; | A59-B72-C6; | A59-B72-C7; | A59-B72-C8; | A59-B72-C9; |
| A60-B72-C1; | A60-B72-C2; | A60-B72-C3; | A60-B72-C4; | A60-B72-C5; | A60-B72-C6; |
| A60-B72-C7; | A60-B72-C8; | A60-B72-C9; | A61-B72-C1; | A61-B72-C2; | A61-B72-C3; |
| A61-B72-C4; | A61-B72-C5; | A61-B72-C6; | A61-B72-C7; | A61-B72-C8; | A61-B72-C9; |
| A62-B72-C1; | A62-B72-C2; | A62-B72-C3; | A62-B72-C4; | A62-B72-C5; | A62-B72-C6; |
| A62-B72-C7; | A62-B72-C8; | A62-B72-C9; | A63-B72-C1; | A63-B72-C2; | A63-B72-C3; |
| A63-B72-C4; | A63-B72-C5; | A63-B72-C6; | A63-B72-C7; | A63-B72-C8; | A63-B72-C9; |
| A64-B72-C1; | A64-B72-C2; | A64-B72-C3; | A64-B72-C4; | A64-B72-C5; | A64-B72-C6; |
| A64-B72-C7; | A64-B72-C8; | A64-B72-C9; | A65-B72-C1; | A65-B72-C2; | A65-B72-C3; |
| A65-B72-C4; | A65-B72-C5; | A65-B72-C6; | A65-B72-C7; | A65-B72-C8; | A65-B72-C9; |
| A66-B72-C1; | A66-B72-C2; | A66-B72-C3; | A66-B72-C4; | A66-B72-C5; | A66-B72-C6; |
| A66-B72-C7; | A66-B72-C8; | A66-B72-C9; | A67-B72-C1; | A67-B72-C2; | A67-B72-C3; |
| A67-B72-C4; | A67-B72-C5; | A67-B72-C6; | A67-B72-C7; | A67-B72-C8; | A67-B72-C9; |
| A68-B72-C1; | A68-B72-C2; | A68-B72-C3; | A68-B72-C4; | A68-B72-C5; | A68-B72-C6; |
| A68-B72-C7; | A68-B72-C8; | A68-B72-C9; | A69-B72-C1; | A69-B72-C2; | A69-B72-C3; |
| A69-B72-C4; | A69-B72-C5; | A69-B72-C6; | A69-B72-C7; | A69-B72-C8; | A69-B72-C9; |
| A70-B72-C1; | A70-B72-C2; | A70-B72-C3; | A70-B72-C4; | A70-B72-C5; | A70-B72-C6; |
| A70-B72-C7; | A70-B72-C8; | A70-B72-C9; | A71-B72-C1; | A71-B72-C2; | A71-B72-C3; |
| A71-B72-C4; | A71-B72-C5; | A71-B72-C6; | A71-B72-C7; | A71-B72-C8; | A71-B72-C9; |
| A1-B73-C1; | A1-B73-C2; | A1-B73-C3; | A1-B73-C4; | A1-B73-C5; | A1-B73-C6; |
| A1-B73-C7; | A1-B73-C8; | A1-B73-C9; | A2-B73-C1; | A2-B73-C2; | A2-B73-C3; |
| A2-B73-C4; | A2-B73-C5; | A2-B73-C6; | A2-B73-C7; | A2-B73-C8; | A2-B73-C9; |
| A3-B73-C1; | A3-B73-C2; | A3-B73-C3; | A3-B73-C4; | A3-B73-C5; | A3-B73-C6; |
| A3-B73-C7; | A3-B73-C8; | A3-B73-C9; | A4-B73-C1; | A4-B73-C2; | A4-B73-C3; |
| A4-B73-C4; | A4-B73-C5; | A4-B73-C6; | A4-B73-C7; | A4-B73-C8; | A4-B73-C9; |
| A5-B73-C1; | A5-B73-C2; | A5-B73-C3; | A5-B73-C4; | A5-B73-C5; | A5-B73-C6; |
| A5-B73-C7; | A5-B73-C8; | A5-B73-C9; | A6-B73-C1; | A6-B73-C2; | A6-B73-C3; |
| A6-B73-C4; | A6-B73-C5; | A6-B73-C6; | A6-B73-C7; | A6-B73-C8; | A6-B73-C9; |
| A7-B73-C1; | A7-B73-C2; | A7-B73-C3; | A7-B73-C4; | A7-B73-C5; | A7-B73-C6; |
| A7-B73-C7; | A7-B73-C8; | A7-B73-C9; | A8-B73-C1; | A8-B73-C2; | A8-B73-C3; |
| A8-B73-C4; | A8-B73-C5; | A8-B73-C6; | A8-B73-C7; | A8-B73-C8; | A8-B73-C9; |
| A9-B73-C1; | A9-B73-C2; | A9-B73-C3; | A9-B73-C4; | A9-B73-C5; | A9-B73-C6; |
| A9-B73-C7; | A9-B73-C8; | A9-B73-C9; | A10-B73-C1; | A10-B73-C2; | A10-B73-C3; |
| A10-B73-C4; | A10-B73-C5; | A10-B73-C6; | A10-B73-C7; | A10-B73-C8; | A10-B73-C9; |
| A11-B73-C1; | A11-B73-C2; | A11-B73-C3; | A11-B73-C4; | A11-B73-C5; | A11-B73-C6; |
| A11-B73-C7; | A11-B73-C8; | A11-B73-C9; | A12-B73-C1; | A12-B73-C2; | A12-B73-C3; |
| A12-B73-C4; | A12-B73-C5; | A12-B73-C6; | A12-B73-C7; | A12-B73-C8; | A12-B73-C9; |
| A13-B73-C1; | A13-B73-C2; | A13-B73-C3; | A13-B73-C4; | A13-B73-C5; | A13-B73-C6; |
| A13-B73-C7; | A13-B73-C8; | A13-B73-C9; | A14-B73-C1; | A14-B73-C2; | A14-B73-C3; |
| A14-B73-C4; | A14-B73-C5; | A14-B73-C6; | A14-B73-C7; | A14-B73-C8; | A14-B73-C9; |
| A15-B73-C1; | A15-B73-C2; | A15-B73-C3; | A15-B73-C4; | A15-B73-C5; | A15-B73-C6; |

-continued

| | | | | | |
|---|---|---|---|---|---|
| A15-B73-C7; | A15-B73-C8; | A15-B73-C9; | A16-B73-C1; | A16-B73-C2; | A16-B73-C3; |
| A16-B73-C4; | A16-B73-C5; | A16-B73-C6; | A16-B73-C7; | A16-B73-C8; | A16-B73-C9; |
| A17-B73-C1; | A17-B73-C2; | A17-B73-C3; | A17-B73-C4; | A17-B73-C5; | A17-B73-C6; |
| A17-B73-C7; | A17-B73-C8; | A17-B73-C9; | A18-B73-C1; | A18-B73-C2; | A18-B73-C3; |
| A18-B73-C4; | A18-B73-C5; | A18-B73-C6; | A18-B73-C7; | A18-B73-C8; | A18-B73-C9; |
| A19-B73-C1; | A19-B73-C2; | A19-B73-C3; | A19-B73-C4; | A19-B73-C5; | A19-B73-C6; |
| A19-B73-C7; | A19-B73-C8; | A19-B73-C9; | A20-B73-C1; | A20-B73-C2; | A20-B73-C3; |
| A20-B73-C4; | A20-B73-C5; | A20-B73-C6; | A20-B73-C7; | A20-B73-C8; | A20-B73-C9; |
| A21-B73-C1; | A21-B73-C2; | A21-B73-C3; | A21-B73-C4; | A21-B73-C5; | A21-B73-C6; |
| A21-B73-C7; | A21-B73-C8; | A21-B73-C9; | A22-B73-C1; | A22-B73-C2; | A22-B73-C3; |
| A22-B73-C4; | A22-B73-C5; | A22-B73-C6; | A22-B73-C7; | A22-B73-C8; | A22-B73-C9; |
| A23-B73-C1; | A23-B73-C2; | A23-B73-C3; | A23-B73-C4; | A23-B73-C5; | A23-B73-C6; |
| A23-B73-C7; | A23-B73-C8; | A23-B73-C9; | A24-B73-C1; | A24-B73-C2; | A24-B73-C3; |
| A24-B73-C4; | A24-B73-C5; | A24-B73-C6; | A24-B73-C7; | A24-B73-C8; | A24-B73-C9; |
| A25-B73-C1; | A25-B73-C2; | A25-B73-C3; | A25-B73-C4; | A25-B73-C5; | A25-B73-C6; |
| A25-B73-C7; | A25-B73-C8; | A25-B73-C9; | A26-B73-C1; | A26-B73-C2; | A26-B73-C3; |
| A26-B73-C4; | A26-B73-C5; | A26-B73-C6; | A26-B73-C7; | A26-B73-C8; | A26-B73-C9; |
| A27-B73-C1; | A27-B73-C2; | A27-B73-C3; | A27-B73-C4; | A27-B73-C5; | A27-B73-C6; |
| A27-B73-C7; | A27-B73-C8; | A27-B73-C9; | A28-B73-C1; | A28-B73-C2; | A28-B73-C3; |
| A28-B73-C4; | A28-B73-C5; | A28-B73-C6; | A28-B73-C7; | A28-B73-C8; | A28-B73-C9; |
| A29-B73-C1; | A29-B73-C2; | A29-B73-C3; | A29-B73-C4; | A29-B73-C5; | A29-B73-C6; |
| A29-B73-C7; | A29-B73-C8; | A29-B73-C9; | A30-B73-C1; | A30-B73-C2; | A30-B73-C3; |
| A30-B73-C4; | A30-B73-C5; | A30-B73-C6; | A30-B73-C7; | A30-B73-C8; | A30-B73-C9; |
| A31-B73-C1; | A31-B73-C2; | A31-B73-C3; | A31-B73-C4; | A31-B73-C5; | A31-B73-C6; |
| A31-B73-C7; | A31-B73-C8; | A31-B73-C9; | A32-B73-C1; | A32-B73-C2; | A32-B73-C3; |
| A32-B73-C4; | A32-B73-C5; | A32-B73-C6; | A32-B73-C7; | A32-B73-C8; | A32-B73-C9; |
| A33-B73-C1; | A33-B73-C2; | A33-B73-C3; | A33-B73-C4; | A33-B73-C5; | A33-B73-C6; |
| A33-B73-C7; | A33-B73-C8; | A33-B73-C9; | A34-B73-C1; | A34-B73-C2; | A34-B73-C3; |
| A34-B73-C4; | A34-B73-C5; | A34-B73-C6; | A34-B73-C7; | A34-B73-C8; | A34-B73-C9; |
| A35-B73-C1; | A35-B73-C2; | A35-B73-C3; | A35-B73-C4; | A35-B73-C5; | A35-B73-C6; |
| A35-B73-C7; | A35-B73-C8; | A35-B73-C9; | A36-B73-C1; | A36-B73-C2; | A36-B73-C3; |
| A36-B73-C4; | A36-B73-C5; | A36-B73-C6; | A36-B73-C7; | A36-B73-C8; | A36-B73-C9; |
| A37-B73-C1; | A37-B73-C2; | A37-B73-C3; | A37-B73-C4; | A37-B73-C5; | A37-B73-C6; |
| A37-B73-C7; | A37-B73-C8; | A37-B73-C9; | A38-B73-C1; | A38-B73-C2; | A38-B73-C3; |
| A38-B73-C4; | A38-B73-C5; | A38-B73-C6; | A38-B73-C7; | A38-B73-C8; | A38-B73-C9; |
| A39-B73-C1; | A39-B73-C2; | A39-B73-C3; | A39-B73-C4; | A39-B73-C5; | A39-B73-C6; |
| A39-B73-C7; | A39-B73-C8; | A39-B73-C9; | A40-B73-C1; | A40-B73-C2; | A40-B73-C3; |
| A40-B73-C4; | A40-B73-C5; | A40-B73-C6; | A40-B73-C7; | A40-B73-C8; | A40-B73-C9; |
| A41-B73-C1; | A41-B73-C2; | A41-B73-C3; | A41-B73-C4; | A41-B73-C5; | A41-B73-C6; |
| A41-B73-C7; | A41-B73-C8; | A41-B73-C9; | A42-B73-C1; | A42-B73-C2; | A42-B73-C3; |
| A42-B73-C4; | A42-B73-C5; | A42-B73-C6; | A42-B73-C7; | A42-B73-C8; | A42-B73-C9; |
| A43-B73-C1; | A43-B73-C2; | A43-B73-C3; | A43-B73-C4; | A43-B73-C5; | A43-B73-C6; |
| A43-B73-C7; | A43-B73-C8; | A43-B73-C9; | A44-B73-C1; | A44-B73-C2; | A44-B73-C3; |
| A44-B73-C4; | A44-B73-C5; | A44-B73-C6; | A44-B73-C7; | A44-B73-C8; | A44-B73-C9; |
| A45-B73-C1; | A45-B73-C2; | A45-B73-C3; | A45-B73-C4; | A45-B73-C5; | A45-B73-C6; |
| A45-B73-C7; | A45-B73-C8; | A45-B73-C9; | A46-B73-C1; | A46-B73-C2; | A46-B73-C3; |
| A46-B73-C4; | A46-B73-C5; | A46-B73-C6; | A46-B73-C7; | A46-B73-C8; | A46-B73-C9; |
| A47-B73-C1; | A47-B73-C2; | A47-B73-C3; | A47-B73-C4; | A47-B73-C5; | A47-B73-C6; |
| A47-B73-C7; | A47-B73-C8; | A47-B73-C9; | A48-B73-C1; | A48-B73-C2; | A48-B73-C3; |
| A48-B73-C4; | A48-B73-C5; | A48-B73-C6; | A48-B73-C7; | A48-B73-C8; | A48-B73-C9; |
| A49-B73-C1; | A49-B73-C2; | A49-B73-C3; | A49-B73-C4; | A49-B73-C5; | A49-B73-C6; |
| A49-B73-C7; | A49-B73-C8; | A49-B73-C9; | A50-B73-C1; | A50-B73-C2; | A50-B73-C3; |
| A50-B73-C4; | A50-B73-C5; | A50-B73-C6; | A50-B73-C7; | A50-B73-C8; | A50-B73-C9; |
| A51-B73-C1; | A51-B73-C2; | A51-B73-C3; | A51-B73-C4; | A51-B73-C5; | A51-B73-C6; |
| A51-B73-C7; | A51-B73-C8; | A51-B73-C9; | A52-B73-C1; | A52-B73-C2; | A52-B73-C3; |
| A52-B73-C4; | A52-B73-C5; | A52-B73-C6; | A52-B73-C7; | A52-B73-C8; | A52-B73-C9; |
| A53-B73-C1; | A53-B73-C2; | A53-B73-C3; | A53-B73-C4; | A53-B73-C5; | A53-B73-C6; |
| A53-B73-C7; | A53-B73-C8; | A53-B73-C9; | A54-B73-C1; | A54-B73-C2; | A54-B73-C3; |
| A54-B73-C4; | A54-B73-C5; | A54-B73-C6; | A54-B73-C7; | A54-B73-C8; | A54-B73-C9; |
| A55-B73-C1; | A55-B73-C2; | A55-B73-C3; | A55-B73-C4; | A55-B73-C5; | A55-B73-C6; |
| A55-B73-C7; | A55-B73-C8; | A55-B73-C9; | A56-B73-C1; | A56-B73-C2; | A56-B73-C3; |
| A56-B73-C4; | A56-B73-C5; | A56-B73-C6; | A56-B73-C7; | A56-B73-C8; | A56-B73-C9; |
| A57-B73-C1; | A57-B73-C2; | A57-B73-C3; | A57-B73-C4; | A57-B73-C5; | A57-B73-C6; |
| A57-B73-C7; | A57-B73-C8; | A57-B73-C9; | A58-B73-C1; | A58-B73-C2; | A58-B73-C3; |
| A58-B73-C4; | A58-B73-C5; | A58-B73-C6; | A58-B73-C7; | A58-B73-C8; | A58-B73-C9; |
| A59-B73-C1; | A59-B73-C2; | A59-B73-C3; | A59-B73-C4; | A59-B73-C5; | A59-B73-C6; |
| A59-B73-C7; | A59-B73-C8; | A59-B73-C9; | A60-B73-C1; | A60-B73-C2; | A60-B73-C3; |
| A60-B73-C4; | A60-B73-C5; | A60-B73-C6; | A60-B73-C7; | A60-B73-C8; | A60-B73-C9; |
| A61-B73-C1; | A61-B73-C2; | A61-B73-C3; | A61-B73-C4; | A61-B73-C5; | A61-B73-C6; |
| A61-B73-C7; | A61-B73-C8; | A61-B73-C9; | A62-B73-C1; | A62-B73-C2; | A62-B73-C3; |
| A62-B73-C4; | A62-B73-C5; | A62-B73-C6; | A62-B73-C7; | A62-B73-C8; | A62-B73-C9; |
| A63-B73-C1; | A63-B73-C2; | A63-B73-C3; | A63-B73-C4; | A63-B73-C5; | A63-B73-C6; |
| A63-B73-C7; | A63-B73-C8; | A63-B73-C9; | A64-B73-C1; | A64-B73-C2; | A64-B73-C3; |
| A64-B73-C4; | A64-B73-C5; | A64-B73-C6; | A64-B73-C7; | A64-B73-C8; | A64-B73-C9; |
| A65-B73-C1; | A65-B73-C2; | A65-B73-C3; | A65-B73-C4; | A65-B73-C5; | A65-B73-C6; |
| A65-B73-C7; | A65-B73-C8; | A65-B73-C9; | A66-B73-C1; | A66-B73-C2; | A66-B73-C3; |
| A66-B73-C4; | A66-B73-C5; | A66-B73-C6; | A66-B73-C7; | A66-B73-C8; | A66-B73-C9; |
| A67-B73-C1; | A67-B73-C2; | A67-B73-C3; | A67-B73-C4; | A67-B73-C5; | A67-B73-C6; |
| A67-B73-C7; | A67-B73-C8; | A67-B73-C9; | A68-B73-C1; | A68-B73-C2; | A68-B73-C3; |

-continued

| | | | | | |
|---|---|---|---|---|---|
| A68-B73-C4; | A68-B73-C5; | A68-B73-C6; | A68-B73-C7; | A68-B73-C8; | A68-B73-C9; |
| A69-B73-C1; | A69-B73-C2; | A69-B73-C3; | A69-B73-C4; | A69-B73-C5; | A69-B73-C6; |
| A69-B73-C7; | A69-B73-C8; | A69-B73-C9; | A70-B73-C1; | A70-B73-C2; | A70-B73-C3; |
| A70-B73-C4; | A70-B73-C5; | A70-B73-C6; | A70-B73-C7; | A70-B73-C8; | A70-B73-C9; |
| A71-B73-C1; | A71-B73-C2; | A71-B73-C3; | A71-B73-C4; | A71-B73-C5; | A71-B73-C6; |
| A71-B73-C7; | A71-B73-C8; | A71-B73-C9; | A1-B74-C1; | A1-B74-C2; | A1-B74-C3; |
| A1-B74-C4; | A1-B74-C5; | A1-B74-C6; | A1-B74-C7; | A1-B74-C8; | A1-B74-C9; |
| A2-B74-C1; | A2-B74-C2; | A2-B74-C3; | A2-B74-C4; | A2-B74-C5; | A2-B74-C6; |
| A2-B74-C7; | A2-B74-C8; | A2-B74-C9; | A3-B74-C1; | A3-B74-C2; | A3-B74-C3; |
| A3-B74-C4; | A3-B74-C5; | A3-B74-C6; | A3-B74-C7; | A3-B74-C8; | A3-B74-C9; |
| A4-B74-C1; | A4-B74-C2; | A4-B74-C3; | A4-B74-C4; | A4-B74-C5; | A4-B74-C6; |
| A4-B74-C7; | A4-B74-C8; | A4-B74-C9; | A5-B74-C1; | A5-B74-C2; | A5-B74-C3; |
| A5-B74-C4; | A5-B74-C5; | A5-B74-C6; | A5-B74-C7; | A5-B74-C8; | A5-B74-C9; |
| A6-B74-C1; | A6-B74-C2; | A6-B74-C3; | A6-B74-C4; | A6-B74-C5; | A6-B74-C6; |
| A6-B74-C7; | A6-B74-C8; | A6-B74-C9; | A7-B74-C1; | A7-B74-C2; | A7-B74-C3; |
| A7-B74-C4; | A7-B74-C5; | A7-B74-C6; | A7-B74-C7; | A7-B74-C8; | A7-B74-C9; |
| A8-B74-C1; | A8-B74-C2; | A8-B74-C3; | A8-B74-C4; | A8-B74-C5; | A8-B74-C6; |
| A8-B74-C7; | A8-B74-C8; | A8-B74-C9; | A9-B74-C1; | A9-B74-C2; | A9-B74-C3; |
| A9-B74-C4; | A9-B74-C5; | A9-B74-C6; | A9-B74-C7; | A9-B74-C8; | A9-B74-C9; |
| A10-B74-C1; | A10-B74-C2; | A10-B74-C3; | A10-B74-C4; | A10-B74-C5; | A10-B74-C6; |
| A10-B74-C7; | A10-B74-C8; | A10-B74-C9; | A11-B74-C1; | A11-B74-C2; | A11-B74-C3; |
| A11-B74-C4; | A11-B74-C5; | A11-B74-C6; | A11-B74-C7; | A11-B74-C8; | A11-B74-C9; |
| A12-B74-C1; | A12-B74-C2; | A12-B74-C3; | A12-B74-C4; | A12-B74-C5; | A12-B74-C6; |
| A12-B74-C7; | A12-B74-C8; | A12-B74-C9; | A13-B74-C1; | A13-B74-C2; | A13-B74-C3; |
| A13-B74-C4; | A13-B74-C5; | A13-B74-C6; | A13-B74-C7; | A13-B74-C8; | A13-B74-C9; |
| A14-B74-C1; | A14-B74-C2; | A14-B74-C3; | A14-B74-C4; | A14-B74-C5; | A14-B74-C6; |
| A14-B74-C7; | A14-B74-C8; | A14-B74-C9; | A15-B74-C1; | A15-B74-C2; | A15-B74-C3; |
| A15-B74-C4; | A15-B74-C5; | A15-B74-C6; | A15-B74-C7; | A15-B74-C8; | A15-B74-C9; |
| A16-B74-C1; | A16-B74-C2; | A16-B74-C3; | A16-B74-C4; | A16-B74-C5; | A16-B74-C6; |
| A16-B74-C7; | A16-B74-C8; | A16-B74-C9; | A17-B74-C1; | A17-B74-C2; | A17-B74-C3; |
| A17-B74-C4; | A17-B74-C5; | A17-B74-C6; | A17-B74-C7; | A17-B74-C8; | A17-B74-C9; |
| A18-B74-C1; | A18-B74-C2; | A18-B74-C3; | A18-B74-C4; | A18-B74-C5; | A18-B74-C6; |
| A18-B74-C7; | A18-B74-C8; | A18-B74-C9; | A19-B74-C1; | A19-B74-C2; | A19-B74-C3; |
| A19-B74-C4; | A19-B74-C5; | A19-B74-C6; | A19-B74-C7; | A19-B74-C8; | A19-B74-C9; |
| A20-B74-C1; | A20-B74-C2; | A20-B74-C3; | A20-B74-C4; | A20-B74-C5; | A20-B74-C6; |
| A20-B74-C7; | A20-B74-C8; | A20-B74-C9; | A21-B74-C1; | A21-B74-C2; | A21-B74-C3; |
| A21-B74-C4; | A21-B74-C5; | A21-B74-C6; | A21-B74-C7; | A21-B74-C8; | A21-B74-C9; |
| A22-B74-C1; | A22-B74-C2; | A22-B74-C3; | A22-B74-C4; | A22-B74-C5; | A22-B74-C6; |
| A22-B74-C7; | A22-B74-C8; | A22-B74-C9; | A23-B74-C1; | A23-B74-C2; | A23-B74-C3; |
| A23-B74-C4; | A23-B74-C5; | A23-B74-C6; | A23-B74-C7; | A23-B74-C8; | A23-B74-C9; |
| A24-B74-C1; | A24-B74-C2; | A24-B74-C3; | A24-B74-C4; | A24-B74-C5; | A24-B74-C6; |
| A24-B74-C7; | A24-B74-C8; | A24-B74-C9; | A25-B74-C1; | A25-B74-C2; | A25-B74-C3; |
| A25-B74-C4; | A25-B74-C5; | A25-B74-C6; | A25-B74-C7; | A25-B74-C8; | A25-B74-C9; |
| A26-B74-C1; | A26-B74-C2; | A26-B74-C3; | A26-B74-C4; | A26-B74-C5; | A26-B74-C6; |
| A26-B74-C7; | A26-B74-C8; | A26-B74-C9; | A27-B74-C1; | A27-B74-C2; | A27-B74-C3; |
| A27-B74-C4; | A27-B74-C5; | A27-B74-C6; | A27-B74-C7; | A27-B74-C8; | A27-B74-C9; |
| A28-B74-C1; | A28-B74-C2; | A28-B74-C3; | A28-B74-C4; | A28-B74-C5; | A28-B74-C6; |
| A28-B74-C7; | A28-B74-C8; | A28-B74-C9; | A29-B74-C1; | A29-B74-C2; | A29-B74-C3; |
| A29-B74-C4; | A29-B74-C5; | A29-B74-C6; | A29-B74-C7; | A29-B74-C8; | A29-B74-C9; |
| A30-B74-C1; | A30-B74-C2; | A30-B74-C3; | A30-B74-C4; | A30-B74-C5; | A30-B74-C6; |
| A30-B74-C7; | A30-B74-C8; | A30-B74-C9; | A31-B74-C1; | A31-B74-C2; | A31-B74-C3; |
| A31-B74-C4; | A31-B74-C5; | A31-B74-C6; | A31-B74-C7; | A31-B74-C8; | A31-B74-C9; |
| A32-B74-C1; | A32-B74-C2; | A32-B74-C3; | A32-B74-C4; | A32-B74-C5; | A32-B74-C6; |
| A32-B74-C7; | A32-B74-C8; | A32-B74-C9; | A33-B74-C1; | A33-B74-C2; | A33-B74-C3; |
| A33-B74-C4; | A33-B74-C5; | A33-B74-C6; | A33-B74-C7; | A33-B74-C8; | A33-B74-C9; |
| A34-B74-C1; | A34-B74-C2; | A34-B74-C3; | A34-B74-C4; | A34-B74-C5; | A34-B74-C6; |
| A34-B74-C7; | A34-B74-C8; | A34-B74-C9; | A35-B74-C1; | A35-B74-C2; | A35-B74-C3; |
| A35-B74-C4; | A35-B74-C5; | A35-B74-C6; | A35-B74-C7; | A35-B74-C8; | A35-B74-C9; |
| A36-B74-C1; | A36-B74-C2; | A36-B74-C3; | A36-B74-C4; | A36-B74-C5; | A36-B74-C6; |
| A36-B74-C7; | A36-B74-C8; | A36-B74-C9; | A37-B74-C1; | A37-B74-C2; | A37-B74-C3; |
| A37-B74-C4; | A37-B74-C5; | A37-B74-C6; | A37-B74-C7; | A37-B74-C8; | A37-B74-C9; |
| A38-B74-C1; | A38-B74-C2; | A38-B74-C3; | A38-B74-C4; | A38-B74-C5; | A38-B74-C6; |
| A38-B74-C7; | A38-B74-C8; | A38-B74-C9; | A39-B74-C1; | A39-B74-C2; | A39-B74-C3; |
| A39-B74-C4; | A39-B74-C5; | A39-B74-C6; | A39-B74-C7; | A39-B74-C8; | A39-B74-C9; |
| A40-B74-C1; | A40-B74-C2; | A40-B74-C3; | A40-B74-C4; | A40-B74-C5; | A40-B74-C6; |
| A40-B74-C7; | A40-B74-C8; | A40-B74-C9; | A41-B74-C1; | A41-B74-C2; | A41-B74-C3; |
| A41-B74-C4; | A41-B74-C5; | A41-B74-C6; | A41-B74-C7; | A41-B74-C8; | A41-B74-C9; |
| A42-B74-C1; | A42-B74-C2; | A42-B74-C3; | A42-B74-C4; | A42-B74-C5; | A42-B74-C6; |
| A42-B74-C7; | A42-B74-C8; | A42-B74-C9; | A43-B74-C1; | A43-B74-C2; | A43-B74-C3; |
| A43-B74-C4; | A43-B74-C5; | A43-B74-C6; | A43-B74-C7; | A43-B74-C8; | A43-B74-C9; |
| A44-B74-C1; | A44-B74-C2; | A44-B74-C3; | A44-B74-C4; | A44-B74-C5; | A44-B74-C6; |
| A44-B74-C7; | A44-B74-C8; | A44-B74-C9; | A45-B74-C1; | A45-B74-C2; | A45-B74-C3; |
| A45-B74-C4; | A45-B74-C5; | A45-B74-C6; | A45-B74-C7; | A45-B74-C8; | A45-B74-C9; |
| A46-B74-C1; | A46-B74-C2; | A46-B74-C3; | A46-B74-C4; | A46-B74-C5; | A46-B74-C6; |
| A46-B74-C7; | A46-B74-C8; | A46-B74-C9; | A47-B74-C1; | A47-B74-C2; | A47-B74-C3; |
| A47-B74-C4; | A47-B74-C5; | A47-B74-C6; | A47-B74-C7; | A47-B74-C8; | A47-B74-C9; |
| A48-B74-C1; | A48-B74-C2; | A48-B74-C3; | A48-B74-C4; | A48-B74-C5; | A48-B74-C6; |
| A48-B74-C7; | A48-B74-C8; | A48-B74-C9; | A49-B74-C1; | A49-B74-C2; | A49-B74-C3; |
| A49-B74-C4; | A49-B74-C5; | A49-B74-C6; | A49-B74-C7; | A49-B74-C8; | A49-B74-C9; |

-continued

| | | | | | |
|---|---|---|---|---|---|
| A50-B74-C1; | A50-B74-C2; | A50-B74-C3; | A50-B74-C4; | A50-B74-C5; | A50-B74-C6; |
| A50-B74-C7; | A50-B74-C8; | A50-B74-C9; | A51-B74-C1; | A51-B74-C2; | A51-B74-C3; |
| A51-B74-C4; | A51-B74-C5; | A51-B74-C6; | A51-B74-C7; | A51-B74-C8; | A51-B74-C9; |
| A52-B74-C1; | A52-B74-C2; | A52-B74-C3; | A52-B74-C4; | A52-B74-C5; | A52-B74-C6; |
| A52-B74-C7; | A52-B74-C8; | A52-B74-C9; | A53-B74-C1; | A53-B74-C2; | A53-B74-C3; |
| A53-B74-C4; | A53-B74-C5; | A53-B74-C6; | A53-B74-C7; | A53-B74-C8; | A53-B74-C9; |
| A54-B74-C1; | A54-B74-C2; | A54-B74-C3; | A54-B74-C4; | A54-B74-C5; | A54-B74-C6; |
| A54-B74-C7; | A54-B74-C8; | A54-B74-C9; | A55-B74-C1; | A55-B74-C2; | A55-B74-C3; |
| A55-B74-C4; | A55-B74-C5; | A55-B74-C6; | A55-B74-C7; | A55-B74-C8; | A55-B74-C9; |
| A56-B74-C1; | A56-B74-C2; | A56-B74-C3; | A56-B74-C4; | A56-B74-C5; | A56-B74-C6; |
| A56-B74-C7; | A56-B74-C8; | A56-B74-C9; | A57-B74-C1; | A57-B74-C2; | A57-B74-C3; |
| A57-B74-C4; | A57-B74-C5; | A57-B74-C6; | A57-B74-C7; | A57-B74-C8; | A57-B74-C9; |
| A58-B74-C1; | A58-B74-C2; | A58-B74-C3; | A58-B74-C4; | A58-B74-C5; | A58-B74-C6; |
| A58-B74-C7; | A58-B74-C8; | A58-B74-C9; | A59-B74-C1; | A59-B74-C2; | A59-B74-C3; |
| A59-B74-C4; | A59-B74-C5; | A59-B74-C6; | A59-B74-C7; | A59-B74-C8; | A59-B74-C9; |
| A60-B74-C1; | A60-B74-C2; | A60-B74-C3; | A60-B74-C4; | A60-B74-C5; | A60-B74-C6; |
| A60-B74-C7; | A60-B74-C8; | A60-B74-C9; | A61-B74-C1; | A61-B74-C2; | A61-B74-C3; |
| A61-B74-C4; | A61-B74-C5; | A61-B74-C6; | A61-B74-C7; | A61-B74-C8; | A61-B74-C9; |
| A62-B74-C1; | A62-B74-C2; | A62-B74-C3; | A62-B74-C4; | A62-B74-C5; | A62-B74-C6; |
| A62-B74-C7; | A62-B74-C8; | A62-B74-C9; | A63-B74-C1; | A63-B74-C2; | A63-B74-C3; |
| A63-B74-C4; | A63-B74-C5; | A63-B74-C6; | A63-B74-C7; | A63-B74-C8; | A63-B74-C9; |
| A64-B74-C1; | A64-B74-C2; | A64-B74-C3; | A64-B74-C4; | A64-B74-C5; | A64-B74-C6; |
| A64-B74-C7; | A64-B74-C8; | A64-B74-C9; | A65-B74-C1; | A65-B74-C2; | A65-B74-C3; |
| A65-B74-C4; | A65-B74-C5; | A65-B74-C6; | A65-B74-C7; | A65-B74-C8; | A65-B74-C9; |
| A66-B74-C1; | A66-B74-C2; | A66-B74-C3; | A66-B74-C4; | A66-B74-C5; | A66-B74-C6; |
| A66-B74-C7; | A66-B74-C8; | A66-B74-C9; | A67-B74-C1; | A67-B74-C2; | A67-B74-C3; |
| A67-B74-C4; | A67-B74-C5; | A67-B74-C6; | A67-B74-C7; | A67-B74-C8; | A67-B74-C9; |
| A68-B74-C1; | A68-B74-C2; | A68-B74-C3; | A68-B74-C4; | A68-B74-C5; | A68-B74-C6; |
| A68-B74-C7; | A68-B74-C8; | A68-B74-C9; | A69-B74-C1; | A69-B74-C2; | A69-B74-C3; |
| A69-B74-C4; | A69-B74-C5; | A69-B74-C6; | A69-B74-C7; | A69-B74-C8; | A69-B74-C9; |
| A70-B74-C1; | A70-B74-C2; | A70-B74-C3; | A70-B74-C4; | A70-B74-C5; | A70-B74-C6; |
| A70-B74-C7; | A70-B74-C8; | A70-B74-C9; | A71-B74-C1; | A71-B74-C2; | A71-B74-C3; |
| A71-B74-C4; | A71-B74-C5; | A71-B74-C6; | A71-B74-C7; | A71-B74-C8; | A71-B74-C9; |
| A1-B75-C1; | A1-B75-C2; | A1-B75-C3; | A1-B75-C4; | A1-B75-C5; | A1-B75-C6; |
| A1-B75-C7; | A1-B75-C8; | A1-B75-C9; | A2-B75-C1; | A2-B75-C2; | A2-B75-C3; |
| A2-B75-C4; | A2-B75-C5; | A2-B75-C6; | A2-B75-C7; | A2-B75-C8; | A2-B75-C9; |
| A3-B75-C1; | A3-B75-C2; | A3-B75-C3; | A3-B75-C4; | A3-B75-C5; | A3-B75-C6; |
| A3-B75-C7; | A3-B75-C8; | A3-B75-C9; | A4-B75-C1; | A4-B75-C2; | A4-B75-C3; |
| A4-B75-C4; | A4-B75-C5; | A4-B75-C6; | A4-B75-C7; | A4-B75-C8; | A4-B75-C9; |
| A5-B75-C1; | A5-B75-C2; | A5-B75-C3; | A5-B75-C4; | A5-B75-C5; | A5-B75-C6; |
| A5-B75-C7; | A5-B75-C8; | A5-B75-C9; | A6-B75-C1; | A6-B75-C2; | A6-B75-C3; |
| A6-B75-C4; | A6-B75-C5; | A6-B75-C6; | A6-B75-C7; | A6-B75-C8; | A6-B75-C9; |
| A7-B75-C1; | A7-B75-C2; | A7-B75-C3; | A7-B75-C4; | A7-B75-C5; | A7-B75-C6; |
| A7-B75-C7; | A7-B75-C8; | A7-B75-C9; | A8-B75-C1; | A8-B75-C2; | A8-B75-C3; |
| A8-B75-C4; | A8-B75-C5; | A8-B75-C6; | A8-B75-C7; | A8-B75-C8; | A8-B75-C9; |
| A9-B75-C1; | A9-B75-C2; | A9-B75-C3; | A9-B75-C4; | A9-B75-C5; | A9-B75-C6; |
| A9-B75-C7; | A9-B75-C8; | A9-B75-C9; | A10-B75-C1; | A10-B75-C2; | A10-B75-C3; |
| A10-B75-C4; | A10-B75-C5; | A10-B75-C6; | A10-B75-C7; | A10-B75-C8; | A10-B75-C9; |
| A11-B75-C1; | A11-B75-C2; | A11-B75-C3; | A11-B75-C4; | A11-B75-C5; | A11-B75-C6; |
| A11-B75-C7; | A11-B75-C8; | A11-B75-C9; | A12-B75-C1; | A12-B75-C2; | A12-B75-C3; |
| A12-B75-C4; | A12-B75-C5; | A12-B75-C6; | A12-B75-C7; | A12-B75-C8; | A12-B75-C9; |
| A13-B75-C1; | A13-B75-C2; | A13-B75-C3; | A13-B75-C4; | A13-B75-C5; | A13-B75-C6; |
| A13-B75-C7; | A13-B75-C8; | A13-B75-C9; | A14-B75-C1; | A14-B75-C2; | A14-B75-C3; |
| A14-B75-C4; | A14-B75-C5; | A14-B75-C6; | A14-B75-C7; | A14-B75-C8; | A14-B75-C9; |
| A15-B75-C1; | A15-B75-C2; | A15-B75-C3; | A15-B75-C4; | A15-B75-C5; | A15-B75-C6; |
| A15-B75-C7; | A15-B75-C8; | A15-B75-C9; | A16-B75-C1; | A16-B75-C2; | A16-B75-C3; |
| A16-B75-C4; | A16-B75-C5; | A16-B75-C6; | A16-B75-C7; | A16-B75-C8; | A16-B75-C9; |
| A17-B75-C1; | A17-B75-C2; | A17-B75-C3; | A17-B75-C4; | A17-B75-C5; | A17-B75-C6; |
| A17-B75-C7; | A17-B75-C8; | A17-B75-C9; | A18-B75-C1; | A18-B75-C2; | A18-B75-C3; |
| A18-B75-C4; | A18-B75-C5; | A18-B75-C6; | A18-B75-C7; | A18-B75-C8; | A18-B75-C9; |
| A19-B75-C1; | A19-B75-C2; | A19-B75-C3; | A19-B75-C4; | A19-B75-C5; | A19-B75-C6; |
| A19-B75-C7; | A19-B75-C8; | A19-B75-C9; | A20-B75-C1; | A20-B75-C2; | A20-B75-C3; |
| A20-B75-C4; | A20-B75-C5; | A20-B75-C6; | A20-B75-C7; | A20-B75-C8; | A20-B75-C9; |
| A21-B75-C1; | A21-B75-C2; | A21-B75-C3; | A21-B75-C4; | A21-B75-C5; | A21-B75-C6; |
| A21-B75-C7; | A21-B75-C8; | A21-B75-C9; | A22-B75-C1; | A22-B75-C2; | A22-B75-C3; |
| A22-B75-C4; | A22-B75-C5; | A22-B75-C6; | A22-B75-C7; | A22-B75-C8; | A22-B75-C9; |
| A23-B75-C1; | A23-B75-C2; | A23-B75-C3; | A23-B75-C4; | A23-B75-C5; | A23-B75-C6; |
| A23-B75-C7; | A23-B75-C8; | A23-B75-C9; | A24-B75-C1; | A24-B75-C2; | A24-B75-C3; |
| A24-B75-C4; | A24-B75-C5; | A24-B75-C6; | A24-B75-C7; | A24-B75-C8; | A24-B75-C9; |
| A25-B75-C1; | A25-B75-C2; | A25-B75-C3; | A25-B75-C4; | A25-B75-C5; | A25-B75-C6; |
| A25-B75-C7; | A25-B75-C8; | A25-B75-C9; | A26-B75-C1; | A26-B75-C2; | A26-B75-C3; |
| A26-B75-C4; | A26-B75-C5; | A26-B75-C6; | A26-B75-C7; | A26-B75-C8; | A26-B75-C9; |
| A27-B75-C1; | A27-B75-C2; | A27-B75-C3; | A27-B75-C4; | A27-B75-C5; | A27-B75-C6; |
| A27-B75-C7; | A27-B75-C8; | A27-B75-C9; | A28-B75-C1; | A28-B75-C2; | A28-B75-C3; |
| A28-B75-C4; | A28-B75-C5; | A28-B75-C6; | A28-B75-C7; | A28-B75-C8; | A28-B75-C9; |
| A29-B75-C1; | A29-B75-C2; | A29-B75-C3; | A29-B75-C4; | A29-B75-C5; | A29-B75-C6; |
| A29-B75-C7; | A29-B75-C8; | A29-B75-C9; | A30-B75-C1; | A30-B75-C2; | A30-B75-C3; |
| A30-B75-C4; | A30-B75-C5; | A30-B75-C6; | A30-B75-C7; | A30-B75-C8; | A30-B75-C9; |
| A31-B75-C1; | A31-B75-C2; | A31-B75-C3; | A31-B75-C4; | A31-B75-C5; | A31-B75-C6; |

-continued

| | | | | | |
|---|---|---|---|---|---|
| A31-B75-C7; | A31-B75-C8; | A31-B75-C9; | A32-B75-C1; | A32-B75-C2; | A32-B75-C3; |
| A32-B75-C4; | A32-B75-C5; | A32-B75-C6; | A32-B75-C7; | A32-B75-C8; | A32-B75-C9; |
| A33-B75-C1; | A33-B75-C2; | A33-B75-C3; | A33-B75-C4; | A33-B75-C5; | A33-B75-C6; |
| A33-B75-C7; | A33-B75-C8; | A33-B75-C9; | A34-B75-C1; | A34-B75-C2; | A34-B75-C3; |
| A34-B75-C4; | A34-B75-C5; | A34-B75-C6; | A34-B75-C7; | A34-B75-C8; | A34-B75-C9; |
| A35-B75-C1; | A35-B75-C2; | A35-B75-C3; | A35-B75-C4; | A35-B75-C5; | A35-B75-C6; |
| A35-B75-C7; | A35-B75-C8; | A35-B75-C9; | A36-B75-C1; | A36-B75-C2; | A36-B75-C3; |
| A36-B75-C4; | A36-B75-C5; | A36-B75-C6; | A36-B75-C7; | A36-B75-C8; | A36-B75-C9; |
| A37-B75-C1; | A37-B75-C2; | A37-B75-C3; | A37-B75-C4; | A37-B75-C5; | A37-B75-C6; |
| A37-B75-C7; | A37-B75-C8; | A37-B75-C9; | A38-B75-C1; | A38-B75-C2; | A38-B75-C3; |
| A38-B75-C4; | A38-B75-C5; | A38-B75-C6; | A38-B75-C7; | A38-B75-C8; | A38-B75-C9; |
| A39-B75-C1; | A39-B75-C2; | A39-B75-C3; | A39-B75-C4; | A39-B75-C5; | A39-B75-C6; |
| A39-B75-C7; | A39-B75-C8; | A39-B75-C9; | A40-B75-C1; | A40-B75-C2; | A40-B75-C3; |
| A40-B75-C4; | A40-B75-C5; | A40-B75-C6; | A40-B75-C7; | A40-B75-C8; | A40-B75-C9; |
| A41-B75-C1; | A41-B75-C2; | A41-B75-C3; | A41-B75-C4; | A41-B75-C5; | A41-B75-C6; |
| A41-B75-C7; | A41-B75-C8; | A41-B75-C9; | A42-B75-C1; | A42-B75-C2; | A42-B75-C3; |
| A42-B75-C4; | A42-B75-C5; | A42-B75-C6; | A42-B75-C7; | A42-B75-C8; | A42-B75-C9; |
| A43-B75-C1; | A43-B75-C2; | A43-B75-C3; | A43-B75-C4; | A43-B75-C5; | A43-B75-C6; |
| A43-B75-C7; | A43-B75-C8; | A43-B75-C9; | A44-B75-C1; | A44-B75-C2; | A44-B75-C3; |
| A44-B75-C4; | A44-B75-C5; | A44-B75-C6; | A44-B75-C7; | A44-B75-C8; | A44-B75-C9; |
| A45-B75-C1; | A45-B75-C2; | A45-B75-C3; | A45-B75-C4; | A45-B75-C5; | A45-B75-C6; |
| A45-B75-C7; | A45-B75-C8; | A45-B75-C9; | A46-B75-C1; | A46-B75-C2; | A46-B75-C3; |
| A46-B75-C4; | A46-B75-C5; | A46-B75-C6; | A46-B75-C7; | A46-B75-C8; | A46-B75-C9; |
| A47-B75-C1; | A47-B75-C2; | A47-B75-C3; | A47-B75-C4; | A47-B75-C5; | A47-B75-C6; |
| A47-B75-C7; | A47-B75-C8; | A47-B75-C9; | A48-B75-C1; | A48-B75-C2; | A48-B75-C3; |
| A48-B75-C4; | A48-B75-C5; | A48-B75-C6; | A48-B75-C7; | A48-B75-C8; | A48-B75-C9; |
| A49-B75-C1; | A49-B75-C2; | A49-B75-C3; | A49-B75-C4; | A49-B75-C5; | A49-B75-C6; |
| A49-B75-C7; | A49-B75-C8; | A49-B75-C9; | A50-B75-C1; | A50-B75-C2; | A50-B75-C3; |
| A50-B75-C4; | A50-B75-C5; | A50-B75-C6; | A50-B75-C7; | A50-B75-C8; | A50-B75-C9; |
| A51-B75-C1; | A51-B75-C2; | A51-B75-C3; | A51-B75-C4; | A51-B75-C5; | A51-B75-C6; |
| A51-B75-C7; | A51-B75-C8; | A51-B75-C9; | A52-B75-C1; | A52-B75-C2; | A52-B75-C3; |
| A52-B75-C4; | A52-B75-C5; | A52-B75-C6; | A52-B75-C7; | A52-B75-C8; | A52-B75-C9; |
| A53-B75-C1; | A53-B75-C2; | A53-B75-C3; | A53-B75-C4; | A53-B75-C5; | A53-B75-C6; |
| A53-B75-C7; | A53-B75-C8; | A53-B75-C9; | A54-B75-C1; | A54-B75-C2; | A54-B75-C3; |
| A54-B75-C4; | A54-B75-C5; | A54-B75-C6; | A54-B75-C7; | A54-B75-C8; | A54-B75-C9; |
| A55-B75-C1; | A55-B75-C2; | A55-B75-C3; | A55-B75-C4; | A55-B75-C5; | A55-B75-C6; |
| A55-B75-C7; | A55-B75-C8; | A55-B75-C9; | A56-B75-C1; | A56-B75-C2; | A56-B75-C3; |
| A56-B75-C4; | A56-B75-C5; | A56-B75-C6; | A56-B75-C7; | A56-B75-C8; | A56-B75-C9; |
| A57-B75-C1; | A57-B75-C2; | A57-B75-C3; | A57-B75-C4; | A57-B75-C5; | A57-B75-C6; |
| A57-B75-C7; | A57-B75-C8; | A57-B75-C9; | A58-B75-C1; | A58-B75-C2; | A58-B75-C3; |
| A58-B75-C4; | A58-B75-C5; | A58-B75-C6; | A58-B75-C7; | A58-B75-C8; | A58-B75-C9; |
| A59-B75-C1; | A59-B75-C2; | A59-B75-C3; | A59-B75-C4; | A59-B75-C5; | A59-B75-C6; |
| A59-B75-C7; | A59-B75-C8; | A59-B75-C9; | A60-B75-C1; | A60-B75-C2; | A60-B75-C3; |
| A60-B75-C4; | A60-B75-C5; | A60-B75-C6; | A60-B75-C7; | A60-B75-C8; | A60-B75-C9; |
| A61-B75-C1; | A61-B75-C2; | A61-B75-C3; | A61-B75-C4; | A61-B75-C5; | A61-B75-C6; |
| A61-B75-C7; | A61-B75-C8; | A61-B75-C9; | A62-B75-C1; | A62-B75-C2; | A62-B75-C3; |
| A62-B75-C4; | A62-B75-C5; | A62-B75-C6; | A62-B75-C7; | A62-B75-C8; | A62-B75-C9; |
| A63-B75-C1; | A63-B75-C2; | A63-B75-C3; | A63-B75-C4; | A63-B75-C5; | A63-B75-C6; |
| A63-B75-C7; | A63-B75-C8; | A63-B75-C9; | A64-B75-C1; | A64-B75-C2; | A64-B75-C3; |
| A64-B75-C4; | A64-B75-C5; | A64-B75-C6; | A64-B75-C7; | A64-B75-C8; | A64-B75-C9; |
| A65-B75-C1; | A65-B75-C2; | A65-B75-C3; | A65-B75-C4; | A65-B75-C5; | A65-B75-C6; |
| A65-B75-C7; | A65-B75-C8; | A65-B75-C9; | A66-B75-C1; | A66-B75-C2; | A66-B75-C3; |
| A66-B75-C4; | A66-B75-C5; | A66-B75-C6; | A66-B75-C7; | A66-B75-C8; | A66-B75-C9; |
| A67-B75-C1; | A67-B75-C2; | A67-B75-C3; | A67-B75-C4; | A67-B75-C5; | A67-B75-C6; |
| A67-B75-C7; | A67-B75-C8; | A67-B75-C9; | A68-B75-C1; | A68-B75-C2; | A68-B75-C3; |
| A68-B75-C4; | A68-B75-C5; | A68-B75-C6; | A68-B75-C7; | A68-B75-C8; | A68-B75-C9; |
| A69-B75-C1; | A69-B75-C2; | A69-B75-C3; | A69-B75-C4; | A69-B75-C5; | A69-B75-C6; |
| A69-B75-C7; | A69-B75-C8; | A69-B75-C9; | A70-B75-C1; | A70-B75-C2; | A70-B75-C3; |
| A70-B75-C4; | A70-B75-C5; | A70-B75-C6; | A70-B75-C7; | A70-B75-C8; | A70-B75-C9; |
| A71-B75-C1; | A71-B75-C2; | A71-B75-C3; | A71-B75-C4; | A71-B75-C5; | A71-B75-C6; |
| A71-B75-C7; | A71-B75-C8; | A71-B75-C9; | | | |

Thus, for example, in the above list the compound denoted as A20-B2-C1 is the product of the combination of group A20 in Table 1 and B2 in Table 2 and C1 in Table 3, namely N-(R)-1-(cyanomethyl-carbamoyl)-2-[2-(1,1-difluoro-methoxy)-phenylmethanesulfonyl]-ethyl}-4-hydroxy-benzamide:

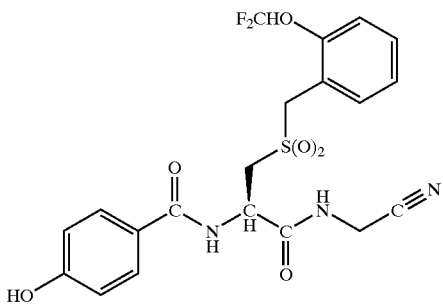

Further preferred are compounds of Formula I selected from a group consisting of:
  N-{(R)-1-(Cyanomethyl-carbamoyl)-2-[2-(1,1-difluoro-methoxy)-phenylmethanesulfonyl]-ethyl}-nicotinamide, (compound denoted as A24-B2-C1);
  N-{(R)-1-(Cyanomethyl-carbamoyl)-2-[2-(1,1-difluoro-methoxy)-phenylmethanesulfonyl]-ethyl}-nicotinamide, (compound denoted as A25-B2-C1);
  Pytidine-2-carboxylic acid-{(R)-1-(cyanomethyl-carbamoyl)-2-[2-(1,1-difluoro-methoxy)-phenylmethanesulfonyl]-ethyl}-amide (compound denoted as A62-B2-C1);
  Pyrazine-2-carboxylic acid-{(R)-1-(cyanomethyl-carbamoyl)-2-[2-(1,1-difluoro-methoxy)-phenylmethanesulfonyl]-ethyl}-amide, (compound denoted as A63-B2-C1);
  N-{(R)-1-(Cyanomethyl-carbamoyl)-2-[2-(1,1-difluoro-methoxy)-phenylmethanesulfonyl]-ethyl}-nicotinamide, (compound denoted as A65-B2-C1);
  2-Amino-N-{(R)-1-(cyanomethyl-carbamoyl)-2-[2-(1,1-difluoro-methoxy)-phenylmethanesulfonyl]-ethyl}-nicotinamide, (compound denoted as A67-B 2—C1);
  6-Amino-N-{(R)-1-(Cyanomethyl-carbamoyl)-2-[2-(1,1-difluoro-methoxy)-phenylmethanesulfonyl]-ethyl}-nicotinamide, (compound denoted as A66-B2-C1);
  3-Hydroxy-pyridine-2-carboxylic acid-{(R)-1-(cyanomethyl-carbamoyl)-2-[2-(1,1-difluoro-methoxy)-phenylmethanesulfonyl]-ethyl}-amide (compound denoted as A68-B2-C1);
  Morpholine-4-carboxylic acid-{(R)-1-(4-cyano-tetrahydro-pyran-4-ylcarbamoyl)-2-[2-1,1-difluoro-methoxy)-phenylmethanesulfonyl]-ethyl}-amide (compound denoted as A2-B2-C4);
  Morpholine-4-carboxylic acid-{(R)-1-(4-cyano-tetrahydro-pyran-4-ylcarbamoyl)-2-[2-(1,1-difluoro-methoxy)-phenylmethanesulfonyl]-ethyl}-amide (compound denoted as A2-B2-C5);
  (R)-N-Cyanomethyl-3-[2-(1,1-difluoro-methoxy)-phenylmethanesulfonyl]-2-(3,3-dimethyl-ureido)-propionamide, (compound denoted as A56-B2-C1);
  {(R)-1-(Cyanomethyl-carbamoyl)-2-[2-(1,1-difluoro-methoxy)-phenylmethane-sulfonyl]-ethyl}-carbamic acid allyl ester, (compound denoted as A53-B2-C1);
  {(R)-1-(Cyanomethyl-carbamoyl)-2-[2-(1,1-difluoro-methoxy)-phenylmethane-sulfonyl]-ethyl}-carbamic acid isobutyl ester, (compound denoted as A51-B2-C1);
  N-{(R)-1-(Cyanomethyl-carbamoyl)-2-[2-(1,1-difluoro-methoxy)-phenylmethane-sulfonyl]-ethyl}-3,4-difluoro-benzamide, (compound denoted as A46-B2-C1);
  N-{(R)-1-(Cyanomethyl-carbamoyl)-2-[2-(1,1-difluoro-methoxy)-phenylmethane-sulfonyl]-ethyl}-3-methyl-benzamide, (compound denoted as A48-B2-C1);
  Thiophene-2-carboxylic acid-{(R)-1-(cyanomethyl-carbamoyl)-2-[2-(1,1-difluoro-methoxy)-phenylmethanesulfonyl]-ethyl}-amide, (compound denoted as A28-B2-C1);
  4-Bromo-N-{(R)-1-(cyanomethyl-carbamoyl)-2-[2-(1,1-difluoro-methoxy)-phenylmethane-sulfonyl]-ethyl}-benzamide, (compound denoted as A43-B2-C1);
  N-{(R)-1-(Cyanomethyl-carbamoyl)-2-[2-(1,1-difluoro-methoxy)-phenylmethane-sulfonyl]-ethyl}-benzamide, (compound denoted as A44-B2-C1);
  N-{(R)-1-(Cyanomethyl-carbamoyl)-2-[2-(1,1-difluoro-methoxy)-phenylmethanesulfonyl]-ethyl}-4-trifluoromethoxy-benzamide, (compound denoted as A45-B2-C1);
  Naphthalene-2-carboxylic acid-{(R)-1-(cyanomethyl-carbamoyl)-2-[2-(1,1-difluoro-methoxy)-phenylmethane-sulfonyl]-ethyl}-amide, (compound denoted as A7-B2-C1);
  (E)-N-{(R)-1-(Cyanomethyl-carbamoyl)-2-[2-(1,1-difluoro-methoxy)-phenylmethanesulfonyl]-ethyl}-3-phenyl-acrylamide, (compound denoted as A59-B2-C1);
  5-Methyl-thiophene-2-carboxylic acid-{(R)-1-(cyanomethyl-carbamoyl)-2-[2-(1,1-difluoro-methoxy)-phenylmethanesulfonyl]-ethyl}-amide, (compound denoted as A31-B2-C1);
  Biphenyl-4-carboxylic acid-{(R)-1-(cyanomethyl-carbamoyl)-2-[2-(1,1-difluoro-methoxy)-phenylmethanesulfonyl]-ethyl}-amide, (compound denoted as A11-B2-C1);
  1H-Indole-5-carboxylic acid-{(R)-1-(cyanomethyl-carbamoyl)-2-[2-(1,1-difluoro-methoxy)-phenylmethanesulfonyl]-ethyl}-amide, (compound denoted as A60-B2-C1);
  Benzo[1,3]dioxole-5-carboxylic acid-{(R)-1-(cyanomethyl-carbamoyl)-2-[2-(1,1-difluoro-methoxy)-phenylmethane-sulfonyl]-ethyl}-amide, (compound denoted as A8-B2-C1);
  Benzo[b]thiophene-2-carboxylic acid-{(R)-1-(cyanomethyl-carbamoyl)-2-[2-(1,1-difluoro-methoxy)-phenylmethane-sulfonyl]-ethyl}-amide, (compound denoted as A35-B2-C1);
  N-{(R)-1-(Cyanomethyl-carbamoyl)-2-[2-(1,1-difluoro-methoxy)-phenylmethane-sulfonyl]-ethyl}-benzamide, (compound denoted as A69-B2-C1);
  Quinoline-3-carboxylic acid-{(R)-1-(cyanomethyl-carbamoyl)-2-[2-(1,1-difluoro-methoxy)-phenylmethanesulfonyl]-ethyl}-amide, (compound denoted as A 13-B2-C1);
  N-{(R)-1-(Cyanomethyl-carbamoyl)-2-[2-(1,1-difluoro-methoxy)-phenylmethane-sulfonyl]-ethyl}-benzamide, (compound denoted as A70-B2-C1);
  4-Chloro-N-{(R)-1-(cyanomethyl-carbamoyl)-2-[2-(1,1-difluoro-methoxy)-phenylmethane-sulfonyl]-ethyl}-benzamide, (compound denoted as A42-B2-C1);
  N-{(R)-1-(Cyanomethyl-carbamoyl)-2-[2-(1,1-difluoro-methoxy)-phenylmethane-sulfonyl]-ethyl}-benzamide, (compound denoted as A41-B2-C1);
  3-Bromo-thiophene-2-carboxylic acid-{(R)-1-(cyanomethyl-carbamoyl)-2-[2-(1,1-difluoro-methoxy)- phenylmethanesulfonyl]-ethyl}-amide, (compound denoted as A33-B2-C1);

3-Chloro-benzo[b]thiophene-2-carboxylic acid-{(R)-1-(cyanomethyl-carbamoyl)-2-[2-(1,1-difluoro-methoxy)-phenylmethanesulfonyl]-ethyl}-amide, (compound denoted as A36-B2-C1);

3-Chloro-thiophene-2-carboxylic acid-{(R)-1-(cyanomethyl-carbamoyl)-2-[2-(1,1-difluoro-methoxy)-phenylmethanesulfonyl]-ethyl}-amide, (compound denoted as A32-B2-C1);

N-{(R)-(Cyanomethyl-carbamoyl)-[2-(1,1-difluoro-methoxy)-phenylmethane-sulfonyl]-ethyl}-benzamide, (compound denoted as A40-B2-C1);

(R)-N-Cyanomethyl-3-[2-(1,1-difluoro-methoxy)-phenylmethanesulfonyl]-2-(naphthalene-2-sulfonylamino)-propionamide, (compound denoted as A38-B2-C1);

Cyclopentanecarboxylic acid-{(R)-1-(cyanomethyl-carbamoyl)-2-[2-(1,1-difluoro-methoxy)-phenylmethanesulfonyl]-ethyl}-amide, (compound denoted as A34-B2-C1);

N-[1R-cyanomethylcarbamoyl-2-(3-trifluromethoxybenzylsulfonyl)ethyl]benzamide, (compound denoted as A1-B2-C1);

N-[1R-cyanomethylcarbamoyl-2-(2-difluoromethoxybenzylsulfonyl)ethyl]benzamide, (compound denoted as A1-B2-C1);

N-[1R-cyanomethylcarbamoyl-2-(2-trifluoromethoxybenzylsulfonyl)ethyl]benzamide, (compound denoted as A1-B42-C1);

N-(1R-cyanomethylcarbamoyl-2-(3-difluoromethoxybenzylsulfonyl)ethyl]benzamide, (compound denoted as A1-B24-C1);

N-[1R-cyanomethylcarbamoyl-2-(2-difluoromethoxybenzylsulfonyl)ethyl]morpholine-4-carboxamide, (compound denoted as A2-B2-C1);

N-[1R-(i-cyanocyclopropylcarbamoyl)-2-(2-difluoromethoxybenzylsulfonyl)ethyl]-morpholine-4-carboxamide, (compound denoted as A2-B2-C3); and the N-oxide derivatives, prodrug derivatives, protected derivatives, individual isomers and mixtures of isomers thereof; and pharmaceutically acceptable salts and solvates (e.g. hydrates) of such compounds and the N-oxide derivatives, prodrug derivatives, protected derivatives, individual isomers and mixtures of isomers thereof.

Particularly preferred are compounds of Formula I selected from a group consisting of:

N-[1R-cyanomethylcarbamoyl-2-(2-difluoromethoxybenzylsulfonyl)ethyl]morpholine-4-carboxamide, (compound denoted as A2-B2-C1);

thiophene-2-carboxylic acid-{(R)-1-(cyanomethyl-carbamoyl)-2-[2-(1,1-difluoro-methoxy)-phenylmethanesulfonyl]-ethyl}-amide, (compound denoted as A28-B2-C1);

thiophene-3-carboxylic acid-{(R)-1-(cyanomethyl-carbamoyl)-2-[2-(1,1-difluoro-methoxy)-phenylmethanesulfonyl]-ethyl}-amide, (compound denoted as A29-B2-C1);

N-{(R)-1-(cyanomethyl-carbamoyl)-2-[2-(1,1-difluoro-methoxy)-phenylmethanesulfonyl]-ethyl}-benzamide, (compound denoted as A49-B2-C1);

morpholine-4-carboxylic acid-{(R)-1-(4-cyano-1-methyl-piperidin-4-ylcabamoyl)-2-[2(1,1-difluoro-methoxy)-phenylmethanesulfonyl]-ethyl}-amide, (compound denoted as A2-B2-C5);

5-methyl-thiophene-2-carboxylic acid-{(R)-1-(cyanomethyl-carbamoyl)-2-[2-(1,1-difluoro-methoxy)-phenylmethanesulfonyl]-ethyl}-amide, (compound denoted as A31-B2-C1);

1H-indole-5-carboxylic acid-{(R)-1-(cyanomethyl-carbamoyl)-2-[2-(1,1-difluoro-methoxy)-phenylmethanesulfonyl]-ethyl}-amide, (compound denoted as A60-B2-C1);

N-{(R)-1-(cyanomethyl-carbamoyl)-2-[2-( 1,1-difluoro-methoxy)-phenylmethanesulfonyl]-ethyl}-3-methyl-benzamide, (compound denoted as A2-B2-C1);

N-{(R)-1-(cyanomethyl-carbamoyl)-2-[2-( 1,1-difluoro-methoxy)-phenylmethanesulfonyl]-ethyl}-3-methyl-benzamide, (compound denoted as A46-B2-C1);

N-{(R)-1-(cyanomethyl-carbamoyl)-2-[2-( 1,1-difluoro-methoxy)-phenylmethanesulfonyl]-ethyl}-isonicotinamide, (compound denoted as A25-B2-C1);

N-[1R-(1-cyanocyclopropyl-carbamoyl)-2-(2-difluoromethoxybenzylsulfonyl)-ethyl]morpholine-4-carboxamide, (compound denoted as A2-B2-C3); and the N-oxide derivatives, prodrug derivatives, protected derivatives, individual isomers and mixtures of isomers thereof; and the pharmaceutically acceptable salts and solvates (e.g. hydrates) of such compounds and the N-oxide derivatives, prodrug derivatives, protected derivatives, individual isomers and mixtures of isomers thereof.

Pharmacology and Utility

The compounds of the invention are selective inhibitors of cathepsin S and, as such, are useful for treating diseases in which cathepsin S activity contributes to the pathology and/or symptomatology of the disease. For example, the compounds of the invention are useful in treating autoimmune disorders, including, but not limited to, juvenile onset diabetes, multiple sclerosis, pemphigus vulgaris, Graves' disease, myasthenia gravis, systemic lupus erythemotasus, rheumatoid arthritis and Hashimoto's thyroiditis, allergic disorders, including, but not limited to, asthma, and allogeneic immune responses, including, but not limited to, organ transplants or tissue grafts.

Cathepsin S also is implicated in disorders involving excessive elastolysis, such as chronic obstructive pulmonary disease (e.g., emphysema), bronchiolitis, excessive airway elastolysis in asthma and bronchitis, pneumonities and cardiovascular disease such as plaque rupture and atheroma. Cathepsin S is implicated in fibril formation and, therefore, inhibitors of cathepsins S are of use in treatment of systemic amyloidosis.

The cysteine protease inhibitory activities of the compounds of the invention can be determined by methods known to those of ordinary skill in the art. Suitable in vitro assays for measuring protease activity and the inhibition thereof by test compounds are known. Typically, the assay measures protease induced hydrolysis of a peptide based substrate. Details of assays for measuring protease inhibitory activity are set forth in Examples 11, 12, 13 and 14, infra.

Administration and Pharmaceutical Compositions

In general, compounds of Formula I will be administered in therapeutically effective amounts via any of the usual and acceptable modes known in the art, either singly or in combination with another therapeutic agent. A therapeutically effective amount may vary widely depending on the severity of the disease, the age and relative health of the subject, the potency of the compound used and other factors. For example, therapeutically effective amounts of a compound of Formula I may range from about 1 micrograms per kilogram body weight (µg/kg) per day to about 1 milligram per kilogram body weight (mg/kg) per day, typically from about 10 µg/kg/day to about 0.1 mg/kg/day. Therefore, a therapeutically effective amount for a 80 kg human patient may range from about 100 µg/day to about 100 mg/day, typically from about 1 µg/day to about 10 mg/day. In general, one of ordinary skill in the art, acting in reliance upon personal knowledge and the disclosure of this Application, will be able to ascertain a therapeutically effective amount of a compound of Formula I for treating a given disease.

The compounds of Formula I can be administered as pharmaceutical compositions by one of the following routes: oral, systemic (e.g., transdermal, intranasal or by suppository) or parenteral (e.g., intramuscular, intravenous or subcutaneous). Compositions can take the form of tablets, pills, capsules, semisolids, powders, sustained release formulations, solutions, suspensions, elixirs, aerosols, or any other appropriate composition and are comprised of, in general, a compound of Formula I in combination with at least one pharmaceutically acceptable excipient. Acceptable excipients are non-toxic, aid administration, and do not adversely affect the therapeutic benefit of the active ingredient. Such excipient may be any solid, liquid, semisolid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, and the like. Liquid and semisolid excipients may be selected from water, ethanol, glycerol, propylene glycol and various oils, including those of petroleum, animal, vegetable or synthetic origin (e.g., peanut oil, soybean oil, mineral oil, sesame oil, and the like). Preferred liquid carriers, particularly for injectable solutions, include water, saline, aqueous dextrose and glycols.

The amount of a compound of Formula I in the composition may vary widely depending upon the type of formulation, size of a unit dosage, kind of excipients and other factors known to those of skill in the art of pharmaceutical sciences. In general, a composition of a compound of Formula I for treating a given disease will comprise from 0.01%w to 10%w, preferably 0.3%w to 1%w, of active ingredient with the remainder being the excipient or excipients. Preferably the pharmaceutical composition is administered in a single unit dosage form for continuous treatment or in a single unit dosage form ad libitum when relief of symptoms is specifically required. Representative pharmaceutical formulations containing a compound of Formula I are described in Example 15.

Chemistry

Processes for Making Compounds of Formula I:

Compounds of the invention may be prepared by the application or adaptation of known methods, by which is meant methods used heretofore or described in the literature, for example those described by R. C. Larock in Comprehensive Organic Transformations, VCH publishers, 1989.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

Compounds of Formula I can be prepared by proceeding as in the following Reaction Scheme 1:

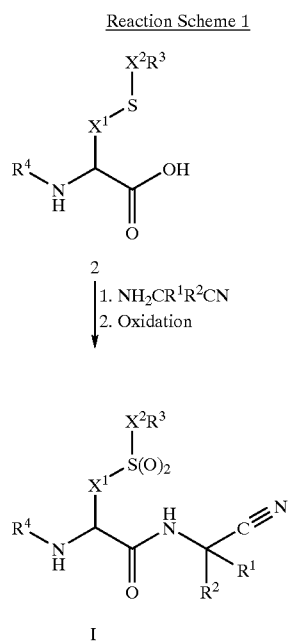

in which each $X^1$, $X^2$, $R^1$, $R^2$, $R^3$ and $R^4$ are as defined for Formula I in the Summary of the Invention.

Compounds of Formula I can be prepared by condensing an acid of Formula 2 with an aminoalkanonitrile of the formula $NH_2CR^1R^2CN$ and then oxidizing. The condensation reaction can be effected with an appropriate coupling agent (e.g., benzotriazol-1-yloxytrispyrrolidinophosphonium hex afluorophosphate (PyBOP®), 1-(3-dimethylaminopropyl)-3-ehtylcarbodiimide hydrochloride (EDCI), O-benzotriazol-1-yl-N,N,N',N'-tetramethyluronium hexafluorophosphate (HBTU), 1,3-dicyclohexylcarbodiimide (DCC), or the like and optionally an appropriate catalyst (e.g., 1-hydroxybenzotriazole (HOBt), 1-hydroxy-7-azabenzotriazole (HOAt), O-(7-azabenzotrizol-1-yl)-1,1,3,3, tetra-methyluroniumhexafluorophosphate (HATU), or the like) and non-nucleophilic base (e.g., N-methylpyrrolidinone, N-methylmorpholine, and the like, or any suitable combination thereof) at ambient temperature and requires 5 to 10 hours to complete.

The oxidation can be carried out with an oxidizing agent (e.g., Oxone®, or the like) in a suitable solvent (e.g., methanol, water, or the like, or any suitable combination thereof) at ambient temperature and requires 16 to 24 hours to complete. A detailed description for the synthesis of a compound of Formula I by the processes in Reaction Scheme 1 is set forth in the Examples 1, 2, 8 and 10, infra.

Compounds of Formula I can be prepared by proceeding as in the following Reaction Scheme 2:

Reaction Scheme 2

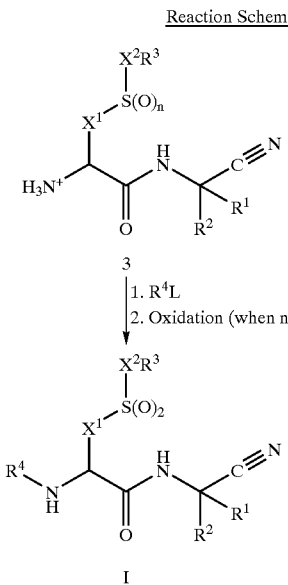

in which n is 0 or 2, L is a leaving group and each $X^1$, $X^2$, $R^1$, $R^2$, $R^3$ and $R^4$ are as defined for Formula I in the Summary of the Invention.

Compounds of Formula I can be prepared by condensing a compound of Formula 3 with a compound of the formula $R^4L$ (e.g., 3-acetylbenzoic acid, nicotinic acid, morpholin-4-ylcarbonyl chloride, or the like) and then oxidizing when n is 0. When L is chloro the condensation can be carried out at ambient temperature in the presence of a suitable non-nucleophilic base (e.g., triethylamine, N-methylmorpholine, or the like) in a suitable solvent (e.g., dichloromethane, tetrahydrofuran, or the like) and requires 16 to 24 hours to complete. When L is hydroxy the condensation typically is effected in the presence of a suitable coupling agent (e.g., (PyBOP®), EDCI, HBTU, DCC, or the like) and optionally an appropriate catalyst (e.g., 1-hydroxybenzotriazole (HOBt), 1-hydroxy-7-azabenzotriazole (HOAt), or the like) in a suitable solvent (e.g., dichloromethane, tetrahydrofuran, or the like, or any suitable combination thereof) at ambient temperature and requires 16 to 24 hours to complete.

The oxidization can be carried out by the process described above for Reaction Scheme 1. Detailed procedures for the syntheses of compounds of Formula I by the processes described in Scheme 2 are set forth in the Examples 3, 4 and 5, infra.

Compounds of Formula I in which $R^4$ is —$NR^{13}R^{14}$ or —$NR^{20}R^{21}$ can be prepared by proceeding as in the following Reaction Scheme 3:

Reaction Scheme 3

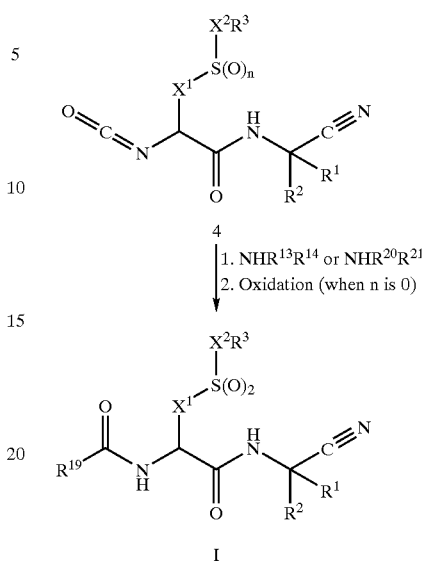

in which $R^{19}$ is —$NR^{13}R^{14}$ or $NR^{20}R^{21}$, wherein $R^{20}$ and $R^{21}$ together with the nitrogen atom to which $R^{20}$ and $R^{21}$ are attached form hetero($C_{5-12}$)cycloalkyl and each $X^1$, $X^2$, $R^1$, $R^2$, $R^3$, $R^{13}$ and $R^{14}$ are as defined in the Summary of the Invention.

Compounds of Formula I in which $R^4$ is —$C(O)NR^{13}R^{14}$ or —$C(O)NR^{20}R^{21}$, wherein $R^{20}$ and $R^{21}$ together with the nitrogen atom to which $R^{20}$ and $R^{21}$ are attached form hetero($C_{5-12}$)cycloalkyl and $R^{13}$ and $R^{14}$ are as defined in the Summary of the Invention can be prepared by condensing a compound of Formula 4 with a compound of the formula $NHR^{13}R^{14}$ or $NHR^{20}R^{21}$, respectively, and then oxidizing when n is 0. The condensation reaction can be carried out at ambient temperature in a suitable solvent (e.g., dichloromethane, or the like) and requires 16 to 24 hours to complete. The oxidization can be carried out by the process described above for Reaction Scheme 1. A detailed description for the synthesis of a compound of Formula I by the processes in Scheme 3 is set forth in the Example 6, infra.

Compounds of Formula I can be prepared by proceeding as in the following Reaction Scheme 4:

Reaction Scheme 4

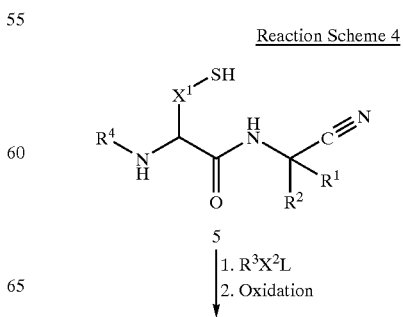

-continued

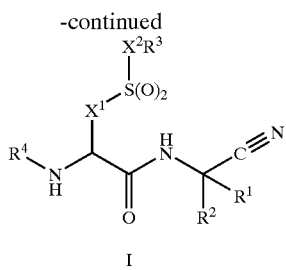

I in which L is a leaving group and each $X^1$, $X^2$, $R^1$, $R^2$, $R^3$ and $R^4$ are as defined for Formula I in the Summary of the Invention.

Compounds of Formula I can be prepared by reacting a compound of Formula 5 with a compound of the formula $R^3X^2L$ and then oxidizing. The reaction is carried out in the presence of base (e.g., potassium hydroxide, or the like) at ambient temperature and requires 2 to 3 hours to complete. The oxidization can be carried out by the process described above for Reaction Scheme 1. A detailed description for the synthesis of a compound of Formula I by the processes in Scheme 4 is set forth in the Examples 7 and 9, infra.

Compounds of Formula 2 can be prepared by reacting a compound of Formula 6:

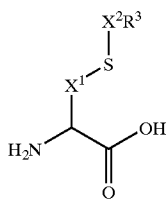

with a compound of the formula $R^4L$, in which L is a leaving group and $X^1$, $X^2$ and $R^3$ are as defined in the Summary of the Invention. The reaction can be carried out in the presence of base (e.g., 1 N aqueous sodium hydroxide, or the like) at about 0.5° C. A detailed description for the synthesis of a compound of Formula 2 by the processes described above is set forth in the References 1 and 7, infra. Compounds of Formula 6 are commercially available or otherwise can be prepared by methods known in the art or analogous to those described elsewhere in this Application.

Compounds of Formula 2 in which $X^1$ is ethylene can be prepared by condensing a diester of Formula 7:

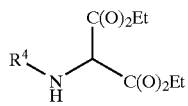

with a compound of the formula $R^3SCH_2CH_2L$ to provide a compound of Formula 8:

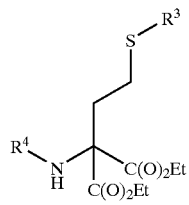

in which L is a leaving group and $R^3$ and $R^4$ are as defined in the Summary of the Invention, decarbalkoxylating to provide a corresponding monoester and then converting the monoester to a corresponding carboxylic acid. The condensation reaction can be carried out in the presence of a suitable nonnucleophilic base (e.g., N-methylpyrrolidone) and lithium hydroxide. The decarbalkoxylation can be effected under strongly basic conditions (e.g., in the presence of 1 N aqueous sodium hydroxide) in a suitable solvent (e.g, methanol) and requires 4 to 6 hours to complete. A detailed description for the synthesis of a compound of Formula 2 by the processes described above is set forth in the Reference 2, infra.

Compounds of Formula 3 can be prepared by condensing a compound of Formula 9:

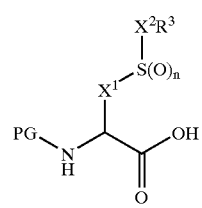

with an aminoalkanonitrile of the formula $NH_2CR^1R^2CN$, in which PG is a protecting group and each $X^1$, $R^1$, $R^2$ and $R^3$ are as defined in the Summary of the Invention, group and each $X^1$, $R^1$, $R^2$ and $R^3$ are as defined in the Summary of the Invention, with an appropriate condensing agent (e.g., N,N-dicyclohexyldiimide, diisopropylcarbodiimide, carbonyldiimidazole, or the like) and a suitable non-nucleophilic base (e.g., N-methylpyrrolidinone, N-methylmorpholine, or the like, or any suitable combination thereof) in a suitable solvent (e.g., dichloromethane, or the like) at ambient temperature and requires 2 to 3 days to complete. Oxidization can be carried out by the process described above for Reaction Scheme 1. Deprotection can be effected by any means which removes the protective group and gives the desired product in reasonable yield. A detailed description of the techniques applicable to the creation of protective groups and their removal can be found in T. W. Greene, *Protective Groups in Organic Synthesis*, 3$^{rd}$ edition, John Wiley & Sons, Inc. 1999. A convenient method of deprotecting is by treatment with a suitable acid (e.g., p-toluenesulfonic acid, or the like) providing the acid addition salt in the process. A detailed description for the synthesis of a compound of Formula 3 by the processes described above is set forth in the References 3, 4 and 5, infra. Compounds of Formula 4 can be prepared by reacting a compound of Formula 3 with phosgene. The reaction is carried out conveniently in a biphasic solvent (e.g., an equal mixture of dichloromethane and saturated sodium bicarbonate solution at ambient temperature. A detailed description for the synthesis of a compound of Formula 4 by the processes described above is set forth in the Reference 6, infra.

Compounds of Formula 5 can be prepared by sequentially condensing an acid of Formula 10:

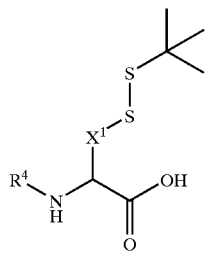

with an aminoalkanonitrile of the formula $NHR^2CR^3R^4CN$ and a compound of the formula $R^4L$ and then deprotecting. The condensation reaction is carried out in a fashion analogous to the process described above for the preparation of the compounds of Formula 3. The condensation reaction with the compound of the formula $R^4L$ is carried out in a fashion analogous to the process described above for the preparation of the compounds of Formula I by Scheme 2. The deprotection can be effected by treatment with a suitable reducing agent (e.g., tris-butyl phosphine, tris-carboxyethyl phosphine, or the like) in the presence of base (e.g., aqueous potassium hydroxide, or the like) in a suitable solvent (e.g., DMIF, or the like) under an inert atmosphere and at ambient temperature and requires 12 to 24 hours. A detailed description for the synthesis of a compound of Formula 5 by the processes decribed above is set forth in the Reference 8, infra.

Additional Processes for Preparing Compounds of Formula I:

A compound of Formula I can be prepared as a pharmaceutically acceptable acid addition salt by reacting the free base form of the compound with a pharmaceutically acceptable inorganic or organic acid. Alternatively, a pharmaceutically acceptable base addition salt of a compound of Formula I can be prepared by reacting the free acid form of the compound with a pharmaceutically acceptable inorganic or organic base. Inorganic and organic acids and bases suitable for the preparation of the pharmaceutically acceptable salts of compounds of Formula I are set forth in the definitions section of this Application. Alternatively, the salt forms of the compounds of Formula I can be prepared using salts of the starting materials or intermediates.

The free acid or free base forms of the compounds of Formula I can be prepared from the corresponding base addition salt or acid addition salt form. For example, a compound of Formula I in an acid addition salt form can be converted to the corresponding free base by treating with a suitable base (e.g., ammonium hydroxide solution, sodium hydroxide, and the like). A compound of Formula I in a base addition salt form can be converted to the corresponding free acid by treating with a suitable acid (e.g., hydrochloric acid, etc).

The N-oxides of compounds of Formula I can be prepared by methods known to those of ordinary skill in the art. For example, N-oxides can be prepared by treating an unoxidized form of the compound of Formula I with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds of Formula I can be prepared from the N-oxide of an appropriate starting material.

Compounds of Formula I in unoxidized form can be prepared from N-oxides of compounds of Formula I by treating with a reducing agent (e.g., sulfur, sulfur dioxide, triphenyl phosphine, lithium borohydride, sodium borohydride, phosphorus trichloride, tribromide, or the like) in an suitable inert organic solvent (e.g., acetonitrile, ethanol, aqueous dioxane, or the like) at 0 to 80° C.

Prodrug derivatives of the compounds of Formula I can be prepared by methods known to those of ordinary skill in the art (e.g., for further details see Saulnier et al.(1994), *Bioorganic and Medicinal Chemistry Letters*, Vol. 4, p. 1985). For example, appropriate prodrugs can be prepared by reacting a non-derivatized compound of Formula I with a suitable carbamylating agent (e.g., 1,1-acyloxyalkylcarbonochloridate, para-nitrophenyl carbonate, or the like).

Protected derivatives of the compounds of Formula I can be made by means known to those of ordinary skill in the art. A detailed description of the techniques applicable to the creation of protecting groups and their removal can be found in T. W. Greene, *Protecting Groups in Organic Synthesis*, $3^{rd}$ edition, John Wiley & Sons, Inc. 1999.

Compounds of the present invention may be conveniently prepared, or formed during the process of the invention, as solvates (e.g. hydrates). Hydrates of compounds of the present invention may be conveniently prepared by recrystallisation from an aqueous/organic solvent mixture, using organic solvents such as dioxin, tetrahydrofuran or methanol.

Compounds of Formula I can be prepared as their individual stereoisomers by reacting a racemic mixture of the compound with an optically active resolving agent to form a pair of diastereoisomeric compounds, separating the diastereomers and recovering the optically pure enantiomer. While resolution of enantiomers can be carried out using covalent diasteromeric derivatives of compounds of Formula I, dissociable complexes are preferred (e.g., crystalline diastereoisomeric salts). Diastereomers have distinct physical properties (e.g., melting points, boiling points, solubilities, reactivity, etc.) and can be readily separated by taking advantage of these dissimilarities. The diastereomers can be separated by chromatography or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques Andre Collet, Samuel H. Wilen, Enantiomers, Racemates and Resolutions, John Wiley & Sons, Inc. (1981).

In summary, the compounds of Formula I are made by a process which comprises:

(A) reacting a compound of Formula 2:

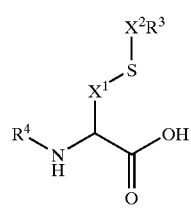

with a compound of the formula $NH_2CR^1R^2CN$, in which $X^1, X^2, R^1, R^2, R^3$ and $R^4$ are as defined in the Summary of the Invention for Formula I; or (B) reacting a compound of Formula 3:

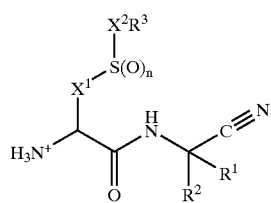

with a compound of the formula R⁴L, in which n is 0 or 2, L is a leaving group and each $X^1$, $X^2$, $R^1$, $R^2$, $R^3$ and $R^4$ are as defined in the Summary of the Invention for Formula I, and then oxidizing when n is 0; or (C) reacting a compound of Formula 4:

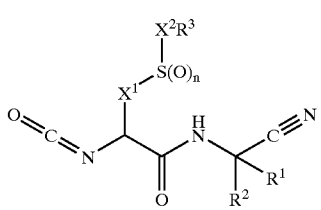

with a compound of formula $NHR^{13}R^{14}$ or $NHR^{20}R^{21}$ to provide a compound of Formula I in which $R^4$ is —C(O)NR$^{13}$R$^{14}$ or —C(O)NR$^2$OR$^{21}$, respectively, wherein n is 0 or 2, $R^{20}$ and $R^{21}$ together with the nitrogen atom to which $R^{20}$ and $R^{21}$ are attached form hetero($C_{5-12}$)cycloalkyl and each $X^1$, $X^2$, $R^1$, $R^2$, $R^3$, $R^{13}$ and $R^{14}$ are as defined in the Summary of the Invention for Formula I, and then oxidizing when n is 0; or (D) reacting a compound of Formula 5:

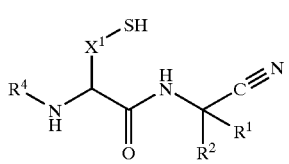

with a compound of $R^3X^2L$ in which L is a leaving group and each $X^1$, $X^2$, $R^1$, $R^2$, $R^3$ and $R^4$ are as defined in the Summary of the Invention for Formula I; and (E) optionally converting a compound of Formula I into a pharmaceutically acceptable salt;

(F) optionally converting a salt form of a compound of Formula I to non-salt form;

(G) optionally converting an unoxidized form of a compound of Formula I into a pharmaceutically acceptable N-oxide;

(H) optionally converting an N-oxide form of a compound of Formula I its unoxidized form;

(I) optionally resolving an individual isomer of a compound of Formula I from a mixture of isomers;

(J) optionally converting a non-derivatized compound of Formula I into a pharmaceutically prodrug derivative; and (K) optionally converting a prodrug derivative of a compound of Formula I to its non-derivatized form.

EXAMPLE

The present invention is further exemplified, but not limited by, the following examples that illustrate the preparation of compounds of Formula I (Examples) and intermediates (References) according to the invention.

Reference 1

2R-Benzoylamino-3-(4-methylbenzylsulfanyl) propionic Acid, a Compound of Formula 2 in which $X^2$ is Methylene, $R^3$ is 4-methylphenyl and $R^4$ is Benzoyl A solution comprised of 2R-amino-3-(4-methylbenzylsulfanyl)propionic acid (2.25 g, 10 mmol) in 1 N aqueous sodium hydroxide (10 mL) was cooled to −5° C. and then treated with benzoyl chloride (1.16 mL, 10 mmol) and 1 N aqueous sodium hydroxide. The reaction was allowed to proceed for 30 minutes and then the mixture was acidified with 1 N aqueous hydrochloric acid (10 mL) to form a precipitate. The precipitate was isolated by filtration to provide 2R-benzoylamino-preciptate was isolated by filtration to provide 2R-benzoylamino-3-(4-methylbenzylsulfanyl)propionic acid (3.38 g, 10 mmol).

Reference 2

2-Benzoylamino-4-phenylsulfanylbutyric Acid, a Compound of Formula 2 in which X is a Bond, R is Phenyl and $R^4$ is Benzoyl A solution comprised of sodium iodide (7.9 g, 52.7 mmol) and 2-chloroethyl phenyl sulfide (4.7 g, 27.2 mmol) in acetone (40 mL) was refluxed for 15 hours. The reaction mixture was cooled, diluted with ice water and extracted with ethyl acetate. The extract was concentrated and the residue was combined with N-methylpyrrolidone (20 mL), lithium hydroxide (1.6 g, 67 mmol) and diethyl 2-benzoylaminomalonate (5 g, 18 mmol). The mixture was stirred at ambient temperature of 15 hours and then poured into cold water. The product was extracted with ethyl acetate and purified by silica gel chromatography to provide diethyl 2-benzoylamino-2-(2-phenylsulfanylethyl)malonate (1.316 g, 3.2 mmol).

The 2-benzoylamino-2-(2-phenylsulfanylethyl)malonate (1.316 g, 3.2 mmol) was dissolved in methanol (10 mL) and the solution was treated with 1 N aqueous sodium hydroxide (7.0 mL) and then stirred at ambient temperature for 4 hours. The mixture was diluted with water and washed with ether (2×). The aqueous layer was cooled on ice, acidified to pH 2 and extracted with ethyl acetate. The extract was dried (MgSO$_4$) and then concentrated. The residue was dissolved in dioxane (30 mL) and the solution was heated at 100° C. for 1 hour and then concentrated. Product was purified from the residue by chromatography on silica gel to provide ethyl 2-benzoylamino-4-phenylsulfanylbutyrate (371 mg, 1.1 mmol).

A solution comprised of ethyl 2-benzoylamino-4-phenylsulfanylbutyrate (340 mg, 1.0 mmol) in methanol (4 mL) was treated with 1 N aqueous sodium hydroxide (2 mL) and stirred at ambient temperature for 3 hours. The reaction mixture was cooled on ice, acidified to pH 1 and then extracted with ethyl acetate. The extract was concentrated to provide 2-benzoylamino-4-phenylsulfanylbutyric acid (304 mg, 1.0 mmol).

Reference 3 tert-Butyl 2-benzylsulfanyl-1R-cyanomethylcarbamoylethylcarbamate

A solution comprised of 3-benzylsulfanyl-2R-tert-butoxycarbonylaminopropionic acid (50 g, 160.6 mmol) and aminoacetonitrile bisulfate (27.2 g, 176.6 mmol) in dichloromethane (400 mL) was cooled in an ice bath and then treated sequentially with carbonyldiimidazole (31.2 g, 192.7 mmol), dichloromethane (250 mL), and N-methylmorpholine (35.3 mL, 321.2 mmol). The mixture was stirred for 5 minutes at 0° C. and 2 days at ambient temperature, filtered, concentrated and partitioned between ethyl acetate and water. The ethyl acetate layer was washed with water, saturated potassium phosphate solution, water, saturated sodium bicarbonate solution and brine, dried ($MgSO_4$), filtered and concentrated. The residue was dried under high vacuum to provide tert-butyl 2-benzylsulfanyl-1R-cyanomethylcarbamoyl-ethylcarbamate (44.1 g, 126.2 mmol) as a white solid.

Reference 4

2R-Amino-3-benzylsulfanyl-N-cyanomethylpropionamide para-toluenesulfonate Salt, a Compound of Formula 3 in which n is 0, $X^2$ is Methylene, $R^1$ and $R^2$ are Both Hydrogen and $R^3$ is Phenyl Toluenesulfonic acid monhydrate (46.7 g, 246 mmol) was dissolved in 2-propanol (200 mL) and the solution was treated with toluene (600 mL). The solvents were removed under reduced pressure and the residue was dissolved in toluene (400 mL). The solution was concentrated under reduced pressure and the residue was dried under high vacuum. The residue was dissolved in an hydrous diethyl ether (200 mL) and the solution was added to a suspension comprised of tert-butyl 2-benzylsulfanyl-1R-cyanomethylcarbamoyl-ethyl-carbamate (42 g, 120 mmol), prepared as in Reference 3, in anhydrous diethyl ether (700 mL). The mixture was stirred at ambient temperature for approximately 12 hours and then the supernatant was decanted. The residue was dissolved in a small amount of dichloromethane and product was precipitated out with diethyl ether to provide 2R-amino-3-benzylsulfanyl-N-cyanomethyl(propionamide para-toluenesulfonate salt (50.7 g, 102 mmol).

Reference 5

2R-Amino-3-benzylsulfonyl-N-cyanomethylpropionamide methanesulfonate Salt, a Compound of Formula 3 in which n is 2, $X^2$ is a Methylene, $R^1$ and $R^2$ are Both Hydrogen and $R^3$ is Phenyl A solution comprised of tert-butyl 2-benzylsulfanyl-1R-cyanomethylcarbamoyl-ethylcarbamate (0.2 g, 0.57 mmol), prepared as in Reference 3, in methanol (8 mL) was treated with of Oxone® (0.526 g, 0.86 mmol) in water (8 mL) and the mixture was stirred at 25° C. for 2 hours. The mixture then was diluted with cold water and the product was extracted with ethyl acetate. The extracts were dried and concentrated. The residue was dissolved in ethyl acetate and product was crystallized out to provide tert-butyl 2-benzylsulfonyl-1R-cyanomethylcarbamoylethylcarbamate (0.158 g 0.41 mmol).

A suspension comprised of tert-butyl 2-benzylsulfonyl-1R-cyanomethylcarbamoyl-ethylcarbamate (5.22 g, 13.7 mmol) in anhydrous tetrahydrofuran (15 mL) was treated with methanesulfonic acid (1.8 mL, 27 mmol) and then the mixture was disluted with additional tetrahydrofuran (20 mL) and methanesulfonic acid (1.8 mL). The mixture was stirred for 16 hours and then diluted with diethyl ether. A resulting precipitate was collected by filtration to provide 2R-amino-3-benzylsulfonyl-N-cyanomethylpropionamide methanesulfonate salt (4.4 g, 11.6 mmol).

Reference 6

3-Benzylsulfanyl-N-cyanomethyl-2R-isocyantopropionamide, a Compound of Formula 4 in which $X^2$ is Methylene, $R^1$ and $R^2$ are Both Hydrogen and $R^3$ is Phenyl A three necked round bottom flask with nitrogen inlet and exit to a 10% sodium hydroxide solution was charged with 2R-amino-3-benzylsulfanyl-N-cyanomethylpropionamide para-toluenesulfonate salt (5 g, 11.8 mmol), prepared as in Reference 4, dichloromethane (120 mL), and saturated sodium bicarbonate solution (120 mL). The mixture was cooled in an ice bath and stirred for 10 minutes. The layers were allowed to separate and then a 20% solution of phosgene (12.4 mL, 23.6 mmol) in toluene was added to the lower layer. The mixture was stirred for 10 minutes. The aqueous phase was separated and extracted with dichloromethane. The combined organic phase was washed with brine, dried ($MgSO_4$), filtered, diluted with toluene (20 mL), concentrated and dried under high vacuum. The residue was dissolved in dichloromethane (15 mL) to provide a stock solution of 3-benzylsulfanyl-N-cyanomethyl-2R-isocyantopropionamide.

Reference 7

(R)-3-[2-(1,1-Difluoro-methoxy)-phenylmethanesulfonyl]-2-[(1-morpholin-4-yl-methanoyl)-amino]-propionic Acid A solution of (R)-2-tert-butoxycarbonylamino-3-((R)-2-tert-butoxycarbonylamino-2-carboxy-ethyldisulfanyl)-propionic acid (i.e., Boc-L-Cystine) (25 g, 56.75 mmol) in DMF (250 mL) was treated with tris(carboxyethyl) phosphine hydrochloride (17.9 g, 62.4 mmol). A solution of KOH (31.8 g, 567 mmol) in water (100 mL) was added over 2 minutes and the exothermic reaction was cooled with a 20° C. water bath. The mixture was stirred for 2 hours at room temperature, diluted with 2-(difluoromethoxy)benzyl bromide and stirred for 2 hours. The mixture was acidified with 1N HCl and extracted with ethyl acetate (3×250 mL). The combined organic layers were washed with brine, dried ($MgSO_4$)and concentrated. The residue was dried under high vacuum and then dissolved in $CH_2Cl_2$ (80 mL). The solution was diluted with trifluoroacetic acid (80 mL) and the mixture was stirred at room temperature for 2.5 hours. All volatile components were removed under vacuum and the residue was dissolved in water (200 mL). The solution was adjusted to pH 6 to 7 with 1N NaOH to give a precipitate, which was collected by filtration, washed with water and dried under vacuum to yield (R)-2-amino-3-[2-(1,1-difluoro-methoxy)-benzylsulfanyl]-propionic acid as white solid (27.5 g).

A mixture of (R)-2-amino-3-[2-(1,1-difluoro-methoxy)-benzylsulfanyl]-propionic acid (5 g, 18.03 mmol) and N-methyl-N-(trimethylsilyl)trifluoroacetamide (8.5 mL, 45.8 mmol) was heated at 70° C. under $N_2$ for 1 hour. All volatile reaction products were removed under vacuum. The residue was dissolved in $CH_2Cl_2$ (10 mL) and the solution treated with morpholinecarbonyl chloride (4.2 mL, 36 mmol). The mixture was stirred at room temperature for 16 hours and then diluted with ethyl acetate (300 mL). The mixture was washed with water (50 mL) and brine (100 mL), dried (MgSO$_4$) and concentrated. The residue was dissolved in methanol (250 mL) and a saturated aqueous solution of Oxone® (35 g, 57 mmol) was added. The mixture was stirred at room temperature for 2 hours. The methanol was removed under vacuum and the remaining aqueous phase was extracted with ethyl acetate (3×200 mL). The combined organic layers were washed with brine, dried (MgSO$_4$) and evaporated. The product was purified by flash chromatography on silica gel (Eluent: ethyl acetate to 10% methanol in ethyl acetate) to yield (R)-3-[2-(1,1-difluoro-methoxy)-phenylmethanesulfonyl]-2-[(1-morpholin-4-yl-methanoyl)-amino]-propionic acid as phenylmethanesulfonyl]-2-[(1-morpholin-4-yl-methanoyl)-amino]-propionic acid as Reference 8

N-[2-tert-Butyldisulfanyl-1R-cyanomethylcarbamoylethyl]morpholine-4-carboxamide

A solution comprised of 2R-amino-3-tert-butyldisulfanylpropionic acid hydrate (25 g, 119 mmol) in sodium hydroxide (1N, 300 mL) was cooled to 0° C. and then treated with 4-morpholinecarbonyl chloride (13.9 mL, 119 mmol) added slowly. The mixture was treated with additional amounts of sodium hydroxide (5N, 100 mL) and 4-morpholinecarbonyl chloride (27.8 mL, 238 mmol), stirred for approximately 12 hours and acidification with concentrated hydrochloric acid. Product was extracted with ethyl acetate and the combined extracts were washed with brine, dried (MgSO$_4$) and concentrated. The product was recrystallized from ethyl acetate/hexane, to provide 3-tert-butyldisulfanyl-2R-morpholin-4-ylcarbonylaminopropionic acid (16.5 g, 51.2 mmol) as a white crystalline solid.

A suspension of 3-tert-butyldisulfanyl-2R-morpholin-4-ylcarbonylaminopropionic acid (16.25 g, 50.4 mmol) in methylene chloride (100 mL) was treated with EDCI (10.6 g, 55.4 mmol), HOBt (8.85 g, 65.5 mmol) and aminoacetonitrile hydrochloride (7.0 g, 75.6 mmol). The mixture then was treated with 4-methylmorpholine (8.31 mL, 75.6 mmol), stirred at ambient temperature for 5 hours and then diluted with ethyl acetate (500 mL). The dilution was washed with saturated aqueous sodium bicarbonate solution, brine, 1N hydrochloric acid and brine, dried (MgSO$_4$) and concentrated. Product was purified from the residue by flash chromatography on silica gel with ethyl acetate as eluent to provide N-[2-tert-butyldisulfanyl-1R-cyanomethylcarbamoylethyl]morpholine-4-carboxamide (7.5 g) as a white solid.

Reference 9

2-(2-Thienyl)aminoacetonitrile Hydrochloride

A mixture of ammonium chloride (24.9 g, 465 mmol) and 2-thiophenecarboxaldehyde (21.2 mL, 227 mmol) in 250 mL diethyl ether was treated with an 80 mL aqueous solution of sodium cyanide (16.7 g, 341 mmol) over 20 minutes. The mixture was allowed to stir for 16 hours. The aqueous layer was removed. The ether layer was washed (2×100 mL) with saturation sodium bicarbonate solution, dried over anhydrous magnesium sulfate, and concentrated. The residue was dissolved in 250 mL diethyl ether and cooled in an ice bath. Hydrogen chloride was bubbled through the solution until precipitation was complete. The salt was filtered and dried under reduced pressure to give 9.8 g of 2-(2-thienyl) aminoacetonitrile hydrochloride.

The following intermediate was provided by proceeding as in reference 9:

Amino-furan-2-yl-acetonitrile

Example 1

N-[(R)-1-(Cyanomethyl-carbamoyl)-2-p-tolylmethanesulfonyl-ethyl]-benzamide

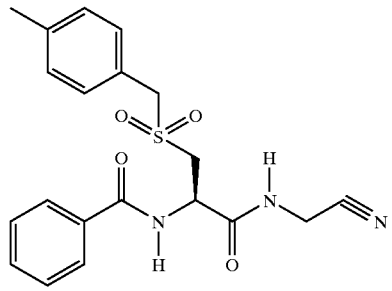

A mixture comprised of 2R-benzoylamino-3-(4-methylbenzylsulfanyl)propionic acid (1.316 g, 3.88 mmol), prepared as in Reference 1, EDCI (0.878 g, 5.56 mmol), HOBt (0.616 g, 4.56 mmol) and aminoacetonitrile bisulfate (0.726 g, 4.71 mmol) in N-methylpyrrolidinone (14 mL) and N-methylmorpholine (1 mL) was stirred at 25° C. for 5 hours. The mixture then was diluted with cold 0.05 N aqueous hydrochloric acid and the product was extracted with ethyl acetate. The extracts were washed with aqueous sodium bicarbonate, dried and concentrated. The residue was dissolved in tert-butylmethyl ether and the product was crystallized from solution to provide N-[1R-cyanomethylcarbamoyl-2-(4-methylbenzylsulfanyl)ethyl] benzamide (0.86 g). Mass Spectrum: m/e 367.9 (theory 367.1). NMR Spectrum (DMSO): 8.82 (t, 1H), 8.69 (d, 1H), 7.88 (d, 2H), 7.5 (m, 3H), 7.16 (d, 2H), 7.08 (d, 2H), 4.7 (m, 1H), 4.2 (d, 2H), 3.7 (s, 2H), 2.75 (m, 2H), 2.1 (s, 3H) ppm.

A solution comprised of N-[1R-cyanomethylcarbamoyl-2-(4-methylbenzylsulfanyl)ethyl]benzamide (0.365 g, 0.99 mmol) in methanol (20 mL) was treated with Oxone® (1.03 g, 1.68 mmol) in water (20 mL) and the mixture was stirred at 25° C. for 16 hours. The mixture then was diluted with cold water and the product was extracted with ethyl acetate. The extracts were dried and concentrated. The residue was dissolved in ethyl acetate and the product was crystallized from solution to provide N-[1R-cyanomethylcarbamoyl-2-(4-methylbenzylsulfonylsulfanyl)ethyl]benzamide (0.229 g 0.57 mmol).

The following compounds of Formula I were provided by proceeding as in Example 1:

N-(2-benzylsulfonyl-1R-cyanomethylcarbamoylethyl) benzamide (Compound 2); Mass Spectrum: m/e 386 (theory 385.4); NMR Spectrum (DMSO). δ: 8.98 (d=9.4 Hz, 1H), 8.87 (t, J=7 Hz, 1H), 7.86 (d, J=8.5 Hz, 2H), 7.6–7.3 (m, 8H), 5.02 (m, 1H), 4.54 (s, 2H), 4.11 (m, 2H), 3.75 (m, 1) 3.54 (dd, 1H), (d, J=5.6 Hz, 2H) ppm; and N-[1R-cyanomethylcarbamoyl-2-(4-methoxybenzylsulfonyl)ethyl]benzamide (Compound 3); Mass Spectrum: m/e 415.9 (theory 415.5); NMR Spectrum (DMSO): δ: 8.96 (d, 1H), 8.79 (t, 1H), 7.87 (d, J=7.4 Hz, 2H), 7.6–7.4 (m, 3H), 7.30 (d, J=10.3 Hz, 2H), 6.94 (d, J=9.9 Hz, 2H), 5.02 (dd, J=10.7 and 3.8 Hz,1H), 4.47 (AB q, J=15.4 Hz, 2H), 4.13 (Br s, 2H), 3.75 (s, 3H), 3.72 (dd, J=15.7 and 3.4 Hz, 1H), 3.50 (dd, J=15.9 and 10.4 Hz, 1H) ppm.

Example 2

N-(3-Phenylsulfonyl-1R-cyanomethylcarbamoylpropyl)benzamide (Compound 4)

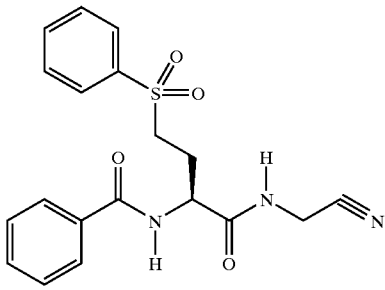

A solution comprised of 2R-benzoylamino-4-phenylsulfanylbutyric acid (150 mg, 0.5 mmol), prepared as in Reference 2, in N-methylpyrrolidone (4 mL) was treated with HOBt (99 mg, 0.8 mmol), EDCI (125 mg, 0.65 mmol), N-methylmorpholine (1.5 mmol) and aminoacetonitrile bisulfate (115 mg, 0.75 mmol). The mixture was stirred 4 hours at ambient temperature and then diluted with cold water. Product was extracted with ethyl acetate and the extract was washed with dilute hydrochloric acid and aqueous sodium bicarbonate, dried and then concentrated to provide N-(3-phenylsulfanyl-1R-cyanomethylcarbamoylpropyl)-benzamide (122 mg, 0.34 mmol).

A solution comprised of N-(3-phenylsulfanyl-1R-cyanomethylcarbamoylpropyl)-benzamide (122 mg, 0.34 mmol) in methanol (7 mL) was treated with Oxone® (317 mg, 1.1 mmol) in water (2 mL) and the mixture was stirred at ambient temperature for 6 hours. The reaction mixture was diluted with aqueous sodium chloride and product was extracted with ethyl acetate. The extract was dried and concentrated. The residue was dissolved in ethyl acetate and the product was crystallized from solution to provide N-(3-phenylsulfonyl-1R-cyanomethylcarbamoylpropyl) benzamide (122 mg, 0.31 mmol). Mass Spectrum: m/e 385.95 (theory 385.49). NMR Spectrum (DMSO): 8.70 (d, J=9.4 Hz, 1H), 8.68 (t, J=6.6 Hz, 1H), 7.95–7.45 (m, 10H), 4.45 (m, 1H), 4.13 d, J=6.1 Hz, 2H), 3.6–3.2 (m, 2H), 2.15–1.95 (m, 2H) ppm.

The following compounds were provided by proceeding as in Example 2:

Morpholine-4-carboxylic acid [(S)-1-(cyanomethyl-carbamoyl)-3-(2-trifluoromethoxy-benzenesulfonyl)-propyl]-amide (Compound 167) NMR $^1$H (DMSO, 300 MHz): 8.53 (t, 5.2 Hz, 1H), 7.98 (d, 8.2 Hz, 1H), 7.89 (t, 6.2 Hz, 1H), 7.65 (m, 2H), 6.78 (d, 8.2 Hz, 1H), 4.20 (m, 1H), 4.08 (d, 3.6 Hz, 2H), 3.55 (m, 4H), 3.40 (m, 2H), 3.24 (m, 4H), 1.98 (m, 1H), 1.82 (m, 1H); MS (M–1)=476.2;

Morpholine-4-carboxylic acid [(S)-3-benzenesulfonyl-1-(cyanomethyl-carbamoyl)-propyl]-amide (Compound 168) NMR $^1$H,(DMSO, 300 MHz) 8.50 (t, 5.1 Hz, 1H), 7.88 (d, 7.1 Hz, 2H), 7.75 (m, 1H), 7.65 (t, 7.1 Hz, 2H), 4.18 (m, 1H), 4.10 (d, 3.5 Hz, 2H), 3.50 (m, 4H), 3.35 (m, 2H), 3.21 (m, 4H), 1.75–2.05 (m, 2H);

Morpholine-4-carboxylic acid [(S)-1-(cyanomethyl-carbamoyl)-3-(4-trifluoromethoxy-benzenesulfonyl)-propyl]-amide (Compound 169) NMR $^1$H,(DMSO, 300 MHz) 8.55 (t, 5.9 Hz, 1H), 8.04 (d, 8.9 Hz, 2H), 7.45 (d, 8.9 Hz, 2H), 7.72 (d, 8.1 Hz, 1H), 4.20 (m, 1H), 4.08 (d, 3.7, Hz, 2H), 3.53 (m, 4H), 3.20–3.45 (m, 6H), 1.75–2.05 (m, 2H); MS (M+1)=479.0;

Thiophene-2-carboxylic acid [(S)-1-(cyanomethyl-carbamoyl)-3-(2-trifluoromethoxy-benzenesulfonyl)-propyl]-amide (Compound 170) NMR $^1$H: (DMSO, 300 MHz) 8.74 (m, 1H), 7.95 (d, 8.8. Hz, 2H), 7.88 (m, 1H), 7.80 (m, 3H), 7.65 (m, 2H), 4.50 (m, 1H), 4.12 (d, 3.6 Hz, 2H), 3.40 (m, 2H), 2.12 (m, 1H), 1.90 (m, 1H); MS (M–1)=474.0;

[(S)-1-(Cyanomethyl-carbamoyl)-3-(2-trifluoromethoxy-phenylsulfanyl)-propyl]-carbamic acid tert-butyl ester (Compound 171) MS (M+1)=465.8.

Example 3

3-Acetyl-N-(2-benzylsulfonyl-1R-cyanomethylcarbamoylethyl)benzamide (Compound 5)

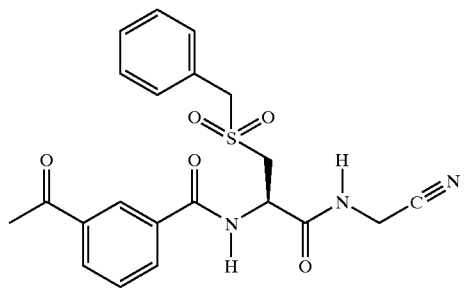

A mixture comprised of 2R-amino-3-benzylsulfanyl-N-cyanomethylpropionamide para-toluenesulfonate salt (845 mg, 2 mmol), prepared as in Reference 4, EDCI (423 mg, 2.2 mmol), HOBt (459 mg, 3 mmol), 3-acetylbenzoic acid (328 mg, 2 mmol) and anhydrous dichloromethane (1.5 mL) was treated with N-methylmorpholine (0.485 mL, 4.4 mmol), stirred for 16 hours and then diluted with ethyl acetate. The mixture was washed with water, 1 N hydrochloric acid, water, sodium bicarbonate solution, water and brine, dried (MgSO$_4$), filtered and concentrated. The residue was stirred vigorously in diethyl ether and a resulting precipitate was collected by filtration and dried under high vacuum to provide 3-acetyl-N-(2-benzylsulfanyl-1R-cyanomethylcarbamoylethyl)benzamide (420 mg, 1.1 mmol).

A solution comprised of 3-acetyl-N-(2-benzylsulfanyl-1R-cyanomethylcarbamoyl-ethyl)benzamide 0.198 g, 0.5 mmol) in methanol (8 mL) was treated with Oxone® (0.46 g, 0.75 mmol) in water (8 mL) and the reaction mixture was stirred at 25° C. for 16 hours. The reaction mixture then was diluted with cold water and the product was extracted with ethyl acetate. The extracts were dried and concentrated. The residue was dissolved in ethyl acetate and the product was crystallized from solution to provide 3-acetyl-N-(2-benzylsulfonyl-1R-cyanomethylcarbamoylethyl)benzamide (0.169 g 0.395 mmol). Mass Spectrum: m/e m$^+$ 428.0, m$^+$ 426.2; NMR Spectrum (CD$_3$OD): 8.49 (m, 1H), 8.16 (m, 1H), 8.09 (m, 1H), 7.61 (m, 1H), 7.45 (m, 2H), 7.37 (m, 3H), 5.21 (dd, J=3.96, 11.14 Hz, 1H), 4.50 (m, 2H), 4.17 (d, J=1.24 Hz, 2H), 3.88 (dd, J=3.96, 15.93 Hz, 1H), 3.54 (dd, J=9.15, 16.23 Hz, 1H).

The following compounds of Formula I were provided by proceeding as in Example 3:

N-(2-benzylsulfonyl-1R-cyanomethylcarbamoylethyl) naphthalene-2-carboxamide (Compound 6); Mass Spectrum: m/e 435.83; NMR Spectrum CDCl$_3$); 8.30 (s, 1H), 7.81 (m, 5H), 7.49 (m, 2H), 7.33 (m, 5H), 5.16 (m, 1H), 4.34 (d, J=2.7 Hz, 2H), 4.09 (s, 2H), 3.55 (m, 2H);

N-(2-benzylsulfonyl-1R-cyanomethylcarbamoylethyl) furan-3-carboxamide (Compound 7); Mass Spectrum: m/e 375.80; NMR Spectrum (CDCl$_3$): 8.00 (m, 1H), 7.45 (m, 3H), 7.40 (m, 4H), 6.65 (m, 1H), 5.10 (m, 1H), 4.41 (m, 2H), 4.14 (m, 2H), 3.70 (m, 1H), 3.31 (m, 1H);

N-(2-benzylsulfonyl-1R-cyanomethylcarbamoylethyl) benzo[1,3]dioxole-5-carboxamide (Compound 8); Mass Spectrum: m/e 429.85; NMR Spectrum (CDCl$_3$): 7.32–7.43 (m, 6H), 7.26 (d, J=1.92 Hz), 6.79 (d, J=7.92 Hz, 1H), 5.99 (s, 2H), 5.10 (dd, J=6.87, 10.02 Hz, 1H), 4.35 (m, 2H), 4.09 (m, 2H), 3.60 (dd, J=6.44, 15.20 Hz, 1H), 3.42 (dd, J=5.45, 16.47 Hz, 1H);

N-(2-benzylsulfonyl-1R-cyanomethylcarbamoylethyl)-3-pyrid-3-ylacrylamide (Compound 9); Mass Spectrum m/e m$^+$ 412.76; $^1$H-NMR (300 MHz, CDCl$_3$, δ ppm), 8.78 (m, 1H), 8.53 (m, 1H), 7.88 (m, 1H), 7.58 (d, J=18 Hz, 1H), 7.36 (m, 6H), 6.63 (m, 1H), 5.08 (m, 1H), 4.36 (m., 2H), 4.10 (d, J=5.8 Hz, 2H), 3.48 (m, 2H);

N-(2-benzylsulfonyl-1R-cyanomethylcarbamoylethyl) benzofuran-2-carboxamide (Compound 10); Mass Spectrum: m/e 425.83; NMR Spectrum (CD$_3$OD): 7.35 (m, 1H), 7.60 (m, 1H), 7.55 (m, 1H), 7.44–7.50 (m, 3H), 7.29–7.39 (m, 4H), 5.23 (dd, J=4.21, 6,44 Hz, 1H), 4.50 (s, 2H), 4.16 (d, J=1.98 Hz), 3.87 (dd, J=4.21, 16.5 Hz), 3.58 (dd, J=8.66, 16.5 Hz);

N-(2-benzylsulfonyl-1R-cyanomethylcarbamoylethyl) furan-2-carboxamide (Compound 11); Mass Spectrum: m/e 375.80; NMR Spectrum (CD$_3$OD): 7.69 (dd, J=0.74, 1.73 Hz, 1H), 7.44 (m, 2H), 7.37 (m, 4H), 7.18 (dd, J=0.74, 2.72 Hz, 1H), 6.61 (dd, J=1.72, 2.60 Hz, 1H), 5.14 (dd, J=4.21, 6.31 Hz, 1H), 4.48 (s, 2H), 4.15 (d, J=1.98 Hz, 2H), 3.82 (dd, J=4.21, 14.85 Hz, 1H), 3.52 (dd, J=8.42, 14.61 Hz, 1H);

tert-butyl 2-benzylsulfonyl-1R-cyanomethylcarbamoylethylcarbamate (Compound 12); Mass Spectrum: m/e 381.84; NMR Spectrum (DMSO): δ: 8.78 (t, J=5.20 Hz, 1H), 7.43 (m, 6H), 4.58 (dd, J=2.97, 8.16 Hz, 1H), 4.52 (s, 2H), 4.13 (dd, J=3.22, 5.44 Hz, 2H), 3.59 (dd, J=3.46, 7.18 Hz, 1H), 3.33 (m, 1H, under H$_2$O), 1.40 (s, 9H);

N-(2-benzylsulfonyl-1R-cyanomethylcarbamoylethyl)-3-phenoxybenzamide (Compound 13); Mass Spectrum: m/e: m$^+$ 477.8, m$^-$ 476.2; NMR Spectrum (CDCl$_3$): 7.62 (m, 1H), 7.3–7.54 (M, 11H), 7.15 (m, 1H), 7.00 (m, 1H), 5.16 (dd, J=5.69, 12.62 Hz, 1H), 4.47 (m, 2H), 4.11 (m, 2H), 3.70 (dd, J=5.44, 15.09 Hz, 1H), 3.33 (dd, J=5.69, 16.20 Hz, 1H);

tert-butyl [3-(2-benzylsulfonyl-1R-cyanomethylcarbamoylethylcarbamoyl)benzyl)-carbamate (Compound 14); Mass Spectrum: m/e m$^+$ 414.8, m$^-$ 513.2; NMR Spectrum (CD$_3$OD): 7.75 (m, 2H), 7.39 (m, 8H), 5.20 (dd, J=3.96, 8.16 Hz, 1H), 4.48 (s, 2H), 4.24 (s, 2H), 4.13 (m, 2H), 3.85 (dd, J=9.36, 16.23 Hz, 1H), 3.55 (dd, J=9.90, 16.20 Hz, 1H);

N-(2-benzylsulfonyl-1R-cyanomethylcarbamoylethyl)-4-hydroxybenzamide (Compound 15); Mass Spectrum: m/e m$^+$ 401.8, m$^-$ 400.0; NMR Spectrum (DMSO): δ: 8.75 (m, 1H), 7.76 (d, J=8.66 Hz, 2H), 7.39 (s, 5H), 6.84 (d, J=8.66 Hz, 2H), 5.02 (m, 1H), 4.55 (s, 2H), 4.13 (m, 2H), 3.77 (m, 1H), 3.53 (m, 1H);

N-(2-benzylsulfonyl-1R-cyanomethylcarbamoylethyl)-3-hydroxybenzamide (Compound 16); Mass Spectrum: m/e m$^+$ 402.0, m$^-$ 400.0; NMR Spectrum (CD$_3$OD): 7.68 (m, 1H), 7.40 (m, 8H), 5.16 (dd, J=4.21, 9.15 Hz, 1H), 4.50 (s, 2H), 4.16 (s, 2H), 3.84 (dd, J=3.96, 16.20 Hz, 1H), 3.55 (dd, J=8.91, 21.99 Hz, 1H);

N-(2-benzylsulfonyl-1R-cyanomethylcarbamoylethyl) thiophene-2-carboxamide (Compound 17); Mass Spectrum m/e: m$^+$ 392.2, m$^-$ 390.2; NMR Spectrum (DMSO): δ: 9.04 (d, J=8.16 Hz, 1H), 8.87 (m, 1H), 7.81 (m, 2H), 7.39 (m, 5H), 7.19 (m, 1H), 5.01 (m, 1H), 4.56 (s, 2H), 4.14 (m, 2H), 3.77 (dd, J=3.46, 16.23 Hz), 3.51 (dd, J=9.15, 15.93 Hz);

N-(2-benzylsulfonyl-1R-cyanomethylcarbamoylethyl) thiophene-3-carboxamide (Compound 18); Mass Spectrum: m/e m$^+$ 392.0, m$^-$ 390.2; NMR Spectrum (DMSO): δ: 8.58 (m, 2H), 8.19 (dd, J=0.99, 4.95 Hz, 1H) 7.62 (m, 1H), 7.53 (dd, J=0.99, 4.95 Hz, 1H), 7.39 (s, 5H), 5.01 (m, 1H), 4.56 (s, 2H), 4.14 (d, J=5.44 Hz, 2H), 3.76 (dd, J=3.46, 12.87 Hz, 1H), 3.51 (dd, J=9.40, 14.60 Hz, 1H);

N-(2-benzylsulfonyl-1R-cyanomethylcarbamoylethyl) quinoline-3-carboxamide (Compound 19); Mass Spectrum: m/e m$^+$ 436.89; $^1$H-NMR (300MHz, CDCl$_3$, δ ppm): 9.20 (m, 1H), 8.77 (m, 1H), 8.02 (t, J=9.5 Hz, 2H), 7.84 (t, J=7.3 Hz, 1H), 7.65 (t, J=7.3 Hz, 1H), 7.43 (m, 2H), 7.34 (m, 3H), 5.23 (m, 1H), 4.18 (m, 2H), 3.83 (m, 1H), 3.46 (m, 1H);

N-(2-benzylsulfonyl-1R-cyanomethylcarbamoylethyl) biphenyl-4-ylcarboxamide (Compound 20); NMR Spectrum (DMSO): δ: 9.05 (d, J=8.17 Hz, 1H), 8.82 (t, J=5.69 Hz, 1H), 7.98 (m, 2H), 7.76 (m, 4H), 7.49 (m, 2H), 7.36 (m, 6H), 5.09 (m, 1H), 4.56 (s,2H), 4.14 (m, 2H), 4.04 (m, 2H), 3.79 (m, 1H), 3.58 (m, 1H);

N-(2-benzylsulfonyl-1R-cyanomethylcarbamoylethyl) quinoline-2-carboxamide (Compound 21); Mass Spectrum m/e m$^+$ 436.2, m$^-$ 435.0, $^1$H-NMR (300 MHz, DMSO-d$_6$, δ ppm) 9.51 (d, J=9.6 Hz, 1H), 8.84 (t, J=6.6 Hz, 1H), 8.63 (d, J=9.33 Hz, 1H), 8.19 (m, 3H), 7.90 (m, 1H), 7.75 (m, 11), 7.38 (m, 5H), 5.18 (m, 1H), 4.58 (dd, J=15.1 Hz, 19.4 Hz, 2H), 4.14 (d, J=6.3 Hz, 2H) 3.81 (d, 6.6 Hz, 2H); and 4-benzoyl-N-(2-benzylsulfonyl-1R-cyanomethylcarbamoylethyl)benzamide (Compound 22); Mass Spectrum: m/e m$^+$ 490.4, m$^-$ 488.2; NMR Spectrum (DMSO): δ: 9.24 (m, 1H), 8.87 (m, 1H), 8.04 (d, J=8.41 Hz, 2H), 7.85 (d, J=8.41 Hz, 2H), 7.75 (m, 3H), 7.59 (m, 2H), 7.41 (s, 5H), 5.10 (m, 1H), 4.60 (s, 2H), 4.16 (m, 2H), 3.81 (m, 1H), 3.57 (m, 1H).

Example 4

N-(2-Benzylsulfonyl-1R-cyanomethylcarbamoylethyl) nicotinamide (Compound 23)

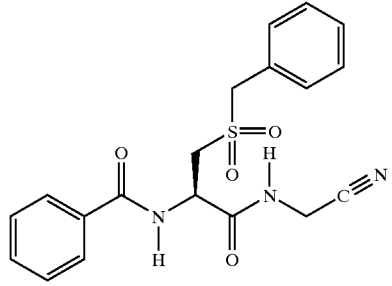

A mixture comprised of 2R-amino-3-benzylsulfonyl-N-cyanomethylpropionamide methanesulfonate salt (377 mg, 1 mmol), prepared as in Reference 5, EDCI (211 mg, 1.1 mmol), HOBt (230 mg, 1.5 mmol), nicotinic acid (123 mg, 1 mmol), and anhydrous dichloromethane (4 mL) was treated with N-methylmorpholine (0.242 mL, 2.2 mmol), stirred for 16 hours and then concentrated. The residue was partitioned between ethyl acetate (150 mL) and water (10 mL) and the ethyl acetate layer was separated and washed with 1 N hydrochloric acid, water, sodium bicarbonate solution, water and brine, dried (MgSO$_4$), filtered and concentrated. The residue was stirred vigorously in diethyl ether and a resulting precipitate was collected by filtration and dried under high vacuum to provide N-(2-benzylsulfonyl-1R-cyanomethylcarbamoylethyl)nicotinamide (236 mg, 0.61 mmol). Mass Spectrum: m/e 387.04. NMR Spectrum (DMSO): δ: 9.23 (d, J=7.92 Hz, 1H), 9.04 (s, 1H), 8.89 (m, 1H), 8.75 (m, 1H), 8.21 (d, J=7.18 Hz, 1H), 7.56 (m, 1H), 7.40 (s, 5H), 5.08 (m, 1H), 4.60 (s, 2H), 4.16 (m, 2H), 3.82 (m, 1H), 3.54 (m, 1H).

Proceeding as in Example 4 provided N-(2-benzylsulfonyl-1R-cyanomethylcarbamoylethyl) isonicotinamide (Compound 24); Mass Spectrum: m/e m$^+$ 386.6, m$^-$ 385.2; NMR Spectrum (DMSO): δ: 9.32 (d, J=7.92 Hz, 1H), 8.90 (m, 1H), 8.79 (m, 2H), 7.80 (m, 2H), 7.42 (s, 5H), 5.08 (m, 1H), 4.60 (s, 2H), 4.17 (m, 2H), 3.83 (m, 1H), 3.56 (m, 1H);

Example 5

N-(2-Benzylsulfonyl-1R-cyanomethylcarbamoylethylmorpholine-4-carboxamide (Compound 25)

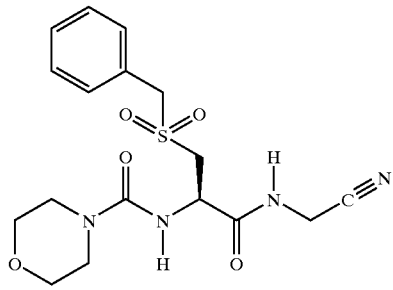

A solution comprised of 2R-amino-3-benzylsulfanyl-N-cyanomethylpropionamide para-toluenesulfonate salt (15 g, 35.5 mmol), prepared as in Reference 4, in anhydrous dichloromethane (200 mL) was cooled in an ice bath and then treated with morpholin-4-ylcarbonyl chloride (5.8 mL, 49.7 mmol) and N-methylmorpholine (11.7 mL, 106.5 mmol). The mixture was stirred at ambient temperature for 16 hours and then diluted with dichloromethane (400 mL). The dilution was washed with water, 1 N hydrochloric acid, water, sodium bicarbonate solution, water and brine, dried (MgSO$_4$), filtered and concentrated. Product was purified from the residue by elution on silica gel chromatography using dichloromethane followed by 1:1 dichloromethane-:ethyl acetate. The purified product was stirred vigorously under ethyl acetate and diethyl ether and a resulting precipitate was collected by filtration to provide N-(2-benzylsulfanyl-1R-cyanomethylcarbamoylethyl-morpholine-4-carboxamide (8.5 g, 23.1 mmol).

A solution comprised of N-(2-benzylsulfanyl-1R-cyanomethylcarbamoylethyl-morpholine-4-carboxamide (6 g, 16.5 mmol) in methanol (460 mL) was treated with Oxone® (15.3 g, 24.8 mmol) in water (460 mL) and the reaction mixture was stirred at 25° C. for 30 minutes. The reaction mixture then was diluted with cold water and the product was extracted with ethyl acetate. The extracts were dried and concentrated. The residue was dissolved in ethyl acetate and the product was crystallized from solution to provide N-(2-benzylsulfonyl-1R-cyanomethylcarbamoyl-ethylmorpholine-4-carboxamide (3.76 g 9.53 mmol). Mass Spectrum: m/e 394.91; NMR Spectrum (DMSO): δ: 8.67 (t, J=5.45 Hz, 1H); 7.39 (m, 5H), 7.12 (d, J=8.17 Hz, 1H), 4.72 (td, J=9.33 Hz, 3.71 Hz, 1H), 4.51 (s, 2H), 4.12 (d, J=5.69 Hz, 2H), 3.61 (dd, J=3.71, 15.9 Hz, 1H), 3.55 (t, J=4.70 Hz, 4H), 3.39 (dd, J=9.16, 15.9 Hz, 1H), 3.30 (m, 4H).

Proceeding as in Example 5 provided N-(2-benzylsulfonyl-1R-cyanomethylcarbamoylethyl)-3-methoxybenzamide (Compound 26); Mass Spectrum: m/e 415.77; NMR Spectrum (CDCl$_3$): 7.31–7.44 (m, 10H), 7.04 (m, 1H), 5.12 (m, 1H), 4.38 (dd, J=7.9, 14.0 Hz, 2H), 4.11 (m, 2H), 3.81 (s, 3H), 3.63 (dd, J=6.19, 11.76 Hz, 1H); 3.40 (dd, J=5.45, 14.86 Hz, 1H).

Example 6

Ethyl 4-(2-Benzylsulfonyl-1R-cyanomethylcarbamoylethylcarbamoyl)piperazine-1-carboxylate (Compound 27),

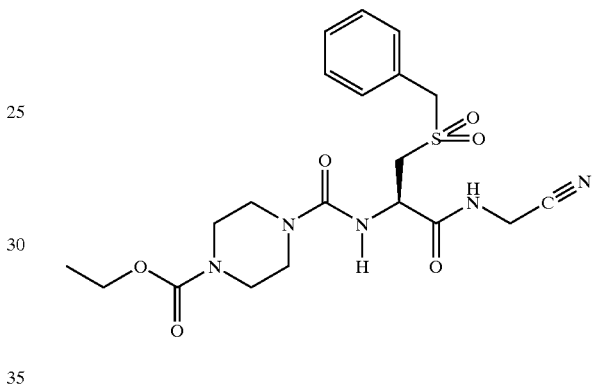

A stock of 3-benzylsulfanyl-N-cyanomethyl-2R-isocyantopropionamide (3 mL), prepared as in Reference 6, was diluted with dichloromethane (20 mL) and the mixture was treated with N-ethoxycarbonylpiperazine (0.69 mL, 2 mmol) and stirred for 16 hours. The mixture then was concentrated and partitioned between ethyl acetate and water. The organic phase was washed with water, 1 N hydrochloric acid, water, sodium bicarbonate solution, water and brine, dried (MgSO$_4$), filtered and concentrated. Product was purified from the residue by elution on silica gel chromatography using 5% methanol in dichloromethane to provide ethyl 4-(2-benzylsulfanyl-1R-cyanomethylcarbamoylethyl-carbamoyl)piperazine-1-carboxylate (382 mg, 0.65 mmol).

A solution comprised of ethyl 4-(2-benzylsulfanyl-1R-cyanomethylcarbamoylethyl-carbamoyl)piperazine-1-carboxylate (0.187 g, 0.43 mmol) in methanol (4 mL) was treated with Oxone® (0.396 g, 0.65 mmol) in water (4 mL) and the reaction mixture was stirred at 25° C. for 3 hours. The reaction mixture then was diluted with cold water and the product was extracted with ethyl acetate. The extracts were dried and concentrated. The residue was dissolved in ethyl acetate and the product was crystallized from solution to provide ethyl 4-2-enzylsulfonyl-1R-cyanomethylcarbamoylethylcarbamoyl)piperazine-1-carboxylate (0.159 0.34 mmol). Mass Spectrum: m/e m$^+$ 466.0, m$^-$ 464.2. NMR Spectrum (DMSO): δ: 8.67 (t, J=5.44, Hz, 1H), 7.40 (s, 5H), 7.18 (d, J=7.92 Hz, 1H), 4.74 (m, 1H), 4.53 (m, 2H), 4.13 (m, 2H), 4.06 (q, J=6.93 Hz, 2H), 3.66 (m, 1H), 3.44 (m, 1H), 3.35 (m, 8H), 1.19 (t, J=6.93, Hz, 3H).

The following compounds of Formula I were provided by proceeding as in Example 6 tert-butyl 4-(2-benzylsulfonyl-1R-cyanomethylcarbamoylethylcarbamoyl)piperazine-1-carboxylate (Compound 28); Mass Spectrum: m/e m+ 493.8, m− 492.2; NMR Spectrum (DMSO): δ: 8.66 (m, 1H), 7.40 (s, 5H), 7.17 (m, 1H), 4.73 (m, 1H), 4.52 (s, 2H), 4.13 (m, 2H), 3.62 (m, 1H), 3.24–3.48 (m, 9H), 1.41 (s, 9H); and N-(2-benzylsulfonyl-1R-cyanomethylcarbamoylethyl)-4-fur-2-ylcarbonylpiperazine-1-carboxamide (Compound 29); Mass Spectrum: m/e m+ 488.4, m− 486.2; NMR Spectrum (DMSO): δ: 8.69 (t, J=5.44 Hz, 1H), 7.86 (m, 1H), 7.40 (s, 5H), 7.03 (d, J=3.22 Hz, 1H), 6.64 (dd, J=1.73, 1.73 Hz, 1H), 4.74 (m, 1H), 4.54 (s, 2H), 4.14 (d, J=5.44 Hz, 2H), 3.67 (m, 4H), 3.45 (m, 4H).

Example 7

N-[1R-Cyanomethylcarbamoyl-2-(2-nitrobenzylsulfonyl)ethyl]morpholine-4-carboxamide (Compound 30),

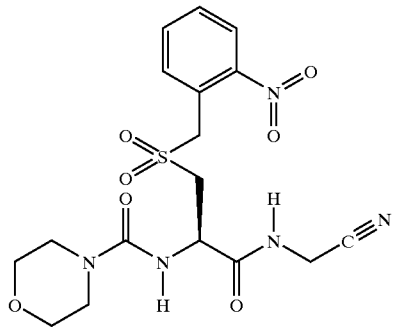

A mixture comprised of N-(2-tert-butyldisulfanyl-1R-cyanomethylcarbamoyl ethyl)morpholine-4-carboxamide (560 mg, 1.6 mmol), provided as in Reference 8, tris-carboxyethyl phosphine (550 mg, 1.9 mmol) and DMF (4.5 mL) was treated with 4M aqueous potassium hydroxide (2 mL) with stirring at 23° C. The mixture was stirred for 3 hours under a nitrogen atmosphere and then treated with 2-nitrobenzyl bromide (830 mg, 3.8 mmol). The mixture was stirred for 16 hours and then diluted with ethyl acetate (200 ml). The organic phase was separated, sequentially washed with brine, saturated sodium bicarbonate and brine, dried (MgSO$_4$) and concentrated under reduced pressure. The residue was dissolved in 1:1 ethyl acetate/hexane and product was crystallized from solution to provide N-[1R-cyanomethylcarbamoyl-2-(2-nitrobenzylsulfanyl)ethyl]morpholine-4-carboxamide (478 mg) as a colorless solid. Mass Spectrum: m/e 399.2 (theory 398). NMR Spectrum (DMSO-d$_6$) δ 8.79 (t, J=5.1 Hz, 1H), 8.69 (d, J=8.1 Hz, 1H), 7.97 (d, J=8.1 Hz, 1H), 7.86 (d, J=8.4 Hz, 2H), 7.58–7.65 (m, 2H), 7.43–7.55 (m, 4H), 4.62 (ddd, J=13.6, 9.2, 5.1 Hz, 1H), 4.12 (d, J=5.5 Hz, 2H), 4.06 (d, J=3.0 Hz, 2H), 2.87 (dd, J=13.5, 5.1, 1H), 2.76 (dd, J=13.6, 9.5 Hz, 1H).

A solution comprised of N-[1R-cyanomethylcarbamoyl-2-(2-nitrobenzylsulfanyl)-ethyl]morpholine-4-carboxamide (50 mg, 0.13 mmol) in methanol (5 mL) was treated with Oxone® (105 g, 0.17 mmol) in water (1 mL) and the reaction mixture was stirred at 25° C. for 16 hours. The reaction mixture then was diluted with cold water and the product was extracted with ethyl acetate. The extracts were dried and concentrated. The residue was dissolved in ethyl acetate and product was crystallized from solution to provide N-[1R-cyanomethylcarbamoyl-2-(2-nitrobenzylsulfonyl)ethyl]morpholine-4-carboxamide (45 g, 0.1 mmol). Mass Spectrum: m/e 431 (theory 430). NMR Spectrum (DMSO-d$_6$) δ 8.99 (d, 1H, J=8.1 Hz), 8.83 (t, J=5.1 Hz, 1H), 8.05 (d, J=8.1 Hz, 1H), 7.86 (d, J=8.1 Hz, 2H), 7.76 (d, J=7 Hz, 1H), 7.64–7.69 (m, 2H), 7.46–7.61 (m, 3H), 5.08 (s, 2H), 5.03 (t, J=6.6 Hz, 1H), 4.13 (s, 2H), 3.83 (d, J=14.3 Hz, 1H), 3.66 (dd, J=14.3, 9.9 Hz, 1H).

The following compounds of Formula I were provided by proceeding as in Example 7:

N-[2-(4-chlorobenzylsulfonyl)-1R-cyanomethylcarbamoylethyl]benzamide (Compound 31); EI MS (M+=420.0); NMR (DMSO): δ 8.96 (d, 1H, J=8.1 Hz), 8.79 (t, 1H, J=5.5 Hz), 7.87 (d, 2H, J=6.2 Hz), 7.39–7.56 (m, 7H), 5.03 (t, J=6.6 Hz), 4.59 (s, 2H), 4.12 (d, 2H, J=5.5 Hz), 3.78 (dd, 1H, J=14.3, 2.9 Hz), 3.54 (dd, 1H, J=14.3, 9.9 Hz);

N-[1R-cyanomethylcarbamoyl-2-(2-methylbenzylsulfonyl)ethyl]benzamide (Compound 32); EI MS (M+=400.2); NMR (DMSO): δ 9.04 (d, 1H, J=8.2 Hz), 8.85 (t, 1H, J=5.4 Hz), 7.90 (d, 2H, J=8.4 Hz), 7.47–7.61 (m, 3H), 7.18–7.34 (m, 4H), 5.11 (t, 1H, J=9.7 Hz), 4.65 (d, 1H, J=13.6 Hz), 4.57 (d, 1H, J=13.6 Hz), 4.16 (d, 2H, J=5.9 Hz), 3.87 (dd, 1H, J=14.3,3.2 Hz), 3.68 (dd, 1H, J=14.6, 9.6 Hz), 2.33 (s, 3H);

N-[1R-cyanomethylcarbamoyl-2-(3,5-dimethylbenzylsulfonyl)ethyl]benzamide (Compound 33); EI MS (M+=414.0); NMR (DMSO): δ 9.01 (d, 1H, J=7.9 Hz), 8.81 (t, 1H, J=5.7 Hz), 7.90 (d, 2H, J=6.7 Hz), 7.48–7.61 (m, 3H), 7.00 (s, 1H), 6.98 (s, 2H), 5.04 (t, 1H, J=11.4 Hz), 4.46 (s, 2H), 4.14 (d, 2H, J=5.4 Hz), 3.76 (dd, 1H, J=14.6, 3.0 Hz), 3.53 (dd, 1H, J=14.3, 9.4 Hz), 2.25 (s, 6H);

N-[1R-cyanomethylcarbamoyl-2-(4-trifluoromethylbenzylsulfonyl)ethyl]benzamide (Compound 34); EI MS (M+=454.0); NMR (DMSO): δ 8.99 (d, 14, J=8.2 Hz), 8.81 (t, 1H, J=5.7 Hz), 7.88 (d, 2H, J=6.7 Hz), 7.79 (d, 2H, J=8.2 Hz), 7.64 (d, 2H, J=8.2 Hz), 7.48–7.58 (m, 3H), 5.08 (t, 1H, J=8.8 Hz), 4.74 (s, 2H), 4.14 (d, 2H, J=6.2 Hz), 3.84 (dd, 1H, J=14.9, 3.5 Hz), 3.60 (dd, 11H, J=14.3, 9.6 Hz);

N-[1R-cyanomethylcarbamoyl-2-(4-trifluoromethoxybenzylsulfonyl)ethyl]benzamide (Compound 35); EI MS (M+=470.2); NMR (DMSO): δ 9.00 (d, 1H, J=8.24 Hz), 8.82 (t, 1H, J=5.6 Hz), 7.89 (d, 2H, J=9.7 Hz), 7.40–7.58 (m, 7H), 5.04–5.11 (m, 1H), 4.65 (s, 2H), 4.15 (s, 1H), 3.82 (dd, 1H, J=14.3,3.2 Hz), 3.59 (dd, 1H, J=12.0, 9.7 Hz);

N-[1R-cyanomethylcarbamoyl-2-(4-trifluoromethylsulfanylbenzylsulfonyl)ethyl]-benzamide (Compound 36); EI MS (M+=486.2); NMR (DMSO): δ 9.02 (d, 1H, J=7.9 Hz), 8.82 (t, 1H, J=5.7 Hz), 7.89 (d, 2H, J=8.4 Hz), 7.76 (d, 2H, J=8.2 Hz), 7.47–7.61 (m, 5H), 5.07 (t, 1H, J=9.4 Hz), 4.70 (s, 2H), 4.15 (d, 2H, =5.7 Hz), 3.84 (dd, 1H,1J=14.6, 3.5 Hz), 3.61 (dd, 1H, J=14.1, 94. Hz);

N-[1R-cyanomethylcarbamoyl-2-(3-nitrobenzylsulfonyl)ethyl]benzamide (Compound 37); EI MS (M+=431.0); NMR (DMSO): δ 8.99 (d, 1H, J=8.0 Hz), 8.82 (t, 1H, J=5.7 Hz), 8.32 (s, 1H), 8.27 (d, 1H, J=8.2 Hz), 7.88 (m, 3H), 7.73 (t, 1H, J=3.1 Hz), 7.47–7.60 (m, 3H), 5.06 (t, 1H, J=11.1 Hz), 4.82 (s, 2H), 4.14 (s, 2H), 3.86 (dd, 1H, J=14.4, 3.2 Hz), 3.62 (dd, 1H, J=14.6, 9.4 Hz);

N-(1R-cyanomethylcarbamoyl-2-pyrid-2-ylmethylsulfonylethyl)benzamide (Compound 38); Mass Spectrum: m/e 387.03 (theory 386.97); NMR Spectrum (DMSO): 9.01 (d, J=9.1 Hz, 1H), 8.79 (t, J=6.3 Hz, 1H), 8.57 (d, J=4.4 Hz, 1H), 7.95–7.8 (m, 3H), 7.6–7.35 (m, 5H), 5.11 (m, 1H), 4.78 (d, J=15.4 Hz, 1H), 4.69 (d, J=15.4 Hz, 1H), 4.14 (d, J=6.1 Hz, 2H), 3.86 (dd, J=3.3 and 16 Hz, 1H), 3.65 (dd, J=11 and 16 Hz, 1H) ppm;

N-(1R-cyanomethylcarbamoyl-2-pyrid-4-ylmethylsulfonylethyl)benzamide (Compound 39); Mass Spectrum: m/e 387.04 (theory 386.97); NMR Spectrum (DMSO): 8.99 (d, J=9.1 Hz, 1H), 8.81 (t, J=6.0 Hz, 1H), 8.60 (d, J=6.6 Hz, 2H), 7.85–7.95 (m, 2H), 7.6–7.45 (m, 3H), 7.42 (d, J=6.6 Hz, 2H), 5.00–5.15 (m, 1H), 4.67 (s, 2H), 4.13 (d, J=6.6 Hz, 2H), 3.84 (dd, J=3.9 and 16 Hz, 1H), 3.59 (dd, J=16 and 10 Hz, 1H) ppm;

N-[1R-cyanomethylcarbamoyl-2-(3,4-dichlorobenzylsulfonyl)ethyl]benzamide (Compound 40); EI MS (M+=454.0); NMR (DMSO); δ8.97 (d, 1H, J=8.1 Hz), 8.80 (t, 1H, J=5.9 Hz), 7.86 (d, 2H, J=7.3 Hz), 7.66–7.70 (m, 2H), 7.46–7.58 (m, 4H), 5.04 (t, 1H, J=7.3 Hz), 4.64 (t, 2H, J=14.3 Hz), 4.13 (s, 2H), 3.81 (d, 1H J=14.7 Hz), 3.56 (dd, 1H, J=14.3, 9.2 Hz);

N-[1R-cyanomethylcarbamoyl-2-(3-methylbenzylsulfonyl)ethyl]benzamide (Compound 41); EI MS (M+=400.0); NMR (DMSO); δ9.00 (d, 1H, J=8.4 Hz), 8.81 (t, 1H, J=5.7 Hz), 7.89 (d, 2H, J=6.6 Hz), 7.47–7.59 (m, 3H), 7.25 (d, 1H, J=6.2 Hz), 7.17 (brS, 3H), 5.02–5.06 (m, 1H), 4.51 (s, 2H), 4.13 (s, 2H), 3.76 (d, 1H, J=14.3 Hz), 3.53 (dd, 1H, J=13.2, 9.5 Hz), 2.28 (s, 3H);

N-[1R-cyanomethylcarbamoyl-2-(4-nitrobenzylsulfonyl)ethyl]benzamide (Compound 42); NMR (DMSO): δ 8.98 (d, 1H, J=7.7 Hz), 8.80 (t, 1H, J=4.8 Hz), 8.25 (d, 2H, J=6.6 Hz), 7.86 (d, 2H, J=7.0 Hz), 7.67 (d, 2H, J=7.0 Hz), 7.45–7.58 (m, 3H), 5.04 (t, 1H, 7.7 Hz), 4.80 (s, 2H), 4.12 (s, 2H), 3.84 (d, 1H, J=16.8 Hz), 3.60 (dd, 1H, J=13.6, 9.5 Hz);

N-[1R-cyanomethylcarbamoyl-2-(2-nitrobenzylsulfonyl)ethyl]benzamide (Compound 43); EI MS (M+=431.2), Theory=430; NMR (DMSO): δ 8.99 (d, 1H, J=8.1 Hz), 8.83 (t, 1H, J=5.1 Hz), 8.05 (d, 1H, J=8.1 Hz), 7.86 (d, 2H, J=8.1 Hz), 7.76 (d, 1H, J=7.0 Hz), 7.64–7.69 (m, 2H), 7.46–7.61 (m, 3H), 5.08 (s, 2H), 5.03 (t, 1H, J=6.6 Hz), 4.13 (s, 2H), 3.83 (d, 1H, J=14.3 Hz), 3.66 (dd, 1H, J=14.3, 9.9 Hz);

N-[1R-cyanomethylcarbamoyl-2-(3-trifluoromethylbenzylsulfonyl)ethyl]benzamide (Compound 44); EI MS (M+=454.1), Theory=453; NMR (DMSO): δ 8.98 (d, 1H, J=7.3 Hz), 8.79 (t, 1H, J=5.1 Hz), 7.85 (d, 2H, J=7.0 Hz, 7.63–7.73 (M, 4H), 7.44–7.54 (m, 3H), 5.04 (t, 1H, J=5.1 Hz), 4.71 (s, 2H), 3.81 (d, 1H, J=13.9 Hz), 3.56 (dd, 1H, J=13.9, 9.2. Hz);

N-[1R-cyanomethylcarbamoyl-2-(3-trifluoromethoxybenzylsulfonyl)ethyl]benzamide (Compound 45); EI MS (M+=470.0), Theory=469; NMR (DMSO): δ 9.00 (d, 1H, J=8.1 Hz), 8.81 (t, 1H, J=5.9 Hz), 7.87 (d, 2H, J=7.3 Hz), 7.40–7.56 (m, 7H), 5.05 (t, 1H, J=5.9 Hz), 4.67 (s, 2H), 4.13 (d, 2H, J=5.5 Hz), 3.81 (d, 1H, J=14.3 Hz), 3.57 (dd, 1H, J=14.3, 9.9 Hz);

N-(1R-cyanomethylcarbamoyl-2-pyrid-3-ylmethylsulfonylethyl)benzamide (Compound 46); Mass Spectrum: m/e 387.02 (theory 386.97); NMR Spectrum (DMSO): 8.99 (d, J=9.1 Hz, 1H), 8.82 (t, J=6.1 Hz, 1H), 8.62–8.54 (m, 2H), 7.94–7.8 (m, 3H), 7.62–7.4 (m, 4H), 5.12–5.0 (m, 1H), 4.66 (s, 2H), 4.14 (d, J=6.6 Hz, 2H), 3.83 (dd, J=3.9 and 16.2 Hz, 1H), 3.59 (dd, J=10.7 and 16 Hz, 1H) ppm;

N-[1R-cyanomethylcarbamoyl-2-(2-methylbenzylsulfonyl)ethyl]morpholine-4-carboxamide (Compound 47); Mass Spectrum: m/e 408.6 (theory 408.48); NMR Spectrum (DMSO): 8.70 (t, J=6.0 Hz, 1H), 7.35–7.1 (m, 5H), 4.84–4.74 (m, 1H), 4.60 (d, J=15 Hz, 1H), 4.52 (d, J=15 Hz, 1H), 4.18 (d, J=17 Hz, 1H), 4.10 (d, J=17 Hz, 1H), 3.70 (dd, J=3.8 and 15.9 Hz, 1H), 3.6–3.5 (m, 5H), 3.4–3.25 (m, 4H), 2.35 (s, 3H).

N-(1R-cyanomethylcarbamoyl)-2-pentafluorobenzylsulfonylethyl)benzamide (Compound 48); MS m/z=476 (M+1); NMR (DMSO): δ 9.0 (d, J=8 Hz, 1H), 8.8 (ddJ=5.5, 3.6, 1H), 7.8 (dJ=7.3, 2H), 7.5 (m, 3H), 4.8 (ddJ=17, 6, 2H), 4.14 (s 1H), 4.11 (s, 1H), 4.02 (s, 1H), 4.01 (s, 1H), 3.99 (dd, 3, 15, 1H), 3.78 (dd (1H), 5.0 (ddd, 3, 10, 8, 1H);

N-(1R-cyanomethylcarbamoyl-2-naphth-2-ylbenzylsulfonyl)ethyl)benzamide (Compound 49); MS m/z=436 (M+1); NMR (DMSO): 6 8.99 (d, 8 Hz, 1H), 8.8 (dd, 3,5,1H), 7.9 (m, 6H), 7.5 (m, 6H), 5.05 (m, 1H), 4.7 (s, 2H), 4.1 (d, 5, 2H), 3.8 (dd, 3,14, 1H), 3.55 (dd, 10, 14, 1H);

N-[1R-cyanomethylcarbamoyl-2-(2-fluorobenzylsulfonyl)ethyl]benzamide (Compound 50); Mass Spectrum: m/e 404.4 (theory 403.43); NMR Spectrum (DMSO): 9.00 (d, J=9 Hz, 1H), 8.82 (t, J=6.3 Hz, 1H), 7.93–7.82 (m, 2H),7.62–7.4 (m, 5H), 7.32–7.18 (m, 2H), 5.14–5.04 (m, 1H), 4.64 (s, 2H), 4.14 (d, 6.9 Hz, 2H), 3.84 (dd, J=3.6 and 11.5 Hz, 1H), 3.67 (dd, J=8.1 and 11 Hz, 1H) ppm;

N-[2-(2-chlorobenzylsulfonyl)-1R-cyanomethylcarbamoylethyl]benzamide (Compound 51); Mass Spectrum: m/e 420.3 (theory 419.88); NMR (DMSO): 9.17 (d, J=9.1 Hz, 1H), 8.94 (t, J=5.8 Hz, 1H), 7.98–7.9 (m, 2H), 7.6–7.32 (m, 7H), 5.15–5.05 (m, 1H), 4.75 (s, 2H), 4.14 (d, J=6.3 Hz, 2H), 3.82 (d, J=6.9 Hz, 2H) ppm;

N-(1R-cyanomethylcarbamoyl-2-prop-2-en-1-ylsulfonylethylbenzamide (Compound 52); Mass Spectrum: m/e 335.7 (theory 335.38); NMR Spectrum (DMSO): 9.00 (d, J=8.1 Hz, 1H), 8.81 (t, J=5.4 Hz, 1H), 7.89 (d, J=7.4 Hz, 2H), 7.64–7.46 (m, 3H), 5.94–5.75 (m, 1H), 5.46 (d, J=4.7 Hz, 1H), 5.41 (s, 1H), 5.06–4.95 (m, 1H), 4.13 (d, J=5.7 Hz, 2H), 4.04–3.9 (m, 2H), 3.75 (dd, J=3.2 and 14.6 Hz, 1H), 3.57 (dd, J=9.4 and 14.6 Hz, 1H) ppm;

N-[2-(2-bromobenzylsulfonyl)-1R-cyanomethylcarbamoylethyl]benzamide (Compound 53); Mass Spectrum: m/e 462.2 (theory 464.34); NMR (DMSO): 9.03 (d, J=8.2 Hz, 1H), 8.84 (t, J=5.4 Hz, 1H), 7.90 (d, J=6.9 Hz, 2H),7.75–7.25 (m, 7H), 5.17–5.05 (m, 1H), 4.75 (s, 2H), 4.15 (d, J=5.7 Hz, 2H), 3.85 (dd, J=3.4 and 14.1 Hz, 1H), 3.73 (dd, J=14.6 and 9.4 Hz, 1H) ppm;

N-[1R-cyanomethylcarbamoyl-2-(2-iodobenzylsulfonyl)ethyl]benzamide (Compound 54); Mass Spectrum: m/e 511.95 (theory 511.34); NMR (DMSO): 9.02 (d, J=9.1 Hz, 1H), 8.83 (t, J=6.0 Hz, 1H), 7.94–7.88 (m, 3H), 7.6–7.37;

N-[2-(4-tert-butylbenzylsulfonyl)-1R-cyanomethylcarbamoylethyl]benzamide (Compound 55); Mass Spectrum: m/e 442.10 (theory 441.55); NMR Spectrum (DMSO): 8.99 (d, J=9.1 Hz, 1H), 8.81 (t; J=6.3 Hz, 1H), 7.94–7.85 (m, 2H), 7.62–7.44 (m, 3H), 7.41 (d, 9 Hz, 2H), 7.30 (d, J=9 Hz, 2H), 5.1–5.02 (m, 1H), 4.51 (s, 2H), 4.13 (d, J=6.6 Hz, 2H), 3.77 (dd, J=3.9 and 16 Hz, 1H), 3.54 (dd, J=7.8 and 16 Hz, 1H), 1.26 (s, 9H) ppm;

N-[1R-cyanomethylcarbamoyl-2-(2-trifluoromethylbenzylsulfonyl)ethyl]benzamide (Compound 56); Mass Spectrum: M+1=454; NMR 270 MHz (DMSO): 8.8 (m, 2H) 8.2–7.8 (m, 7H), 5.7 (ddd, 8,8,4, 1H) 5.2 (S,2H) 4.6 (DD, 5,3, 2H) 4.4 (dd 14, 4, 1H) 4.2 (dd 14, 8, 1H);

N-[1R-cyanomethylcarbamoyl)-2-(2-cyanobenzylsulfonyl)ethyl]benzamide (Compound 57); Mass Spectrum: M+1=454; NMR 270 MHz. (acetone):

8–7.4 (m, 9H) 5.2 (m, 1H), 4.8 (S, 2H) 4.2 (s, 2H) 4.0 (dd 14, 4, 1H) 3.8 (ddd 14, 9, 2,1H);

N-[2-(4-bromobenzylsulfonyl)-1R-cyanomethylcarbamoylethyl]benzamide (Compound 58); Mass Spectrum: (M+H$^+$) 464, 466; (M–H$^+$) 462, 464;

N-[2-(3-chlorobenzylsulfonyl)-1R-cyanomethylcarbamoylethyl]benzamide (Compound 59); Mass Spectrum: (M+H$^+$) 420, 422; (M–H$^+$) 418, 420; $^1$H NMR: (DMSO) 8.98 (d, J=8.2 Hz, 1H), 8.81 (t, J=6 Hz, 1H), 7.88 (m, 2H), 7.60–7.35 (m, 7H), 5.05 (m, 1H), 4.62 (s, 2H), 4.14 (m, 2H), 3.81 (dd, J=3.4 Hz, J=14.3 Hz, 1H), 3.56 (dd, J=9.4 Hz, J=14.5 Hz, 1H);

N-[1R-cyanomethylcarbamoyl-2-(3-fluorobenzylsulfonyl)ethyl]benzamide (Compound 60); Mass Spectrum: (M+H$^+$) 404; (M–H$^+$) 402; $^1$H NMR: (DMSO) 8.99 (d, J=7.9 Hz, 1H), 8.81 (t, J=6 Hz, 1H), 7.87 (m, 2H), 7.60–7.40 (m, 4H), 7.28–7.20 (m, 3H), 5.05 (m, 1H), 4.62 (s, 2H), 4.13 (m, 2H), 3.81 (dd, J=3.2 Hz, J=14.3 Hz, 1H), 3.56 (dd, J=9.4 Hz, J=14.5 Hz, 1H);

N-[2-(3-chloro-2-fluorobenzylsulfonyl)-1R-cyanomethylcarbamoylethyl]benzamide (Compound 61); Mass Spectrum: (M+H$^+$) 438, 440; (M–H$^+$) 436, 438; $^1$H-NMR: (DMSO, δ) 9.00 (d, J=8.4 Hz, 1H), 8.84 (t, J=5.4 Hz, H), 7.88 (d, J=6.8 Hz, 2H), 7.65–7.42 (m, 5H), 7.28 (t, J=7.7 Hz, 1H), 5.08 (m, 1H), 4.72 (s, 2H), 4.15 (m, 2H), 3.90 (dd, J=3 Hz, J=14.4 Hz, 1H), 3.70 (dd, J=9.9 Hz, J=14.4 Hz, 1H);

N-[1-cyanomethylcarbamoyl-2-(2-fluoro-3-methylbenzylsulfonyl)ethyl]benzamide (Compound 62); Mass Spectrum: (M+H$^+$) 422; (M–H$^+$) 420; $^1$H NMR: (DMSO) 8.99 (d, J=7.9 Hz, 1H), 8.81 (t, J=6 Hz, 1H), 7.88 (m, 2H), 7.60–7.45 (m, 3H), 7.37–7.28 (m, 3H), 5.07 (m, 1H), 4.65 (s, 2H), 4.14 (m, 2H), 3.87 (dd, J=3.2 Hz, J=14.3 Hz, 1H), 3.70 (dd, , J=9.4 Hz, J=14.5 Hz, 1H);

N-[1-cyanomethylcarbamoyl)-2-(2,5-difluorobenzylsulfonyl)ethyl]benzamide (Compound 63); Mass Spectrum: (M+H$^+$) 422; (M–H$^+$) 420; $^1$H-NMR: (DMSO, δ) 9.00 (d, J=8.2 Hz, 1H), 8.84 (t, J=5.6 Hz, 1H), 7.87 (d, J=8 Hz, 2H), 7.60–7.45 (m, 4H), 7.19 (t, J=8 Hz, 1H), 5.10 (m, 1H), 4.68 (s, 2H), 4.15 (m, 2H), 3.90 (dd, J=3.5 Hz, J=14.4 Hz, 1H), 3.76 (dd, J=9.9 Hz, J=14.4 Hz, 1H);

N-[1R-cyanomethylcarbamoyl)-2-(4-iodobenzylsulfonyl)ethyl]benzamide (Compound 64); Mass Spectrum: (M+H$^+$) 512; (M–H$^+$) 510; $^1$H NMR: (DMSO) 8.99 (d, J=7.9 Hz, 1H), 8.81 (t, J=6 Hz, 1H), 7.87 (m, 2H), 7.77 (d, J=8.2 Hz, 2H), 7.57–7.46 (m, 3H), 7.19 (d, J=8.2 Hz, 2H), 5.04 (m, 1H), 4.55 (s, 2H), 4.13 (m, 2H), 3.78 (dd, J=3.2 Hz, J=14.3 Hz, 1H), 3.53 (dd, J=9.4 Hz, J=14.5 Hz, 1H);

N-[1R-cyanomethylcarbamoyl)-2-(3-iodobenzylsulfonyl)ethyl]benzamide (Compound 65); Mass Spectrum: (M+H$^+$) 512; (M–H$^+$) 510; $^1$H NMR: (DMSO) 8.99 (d, J=8.2 Hz, 1H), 8.80 (t, J=6 Hz, 1H), 7.88 (m, 2H), 7.78–7.73 (m, 2H), 7.60–7.46 (m, 3H), 7.41 (d, J=7.7 Hz, 1H), 7.20 (t, J=7.7 Hz, 1H), 5.06 (m, 1H), 4.57 (s, 2H), 4.14 (m, 2H), 3.80 (dd, J=3.4 Hz, J=14.3 Hz, 1H), 3.53 (dd, J=9.9 Hz, J=14.5 Hz, 1H);

N-[1R-cyanomethylcarbamoyl-2-(2-difluoromethoxybenzylsulfonyl)ethyl]benzamide (Compound 66); Mass Spectrum: (M+H$^+$) 452; (M–H$^+$) 450; $^1$H-NMR: (DMSO, δ) 8.99 (d, J=8.2 Hz, 1H), 8.82 (t, J=5.5 Hz, 1H), 7.89 (d, J=8.2 Hz, 2H), 7.60–7.44 (m, 5H), 7.29 (t, J=5.5 Hz, 1H), 7.26 (t, J=5.5 Hz, 1H) 7.13 (t, J$_{H,F}$=74 Hz, 1H) 5.08 (m, 1H), 4.61 (s, 2H), 4.14 (m, 2H), 3.80 (dd, J=2.7 Hz, J=14.4 Hz, 1H), 3.76 (dd, J=9.7 Hz, J=14.4 Hz, 1H);

N-[1R-cyanomethylcarbamoyl-2-(2,5-dichlorobenzylsulfonyl)ethyl]benzamide (Compound 67); Mass Spectrum: (M+H$^+$) 454, 456; (M–H$^+$) 452, 454; $^1$H NMR (DMSO) 9.02 (d, J=8.4 Hz, 1H), 8.85 (t, J=5.4 Hz, 1H), 7.89 (m, 2H), 7.61–7.46 (m, 6H), 5.11 (m, 1H), 4.76 (s, 2H), 4.15 (m, 2H), 3.88 (dd, J=3.4 Hz, J=14.3 Hz, 1H), 3.73 (dd, J=9.9 Hz, J=14.5 Hz, 1H);

N-[2-(3-bromobenzylsulfonyl)-1-cyanomethylcarbamoylethyl]benzamide (Compound 68); Mass Spectrum: (M+H$^+$) 464, 466; (M–H$^+$) 462, 464; $^1$H-NMR (DMSO, δ) 8.99 (d, J=8.2 Hz, 1H), 8.80 (t, J=5.6 Hz, 1H), 7.87 (d, J=8.2 Hz, 2H), 7.62–7.34 (m, 7H), 5.05 (m, 1H), 4.61 (s, 2H), 4.14 (m, 2H), 3.80 (dd, J=3.2 Hz, J=14.4 Hz, 1H), 3.56 (dd, J=9.7 Hz, J=14.4 Hz, 1H);

N-[1R-cyanomethylcarbamoyl-2-(3-cyanobenzyl)ethyl]benzamide (Compound 69); Mass Spectrum: (M+H$^+$) 411; (M–H$^+$) 409; $^1$H NMR: (DMSO) 8.98 (d, J=8.2 Hz, 1H), 8.81 (t, J=5.4 Hz, 1H), 7.90–7.46 (m, 9H), 5.05 (m, 1H), 4.68 (s, 2H), 4.14 (m, 2H), 3.82 (dd, J=3.2 Hz, J=14.3 Hz, 1H), 3.58 (dd, J=9.4 Hz, J=14.5 Hz, 1H);

N-[1R-cyanomethylcarbamoyl-2-(4-cyanobenzylsulfonyl)ethyl]benzamide (Compound 70); Mass Spectrum: (M+H$^+$) 411; (M–H$^+$) 409; $^1$H NMR: (DMSO) 8.98 (d, J=8.2 Hz, 1H), 8.81 (t, J=5.4 Hz, 1H), 7.91–7.85 (m, 4H), 7.61–7.46 (m, 5H), 5.06 (m, 1H), 4.74 (s, 2H), 4.13 (m, 2H), 3.83 (dd, J=3.2 Hz, J=14.3 Hz, 1H), 3.58 (dd, J=9.4 Hz, J=14.5 Hz, 1H);

N-[1R-cyanomethylcarbamoyl-2-(2-fluoro-6-nitrobenzylsulfonyl)ethyl]benzamide (Compound 71); Mass Spectrum: (M+H$^+$) 449; (M–H$^+$) 447;: $^1$H NMR: (DMSO) 9.01 (d, J=8.2 Hz, 1H), 8.87 (t, J=5.4 Hz, 1H), 7.94–7.46 (m, 8H), 5.11–5.03 (m, 3H), 4.15 (m, 2H), 3.93 (dd, J=3.4 Hz, J=14.3 Hz, 1H), 3.80 (dd, J=9.7 Hz, J=14.5 Hz, 1H);

N-[2-(2-bromo-5-fluorobenzylsulfonyl)-1R-cyanomethylcarbamoylethyl]benzamide (Compound 72); Mass Spectrum: (M+H$^+$) 482, 484; (M–H$^+$) 480, 482; $^1$H-NMR: (DMSO, δ) 9.02 (d, J=7.9 Hz, 1H), 8.85 (t, J=5.4 Hz, 1H), 7.88 (d, J=8.2 Hz, 2H), 7.74 (dd, J=5.4 Hz, J=8.9 Hz, 1H) 7.60–7.46 (m, 3H), 7.40 (dd, J=3.2 Hz, J=10.8 Hz, 1H) 7.25 (dt, J=3.2 Hz, J=8.5 Hz, 1H) 5.10 (m, 1H), 4.77 (s, 2H), 4.15 (m, 2H), 3.88 (dd, J=3.7 Hz, J=14.4 Hz, 1H), 3.73 (dd, J=9.7 Hz, J=14.4 Hz, 1H);

N-[1R-cyanomethylcarbamoyl-2-(2,3-difluorobenzylsulfonyl)ethyl]benzamide (Compound 73); Mass Spectrum: (M+H$^+$) 422; (M–H$^+$) 420; $^1$H-NMR: (DMSO, δ) 9.00 (d, J=8.2 Hz, 1H), 8.83 (t, J=5.6 Hz, 1H), 7.87 (d, J=8.2 Hz, 2H), 7.60–7.22 (m, 6H), 5.08 (m, 1H), 4.72 (s, 2H), 4.15 (m, 2H), 3.89 (dd, J=3.0 Hz, J=14.4 Hz, 1H), 3.70 (dd, J=9.9 Hz, J=14.4 Hz, 1H);

N-[2-biphenyl-2-ylmethylsulfonyl)-1R-cyanomethylcarbamoylethyl]benzamide (Compound 74); Mass Spectrum: (M+H$^+$) 462; (M–H$^+$) 460; $^1$H-NMR: (DMSO, δ) 8.90 (d, J=8.4 Hz, H), 8.78 (t, J=5.4 Hz, 1H), 7.83 (d, J=7.9 Hz, 2H), 7.60–7.28 (m, 12H), 4.93 (m, 1H), 4.51 (s, 2H), 4.11 (m, 2H), 3.61 (dd, J=3.2 Hz, J=14.4 Hz, 1H), 3.52 (dd, J=9.7 Hz, J=14.4 Hz, 1H);

N-[1R-cyanomethylcarbamoyl)-2-(2,4-difluorobenzylsulfonyl)ethyl]benzamide (Compound 75); Mass Spectrum: (M+H$^+$) 422; (M–H$^+$) 420; $^1$H NMR: (DMSO) 8.99 (d, J=8.2 Hz, 1H), 8.83 (t, J=5.4 Hz, 1H), 7.88 (m, 2H), 7.60–7.12 (m, 6H), 5.07 (m, 1), 4.63 (s, 2H), 4.14 (m, 2H), 3.85 (dd, J=3.2 Hz, J=14.3 Hz, 1H), 3.67 (dd, , J=9.5 Hz, J=14.5 Hz, 1H);

N-[1R-cyanomethylcarbamoyl-2-(4-fluorobenzylsulfonyl)ethyl]benzamide (Compound 76); Mass Spectrum: (M+H$^+$) 404; (M–H$^+$) 402; $^1$H NMR:

(DMSO) 8.98 (d, J=8.2 Hz, 1H), 8.80 (t, J=5.4 Hz, 1H), 7.88 (m, 2H), 7.60–7.40 (m, 5H), 7.23 (t, J=8.9 Hz, 2H), 5.04 (m, 1H), 4.58 (s, 2H), 4.13 (m, 2H), 3.78 (dd, J=3.2 Hz, J=14.3 Hz, 1H), 3.54 (dd, J=9.5 Hz, J=14.5 Hz, 1H);

N-[1-R-cyanomethylcarbamoyl-2-(3,4-difluorobenzylsulfonyl)ethyl]benzamide (Compound 77); Mass Spectrum: (M+H$^+$) 422; (M−H$^+$);

N-[1R-cyanomethylcarbamoyl-2-(2,3,4-trifluorobenzylsulfonyl)ethyl]benzamide (Compound 78); Mass Spectrum: (M+H$^+$) 440; (M−H$^+$) 438;

N-[1R-cyanomethylcarbamoyl-2-(2,4,6-trifluorobenzylsulfonyl)ethyl]benzamide (Compound 79); Mass Spectrum: (M+H$^+$) 440; (M−H$^+$) 438; $^1$H-NMR: (DMSO, δ) 9.01 (d, J=8.2 Hz, 1H), 8.85 (t, J=5.4 Hz, 1H), 7.88 (d, J=7.4 Hz, 2H), 7.60–7.46 (m, 3H), 7.31 (t, J=8.7 Hz, 2H), 5.10 (m, 1H), 4.66 (s, 2H), 4.15 (m, 2H), 3.91 (dd, J=2.5 Hz, J=14.4 Hz, 1H), 3.76 (dd, J=9.7 Hz, J=14.4 Hz, 1H);

N-[1R-cyanomethylcarbamoyl-2-(2.4,5-trifluorobenzylsulfonyl)ethyl]benzamide (Compound 80); Mass Spectrum: (M+H$^+$) 440; (M−H$^+$) 438; $^1$H NMR: (DMSO) 8.98 (d, J=8.2 Hz, 1H), 8.83 (t, J=5.4 Hz, 1H), 7.88 (m, 2H), 7.71–7.46 (m, 5H), 5.07 (m, 1H), 4.64 (s, 2H), 4.14 (m, 2H), 3.87 (dd, J=3.4 Hz, J=14.3 Hz, 1H), 3.69 (dd, , J=9.5 Hz, J=14.5 Hz, 1H);

N-[1R-cyanomethylcarbamoyl-2-(2,3,6-trifluorobenzylsulfonyl)ethyl]benzamide (Compound 81); Mass Spectrum: (M+H$^+$) 440; (M−H$^+$) 438; $^1$H NMR: (DMSO) 9.01 (d, J=8.2 Hz, 1H), 8.85 (t, J=5.4 Hz, 1H), 7.88 (m, 2H), 7.66–7.46 (m, 4H), 7.29–7.20 (m, 1H), 5.11 (m, 1H), 4.76 (s, 2H), 4.15 (m, 2H), 3.96 (dd, J=3.4 Hz, J=14.3 Hz, 1H), 3.78 (dd, J=9.5 Hz, J=14.5 Hz, 1H);

N-[2-(2-chloro-5-trifluoromethylbenzylsulfonyl)-1R-cyanomethylcarbamoylethy]-benzamide (Compound 82); Mass Spectrum: (M+H$^+$) δ487, 489; (M−H$^+$) 485, 487; $^1$H-NMR: (DMSO, o) 9.04 (d, J=8.2 Hz, 1H), 8.86 (t, J=5.4 Hz, 1H), 7.92–7.87 (m, 3H), 7.79 (s, 2H), 7.60–7.44 (m, 3H), 5.11 (m, 1H), 4.92 d, J=13.6 Hz, 1H), 4.86 (d, J=13.6 Hz, 1H), 4.15 (m, 2H), 3.92 (dd, J=3.2 Hz, J=14.6 Hz, 1H), 3.75 (dd, J=9.9 Hz, J=14.4 Hz, 1H);

N-[2-(2,4-bistrifluoromethylbenzylsulfonyl)-1R-cyanomethylcarbamoylethyl]-benzamide (Compound 83); Mass Spectrum: (M+H$^+$) 522; (M−H$^+$) 520; $^1$H NMR (DMSO) 9.04 (d, J=8.2 Hz, 1H), 8.87 (t, J=5.4 Hz, 1H), 8.17 (d, J=8.4 Hz, 1H), 809 (s, 1H), 7.94–7.87 (m, 3H), 7.60–7.46 (m, 3H), 5.12 (m, 1H), 4.96 (d, J=14.3 Hz, 1H), 4.88 (d, J=14.3 Hz, 1H), 4.16 (m, 2H), 3.97 (dd, J=3.4 Hz, J=14.3 Hz, 1H), 3.82 (dd, J=9.5 Hz, J=14.5 Hz, 1H);

N-[1R-cyanomethylcarbamoyl-2-(2-fluoro-6-trifluoromethylbenzylsulfonyl)ethyl]-benzamide (Compound 84); Mass Spectrum: (M+H$^+$) 472; (M−H$^+$) 470; $^1$H-NMR: (DMSO, δ) 9.01 (d, J=8.4 Hz, 1H), 8.85 (t, J=5.5 Hz, 1H), 7.87 (d, J=7.4 Hz, 2H), 7.70–7.45 (m, 6H), 5.08 (m, 1H), 4.80 (s, 2H), 4.13 (m, 2H), 3.97–3.75 (m, 2H);

N-[1R-cyanomethylcarbamoyl-2-(2-fluoro-3-trifluoromethylbenzylsulfonyl)ethyl]-benzamide (Compound 85); Mass Spectrum: (M+H$^+$) 472; (M−H$^+$) 470; $^1$H NMR: (DMSO) 9.02 (d, J=8.2 Hz, 1H), 8.84 (t, J=5.4 Hz, 1H), 7.90–7.78 (m, 4H), 7.60–7.44 (m, 4H), 5.10 (m, 1H), 4.79 (s, 2H), 4.15 (m, 2H), 3.92 (dd, J=3.4 Hz, J=14.3 Hz, 1H), 3.72 (dd, J=9.5 Hz, J=14.5 Hz, 1H);

N-[1R-cyanomethylcarbamoyl-2-(3-trifluoromethylsulfanylbenzylsulfonyl)ethyl)-benzamide (Compound 86); Mass Spectrum: (M+H$^+$) 486; (M−H$^+$) 484; $^1$H-NMR: (DMSO, δ) 9.00 (d, J=8.2 Hz, 1H), 8.80 (t, J=5.4 Hz, 1H), 7.90–7.46 (m, 9H), 5.05 (m, 1H), 4.70 (s, 2H), 4.13 (m, 2H), 3.82 (dd, J=3.2 Hz, J=14.9 Hz, 1H), 3.58 (dd, J=9.7 Hz, J=14.6 Hz, 1H);

N-[1-R-cyanomethylcarbamoyl-2-(2-fluoro-4-trifluoromethylbenzylsulfonyl)ethyl]-benzamide (Compound 87); Mass Spectrum: (M+H$^+$) 472; (M−H$^+$) 470; $^1$H NMR: (DMSO) 9.00 (d, J=8.2 Hz, 1H), 8.84 (t, J=5.4 Hz, 1H), 7.90–7.46 (m, 8H), 5.10 (m, 1H), 4.78 (s, 2H), 4.15 (m, 2H), 3.92 (dd, J=3.2 Hz, J=14.3 Hz, 1H), 3.71 (dd, , J=9.5 Hz, J=14.5 Hz, 1H);

N-[1R-cyanomethylcarbamoyl-2-(2,3,5-trifluorobenzylsulfonyl)ethyl]benzamide (Compound 88); Mass Spectrum: (M+H$^+$) 440; (M−H$^+$) 438; $^1$H NMR: (DMSO) 8.99 (d, J=8.2 Hz, 1H), 8.84 (t, J=5.4 Hz, 1H), 7.88 (m, 2H), 7.69–7.46 (m, 4H), 7.25–7.18 (m, 1H), 5.08 (m, 1H), 4.75 (s, 2H), 4.15 (m, 2H), 3.92 (dd, J=3.2 Hz, J=14.3 Hz, 1H), 3.71 (dd, , J=9.5 Hz, J=14.5 Hz, 1H);

N-[1R-cyanomethylcarbamoyl-2-(2-trifluoromethylbenzylsulfonyl)ethyl]-benzamide (Compound 89); Mass Spectrum Spectrum: (M+H$^+$) 486; (M−H$^+$) 484; $^1$H-NMR: (DMSO, δ) 9.04 (d, J=8.2 Hz, 1H), 8.87 (t, J=5.6 Hz, 1H), 7.92–7.46 (m, 9H), 5.11 (m, 1H), 4.92 (s, 2H), 4.15 (m, 2H), 3.90 (dd, J=3.5 Hz, J=14.8 Hz, 1H), 3.77 (dd, J=9.7 Hz, J=14.6 Hz, 1H);

N-[1R-cyanomethylcarbamoyl-2-(4-fluoro-2-trifluoromethylbenzylsulfonyl)ethyl]-benzamide (Compound 90); Mass Spectrum: (M+H$^+$) 472; (M−H$^+$) 470; $^1$H NMR: (DMSO) 9.01 (d, J=8.2 Hz, 1H), 8.86 (t, J=5.4 Hz, 1H), 7.89 (m, 2H), 7.75–7.46 (m, 6H), 5.09 (m, 1H), 4.80 (d, J=14.3 Hz, 1H), 4.73 (d, J=14.3 Hz, 1H), 4.15 (m, 2H), 3.90 (dd, J=3.2 Hz, J=14.3 Hz, 1H), 3.77 (dd, J=9.5 Hz, J=14.5 Hz, 1H);

N-[1R-cyanomethylcarbamoyl-2-(2-fluoro-5-trifluoromethylbenzylsulfonyl)ethyl]-benzamide (Compound 91); Mass Spectrum: (M+H$^+$) 472; (M−H$^+$) 470; $^1$H NMR: (DMSO) 9.01 (d, J=8.2 Hz, 1H), 8.84 (t, J=5.4 Hz, 1H), 7.91–7.84 (m, 4H), 7.60–7.46 (m, 4H), 5.10 (m, 1H), 4.78 (s, 2H), 4.14 (m, 2H), 3.91 (dd, J=3.2 Hz, J=14.3 Hz, 1H), 3.71 (dd, J=9.5 Hz, J=14.5 Hz, 1H);

N-[1R-cyanomethylcarbamoyl-2-(2-trifluoromethoxybenzylsulfonyl)ethyl]benzamide (Compound 92); Mass Spectrum: (M+H$^+$) 470; (M−H$^+$) 468; $^1$H-NMR: (DMSO, δ) 9.01 (d, J=7.9 Hz, 1H), 8.84 (t, J=5.3 Hz, 1H), 7.89 (d, J=7.7 Hz, 2H) 7.60–7.40 (m, 7H), 5.10 (m, 1H), 4.67 (s, 2H), 4.14 (m, 2H), 3.86 (dd, J=3.2 Hz, J=14.4 Hz, 1H), 3.70 (dd, J=9.9 Hz, J=14.4 Hz, 1H);

N-{(R)-1-(Cyanomethyl-carbamoyl)-2-[4-(1,1-difluoro-methoxy)-phenylmethane-sulfonyl]-ethyl}-benzamide (Compound 93); Mass Spectrum: (M+H$^+$) 452; (M−H$^+$) 450; $^1$H NMR: (DMSO) 8.99 (d, J=8.2 Hz, 1H), 8.80 (t, J=5.4 Hz, 1H), 7.88 (m, 2H), 7.60–7.42 (m, 5H), 7.27 (t, $J_{H,F}$=74 Hz, 1H), 7.20 (d, J=8.4 Hz, 1H), 5.05 (m, 1H), 4.58 (s, 2H), 4.14 (m, 2H), 3.79 (dd, J=3.2 Hz, J=14.3 Hz, 1H), 3.55 (dd, J=9.5 Hz, J=14.5 Hz, 1H);

N-[2-(3,5-bistrifluoromethylbenzylsulfonyl)-1R-cyanomethylcarbamoylethyl]-benzamide (Compound 94); Mass Spectrum: (M+H$^+$) 522; (M−H$^+$) 520; $^1$H NMR (DMSO) 9.00 (d, J=8.2 Hz, 1H), 8.82 (t, J=5.6 Hz, 1H), 8.17 (s, 1H), 8.13 (s, 2H), 7.88 (m, 2H), 7.60–7.46 (m, 3H), 5.07 (m, 1H), 4.89 (s, 2H), 4.14 (m, 2H), 3.88 (dd, J=3.2 Hz, J=14.3 Hz, 1H), 3.63 (dd, J=9.5 Hz, J=14.5 Hz, 1H);

N-[1R-cyanomethylcarbamoyl-2-(2-methoxybenzylsulfonyl)ethyl]benzamide (Compound 95); Mass Spectrum: M+1=416; NMR 270 MHz (DMSO): 8.3 (dd, 6, 1, 2H) 8–7.8 (m, 6H) 7.5 (d, 8, 1H) 7.4 (dd 8, 7, 1H) 5.6 (dd, 9, 3, 1H) 5.0 (d, 14, 1H) 4.6 (dd, 5,3, 2H) 4.8 (d 14, 1H) 4.6 (S, 2H) 4.2 (dd, 15, 3, 11H) 3.8 (dd, 15, 9, 1H);

N-[1R-cyanomethylcarbamoyl-2-(2,6-dichlorobenzylsulfonyl)ethyl]benzamide (Compound 96); Mass Spectrum: M+1=454; NMR 270 MHz (acetone): 7.8 (d, 7, 2H) 7.4 (m, 6H) 5.3 (dd, 9, 3, 1H) 5.0 (d, 5, 2H) 4.2 (d, 3, 2H) 4.1 (dd 14, 3, 1H), 3.9 (dd, 14, 9, 11H);

N-(1R-cyanomethylcarbamoyl-3-prid-4-ylsulfonylpropyl)benzamide (Compound 97) MS: (M−1)= 385; NMR (1H): 8.95 (m, 2H), 8.72 (m, 2H), 7.88 (t, 2.2 Hz, 2H), 7.78 (d, 1.7 Hz, 2H), 7.45–7.58 (m, 3H), 4.55 (m, 1H), 4.11 (d, 5.6 Hz, 2H), 3.51 (m, 2H), 2.10 (m, 2H);

N-(1R-cyanomethylcarbamoyl)-3-pyrid-2-ylsulfonylpopyl)benzamide (Compound 98) MS: (M−1)= 385; NMR: (1H): 8.6–8.77 (m, 2H), 8.18 (dt, 1.7, 7.6 Hz, 1H), 8.06 (d, 7.6 Hz, 1 H), 7.88 (d, 6.9 Hz, 2H), 7.72 (m, 1H), 7.45–7.58 (m, 4H), 4.12 (t, 2.7 Hz, 2H), 4.55 (m, 1H), 3.45–3.60 (m, 2H), 1.95–2.25 (m, 2H);

N-(1R-cyanomethylcarbamoyl-2-(3-difluoromethoxybenzylsulfonyl)ethyl]benzamide (Compound 99); Mass Spectrum: (M+H$^+$) 452; (M−H$^+$) 450; $^1$H-NMR: (DMSO, δ) 8.99 (d, J=8.2 Hz, 1H), 8.81 (t, J=6.2 Hz, 1H), 7.87 (d, J=8.2 Hz, 2H), 7.60–7.18 (m, 7H), 7.22 (t, J$_{H,F}$=74 Hz, 1H), 5.05 (m, 1H), 4.62 (s, 2H), 4.14 (m, 2H), 3.81 (dd, J=2.7 Hz, J=14.5 Hz, 1H), 3.57 (dd, J=9.7 Hz, J=14.4 Hz, 1H);

N-[1R-cyanomethylcarbamoyl-2-(4-fluoro-3-trifluoromethylbenzylsulfonyl)ethyl]-benzamide (Compound 100); Mass Spectrum: (M+H$^+$) 472; (M−H$^+$) 470; $^1$H NMR: (DMSO) 8.98 (d, J=8.2 Hz, 1H), 8.81 (t, J=5.6 Hz, 1H), 7.90–7.75 (m, 4H), 7.62–7.46 (m, 4H), 5.05 (m, 1H), 4.72 (s, 2H), 4.14 (m, 2H), 3.84 (dd, J=3.2 Hz, J=14.3 Hz, 1H), 3.58 (dd, , J=9.5 Hz, J=14.5 Hz, 1H);

4-(2R-benzoylamino-2-cyanomethylcarbamoylethylsulfonylmethyl)benzoic acid (Compound 101); Mass Spectrum: (M+H$^+$) 430; (M−H$^+$) 428; $^1$H NMR: (DMSO) 8.98 (d, J=8.2 Hz, 1H), 8.81 (t, J=5.6 Hz, 1H), 7.95 (d, J=8.2 Hz, 2H), 7.88 (m, 2H), 7.60–7.46 (m, 5H), 5.06 (m, 1H), 4.69 (s, 2H), 4.13 (m, 2H), 3.81 (dd, J=3.2 Hz, J=14.3 Hz, 1H), 3.57 (dd, , J=9.5 Hz, J=14.5 Hz, 1H) and N-[1R-(1-cyanocyclopropylcarbamoyl)-2-benzylsulfonylethyl]morpholine-4-carboxamide (Compound 103).

Example 8

N-[R-(1-Cyanocyclopropylcarbamoyl)-2-(2-difluoromethoxybenzylsulfonyl)ethyl]-morpholine-4-carboxamide (Compound 104);

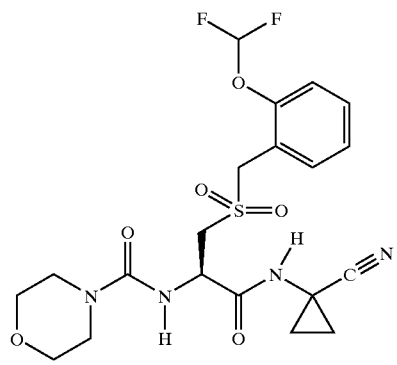

A mixture of (R)-3-[2-(1,1-difluoro-methoxy)-phenylmethanesulfonyl]-2-[(1-morpholin-4-yl-methanoyl)-amino]-propionic acid (200 mg, 0.473 mmol), prepared as in Reference 7, in CH$_2$Cl$_2$ (3 mL), HATU (270 mg, 0.71 mmol) and HOAt (64.3 mg, 0.473 mmol) was treated with 1-aminocyclopropanecarbonitrile (116 mg, 0.71 mmol) and N-methylmorpholine (0.156 mL, 1.42 mmol) and then DMF (3 mL) to obtain a homogenous solution. The mixture was stirred at room temperature for 16 hours, diluted with ethyl acetate (150 mL), washed with saturated aqueous NaHCO$_3$ and then brine, dried (MgSO$_4$) and concentrated to provide N-[1R-(1-cyanocycloprolylcarbamoyl)-2-(2-difluoromethoxybenzylsulfonyl)ethyl]-morpholine-4-carboxamide. The product was purified by flash chromatography. $^1$H NMR: (DMSO) 8.99 (s, 1H), 7.50–7.23 (m, 4H), 7.13 (t, J$_{H,F}$32 74 Hz, 1H), 7.03 (d, J=8.4 Hz, 4.64 (m, 1H), 4.55 (s, 2H), 3.64–3.24 (m, 10H), 1.47 (m, 2H), 1.14 (m, 2H).

Example 9

N-[1R-Cyanomethylcarbamoyl-2-(2-difluoromethoxybenzylsulfonyl)ethyl]morpholine-4-carboxamide (Compound 102)

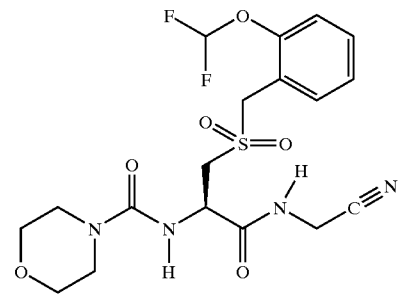

A solution of N-[2-tert-butyldisulfanyl-1R-cyanlomethylcarbamoylethyl]morpholine-4-carboxamide (7.37 g, 20.4 mmol), provided as in Reference 8, in DMF (80 mL) was treated sequentially with tris(carboxyethyl)phosphine hydrochloride (7.03 g, 24.53 mmol) and aqueous potassium hydroxide solution (5N, 20 mL). The mixture was stirred for 5 hours and then treated with 2-difluoromethoxybenzyl bromide (14.54 g, 61.3 mmol). The mixture was stirred for 3 hours and then acidified with 1N hydrochloric acid. Product was extracted with ethyl acetate (3×150 mL) and the combined extracts were washed with brine, dried (MgSO$_4$) and concentrated. The residue was dissolved in methanol (500 mL) and then a saturated aqueous solution of Oxone® (200 mL) was added in one portion. The mixture was stirred for 2 hours and then concentrated under vacuum. Product was extracted from the residue with ethyl acetate (3×150 mL). The combined extracts were washed with brine, dried (MgSO$_4$) and concentrated. Crude product was crystallized from ethyl acetate/hexane to provide N-[1R-cyanomethylcarbamoyl-2-(2-difluoromethoxybenzylsulfonyl)ethyl]morpholine-4-carboxamide (5.45 g) as a white crystalline solid. Mass Spectrum: (M+H$^+$) 461; (M−H$^+$) 459. $^1$H-NMR: (DMSO, δ) 8.69 (t, J=5.4 Hz, 1H), 7.54–7.09 (m, 4H), 7.14 (t, J$_{H,F}$=74 Hz, 1H), 4.73 (m, 1H), 4.56 (s, 2H), 4.13 (s, 2H), 3.68–3.25 (m, 10H).

Example 10

Morpholine-4-carboxylic Acid {(R)-1-(4-Cyano-1-methyl-piperidin-4-ylcarbamoyl)-2-[2-(1,1-difluoro-methoxy)-phenylmethanesulfonyl]-ethyl}-amide (Compound 121)

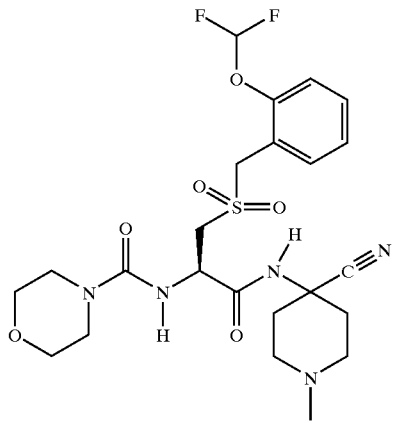

A solution of (R)-3-[2-(1,1-difluoro-methoxy)-phenylmethanesulfonyl]-2-[(1-morpholin-4-ylmethanoyl) amino]propionic acid (200 mg, 0.473 mmol), provided as in Reference 1, in $CH_2Cl_2$ (3 mL) was combined with HATU (270 mg, 0.71 mmol), HOAt (64.3 mg, 0.473 mmol), 4-amino-1-methyl-piperidine-4-carbonitrile (98 mg, 0.71 mmol), N-methylmorpholine (0.156 mL, 1.42 mmol) and them DMF (3 mL) to obtain a homogenous solution. The mixture was stirred at room temperature for 16 hours, diluted with ethyl acetate (150 mL), washed with saturated aqueous $NaHCO_3$ and then brine, dried ($MgSO_4$) and concentrated. The product was purified from the residue by flash chromatography to provide morpholine-4-carboxylic acid {(R)-1-(4-cyano-1-methyl-piperidin4-ylcarbamoyl)-2-[2-(1, 1-difluoro-methoxy-phenylmethanesulfonyl]-ethyl}-amide. $^1$H NMR: (DMSO) 8.62 (s, 1H), 7.51–7.23 (m, 4H), 7.13 (t, $J_{H,F}$=74 Hz, 1H), 7.06 (d, J=8.6 Hz, 1H), 4.70 (m, 1H), 4.57 (s, 2H), 3.57–3.25 (m, 10 H), 2.62–1.82 (m, 1H).

The following compounds of Formula I are provided by the methods described in this Application:

N-[1R-cyanomethylcarbamoyl-2-(3,5-dimethylisoxazol-4-ylmethylsulfonyl)ethyl]-benzamide (Compound 105); $^1$H NMR: (DMSO) 9.02 (d, J=8.4 Hz, 1H), 8.83 (t, J=5.6 Hz, 1H), 7.89 (m, 2H), 7.60–7.46 (m, 3H), 5.10 (m, 2H), 4.51 (d, J=14.5 Hz, 1H), 4.41 (d, J=14.5 Hz, 1H), 4.15 (m, 2H), 3.89 (dd, J=3.4 Hz, J=14.5 Hz, 1H), 3.66 (dd, J=9.5 Hz, J=14.5 Hz, 1H), 2.37 (s, 3H), 2.18 (s, 3H). MS: ($M^+$+1) 430;

N-[2-(5-chlorothien-2-ylmethylsulfonyl)-1R-cyanomethylcarbomoylethyl]benzamide (Compound 106); $^1$H NMR: (DMSO) 900 (d, J=8.2 Hz, 1H), 8.80 (t, J=5.6 Hz, 1H), 7.88 (m, 2H), 7.60–7.46 (m, 3H), 7.09 (d, J=3.7 Hz, 1H), 7.04 (d, J=3.7 Hz, 1H), 5.03 (m, 1H), 4.87 (d, J=14.7 Hz, 1H), 4.80 (d, J=14.7 Hz, 1H), 4.13 (m, 2H), 3.84 (dd, J=3.2 Hz, J=14.3 Hz, 1H), 3.59 (dd, J=9.5 Hz, J=14.5 Hz, 1H). MS: ($M^+$+1) 426;

N-[1R-cyanomethylcarbamoyl-2-(2-fluoro-3-methylbenzylsulfonyl)ethyl]benzamide (Compound 107); Mass Spectrum: (M+H$^+$) 418; (M−H$^+$) 416; $^1$H-NMR: (DMSO, δ) 8.99 (d, J=7.9 Hz, 1H), 8.82 (t, J=5.7 Hz, 1H), 7.87 (d, J=8.2 Hz, 2H), 7.60–7.45 (m, 3H), 7.34–7.25 (m, 2H), 7.12 (t, J=7.5 Hz, 1H), 5.07 (m, 1H), 4.61 (s, 2H), 4.14 (m, 2H), 3.86 (dd, J=3.2 Hz, J=14.4 Hz, 1H), 3.66 (dd, J=9.7 Hz, J=14.4 Hz, 1H), 2.23 (s, 3H);

N-[1-(Cyanomethyl-carbamoyl)-2-(1-oxy-pyridin-2-ylmethanesulfonyl)-ethyl]-benzamide (Compound 108) Mass Spec: MW=402.4, (M+1)=403.0;

N-{(R)-1-(Cyanomethyl-carbamoyl)-2-[2-(1,1-difluoro-methoxy)-phenylmethane-sulfonyl]-ethyl}-1-oxy-nicotinamide (Compound 109); $^1$H NMR: (DMSO) 9.32 (d, J=8.2 Hz, 1H), 8.91 (t, J=5.6 Hz, 1H), 8.62 (s, 1H), 8.39 (d, J=6.4 Hz, 1H), 7.70 (d, J=8.2 Hz, 11), 7.58–7.44 (m, 3H), 7.32–7.24 (m, 2H), 7.14 (t, $J_{H,F}$=74 Hz, 1H), 5.05 (m, 1H), 4.62 (s, 2H), 4.16 (m, 2H), 3.83 (dd, J=3.0 Hz, J=14.5 Hz, 1H), 3.58 (dd, , J=10.00 Hz, J=14.5 Hz, 1H). MS: ($M^+$+1) 469;

N-{(R)-1-(Cyanomethyl-carbamoyl)-2-[2-(1,1-difluoro-methoxy)-phenylmethane-sulfonyl]-ethyl}-nicotinamide (Compound 110); $^1$H NMR: (DMSO) 9.21 (d, J=7.9 Hz, 1H), 9.03 (s, 1H), 8.88 (t, J=5.4 Hz, 1H), 8.73 (dd, J=1.5 Hz, J=4.7 Hz, 1H), 8.20 (m, 1H), 7.57–7.44 (m, 3H), 7.32–7.23 (m, 2H), 7.13 (t, $J_{H,F}$=74 Hz, 1H), 5.10 (m, 1H), 4.62 (s, 2H), 4.15 (m, 2H), 3.84 (dd, J=3.0 Hz, J=14.5 Hz, 1H), 3.62 (dd, J=10.0 Hz, J=14.5 Hz, 1H). MS: ($M^+$+1) 453;

N-{(R)-1-(Cyanomethyl-carbamoyl)-2-[2-(1,1-difluoro-methoxy)-phenylmethane-sulfonyl]-ethyl}-isonicotinamide (Compound 111); $^1$H NMR: (DMSO) 9.31 (d, J=8.4 Hz, 1H), 8.90 (t, J=5.4 Hz, 1H), 8.77–8.75 (m, 2H), 8.78–8.76 (m, 2H), 7.52–7.44 (m, 2H), 7.32–7.23 (m, 2H), 7.14 (t, $J_{H,F}$=74 Hz, 1H), 5.09 (m, 1H), 4.62 (s, 2H), 4.15 (m, 2H), 3.83 (dd, J=3.0 Hz, J=14.5 Hz, 1H), 3.63 (dd, J=10.0 Hz, J=14.5 Hz, 1H). MS: ($M^+$+1) 453;

N-{(R)-1-(Cyanomethyl-carbamoyl)-2-[2-(1,1-difluoro-methoxy)-phenylmethanesulfonyl]-ethyl}-1-oxy-isonicotinamide (Compound 112); $^1$H NMR: (DMSO) 9.25 (d, J=8.2 Hz, 1H), 8.90 (t, J=5.4 Hz, 1H), 8.35 (d, J=7.2 Hz, 2H), 2H), 7.82 (d, J=7.2 Hz, 2H), 7.52–7.44 (m, 2H), 7.32–7.23 (m, 2H), 7.13 (t, $J_{H,F}$=74 Hz, 1H), 5.05 (m, 1H), 4.61 (s, 2H), 4.15 (m, 2H), 3.82 (dd, J=3.0 Hz, J=14.5 Hz, 1H), 3.60 (dd, J=10.0 Hz, J=14.5 Hz, 1H). MS: ($M^+$+1) 469;

Pyridine-2-carboxylic acid {(R)-1-(cyanomethyl-carbamoyl)-2-[2-(1,1-difluoro-methoxy)-phenylmethanesulfonyl]-ethyl}-amide (Compound 113); $^1$H NMR: (DMSO) 9.34 (d, J=8.8 Hz, 1H), 8.78 (t, J=5.4 Hz, 1H), 8.68 (d, J=4.7 Hz, 1H), 8.09–7.99 (m, 2H), 7.64 (t, J=6.2 Hz, 1H), 7.49–7.43 (m, 2H), 7.30–7.22 (m, 2H), 7.10 (t, $J_{H,F}$=74 Hz, 1H), 5.13 (m, 1H), 4.58 (s, 2H), 4.12 (m, 2H), 3.93–3.77 (m, 2H). MS: ($M^+$+1) 453;

Pyrazine-2-carboxylic acid {(R)-1-(cyanomethyl-carbamoyl)-2-[2-(1,1-difluoro-methoxy)-phenylmethanesulfonyl]-ethyl}-amide (Compound 114); $^1$H NMR: (DMSO) 9.46 (d, J=8.7 Hz, 1H), 9.22 (d, J=1.5 Hz, 1H), 8.91 (d, J=2.5 Hz, 1H), 8.82–8.77 (m, 2H), 7.51–7.43 (m, 2H), 7.31–7.21 (m, 2H), 7.11 (t, $J_{H,F}$=74 Hz, 1H), 5.16 (m, 1H), 4.58 (s, 2H), 4.13 (m, 2H), 3.91–3.78 (m, 2H). MS: ($M^+$+1) 454;

N-{(R)-1-(Cyanomethyl-carbamoyl)-2-[2-(1,1-difluoro-methoxy)-phenylmethane-sulfonyl]-ethyl}-2-hydroxy-nicotinamide (Compound 115); $^1$H NMR: (DMSO) 10.38 (d, J=7.8 Hz, 1H), 8.88 (t, J=5.4 Hz, 1H), 8.32 (dd, J=1.5 Hz, J=7.2 Hz, 1H), 7.74 (m, 1H), 7.53–7.44 (m, 2H), 7.32–7.23 (m, 2H), 7.11 (t, $J_{H,F}$=74 Hz, 1H), 6.49 (t, J=6.6 Hz, 1H), 5.07 (m, 1H), 4.59 (s, 2H), 4.13 (m, 2H), 3.73 (d, J=6.4 Hz, 2H). MS: ($M^+$+1) 469;

N-{(R)-1-(Cyanomethyl-carbamoyl)-2-[2-(1,1-difluoro-methoxy)-phenylmethane-sulfonyl]-ethyl}-6-hydroxy-nicotinamide (Compound 116); $^1$H NMR: (DMSO) 12.03 (s, 1H), 8.83–8.77 (m, 2H), 8.01 (d, J=2.2 Hz, 1H), 7.84 (dd, J=2.5 Hz, J=9.4 Hz, 1H), 7.52–7.44 (m, 2H), 7.32–7.23 (m, 2H), 7.13 (t, $J_{H,F}$=74 Hz, 1H), 6.38 (d, J=9.6 Hz, 1H), 4.99

(m, 1H), 4.59 (s, 2H), 4.13 (m, 2H), 3.78 (dd, J=3.0 Hz, J=14.5 Hz, 1H), 3.55 (dd, J=10.0 Hz, J=14.5 Hz, 1H). MS: (M$^+$+1) 469;

2-Amino-N-{(R)-1-(cyanomethyl-carbamoyl)-2-[2-(1,1-difluoro-methoxy)-phenylmethane-sulfonyl]-ethyl}-nicotinamide (Compound 117); $^1$H NMR: (DMSO) 8.91 (d, J=7.9 Hz, 1H), 8.82 (t, J=5.4 Hz, 1H), 8.10 (d, J=3.7 Hz, 1H), 7.94 (d, J=7.7 Hz, 1H), 7.52–7.44 (m, 2H), 7.32–7.23 (m, 2H), 7.13 (t, $J_{H,F}$=74 Hz, 1H), 7.05 (s, 2H), 6.61 (dd, J=4.7 Hz, J=7.4 Hz, 1H), 5.03 (m, 1H), 4.60 (s, 2H), 4.13 (m, 2H), 3.80 (dd, J=3.0 Hz, J=14.5 Hz, 1H), 3.62 (dd, J=10.0 Hz, J=14.5 Hz, 1H). MS: (M$^+$+1) 468;

6-Amino-N-{(R)-1-(cyanomethyl-carbamoyl)-2-[2-(1,1-difluoro-methoxy)-phenylmethanesulfonyl]-ethyl}-nicotinamide (Compound 118); $^1$H NMR: (DMSO) 8.76 (t, J=5.4 Hz, 1H), 8.66 (d, J=8.4 Hz, 1H), 8.48 (s, 1H), 7.81 (d, J=8.5 Hz, 1H), 7.52–7.44 (m, 2H), 7.32–7.23 (m, 2H), 7.12 (t, $J_{H,F}$=74 Hz, 1H), 6.56 (s, 2H), 6.43 (d, J=8.7 Hz, 1H), 5.02 (m, 1H), 4.58 (s, 2H), 4.12 (m, 2H), 3.77 (dd, J=3.0 Hz, J=14.5 Hz, 1H), 3.61 (dd, J=10.0 Hz, J=14.5 Hz, 1H). MS: (M$^+$+1) 468;

3-Hydroxy-pyridine-2-carboxylic acid {(R)-1-(cyanomethyl-carbamoyl)-2-[2-(1,1-difluoro-methoxy)-phenylmethanesulfonyl]-ethyl}-amide (Compound 119); $^1$H NMR: NMR: (DMSO) 12.04 (s, 1H), 9.64 (d, J=9.2 Hz, 1H), 8.84 (t, J=5.4 Hz, 1H), 8.20 (d, J=4.5 Hz, 1H), 7.57 (dd, J=4.5 Hz, J=8.7 Hz, 1H), 7.52–7.44 (m, 3H), 7.31–7.22 (m, 2H), 7.11 (t, $J_{H,F}$=74 Hz, 1H), 5.15 (m, 1H), 4.60 (s, 2H), 4.14 (m, 2H), 3.94–3.81 (m, 2H). MS: (M$^+$+1) 469;

Morpholine-4-carboxylic acid {(R)-1-(4-cyano-tetrahydro-pyran-4-ylcarbamoyl)-2-[2-(1,1-difluoro-methoxy)-phenylmethanesulfonyl]-ethyl}amide (Compound 120); $^1$H NMR: (DMSO) 8.75 (s, 1H), 7.51–7.44 (m, 2H), 7.32–7.23 (m, 2H), 7.13 (t, $J_{H,F}$=74 Hz, 1H), 7.04 (d, J=8.4 Hz, 1H), 4.72 (m, 1H), 4.57 (s, 2H), 3.78 (m, 2H), 3.60–3.25 (m, 12H), 2.24–2.10 (m, 2H), 1.98–1.84 (m, 2H). MS: (M$^+$+1) 531;

(R)-N-Cyanomethyl-3-[2-(1,1-difluoro-methoxy)-phenylmethanesulfonyl]-2-(3-pyridin-3-yl-ureido)-propionamide (Compound 122); $^1$H NMR: (DMSO) 9.08 (s, 1H), 8.90 (t, J=5.4 Hz, 1H), 8.55 (d, J=2.5 Hz, 1H), 8.14 (dd, J=1.2 Hz, J=4.7 Hz, 1H), 7.90 (m, 1H), 7.52–7.44 (m, 2H), 7.32–7.23 (m, 3H), 7.14 (t, $J_{H,F}$=74 Hz, 1H), 6.84 (d, J=8.9 Hz, 1H), 4.84 (m, 1H), 4.61 (s, 2H), 4.15 (m, 2H), 3.70 (dd, J=4.2 Hz, J=14.5 Hz, 1H), 3.60 (dd, J=8.4 Hz, J=14.5 Hz, 1H). MS: (M$^+$+1) 468;

(R)-N-Cyanomethyl-3-[2-(1,1-difluoro-methoxy)-phenylmethanesulfonyl]-2-(3-pyridin-4-yl-ureido)-propionamide (Compound 123); $^1$H NMR: (DMSO) 9.34 (s, 1H), 8.92 (t, J=5.4 Hz, 1H), 8.31 (d, J=5.9 Hz, 2H), 7.52–7.37 (m, 4H), 7.32–7.23 (m, 2H), 7.14 (t, $J_{H,F}$=74 Hz, 1H), 6.92 (d, J=8.4 Hz, 1H), 4.84 (m, 1H), 4.61 (s, 2H), 4.15 (m, 2H), 3.71 (dd, J=4.2 Hz, J=14.5 Hz, 1H), 3.61 (dd, J=8.4 Hz, J=14.5 Hz, 1H). MS: (M$^+$+1) 468;

(R)-N-Cyanomethyl-3-[2-(1.1-difluoro-methoxy)-phenylmethanesulfonyl]-2-(3-isopropyl-ureido)-propionamide (Compound 124); $^1$H NMR: (DMSO) 8.76 (t, J=5.4 Hz, 1H), 7.52–7.44 (m, 2H), 7.32–7.23 (m, 2H), 7.13 (t, $J_{H,F}$=74 Hz, 1H), 6.31 (d, J=8.7 Hz, 1H), 6.15 (d, J=7.7 Hz, 1H), 4.71 (m, 1H), 4.55 (s, 2H), 4.12 (m, 2H), 3.75–3.40 (m, 3H), 1.03 (d, J=6.4 Hz, 6H). MS: (M$^+$+1) 433;

(R)-N-Cyanomethyl-3-[2-(1,1-difluoro-methoxy)-phenylmethanesulfonyl]-2-(3,3-dimethyl-ureido)-propionamide (Compound 125); $^1$H NMR: (DMSO) 8.65 (t, J=5.4 Hz, 1H), 7.52–7.44 (m, 2H), 7.32–7.23 (m, 2H), 7.13 (t, $J_{H,F}$=74 Hz, 1H), 6.84 (d, J=7.0 Hz, 1H), 4.71 (m, 1H), 4.55 (s, 2H), 4.11 (m, 2H), 3.68–3.51 (m, 2H), 2.82 (s, 6H). MS: (M$^+$+1) 419;

(R)-2-Acetylamino-N-cyanomethyl-3-phenylmethanesulfonyl-propionamide (Compound 126);

N-[(R)-1-(Cyanomethyl-carbamoyl)-2-phenylmethanesulfonyl-ethyl]-2-methoxy-benzamide (Compound 127);

N-[(S)-1-(Cyanomethyl-carbamoyl)-3-phenylmethanesulfonyl-propyl]-benzamide (Compound 128); $^1$H NMR: (DMSO) 8.7 (m, 2H), 7.91 (d, J=7 Hz, 2H), 7.5, (m, 3H), 7.35 (m, 5H), 4.56 (m, 1H), 4.51 (s, 2H), 4.15 (d, J=6 Hz, 2H), 3.1 (m, 2H), 2.2 (m, 2H). MS: (m/e)=400.2;

Morpholine-4-carboxylic acid {(R)-1-[(1,1-dicyano-methyl)-carbamoyl]-2-phenyl-methanesulfonyl-ethyl}-amide (Compound 129);

2-(2-Benzenesulfonyl-ethyl)-N-benzyl-N'-cyanomethyl-malonamide (Compound 130); $^1$H NMR: (DMSO) 8.57 (t, J=6 Hz, 1H), 8.43 (t, J=6 Hz, 1H), 7.86 (d, J=7 Hz, 2H), 7.79 (t, J=5 Hz, 1H), 7.68 (t, J=8 Hz, 1H), 7.15 (m, 5H), 4.26 (d, J=6 Hz, 2H), 4.13 (d, J=6 Hz, 2H), 3.35 (m, 1H), 3.19 (m, 2H), 2.00 (m, 2H). MS: (M/e)=400.04;

{(R)-1-(Cyanomethyl-carbamoyl)-2-[2-(1,1-difluoro-methoxy)-phenylmethane-sulfonyl]-ethyl}-carbamic acid methyl ester (Compound 131); $^1$H NMR: (DMSO) 8.87 (t, J=5.4 Hz, 1H), 7.75 (d, J=8.6 Hz, 1H), 7.52–7.44 (m, 2H), 7.32–7.23 (m, 2H), 7.14 (t, $J_{H,F}$=74 Hz, 1H), 4.62 (m, 1H), 4.57 (s, 2H), 4.12 (m, 2H), 3.66 (dd, J=3.2 Hz, J=14.5 Hz, 1H), 3.57 (s, 3H), 3.42 (dd, J=9.4 Hz, J=14.5 Hz, 1H). MS: (M$^+$+1) 406;

{(R)-1-(Cyanomethyl-carbamoyl)-2-[2-(1,1-difluoro-methoxy)-phenylmethane-sulfonyl]-ethyl}-carbamic acid allyl ester (Compound 132); $^1$H NMR: (DMSO) 8.87 (t, J=5.4 Hz, 1H), 7.84 (d, J=8.6 Hz, 1H), 7.52–7.44 (m, 2H), 7.32–7.23 (m, 2H), 7.14 (t, $J_{H,F}$=74 Hz, 1H), 5.90 (m, 1H), 5.31 (d, J=17 Hz, 1H), 5.18 (d, J=10.6 Hz, 1H), 4.62 (m, 1H), 4.57 (s, 2H), 4.51 (m, 2H), 4.12 (m, 2H), 3.66 (dd, J=3.2 Hz, J=14.5 Hz, 1H), 3.44 (dd, J=9.4 Hz, J=14.5 Hz, 1H). MS: (M$^+$+1) 432;

{(R)-1-(Cyanomethyl-carbamoyl)-2-[2-(1,1-difluoro-methoxy)-phenylmethane-sulfonyl]-ethyl}-carbamic acid isopropyl ester (Compound 133); $^1$H NMR: (DMSO) 8.80 (t, J=5.4 Hz, 1H), 7.60 (d, J=8.4 Hz, 1H), 7.52–7.44 (m, 2H), 7.32–7.23 (m, 2H), 7.14 (t, $J_{H,F}$=74 Hz, 1H), 4.77 (sept, J=6.4 Hz, 1H), 4.62 (m, 1H), 4.56 (s, 2H), 4.13 (m, 2H), 3.64 (dd, J=3.2 Hz, J=14.5 Hz, 1H), 3.43 (dd, J=9.4 Hz, J=14.5 Hz, 1H), 1.19 (d, J=6.4 Hz, 3H), 1.16 (d, J=6.4 Hz, 3H). MS: (M$^+$+1) 434;

{(R)-1-(Cyanomethyl-carbamoyl)-2-[2-(1,1-difluoro-methoxy)-phenylmethane-sulfonyl]-ethyl}-carbamic acid isobutyl ester (Compound 134); $^1$H NMR: (DMSO) 8.82 (t, J=5.4 Hz, 1H), 7.71 (d, J=8.7 Hz, 1H), 7.52–7.44 (m, 2H), 7.32–7.23 (m, 2H), 7.14 (t, $J_{H,F}$=74 Hz, 1H), 4.61 (m, 1H), 4.56 (s, 2H), 4.13 (m, 2H), 3.86–3.69 (m, 2H), 3.65 (dd, J=3.4 Hz, J=14.5 Hz, 1H), 3.44 (dd, J=9.6 Hz, J=14.5 Hz, 1H), 1.84 (sept, J=6.4 Hz, 1H), 0.88 (d, J=6.6 Hz, 6H). MS: (M$^+$+1) 448;

(R)-N-Cyanomethyl-2-(1-oxo-1,3-dihydro-isoindol-2-yl)-3-phenylmethanesulfonyl-propionamide (Compound 135); $^1$H NMR: (DMSO) 8.93 (t, J=5.4 Hz, 1H), 7.72 (d, J=7.7 Hz, 1H), 7.64–7.36 (m, 8H), 5.32 (m, 1H), 4.65–5.52 (m, 3H), 4.43 (d, J=17 Hz, 1H), 4.12 (m, 2H), 3.92–3.77 (m, 2H). MS: (M$^+$+1) 398;

N-{(R)-1-(Cyanomethyl-carbamoyl)-2-[2-(1,1-difluoro-methoxy)-phenylmethane-sulfonyl]-ethyl}-3,4-difluoro-benzamide (Compound 136); $^1$H NMR: (DMSO) 9.12 (d, J=8.2 Hz, 1H), 8.87 (t, J=5.4 Hz, 1H), 7.90 (m, 1H), 7.76 (m, 1H), 7.65–7.44 (m, 3H), 7.32–7.23 (m, 2H), 7.13 (t, $J_{H,F}$=74 Hz, 1H), 5.06 (m, 1H), 4.61 (s, 2H), 4.14 (m, 2H), 3.82 (dd, J=3.2 Hz, J=14.5 Hz, 1H), 3.61 (dd, J=10.0 Hz, J=14.5 Hz, 1H). MS: (M$^+$+1) 488;

N-{(R)-1-(Cyanomethyl-carbamoyl)-2-[2-(1,1-difluoro-methoxy)-phenylmethane-sulfonyl]-ethyl}-3,4-dimethoxy-benzamide (Compound 137); $^1$H NMR: (DMSO) 8.86 (d, J=8.2 Hz, 1H), 8.80 (t, J=5.4 Hz, 1H), 7.54–7.44 (m, 4H), 7.32–7.23 (m, 2H), 7.12 (t, $J_{H,F}$=74 Hz, 1H), 7.05 (d, J=8.4 Hz, 1H), 5.05 (m, 1H), 4.59 (s, 2H), 4.13 (m, 2H), 3.81 (s, 3H), 3.80 (s, 3H), 3.79 (dd, J=3.2 Hz, J=14.5 Hz, 1H), 3.64 (dd, J=10.0 Hz, J=14.5 Hz, 1H). MS: (M$^+$+1) 512;

N-{(R)-1-(Cyanomethyl-carbamoyl)-2-[2-(1,1-difluoro-methoxy)-phenylmethane-sulfonyl]-ethyl}-3-methyl-benzamide (Compound 138); $^1$H NMR: (DMSO) 8.94 (d, J=8.2 Hz, 1H), 8.80 (t, J=5.4 Hz, 1H), 7.71–7.64 (m, 2H), 7.52–7.23 (m, 6H), 7.13 (t, $J_{H,F}$=74 Hz, 1H), 5.07 (m, 1H), 4.60 (s, 2H), 4.13 (m, 2H), 3.81 (dd, J=3.2 Hz, J=14.5 Hz, 1H), 3.65 (dd, J=10.0 Hz, J=14.5 Hz, 1H), 2.37 (s, 3H). MS: (M$^+$+1) 466;

Thiophene-3-carboxylic acid {(R)-1-(cyanomethyl-carbamoyl)-2-[2-(1,1-difluoro-methoxy)-phenylmethanesulfonyl]-ethyl}-amide (Compound 139); $^1$H NMR: (DMSO) 8.86 (d, J=8.2 Hz, 1H), 8.84 (t, J=5.4 Hz, 1H), 8.18 (dd, J=1.0 Hz, J=2.7 Hz, 1H), 7.61 (dd, J=2.9 Hz, J=4.9 Hz, 1H), 7.53–7.44 (m, 3H), 7.32–7.23 (m, 2H), 7.12 (t, $J_{H,F}$=74 Hz, 1H), 5.02 (m, 1H), 4.59 (s, 2H), 4.13 (m, 2H), 3.79 (dd, J=3.2 Hz, J=14.5 Hz, 1H), 3.60 (dd, J=10.0 Hz, J=14.5 Hz, 1H). MS: (M$^+$+1) 458;

N-{(R)-1-(Cyanomethyl-carbamoyl)-2-[2-(1,1-difluoro-methoxy)-phenylmethane-sulfonyl]-ethyl}-4-fluoro-benzamide (Compound 140); $^1$H NMR: (DMSO) 9.03 (d, J=8.2 Hz, 1H), 8.84 (t, J=5.4 Hz, 1H), 7.97–7.92 (m, 2H), 7.53–7.23 (m, 6H), 7.13 (t, $J_{H,F}$=74 Hz, 1H), 5.07 (m, 1H), 4.61 (s, 2H), 4.14 (m, 2H), 3.81 (dd, J=3.2 Hz, J=14.5 Hz, 1H), 3.64 (dd, J=10.0 Hz, J=14.5 Hz, 1H). MS: (M$^+$+1) 470;

4-Methyl-pentanoic acid {(R)-1-(cyanomethyl-carbamoyl)-2-[2-(1,1-difluoro-methoxy)-phenylmethanesulfonyl]-ethyl}-amide (Compound 141); $^1$H NMR: (DMSO) 8.73 (t, J=5.4 Hz, 1H), 8.41 (d, J=8.4 Hz, 1H), 7.53–7.44 (m, 2H), 7.32–7.23 (m, 2H), 7.14 (t, $J_{H,F}$=74 Hz, 1H), 4.83 (m, 1H), 4.56 (s, 2H), 4.12 (m, 2H), 3.67 (dd, J=3.9 Hz, J=14.5 Hz, 1H), 3.39 (dd, J=9.0 Hz, J=14.5 Hz, 1H), 2.14 (t, J=7.4 Hz, 2H), 1.58–1.35 (m, 3H), 0.84 (d, J=6.4 Hz, 6H). MS: (M$^+$+1) 446;

Thiophene-2-carboxylic acid {(R)-1-(cyanomethyl-carbamoyl)-2-[2-(1,1-difluoro-methoxy)-phenylmethanesulfonyl]-ethyl}-amide (Compound 142); $^1$H NMR: (DMSO) 9.02 (d, J=8.2 Hz, 1H), 8.87 (t, J=5.4 Hz, 1H), 7.80 (m, 2H), 7.53–7.44 (m, 2H), 7.32–7.23 (m, 2H), 7.18 (dd, J=3.9 Hz, J=4.9 Hz, 1H), 7.12 (t, $J_{H,F}$=74 Hz, 1H), 5.02 (m, 1H), 4.60 (s, 2H), 4.14 (m, 2H), 3.80 (dd, J=3.2 Hz, J=14.5 Hz, 1H), 3.61 (dd, J=10.0 Hz, J=14.5 Hz, 1H). MS: (M$^+$+1) 458;

4-Bromo-N-{(R)-1-(cyanomethyl-carbamoyl)-2-[2-(1,1-difluoro-methoxy)-phenyl-methanesulfonyl]-ethyl}-benzamide (Compound 143); $^1$H NMR: (DMSO) 9.08 (d, J=8.2 Hz, 1H), 8.84 (t, J=5.4 Hz, 1H), 7.82 (d, J=8.7 Hz, 2H), 7.72 (d, J=8.7 Hz, 2H), 7.53–7.44 (m, 2H), 7.32–7.23 (m, 2H), 7.13 (t, $J_{H,F}$=74 Hz, 1H), 5.06 (m, 1H), 4.60 (s, 2H), 4.14 (m, 2H), 3.81 (dd, J=3.2 Hz, J=14.5 Hz, 1H), 3.62 (dd, J=10.0 Hz, J=14.5 Hz, 1H). MS: (M$^+$+1) 530, 532;

N-{(R)-1-(Cyanomethyl-carbamoyl)-2-[2-(1,1-difluoro-methoxy)-phenylmethane-sulfonyl]-ethyl}-4-methoxy-benzamide (Compound 144); $^1$H NMR: (DMSO) 8.83 (d, J=8.2 Hz, 1H), 8.78 (t, J=5.4 Hz, 1H), 7.86 (d, J=8.6 Hz, 2H), 7.52–7.44 (m, 2H), 7.32–7.23 (m, 2H), 7.12 (t, $J_{H,F}$=74 Hz, 1H), 7.02 (d, J=8.7 Hz, 2H), 5.05 (m, 1H), 4.59 (s, 2H), 4.13 (m, 2H), 3.81 (s, 3H), 3.79 (dd, J=3.2 Hz, J=14.5 Hz, 1H), 3.64 (dd, J=10.0 Hz, J=14.5 Hz, 1H). MS: (M$^+$+1) 482;

N-{(R)-1-(Cyanomethyl-carbamoyl)-2-[2-(1,1-difluoro-methoxy)-phenylmethane-sulfonyl]-ethyl}-4-trifluoromethoxy-benzamide (Compound 145); $^1$H NMR: (DMSO) 9.12 (d, J=8.2 Hz, 1H), 8.85 (t, J=5.4 Hz, 1H), 8.00 (d, J=8.6 Hz, 2H), 7.54–7.44 (m, 4H), 7.32–7.23 (m, 2H), 7.13 (t, $J_{H,F}$=74 Hz, 1H), 5.08 (m, 1H), 4.61 (s, 2H), 4.14 (m, 2H), 3.82 (dd, J=3.2 Hz, J=14.5 Hz, 1H), 3.63 (dd, J=10.0 Hz, J=14.5 Hz, 1H). MS: (M$^+$+1) 536;

Naphthalene-2-carboxylic acid {(R)-1-(cyanomethyl-carbamoyl)-2-[2-(1,1-difluoro-methoxy)-phenylmethanesulfonyl]-ethyl}-amide (Compound 146); $^1$H NMR: (DMSO) 9.18 (d, J=8.2 Hz, 1H), 8.87 (t, J=5.4 Hz, 1H), 8.49 (s, 1H), 8.05–7.94 (m, 4H), 7.66–7.57 (m, 2H), 7.53–7.44 (m, 2H), 7.32–7.23 (m, 2H), 7.13 (t, $J_{H,F}$=74 Hz, 1H), 5.14 (m, 1H), 4.63 (s, 2H), 4.16 (m, 2H), 3.85 (dd, J=3.2 Hz, J=14.5 Hz, 1H), 3.69 (dd, J=10.0 Hz, J=14.5 Hz, 1H). MS: (M$^+$+1) 502;

(E)-N-{(R)-1-(Cyanomethyl-carbamoyl)-2-[2-(1,1-difluoro-methoxy)-phenylmethane-sulfonyl]-ethyl}-3-phenyl-acrylamide (Compound 147); $^1$H NMR: (DMSO) 8.88 (t, J=5.4 Hz, 1H), 8.78 (d, J=8.2 Hz, 1H), 7.61–7.38 (m, 8H), 7.32–7.23 (m, 2H), 7.14 (t, $J_{H,F}$=74 Hz, 1H), 6.66 (d, J=16 Hz, 1H), 4.99 (m, 1H), 4.60 (s, 2H), 4.14 (m, 2H), 3.75 (dd, J=3.2 Hz, J=14.5 Hz, 1H), 3.49 (dd, J=10.0 Hz, J=14.5 Hz, 1H). MS: (M$^+$+1) 478;

5-Methyl-thiophene-2-carboxylic acid {(R)-1-(cyanomethyl-carbamoyl)-2-[2-(1,1-difluoro-methoxy)-phenylmethanesulfonyl]-ethyl}-amide (Compound 148); $^1$H NMR: (DMSO) 8.87 (d, J=8.2 Hz, 1H), 8.84 (t, J=5.4 Hz, 1H), 7.59 (d, J=3.7 Hz, 1H), 7.52–7.44 (m, 2H), 7.32–7.23 (m, 2H), 7.12 (t, $J_{H,F}$=74 Hz, 1H), 6.86 (m, 1H), 4.99 (m, 1H), 4.58 (s, 2H), 4.13 (m, 2H), 3.78 (dd, J=3.4 Hz, J=14.5 Hz, 1H), 3.63 (dd, J=10.0 Hz, J=14.5 Hz, 1H), 2.47 (s, 3H). MS: (M$^+$+1) 472;

Biphenyl-4-carboxylic acid {(R)-1-(cyanomethyl-carbamoyl)-2-[2-(1,1-difluoro-methoxy)-phenylmethanesulfonyl]-ethyl}-amide (Compound 149); $^1$H NMR: (DMSO) 9.06 (d, J=8.4 Hz, 1H), 8.86 (t, J=5.4 Hz, 1H), 7.98 (d, J=8.4 Hz, 2H), 7.81 (d, J=8.4 Hz, 2H), 7.74 (d, J=7.4 Hz, 2H), 7.53–7.38 (m, 5H), 7.32–7.23 (m, 2H), 7.14 (t, $J_{H,F}$=74 Hz, 1H), 5.11 (m, 1H), 4.61 (s, 2H), 4.15 (m, 2H), 3.83 (dd, J=3.2 Hz, J=14.5 Hz, 1H), 3.68 (dd, J=10.0 Hz, J=14.5 Hz, 1H). MS: (M$^+$+1) 528;

1H-Indole-5-carboxylic acid {(R)-1-(cyanomethyl-carbamoyl)-2-[2-(1,1-difluoro-methoxy)-phenylmethanesulfonyl]-ethyl}-amide; (Compound 150); $^1$H NMR: (DMSO) 11.36 (s, 1H), 8.83 (d, J=8.2 Hz, 1H), 8.78 (t, J=5.4 Hz, 1H), 8.18 (s, 1H), 7.66 (dd, J=1.7 Hz, J=8.4 Hz, 1H), 7.53–7.42 (m, 4H), 7.32–7.23 (m, 2H), 7.12 (t, $J_{H,F}$=74 Hz, 1H), 6.55 (m, 1H), 5.10 (m, 1H), 4.60 (s, 2H), 4.14 (m, 2H), 3.80 (dd, J=3.5 Hz, J=14.5 Hz, 1H), 3.70 (dd, J=9.2 Hz, J=14.5 Hz, 1H). MS: (M$^+$+1) 491;

Benzo[1,3]dioxole-5-carboxylic acid {(R)-1-(cyanomethyl-carbamoyl)-2-[2-(1,1-difluoro-methoxy)-phenylmethanesulfonyl]-ethyl}-amide (Compound 151); $^1$H NMR: (DMSO) 8.83 (d, J=8.2 Hz, 1H), 8.79 (t, J=5.4 Hz, 1H), 7.52–7.39 (m, 4H), 7.32–7.23 (m, 2H), 7.13 (t, $J_{H,F}$=74 Hz, 1H), 7.02 (d, J=8.2 Hz, 1H), 6.10 (s, 2H), 5.03 (m, 1H), 4.59 (s, 2H), 4.13 (m, 2H), 3.78 (dd, J=3.2 Hz, J=14.5 Hz, 1H), 3.62 (dd, J=10.0 Hz, J=14.5 Hz, 1H). MS: (M$^+$+1) 496;

Benzo[b]thiophene-2-carboxylic acid {(R)-1-(cyanomethyl-carbamoyl)-2-[2-(1,1-difluoro-methoxy)- phenylmethanesulfonyl]-ethyl}-amide (Compound 152); ¹H NMR: (DMSO) 9.30 (d, J=8.2 Hz, 1H), 8.92 (t, J=5.4 Hz, 1H), 8.12 (s, 1H), 8.06–7.97 (m, 2H), 7.53–7.40 (m, 4H), 7.32–7.23 (m, 2H), 7.13 (t, $J_{H,F}$=74 Hz, 1H), 5.07 (m, 1H), 4.62 (s, 2H), 4.16 (m, 2H), 3.83 (dd, J=3.2 Hz, J=14.5 Hz, 1H), 3.63 (dd, J=10.0 Hz, J=14.5 Hz, 1H). MS: (M⁺+1) 508;

N-{(R)-1-(Cyanomethyl-carbamoyl)-2-[2-(1,1-difluoro-methoxy)-phenylmethane-sulfonyl]-ethyl}-3-phenoxy-benzamide (Compound 153); ¹H NMR: (DMSO) 9.04 (d, J=8.2 Hz, 1H), 8.82 (t, J=5.4 Hz, 1H), 7.66 (d, J=8.2 Hz, 1H), 7.55–7.37 (m, 6H), 7.32–7.14 (m, 4H), 7.12 (t, $J_{H,F}$=74 Hz, 1H), 7.03 (d, J=7.7 Hz, 2H), 5.05 (m, 1H), 4.59 (s, 2H), 4.13 (m, 2H), 3.79 (dd, J=3.2 Hz, J=14.5 Hz, 1H), 3.63 (dd, J=10.0 Hz, J=14.5 Hz, 1H). MS: (M⁺+1) 544;

Quinoline-3-carboxylic acid {(R)-1-(cyanomethyl-carbamoyl)-2-[2-(1,1-difluoro-methoxy)-phenylmethanesulfonyl]-ethyl}-amide (Compound 154); ¹H NMR: (DMSO) 9.40 (d, J=8.2 Hz, 1H), 9.30 (d, J=2.2 Hz, 1H), 8.95 (t, J=5.4 Hz, 1H), 8.84 (d, J=2.0 Hz, 1H), 8.12 (dd, J=3.7 Hz, J=7.9 Hz, 2H), 7.89 (t, J=7.4 Hz, 1H), 7.71 (t, J=7.7 Hz, 1H), 7.54–7.44 (m, 2H), 7.32–7.23 (m, 2H), 7.14 (t, $J_{H,F}$=74 Hz, 1H), 5.17 (m, 1H), 4.65 (s, 2H), 4.17 (m, 2H), 3.88 (dd, J=3.0 Hz, J=14.5 Hz, 1H), 3.63 (dd, J=10.0 Hz, J=14.5 Hz, 1H). MS: (M⁺+1) 503;

N-{(R)-1-(Cyanomethyl-carbamoyl)-2-[2-(1,1-difluoro-methoxy)-phenylmethane-sulfonyl]-ethyl}-3-(1-phenyl-methanoyl)-benzamide (Compound 155); ¹H NMR: (DMSO) 9.22 (d, J=8.2 Hz, 1H), 8.87 (t, J=5.4 Hz, 1H), 8.27 (s, 1H), 8.17 (d, J=7.9 Hz, 1H), 7.90 (d, J=7.9 Hz, 1H), 7.78–7.66 (m, 4H), 7.59–7.44 (m, 4H), 7.32–7.23 (m, 2H), 7.13 (t, $J_{H,F}$=74 Hz, 1H), 5.09 (m, 1H), 4.61 (s, 2H), 4.14 (m, 2H), 3.82 (dd, J=3.2 Hz, J=14.5 Hz, 1H), 3.65 (dd, J=10.0 Hz, J=14.5 Hz, 1H). MS: (M⁺+1) 556;

4-Chloro-N-{(R)-1-(cyanomethyl-carbamoyl)-2-[2-(1,1-difluoro-methoxy)-phenyl-methanesulfonyl]-ethyl}-benzamide (Compound 156); ¹H NMR: (DMSO) 9.08 (d, J=8.2 Hz, 1H), 8.84 (t, J=5.4 Hz, 1H), 7.89 (d, J=8.4 Hz, 2H), 7.58 (d, J=8.4 Hz, 2H), 7.52–7.44 (m, 2H), 7.32–7.23 (m, 2H), 7.13 (t, $J_{H,F}$=74 Hz, 1H), 5.07 (m, 1H), 4.06 (s, 2H), 4.14 (m, 2H), 3.81 (dd, J=3.2 Hz, J=14.5 Hz, 1H), 3.63 (dd, J=10.0 Hz, J=14.5 Hz, 1H). MS: (M⁺+1) 486, 488;

N-{(R)-1-(Cyanomethyl-carbamoyl)-2-[2-(1,1-difluoro-methoxy)-phenylmethane-sulfonyl]-ethyl}-3-fluoro-4-methoxy-benzamide (Compound 157); ¹H NMR: (DMSO) 8.94 (d, J=8.2 Hz, 1H), 8.83 (t, J=5.4 Hz, 1H), 7.75–7.68 (m, 2H), 7.52–7.44 (m, 2H), 7.32–7.23 (m, 3H), 7.13 (t, $J_{H,F}$=74 Hz, 1H), 5.05 (m, 1H), 4.59 (s, 2H), 4.13 (m, 2H), 3.90 (s, 3H), 3.80 (dd, J=3.2 Hz, J=14.5 Hz, 1H), 3.62 (dd, J=10.0 Hz, J=14.5 Hz, 1H). MS: (M⁺+1) 500;

3-Bromo-thiophene-2-carboxylic acid {(R)-1-(cyanomethyl-carbamoyl)-2-[2-(1,1-difluoro-methoxy)-phenylmethanesulfonyl]-ethyl}-amide (Compound 158); ¹H NMR: (DMSO) 8.89 (t, J=5.4 Hz, 1H), 8.59 (d, J=8.2 Hz, 1H), 7.86 (d, J=5.2 Hz, 1H), 7.53–7.44 (m, 2H), 7.32–7.23 (m, 2H), 7.21 (d, J=5.2 Hz, 1H), 7.13 (t, $J_{H,F}$=74 Hz, 1H), 5.04 (m, 1H), 4.61 (s, 2H), 4.16 (m, 2H), 3.79 (dd, J=3.5 Hz, J=14.5 Hz, 1H), 3.70 (dd, J=9.0 Hz, J=14.5 Hz, 1H). MS: (M⁺+1) 536, 538;

3-Chloro-benzo[b]thiophene-2-carboxylic acid {(R)-1-(cyanomethyl-carbamoyl)-2-[2-(1,1-difluoro-methoxy)-phenylmethanesulfonyl]-ethyl}-amide (Compound 159); ¹H NMR: (DMSO) 8.96 (t, J=5.4 Hz, 1H), 8.82 (d, J=8.2 Hz, 1H), 8.17–8.10 (m, 1H), 7.96–7.89 (m, 1H), 7.64–7.56 (m, 2H), 7.54–7.44 (m, 2H), 7.32–7.23 (m, 2H), 7.14 (t, $J_{H,F}$=74 Hz, 1H), 5.14 (m, 1H), 4.64 (s, 2H), 4.19 (m, 2H), 3.88–3.373 (m, 2H). MS: (M⁺+1) 542, 544;

3-Chloro-thiophene-2-carboxylic acid {(R)-1-(cyanomethyl-carbamoyl)-2-[2-(1,1-difluoro-methoxy)-phenylmethanesulfonyl]-ethyl}-amide (Compound 160); ¹H NMR: (DMSO) 8.88 (t, J=5.4 Hz, 1H), 8.49 (d, J=8.2 Hz, 1H), 7.90 (d, J=5.4 Hz, 1H), 7.52–7.44 (m, 2H), 7.32–7.23 (m, 2H), 7.18 (d, J=5.4 Hz, 1H), 7.13 (t, $J_{H,F}$=74 Hz, 1H), 5.05 (m, 1H), 4.61 (s, 2H), 4.16 (m, 2H), 3.82–3.70 (m, 2H). MS: (M⁺+1) 492, 494;

N-{(R)-(Cyanomethyl-carbamoyl)-2-[2-(1,1-difluoro-methoxy)-phenylmethanesulfonyl]-ethyl}-trifluoromethyl-benzamide (Compound 161); ¹H NMR: (DMSO) 9.24 (d, J=8.2 Hz, 1H), 8.88 (t, J=5.4 Hz, 1H), 8.07 (d, J=8.2 Hz, 2H), 7.90 (d, J=8.4 Hz, 2H), 7.53–7.44 (m, 2H), 7.32–7.23 (m, 2H), 7.13 (t, $J_{H,F}$=74 Hz, 1H), 5.11 (m, 1H), 4.62 (s, 2H), 4.15 (m, 2H), 3.83 (dd, J=3.2 Hz, J=14.5 Hz, 1H), 3.64 (dd, J=10.0 Hz, J=14.5 Hz, 1H). MS: (M⁺+1) 520;

Quinoline-2-carboxylic acid {(R)-1-(cyanomethyl-carbamoyl)-2-[2-(1,1-difluoro-methoxy)-phenylmethanesulfonyl]-ethyl}-amide (Compound 162); ¹H NMR: (DMSO) 9.51 (d, J=8.2 Hz, 1H), 8.85 (t, J=5.4 Hz, 1H), 8.60 (d, J=8.4 Hz, 1H), 8.20 (d, J=8.4 Hz, 1H), 8.16–8.08 (m, 2H), 7.89 (t, J=7.0 Hz, 1H), 7.74 (t, J=7.0 Hz, 1H), 7.53–7.44 (m, 2H), 7.32–7.23 (m, 2H), 7.11 (t, $J_{H,F}$=74 Hz, 1H), 5.21 (m, 1H), 4.62 (s, 2H), 4.14 (m, 2H), 4.00–3.82 (m, 2H). MS: (M⁺+1) 503;

(R)-2-Benzenesulfonylamino-N-cyanomethyl-3-[2-(1,1-difluoro-methoxy)-phenylmethanesulfonyl]-propionamide (Compound 163); ¹H NMR: (DMSO) 9.02 (t, J=5.4 Hz, 1H), 8.57 (d, J=9.2 Hz, 1H), 8.77 (m, 2H), 7.65–7.23 (m, 7H), 7.11 (t, $J_{H,F}$=74 Hz, 1H), 4.52 (d, J=13.6 Hz, 1H), 4.44 (d, J=13.6 Hz, 1H), 4.38 (m, 1H), 4.01–3.85 (m, 2H), 3.47 (dd, J=5.9 Hz, J=14.5 Hz, 1H), 3.22 (dd, J=7.2 Hz, J=14.5 Hz, 1H). MS: (M⁺+1) 488;

(R)-N-Cyanomethyl-3-[2-(1,1-difluoro-methoxy)-phenylmethanesulfonyl]-2-(naphthalene-2-sulfonylamino)-propionamide (Compound 164); ¹H NMR: (DMSO) 9.05 (t, J=5.4 Hz, 1H), 8.67 (d, J=9.0 Hz, 1H), 8.43 (s, 1H), 8.14–8.01 (m, 3H), 7.78 (dd, J=2.0 Hz, J=8.6 Hz, 1H), 7.74–6.63 (m, 2H), 7.46–7.39 (m, 1H), 7.27–7.14 (m, 3H), 7.07 (t, $J_{H,F}$=74 Hz, 1H), 4.52–4.37 (m, 3H), 3.86 (m, 2H), 3.49 (dd, J=5.7 Hz, J=14.5 Hz, 1H), 3.26 (dd, J=7.2 Hz, J=14.5 Hz, 1H). MS: (M⁺+1) 538;

(R)-N-Cyanomethyl-3-[2-(1,1-difluoro-methoxy)-phenylmethanesulfonyl]-2-(thiophene-2-sulfonylamino)-propionamide (Compound 165); ¹H NMR: (DMSO) 9.06 (t, J=5.4 Hz, 1H), 8.78 (d, J=9.1 Hz, 1H), 7.91 (d, J=4.9 Hz, 1H), 7.57 (d, J=3 Hz, 1H), 7.51–7.40 (m, 2H), 7.32–7.23 (m, 2H), 7.12 (m, 1H), 7.11 (t, $J_{H,F}$=74 Hz, 1H), 4.54 (d, J=13.8 Hz, 1H), 4.47 (d, J=13.8 Hz, 1H), 4.42 (m, 1H), 4.10–3.95 (m, 2H), 3.50 (dd, J=5.9 Hz, J=14.5 Hz, 1H), 3.24 (dd, J=7.2 Hz, J=14.5 Hz, 1H). MS: (M⁺+1) 494;

Cyclopentanecarboxylic acid {(R)-1-(cyanomethyl-carbamoyl)-2-[2-(1,1-difluoro-methoxy)-phenylmethanesulfonyl]-ethyl}-amide (Compound 166); ¹H NMR: (DMSO) 8.69 (t, J=5.4 Hz, 1H), 8.34 (d, J=8.4 Hz, 1H), 7.52–7.44 (m, 2H), 7.33–7.23 (m, 2H), 7.14 (t, $J_{H,F}$=74 Hz, 1H), 4.84 (m, 1H), 4.56 (s, 2H), 4.12 (m, 2H), 3.67 (dd, J=3.9 Hz, J=14.5 Hz, 1H), 3.41 (dd, J=9.2 Hz, J=14.5 Hz, 1H), 2.62 (m, 1H), 1.76–1.45 (m, 8H). MS: (M⁺+1) 444;

Morpholine-4-carboxylic acid {(R)-1-[(1-cyano-1-thiophen-2-yl-methyl)-carbamoyl]-2-phenylmethanesulfonyl-ethyl}-amide (Compound 172); ¹H-NMR (CdCl3) delta (ppm): 8.17 (m, 1H), 7.40 (m, 5H), 7.35 (t, J=1.0 Hz, 1H), 7.28, 7.26 (t, J=1.0 Hz, 1H), 7.02–7.00 (d, J=3.5 Hz, 1H), 6.17 (d, J=7.9 Hz, 1H), 5.98 (m, 1H), 4.90 (m, 1H), 4.50 (dd, J=8.9, 9.1 Hz, 1H), 4.35

(dd, J=6.2, 5.7 Hz, 1H), 3.65 (m, 5H), 3.20–3.40 (m, 5H); MS M+=476.8 M−=474.8; and Morpholine-4-carboxylic acid {(R)-1-[(1-cyano-1-furan-2-yl-methyl)-carbamoyl]-2-phenylmethanesulfonyl-ethyl}-amide (Compound 174) $^1$H NMR (DMSO, 300 MHz) 9.9 and 9.36 pair of diastereomers (pair of doublets, J=3.5 Hz, 1H), 7.37 (m, 5H), 7.08 (m, 1H), 7.36 (t, 3.5 Hz, 1H), 6.16 (d, 7.4 Hz, 1H), 6.11 (m, 1H), 4.72, (m, 1H), 4.49 (d, 5.9 Hz, 2H), 3.2–3.7 (m, 10H), 2.26 (s, 3H); MS (M−1)=472.8

Example 11

Cathepsin S Assay

Solutions of test compounds in varying concentrations were prepared in 10 μL of dimethyl sulfoxide (DMSO) and then diluted into assay buffer (40 μL, comprising: MES, 50 mM (pH 6.5); EDTA, 2.5 mM; and NaCl, 100 mM). Human cathepsin S (0.158 pMoles in 25 μL of assay buffer) was added to the dilutions. The assay solutions were mixed for 5–10 seconds on a shaker plate, covered and incubated for 30 minutes at ambient temperature. Z-Val-Val-Arg-AMC (9 nMoles in 25 μL of assay buffer) was added to the assay solutions and hydrolysis was followed spectrophotometrically at (λ460 nm) for 5 minutes. Apparent inhibition constants ($K_i$) were calculated from the enzyme progress curves using standard mathematical models.

Example 12

Cathepsin B Assay

Solutions of test compounds in varying concentrations were prepared in 10 μL of dimethyl sulfoxide (DMSO) and then diluted into assay buffer (40 μL, comprising: N,N-bis (2-hydroxyethyl)-2-aminoethanesulfonic acid (BES), 50 mM (pH 6); polyoxyethylenesorbitan monolaurate, 0.05%; and dithiothreitol (DTr), 2.5 mM). Human cathepsin B (0.025 pMoles in 25 μL of assay buffer) was added to the dilutions. The assay solutions were mixed for 5–10 seconds on a shaker plate, covered and incubated for 30 minutes at ambient temperature. Z-FR-AMC (20 nMoles in 25 μL of assay buffer) was added to the assay solutions and hydrolysis was followed spectrophotometrically at (λ460 nm) for 5 minutes. Apparent inhibition constants ($K_i$) were calculated from the enzyme progress curves using standard mathematical models.

Example 13

Cathepsin K Assay

Solutions of test compounds in varying concentrations were prepared in 10 μL of dimethyl sulfoxide (DMSO) and then diluted into assay buffer (40 μL, comprising: MES, 50 mM (pH 5.5); EDTA, 2.5 mM; and DTT, 2.5 mM). Human cathepsin K (0.0906 pMoles in 25 μL of assay buffer) was added to the dilutions. The assay solutions were mixed for 5–10 seconds on a shaker plate, covered and incubated for 30 minutes at ambient temperature. Z-Phe-Arg-AMC (4 nMoles in 25 μL of assay buffer) was added to the assay solutions and hydrolysis was followed spectrophotometrically at (λ460 nm) for 5 minutes. Apparent inhibition constants ($K_i$) were calculated from the enzyme progress curves using standard mathematical models.

Example 14

Cathepsin L Assay

Solutions of test compounds in varying concentrations were prepared in 10 μL of dimethyl sulfoxide (DMSO) and then diluted into assay buffer (40 μL, comprising: MES, 50 mM (pH 5.5); EDTA, 2.5 mM; and DTT, 2.5 mM). Human cathepsin L (0.05 pMoles in 25 μl of assay buffer) was added to the dilutions. The assay solutions were mixed for 5–10 seconds on a shaker plate, covered and incubated for 30 minutes at ambient temperature. Z-Phe-Arg-AMC (1 nMoles in 25 μL of assay buffer) was added to the assay solutions and hydrolysis was followed spectrophotometrically at (λ460 nm) for 5 minutes. Apparent inhibition constants ($K_i$) were calculated from the enzyme progress curves using standard mathematical models.

Compounds of the invention were tested according to the above-described assays for protease inhibition and observed to exhibit selective cathepsin S inhibitory activity. For example, the compounds of the invention were found to inhibit cathepsin S protease activity at concentrations that are least 50 fold less than those concentrations required to produce an equiactive inhibition of cathepsin K protease activity. The apparent inhibition constants ($K_i$) for compounds of the invention, against Cathepsin S, were in the range from about $10^{-10}$M to about $10^{-7}$M.

Example 15

Representative Pharmaceutical Formulations Containing a Compound of Formula I

| ORAL FORMULATION | |
|---|---|
| Compound of Formula I | 10–100 mg |
| Citric Acid Monohydrate | 105 mg |
| Sodium Hydroxide | 18 mg |
| Flavoring | |
| Water | q.s. to 100 mL |
| INTRAVENOUS FORMULATION | |
| Compound of Formula I | 0.1–10 mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |
| TABLET FORMULATION | |
| Compound of Formula I | 1% |
| Microcrystalline Cellulose | 73% |
| Stearic Acid | 25% |
| Colloidal Silica | 1%. |

We claim:
1. A compound of Formula II:

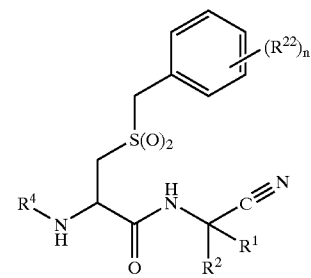

II in which:
n is 1, 2, 3, 4 or 5;
$R^1$ is hydrogen and $R^2$ is cyano, hetero($C_5$)aryl or ($C_{1-4}$) alkyl-substituted hetero($C_5$)aryl or both $R^1$ and $R^2$ are hydrogen, halo, ($C_{1-4}$)alkyl or —$X^3OR^9$, wherein $X^3$ and $R^9$ are as defined below, or $R^1$ and $R^2$ together with the carbon atom to which both $R^1$ and $R^2$ are attached form $(C_{3-8})$cycloalkylene or $(C_{3-8})$heterocycloalkylene; $R^{22}$ at the first occurrence is selected from a group consisting of nitro, —$X^3NR^9R^9$, —$X^3SR^9$, —$X^3C(O)NR^9R^9$, —$X^3C(O)OR^9$, —$X^3S(O)R^{10}$, —$X^3S(O)_2R^{10}$, —$X^3C(O)R^{10}$ and —$X^3OR^{23}$, wherein $X^3$ is a bond or $(C_{1-2})$alkylene, $R^9$ at each occurrence independently is hydrogen, $(C_{1-3})$alkyl or halo-substituted $(C_{1-3})$alkyl, $R^{10}$ is $(C_{1-3})$alkyl or halo-substituted $(C_{1-3})$alkyl and $R^{23}$ is halo-substituted $(C_{1-3})$alkyl and $R^{22}$ at each other occurrence, independently is selected from a group consisting of $(C_{1-4})$alkyl, cyano, halo, halo-substituted $(C_{1-4})$alkyl, nitro, —$X^3NR^9R^9$, —$X^3OR^9$, —$X^3SR^9$, —$X^3C(O)NR^9R^9$, —$X^3C(O)OR^9$, —$X^3S(O)R^{10}$, —$X^3S(O)_2R^{10}$ and —$X^3C(O)R^{10}$, wherein $X^3$, $R^9$ and $R^{10}$ are as defined above; and $R^4$ is —$C(O)X^4R^{11}$ or —$S(O)_2X^4R^{11}$, wherein $X^4$ is a bond, —O— or —$NR^{12}$—, wherein $R^{12}$ is hydrogen or $(C_{1-6})$alkyl, and $R^{11}$ is (i) $(C_{1-6})$alkyl optionally substituted by —$OR^{13}$, —$SR^{13}$, —$S(O)R^{13}$, —$S(O)_2R^{13}$, —$C(O)R^{13}$, —$C(O)OR^{13}$, —$C(O)R^{13}R^{14}$, —$NR^{13}R^{14}$, —$NR^{14}C(O)R^{13}$, —$NR^{14}C(O)OR^{13}$, —$NR^{14}C(O)NR^{13}R^{14}$ or —$NR^{14}C(NR^{14})NR^{13}R^{14}$, wherein $R^{13}$ is $(C_{3-12})$cycloalkyl$(C_{0-3})$alkyl, hetero$(C_{5-12})$cycloalkyl$(C_{0-3})$alkyl, $(C_{6-12})$aryl$(C_{0-3})$alkyl hetero$(C_{5-12})$aryl$(C_{0-3})$alkyl, $(C_{9-12})$bicycloaryl$(C_{0-3})$alkyl or hetero$(C_{8-12})$bicycloaryl$(C_{0-3})$alkyl, and $R^{14}$ at each occurrence independently is hydrogen or $(C_{1-6})$alkyl, or (ii) $(C_{3-12})$cycloalkyl$(C_{0-3})$alkyl, hetero$(C_{5-12})$cycloalkyl$(C_{0-3})$alkyl, $(C_{6-12})$aryl$(C_{0-3})$alkyl, hetero$(C_{5-12})$aryl$(C_{0-3})$alkyl, $(C_{9-12})$bicycloaryl$(C_{0-3})$alkyl or hetero$(C_{8-12})$bicycloaryl$(C_{0-3})$alkyl or (iii) $(C_{3-6})$cycloalkyl$(C_{0-3})$alkyl, hetero$(C_{5-6})$cycloalkyl$(C_{0-3})$alkyl, phenyl$(C_{0-3})$alkyl or hetero$(C_{5-6})$aryl$(C_{0-3})$alkyl substituted by —$X^5OR^{15}$, —$X^5SR^{15}$, —$X^5S(O)R^{15}$, —$X^5S(O)_2R^{15}$, —$X^5(O)R^{15}$, —$X^5C(O)OR^{15}$, —$X^5C(O)NR^{15}R^{16}$, —$X^5NR^{15}R^{16}$, —$X^5NR^{16}C(O)R^{15}$, —$X^5NR^{16}C(O)OR^{15}$, —$X^5NR^{16}C(O)NR^{15}R^{16}$ OR —$X^5NR^{16}C(NR^{16})NR^{15}R^{16}$, wherein $X^5$ is a bond or methylene, $R^{15}$ is $(C_{3-6})$cycloalkyl$(C_{0-3})$alkyl, hetero$(C_{5-6})$cycloalkyl$(C_{1-6})$alkyl; wherein $R^4$ phenyl$(C_{0-3})$alkyl or hetero$(C_{5-6})$aryl$(C_{0-3})$alkyl and $R^{16}$ is hydrogen or $(C_{1-6})$alkyl; wherein $R^4$ optionally further contains 1 to 5 substituents which when occurring within an alicyclic or aromatic ring system are radicals independently selected from a group consisting of $(C_{1-6})$alkyl, $(C_{1-6})$alkylidene, cyano, halo, halo-substituted $(C_{1-3})$alkyl, nitro, —$X^5NR^{17}R^{17}$, —$X^5NR^{17}C(O)OR^{17}$, —$X^5NR^{17}C(O)NR^{17}R^{17}$, —$X^5NR^{17}C(NR^{17})NR^{17}R^{17}$, —$X^5OR^{17}$, —$X^5SR^{17}$, —$X^5C(O)OR^{17}$, —$X^5C(O)NR^{17}R^{17}$, —$X^5S(O)_2NR^{17}R^{17}$, —$X^5P(O)(OR^{17})OR^{17}$, —$X^5P(O)(OR^{17})OR^{17}$, —$X^5NR^{17}C(O)R^{17}$, —$X^5S(O)R^{18}$, —$X^5S(O)_2R^{18}$ and —$X^5C(O)R^{18}$ and when occurring within an aliphatic moiety are radicals independently selected from a group consisting of cyano, halo, nitro, —$NR^{14}R^{17}$, —$NR^{17}C(O)OR^{17}$, —$NR^{17}C(O)NR^{17}R^{17}$, —$NR^{17}C(NR^{17})NR^{17}R^{17}$, —$OR^{17}$, —$SR^{17}$, —$C(O)OR^{17}$, —$C(O)NR^{17}R^{17}$, —$S(O)_2NR^{17}R^{17}$, —$P(O)(OR^{17})OR^{17}$, —$OP(O)(OR^{17})OR^{17}$, —$NR^{17}C(O)R^{18}$, —$S(O)R^{18}$, —$S(O)_2R^{18}$ and —$C(O)R^{18}$, wherein $X^5$ is a bond or $(C_{1-6})$alkylene, $R^{17}$ at each occurrence independently is hydrogen, $(C_{1-6})$alkyl or halo-substituted $(C_{1-3})$alkyl and $R^{18}$ is $(C_{1-6})$alkyl or halo-substituted $(C_{1-3})$alkyl; and the N-oxide derivatives, individual isomers or mixtures of isomers thereof; or the pharmaceutically acceptable salts or solvates of such compounds or the N-oxide derivatives, individual isomers or mixtures of isomers thereof.

2. The compound of claim 1 in which n is 1 or 2, $R^1$ represents hydrogen and $R^2$ represents hydrogen, hetero$(C_5)$aryl or $(C_{1-4})$alkyl-substituted hetero$(C_5)$aryl or $R^1$ and $R^2$ together with the carbon atom to which both $R^1$ and $R^2$ are attached form $(C_{3-5})$cycloalkylene or $(C_{5-6})$heterocycloalkylene, $R^3$ at the first occurence is selected from a group consisting of difluoromethoxy, trifluoromethoxy, trifluorosulfanyl and nitro and $R^3$ at the second occurrence, if present, is selected from a group consisting of $(C_{1-4})$alkyl, bromo, carboxy, chloro, cyano, difluoromethoxy, fluoro, iodo, methoxy, nitro, trifluoromethoxy, trifluoromethyl and trifluorosulfanyl and $R^4$ is —$C(O)X^4R^{11}$ or —$S(O)_2X^4R^{11}$, wherein $X^4$ is a bond, —O— or —$N^{12}$—, wherein $R^{12}$ is hydrogen or $(C_{1-6})$alkyl, and $R^{11}$ is $(C_{1-6})$alkyl, $(C_{3-12})$cycloalkyl$(C_{0-3})$alkyl, hetero$(C_{5-12})$cycloalkyl$(C_{0-3})$alkyl, $(C_{6-10})$aryl$(C_{0-3})$alkyl, hetero$(C_{5-10})$aryl$(C_{0-3})$alkyl, hetero$(C_{8-12})$bicycloaryl$(C_{0-3})$alkyl, or phenyl$(C_{0-3})$alkyl, wherein the phenyl is substituted by —$X^5OR^{15}$ or —$X^5C(O)R^{15}$, wherein $X^5$ is a bond or methylene and $R^{15}$ is phenyl$(C_{0-3})$alkyl, wherein within $R^4$ any aryl or heteroaryl group optionally is substituted in the ring by 1 to 2 substituents selected from $(C_{1-6})$alkyl, halo, halo-substituted $(C_{1-3})$alkyl, —$X^5NR^{17}R^{17}$ and —$X^5OR^{17}$, wherein $X^5$ is a bond or $(C_{1-6})$alkylene, $R^{17}$ is hydrogen, $(C_{1-6})$alkyl or halo-substituted $(C_{1-3})$alkyl; and the N-oxide derivatives, individual isomers or mixtures of isomers thereof; or the pharmaceutically acceptable salts or solvates of such compounds or the N-oxide derivatives, individual isomers or mixtures of isomers thereof.

3. The compound of claim 2 in which $R^{22}$ at the first occurrence is nitro or difluoromethoxy in the ortho or meta position and $R^4$ is allyloxycarbonyl, 2-aminopyridinylcarbonyl, benzo[1,3]dioxolylcarbonyl, benzothienyl, benzoyl, 3-benzoylbenzoyl, 4-bromobenzoyl, 3-bromothienyl, biphenylylcarbonyl, 3-chlorobenzothienyl, 4-chlorobenzoyl, 3-chlorothienyl, cyclopentylcarbonyl, 3,4-difluorobenzoyl, dimethylcarbamoyl, 3,4-dimethoxybenzoyl, 4-fluorobenzoyl, 3-fluoro-4-hydroxybenzoyl, 2-hydroxypyridinylcarbonyl, 3-hydroxypyridinylcarbonyl, indolylcarbonyl, isobutyloxycarbonyl, isopropylcarbamoyl, isopropyloxycarbonyl, 4-methoxybenzoyl, methoxycarbonyl, 3-methylbenzoyl, 2-methylthienylcarbonyl, 4-methylvaleryl, morpholin-1-ylcarbonyl, naphthalenylcarbonyl, napthalenylsulfonyl, phenoxycarbonyl, phenylacryloyl, phenylsulfonyl, pyrazinylcarbonyl, pyridinylcarbonyl, quinolyl, thienylcarbonyl, thienylsulfonyl, 4-trifluoromethoxybenzoyl or 4-trifluoromethylbenzoyl; and the N-oxide derivastives, individual isomers or mixtures of isomers thereof; or the pharmaceutically acceptable salts or solvates of such compounds or the N-oxide derivatives, individual isomers or mixtures of isomers thereof.

4. The compound of claim 3 in which $R^{22}$ at the first occurrence is nitro or difluoromethoxy in the ortrho position and $R^4$ is benzoyl, indolyl, morpholin-4-ylcarbonyl, thienylcarbonyl or pyridinylcarbonyl optionally substituted in the ring by 1 to 2 substituents selected from fluoro and methyl; and the N-oxide derivatives, individual isomers or mixtures of isomers thereof; or the pharmaceutically acceptable salts or solvates of such compounds or the N-oxide derivatives, individual isomers or mixtures of isomers thereof.

5. The compound of claim 4 selected from a group consisting of:

N-[1R-cyanomethylcarbamoyl-2-(2-difluoromethoxybenzylsulfonyl)ethyl]-morpholine-4-carboxamide;

thiophene-2-carboxylic acid-{(R)-1-(cyanomethyl-carbamoyl)-2-[2-(1,1-difluoro-methoxy)-phenylmethanesulfonyl]ethyl}-amide;

thiophene-3-carboxylic acid-{(R)-1-(cyanomethyl-carbamoyl)-2-[2-(1,1-difluoro-methoxy)-phenylmethanesulfonyl]-ethyl}-amide;

N-{(R)-1-(cyanomethyl-carbamoyl)-2-[2-(1,1-difluoro-methoxy)-phenylmethanesulfonyl]-ethyl}-4-fluoro-benzamide;

morpholine-4-carboxylic acid-{(R)-1-(4-cyano-1-methyl-piperidin-4-ylcarbamoyl)-2-[2-(1,1-difluoro-methoxy)-phenylmethanesulfonyl]-ethyl}-amide;

5-methyl-thiophene-2-carboxylic acid-{(R)-1-(cyanomethyl-carbamoyl)-2-[2-(1,1-difluoro-methoxy)-phenylmethanesulfonyl]-ethyl}-amide;

1H-indole-5-carboxylic acid-{(R)-1-(cyanomethyl-carbamoyl)-2-[2-(1,1-difluoro-methoxy)-phenylmethanesulfonyl]-ethyl}-amide;

N-{(R)-1-(cyanomethyl-carbamoyl)-2-[2-(1,1-difluoro-methoxy)-phenylmethanesulfonyl]-ethyl}-3-methyl-benzamide;

N-{(R)-1-(cyanomethyl-carbamoyl)-2-[2-(1,1-difluoro-methoxy)-phenylmethanesulfonyl]-ethyl}-3,4-difluoro-benzamide;

N-{(R)-1-(cyanomethyl-carbamoyl)-2-[2-(1,1-difluoro-methoxy)-phenylmethanesulfonyl]ethyl}-isonicotinamide;

N-[1R-(1-cyanacyclopropylcarbamoyl)-2-(2-difluoromethoxybenzylsulfonyl)-ethyl]morpholine-4-carboxamide; and the N-oxide derivatives, individual isomers or mixtures of isomers thereof; or the pharmaceutically acceptable sales or solvates of such compounds or the N-oxide derivatives, individual isomers or mixtures of isomers thereof.

6. A pharmaceutical composition comprising a therapeutically effective amount of a compound of claim 1 in combination with a pharmaceutically acceptable excipient.

7. A method for treating a disease in an animal in which cathepsin S protease activity can contribute to the pathology or symptomatology of the disease, which method comprises administering to the animal a therapeutically effective amount of compound of claim 1 or a N-oxide derivative or individual isomer or mixture of isomers thereof; or a pharmaceutically acceptable sale or solvate of such compounds or the N-oxide derivatives, individual isomers or mixtures of isomers thereof.

8. The method of claim 7 in which the disease is an autoimmune disorder, allergic disorder, allogeneic immune response, a disorder involving excessive elastolysis, cardiovascular disorders or a disorder involving fibril formation.

9. The method of claim 8 in which the disorder is selected from the juvenile onset diabetes, multiple sclerosis, pemphigus vulgaris, Graves' disease, myasthenia gravis, systemic lupus eryihernotaus, rheumatoid arthritis, Hashimoto's thyroiditis, asthmua, organ transplant or tissue graft rejections, chronic obstructive pulmonary disease, bronchiolitis, excessive airway elastolysis in asthma and bronchitis, pneumonities, plaque rupture, atheroma and systemic amyloidosis.

* * * * *